United States Patent
Ren et al.

(10) Patent No.: US 9,227,978 B2
(45) Date of Patent: Jan. 5, 2016

(54) COVALENT INHIBITORS OF KRAS G12C

(71) Applicant: Araxes Pharma LLC, San Diego, CA (US)

(72) Inventors: Pingda Ren, San Diego, CA (US); Yi Liu, San Diego, CA (US); Liansheng Li, San Diego, CA (US); Jun Feng, San Diego, CA (US); Tao Wu, Carlsbad, CA (US)

(73) Assignee: Araxes Pharma LLC, La Jolla, CA (US)

( * ) Notice: Subject to any disclaimer, the term of this patent is extended or adjusted under 35 U.S.C. 154(b) by 0 days.

(21) Appl. No.: 14/212,656

(22) Filed: Mar. 14, 2014

(65) Prior Publication Data

US 2014/0288045 A1 Sep. 25, 2014

Related U.S. Application Data

(60) Provisional application No. 61/852,123, filed on Mar. 15, 2013, provisional application No. 61/889,480, filed on Oct. 10, 2013.

(51) Int. Cl.
| | |
|---|---|
| *A61K 31/496* | (2006.01) |
| *C07D 403/04* | (2006.01) |
| *C07D 487/10* | (2006.01) |
| *C07D 211/62* | (2006.01) |
| *C07D 213/64* | (2006.01) |
| *C07D 487/04* | (2006.01) |
| *C07D 295/16* | (2006.01) |
| *C07D 205/04* | (2006.01) |
| *C07D 401/04* | (2006.01) |
| *C07D 285/14* | (2006.01) |
| *G01N 33/58* | (2006.01) |
| *C07D 213/74* | (2006.01) |
| *C07D 231/40* | (2006.01) |
| *C07D 401/12* | (2006.01) |
| *C07D 237/04* | (2006.01) |
| *C07D 403/06* | (2006.01) |
| *C07D 405/06* | (2006.01) |
| *C07D 419/12* | (2006.01) |
| *C07D 471/04* | (2006.01) |
| *C07D 285/16* | (2006.01) |
| *C07D 211/56* | (2006.01) |
| *C07D 211/58* | (2006.01) |
| *C07D 211/60* | (2006.01) |

(52) U.S. Cl.
CPC ............ *C07D 487/10* (2013.01); *C07D 205/04* (2013.01); *C07D 211/56* (2013.01); *C07D 211/58* (2013.01); *C07D 211/60* (2013.01); *C07D 211/62* (2013.01); *C07D 213/64* (2013.01); *C07D 213/74* (2013.01); *C07D 231/40* (2013.01); *C07D 237/04* (2013.01); *C07D 285/14* (2013.01); *C07D 285/16* (2013.01); *C07D 295/16* (2013.01); *C07D 401/04* (2013.01); *C07D 401/12* (2013.01); *C07D 403/04* (2013.01); *C07D 403/06* (2013.01); *C07D 405/06* (2013.01); *C07D 419/12* (2013.01); *C07D 471/04* (2013.01); *C07D 487/04* (2013.01); *G01N 33/58* (2013.01)

(58) Field of Classification Search
CPC ............................. A61K 31/496; C07D 403/04
USPC ................. 544/358, 359; 514/252.12, 252.13
See application file for complete search history.

(56) References Cited

U.S. PATENT DOCUMENTS

| | | | |
|---|---|---|---|
| 4,649,219 A | 3/1987 | Itoh et al. | |
| 5,033,252 A | 7/1991 | Carter | |
| 5,052,558 A | 10/1991 | Carter | |
| 5,323,907 A | 6/1994 | Kalvelage | |
| 5,731,352 A | 3/1998 | Lesieur et al. | |
| 5,861,510 A | 1/1999 | Piscopio et al. | |
| 5,863,949 A | 1/1999 | Robinson et al. | |
| 6,214,872 B1 | 4/2001 | Robinson | |
| 8,399,454 B2 * | 3/2013 | Bian et al. | 514/217.05 |
| 8,426,401 B2 * | 4/2013 | Bian et al. | 514/210.18 |
| 8,604,017 B2 * | 12/2013 | Bian et al. | 514/210.18 |
| 8,697,684 B2 * | 4/2014 | Bian et al. | 514/210.18 |
| 8,741,887 B2 * | 6/2014 | Bian et al. | 514/210.18 |
| 2003/0022344 A1 | 1/2003 | Williams et al. | |
| 2005/0227997 A1 | 10/2005 | Noe et al. | |
| 2008/0004348 A1 | 1/2008 | Yous et al. | |
| 2009/0054402 A1 | 2/2009 | Wang et al. | |
| 2010/0331300 A1 | 12/2010 | Bian et al. | |
| 2011/0269244 A1 | 11/2011 | Petter et al. | |

FOREIGN PATENT DOCUMENTS

| | | |
|---|---|---|
| EP | 0 606 046 A1 | 7/1994 |
| EP | 0 780 386 A1 | 6/1997 |
| EP | 0 818 442 A2 | 1/1998 |
| EP | 0 931 788 A2 | 7/1999 |
| EP | 1 004 578 A1 | 5/2000 |
| GB | 939516 A | 10/1963 |
| WO | 90/05719 A1 | 5/1990 |
| WO | 96/27583 A1 | 9/1996 |
| WO | 96/33172 A1 | 10/1996 |

(Continued)

OTHER PUBLICATIONS

Barbe et al., "Highly Chemoselective Metal-Free Reduction of Tertiary Amides," *J. Am. Chem. Soc.* 130:18-19, 2008.

(Continued)

*Primary Examiner* — Golam M M Shameem
(74) *Attorney, Agent, or Firm* — Seed IP Law Group PLLC

(57) ABSTRACT

Irreversible inhibitors of G12C mutant K-Ras protein are provided. Also disclosed are methods to modulate the activity of G12C mutant K-Ras protein and methods of treatment of disorders mediated by G12C mutant K-Ras protein.

24 Claims, 8 Drawing Sheets

(56) References Cited

FOREIGN PATENT DOCUMENTS

| WO | 98/03516 A1 | 1/1998 |
|---|---|---|
| WO | 98/07697 A1 | 2/1998 |
| WO | 98/30566 A1 | 7/1998 |
| WO | 98/33768 A1 | 8/1998 |
| WO | 98/34915 A1 | 8/1998 |
| WO | 98/34918 A1 | 8/1998 |
| WO | 98/57948 A1 | 12/1998 |
| WO | 99/29667 A1 | 6/1999 |
| WO | 99/52889 A1 | 10/1999 |
| WO | 99/52910 A1 | 10/1999 |
| WO | 2013/155223 A1 | 10/2013 |
| WO | 2014/143659 A1 | 9/2014 |
| WO | 2015/054572 A1 | 4/2015 |

OTHER PUBLICATIONS

Bégué et al., "Ions α-Cetocarbenium. Influence De La Structure Sur L'Evolution Des Ions α-Cetocyclohexylcarbenium," *Tetrahedron* 31(20):2205-2511, 1975. (English Abstract Only).

Kelly et al., "Synthesis of Isomeric 3-Piperidinyl and 3-Pyrrolidinyl Benzo[5,6]cyclohepta[1,2-*b*]pyridines: Sulfonamido Derivatives as Inhibitors of Ras Prenylation," *Bioorganic & Medicinial Chemistry* 6:673-686, 1998.

Liansheng Li et al., "Inhibitors of Kras G12C," filed Oct. 10, 2014, U.S. Appl. No. 14/511,425, 353 pages.

Liu et al., "*Polygonatum cyrtonema* lectin induces murine fibrosarcoma L929 cell apoptosis and autophagy via blocking Ras-Raf and PI3K-Akt signaling pathways," *Biochimie* 92:1934-1938, 2010.

Loboda et al., "A gene expression signature of RAS pathway dependence predicts response to PI3K and RAS pathway inhibitors and expands the population of RAS pathway activated tumors," *BMC Medical Genomics* 3(26):1-11, 2010.

Pédeboscq et al., "Synthesis and evaluation of apoptosis induction of thienopyrimidine compounds on KRAS and BRAF mutated colorectal cancer cell lines," *Bioorganic & Medicinial Chemistry* 20:6724-6731, 2012.

PubChem Compound, "(4-hydroxypiperidin-1-y1)-pyridin-4-ylmethanone: AC1L5BNJ," retrieved on Feb. 17, 2014, from http://pubchem.ncbi.nlm.nih.gov/summary/summary.cgi?cid=76837, Jul. 8, 2005, 5 pages.

Tsubaki et al., "Reduction of metastasis, cell invasion, and adhesion in mouse osteosarcoma by YM529/ONO-5920-induced blockade of the Ras/MEK/ERK and Ras/PI3K/Akt pathway," *Toxicology and Applied Pharmacology* 259(3):402-410, Jan. 2012.

Appel et al., "Supramolecular Cross-Linked Networks via Host-Guest Complexation with Cucurbit[8]uril," *J. Am. Chem. Soc.* 132(40):14251-14260, Jul. 2010.

Johnson et al., "The Chemistry of β-Bromopropionyl Isocyanate. I. Synthesis of 1-Aryldihydrouracils," *The Journal of Organic Chemistry* 24(9):1391-1392, Sep. 1959.

Le Picard et al., "Design and Synthesis of Naphthalenic Derivatives as Potential Inhibitors of Hydroxyindole-*O*-methyltransferase," *Pharm. Pharmacol. Commun.* 5:183-188, 1999.

Palmioli et al., "Selective cytotoxicity of a bicyclic Ras inhibitor in cancer cells expressing $K\text{-}Ras^{G13D}$," *Biochemical and Biophysical Research Communications* 386(4):593-597, Sep. 2009.

Peri et al., "Arabinose-derived bicyclic amino acids: synthesis, conformational analysis and construction of an $\alpha_v\beta_3$-selective RGD peptide," *J. Am. Chem. Soc., Perkins Trans* 1(5):638-644, Feb. 2002.

Peri et al., "Sugar-Derived Ras Inhibitors: Group Epitope Mapping by NMR Spectroscopy and Biological Evaluation," *Eur. J. Org. Chem.* 2006(16):3707-3720, Aug. 2006.

Peri et al., "Synthesis of bicyclic sugar azido acids and their incorporation in cyclic peptides," *Chem. Commun.* 23:2303-2304, Jan. 2000.

PubChem Compound, "(2S,6R)-hexahydrofuro[3,2-b]furan-2,6-diyl dicarbonochloridate:Compound Summary CID 53396983," Oct. 30, 2011, retrieved from http://pubchem.ncbi.nlm.nih.gov/compound/53396983, 6 pages.

PubChem Compound, "Compound Summary for CID 21765509: Molecular Formula $C_{18}H_{21}N_5O_8$," Dec. 5, 2007, retrieved from http://pubchem.ncbi.nlm.nih.gov/compound/21765509, 4 pages.

PubChem Compound, "Compound Summary for CID 21765511: Molecular Formula $C_{18}H_{21}N_5O_8$," Dec. 5, 2007, retrieved from http://pubchem.ncbi.nlm.nih.gov/compound/21765511, 4 pages.

PubChem Compound, "Compound Summary for CID 60018735: Molecular Formula $C_{30}H_{30}O_{13}$," Aug. 20, 2012, retrieved from http://pubchem.ncbi.nlm.nih.gov/compound/60018735#section=Top, 1 page.

PubChem Compound, "Compound Summary for CID 72623693: AGN-PC-0D83J7," Jan. 9, 2014, retrieved from http://pubchem.ncbi.nlm.nih.gov/compound/72623693, 6 pages.

PubChem Compound, "Compound Summary for CID 9897840: Molecular Formula $C_{50}H_{46}O_{20}$," Oct. 25, 2006, retrieved from http://pubchem.ncbi.nlm.nih.gov/compound/9897840, 6 pages.

Sasaki et al., "Selective Formation of Stable Triplexes Including a TA or a CG Interrupting Site with New Bicyclic Nucleoside Analogues (WNA)," *J. Am. Chem. Soc.* 126(2):516-528, Jan. 2004.

Streuff et al., "First asymmetric aminohydroxylation of acrylamides," *Tetrahedron: Asymmetry* 16(21):3492-3496, Oct. 2005.

Tulshian et al., "Synthesis and Phosphodiesterase Activity of Carboxylic Acid Mimetics of Cyclic Guanosine 3',5'-Monophosphate," *J. Med. Chem.* 36(9):1210-1220, Jan. 1993.

Wu et al., "Stereoselective synthesis of dioxabicycles from 1-*C*-allyl-2-*O*-benzyl-glycosides—An intramolecular cyclization between 2-*O*-benzyl oxygen and the allyl double bond," *Can. J. Chem.* 84(1):597-602, Jan. 2006.

* cited by examiner

| Oncogene | Tumor Type | Cumulative Mutation Frequency (All Tumors) |
|---|---|---|
| Bcr-Abl | 90% CML | <1% |
| EGFR | 10% NSCLC | <5% |
| ALK | 5% NSCLC | <1% |
| B-Raf | 66% Melanoma | <5% |
| Flt3 | 25% AML | <1% |
| PI3kα | 25% Breast; 25% Endometrial; 15% CRC | 15-20% |
| K-Ras | >80% Pancreatic; >40% colon >20% lung | ~20% |

FIG. 3

COVALENT INHIBITORS OF KRAS G12C

BACKGROUND

Technical Field

Ras represents a group of closely related monomeric globular protein of 189 amino acids (21 kDa molecular mass) which is associated with the plasma membrane and which binds either GDP or GTP. Ras acts as a molecular switch. When Ras contains bound GDP it is in the resting or off position and is "inactive". In response to exposure of the cell to certain growth promoting stimuli, Ras is induced to exchange its bound GDP for a GTP. With GTP bound, Ras is "switched on" and is able to interact with and activate other proteins (its "downstream targets"). The Ras protein itself has a very low intrinsic ability to hydrolyze GTP back to GDP, thus turning itself into the off state. Switching Ras off requires extrinsic proteins termed GTPase-activating proteins (GAPs) that interact with Ras and greatly accelerate the conversion of GTP to GDP. Any mutation in Ras which affects its ability to interact with GAP or to convert GTP back to GDP will result in a prolonged activation of the protein and consequently a prolonged signal to the cell telling it to continue to grow and divide. Because these signals result in cell growth and division, overactive Ras signaling may ultimately lead to cancer.

Structurally, Ras proteins contain a G domain which is responsible for the enzymatic activity of Ras—the guanine nucleotide binding and the hydrolysis (GTPase reaction). It also contains a C-terminal extension, known as the CAAX box, which may be post-translationally modified and is responsible for targeting the protein to the membrane. The G domain is approximately 21-25 kDa in size and it contains a phosphate binding loop (P-loop). The P-loop represents the pocket where the nucleotides are bound in the protein, and this is the rigid part of the domain with conserved amino acid residues which are essential for nucleotide binding and hydrolysis (Glycine 12, Threonine 26 and Lysine 16). The G domain also contains the so called Switch I (residues 30-40) and Switch II (residues 60-76) regions, both of which are the dynamic parts of the protein which are often represented as the "spring-loaded" mechanism because of their ability to switch between the resting and loaded state. The key interaction is the hydrogen bonds formed by Threonine-35 and glycine-60 with the γ-phosphate of GTP which maintain Switch 1 and Switch 2 regions respectively in their active conformation. After hydrolysis of GTP and release of phosphate, these two relax into the inactive GDP conformation.

The most notable members of the Ras subfamily are HRAS, KRAS and NRAS, mainly for being implicated in many types of cancer. However, there are many other members including DIRAS1; DIRAS2; DIRAS3; ERAS; GEM; MRAS; NKIRAS1; NKIRAS2; NRAS; RALA; RALB; RAP1A; RAP1B; RAP2A; RAP2B; RAP2C; RASD1; RASD2; RASL10A; RASL10B; RASL11A; RASL11B; RASL12; REM1; REM2; RERG; RERGL; RRAD; RRAS; RRAS2.

Mutations in any one of the three main isoforms of RAS (H-Ras, N-Ras, or K-Ras) genes are among the most common events in human tumorigenesis. About 30% of all human tumors are found to carry some mutation in Ras genes. Remarkably, K-Ras mutations are detected in 25-30% of tumors. By comparison, the rates of oncogenic mutation occurring in the N-Ras and H-Ras family members are much lower (8% and 3% respectively). The most common K-Ras mutations are found at residue G12 and G13 in the P-loop and at residue Q61.

G12C is a frequent mutation of K-Ras gene (glycine-12 to cysteine). This mutation had been found in about 13% of cancer occurrences, about 43% of lung cancer occurrences, and in almost 100% of MYH-associates polyposis (familial colon cancer syndrome). However targeting this gene with small molecules is a challenge. Accordingly, there is a need in the art for small molecules for targeting Ras (e.g., K-Ras, H-Ras and/or N-Ras) and use of the same for treatment of various diseases, such as cancer. The present invention provides these and other related advantages.

BRIEF SUMMARY

The present invention provides compounds which are capable of modulating G12C mutant K-Ras, H-Ras and/or N-Ras proteins. In some instances, the compound acts as an electrophile capable of forming a covalent bond with the cysteine residue at position 12 of a K-Ras, H-Ras or N-Ras G12C mutant protein.

In some aspects of the invention, the compounds described herein are included in pharmaceutical compositions. In some embodiments, the pharmaceutical composition comprises a pharmaceutically acceptable carrier. In some aspects of the invention, the pharmaceutical composition is suitable for oral administration. In some embodiments, the pharmaceutical composition is suitable for injection.

In one aspect, a method is provided. The method comprises a method of regulating activity of a K-Ras, H-Ras or N-Ras G12C mutant protein wherein the method comprises reacting the K-Ras, H-Ras or N-Ras G12C mutant protein with any of the compounds described herein. In some embodiments, the method inhibits proliferation of a cell population by contacting the cell population with any of the compounds described herein. In some embodiments, the method of inhibiting proliferation of a cell is measured as a decrease in cell viability of the cell population.

In one aspect, a method of treating a disorder in a subject is provided. The method of treating a disorder in a subject comprises: (a) determining if the subject has a K-Ras, H-Ras or N-Ras G12C mutation; and (b) if the subject is determined to have the K-Ras, H-Ras or N-Ras G12C mutation then administering to the subject a therapeutically effective dose of a pharmaceutical composition comprising at least one compound described herein. In some embodiments, the disorder is a cancer. In some embodiments, the cancer is pancreatic cancer, colon cancer, MYH associated polyposis, colorectal cancer, lung cancer or NSCLC.

In one aspect, a method of preparing a labeled K-Ras, H-Ras or N-Ras G12C mutant protein is provided. The method of preparing a labeled K-Ras, H-Ras or N-Ras G12C mutant comprises reacting the K-Ras, H-Ras or N-Ras G12C mutant with a compound described herein, resulting in a labeled K-Ras, H-Ras or N-Ras G12C protein.

In one aspect, a compound of Formula I having is provided:

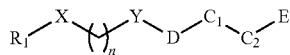

wherein X is O or NH, S, or $CR_{23}$, $R_{24}$; Y is $CH_2$, $CHR_{22}$, CO, SO, or $SO_2$; n is an integer of value 1-6; R1 is aryl or heteroaryl, each of which is unsubstituted or substituted by one or more independent R2 substituents; R2 is halogen, —OH, oxo, alkoxy, alkyl, cycloalkyl, heteroalkyl, heterocycloalkyl, aryl, heteroaryl, arylene, or heteroarylene, each of which is unsubstituted or substituted by one or more independent R3 substituents; R3 is halogen, OH, cyano, alkyl, alkoxy, cycloalkyl, heteroalkyl, heterocycloalkyl, aryl, heteroaryl, arylene, or heteroarylene, each of which is unsubstituted or substituted by one or more independent R4 substituents; R4 is halogen, OH, cyano, alkyl, alkoxy, cycloalkyl, heteroalkyl, heterocycloalkyl, aryl, heteroaryl, arylene, or heteroarylene; C1 is alkyl, cycloalkyl, heterocycloalkyl, arylene, heteroarylene, or heterocycloalkylene; each of which may be substituted with a R5 substituent; C2 is a bond, cycloalkyl, heterocycloalkyl, arylene, heteroarylene, cycloalkylene, or heterocycloalkylene, wherein C1 and C2 may form a fused or spiro bicyclic ring; D is a bond, —NH—CH2-, —NH—, or —CH2-; R5 is OH, alkyl, or —CH2OH; and E is an electrophile capable of forming a covalent bond with the cysteine residue at position 12 of a K-Ras G12C mutant protein.

In some embodiments, the compound of Formula 1 has an O at position X. In other embodiments, the X represents a NH group.

In some embodiments, the compound of Formula 1 has a bond at position D. In other embodiments, D is a NH group. In other embodiments, the compound of Formula 1 has —NH—CH2- at position D connected to —NH—CH2- connected to the carbonyl carbon.

In some embodiments, the compound of Formula 1 has a group at position E that is selected from the group consisting of:

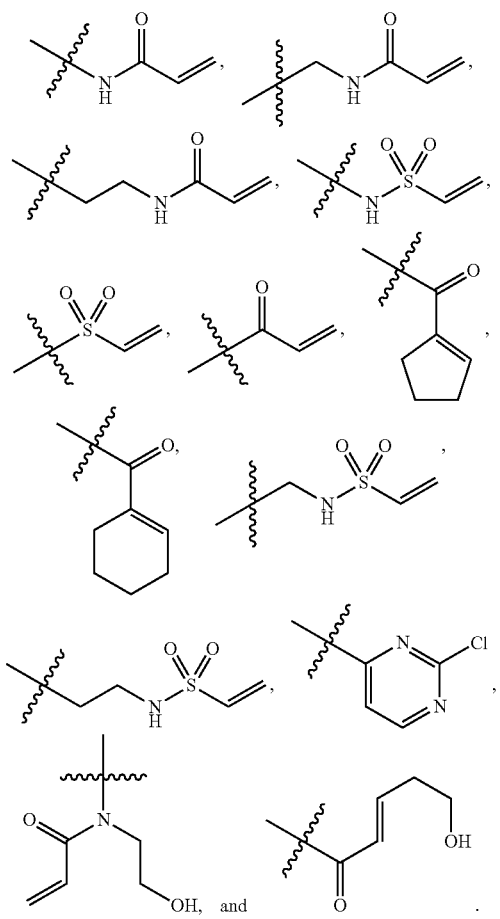

In some embodiments, the compound of Formula 1 has a phenyl moiety is at position R1 and the phenyl moiety position R1 is unsubstituted or substituted by one or more independent R2 substituents. In other embodiments, the compound of Formula 1 has a benzothiadiazolyl moiety is at position R1 and is unsubstituted or substituted by one or more independent R2 substituents. In other embodiments, the compound of Formula 1 has a naphthalenyl moiety is at position R1 and is unsubstituted or substituted by one or more independent R2 substituents. In other embodiments, the compound of Formula 1 has an imidazopyridinyl moiety is at position R1 and is unsubstituted or substituted by one or more independent R2 substituents.

In some embodiments, the compound of Formula 1 has a halogen at position R2. In other embodiments, the compound of Formula 1 has an OH at position R2. In other embodiments, the compound of Formula 1 has an OMe at position R2. In other embodiments, the compound of Formula 1 has an aryl or heteroaryl moiety at position R2 that is unsubstituted or substituted by one or more independent R3 substituents. In other embodiments, the compound of Formula 1 has a phenyl, pyridinyl, or thiophenyl moiety at position R2 that is unsubstituted or substituted by one or more independent R3 substituents.

In some embodiments, the compound of Formula 1 has a fused bicyclic ring structure at the —C1-C2- position. In some embodiments, the compound of Formula 1 has a

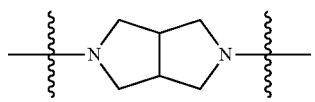 [SMILES: *N1CC2CN(*)CC2C1]

at the —C1-C2 position. In other embodiments, the compound of Formula 1 has a

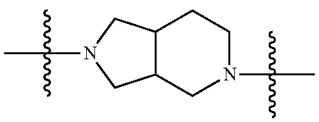

at the —C1-C2 position. In other embodiments, the compound of Formula 1 has

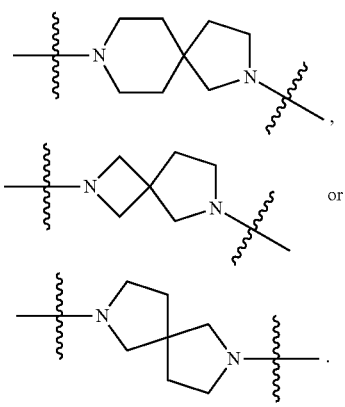

at the —C1-C2 position.

In some embodiments, the compound of Formula 1 has group at $C_1$ that is selected from the group consisting of:

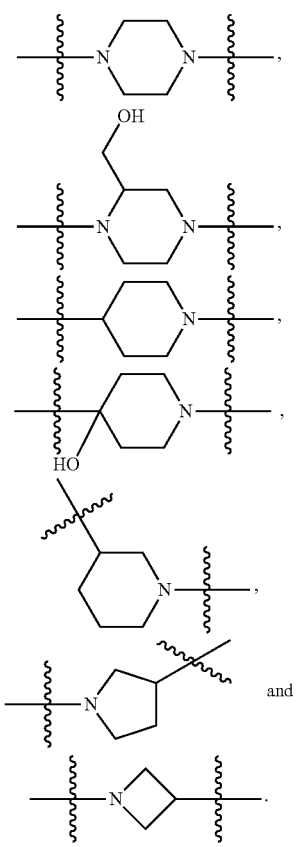

In some embodiments, the compound of Formula 1 has group at $C_2$ that is selected from the group consisting of:

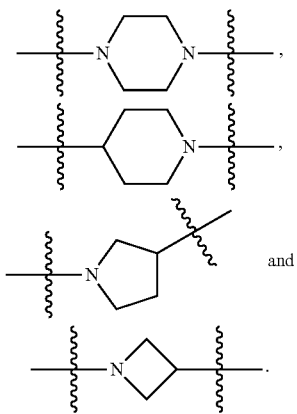

In some embodiments, the compound of Formula 1 is selected from the compounds shown in Table 1.

In another aspect, a composition is provided; the composition comprises a compound of Formula II having the structure of

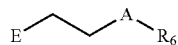

wherein A is —CH2-, —O—, or —NH—; $R_6$ is aryl or heteroaryl, each of which is unsubstituted or substituted by one or more independent R7 substituents; R7 is halogen, —OH, OR10, NR11R12, alkyl, oxo, cycloalkyl, heteroalkyl, heterocycloalkyl, aryl, heteroaryl, arylene, or heteroarylene, each of which is unsubstituted or substituted by one or more independent R8 substituents; R8 is halogen, OH, cyano, alkyl, alkoxy, cycloalkyl, heteroalkyl, heterocycloalkyl, aryl, heteroaryl, arylene, or heteroarylene, each of which is unsubstituted or substituted by one or more independent R9 substituents; R10, R11 and R12 are independently hydrogen, alkyl, cycloalkyl, heteroalkyl, heterocycloalkyl, aryl, or heteroaryl, each of which is unsubstituted or substituted by one or more independent R13 substituents; R9 and R13 are independently halogen, OH, cyano, alkyl, alkoxy, cycloalkyl, heteroalkyl, heterocycloalkyl, aryl, heteroaryl, arylene, or heteroarylene; E is an electrophile capable of forming a covalent bond with the cysteine residue at position 12 of a K-Ras G12C mutant protein.

In some embodiments, the E of the Formula II compound represents

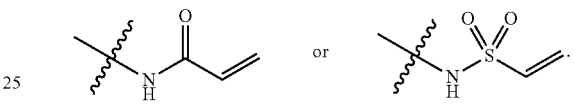

In some embodiments, the R1 of the Formula II compound represents an aryl, unsubstituted or substituted by one or more independent R2 substituents. In other embodiments, the R1 of the Formula II compound is a heteroaryl, unsubstituted or substituted by one or more independent R2 substituents. In some embodiments, the R1 of the Formula II compound represents a phenyl moiety unsubstituted or substituted by one or more independent R2 substituents. In some embodiments, the R1 of the Formula II compound represents a pyridinyl moiety unsubstituted or substituted by one or more independent R2 substituents.

In some embodiments, the A of the Formula II compound is O. In other embodiments, the A of the Formula II compound is NH.

In some embodiments, the Formula II compound is selected from the compounds shown in Table 2.

In another aspect, a compound is provided; the compound of Formula III having the structure of:

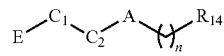

wherein A is a bond, O, NH, or —C(O)—; n is 0 or 2; R14 is cycloalkyl, heterocycloalkyl, aryl, or heteroaryl, each of which is unsubstituted or substituted by one or more independent R15 substituents; R15 is halogen, OR18, NR19R20, oxo, alkyl, cycloalkyl, heteroalkyl, heterocycloalkyl, aryl, heteroaryl, arylene, or heteroarylene, each of which is unsubstituted or substituted by one or more independent R16 substituents; R16 is halogen, OH, alkyl, alkoxy, cyano cycloalkyl, heteroalkyl, heterocycloalkyl, aryl, heteroaryl, arylene, or heteroarylene, each of which is unsubstituted or substituted by one or more independent R17 substituents; R18, R19 and R20 are independently hydrogen, alkyl, cycloalkyl, heteroalkyl, heterocycloalkyl, aryl, heteroaryl, arylene, or heteroarylene, each of which is unsubstituted or substituted by one or more independent R21 substituents; R17 and R21 are independently halogen, OH, cyano, alkyl, alkoxy, cycloalkyl, heteroalkyl, heterocycloalkyl, aryl, heteroaryl, arylene, or heteroarylene; C1 is cycloalkyl or heterocycloalkyl; C2 is a bond, cycloalkyl, heterocycloalkyl, arylene, or heteroarylene; wherein C1 and C2 may form a fused or spiro bicyclic ring; and E is an electrophile capable of forming a covalent bond with the cysteine residue at position 12 of a K-Ras G12C mutant protein.

In some embodiments, the A of the Formula III compound represents O. In other embodiments, the A of the Formula III compound represents —C(O)—. In other embodiments, the A of the Formula III compound represents a bond.

In some embodiments, the n of the Formula III compound represents 0. In other embodiments, the n of the Formula III compound represents 1. In other embodiments, the n of the Formula III compound represents 2.

In some embodiments, the C2 of the Formula III compound represents a bond. In some embodiments, the C2 of the Formula III compound represents a pyridinyl.

In some embodiments the C1 of the Formula III compound is selected from the group consisting of:

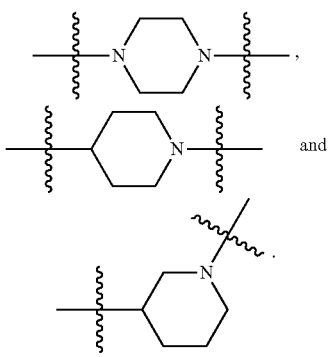

In some embodiments, the R1 of the Formula III compound is an aryl or heteroaryl moiety unsubstituted or substituted by one or more independent R2 substituents. In other embodiments, the R1 of the Formula III compound is a phenyl moiety unsubstituted or substituted by one or more independent R2 substituents. In other embodiments, the R1 of the Formula III compound is

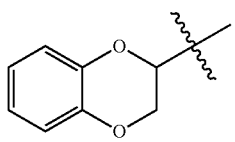

In other embodiments, R1 of the Formula III compound represents

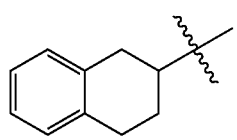

In other embodiments, R1 represents a pyridinyl moiety unsubstituted or substituted by one or more independent R2 substituents. In other embodiments, the R1 of the Formula III compound represents

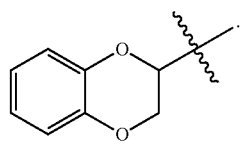 [SMILES: *C1COc2ccccc2O1]

In other embodiments, the R1 of the Formula III compound represents

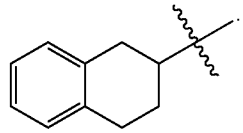 [SMILES: *C1CCc2ccccc2C1]

In some embodiments, the R2 of the Formula III compound represents a halogen. In other embodiments, the R2 of the Formula III compound represents an alkyl. In other embodiments, the R2 of the Formula III compound represents a —CH3.

In some embodiments, the E of the Formula III compound represents:

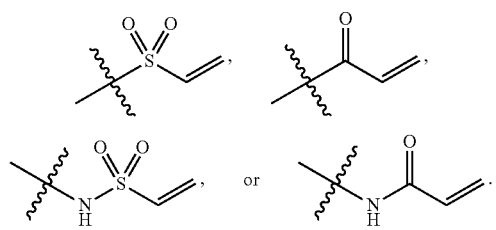

In some embodiments, the Formula III compound is selected from the compounds shown in Table 3.

In another aspect, a composition is provided; the composition comprises a compound shown in Table 4.

In other embodiments, a compound of structure (V) is provided:

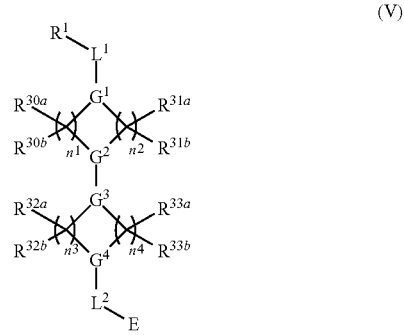

(V)

or a pharmaceutically acceptable salt, tautomer, stereoisomer or prodrug thereof, wherein $R^1$, $L^1$, $L^2$, E, G1, G2, G3, G4, $R^{30a}$, $R^{30b}$, $R^{31a}$, $R^{31b}$, $R^{32a}$, $R^{32b}$, $R^{33a}$, $R^{33b}$, $n^1$, $n^2$, $n^3$ and $n^4$ are as defined herein.

Also provided in various different embodiments is a compound of structure (VI):

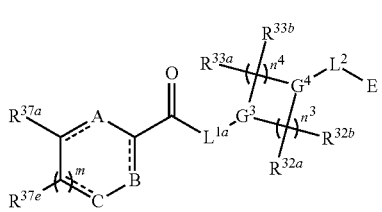

or a pharmaceutically acceptable salt, tautomer, stereoisomer or prodrug thereof, wherein A, B, C, $L^{1a}$, $L^2$, E, $G^3$, $G^4$, $R^{32a}$, $R^{32b}$, $R^{33a}$, $R^{33b}$, $R^{37a}$, $R^{37e}$, $n^3$, $n^4$ and m are as defined herein, These and other aspects of the invention will be apparent upon reference to the following detailed description. To this end, various references are set forth herein which describe in more detail certain background information, procedures, compounds and/or compositions, and are each hereby incorporated by reference in their entirety.

BRIEF DESCRIPTION OF THE SEVERAL VIEWS OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 3 Shows some common oncogenes, their respective tumor type and cumulative mutation frequencies (all tumors).

DETAILED DESCRIPTION

Figure 1:
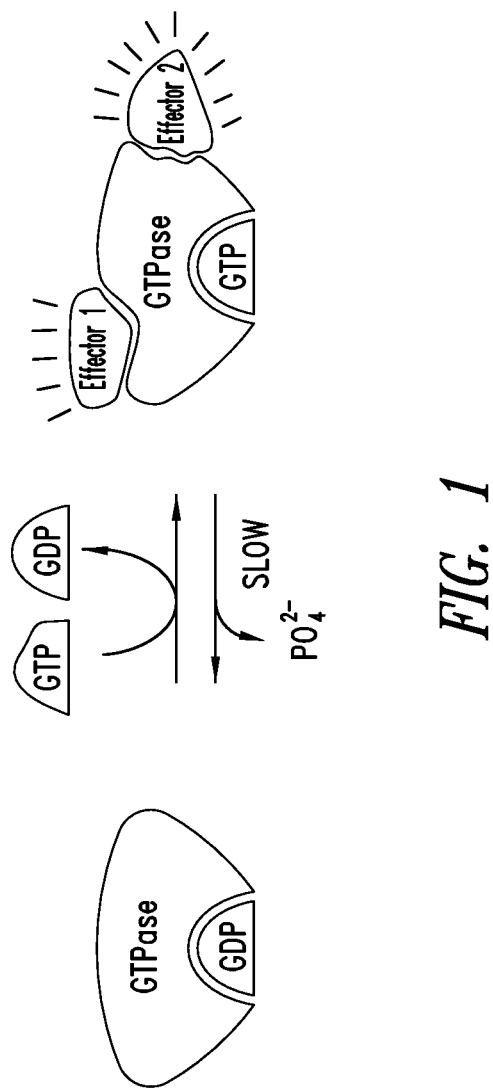
FIG. 1 Shows the enzymatic activity of Ras.
Figure 2:
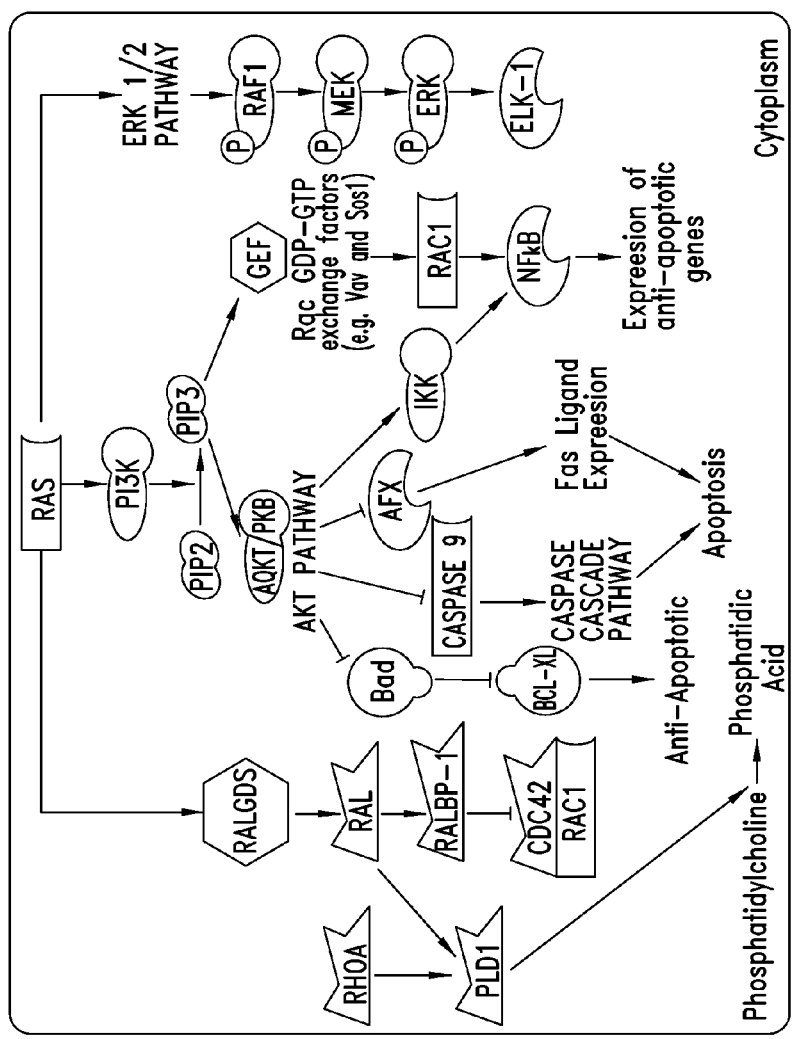
FIG. 2 shows a signal transduction pathway for Ras.

Unless defined otherwise, all technical and scientific terms used herein have the same meaning as is commonly understood by one of skill in the art to which this invention belongs. All patents and publications referred to herein are incorporated by reference.

As used in the specification and claims, the singular form "a", "an" and "the" include plural references unless the context clearly dictates otherwise.

"Amino" refers to the —$NH_2$ radical.

"Carboxy" or "carboxyl" refers to the —$CO_2H$ radical.

"Cyano" refers to the —CN radical.

"Hydroxy" or "hydroxyl" refers to th —OH radical.

"Imino" refers to the =NH substituent.

"Nitro" refers to the —$NO_2$ radical.

"Oxo" refers to the =O substituent.

"Thioxo" refers to the =S substituent.

"Alkyl" refers to a straight or branched hydrocarbon chain radical consisting solely of carbon and hydrogen atoms, which is saturated or unsaturated (i.e., contains one or more double and/or triple bonds), having from one to twelve carbon atoms ($C_1$-$C_{12}$ alkyl), preferably one to eight carbon atoms ($C_1$-$C_8$ alkyl) or one to six carbon atoms ($C_1$-$C_6$ alkyl), and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, ethenyl, prop-1-enyl, but-1-enyl, pent-1-enyl, penta-1,4-dienyl, ethynyl, propynyl, butynyl, pentynyl, hexynyl, and the like. Alkyl includes alkenyls (one or more carbon-carbon double bonds) and alkynyls (one or more carbon-carbon triple bonds). Unless stated otherwise specifically in the specification, an alkyl group is optionally substituted.

"Alkylene" or "alkylene chain" refers to a straight or branched divalent hydrocarbon chain linking the rest of the molecule to a radical group, consisting solely of carbon and hydrogen, which is saturated or unsaturated (i.e., contains one or more double and/or triple bonds), and having from one to twelve carbon atoms, e.g., methylene, ethylene, propylene, n-butylene, ethenylene, propenylene, n-butenylene, propynylene, n-butynylene, and the like. The alkylene chain is attached to the rest of the molecule through a single or double bond and to the radical group through a single or double bond. The points of attachment of the alkylene chain to the rest of the molecule and to the radical group can be through one carbon or any two carbons within the chain. Unless stated otherwise specifically in the specification, an alkylene chain is optionally substituted.

"Alkenylene" is an alkylene, as defined above, which comprises one or more carbon-carbon double bonds. Unless stated otherwise specifically in the specification, an alkenylene is optionally substituted.

"Alkylenecarbonyl" refers to a radical of the formula —C(=O)$R_a$—, where $R_a$ is an alkylene chain as defined above. Unless stated otherwise specifically in the specification, an alkylenecarbonyl is optionally substituted.

"Alkenylenecarbonyl" refers to an alkylenecarbonyl, as defined above, which comprises one or more carbon-carbon double bonds. Unless stated otherwise specifically in the specification, an alkenylenecarbonyl is optionally substituted.

"Alkoxy" refers to a radical of the formula —$OR_a$ where $R_a$ is an alkyl radical as defined above containing one to twelve carbon atoms. Unless stated otherwise specifically in the specification, an alkoxy group is optionally substituted.

"Alkylamino" refers to a radical of the formula —$NHR_a$ or —$NR_aR_a$ where each $R_a$ is, independently, an alkyl radical as defined above containing one to twelve carbon atoms. Unless stated otherwise specifically in the specification, an alkylamino group is optionally substituted.

"Aminoalkyl" refers to an alkyl group comprising at least one amino substituent. The amino substituent can be on a tertiary, secondary or primary carbon. Unless stated otherwise specifically in the specification, an aminoalkyl group is optionally substituted.

"Alkylaminoalkyl" refers to an alkyl group comprising at least one alkylamino substituent. The alkylamino substituent can be on a tertiary, secondary or primary carbon. Unless stated otherwise specifically in the specification, an alkylaminoalkyl group is optionally substituted.

"Aminocarbonyl" refers to a radical of the formula —C(=O)$NR_aR_b$, where $R_a$ and $R_b$ are each independently H or alkyl. Unless stated otherwise specifically in the specification, an alkoxy group is optionally substituted.

"Aryl" refers to a hydrocarbon ring system radical comprising hydrogen, 6 to 18 carbon atoms and at least one aromatic ring. For purposes of this invention, the aryl radical is a monocyclic, bicyclic, tricyclic or tetracyclic ring system, which may include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl radicals that are optionally substituted.

"Arylene" refers to a divalent aryl group which links the rest of the molecule (e.g., compound of structure I-VI) to a radical group and/or to the rest of the molecule. Unless stated specifically otherwise, an arylene is optionally substituted.

"Aralkyl" refers to a radical of the formula —$R_b$—$R_c$ where $R_b$ is an alkylene chain as defined above and $R_c$ is one or more aryl radicals as defined above, for example, benzyl, diphenylmethyl and the like. Unless stated otherwise specifically in the specification, an aralkyl group is optionally substituted.

"Carboxyalkyl" refers to a radical of the formula —$R_b$—$R_c$ where $R_b$ is an alkylene chain as defined above and $R_c$ is a carboxy group as defined above. Unless stated otherwise specifically in the specification, carboxyalkyl group is optionally substituted.

"Cyanoalkyl" refers to a radical of the formula —$R_b$—$R_c$ where $R_b$ is an alkylene chain as defined above and $R_c$ is a cyano group as defined above. Unless stated otherwise specifically in the specification, a cyanoalkyl group is optionally substituted.

"Cycloalkyl" or "carbocyclic ring" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, 7,7-dimethyl-bicyclo[2.2.1]heptanyl, and the like. A "cycloalkenyl" is a cycloalkyl comprising one or more carbob-carbon double bonds within the ring. Unless otherwise stated specifically in the specification, a cycloalkyl (or cycloalkenyl) group is optionally substituted.

The term "bicycloalkyl" refers to a structure consisting of two cycloalkyl moieties, unsubstituted or substituted, that have two or more atoms in common. If the cycloalkyl moieties have exactly two atoms in common they are said to be "fused". Examples include, but are not limited to, bicyclo[3.1.0]hexyl, perhydronaphthyl, and the like. If the cycloalkyl moieties have more than two atoms in common they are said to be "bridged". Examples include, but are not limited to, bicyclo[3.2.1]heptyl ("norbornyl"), bicyclo[2.2.2]octyl, and the like.

As used herein, the term "heteroatom" or "ring heteroatom" is meant to include oxygen (O), nitrogen (N), sulfur (S), and phosphorus (P).

The term "heteroalkyl," by itself or in combination with another term, means, unless otherwise stated, a straight or branched chain, or cyclic hydrocarbon radical, or combinations thereof, comprising of at least one carbon atoms and at least one heteroatom selected from the group comprising of O, N, P, Si and S, and wherein the nitrogen, phosphorus, and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. The alkyl portion of the moiety is unsubstituted or substituted.

"Heteroalkylene" refers to an alkylene group comprising at least one heteroatom (e.g., N, O or S). In some embodiments, the heteroatom is within the alkylene chain (i.e., the heteroalkylene comprises at least one carbon-heteroatom-carbon bond. In other embodiments, the heteroatom is at a terminus of the alkylene and thus serves to join the alkylene to the remainder of the molecule (e.g., M1-H-A-M2, where M1 and M2 are portions of the a molecule, H is a heteroatom and A is an alkylene). Unless stated otherwise specifically in the specification, a heteroalkylene is optionally substituted.

"Heteroalkylenecarbonyl" refers to a radical of the formula —C(=O)$R_a$—, where $R_a$ is a heteroalkylene chain as defined above. Unless stated otherwise specifically in the specification, a heteroalkylenecarbonyl is optionally substituted.

The term "heterobicycloalkyl" refers to a bicycloalkyl structure, which is unsubstituted or substituted, in which at least one carbon atom is replaced with a heteroatom independently selected from oxygen, nitrogen, and sulfur.

The term "spiroalkyl" refers to a structure, which is unsubstituted or substituted, which comprises at least two cycloalkyl units joined at single carbon. In various embodiments the spiroalkyl rings can be 1-18 carbons.

The term "heterospiroalkyl" refers to a spiroalkyl structure, which is unsubstituted or substituted, in which at least one carbon atom is replaced with a heteroatom independently selected from oxygen, nitrogen, and sulfur.

"Cycloalkylalkyl" refers to a radical of the formula —$R_b R_d$ where $R_b$ is an alkylene chain as defined above and $R_d$ is a cycloalkyl radical as defined above. Unless stated otherwise specifically in the specification, a cycloalkylalkyl group is optionally substituted.

"Fused" refers to any ring structure described herein which is fused to an existing ring structure in the compounds of the invention. When the fused ring is a heterocyclyl ring or a heteroaryl ring, any carbon atom on the existing ring structure which becomes part of the fused heterocyclyl ring or the fused heteroaryl ring is replaced with a nitrogen atom.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group is optionally substituted.

"Heterocyclyl" or "heterocyclic ring" refers to a stable 3- to 18-membered non-aromatic ring radical which consists of two to twelve carbon atoms and from one to six heteroatoms selected from the group consisting of nitrogen, oxygen and sulfur. Unless stated otherwise specifically in the specification, the heterocyclyl radical is a monocyclic, bicyclic, tricyclic or tetracyclic ring system, which may include fused or bridged ring systems; and the nitrogen, carbon or sulfur atoms in the heterocyclyl radical is optionally oxidized; the nitrogen atom is optionally quaternized; and the heterocyclyl radical is partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxothiomorpholinyl, and 1,1-dioxo-thiomorpholinyl. Unless stated otherwise specifically in the specification. Unless stated otherwise specifically in the specification, a heterocyclyl group is optionally substituted.

"Heterocycloalkylene" refers to a divalent saturated heterocyclyl group which links the rest of the molecule (e.g., compound of structure I-VI) to a radical group and/or to the rest of the molecule. Unless stated specifically otherwise, a heterocycloalkylene is optionally substituted.

"Heterocycloalkylenecarbonyl" refers to a radical of the formula —$R_aC(=O)$—, wherein $R_a$ is a heterocycloalkylene as defined above. Unless stated specifically otherwise, a heterocycloalkylenecarbonyl is optionally substituted.

"N-heterocyclyl" refers to a heterocyclyl radical as defined above containing at least one nitrogen and where the point of attachment of the heterocyclyl radical to the rest of the molecule is through a nitrogen atom in the heterocyclyl radical. Unless stated otherwise specifically in the specification, a N-heterocyclyl group is optionally substituted.

"Heterocyclylalkyl" or "heterocycloalkyl" refers to a radical of the formula —$R_bR_e$ where $R_b$ is an alkylene chain as defined above and $R_e$ is a heterocyclyl radical as defined above, and if the heterocyclyl is a nitrogen-containing heterocyclyl, the heterocyclyl is optionally attached to the alkyl radical at the nitrogen atom. Unless stated otherwise specifically in the specification, a heterocyclylalkyl group is optionally substituted.

"Heteroaryl" refers to a 5- to 14-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). Unless stated otherwise specifically in the specification, a heteroaryl group is optionally substituted.

"Heteroarylene" refers to a divalent saturated heteroaryl group which links the rest of the molecule (e.g., compound of structure I-VI) to a radical group and/or to the rest of the molecule. Unless stated specifically otherwise, a heteroarylene is optionally substituted.

"Heteroarylenecarbonyl" refers to a radical of the formula —$R_aC(=O)$—, wherein $R_a$ is a heteroarylene as defined above. Unless stated specifically otherwise, a heteroarylenecarbonyl is optionally substituted.

"N-heteroaryl" refers to a heteroaryl radical as defined above containing at least one nitrogen and where the point of attachment of the heteroaryl radical to the rest of the molecule is through a nitrogen atom in the heteroaryl radical. Unless stated otherwise specifically in the specification, an N-heteroaryl group is optionally substituted.

"Heteroarylalkyl" refers to a radical of the formula —$R_bR_f$ where $R_b$ is an alkylene chain as defined above and $R_f$ is a heteroaryl radical as defined above. Unless stated otherwise specifically in the specification, a heteroarylalkyl group is optionally substituted.

"Hydroxylalkyl" refers to an alkyl group comprising at least one hydroxyl substituent. The —OH substituent may be on a primary, secondary or tertiary carbon. Unless stated otherwise specifically in the specification, a hydroxylalkyl group is optionally substituted.

"Thioalkyl" refers to a radical of the formula —$SR_a$ where $R_a$ is an alkyl radical as defined above containing one to twelve carbon atoms. Unless stated otherwise specifically in the specification, a thioalkyl group is optionally substituted.

The term "substituted" used herein means any of the above groups (e.g., alkyl, alkylene, alkenylene, alkenylenecarbonyl, alkoxy, alkylamino, aminoalkyl, alkylaminoalkyl, thioalkyl, aryl, arylene, aralkyl, carboxyalkyl, cyanoalkyl, cycloalkyl, cycloalkylalkyl, heteroalkyl, heteroalkylene, heteroalkylenecarbonyl, heterobicycloalkyl, spiroalkyl, heterospiroalkyl, haloalkyl, heterocyclyl, heterocycloalkylene, heterocycloalkylenecarbonyl, N-heterocyclyl, heterocyclylalkyl, heteroaryl, heteroarylene, heteroarylenecarbonyl, N-heteroaryl, hydroxylalkyl, thioalkyl and/or heteroarylalkyl) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —$NR_gR_h$, —$NR_gC(=O)R_h$, —$NR_gC(=O)NR_gR_h$, —$NR_gC(=O)OR_h$, —$NR_gSO_2R_h$, —$OC(=O)N\ R_gR_h$, —$OR_g$, —$SR_g$, —$SOR_g$, —$SO_2R_g$, —$OSO_2R_g$, —$SO_2OR_g$, =$NSO_2R_g$, and —$SO_2NR_gR_h$. "Substituted also means any of the above groups in which one or more hydrogen atoms are replaced with —$C(=O)R_g$, —$C(=O)OR_g$, —$C(=O)NR_gR_h$, —$CH_2SO_2R_g$, —$CH_2SO_2NR_gR_h$. In the foregoing, $R_g$ and $R_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl group. In addition, each of the foregoing substituents is optionally substituted with one or more of the above substituents.

"Electrophile" or "electrophilic moiety" is any moiety capable of reacting with a nucleophile (e.g., a moiety having a lone pair of electrons, a negative charge, a partial negative charge and/or an excess of electrons, for example a —SH group). Electrohiles typically are electron poor or comprise atoms which are electron poor. In certain embodiments an electrohile contains a positive charge or partial positive charge, has a resonance structure which contains a positive charge or partial positive charge or is a moiety in which delocalization or polarization of electrons results in one or more atom which contains a positive charge or partial positive charge. In some embodiments, the electrophiles comprise conjugated double bonds, for example an α,β-unsaturated carbonyl or α,β-unsaturated thiocarbonyl compound.

The term "effective amount" or "therapeutically effective amount" refers to that amount of a compound described herein that is sufficient to effect the intended application including but not limited to disease treatment, as defined below. The therapeutically effective amount may vary depending upon the intended treatment application (in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g. reduction of platelet adhesion and/or cell migration. The specific dose will vary depending on the particular compounds chosen, the dosing regimen to be followed, whether it is administered in combination with other compounds, timing of administration, the tissue to which it is administered, and the physical delivery system in which it is carried.

As used herein, "treatment" or "treating" refer to an approach for obtaining beneficial or desired results with respect to a disease, disorder or medical condition including but not limited to a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the subject, notwithstanding that the subject may still be afflicted with the underlying disorder. In certain embodiments, for prophylactic benefit, the compositions are administered to a subject at risk of developing a particular disease, or to a subject reporting one or more of the physiological symptoms of a disease, even though a diagnosis of this disease may not have been made.

A "therapeutic effect," as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The term "co-administration," "administered in combination with," and their grammatical equivalents, as used herein, encompass administration of two or more agents to an animal, including humans, so that both agents and/or their metabolites are present in the subject at the same time. Co-administration includes simultaneous administration in separate compositions, administration at different times in separate compositions, or administration in a composition in which both agents are present.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

The terms "antagonist" and "inhibitor" are used interchangeably, and they refer to a compound having the ability to inhibit a biological function of a target protein, whether by inhibiting the activity or expression of the protein, such as K-Ras, H-Ras or N-Ras G12C. Accordingly, the terms "antagonist" and "inhibitors" are defined in the context of the biological role of the target protein. While preferred antagonists herein specifically interact with (e.g. bind to) the target, compounds that inhibit a biological activity of the target protein by interacting with other members of the signal transduction pathway of which the target protein is a member are also specifically included within this definition. A preferred biological activity inhibited by an antagonist is associated with the development, growth, or spread of a tumor.

The term "agonist" as used herein refers to a compound having the ability to initiate or enhance a biological function of a target protein, whether by inhibiting the activity or expression of the target protein. Accordingly, the term "agonist" is defined in the context of the biological role of the target polypeptide. While preferred agonists herein specifically interact with (e.g. bind to) the target, compounds that initiate or enhance a biological activity of the target polypeptide by interacting with other members of the signal transduction pathway of which the target polypeptide is a member are also specifically included within this definition.

As used herein, "agent" or "biologically active agent" refers to a biological, pharmaceutical, or chemical compound or other moiety. Non-limiting examples include a simple or complex organic or inorganic molecule, a peptide, a protein, an oligonucleotide, an antibody, an antibody derivative, antibody fragment, a vitamin derivative, a carbohydrate, a toxin, or a chemotherapeutic compound. Various compounds can be synthesized, for example, small molecules and oligomers (e.g., oligopeptides and oligonucleotides), and synthetic organic compounds based on various core structures. In addition, various natural sources can provide compounds for screening, such as plant or animal extracts, and the like.

"Signal transduction" is a process during which stimulatory or inhibitory signals are transmitted into and within a cell to elicit an intracellular response. A modulator of a signal transduction pathway refers to a compound which modulates the activity of one or more cellular proteins mapped to the same specific signal transduction pathway. A modulator may augment (agonist) or suppress (antagonist) the activity of a signaling molecule.

An "anti-cancer agent", "anti-tumor agent" or "chemotherapeutic agent" refers to any agent useful in the treatment of a neoplastic condition. One class of anti-cancer agents comprises chemotherapeutic agents. "Chemotherapy" means the administration of one or more chemotherapeutic drugs and/or other agents to a cancer patient by various methods, including intravenous, oral, intramuscular, intraperitoneal, intravesical, subcutaneous, transdermal, buccal, or inhalation or in the form of a suppository.

The term "cell proliferation" refers to a phenomenon by which the cell number has changed as a result of division. This term also encompasses cell growth by which the cell morphology has changed (e.g., increased in size) consistent with a proliferative signal.

The term "selective inhibition" or "selectively inhibit" refers to a biologically active agent refers to the agent's ability to preferentially reduce the target signaling activity as compared to off-target signaling activity, via direct or indirect interaction with the target.

"Subject" refers to an animal, such as a mammal, for example a human. The methods described herein can be useful in both human therapeutics and veterinary applications. In some embodiments, the subject is a mammal, and in some embodiments, the subject is human.

"Mammal" includes humans and both domestic animals such as laboratory animals and household pets (e.g., cats, dogs, swine, cattle, sheep, goats, horses, rabbits), and non-domestic animals such as wildlife and the like.

"Radiation therapy" means exposing a subject, using routine methods and compositions known to the practitioner, to radiation emitters such as alpha-particle emitting radionuclides (e.g., actinium and thorium radionuclides), low linear energy transfer (LET) radiation emitters (i.e. beta emitters), conversion electron emitters (e.g. strontium-89 and samarium-153-EDTMP, or high-energy radiation, including without limitation x-rays, gamma rays, and neutrons.

An "anti-cancer agent", "anti-tumor agent" or "chemotherapeutic agent" refers to any agent useful in the treatment of a neoplastic condition. One class of anti-cancer agents comprises chemotherapeutic agents. "Chemotherapy" means the administration of one or more chemotherapeutic drugs and/or other agents to a cancer patient by various methods, including intravenous, oral, intramuscular, intraperitoneal, intravesical, subcutaneous, transdermal, buccal, or inhalation or in the form of a suppository.

"Prodrug" is meant to indicate a compound that may be converted under physiological conditions or by solvolysis to a biologically active compound described herein (e.g., compound of structure (I)). Thus, the term "prodrug" refers to a precursor of a biologically active compound that is pharmaceutically acceptable. In some aspects, a prodrug is inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam). A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein. The term "prodrug" is also meant to include any covalently bonded carriers, which release the active compound in vivo when such prodrug is administered to a mammalian subject. Prodrugs of an active compound, as described herein, are typically prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of a hydroxy functional group, or acetamide, formamide and benzamide derivatives of an amine functional group in the active compound and the like.

The term "in vivo" refers to an event that takes place in a subject's body.

The invention disclosed herein is also meant to encompass all pharmaceutically acceptable compounds of structure (I) being isotopically-labeled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. These radiolabelled compounds could be useful to help determine or measure the effectiveness of the compounds, by characterizing, for example, the site or mode of action, or binding affinity to pharmacologically important site of action. Certain isotopically-labeled compounds of structure (I), for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence are preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labeled compounds of structure (I) can generally be prepared by conventional techniques known to those skilled in the art or by processes analogous to those described in the Preparations and Examples as set out below using an appropriate isotopically-labeled reagent in place of the non-labeled reagent previously employed.

The invention disclosed herein is also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, the invention includes compounds produced by a process comprising administering a compound of this invention to a mammal for a period of time sufficient to yield a metabolic product thereof. Such products are typically identified by administering a radiolabelled compound of the invention in a detectable dose to an animal, such as rat, mouse, guinea pig, monkey, or to human, allowing sufficient time for metabolism to occur, and isolating its conversion products from the urine, blood or other biological samples.

"Stable compound" and "stable structure" are meant to indicate a compound that is sufficiently robust to survive isolation to a useful degree of purity from a reaction mixture, and formulation into an efficacious therapeutic agent.

Often crystallizations produce a solvate of the compound of the invention. As used herein, the term "solvate" refers to an aggregate that comprises one or more molecules of a compound of the invention with one or more molecules of solvent. In some embodiments, the solvent wise water, in which case the solvate is a hydrate. Alternatively, in other embodiments, the solvent is an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. In some aspects, the compound of the invention is a true solvate, while in other cases, the compound of the invention merely retains adventitious water or is a mixture of water plus some adventitious solvent.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients therefor.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

The compounds of the invention, or their pharmaceutically acceptable salts may contain one or more asymmetric centers and may thus give rise to enantiomers, diastereomers, and other stereoisomeric forms that are defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centres of geometric asymmetry, and unless specified otherwise, it is intended that the compounds include both E and Z geometric isomers. Likewise, all tautomeric forms are also intended to be included.

The present invention includes all manner of rotamers and conformationally restricted states of a compound of the invention.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule. The present invention includes tautomers of any said compounds.

The chemical naming protocol and structure diagrams used herein are a modified form of the I.U.P.A.C. nomenclature system, using the ACD/Name Version 9.07 software program and/or ChemDraw Ultra Version 11.0.1 software naming program (CambridgeSoft). For complex chemical names employed herein, a substituent group is typically named before the group to which it attaches. For example, cyclopropylethyl comprises an ethyl backbone with a cyclopropyl substituent. Except as described below, all bonds are identified in the chemical structure diagrams herein, except for all bonds on some carbon atoms, which are assumed to be bonded to sufficient hydrogen atoms to complete the valency.

Compounds

In an aspect, the invention provides compounds which are capable of selectively binding to and/or modulating a G12C mutant K-Ras, H-Ras or N-Ras protein. In some embodiments, the compounds modulate the G12C mutant K-Ras, H-Ras or N-Ras protein by reaction with an amino acid. In some embodiment the compounds of the invention selectively react with the G12C mutant K-Ras, H-Ras or N-Ras proteins by forming an irreversible covalent bond with the cysteine at the 12 position. By binding to the Cystine 12 the compounds of the invention may lock the switch II of the G12C mutant K-Ras, H-Ras or N-Ras into an inactive stage. This inactive stage may be distinct from those observed for GTP and GDP bound K-Ras, H-Ras or N-Ras. Some compounds of the invention are also able to perturb the switch I conformation. Because effector binding to K-Ras, H-Ras or N-Ras is highly sensitive to the conformation of switch I and II, the irreversible binding of these compounds may disrupt K-Ras, H-Ras or N-Ras downstream signaling.

In some embodiments, the invention provides a compound of Formula I

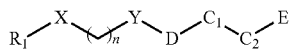

Formula I

In various embodiments Y is —$CH_2$—, —$CHR_{22}$—, CO, SO or $SO_2$. In some embodiments Y is —$CH_2$—. In some embodiments Y is —$CHR_{22}$—. In some embodiments Y is CO. In some embodiments Y is SO. In some embodiments Y is $SO_2$.

In various embodiments n is an integer with value 1-6. In some cases n is 1. In some cases n is 2. In some cases n is 3. In some cases n is 4. In some cases n is 5. In some cases n is 6.

$R_1$ is aryl or heteroaryl each of which is unsubstituted or substituted by one or more independent $R_2$ substituents. In some embodiments $R_1$ is substituted aryl. In some cases $R_1$ is unsubstituted aryl. In some cases $R_1$ is substituted heteroaryl. In some cases $R_1$ is unsubstituted heteroaryl. In some embodiments $R_1$ an aryl group substituted with one or more $R_3$ groups. In some embodiments $R_1$ a heteroaryl group substituted with one or more $R_3$ groups. In some embodiments $R_1$ is a substituted or unsubstituted phenyl group. In some embodiments $R_1$ is an unsubstituted benzyl group. In some embodiments $R_1$ is a phenyl group substituted with one or more independent $R_2$ substituents. In some embodiments $R_1$ is an unsubstituted benzothiadiazolyl group. In some embodiments $R_1$ is a benzothiadiazolyl group substituted with one or more independent $R_2$ substituents. In some embodiments $R_1$ is an unsubstituted benzothiadiazolyl group. In some embodiments $R_1$ is a benzothiadiazolyl group substituted with one or more independent $R_2$ substituents. In some embodiments $R_1$ is an unsubstituted naphthalenyl group. In some embodiments $R_1$ is a naphthalenyl group substituted with one or more independent $R_2$ substituents. In some embodiments $R_1$ is an imidazopyridinyl naphthalenyl group. In some embodiments $R_1$ is an imidazopyridinyl group substituted with one or more independent $R_2$ substituents.

In some embodiments, $R_1$ is an unsubstituted phenyl group. In some embodiments, $R_1$ is a substituted phenyl group (Formula Ia). In some embodiments $R_1$ is a phenyl group with a halogen substituent at the 4-position of the phenyl ring. In some embodiments, $R_1$ is a phenyl substituted with a substituted or unsubstituted aryl at the 5-position. In some embodiments, $R_1$ is a phenyl substituted with a substituted or unsubstituted heteroaryl at the 5-position. In some embodiments, $R_1$ is a phenyl substituted with a substituted or unsubstituted cycloalkyl at the 5-position. In some embodiments, $R_1$ is a phenyl substituted with a substituted or unsubstituted heterocycloaryl (heteroaryl) at the 5-position. In some embodiments $R_1$ is a phenyl with an alkoxy substituent at the 2 position of the phenyl ring. In some embodiments $R_1$ is a phenyl with methoxy substituent at the 2 position of the phenyl ring. In some embodiments $R_1$ is a phenyl group with a methoxy substituent at the 2 position, a halogen substituent at the 4 position and an aryl or heteroaryl substituent (both of which are substituted or unsubstituted) at the 5 position of the phenyl ring.

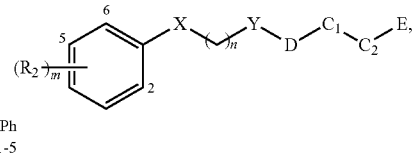

Formula Ia $R_1$ = Ph
m = 1-5

In some embodiments, $R_1$ is capable of reversible interaction with K-Ras, H-Ras or N-Ras G12C mutant protein. In some embodiments $R_1$ has high affinity towards K-Ras, H-Ras or N-Ras and is highly specific towards G12C K-Ras, H-Ras or N-Ras. In some embodiments $R_1$ is capable of hydrophobic interaction with K-Ras, H-Ras or N-Ras G12C. In some embodiments $R_1$ is able to form hydrogen bonds with various residues of G12C K-Ras, H-Ras or N-Ras protein. In some embodiments $R_1$ interacts with one or more of G10, R68, Y71, Y96 or Q99 residues in K-Ras G12C (FIG. 1). In some embodiments $R_1$ interacts with the G10 residue of K-Ras G12C. In some embodiments $R_1$ interacts with the R68 residue of K-Ras G12C. In some embodiments $R_1$ interacts with the Y71 residue of K-Ras G12C. In some embodiments $R_1$ interacts with the Y96 residue of K-Ras G12C. In some embodiments $R_1$ interacts with the Q99 residue of K-Ras G12C.

$R_2$ is, at each occurrence, independently halogen, oxo, hydroxy, substituted or unsubstituted alkoxy, substituted or unsubstituted alkyl, substituted or unsubstituted cycloalkyl, substituted or unsubstituted heteroalkyl, substituted or unsubstituted heterocycloalkyl, aryl, substituted or unsubstituted heteroaryl, substituted or unsubstituted arylene, or substituted or unsubstituted arylene heteroarylene, each of which is unsubstituted or substituted by one or more independent $R_3$ substituents. In some embodiments $R_2$ is halogen. In some embodiments, $R_2$ is hydroxy. In some embodiments $R_2$ is an alkoxy group substituted with one or more $R_3$ substituents. In some embodiments $R_2$ is an unsubstituted alkoxy group. In some embodiments $R_3$ is an alkyl group substituted with one or more $R_3$ groups. In some embodiments $R_2$ is an unsubstituted alkyl group. In some embodiments $R_2$ is a heteroalkyl group substituted with one or more $R_3$ groups. In some embodiments $R_2$ is an unsubstituted heteroalkyl group. In some embodiments $R_2$ a cycloalkyl group substituted with one or more $R_3$ groups. In some embodiments $R_2$ is an unsubstituted cycloalkyl group. In some embodiments $R_2$ is a heterocycloalkyl substituted with one or more $R_3$ groups. In some embodiments $R_2$ is an unsubstituted heterocycloalkyl group. In some embodiments $R_2$ is an aryl substituted with one or more $R_3$ groups. In some embodiments $R_2$ is an unsubstituted aryl group. In some embodiments $R_2$ is a heteroaryl group substituted with one or more $R_3$ groups. In some embodiments $R_2$ unsubstituted a heteroaryl group. In some embodiments $R_2$ is an arylene substituted with one or more $R_3$ groups. In some embodiments $R_2$ is an unsubstituted arylene group. In some embodiments $R_2$ is a heteroarylene group substituted with one or more $R_3$ groups. In some embodiments $R_2$ unsubstituted a heteroarylene group. In some embodiments $R_2$ is halogen. In some embodiments $R_2$ is hydroxy. In some embodiments $R_2$ is alkoxy. In some embodiments $R_2$ is methoxy. In some embodiments R2 is oxo.

$R_3$ is halogen, OH, cyano, substituted or unsubstituted alkyl, substituted or unsubstituted alkoxy, substituted or unsubstituted cycloalkyl, substituted or unsubstituted heteroalkyl, substituted or unsubstituted cycloheteroalkyl, substituted or unsubstituted aryl, substituted or unsubstituted heteroaryl, substituted or unsubstituted arylene, substituted or unsubstituted heteroarylene. In some embodiments $R_3$ is halogen. In some embodiments $R_3$ is hydroxy. In some embodiments $R_3$ is cyano. In some embodiments $R_3$ is unsubstituted alkyl. In some embodiments $R_3$ is an alkyl substituted with one or more $R_4$ groups. In some embodiments $R_3$ is unsubstituted alkoxy. In some embodiments $R_3$ is an alkoxy substituted with one or more $R_4$ groups. In some embodiments $R_3$ is unsubstituted cycloalkyl. In some embodiments $R_3$ is a cycloalkyl substituted with one or more $R_4$ groups. In some embodiments $R_3$ is unsubstituted hetero alkyl. In some embodiments $R_3$ is a hetero alkyl substituted with one or more $R_4$ groups. In some embodiments $R_3$ is unsubstituted heterocycloalkyl. In some embodiments $R_3$ is a heterocycloalkyl substituted with one or more $R_4$ groups. In some embodiments $R_3$ is unsubstituted aryl. In some embodiments $R_3$ is an aryl substituted with one or more $R_4$ groups. In some embodiments $R_3$ is unsubstituted heteroaryl. In some embodiments $R_3$ is a heteroaryl substituted with one or more $R_4$ groups. In some embodiments $R_3$ is unsubstituted arylene. In some embodiments $R_3$ is an arylene substituted with one or more $R_4$ groups. In some embodiments $R_3$ is unsubstituted heteroarylene. In some embodiments $R_3$ is a heteroarylene substituted with one or more $R_4$ groups. In some embodiments $R_3$ is halogen. In some embodiments $R_3$ is hydroxyl. In some embodiments $R_3$ is cyano.

In various embodiments $R_4$ is halogen, OH, cyano, alkyl, alkoxy, cycloalkyl, heteroalkyl, heterocycloalkyl, aryl, heteroaryl, arylene, or heteroarylene moiety. In some embodiments $R_4$ is halogen. In some embodiments $R_4$ is hydroxyl. In some embodiments $R_4$ is cyano. In some embodiments $R_4$ is an alkyl. In some embodiments $R_4$ is an alkoxy. In some embodiments $R_4$ is a cycloalkyl. In some embodiments $R_4$ is heteroalkyl. In some embodiments $R_4$ is heterocycloalkyl. In some embodiments $R_4$ is aryl. In some embodiments $R_4$ is heteroaryl. In some embodiments $R_4$ is arylene, in some embodiments $R_4$ is heteroarylene.

In various embodiments $C_1$ is a substituted or unsubstituted alkyl, substituted or unsubstituted cycloalkylene, substituted or unsubstituted heterocycloalkylene, substituted or unsubstituted arylene, or substituted or unsubstituted heteroarylene. In some embodiments $C_1$ is a cycloalkylene substituted with one or more $R_5$ groups. In some embodiments $C_1$ is an unsubstituted cycloalkylene. In some embodiments $C_1$ is a heterocycloalkylene substituted with one or more $R_5$ groups. In some embodiments $C_1$ is an unsubstituted heterocycloalkylene. In some embodiments $C_1$ is an arylene substituted with one or more $R_5$ groups. In some embodiments $C_1$ is an unsubstituted arylene. In some embodiments $C_1$ is a heteroarylene substituted with one or more $R_5$ groups. In some embodiments $C_1$ is an unsubstituted heteroarylene. In some embodiments $C_1$ is selected from:

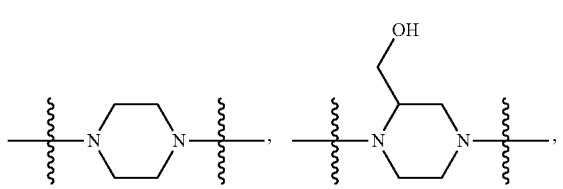

In some embodiments, $C_1$ is

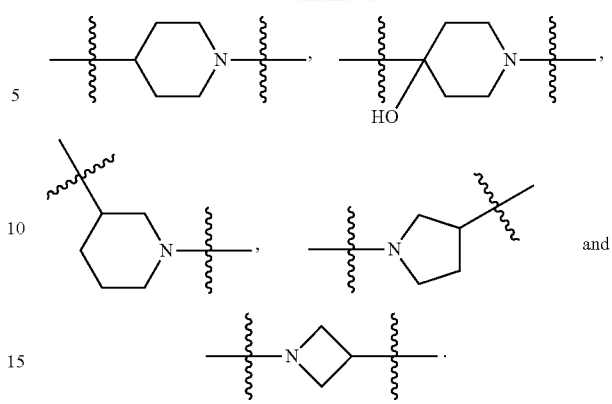

In some embodiments $R_5$ is —OH. In some embodiments $R_5$ is —CH$_2$OH. In some embodiment $R_5$ is alkyl. In some embodiments $R_5$ is methyl.

In various embodiments $C_2$ is a bond, a cycloalkylene, heterocycloalkylene, arylene, or heteroarylene. In some embodiments $C_2$ is a bond. In some embodiments $C_2$ is an unsubstituted cycloalkylene. In some embodiments $C_2$ is an unsubstituted heterocycloalkylene. In some embodiments $C_2$ is an unsubstituted arylene. In some embodiments $C_2$ is an unsubstituted heteroarylene. In some embodiments $C_2$ is selected from:

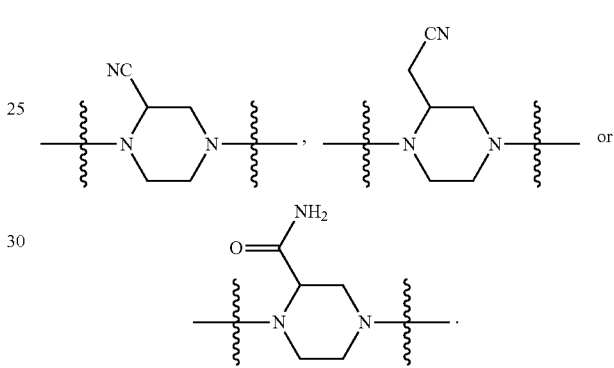

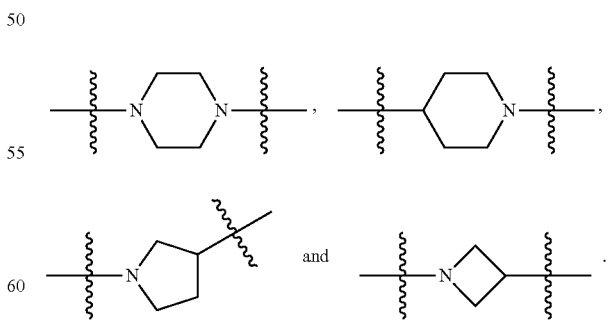

In some embodiments, C1 and C2 form a fused or spiro bicyclic ring. In some embodiments —C1-C2- form a fused bicylic ring. In some embodiments —C1-C2- form a spiro bicyclic ring. In some embodiments —C1-C2- is In some embodiments —C1-C2- is

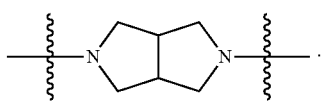 [SMILES: *N1CC2CN(*)CC2C1]

In some embodiments —C1-C2- is

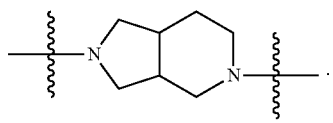 [SMILES: *N1CCC2CN(*)CC2C1]

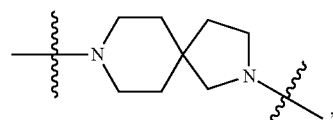

or

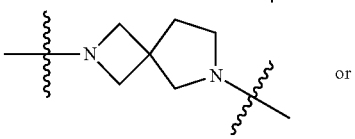

In various embodiments X is O, NH, S or $CR_{23}R_{24}$. In some embodiments X is O. In some embodiments X is NH. In various embodiments X is S. In various embodiments X is $CR_{23}R_{24}$.

In various embodiments D is a bond, —NH—CH$_2$—, —NH—, or —CH$_2$-. In various embodiments D is a bond. In various embodiments D is —NH—CH$_2$. In various embodiments D is —NH—. In various embodiments D is —CH$_2$—.

$R_{22}$, $R_{23}$ and $R_{24}$ are each independently hydrogen, halogen, —OH, alkyl, cycloalkyl, aryl, heteroaryl, heteroalkyl, or heterocycloalkyl.

In some embodiments E is an electrophile capable of bonding with a K-Ras, H-Ras or N-Ras protein comprising G12C mutation. In some embodiments, the electrophile E is capable of forming an irreversible covalent bond with a G12C mutant K-Ras, H-Ras or N-Ras protein. In some cases, the electrophile E binds with the cysteine residue at the position 12 of a G12C mutant K-Ras, H-Ras or N-Ras protein. In some cases E is selected from:

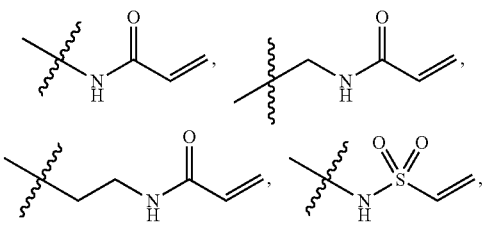

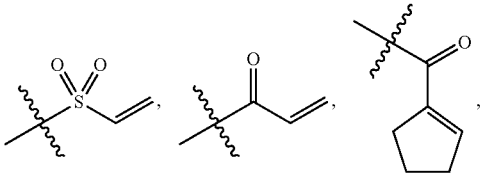

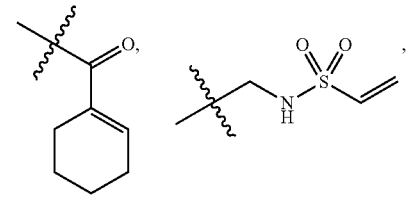

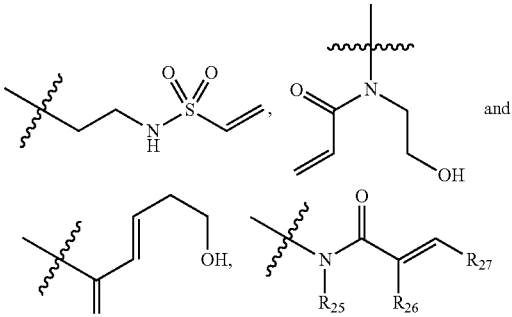

R1 = alkyl; R2 = CN, alkyl, R3 = alkyl; $R_{26}$ and $R_{27}$ can form cyclo alkene In some embodiments E is

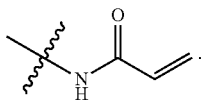 [SMILES: *NC(=O)C=C]

In some embodiments E is

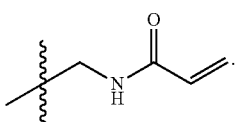

In some embodiments E is

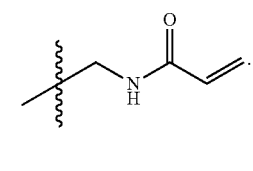 [SMILES: *CNC(=O)C=C]

In some embodiments E is

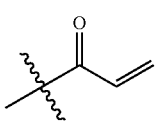 [SMILES: *C(=O)C=C]

In some embodiments E is

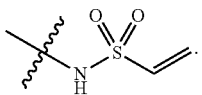 [SMILES: *NS(=O)(=O)C=C]

In some embodiments the invention provides compounds of Formula I as shown in Table 1.

In some embodiments, the invention provides compounds of Formula II

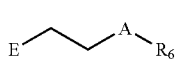

Formula II

In various embodiments A is $CH_2$, O— or NH. In some embodiments A is $CH_2$. In some embodiments A is O. In some embodiments A is NH.

In various embodiments $R_6$ is aryl or heteroaryl moiety, each of which is either unsubstituted or substituted with one or more $R_7$ groups. In some embodiments $R_6$ is an unsubstituted aryl. In some embodiments $R_6$ is an aryl substituted with one or more $R_7$ groups. In some embodiments $R_6$ is an unsubstituted heteroaryl. In some embodiments $R_6$ is a heteroaryl substituted with one or more $R_7$ groups. In some embodiments $R_6$ is a substituted or unsubstituted phenyl moiety. In some embodiments $R_6$ is an unsubstituted phenyl moiety. In some embodiments $R_6$ is a phenyl moiety substituted with one or more $R_7$ substituents. In some embodiments $R_6$ is a substituted or unsubstituted pyridinyl moiety. In some embodiments $R_6$ is an unsubstituted pyridinyl moiety. In some embodiments $R_6$ is a pyridinyl moiety substituted with one or more $R_7$ substituents.

$R_7$ is halogen, —OH, $OR_{10}$, $NR_{11}R_{12}$, oxo, unsubstituted or substituted alkyl, unsubstituted or substituted cycloalkyl, unsubstituted or substituted heteroalkyl, unsubstituted or substituted heterocycloalkyl, unsubstituted or substituted aryl, unsubstituted or substituted heteroaryl, unsubstituted or substituted arylene, or unsubstituted or substituted heteroarylene. In some embodiments $R_7$ is a halogen. In some embodiments $R_7$ is OH. In some embodiments $R_7$ is OR10. In some embodiments $R_7$ is $NR_{11}R_{12}$. In some embodiments $R_7$ is unsubstituted alkyl. In some embodiments $R_7$ is a alkyl substituted with one or more $R_8$ substituents. In some embodiments $R_7$ is unsubstituted cycloalkyl. In some embodiments $R_7$ is a cycloalkyl substituted with one or more $R_8$ substituents. In some embodiments $R_7$ is unsubstituted heteroalkyl. In some embodiments $R_7$ is a heteroalkyl substituted with one or more $R_8$ substituents. In some embodiments $R_7$ is unsubstituted heterocycloalkyl. In some embodiments $R_7$ is a heterocycloalkyl substituted with one or more $R_8$ substituents. In some embodiments $R_7$ is unsubstituted aryl. In some embodiments $R_7$ is a aryl substituted with one or more $R_8$ substituents. In some embodiments $R_7$ is unsubstituted heteroaryl. In some embodiments $R_7$ is a heteroaryl substituted with one or more $R_8$ substituents. In some embodiments $R_7$ is unsubstituted arylene. In some embodiments $R_7$ is a arylene substituted with one or more $R_8$ substituents. In some embodiments $R_7$ is unsubstituted heteroarylene. In some embodiments $R_7$ is a heteroarylene substituted with one or more $R_8$ substituents.

In various embodiments $R_8$ is halogen, OH, cyano, unsubstituted or substituted alkyl, unsubstituted or substituted alkoxy, unsubstituted or substituted cycloalkyl, unsubstituted or substituted heteroalkyl, unsubstituted or substituted heterocycloalkyl, unsubstituted or substituted aryl, unsubstituted or substituted heteroaryl, unsubstituted or substituted arylene, or unsubstituted or substituted heteroarylene. In some embodiments $R_8$ is halogen. In some embodiments $R_8$ is OH. In some embodiments $R_8$ is cyano. In some embodiments $R_8$ is unsubstituted alkyl. In some embodiments $R_8$ is a alkyl substituted with one or more $R_g$ groups. In some embodiments $R_8$ is unsubstituted alkoxy. In some embodiments $R_8$ is a alkoxy substituted with one or more $R_g$ groups. In some embodiments $R_8$ is unsubstituted cycloalkyl. In some embodiments $R_8$ is a cycloalkyl substituted with one or more $R_9$ groups. In some embodiments $R_8$ is unsubstituted heteroalkyl. In some embodiments $R_8$ is a heteroalkyl substituted with one or more $R_9$ groups. In some embodiments $R_8$ is unsubstituted heterocycloalkyl. In some embodiments $R_8$ is a heterocycloalkyl substituted with one or more $R_9$ groups. In some embodiments $R_8$ is unsubstituted aryl. In some embodiments $R_8$ is a aryl substituted with one or more $R_9$ groups. In some embodiments $R_8$ is unsubstituted heteroaryl. In some embodiments $R_8$ is a heteroaryl substituted with one or more $R_9$ groups. In some embodiments $R_8$ is unsubstituted arylene. In some embodiments $R_8$ is a arylene substituted with one or more $R_9$ groups. In some embodiments $R_8$ is unsubstituted heteroarylene. In some embodiments $R_8$ is a heteroarylene substituted with one or more $R_9$ groups.

In various embodiments, $R_{10}$ is hydrogen, unsubstituted or substituted alkyl, unsubstituted or substituted cycloalkyl, unsubstituted or substituted heteroalkyl, unsubstituted or substituted heterocycloalkyl, unsubstituted or substituted aryl, or unsubstituted or substituted heteroaryl. In some embodiments $R_{10}$ is hydrogen. In some embodiments $R_{10}$ is unsubstituted alkyl. In some embodiments $R_{10}$ is alkyl substituted with one or more $R_{13}$ groups. In some embodiments $R_{10}$ is unsubstituted cycloalkyl. In some embodiments $R_{10}$ is cycloalkyl substituted with one or more $R_{13}$ groups. In some embodiments $R_{10}$ is unsubstituted heteroalkyl. In some embodiments $R_{10}$ is heteroalkyl substituted with one or more $R_{13}$ groups. In some embodiments $R_{10}$ is unsubstituted heterocycloalkyl. In some embodiments $R_{10}$ is heterocycloalkyl substituted with one or more $R_{13}$ groups. In some embodiments $R_{10}$ is unsubstituted aryl. In some embodiments $R_{10}$ is aryl substituted with one or more $R_{13}$ groups. In some embodiments $R_{10}$ is unsubstituted heteroaryl. In some embodiments $R_{10}$ is heteroaryl substituted with one or more $R_{13}$ groups.

In various embodiments, $R_{11}$ is hydrogen, unsubstituted or substituted alkyl, unsubstituted or substituted cycloalkyl, unsubstituted or substituted heteroalkyl, unsubstituted or substituted heterocycloalkyl, unsubstituted or substituted aryl, or unsubstituted or substituted heteroaryl. In some embodiments $R_{11}$ is hydrogen. In some embodiments $R_{11}$ is unsubstituted alkyl. In some embodiments $R_{11}$ is alkyl substituted with one or more $R_{13}$ groups. In some embodiments $R_{11}$ is unsubstituted cycloalkyl. In some embodiments $R_{11}$ is cycloalkyl substituted with one or more $R_{13}$ groups. In some embodiments $R_{11}$ is unsubstituted heteroalkyl. In some embodiments $R_{11}$ is heteroalkyl substituted with one or more $R_{13}$ groups. In some embodiments $R_{11}$ is unsubstituted heterocycloalkyl. In some embodiments $R_{11}$ is heterocycloalkyl substituted with one or more $R_{13}$ groups. In some embodiments $R_{11}$ is unsubstituted aryl. In some embodiments $R_{11}$ is aryl substituted with one or more $R_{13}$ groups. In some embodiments $R_{11}$ is unsubstituted heteroaryl. In some embodiments $R_{11}$ is heteroaryl substituted with one or more $R_{13}$ groups.

In various embodiments, $R_{12}$ is hydrogen, unsubstituted or substituted alkyl, unsubstituted or substituted cycloalkyl, unsubstituted or substituted heteroalkyl, unsubstituted or substituted heterocycloalkyl, unsubstituted or substituted aryl, or unsubstituted or substituted heteroaryl. In some embodiments $R_{12}$ is hydrogen. In some embodiments $R_{12}$ is unsubstituted alkyl. In some embodiments $R_{12}$ is alkyl substituted with one or more $R_{13}$ groups. In some embodiments $R_{12}$ is unsubstituted cycloalkyl. In some embodiments $R_{12}$ is cycloalkyl substituted with one or more $R_{13}$ groups. In some embodiments $R_{12}$ is unsubstituted heteroalkyl. In some embodiments $R_{12}$ is heteroalkyl substituted with one or more $R_{13}$ groups. In some embodiments $R_{12}$ is unsubstituted heterocycloalkyl. In some embodiments $R_{12}$ is heterocycloalkyl substituted with one or more $R_{13}$ groups. In some embodiments $R_{12}$ is unsubstituted aryl. In some embodiments $R_{12}$ is aryl substituted with one or more $R_{13}$ groups. In some embodiments $R_{12}$ is unsubstituted heteroaryl. In some embodiments $R_{12}$ is heteroaryl substituted with one or more $R_{13}$ groups.

In various embodiments $R_9$ is halogen, OH, cyano, alkyl, alkoxy, cycloalkyl, heteroalkyl, heterocycloalkyl, aryl, heteroaryl, arylene, or heteroarylene. In various embodiments $R_9$ is halogen. In various embodiments $R_9$ is OH. In various embodiments $R_9$ is cyano. In various embodiments $R_9$ is alkyl. In various embodiments $R_9$ is cycloalkyl. In various embodiments $R_9$ is heteroalkyl. In various embodiments $R_9$ is heterocycloalkyl. In various embodiments $R_9$ is aryl. In various embodiments $R_9$ is heteroaryl. In various embodiments $R_9$ is arylene. In various embodiments $R_9$ is heteroarylene.

In various embodiments $R_{13}$ is halogen, OH, cyano, alkyl, alkoxy, cycloalkyl, heteroalkyl, heterocycloalkyl, aryl, heteroaryl, arylene, or heteroarylene. In various embodiments $R_{13}$ is halogen. In various embodiments $R_{13}$ is OH. In various embodiments $R_{13}$ is cyano. In various embodiments $R_{13}$ is alkyl. In various embodiments $R_{13}$ is cycloalkyl. In various embodiments $R_{13}$ is heteroalkyl. In various embodiments $R_{13}$ is heterocycloalkyl. In various embodiments $R_{13}$ is aryl. In various embodiments $R_{13}$ is heteroaryl. In various embodiments $R_{13}$ is arylene. In various embodiments $R_{13}$ is heteroarylene.

In some embodiments E is an electrophile capable of bonding with a K-Ras, H-Ras or N-Ras protein comprising G12C mutation. In some embodiments, the electrophile E is capable of forming an irreversible covalent bond with a G12C mutant K-Ras, H-Ras or N-Ras protein. In some cases, the electrophile E binds with the cysteine residue at the position 12 of a G12C mutant K-Ras, H-Ras or N-Ras protein.

In some cases E has the general structure

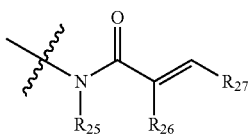

wherein:
$R_{25}$ is alkyl;
$R_{26}$ is cyano or alkyl or $R_{26}$ joins with $R_{27}$ to form a cycloalkene; and
$R_{27}$ is alkyl or $R_{27}$ joins with $R_{26}$ to form a cycloalkene.

In some cases E is selected from:

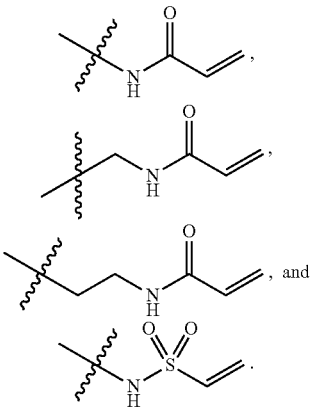

In some embodiments E is

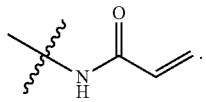 [SMILES: *NC(=O)C=C]

In some embodiments E is

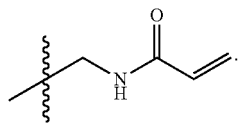 [SMILES: *CNC(=O)C=C]

In some embodiments E is

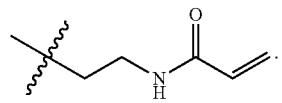 [SMILES: *CCNC(=O)C=C]

In some embodiments E is

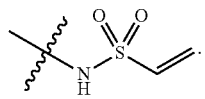 [SMILES: *NS(=O)(=O)C=C]

In some embodiments, $R_6$ is capable of reversible interaction with K-Ras, H-Ras or N-Ras G12C mutant protein. In some embodiments $R_6$ moiety has high affinity towards K-Ras, H-Ras or N-Ras and is highly specific towards G12C K-Ras, H-Ras or N-Ras. In some embodiments $R_6$ is capable of hydrophobic interaction with K-Ras, H-Ras or N-Ras G12C. In some embodiments $R_6$ is able to form hydrogen bonds with various residues of G12C K-Ras, H-Ras or N-Ras protein. In some embodiments $R_6$ interacts with one or more of G10, R68, Y71, Y96 or Q99 residues in K-Ras G12C (FIG. 1). In some embodiments, $R_6$ moiety interacts with the G10 residue of K-Ras G12C. In some embodiments $R_6$ interacts with the R68 residue of K-Ras G12C. In some embodiments $R_6$ interacts with the Y71 residue of K-Ras G12C. In some embodiments $R_6$ interacts with the Y96 residue of K-Ras G12C. In some embodiments $R_6$ interacts with the Q99 residue of K-Ras G12C.

In some embodiments, the

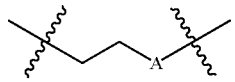

unit in Formula II provides proper length and geometry to the compound such that the electrophile E interacts with the cysteine residue at the 12 position in G12C K-Ras, H-Ras or N-Ras protein. In some embodiments the

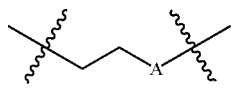

also interacts with other protein backbone residues.

In some embodiments the invention provides compounds of Formula II as shown in Table 2.

In some embodiments, the invention provides compounds of Formula III

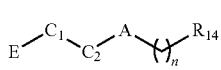

Formula III

In various embodiments A is a bond, O, NH or —(CO)—. In some embodiments A is a bond. In some embodiments A is O. In some embodiments A is NH. In some embodiments A is —C(O)—.

In various embodiments n is 0 or 1. In some cases n is 0. In some cases n is 1.

In various embodiments $R_{14}$ is cycloalkyl, heterocycloalkyl, aryl or heteroaryl moiety. In some embodiments $R_{14}$ is an unsubstituted cycloalkyl. In some embodiments $R_{14}$ is cycloalkyl substituted with one or more $R_{15}$ groups. In some embodiments $R_{14}$ is an unsubstituted heterocycloalkyl. In some embodiments $R_{14}$ is hetero cycloalkyl substituted with one or more $R_{15}$ groups. In some embodiments $R_{14}$ is an unsubstituted aryl. In some embodiments $R_{14}$ is aryl substituted with one or more $R_{15}$ groups. In some embodiments $R_{14}$ is an unsubstituted heteroaryl. In some embodiments $R_{14}$ is heteroaryl substituted with one or more $R_{15}$ groups. In some embodiments $R_{14}$ is an unsubstituted phenyl. In some embodiments $R_{14}$ is phenyl substituted with one or more $R_{15}$ groups.

In various embodiments $R_{15}$ is halogen, $OR_{18}$, $NR_{19}R_{20}$, oxo, alkyl, alkoxy, cycloalkyl, heteroalkyl, heterocycloalkyl, aryl, heteroaryl, arylene, or heteroarylene, each of which is unsubstituted or substituted by one or more independent $R_3$ substituents. In some embodiments $R_{15}$ is halogen. In some embodiments $R_{15}$ is cyano. In some embodiments $R_{15}$ is $NR_{19}R_{20}$. In some embodiments $R_{15}$ is oxo. In some embodiments $R_{15}$ is $OR_{18}$. In some embodiments $R_{15}$ is unsubstituted alkyl. In some embodiments $R_{15}$ is a alkyl substituted with one or more $R_{16}$ groups. In some embodiments $R_{15}$ is unsubstituted alkoxy. In some embodiments $R_{15}$ is a alkoxy substituted with one or more $R_{16}$ groups. In some embodiments $R_{15}$ is unsubstituted cycloalkyl. In some embodiments $R_{15}$ is a cycloalkyl substituted with one or more $R_{16}$ groups. In some embodiments $R_{15}$ is unsubstituted heteroalkyl. In some embodiments $R_{15}$ is a heteroalkyl substituted with one or more $R_{16}$ groups. In some embodiments $R_{15}$ is unsubstituted heterocycloalkyl. In some embodiments $R_{15}$ is a heterocycloalkyl substituted with one or more $R_{16}$ groups. In some embodiments $R_{15}$ is unsubstituted aryl. In some embodiments $R_{15}$ is a aryl substituted with one or more $R_{16}$ groups. In some embodiments $R_{15}$ is unsubstituted heteroaryl. In some embodiments $R_{15}$ is a heteroaryl substituted with one or more $R_{16}$ groups. In some embodiments $R_{15}$ is unsubstituted arylene. In some embodiments $R_{15}$ is a arylene substituted with one or more $R_{16}$ groups. In some embodiments $R_{15}$ is unsubstituted heteroarylene. In some embodiments $R_{15}$ is a heteroarylene substituted with one or more $R_{16}$ groups In various embodiments $R_{16}$ is halogen, OH, oxo, cyano alkyl, alkoxy, cycloalkyl, heteroalkyl, heterocycloalkyl, aryl, heteroaryl, arylene, or heteroarylene, each of which is unsubstituted or substituted by one or more independent $R_{17}$ substituents. In some embodiments $R_{16}$ is halogen. In some embodiments $R_{16}$ is OH. In some embodiments $R_{16}$ is cyano. In some embodiments $R_{16}$ is unsubstituted alkyl. In some embodiments $R_{16}$ is a alkyl substituted with one or more $R_{17}$ groups. In some embodiments $R_{16}$ is unsubstituted alkoxy. In some embodiments $R_{16}$ is a alkoxy substituted with one or more $R_{17}$ groups. In some embodiments $R_{16}$ is unsubstituted cycloalkyl. In some embodiments $R_{16}$ is a cycloalkyl substituted with one or more $R_{17}$ groups. In some embodiments $R_{16}$ is unsubstituted heteroalkyl. In some embodiments $R_{16}$ is a heteroalkyl substituted with one or more $R_{17}$ groups. In some embodiments $R_{16}$ is unsubstituted heterocycloalkyl. In some embodiments $R_{16}$ is a heterocycloalkyl substituted with one or more $R_{17}$ groups. In some embodiments $R_{16}$ is unsubstituted aryl. In some embodiments $R_{16}$ is a aryl substituted with one or more $R_{17}$ groups. In some embodiments $R_{16}$ is unsubstituted heteroaryl. In some embodiments $R_{16}$ is a heteroaryl substituted with one or more $R_{17}$ groups. In some embodiments $R_{16}$ is unsubstituted arylene. In some embodiments $R_{16}$ is a arylene substituted with one or more $R_{17}$ groups. In some embodiments $R_{16}$ is unsubstituted heteroarylene. In some embodiments $R_{16}$ is a heteroarylene substituted with one or more $R_{17}$ groups.

In various embodiments, $R_{18}$ is hydrogen, unsubstituted or substituted alkyl, unsubstituted or substituted cycloalkyl, unsubstituted or substituted heteroalkyl, unsubstituted or substituted heterocycloalkyl, unsubstituted or substituted aryl, or unsubstituted or substituted heteroaryl. In some embodiments $R_{18}$ is hydrogen. In some embodiments $R_{18}$ is unsubstituted alkyl. In some embodiments $R_{18}$ is alkyl substituted with one or more $R_{21}$ groups. In some embodiments $R_{18}$ is unsubstituted cycloalkyl. In some embodiments $R_{18}$, is cycloalkyl substituted with one or more $R_{21}$ groups. In some embodiments $R_{18}$, is unsubstituted heteroalkyl. In one embodiments $R_{18}$ is heteroalkyl substituted with one or more $R_{21}$ groups. In some embodiments $R_{18}$ is unsubstituted heterocycloalkyl. In some embodiments $R_{18}$ is heterocycloalkyl substituted with one or more $R_{21}$ groups. In some embodiments $R_{18}$, is unsubstituted aryl. In some embodiments $R_{18}$ is aryl substituted with one or more $R_{21}$ groups. In some embodiments $R_{18}$ is unsubstituted heteroaryl. In some embodiments $R_{18}$, is heteroaryl substituted with one or more $R_{21}$ groups.

In various embodiments, $R_{19}$ is hydrogen, unsubstituted or substituted alkyl, unsubstituted or substituted cycloalkyl, unsubstituted or substituted heteroalkyl, unsubstituted or substituted heterocycloalkyl, unsubstituted or substituted aryl, or unsubstituted or substituted heteroaryl. In some embodiments $R_{19}$ is hydrogen. In some embodiments $R_{19}$ is unsubstituted alkyl. In some embodiments $R_{19}$ is alkyl substituted with one or more $R_{21}$ groups. In some embodiments $R_{19}$ is unsubstituted cycloalkyl. In some embodiments $R_{19}$ is cycloalkyl substituted with one or more $R_{21}$ groups. In some embodiments $R_{19}$ is unsubstituted heteroalkyl. In some embodiments $R_{19}$ is heteroalkyl substituted with one or more $R_{21}$ groups. In some embodiments $R_{19}$ is unsubstituted heterocycloalkyl. In some embodiments $R_{19}$ is heterocycloalkyl substituted with one or more $R_{21}$ groups. In some embodiments $R_{19}$ is unsubstituted aryl. In some embodiments $R_{19}$ is aryl substituted with one or more $R_{21}$ groups. In some embodiments $R_{19}$ is unsubstituted heteroaryl. In some embodiments $R_{19}$ is heteroaryl substituted with one or more $R_{21}$ groups.

In various embodiments $R_{20}$ is hydrogen, unsubstituted or substituted alkyl, unsubstituted or substituted cycloalkyl, unsubstituted or substituted heteroalkyl, unsubstituted or substituted heterocycloalkyl, unsubstituted or substituted aryl, or unsubstituted or substituted heteroaryl. In some embodiments $R_{20}$ is hydrogen. In some embodiments $R_{20}$ is unsubstituted alkyl. In some embodiments $R_{20}$ is alkyl substituted with one or more $R_{21}$ groups. In some embodiments $R_{20}$ is unsubstituted cycloalkyl. In some embodiments $R_{20}$ is cycloalkyl substituted with one or more $R_{13}$ groups. In some embodiments $R_{20}$ is unsubstituted heteroalkyl. In some embodiments $R_{20}$ is heteroalkyl substituted with one or more $R_{21}$ groups. In some embodiments $R_{20}$ is unsubstituted heterocycloalkyl. In some embodiments $R_{20}$ is heterocycloalkyl substituted with one or more $R_{21}$ groups. In some embodiments $R_{20}$ is unsubstituted aryl. In some embodiments $R_{20}$ is aryl substituted with one or more $R_{21}$ groups. In some embodiments $R_{20}$ is unsubstituted heteroaryl. In some embodiments $R_{20}$ is heteroaryl substituted with one or more $R_{21}$ groups.

In various embodiments $R_{17}$ is halogen, OH, cyano, alkyl, alkoxy, cycloalkyl, heteroalkyl, heterocycloalkyl, aryl, heteroaryl, arylene, or heteroarylene. In various embodiments $R_{17}$ is halogen. In various embodiments $R_{17}$ is OH. In various embodiments $R_{17}$ is cyano. In various embodiments $R_{17}$ is alkyl. In various embodiments $R_{17}$ is cycloalkyl. In various embodiments $R_{17}$ is heteroalkyl. In various embodiments $R_{17}$ is heterocycloalkyl. In various embodiments $R_{17}$ is aryl. In various embodiments $R_{17}$ is heteroaryl. In various embodiments $R_{17}$ is arylene. In various embodiments $R_{17}$ is heteroarylene.

In various embodiments $R_{21}$ is halogen, OH, cyano, alkyl, alkoxy, cycloalkyl, heteroalkyl, heterocycloalkyl, aryl, heteroaryl, arylene, or heteroarylene. In various embodiments $R_{21}$ is halogen. In various embodiments $R_{21}$ is OH. In various embodiments $R_{21}$ is cyano. In various embodiments $R_{21}$ is alkyl. In various embodiments $R_{21}$ is cycloalkyl. In various embodiments $R_{21}$ is heteroalkyl. In various embodiments $R_{21}$ is heterocycloalkyl. In various embodiments $R_{21}$ is aryl. In various embodiments $R_{21}$ is heteroaryl. In various embodiments $R_{21}$ is arylene. In various embodiments $R_{21}$ is heteroarylene.

In various embodiments $C_1$ is a substituted or unsubstituted alkyl, embodiments $C_1$ is a substituted or unsubstituted cycloalkylene, substituted or unsubstituted heterocycloalkylene, substituted or unsubstituted arylene, or substituted or unsubstituted heteroarylene. In some embodiments $C_1$ is a cycloalkylene substituted with one or more $R_5$ groups. In some embodiments $C_1$ is an unsubstituted cycloalkylene. In some embodiments $C_1$ is a heterocycloalkylene substituted with one or more $R_5$ groups. In some embodiments $C_1$ is an unsubstituted heterocycloalkylene. In some embodiments $C_1$ is an arylene substituted with one or more $R_5$ groups. In some embodiments $C_1$ is an unsubstituted arylene. In some embodiments $C_1$ is a heteroarylene substituted with one or more $R_5$ groups. In some embodiments $C_1$ is an unsubstituted heteroarylene. In some embodiments $C_1$ is selected form the group consisting of

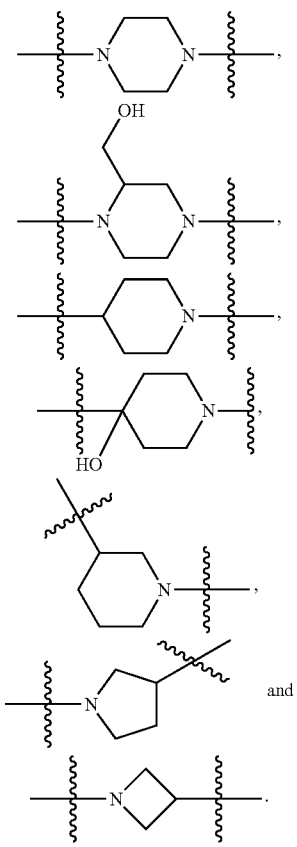

In some embodiments, $C_1$ is

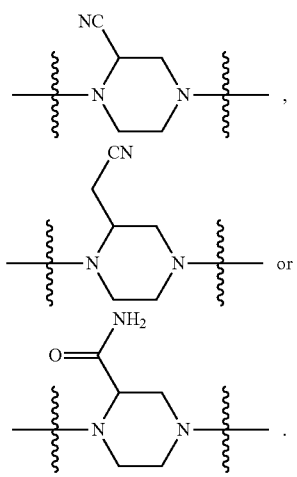

In some embodiments $R_5$ is —OH. In some embodiments $R_5$ is —CH$_2$OH, in some embodiments R5 is alkyl.

In various embodiments $C_2$ is a bond, a cycloalkylene, heterocycloalkylene, arylene, or heteroarylene. In some embodiments $C_2$ is a bond. In some embodiments $C_2$ is an unsubstituted cycloalkylene. In some embodiments $C_2$ is an unsubstituted heterocycloalkylene. In some embodiments $C_2$ is an unsubstituted arylene. In some embodiments $C_2$ is an unsubstituted heteroarylene. In some embodiments $C_2$ is selected form the group consisting of

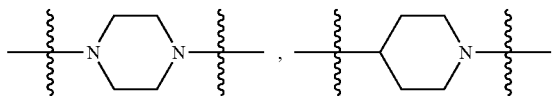

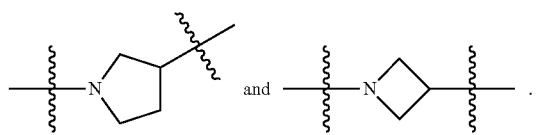

In some embodiments, C1 and C2 form a fused or spiro bicyclic ring. In some embodiments —C1-C2- form a fused bicylic ring. In some embodiments —C1-C2 form a spiro bicyclic ring. In some embodiments —C1-C2- is

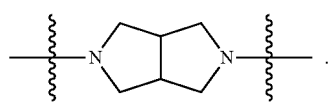 [SMILES: *N1CC2CN(*)CC2C1]

In some embodiments —C1-C2- is

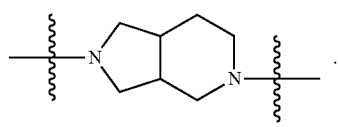 [SMILES: *N1CCC2CN(*)CC2C1]

In some embodiments —C1-C2- is

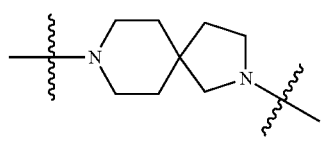

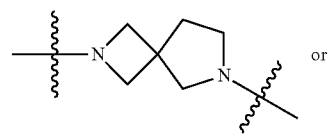

or

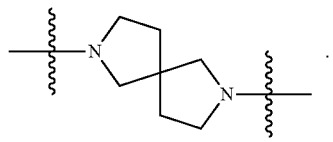

In some embodiments E is an electrophile capable of bonding with a K-Ras, H-Ras or N-Ras protein comprising G12C mutation. In some embodiments, the electrophile E is capable of forming an irreversible covalent bond with a G12C mutant K-Ras, H-Ras or N-Ras protein. In some cases E is the general structure

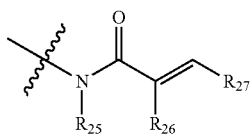

$R_{25}$ is alkyl. $R_{26}$ is cyano or alkyl. $R_{27}$ is alkyl. $R_{26}$ and $R_{27}$ can form cycloalkene.

In some of the foregoing embodiments of compounds of Formula III, E is selected from:

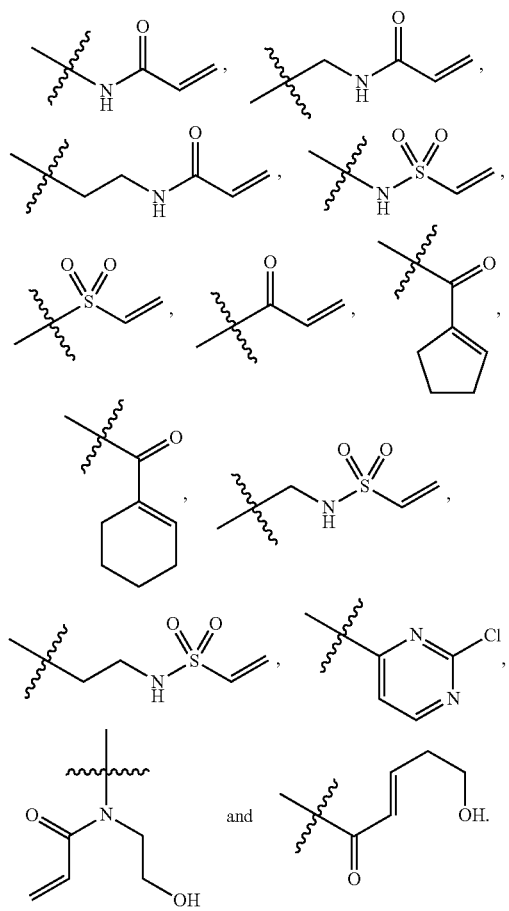

In some embodiments E is

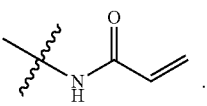 [SMILES: *NC(=O)C=C]

In some embodiments E is

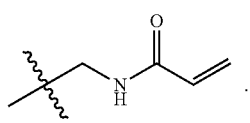 [SMILES: *CNC(=O)C=C]

In some embodiments E is

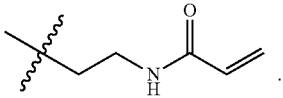 [SMILES: *CCNC(=O)C=C]

In some embodiments E is

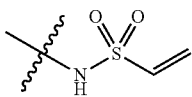

In some embodiments, $R_{14}$ is capable of reversible interaction with K-Ras, H-Ras or N-Ras G12C mutant protein. In some embodiments $R_{14}$ moiety has high affinity towards K-Ras, H-Ras or N-Ras and is highly specific towards G12C K-Ras, H-Ras or N-Ras. In some embodiments $R_{14}$ is capable of hydrophobic interaction with K-Ras, H-Ras or N-Ras G12C. In some embodiments $R_{14}$ is able to form hydrogen bonds with various residues of G12C K-Ras, H-Ras or N-Ras protein. In some embodiments $R_{14}$ interacts with one or more of G10, R68, Y71, Y96 or Q99 residues in K-Ras G12C (FIG. 1). In some embodiments, $R_{14}$ moiety interacts with the G10 residue of K-Ras G12C. In some embodiments $R_{14}$ interacts with the R68 residue of K-Ras G12C. In some embodiments $R_{14}$ interacts with the Y71 residue of K-Ras G12C. In some embodiments $R_{14}$ interacts with the Y96 residue of K-Ras G12C. In some embodiments $R_{14}$ interacts with the Q99 residue of K-Ras G12C.

In some embodiments, the

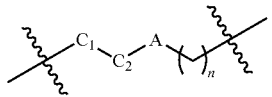

unit in Formula III provides proper length and geometry to the compound such that the electrophile E is able to interact with the cysteine residue at the 12 position in G12C K-Ras, H-Ras or N-Ras protein. In some embodiments the

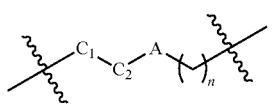

also interacts with other protein backbone residues.

In some embodiments the invention provides compounds of Formula III as shown in Table 3.

In some embodiments the invention provides compounds shown in Table 4.

In still other embodiments, the invention provides a compound having the following structure (V):

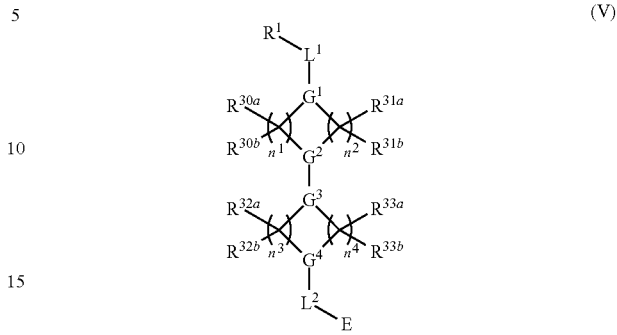

or a pharmaceutically acceptable salt, tautomer, stereoisomer or prodrug thereof, wherein:

$R^1$ is aryl or heteroaryl;

$R^{30a}$ and $R^{30b}$ are, at each occurrence, independently H, —OH, —NH$_2$, —CO$_2$H, cyano, cyanoalkyl, C$_1$-C$_6$alkyl, C$_3$-C$_8$cycloalkyl, hydroxylalkyl, aminoalkyl, carboxylalkyl or aminocarbonyl; or $R^{30a}$ and $R^{30b}$ join to form a carbocyclic or heterocyclic ring; or $R^{30a}$ is H, —OH, —NH$_2$, —CO$_2$H, cyano, C$_1$-C$_6$alkyl, C$_3$-C$_8$cycloalkyl, hydroxylalkyl, aminoalkyl, carboxylalkyl or aminocarbonyl and $R^{30b}$ joins with $R^{31b}$ to form a carbocyclic or heterocyclic ring;

$R^{31a}$ and $R^{31b}$ are, at each occurrence, independently H, —OH, —NH$_2$, —CO$_2$H, cyano, cyanoalkyl, C$_1$-C$_6$alkyl, C$_3$-C$_8$cycloalkyl, hydroxylalkyl, aminoalkyl, carboxylalkyl or aminocarbonyl; or $R^{31a}$ and $R^{31b}$ join to form a carbocyclic or heterocyclic ring; or $R^{31a}$ is H, —OH, —NH$_2$, —CO$_2$H, cyano, C$_1$-C$_6$alkyl, C$_3$-C$_8$cycloalkyl, hydroxylalkyl, aminoalkyl, carboxylalkyl or aminocarbonyl and $R^{31b}$ joins with $R^{30b}$ to form a carbocyclic or heterocyclic ring;

$R^{32a}$ and $R^{32b}$ are, at each occurrence, independently H, —OH, —NH$_2$, —CO$_2$H, cyano, cyanoalkyl, C$_1$-C$_6$alkyl, C$_3$-C$_8$cycloalkyl, hydroxylalkyl, aminoalkyl, carboxylalkyl or aminocarbonyl; or $R^{32a}$ and $R^{32b}$ join to form a carbocyclic or heterocyclic ring; or $R^{32a}$ is H, —OH, —NH$_2$, —CO$_2$H, cyano, C$_1$-C$_6$alkyl, C$_3$-C$_8$cycloalkyl, hydroxylalkyl, aminoalkyl, carboxylalkyl or aminocarbonyl and $R^{32b}$ joins with $R^{33b}$ to form a carbocyclic or heterocyclic ring;

$R^{33a}$ and $R^{33b}$ are, at each occurrence, independently H, —OH, —NH$_2$, —CO$_2$H, cyano, cyanoalkyl, C$_1$-C$_6$alkyl, C$_3$-C$_8$cycloalkyl, hydroxylalkyl, aminoalkyl, carboxylalkyl or aminocarbonyl; or $R^{33a}$ and $R^{33b}$ join to form a carbocyclic or heterocyclic ring; or $R^{33a}$ is H, —OH, —NH$_2$, —CO$_2$H, cyano, C$_1$-C$_6$alkyl, C$_3$-C$_8$cycloalkyl, hydroxylalkyl, aminoalkyl, carboxylalkyl or aminocarbonyl and $R^{33b}$ joins with $R^{32b}$ to form a carbocyclic or heterocyclic ring;

$L^1$ is carbonyl, —NHC(=O)—, alkylene, alkenylene, heteroalkylene, heterocycloalkylene, heteroarylene, alkylenecarbonyl, alkenylenecarbonyl, heteroalkylenecarbonyl, heterocycloalkylenecarbonyl or heteroarylenecarbonyl;

$L^2$ is a bond or alkylene;

$G^1$, $G^2$, $G^3$ and $G^4$ are each independently N or CR, where R is H, cyano, halo or C$_1$-C$_6$alkyl;

$n^1$, $n^2$, $n^3$ and $n^4$ are each independently 1, 2 or 3; and

E is an electrophilic moiety capable of forming a covalent bond with the cysteine residue at position 12 of a K-Ras, H-Ras or N-Ras G12C mutant protein.

In some embodiments of the compounds of structure V, $L^1$ is carbonyl, —NHC(=O)—, alkylene, heteroalkylene, alkylenecarbonyl or heteroalkylenecarbonyl;

In some other embodiments, the compound has the following structure (Va):

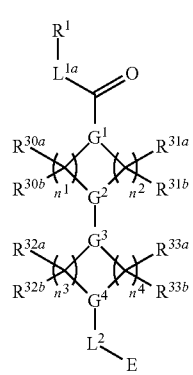

(Va)

wherein:

L$^{1a}$ is a bond, —NH—, alkylene, alkeneylene, heteroalkylene, heterocycloalkylene or heteroarylene.

In other embodiments of compound (Va), L$^{1a}$ is a bond, —NH—, alkylene or heteroalkylene In some more embodiments, the compound has the following structure (Vb):

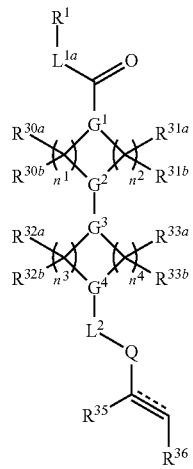

(Vb)

wherein:

Q is —C(=O)—, —NR$^{34}$C(=O)—, —S(=O)$_2$— or —NR$^{34}$S(=O)$_2$—;

R$^{34}$ is H, C$_1$-C$_6$alkyl or hydroxylalkyl;

≡ is a carbon-carbon double bond or a carbon-carbon triple bond; and

R$^{35}$ and R$^{36}$ are each independently H, cyano, C$_1$-C$_6$alkyl, aminoalkyl, alkylaminoalkyl, or hydroxylalkyl or R$^{35}$ and R$^{36}$ join to form a carbocyclic or heterocyclic ring when ≡ is a double bond; or R$^{35}$ is absent and R$^{36}$ is H, C$_1$-C$_6$alkyl, aminoalkyl, alkylaminoalkyl or hydroxylalkyl when ≡ is a triple bond.

In some different embodiments, the compound has one of the following structures (Vc), (Vd), (Ve) or (Vf):

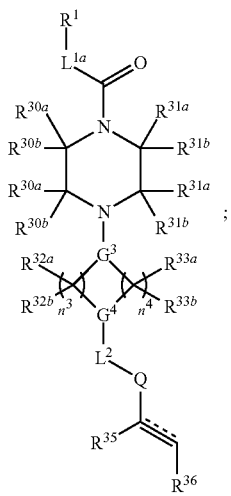

(Vc)

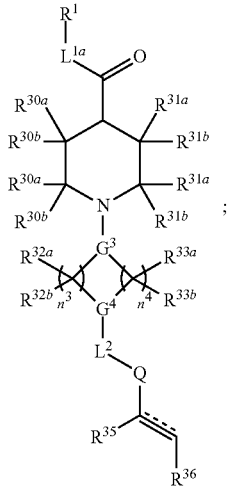

(Vd)

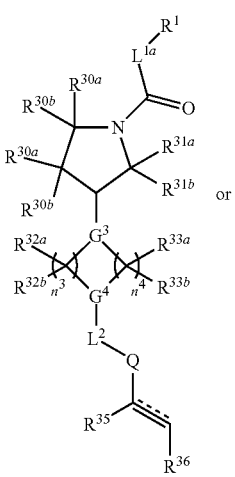

(Ve)

or (Vf)
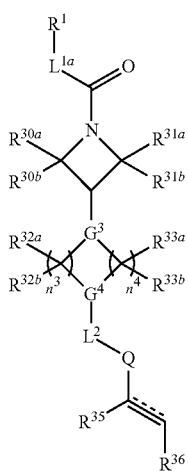
(Vi)
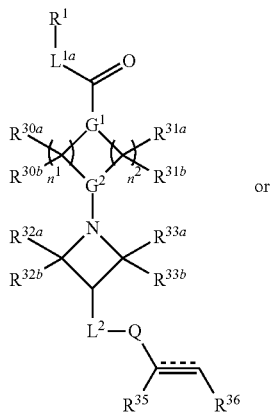
or
In still other embodiments, wherein the compound has one of the following structures (Vg), (Vh), (Vi) or (Vj):
(Vg)
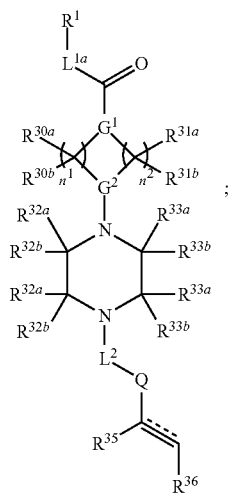
;
(Vj)
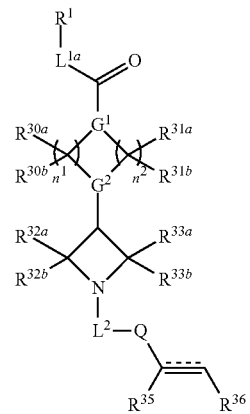
In some other embodiments, the compound has one of the following structures (Vk), (Vl), (Vm), (Vn); (Vo) or (Vp):
(Vh)
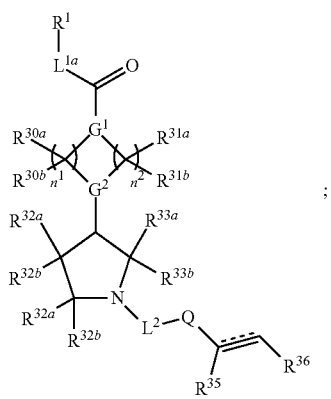
;
(Vk)
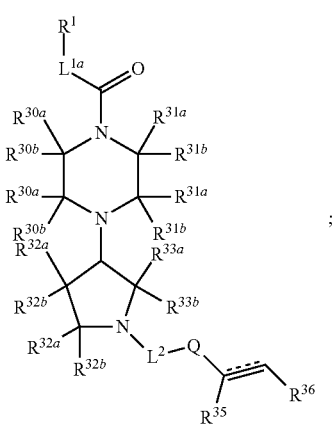
;

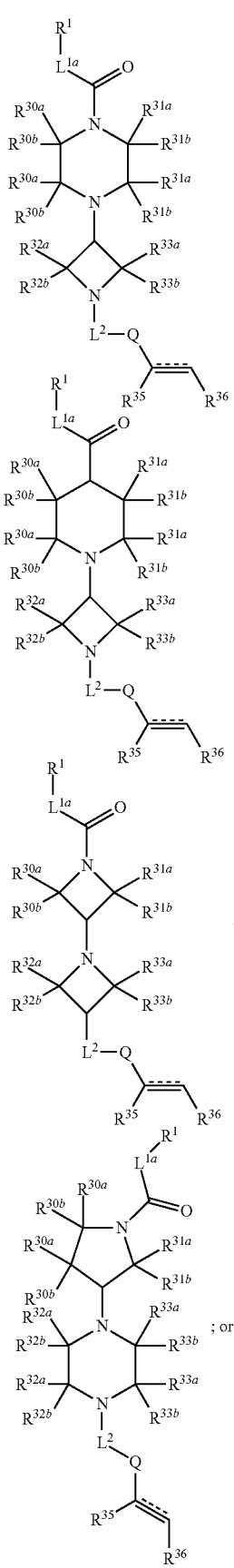

(Vl)

(Vm)

(Vn)

(Vo)

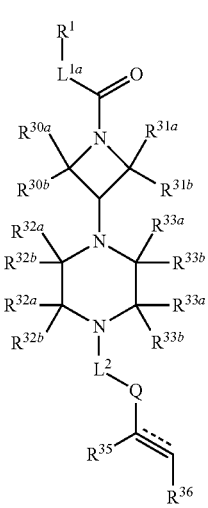

(Vp)

In various other embodiments, $R^1$ is aryl. For example, in some embodiments the aryl is bicyclic, such as a fused bicyclic aryl. In some more specific embodiments, the aryl is naphthyl.

In various other embodiments, the aryl is monocyclic. For example, in some embodiments the aryl is phenyl.

In some of the foregoing embodiments, the aryl is unsubstituted. In other of the foregoing embodiments, the aryl is substituted with one or more substituents. For example, in some embodiments the substituents are selected from halo, hydroxyl, cyano, aminocarbonyl, formyl, $C_1$-$C_6$alkyl, $C_1$-$C_6$alkylsulfonyl, $C_1$-$C_6$haloalkyl, $C_3$-$C_8$cycloalkyl, $C_1$-$C_6$alkoxy, $C_1$-$C_6$hydroxylalkyl, $C_1$-$C_6$alkoxyalkyl, $C_1$-$C_6$-aminoalkyl, aliphatic heterocyclyl, heteroaryl and aryl.

In other embodiments, the aryl substituents are selected from fluoro, chloro, bromo, iodo, hydroxyl, cyano, methyl, ethyl, isopropyl, methylsulfonyl, methoxy, aminocarbonyl, trifluoromethyl, 2,2,2-trifluorethyl, cyclobutyl, cyclopropyl and phenyl, wherein the cyclopropyl and phenyl are optionally substituted with one or more substituents selected from $C_1$-$C_6$alkyl, halo, hydroxyl and cyano In some different embodiments, the substituents are selected from fluoro, chloro, bromo, iodo, hydroxyl, cyano, methyl, ethyl, methylsulfonyl, methoxy, aminocarbonyl, trifluoromethyl, cyclopropyl and phenyl, wherein the cyclopropyl and phenyl are optionally substituted with one or more substituents selected from halo, hydroxyl and cyano.

In other exemplary embodiments, the aryl substituents are selected from fluoro, chloro, bromo, iodo, hydroxyl, methyl, ethyl, cyclobutyl and cyclopropyl, wherein the cyclopropyl is optionally substituted with one or more substituents selected from $C_1$-$C_6$alkyl, halo, hydroxyl and cyano In some more embodiments, the substituents are selected from fluoro, chloro, bromo, iodo, hydroxyl, methyl, ethyl and cyclopropyl, wherein the cyclopropyl is optionally substituted with one or more substituents selected from halo, hydroxyl and cyano.

In still more embodiments, the substituents are selected from fluoro, chloro, bromo, hydroxyl and cyclopropyl, wherein the cyclopropyl is optionally substituted with one or more substituents selected from $C_1$-$C_6$alkyl, halo, hydroxyl and cyano.

In some more specific embodiments, the substituents are selected from fluoro, chloro, bromo, hydroxyl and cyclopropyl, wherein the cyclopropyl is optionally substituted with one or more substituents selected from halo, hydroxyl and cyano. For example, in some embodiments the cyclopropyl comprises a geminal difluoro substitution.
In still other embodiments, $R^1$ has one of the following structures:
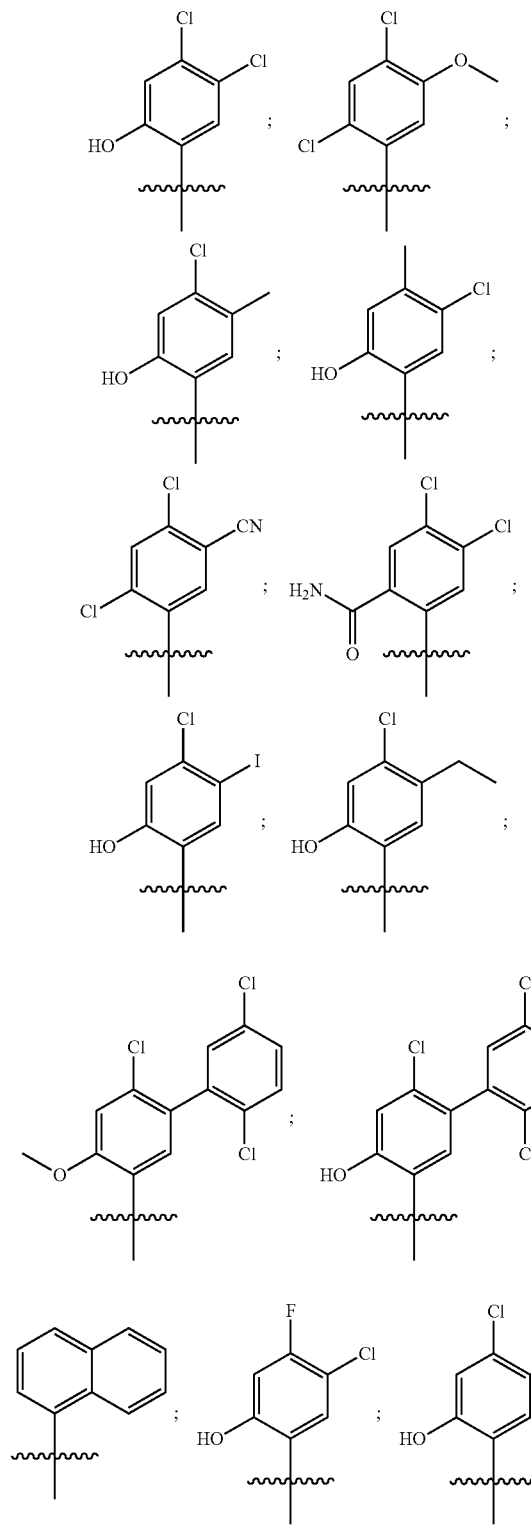
-continued
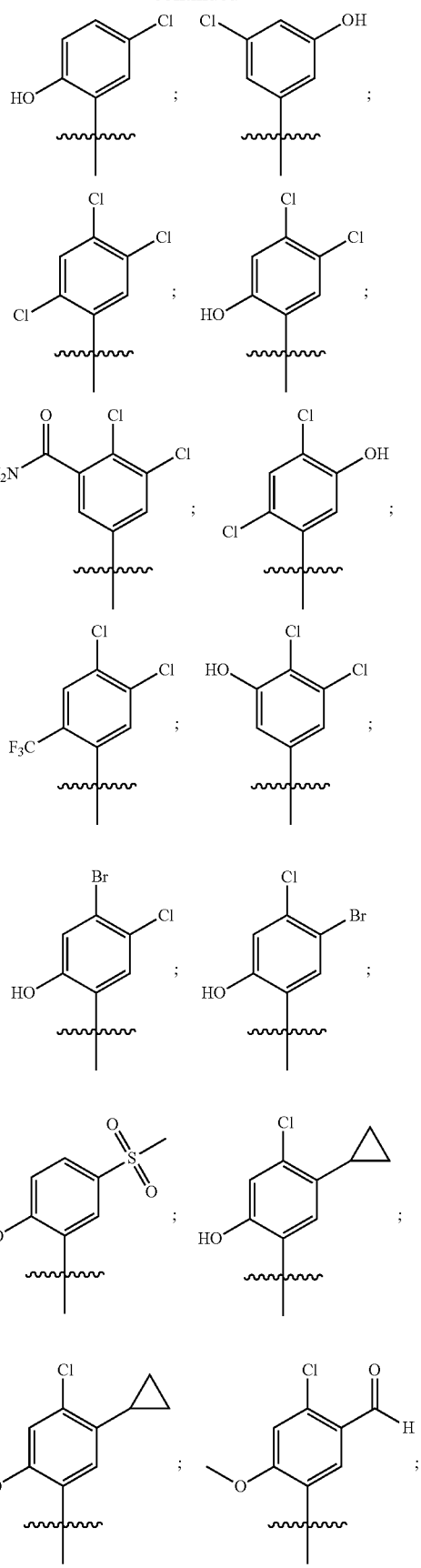

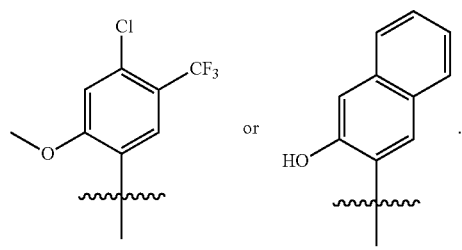
In still other embodiments, R$^1$ has one of the following structures:
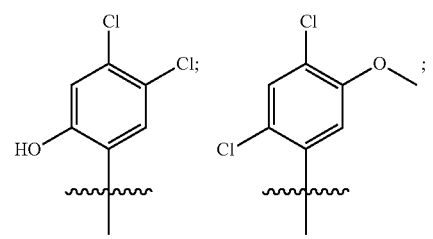
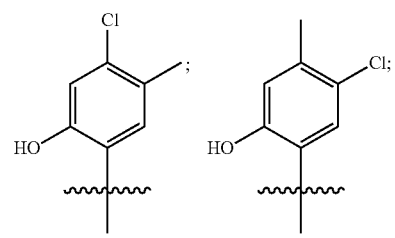
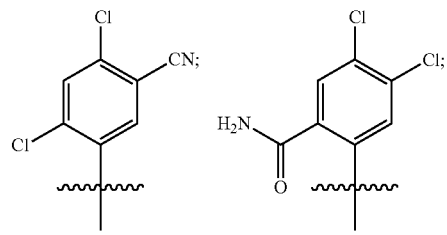
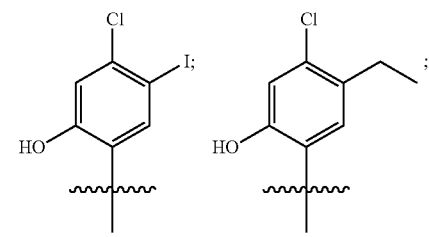
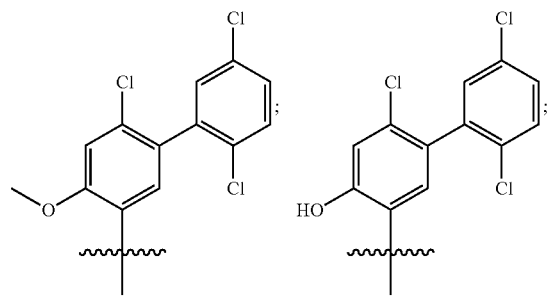
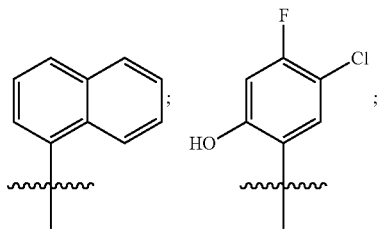
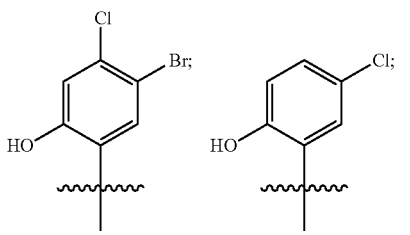
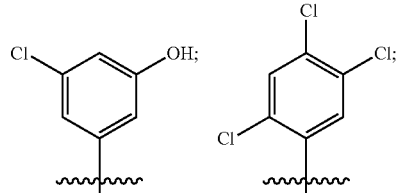
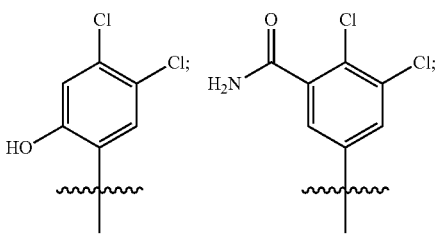
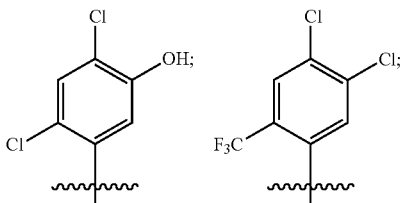
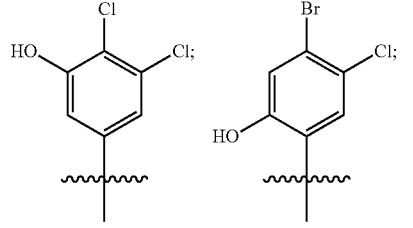
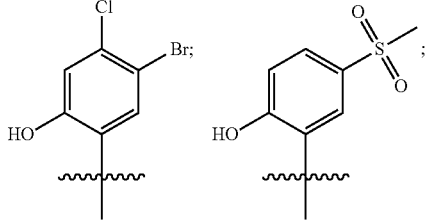

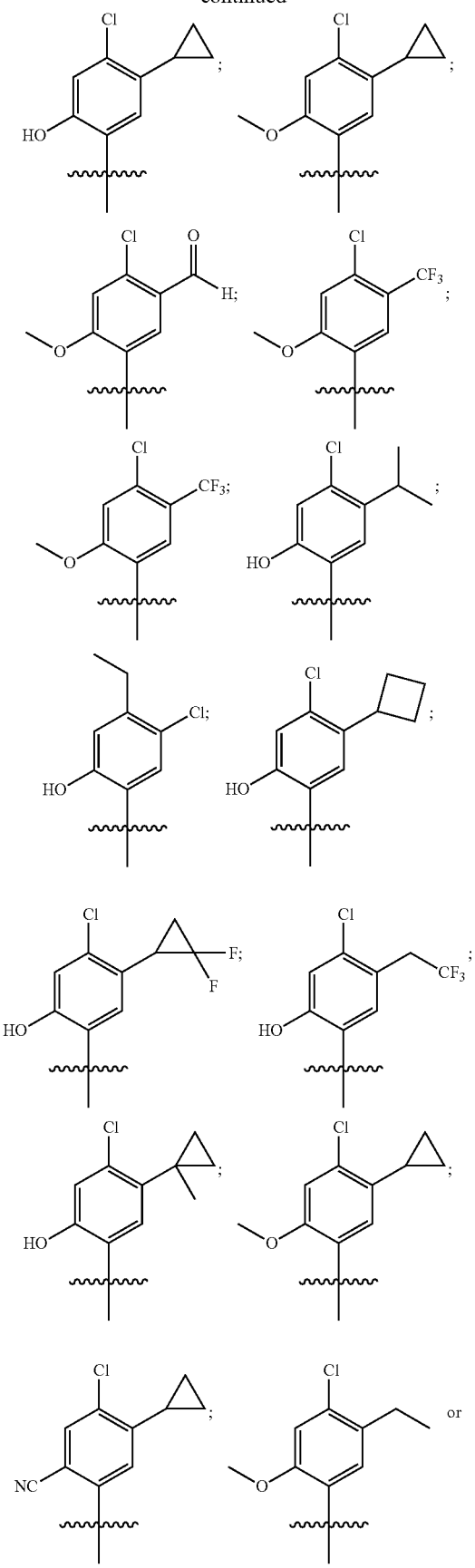

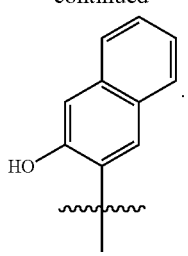

In still other embodiments, $R^1$ is heteroaryl. For example, in some embodiments the heteroaryl is bicyclic, such as a fused bicyclic heteroaryl.

In some more embodiments, the heteroaryl is monocyclic.

In some of the foregoing embodiments, the heteroaryl comprises nitrogen, sulfur or a combination thereof. For example, in some embodiments the heteroaryl is dihydroquinoxalinyl, indoleyl, benzoimidazolyl, pyridinyl or thiazolyl.

In some embodiments, the heteroaryl is unsubstituted. In some other embodiments, the heteroaryl is substituted with one or more substituents. In some embodiments, the substituents are selected from $C_1$-$C_6$alkyl, halo and oxo. For example, in some embodiments the substituents are selected from halo and oxo. In other embodiments, the substituents are selected from ethyl and chloro. In some more specific embodiments, the substituents are chloro.

In some embodiments of the forgoing compounds of structure (V), $R^1$ has one of the following structures:

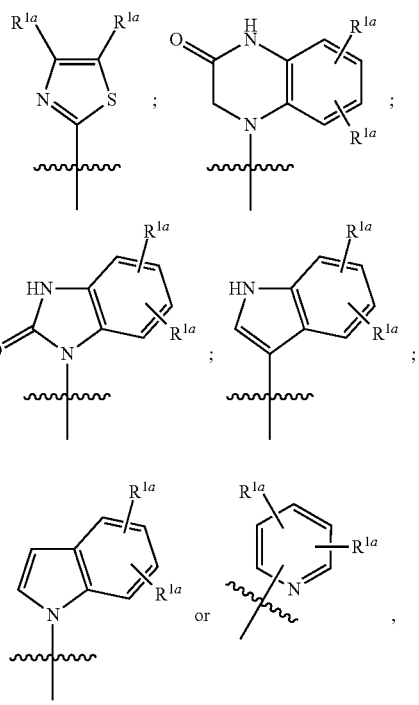

wherein $R^{1a}$ is, at each occurrence, independently H, $C_1$-$C_6$alkyl or halo.

In various other embodiments, $R^1$ has one of the following structures:

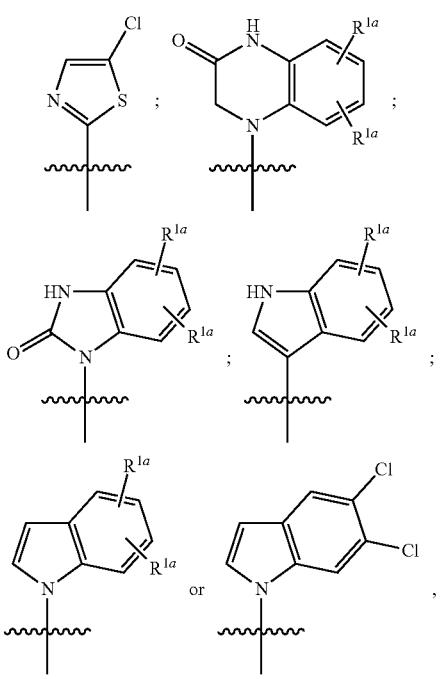

wherein $R^{1a}$ is, at each occurrence, independently H or halo.

In still other embodiments of structure (V), $R^1$ has one of the following structures:

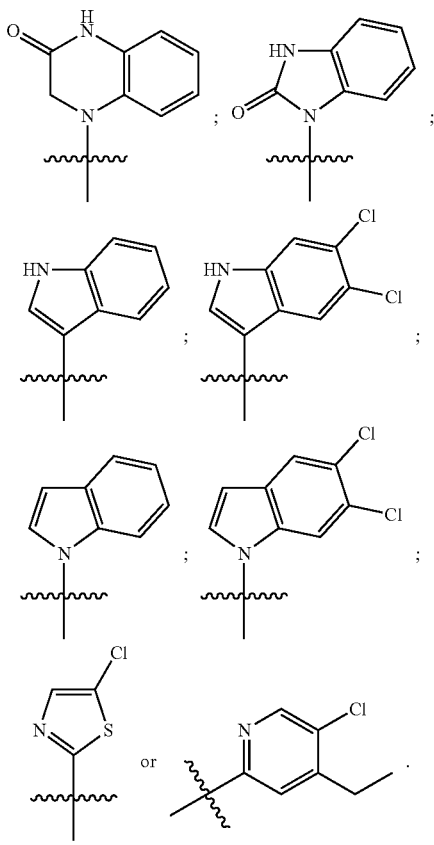

In some embodiments, Q is —C(=O)—. In some other embodiments, Q is —S(=O)$_2$—. In still other embodiments, Q is —NR$^{34}$C(=O)—. In still more other embodiments, Q is —NR$^{34}$S(=O)$_2$—.

In some more specific embodiments, $R^{34}$ is H. For example, in some embodiments $R^{34}$ is hydroxylalkyl, such as 2-hydroxylalkyl.

In other of the foregoing embodiments, at least one of $R^{35}$ or $R^{36}$ is H. For example, in some embodiment search of $R^{35}$ and $R^{36}$ are H.

In various other embodiments, $R^{36}$ is alkylaminoalkyl. For example, in some embodiments $R^{36}$ has the following structure:

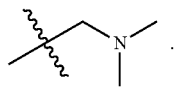 [SMILES: *CN(C)C]

In some different embodiments, $R^{36}$ is hydroxylalkyl, for example 2-hydroxylalkyl In various other embodiments, $R^{35}$ and $R^{36}$ join to form a ring. In some of these embodiments, the ring is a cyclopentene, cyclohexene or phenyl ring.

In other of the foregoing embodiments, E has one of the following structures:

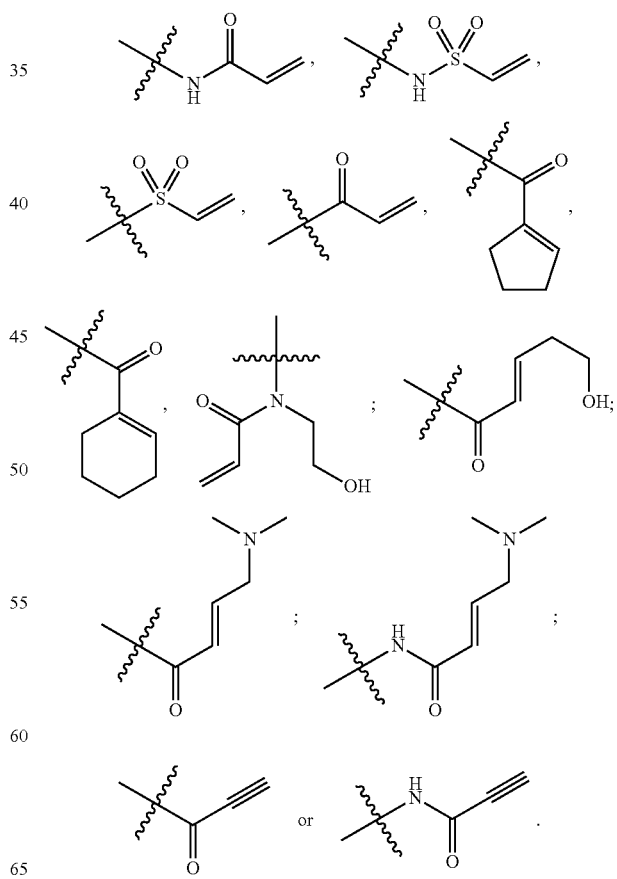

In some embodiments, E is

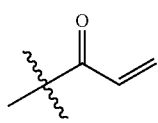

In some more of the foregoing embodiments, $L_1$ is heteroalkylene. In some more embodiments, the heteroalkylene is unsubstituted. In some different embodiments, the heteroalkylene is substituted.

In various other embodiments, $L^1$ is aminoalkylene. For example, in some embodiments $L^1$ is —CH$_2$CH$_2$NH—.

In other embodiments of the foregoing, $L^1$ is heterocycloalkylene or heteroarylene. In some embodiments, the heterocycloalkylene or heteroarylene is unsubstituted. In other embodiments, the heterocycloalkylene or heteroarylene is substituted. In some further embodiments, $L^1$ has one of the following structures:

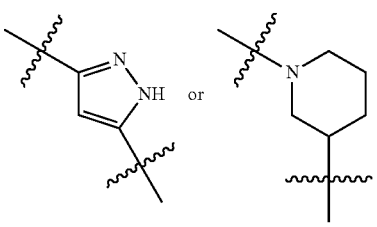

In some different embodiments, $L^{1a}$ is a bond.

In some embodiments, $L^{1a}$ is alkylene, alkenylene, heteroalkylene or heterocycloalkylene. In some other embodiments, $L^{1a}$ is alkylene or heteroalkylene. In some of these embodiments, $L^{1a}$ is substituted alkylene. In various other embodiments $L^{1a}$ is unsubstituted alkylene. For example, in some embodiments $L^{1a}$ is

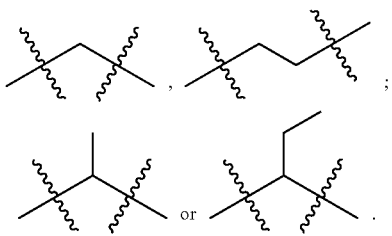

In some different embodiments, $L^{1a}$ is substituted heteroalkylene. In some other embodiments, $L^{1a}$ is unsubstituted heteroalkylene. In some of the foregoing embodiments, $L^{1a}$ is aminoalkylene or thioalkylene, for example aminoalkylene. For example, in some embodiments $L^{1a}$ has one of the following structures:

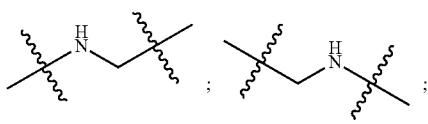

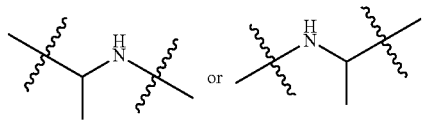

In other embodiments, $L^{1a}$ is

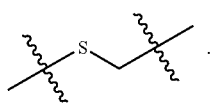 [SMILES: *CS*]

In other embodiments, $L^{1a}$ is substituted alkenylene. In different embodiments, $L^{1a}$ is unsubstituted alkenylene. In some more specific embodiments, $L^{1a}$ has the following structure:

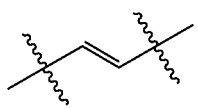

In yet other embodiments, $L^{1a}$ is substituted heterocycloalkylene. In some other embodiments, $L^{1a}$ is unsubstituted heterocycloalkylene. For Example, in some embodiments, $L^{1a}$ has the following structure:

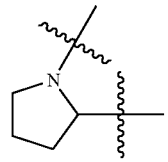

In some of the foregoing embodiments, $L^2$ is a bond.
In various other embodiments, $L^2$ is substituted alkylene. In still other embodiments, $L^2$ is unsubstituted alkylene.

In various embodiments of any of the foregoing compounds of structure (V):

$R^{30a}$ and $R^{30b}$ are, at each occurrence, independently H, —OH, —NH$_2$, —CO$_2$H, cyano, cyanoalkyl, C$_1$-C$_6$alkyl, C$_3$-C$_8$cycloalkyl, hydroxylalkyl, aminoalkyl, carboxylalkyl or aminocarbonyl;

$R^{31a}$ and $R^{31b}$ are, at each occurrence, independently H, —OH, —NH$_2$, —CO$_2$H, cyano, cyanoalkyl, C$_1$-C$_6$alkyl, C$_3$-C$_8$cycloalkyl, hydroxylalkyl, aminoalkyl, carboxylalkyl or aminocarbonyl;

$R^{32a}$ and $R^{32b}$ are, at each occurrence, independently H, —OH, —NH$_2$, —CO$_2$H, cyano, cyanoalkyl, C$_1$-C$_6$alkyl, C$_3$-C$_8$cycloalkyl, hydroxylalkyl, aminoalkyl, carboxylalkyl or aminocarbonyl; and $R^{33a}$ and $R^{33b}$ are, at each occurrence, independently H, —OH, —NH$_2$, —CO$_2$H, cyano, cyanoalkyl, C$_1$-C$_6$alkyl, C$_3$-C$_8$cycloalkyl, hydroxylalkyl, aminoalkyl, carboxylalkyl or aminocarbonyl.

In other embodiments, $R^{30a}$, $R^{30b}$, $R^{31a}$, $R^{31b}$, $R^{32a}$, $R^{32b}$, $R^{33a}$ and $R^{33b}$ are selected from H, C$_1$-C$_6$alkyl, hydroxylalkyl, cyano, cyanoalkyl and aminocarbonyl, for example H, C$_1$-C$_6$alkyl, hydroxylalkyl, cyano, and aminocarbonyl or in other embodiments H, C$_1$-C$_6$alkyl and hydroxylalkyl.

In some of the foregoing embodiments, at least one of $R^{30a}$, $R^{30b}$, $R^{31a}$, $R^{31b}$ $R^{32a}$, $R^{32b}$, $R^{33a}$ or $R^{33b}$ is H. For example, in some embodiments each of $R^{30a}$, $R^{30b}$, $R^{31a}$, $R^{31b}$, $R^{32a}$, $R^{32b}$, $R^{33a}$ or $R^{33b}$ is H.

In some other of the foregoing embodiments, at least one of $R^{30a}$, $R^{30b}$, $R^{31a}$, $R^{31b}$, $R^{32a}$, $R^{32b}$, $R^{33a}$ or $R^{33b}$ is hydroxylalkyl.

In still other of the foregoing embodiments, at least one of $R^{30a}$, $R^{30b}$, $R^{31a}$, $R^{31b}$, $R^{32a}$, $R^{32b}$, $R^{33a}$ or $R^{33b}$ is cyano.

In still more of the foregoing embodiments of compound (V), at least one of $R^{30a}$, $R^{30b}$, $R^{31a}$, $R^{31b}$, $R^{32a}$, $R^{32b}$, $R^{33a}$ or $R^{33b}$ is aminocarbonyl.

In other embodiments, at least one of $R^{30a}$, $R^{30b}$, $R^{31a}$, $R^{31b}$, $R^{32a}$, $R^{32b}$, $R^{33a}$ or $R^{33b}$ is $C_1$-$C_6$alkyl.

In some embodiments, $R^{30a}$ and $R^{30b}$ join to form a carbocyclic or heterocyclic ring. In different embodiments, $R^{31}$ and $R^{31b}$ join to form a carbocyclic or heterocyclic ring. In more embodiments, $R^{32a}$ and $R^{32b}$ join to form a carbocyclic or heterocyclic ring. In yet other embodiments, $R^{33a}$ and $R^{33b}$ join to form a carbocyclic or heterocyclic ring.

In even other embodiments, $R^{30a}$ is H, —OH, —NH$_2$, —CO$_2$H, cyano, $C_1$-$C_6$alkyl, $C_3$-$C_8$cycloalkyl, hydroxylalkyl, aminoalkyl, carboxylalkyl or aminocarbonyl and $R^{30b}$ joins with $R^{31b}$ to form a carbocyclic or heterocyclic ring.

In more embodiments, $R^{31a}$ is H, —OH, —NH$_2$, —CO$_2$H, cyano, $C_1$-$C_6$alkyl, $C_3$-$C_8$cycloalkyl, hydroxylalkyl, aminoalkyl, carboxylalkyl or aminocarbonyl and $R^{31b}$ joins with $R^{30b}$ to form a carbocyclic or heterocyclic ring.

In other embodiments, $R^{32a}$ is H, —OH, —NH$_2$, —CO$_2$H, cyano, $C_1$-$C_6$alkyl, $C_3$-$C_8$cycloalkyl, hydroxylalkyl, aminoalkyl, carboxylalkyl or aminocarbonyl and $R^{32b}$ joins with $R^{33b}$ to form a carbocyclic or heterocyclic ring.

In still more embodiments, $R^{33a}$ is H, —OH, —NH$_2$, —CO$_2$H, cyano, $C_1$-$C_6$alkyl, $C_3$-$C_8$cycloalkyl, hydroxylalkyl, aminoalkyl, carboxylalkyl or aminocarbonyl and $R^{33b}$ joins with $R^{32b}$ to form a carbocyclic or heterocyclic ring.

In some other embodiments, the compound is selected from a compound in Table 5.

Compounds of structure V are prepared according to procedures well-known or derivable by one of ordinary skill in the art, for example by procedures analogous to those exemplified in Examples 8, 9, 18 and other examples provided below. Each of the compounds in Table 5 was prepared in such a manner and analyzed by mass spectrometry and/or $^1$H NMR. The mass spectrum ([M+H$^+$] or [M+Na$^+$]) and/or NMR spectrum was found to be consistent with the structures in Table V.

General Reaction Scheme I illustrates an exemplary procedure for preparing compounds of structure (V).

General Reaction Scheme I

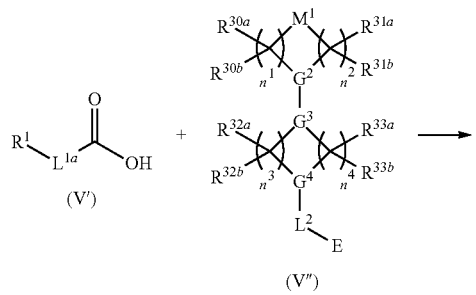

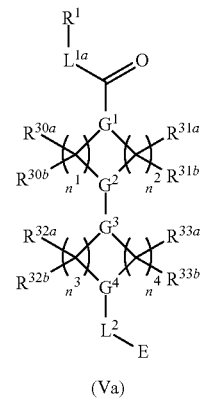

Referring to General Reaction Scheme I, (V') and (VI') are available from commercial sources and/or are easily prepared according to procedures known in the art. All variables on (V') and (V'''), with the exception of $M^1$, are as defined above. In some procedures, $M^1$ is NH. Briefly, an appropriately substituted acid (V') is activated and reacted with an appropriately substituted heterocycle (V''') under appropriate coupling conditions. The $L^2$-E moiety may be present in (V''') as illustrated or may be installed after coupling For example $L^2$-E may be installed before or after coupling via acylation (or thioacylation) using a reagent such as an acid chloride or thionyl chloride.

It should be noted that variations of the above procedure are possible, some of which are exemplified in the examples. For example, in some procedures (V''') is monocyclic and the second cyclic moiety is added after the compouling step. In other procedures, the acid moiety is present on the cyclic moiety (V''') and $R^1$ is appropriately substituted with a nucleophilic moiety to enable coupling to form (Va).

Various other options are available to one of ordinary skill in the art to add various substituents and or modify or reorder the above described steps to arrive at different embodiments of compounds of structure V. It should also ne noted that various substitutions on (V') and/or (V''') can be present during the coupling step (in protected or unprotected form) or the substituents can be added after (V') and (V''') are coupled. Methods for inclusion of these substituents are known in the art.

It is understood that although an exemplary procedure for prepare (Va) is provided above, other compounds of structure (V) can be prepared by analogous methods. For example, the carbonyl of (Va) may be reduced to form compounds of structure (V) wherein $L^1$ does not comprise a carbonyl. Embodiments wherein $L^1$ is heterocycloalkylene or heteroarylene can be prepared from analogous methods, for example by use of Buchwald chemistry to include the heterocycloalkylene or heteroarylene portion. Other methods for preparation of different compounds of structure (V) are known in the art.

Briefly, an appropriately substituted acid is reacted with an appropriately substituted heterocycle under amide coupling conditions. Acylation (or thioacylation) using a reagent such as an acid chloride or thionyl chloride results in compounds of structure V. Various options are available to one of ordinary skill in the art to add various substituents and/or modify or reorder the above described steps to arrive at different embodiments of compounds of structure V. The appropriate acid is purchased commercially or made according to well-known procedures.

In still other embodiments, the invention provides a compound having the following structure (VI):

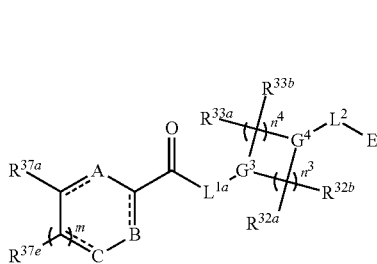

(VI)

or a pharmaceutically acceptable salt, tautomer, stereoisomer or prodrug thereof, wherein:

A is $CR^{37b}$, N or $NR^{38a}$;

B is $CR^{37c}$, N, $NR^{38b}$ or S

C is $CR^{37d}$, N, $NR^{38c}$ or S $G^3$ and $G^4$ are each independently N or CR, wherein R is H, cyano, halo or $C^1$-$C^6$alkyl;

$L^{1a}$ is a bond, —NH—, alkylene or heteroalkylene $L^2$ is a bond or alkylene;

$R^{32a}$ and $R^{32b}$ are, at each occurrence, independently H, —OH, —NH$_2$, —CO$_2$H, cyano, cyanoalkyl, $C_1$-$C_6$alkyl, $C_3$-$C_8$cycloalkyl, hydroxylalkyl, aminoalkyl, carboxylalkyl or aminocarbonyl; or $R^{32a}$ and $R^{32b}$ join to form a carbocyclic or heterocyclic ring; or $R^{32a}$ is H, —OH, —NH$_2$, —CO$_2$H, cyano, $C_1$-$C_6$alkyl, $C_3$-$C_8$cycloalkyl, hydroxylalkyl, aminoalkyl, carboxylalkyl or aminocarbonyl and $R^{32b}$ joins with $R^{33b}$ to form a carbocyclic or heterocyclic ring;

$R^{33a}$ and $R^{33b}$ are, at each occurrence, independently H, —OH, —NH$_2$, —CO$_2$H, cyano, cyanoalkyl, $C_1$-$C_6$alkyl, $C_3$-$C_8$cycloalkyl, hydroxylalkyl, aminoalkyl, carboxylalkyl or aminocarbonyl; or $R^{33a}$ and $R^{33b}$ join to form a carbocyclic or heterocyclic ring; or $R^{33a}$ is H, —OH, —NH$_2$, —CO$_2$H, cyano, $C_1$-$C_6$alkyl, $C_3$-$C_8$cycloalkyl, hydroxylalkyl, aminoalkyl, carboxylalkyl or aminocarbonyl and $R^{33b}$ joins with $R^{32b}$ to form a carbocyclic or heterocyclic ring;

$R^{37a}$, $R^{37b}$, $R^{37c}$, $R^{37d}$ and $R^{37e}$ are each independently H, halo, oxo, hydroxyl, cyano, aminocarbonyl, formyl, $C_1$-$C_6$alkyl, $C_1$-$C_6$alkylsulfonyl, $C_1$-$C_6$haloalkyl, $C_3$-$C_8$cycloalkyl, $C_1$-$C_6$alkoxy, $C_1$-$C_6$hydroxylalkyl, $C_1$-$C_6$alkoxyalkyl, $C_1$-$C_6$-aminoalkyl, heterocyclyl or aryl;

$R^{38a}$, $R^{38b}$ and $R^{38c}$ are each independently H, $C_1$-$C_6$alkyl or aryl;

$n^3$ and $n^4$ are each independently 1, 2 or 3 m is 0 or 1;

═ is a single or double bond such that all valences are satisfied; and

E is an electrophilic moiety capable of forming a covalent bond with the cysteine residue at position 12 of a K-Ras, H-Ras or N-Ras G12C mutant protein.

In various other embodiments, the compound has one of the following structures (VIa), (VIb), (VIc), (VId), (VIe), (VIf) or (VIg):

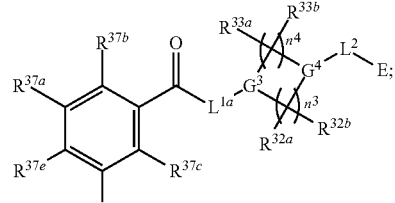

(VIa)

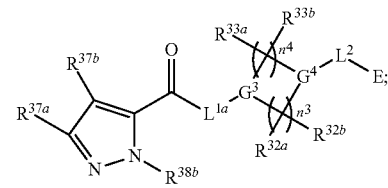

(VIb)

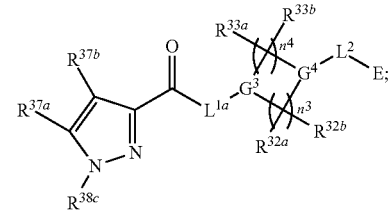

(VIc)

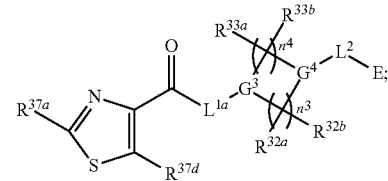

(VId)

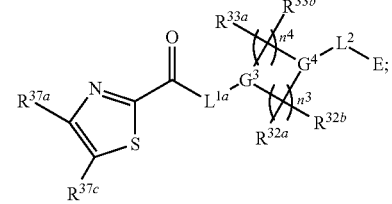

(VIe)

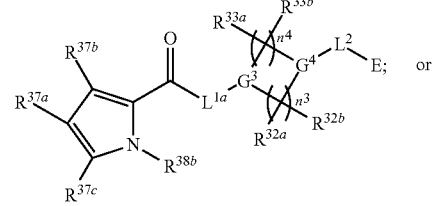

(VIf) or

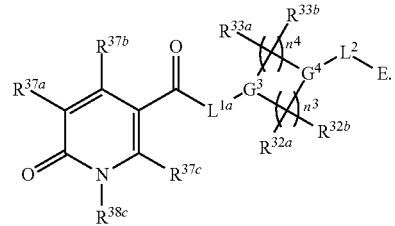

(VIg)

In some different embodiments, the compound has one of the following structures (VIa'), (VIb'), (VIc'), (VId'), (VIe'), (VIf') or (VIg'):

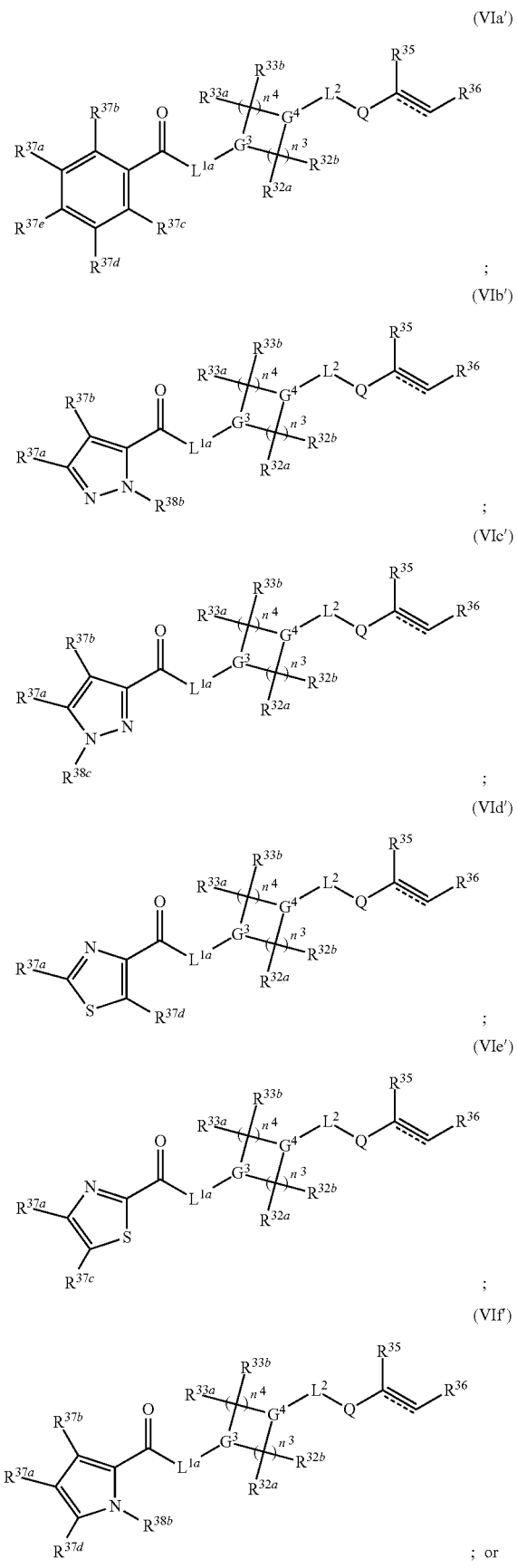

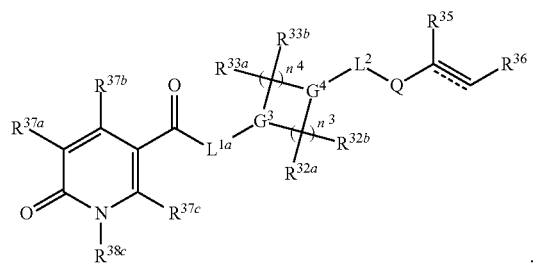

wherein:

Q is —C(=O)—, —NR³⁴C(=O)—, —S(=O)₂— or —NR³⁴S(=O)₂—;

R³⁴ is H, C₁-C₆alkyl or hydroxylalkyl:

≡ is a carbon-carbon double bond or a carbon-carbon triple bond; and

R³⁵ and R³⁶ are each independently H, cyano, C₁-C₆alkyl, aminoalkyl, alkylaminoalkyl, or hydroxylalkyl or R³⁵ and R³⁶ join to form a carbocyclic or heterocyclic ring when ≡ a double bond; or R³⁵ is absent and R³⁶ is H, C₁-C₆alkyl, aminoalkyl, alkylaminoalkyl or hydroxylalkyl when ≡ is a triple bond.

In some specific embodiments of the foregoing compounds of structure (VI), and substructures thereof, R³⁷ᵃ is halo, aryl or heteroaryl. In further such embodiments, R³⁵ and R³⁶ are each H.

In various other embodiments, G³ is N and G⁴ is CR, for example CH.

In some different embodiments, G³ is CR, for example, CH, and G⁴ is N.

In still other embodiments, G³ is N and G⁴ is N.

In various other embodiments, n³ is 2 and n⁴ is 2. In still other embodiments, n³ is 1 and n⁴ is 1. In some more embodiments, n³ is 2 and n⁴ is 1.

In other of the foregoing embodiments, R³⁷ᵃ, R³⁷ᵇ, R³⁷ᶜ, R³⁷ᵈ and R³⁷ᵉ are each independently H, —OH, halo, oxo, C₁-C₆alkyl, C₁-C₆alkoxy, heterocyclyl or aryl.

In still other embodiments, R³⁷ᵃ, R³⁷ᵇ, R³⁷ᶜ, R³⁷ᵈ and R³⁷ᵉ are each independently H, —OH, fluoro, chloro, bromo, iodo, oxo, methyl, methoxy, heteroaryl or aryl.

In some embodiments, R³⁷ᵃ or R³⁷ᵉ is aryl. In some more specific embodiments, R³⁷ᵃ is aryl, such as phenyl.

In some different embodiments, the aryl is unsubstituted. In some other embodiments, the aryl is substituted. For example, in some embodiments the aryl is substituted with one or more halo substituents. In some of these embodiments, the halo substituents are selected from fluoro and chloro.

In still other embodiments, R³⁷ᵃ is heteroaryl. In some of these embodiments, the heteroaryl is unsubstituted. In various other embodiments, the heteroaryl is substituted. In some more embodiments, the heteroaryl comprises nitrogen, sulfur or a combination thereof.

In some more specific embodiments, the heteroaryl is thiophenyl.

In other of the foregoing embodiments, R³⁷ᵃ is halo. For example, in some embodiments halo is chloro, bromo or iodo.

In some embodiments, R³⁷ᵃ or R³⁷ᵉ has one of the following structures:

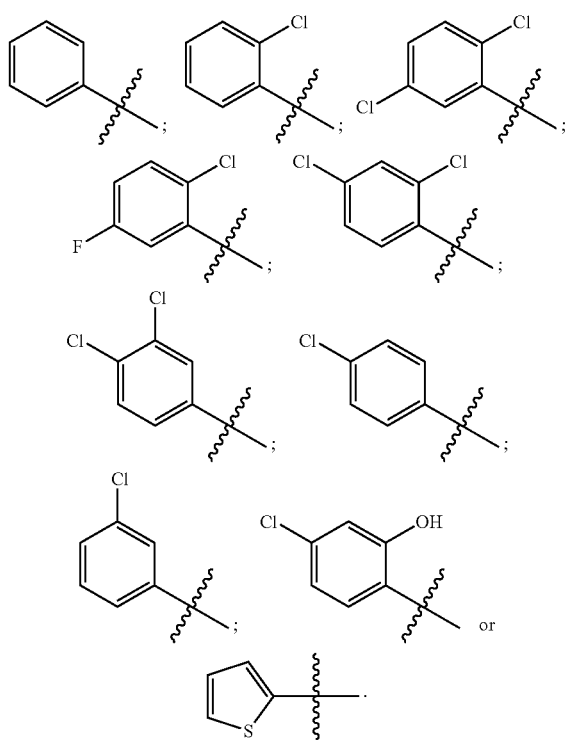

In still other embodiments, $R^{37a}$ has one of the following structures:

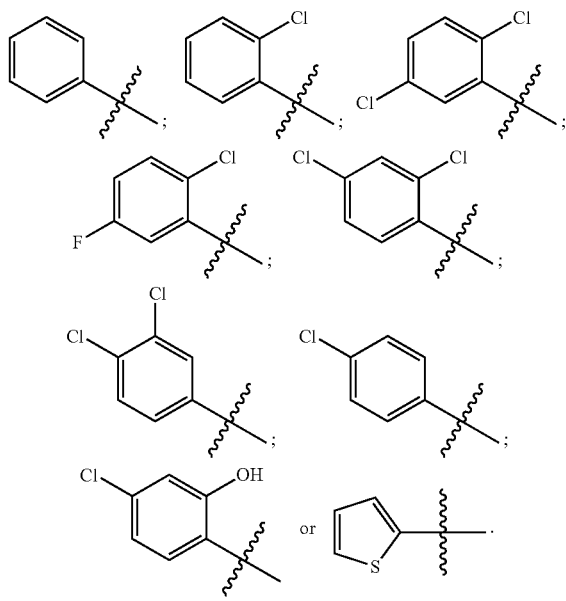

In various different embodiments, $R^{38a}$, $R^{38b}$ and $R^{38}$ are each independently H or aryl. In still other embodiments, $R^{38a}$, $R^{38b}$ and $R^{38}$ are each independently H.

In some other different embodiments, $R^{38c}$ is aryl. For example, in some embodiments the aryl is substituted with one or more halo substituents. In some of these embodiments, halo is chloro.

In some other embodiments of the compounds of structure (VI), Q is —C(=O)—. In some other embodiments, Q is —S(=O)$_2$—. In still other embodiments, Q is —NR$^{34}$C(=O)—. In still more other embodiments, Q is —NR$^{34}$S(=O)$_2$—.

In some more specific embodiments, $R^{34}$ is H. For example, in some embodiments $R^{34}$ is hydroxylalkyl, such as 2-hydroxylalkyl.

In other of the foregoing embodiments, at least one of $R^{35}$ or $R^{36}$ is H. For example, in some embodiment search of $R^{35}$ and $R^{36}$ are H.

In various other embodiments, $R^{36}$ is alkylaminoalkyl. For example, in some embodiments $R^{36}$ has the following structure:

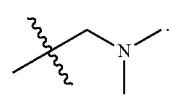 [SMILES: *CN(C)C]

In some different embodiments, $R^{36}$ is hydroxylalkyl, for example 2-hydroxylalkyl In various other embodiments, $R^{35}$ and $R^{36}$ join to form a ring. In some of these embodiments, the ring is a cyclopentene, cyclohexene or phenyl ring.

In other of the foregoing embodiments, E has one of the following structures:

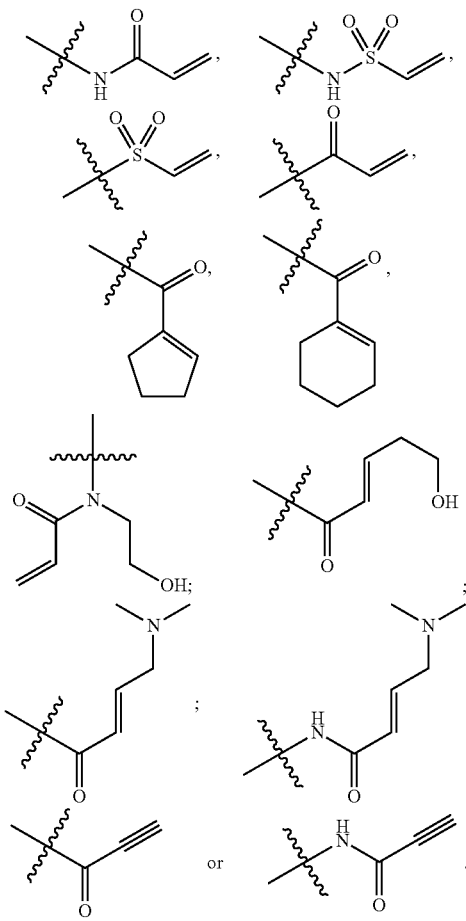

In some embodiments, E is

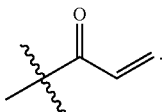 [SMILES: *C(=O)C=C]

In some more of the foregoing embodiments, $L^1$ is heteroalkylene. In some more embodiments, the heteroalkylene is unsubstituted. In some different embodiments, the heteroalkylene is substituted.

In various other embodiments, $L^1$ is aminoalkylene. For example, in some embodiments $L^1$ is —CH$_2$CH$_2$NH—.

In some different embodiments, $L^{1a}$ is a bond.

In some embodiments, $L^{1a}$ is alkylene, alkenylene, heteroalkylene or heterocycloalkylene. In some other embodiments, $L^{1a}$ is alkylene or heteroalkylene. In some of these embodiments, $L^{1a}$ is substituted alkylene. In various other embodiments, $L^{1a}$ is unsubstituted alkylene. For example, in some embodiments $L^{1a}$ is

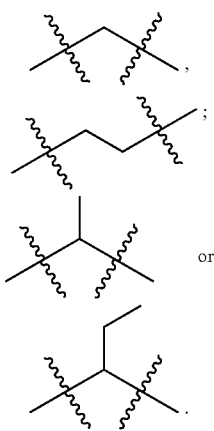

In some different embodiments, $L^{1a}$ is substituted heteroalkylene. In some other embodiments, $L^{1a}$ is unsubstituted heteroalkylene. In some of the foregoing embodiments, $L^{1a}$ is aminoalkylene or thioalkylene, for example aminoalkylene. For example, in some embodiments $L^{1a}$ has one of the following structures:

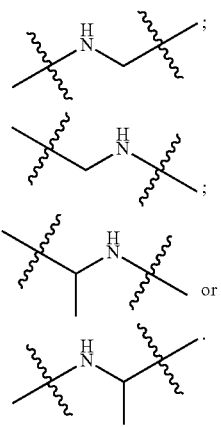

In other embodiments, $L^{1a}$ is

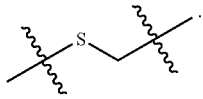 [SMILES: *CS*]

In other embodiments, $L^{1a}$ is substituted alkenylene. In different embodiments, $L^{1a}$ is unsubstituted alkenylene. In some more specific embodiments, $L^{1a}$ has the following structure:

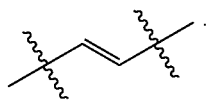 [SMILES: */C=C/*]

In yet other embodiments, $L^{1a}$ is substituted heterocycloalkylene. In some other embodiments, $L^{1a}$ is unsubstituted heterocycloalkylene. For Example, in some embodiments, $L^{1a}$ has the following structure:

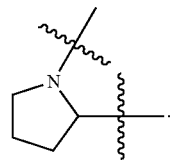 [SMILES: *C1CCCN1*]

In some of the foregoing embodiments, $L^2$ is a bond.

In various other embodiments, $L^2$ is substituted alkylene. In still other embodiments, $L^2$ is unsubstituted alkylene.

In some embodiments of any of the foregoing compounds of structure (VI):

$R^{32a}$ and $R^{32b}$ are, at each occurrence, independently H, —OH, —NH$_2$, —CO$_2$H, cyano, cyanoalkyl, C$_1$-C$_6$alkyl, C$_3$-C$_8$cycloalkyl, hydroxylalkyl, aminoalkyl, carboxylalkyl or aminocarbonyl; and $R^{33a}$ and $R^{33b}$ are, at each occurrence, independently H, —OH, —NH$_2$, —CO$_2$H, cyano, cyanoalkyl, C$_1$-C$_6$alkyl, C$_3$-C$_8$cycloalkyl, hydroxylalkyl, aminoalkyl, carboxylalkyl or aminocarbonyl.

In other embodiments, $R^{32a}$, $R^{32b}$, $R^{33a}$ or $R^{33b}$ are selected from H, C$_1$-C$_5$alkyl, hydroxylalkyl, cyano, cyanoalkyl and aminocarbonyl, for example H, hydroxyl alkyl and cyano.

In other of the foregoing embodiments, at least one of $R^{32a}$, $R^{32b}$, $R^{33a}$ or $R^{33b}$ is H. For example, in some embodiments each of $R^{32a}$, $R^{32b}$, $R^{33a}$ or $R^{33b}$ is H.

In other of the foregoing embodiments, at least one of $R^{32a}$, $R^{32b}$, $R^{33a}$ or $R^{33b}$ is hydroxylalkyl.

In still other embodiments, at least one of $R^{32a}$, $R^{32b}$, $R^{33a}$ or $R^{33b}$ is cyano.

In some other different embodiments, least one of $R^{32a}$, $R^{32b}$, $R^{33a}$ or $R^{33b}$ is aminocarbonyl.

In some embodiments, $R^{32a}$ and $R^{32b}$ join to form a carbocyclic or heterocyclic ring. In other embodiments, $R^{33a}$ and $R^{33b}$ join to form a carbocyclic or heterocyclic ring.

In different embodiments, $R^{32a}$ is H, —OH, —NH$_2$, —CO$_2$H, cyano, C$_1$-C$_6$alkyl, C$_3$-C$_8$cycloalkyl, hydroxylalkyl, aminoalkyl, carboxylalkyl or aminocarbonyl and $R^{32b}$ joins with $R^{33b}$ to form a carbocyclic or heterocyclic ring.

In still other embodiments, $R^{33a}$ is H, —OH, —NH$_2$, —CO$_2$H, cyano, C$_1$-C$_6$alkyl, C$_3$-C$_8$cycloalkyl, hydroxylalkyl, aminoalkyl, carboxylalkyl or aminocarbonyl and $R^{33b}$ joins with $R^{32b}$ to form a carbocyclic or heterocyclic ring.

In some more specific embodiments, the compound is selected from a compound in Table 6.

Compounds of structure VI are prepared according to procedures well-known or derivable by one of ordinary skill in the art, for example by procedures analogous to those exemplified in Examples 13, 17, 19, 20, 22 and other examples provided below. Each of the compounds in Table 6 was prepared in such a manner and analyzed by mass spectrometry and/or $^1$H NMR. The mass spectrum ([M+H$^+$] or [M+Na$^+$]) and/or NMR spectrum was found to be consistent with the structures in Table VI.

General Reaction Scheme II illustrates an exemplary procedure for preparing compounds of structure (VI).

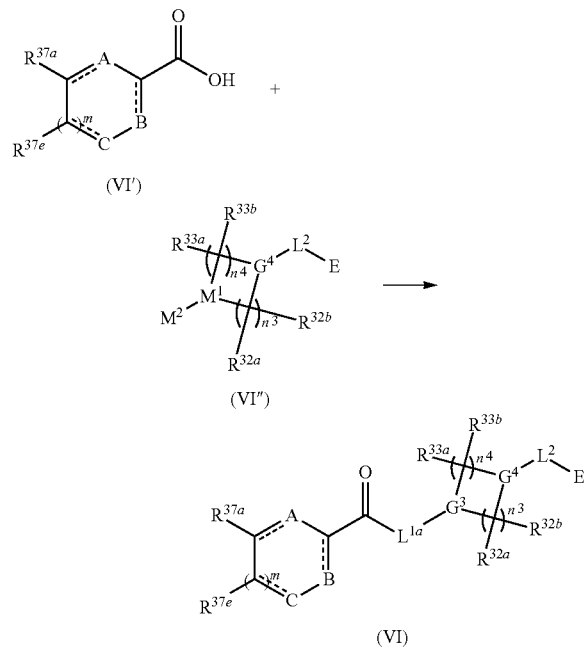

Referring to General Reaction Scheme II, (VI') and (VI") are available from commercial sources and/or are easily prepared according to procedures known in the art. All variables on (VI') and (VI"), with the exception of M$^1$ and M$^2$, are as defined above. In some procedures, M$^1$ is NH and M$^2$ is absent. In other procedures M$^1$ is N or CH and M$^2$ is a precursor to L$^{1a}$ which reacts with an activated acid. For example, in various procedures M$^2$ is NH$_2$, aminoalkyl or other heterosubstituted alkyl. Embodiments where M$^2$ comprises a carbanion (or M$^1$ is a carbanion) are also contemplated such that L$^1$ is alkylene. Briefly, an appropriately substituted acid (VI') is activated and reacted with an appropriately substituted heterocycle (VI") under appropriate coupling conditions. The L$^2$-E moiety may be present in (VI") as illustrated or may be installed after coupling For example L2-E may be installed before or after coupling via acylation (or thioacylation) using a reagent such as an acid chloride or thionyl chloride.

It should be noted that variations of the above procedure are possible, some of which are exemplified in the examples. For example, in some procedures, the acid moiety is present on the cyclic moiety (VI') and (VI') is appropriately substituted with a nucleophilic moiety to enable coupling to form (VI). Other methods of bond formation, which do not require reaction of an activated acid are also available for preparation of the compounds. It should also ne noted that various substitutions on (VI') and/or (VI") can be present during the coupling step (in protected or unprotected form) or the substituents can be added after (VI') and (VI") are coupled. Methods for inclusion of these substituents are known in the art.

Various options are available to one of ordinary skill in the art to add various substituents and or modify or reorder the above described steps to arrive at different embodiments of compounds of structure VI. The appropriate acid is purchased commercially or made according to well-known procedures.

It will also be appreciated by those skilled in the art that in the processes described herein (e.g., General Reaction Scheme I and II and the below examples) the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters. Protecting groups may be added or removed in accordance with standard techniques, which are known to one skilled in the art and as described herein. The use of protecting groups is described in detail in Green, T. W. and P. G. M. Wutz, *Protective Groups in Organic Synthesis* (1999), 3rd Ed., Wiley. As one of skill in the art would appreciate, the protecting group may also be a polymer resin such as a Wang resin, Rink resin or a 2-chlorotrityl-chloride resin.

It will also be appreciated by those skilled in the art, although such protected derivatives of compounds of this invention may not possess pharmacological activity as such, they may be administered to a mammal and thereafter metabolized in the body to form compounds of the invention which are pharmacologically active. Such derivatives may therefore be described as "prodrugs". All prodrugs of compounds of this invention are included within the scope of the invention.

It is also understood that one skilled in the art may be able to make these compounds by similar methods or by combining other methods known to one skilled in the art. It is further understood that one skilled in the art would be able to make, in a similar manner as described below, other compounds of the invention not specifically illustrated below by using the appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, for example, Advanced Organic Chemistry: Reactions, Mechanisms, and Structure, 5th edition (Wiley, December 2000)) or prepared as described in this invention.

TABLE 1

| Compound Number I- | Structure |
|---|---|
| 1 | 2-((2,4-dichloro-5-hydroxyphenyl)amino)-N-(1-acryloylpiperidin-4-yl)acetamide |
| 2 | N-(6-chloro-5'-fluoro-4-hydroxy-[1,1'-biphenyl]-3-yl)-2-(4-acryloylpiperazin-1-yl)-2-oxoethanamine derivative |
| 3 | N-(2',5-dichloro-5'-fluoro-4-methoxy-[1,1'-biphenyl]-3-yl)-2-(4-acryloylpiperazin-1-yl)-2-oxoethanamine derivative |
| 4 | N-(3'-cyano-6-chloro-4-methoxy-[1,1'-biphenyl]-3-yl)-2-(4-acryloylpiperazin-1-yl)-2-oxoethanamine derivative |
| 5 | 2-((2,4-dichloro-5-hydroxyphenyl)amino)-N-(1-(vinylsulfonyl)piperidin-4-yl)acetamide |

TABLE 1-continued

| Compound Number I- | Structure |
| --- | --- |
| 6 | 4,5-dichloro-2-hydroxyphenyl-NH-CH2-C(=O)-NH-[(3S)-piperidin-3-yl]-N-S(=O)2-CH=CH2 |
| 7 | 4,5-dichloro-2-hydroxyphenyl-NH-CH2-C(=O)-NH-CH2-[piperidin-4-yl]-N-S(=O)2-CH=CH2 |
| 8 | 4,5-dichloro-2-hydroxyphenyl-NH-CH2-C(=O)-NH-CH2-[piperidin-4-yl]-N-C(=O)-CH=CH2 |
| 9 | 4,5-dichloro-2-hydroxyphenyl-NH-CH2-C(=O)-NH-[(3R)-piperidin-3-yl]-N-S(=O)2-CH=CH2 |
| 10 | 4,5-dichloro-2-hydroxyphenyl-NH-CH2-C(=O)-NH-[(3S)-piperidin-3-yl]-N-C(=O)-CH=CH2 |
| 11 | 4,5-dichloro-2-hydroxyphenyl-NH-CH2-C(=O)-NH-[(3R)-piperidin-3-yl]-N-C(=O)-CH=CH2 |

TABLE 1-continued

| Compound Number I- | Structure |
|---|---|
| 12 | 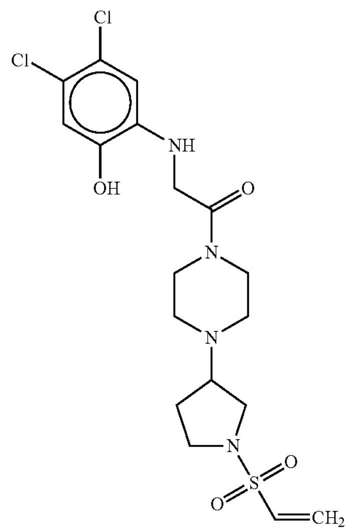 |
| 13 | 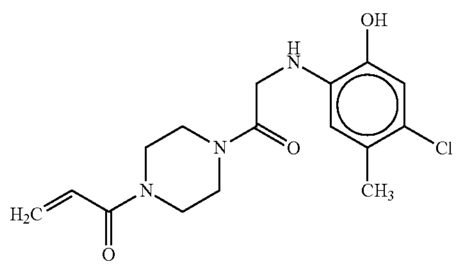 |
| 14 | 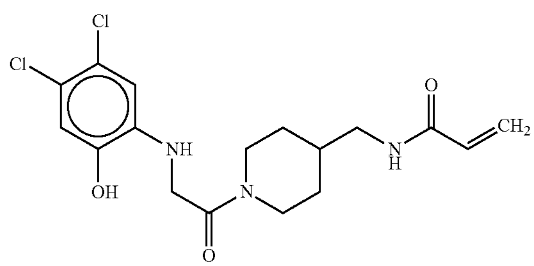 |
| 15 | 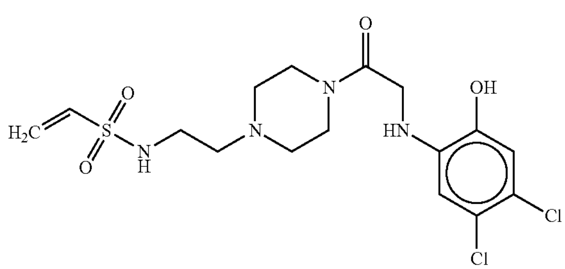 |
| 16 | 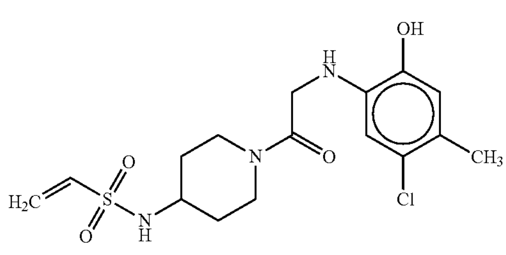 |

TABLE 1-continued

| Compound Number I- | Structure |
| --- | --- |
| 17 | 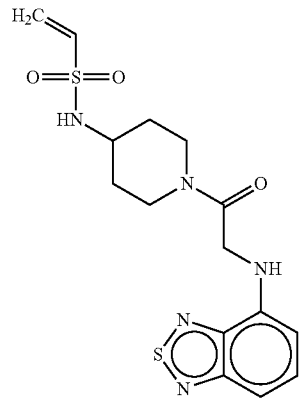 |
| 18 | 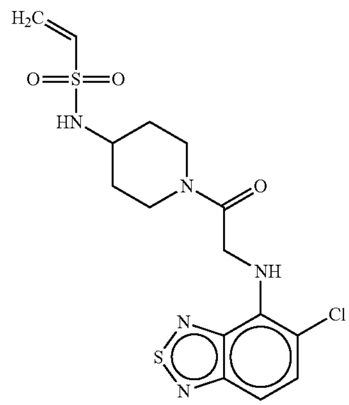 |
| 19 | 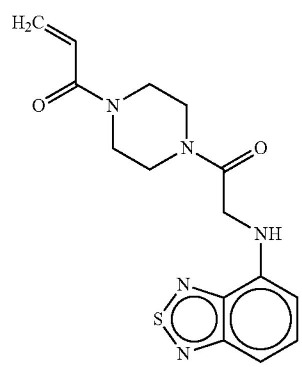 |
| 20 | 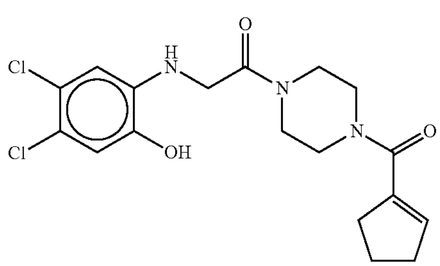 |

TABLE 1-continued
| Compound Number I- | Structure |
|---|---|
| 21 | 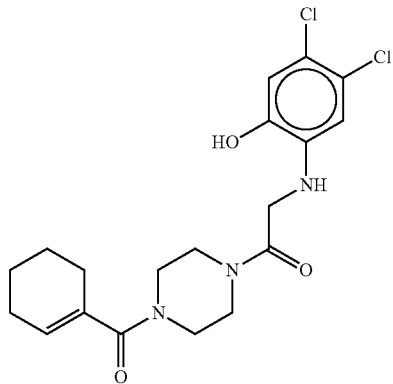 |
| 22 | 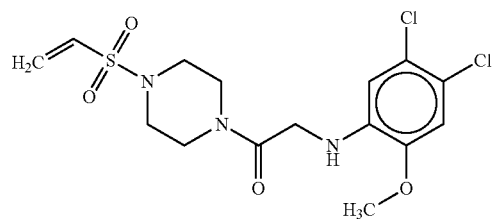 |
| 23 | 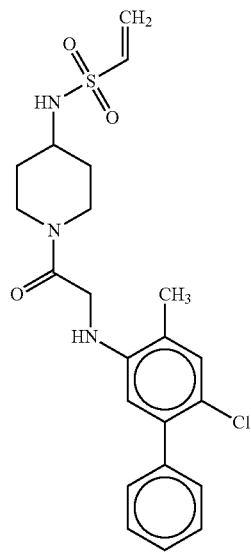 |

TABLE 1-continued

| Compound Number I- | Structure |
|---|---|
| 24 | *[Chemical structure: 4,5-dichloro-2-hydroxyphenyl-NH-CH2-C(O)-N(azetidine)-piperazine-C(O)-CH=CH2]* |
| 25 | *[Chemical structure: H2C=CH-S(O)2-N(piperazine)-C(O)-CH2-NH-(2-iodo-4,5-dichlorophenyl)]* |
| 26 | *[Chemical structure: 4,5-dichloro-2-hydroxyphenyl-NH-CH2-C(O)-N(azetidine)-piperazine-S(O)2-CH=CH2]* |

TABLE 1-continued

| Compound Number I- | Structure |
|---|---|
| 27 | 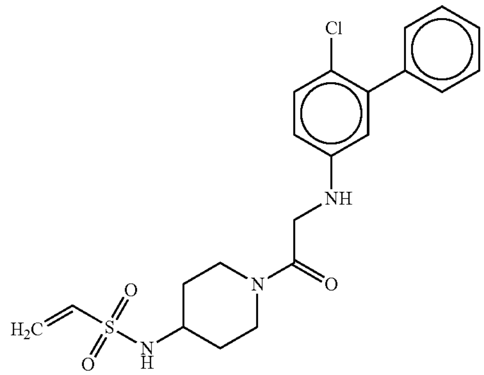 |
| 28 | 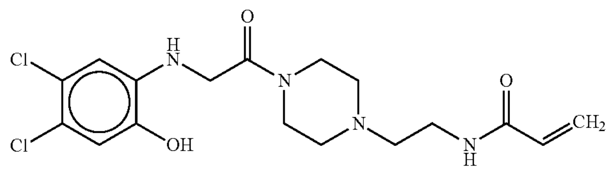 |
| 29 | 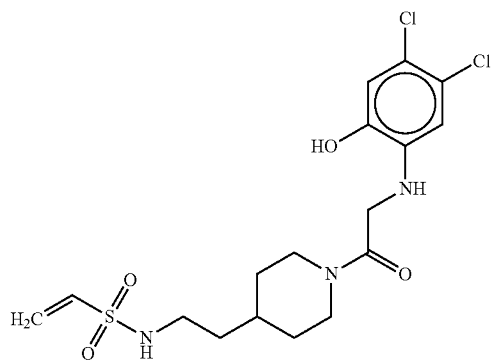 |
| 30 | 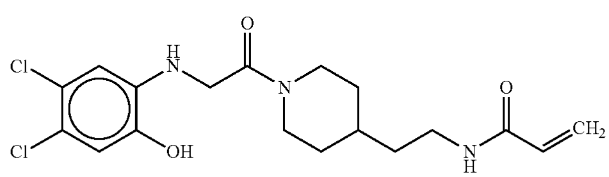 |
| 31 | 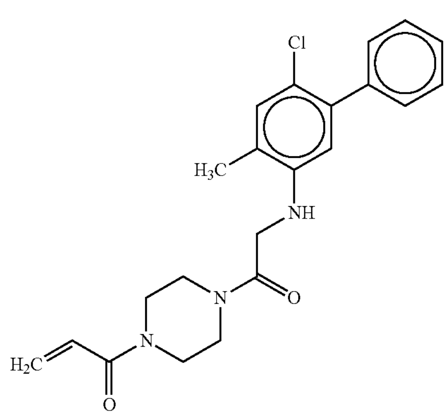 |

TABLE 1-continued
| Compound Number I- | Structure |
|---|---|
| 32 | 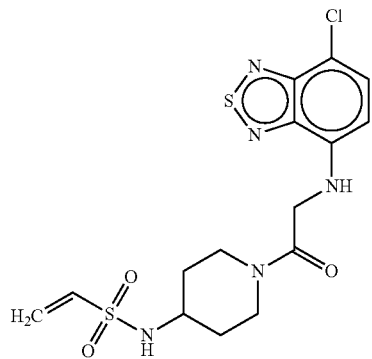 |
| 33 | 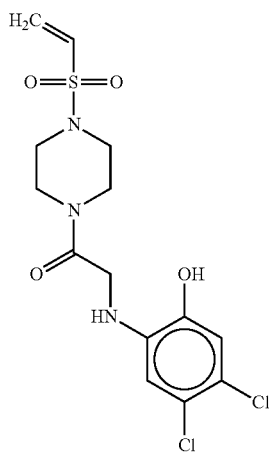 |
| 34 | 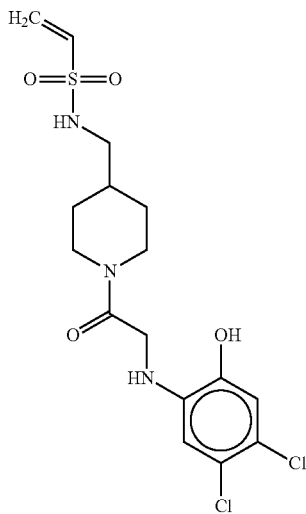 |

TABLE 1-continued

| Compound Number I- | Structure |
|---|---|
| 35 | 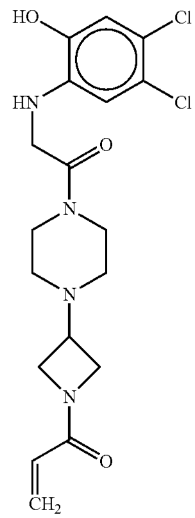 |
| 36 | 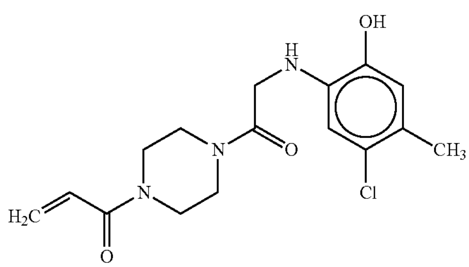 |
| 37 | 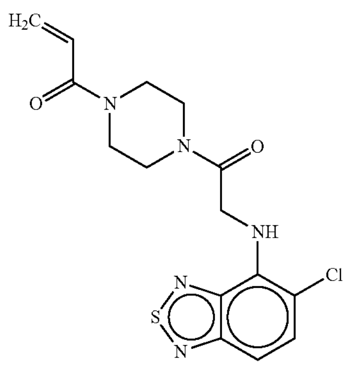 |
| 38 | 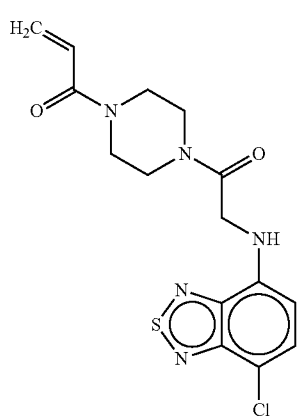 |

TABLE 1-continued
| Compound Number I- | Structure |
|---|---|
| 39 | 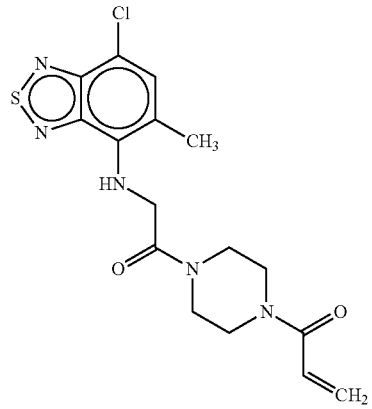 |
| 40 | 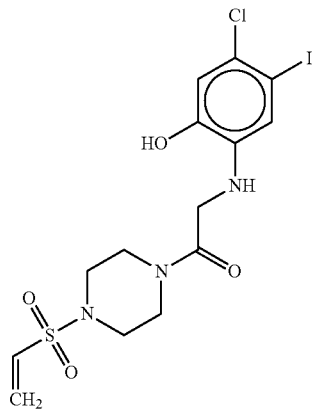 |
| 41 | 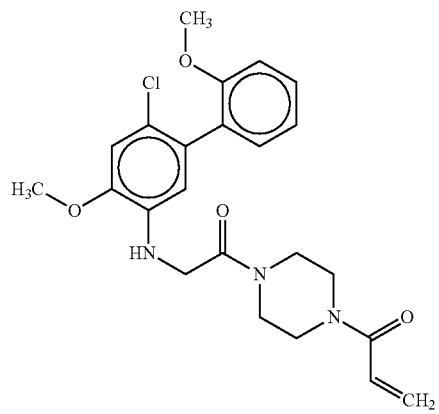 |

TABLE 1-continued
| Compound Number I- | Structure |
|---|---|
| 42 | 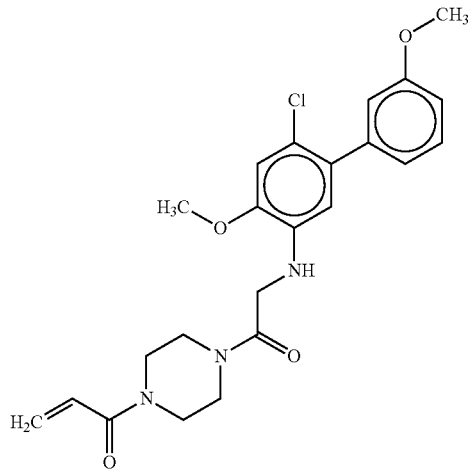 |
| 43 | 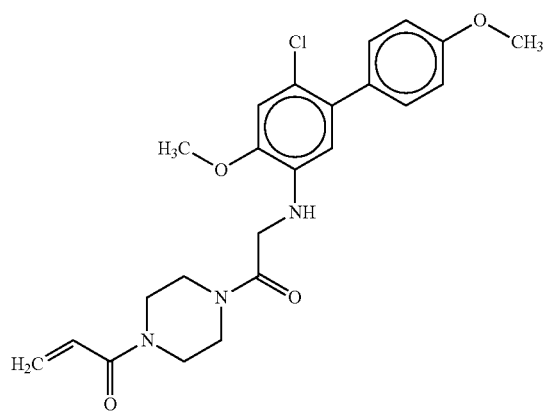 |
| 44 | 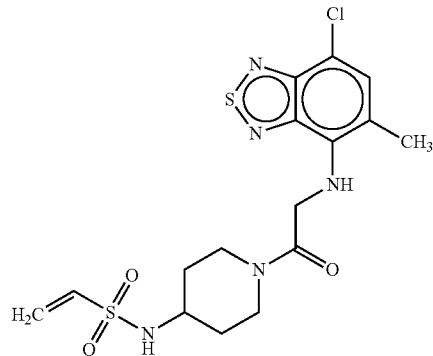 |

TABLE 1-continued
| Compound Number I- | Structure |
|---|---|
| 45 | 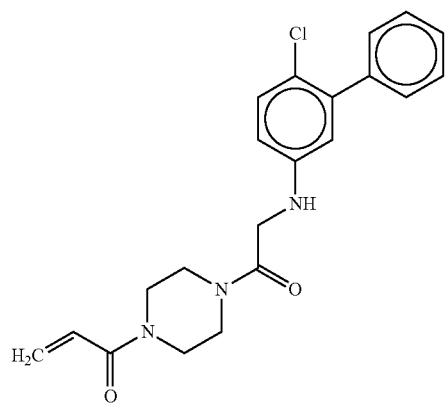 |
| 46 | 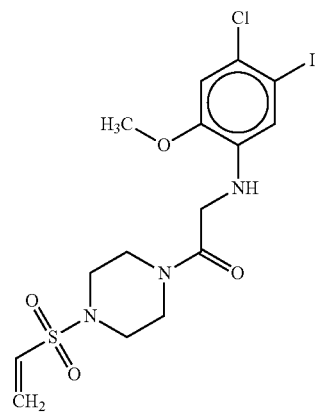 |
| 47 | 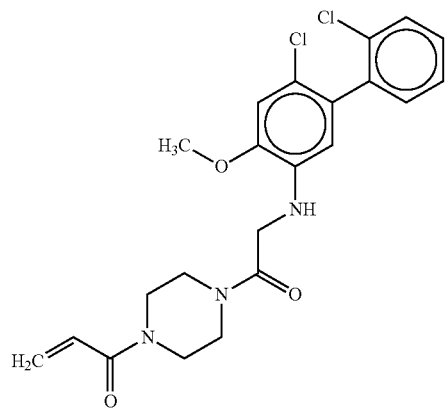 |

TABLE 1-continued
| Compound Number I- | Structure |
| --- | --- |
| 48 | 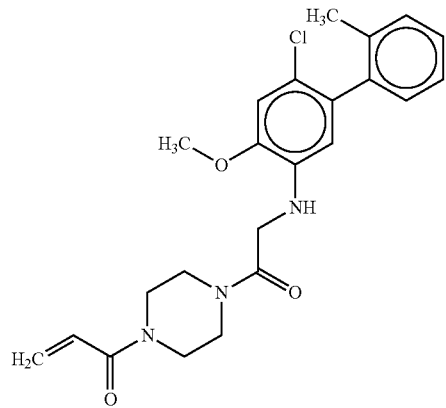 |
| 49 | 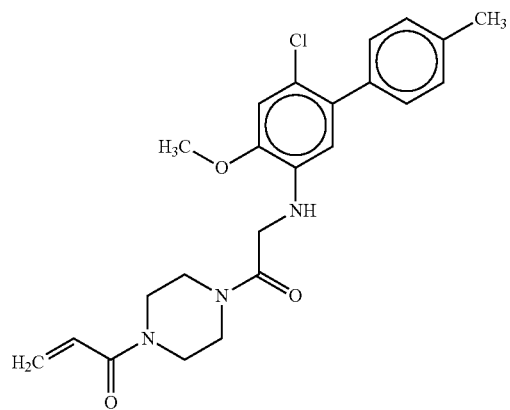 |
| 50 | 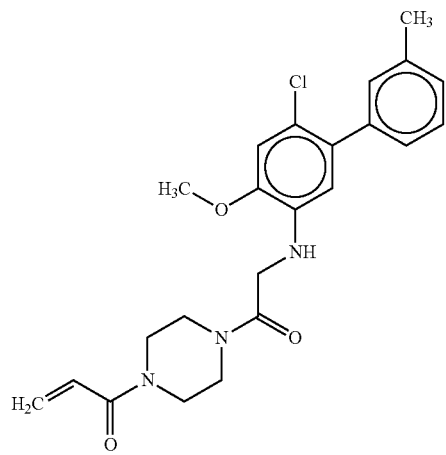 |

TABLE 1-continued
| Compound Number I- | Structure |
|---|---|
| 51 | 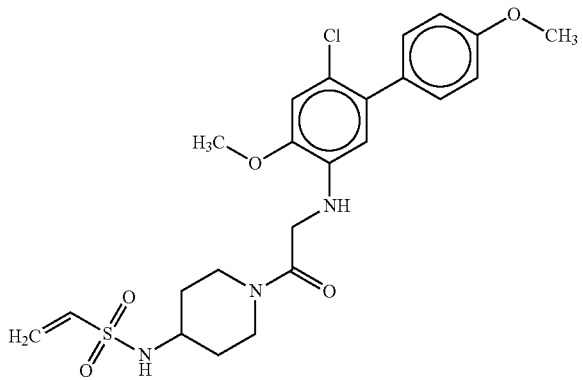 |
| 52 | 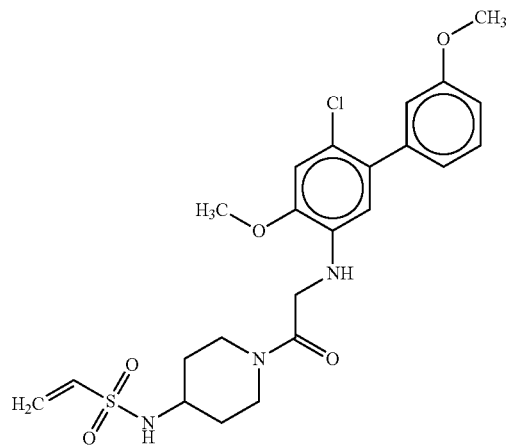 |
| 53 | 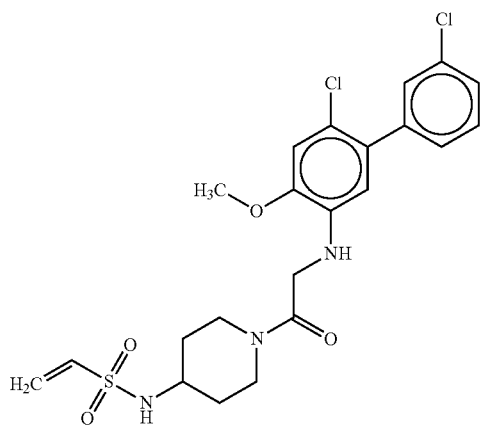 |

TABLE 1-continued
| Compound Number I- | Structure |
|---|---|
| 54 | 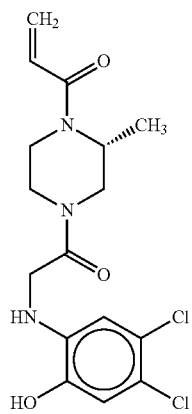 |
| 55 | 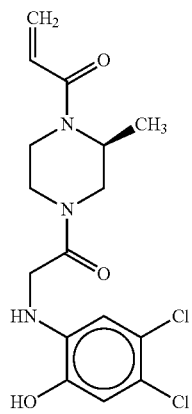 |
| 56 | 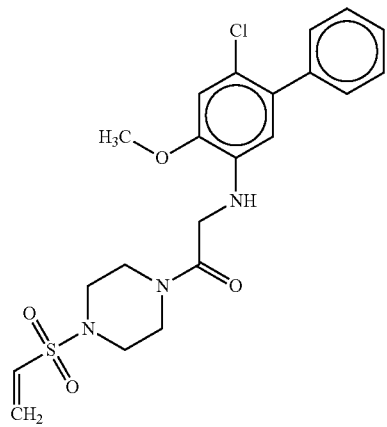 |

TABLE 1-continued

| Compound Number I- | Structure |
|---|---|
| 57 | *(structure: 4,5-dichloro-2-hydroxyphenyl-NH-CH2-C(=O)-N-piperidine with 3-NH-SO2-CH=CH2 substituent)* |
| 58 | *(structure: 3,5-dichloro-2-hydroxyphenyl-NH-CH2-C(=O)-N-piperidine with 4-NH-SO2-CH=CH2 substituent)* |
| 59 | *(structure: 4,5-dichloro-2-hydroxyphenyl-NH-CH2-C(=O)-N-piperazine-N-pyrrolidine-N-C(=O)-CH=CH2)* |

TABLE 1-continued
| Compound Number I- | Structure |
| --- | --- |
| 60 | 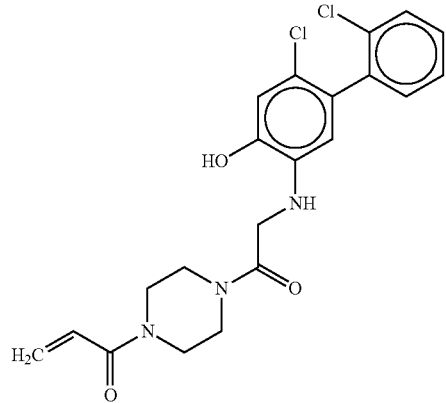 |
| 61 | 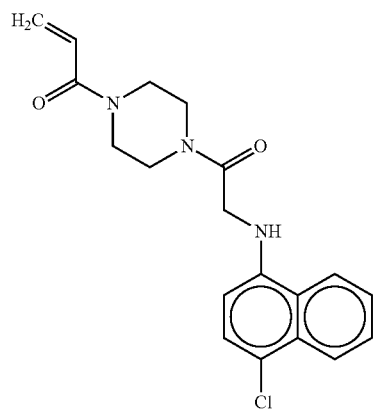 |
| 62 | 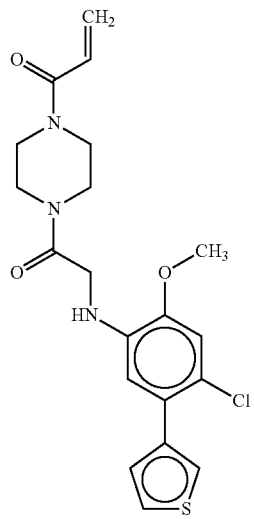 |

101 102
TABLE 1-continued
| Compound Number I- | Structure |
|---|---|
| 63 | 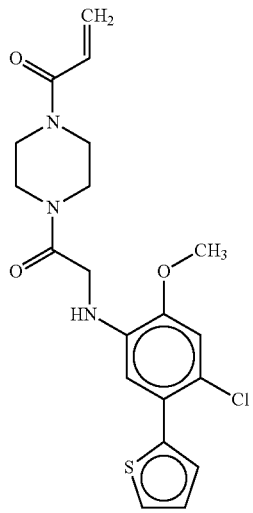 |
| 64 | 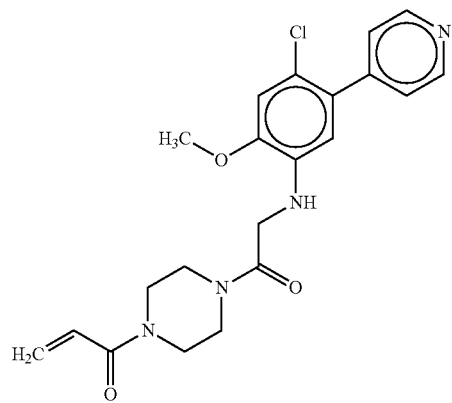 |
| 65 | 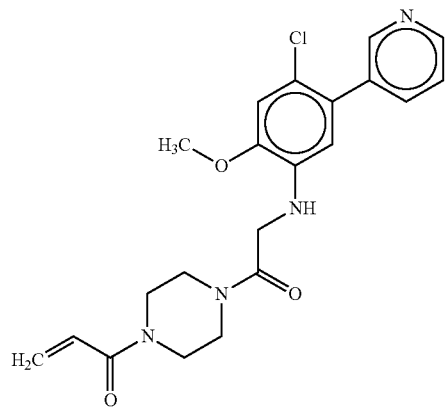 |

TABLE 1-continued
| Compound Number I- | Structure |
|---|---|
| 66 | 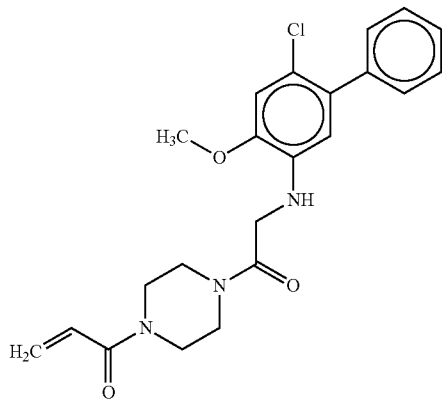 |
| 67 | 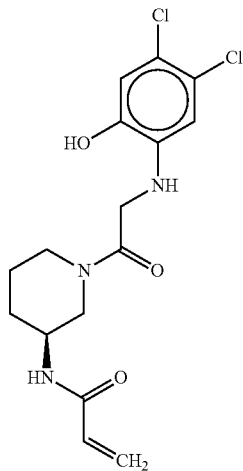 |
| 68 | 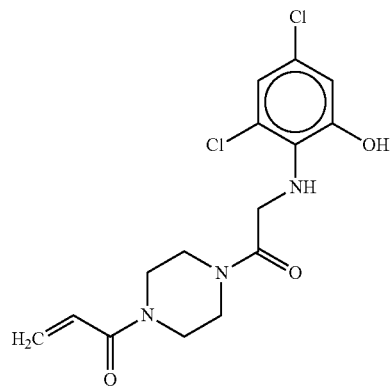 |

TABLE 1-continued
| Compound Number I- | Structure |
|---|---|
| 69 | 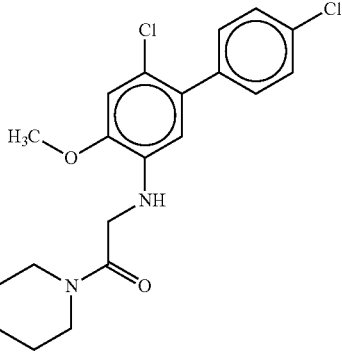 |
| 70 | 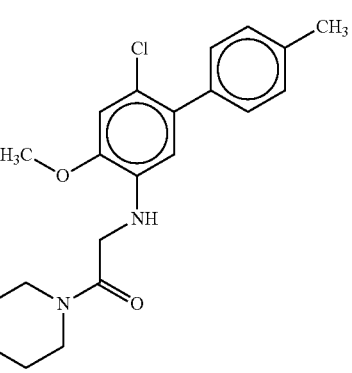 |
| 71 | 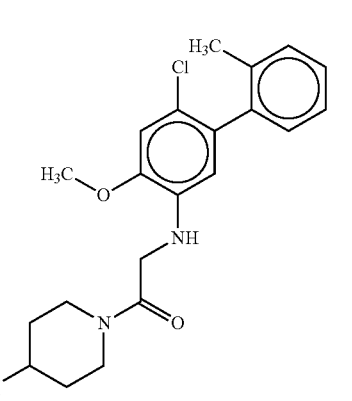 |
| 72 | 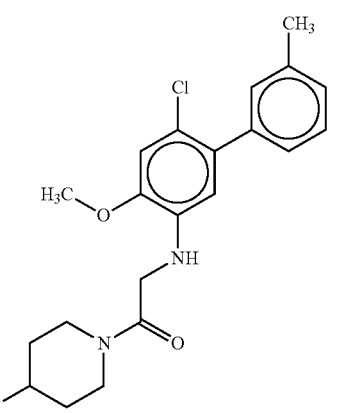 |

TABLE 1-continued
| Compound Number I- | Structure |
|---|---|
| 73 | 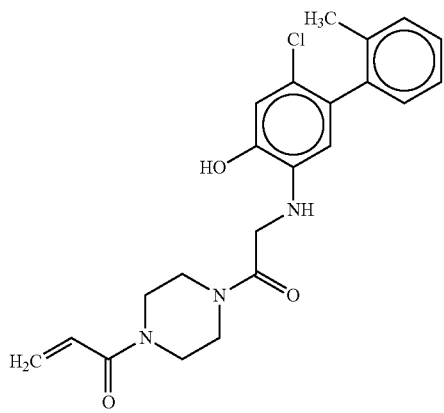 |
| 74 | 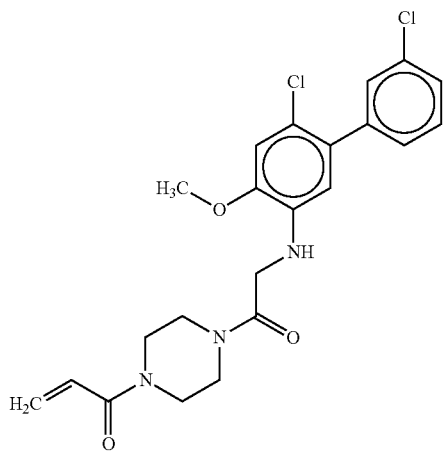 |
| 75 | 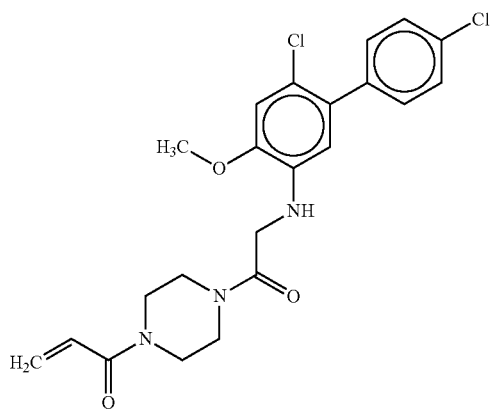 |

TABLE 1-continued
| Compound Number I- | Structure |
|---|---|
| 76 | 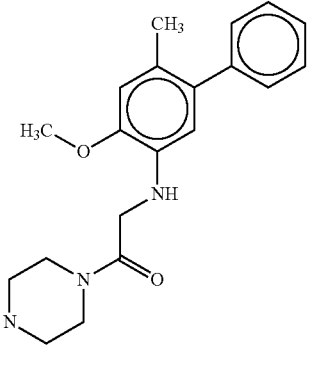 |
| 77 | 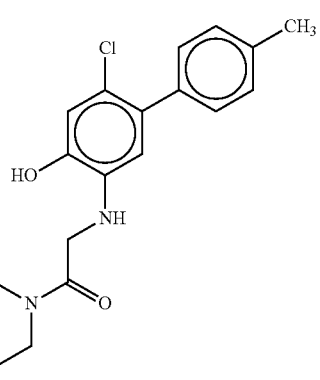 |
| 78 | 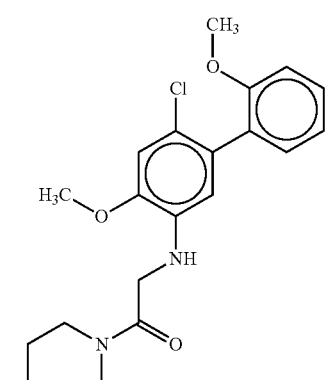 |
| 79 | 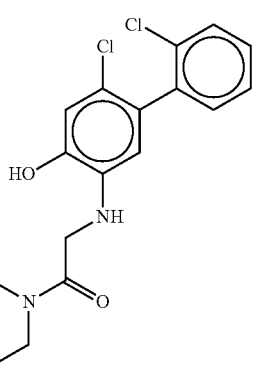 |

TABLE 1-continued
| Compound Number I- | Structure |
|---|---|
| 80 | 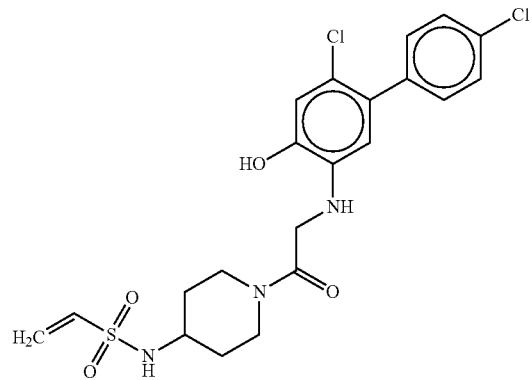 |
| 81 | 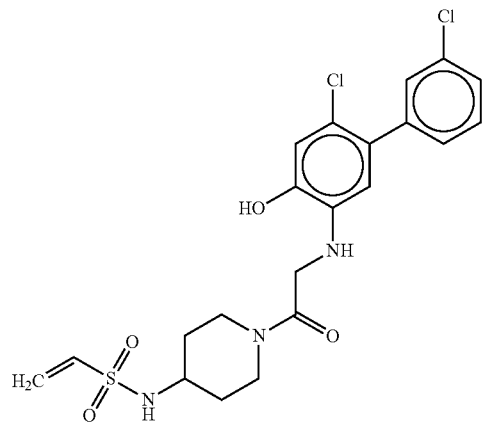 |
| 82 | 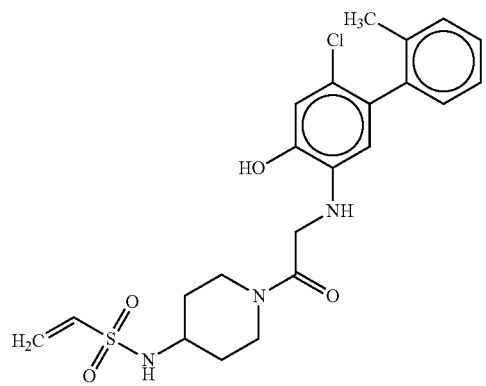 |

TABLE 1-continued
| Compound Number I- | Structure |
|---|---|
| 83 | 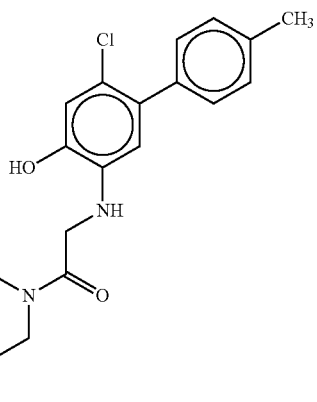 |
| 84 | 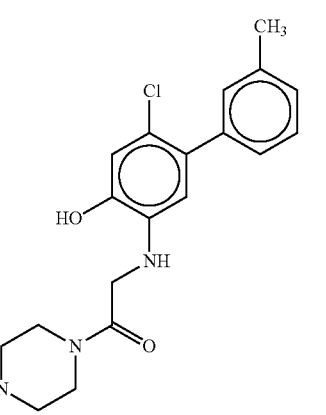 |
| 85 | 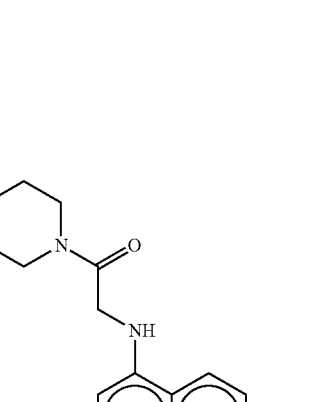 |
| 86 | 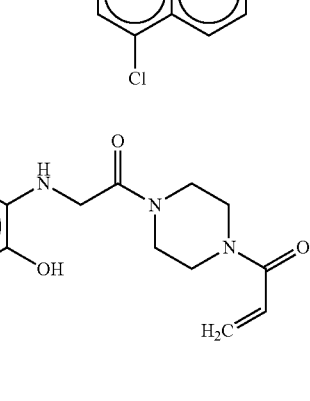 |

TABLE 1-continued

| Compound Number I- | Structure |
|---|---|
| 87 | *(structure image)* |
| 88 | *(structure image)* |
| 89 | *(structure image)* |
| 90 | *(structure image)* |
| 91 | *(structure image)* |
| 92 | *(structure image)* |

TABLE 1-continued

| Compound Number I- | Structure |
|---|---|
| 93 | 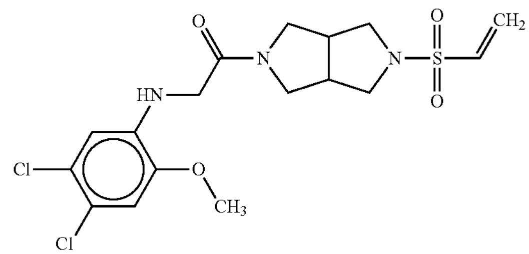 |
| 94 | 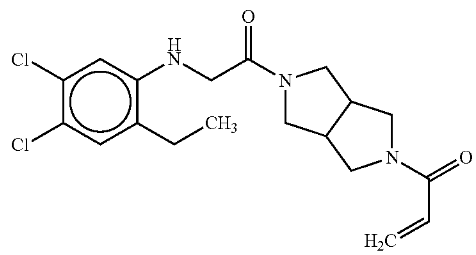 |
| 95 | 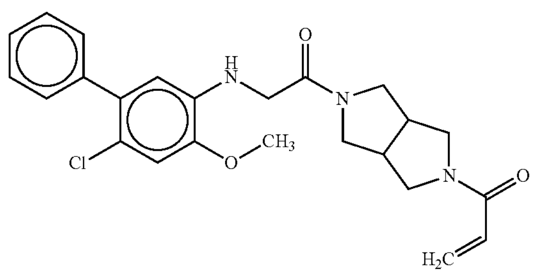 |
| 96 | 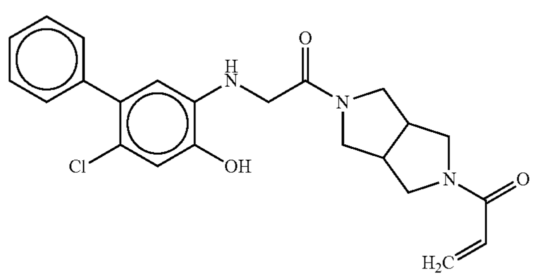 |
| 97 | 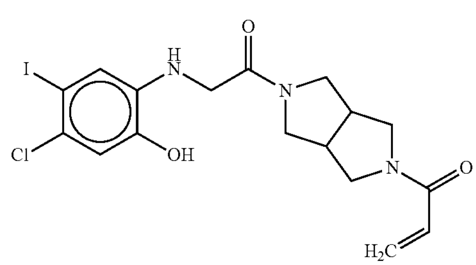 |
| 98 | 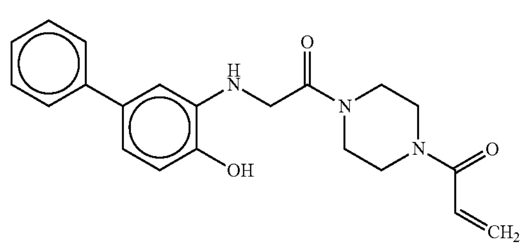 |

TABLE 1-continued

| Compound Number I- | Structure |
| --- | --- |
| 99 | 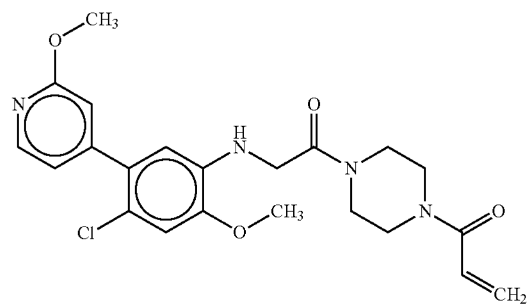 |
| 100 | 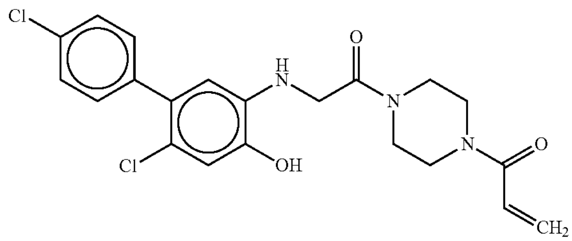 |
| 101 | 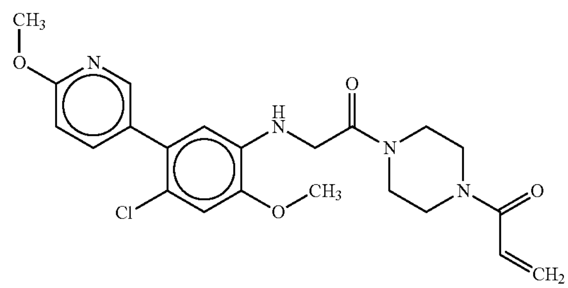 |
| 102 | 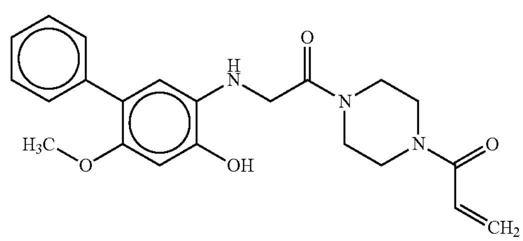 |
| 103 | 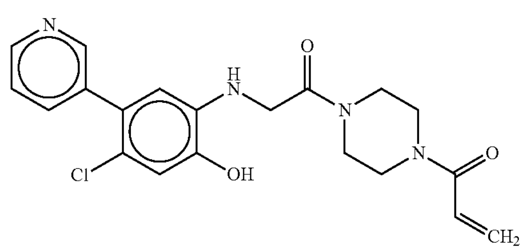 |
| 104 | 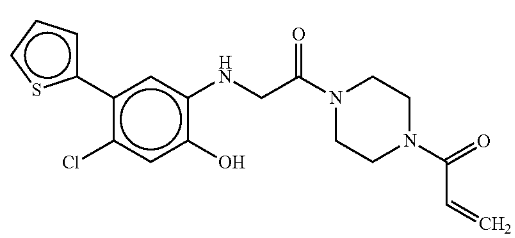 |

TABLE 1-continued
| Compound Number I- | Structure |
|---|---|
| 105 | 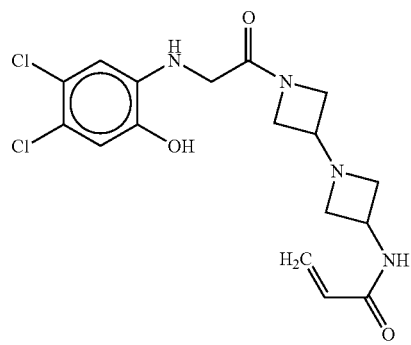 |
| 106 | 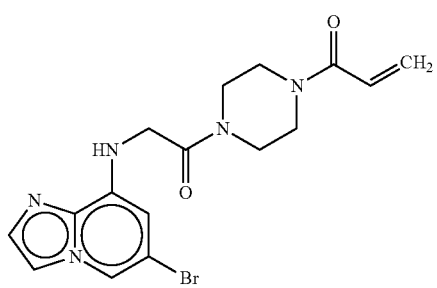 |
| 107 | 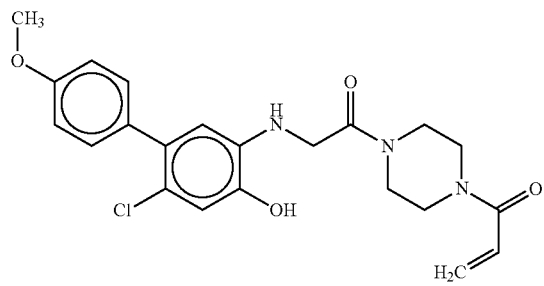 |
| 108 | 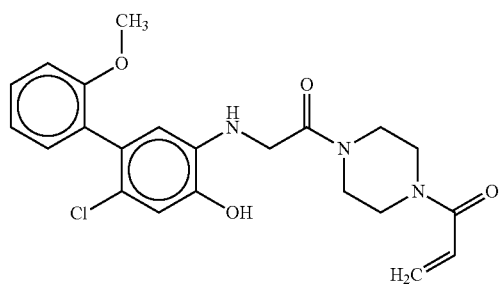 |
| 109 | 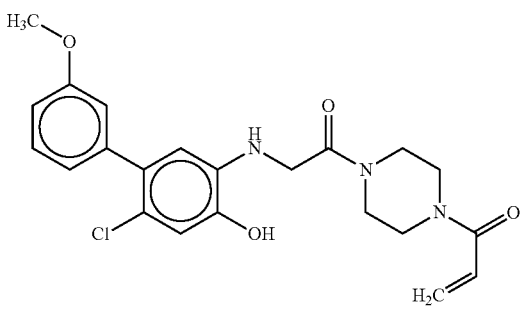 |

TABLE 1-continued
| Compound Number I- | Structure |
|---|---|
| 110 | 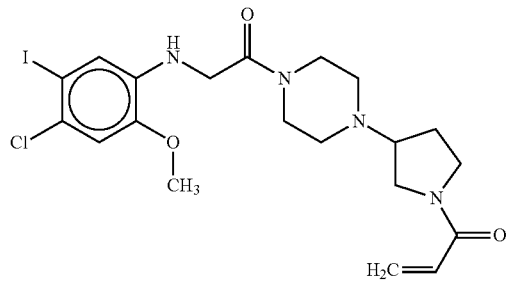 |
| 111 | 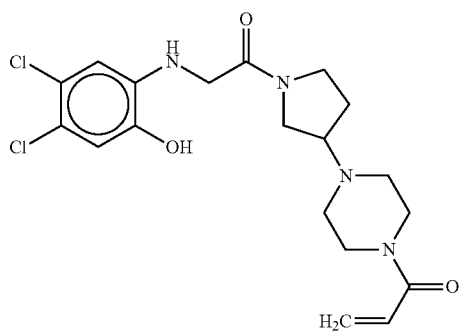 |
| 112 | 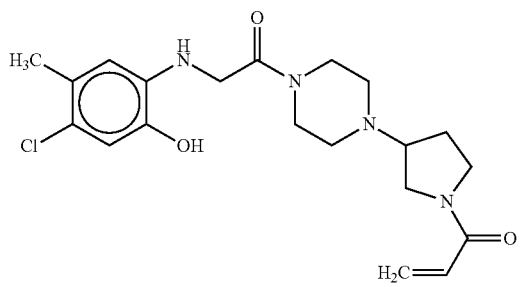 |
| 113 | 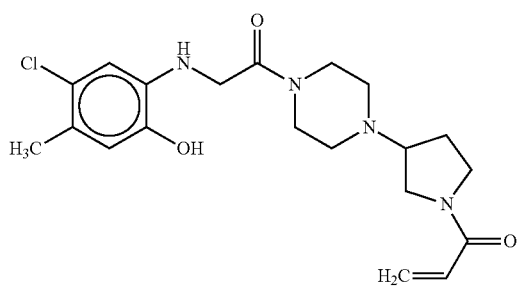 |
| 114 | 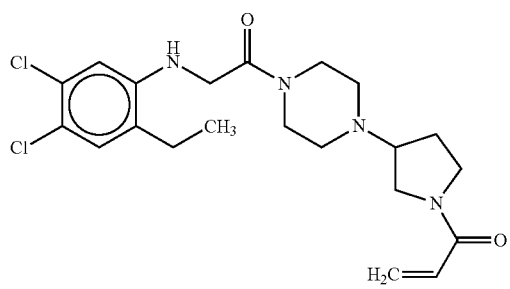 |

TABLE 1-continued
| Compound Number I- | Structure |
|---|---|
| 115 | 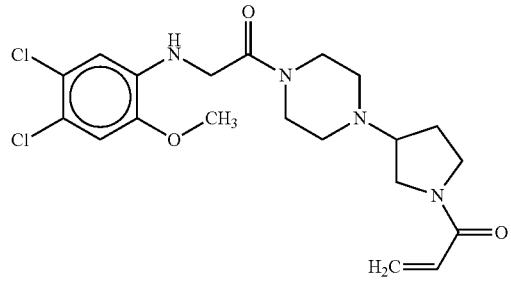 |
| 116 | 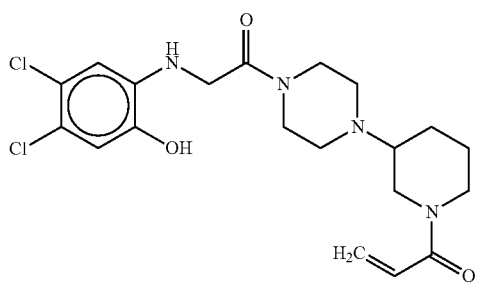 |
| 117 | 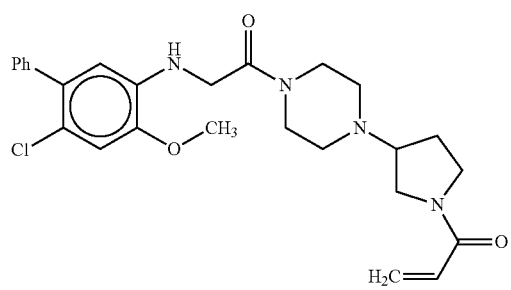 |
| 118 | 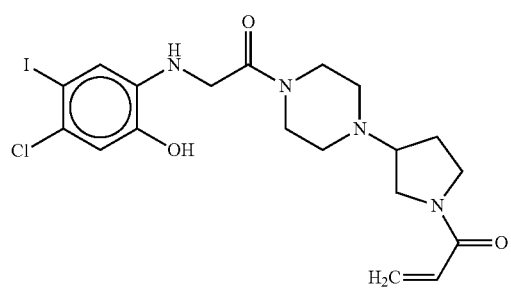 |
| 119 | 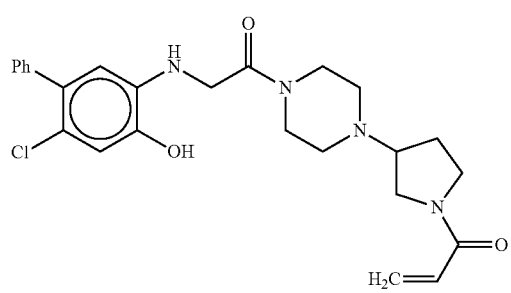 |

TABLE 1-continued
| Compound Number I- | Structure |
|---|---|
| 120 | 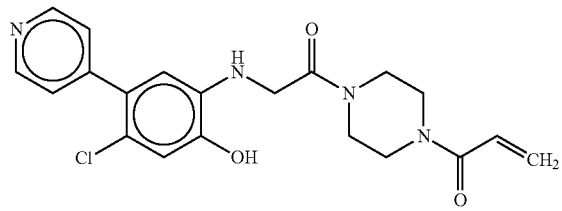 |
| 121 | 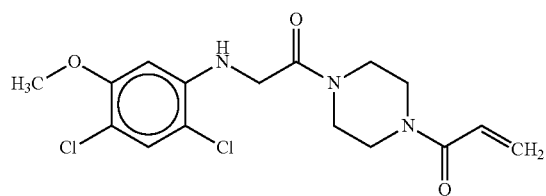 |
| 122 | 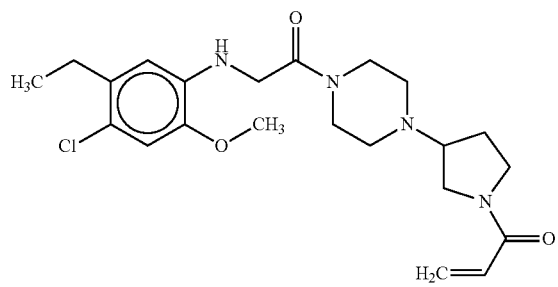 |
| 123 | 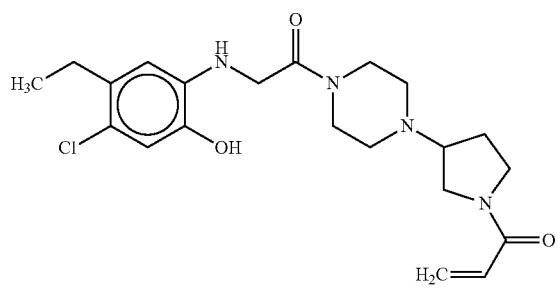 |
| 124 | 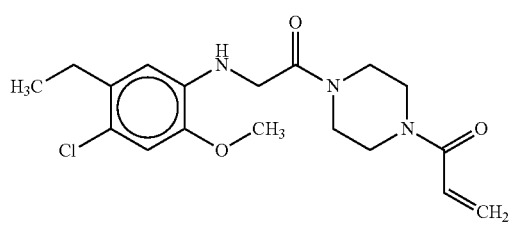 |
| 125 | 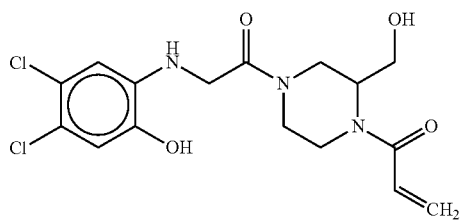 |

TABLE 1-continued

| Compound Number I- | Structure |
|---|---|
| 126 | 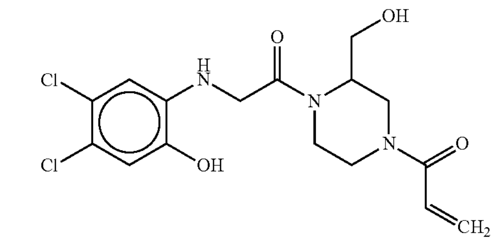 |
| 127 | 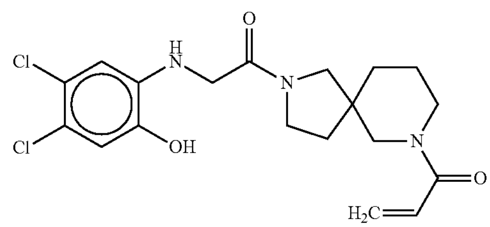 |
| 128 | 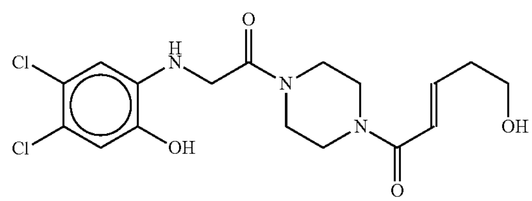 |
| 129 | 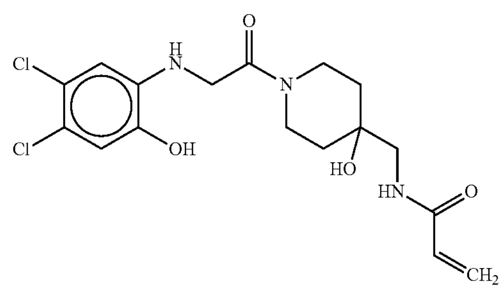 |
| 130 | 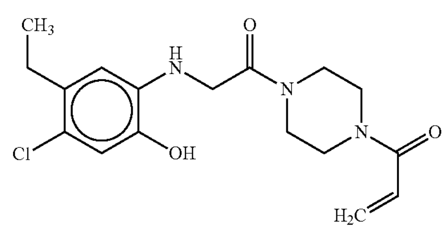 |
| 131 | 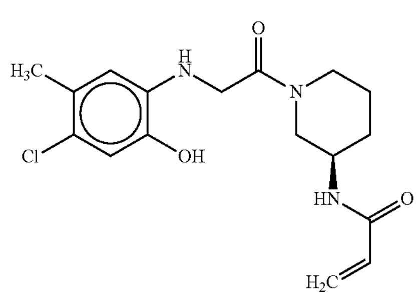 |

TABLE 1-continued
| Compound Number I- | Structure |
|---|---|
| 132 | 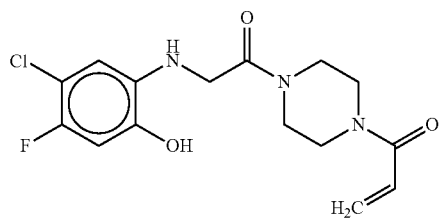 |
| 133 | 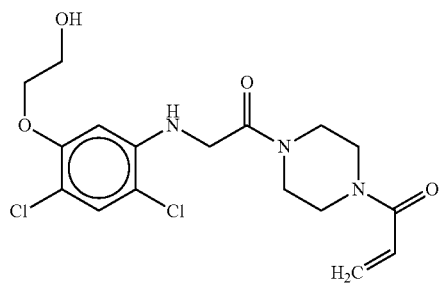 |
| 134 | 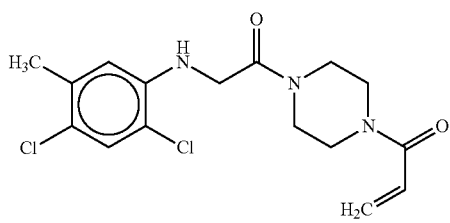 |
| 135 | 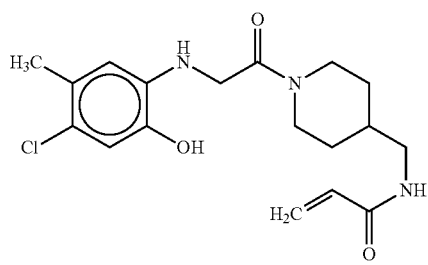 |
| 136 | 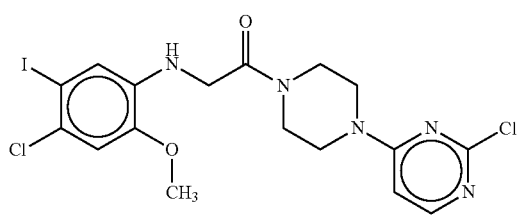 |
| 137 | 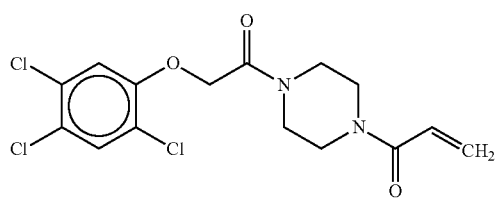 |

TABLE 1-continued
| Compound Number I- | Structure |
|---|---|
| 138 | 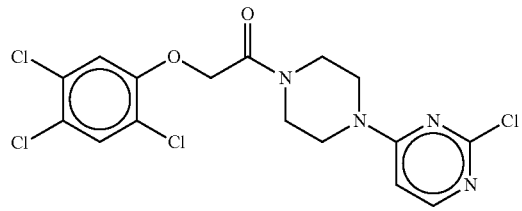 |
| 139 | 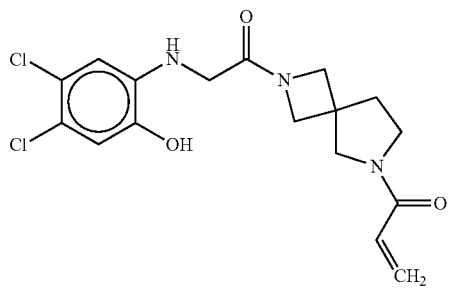 |
| 140 | 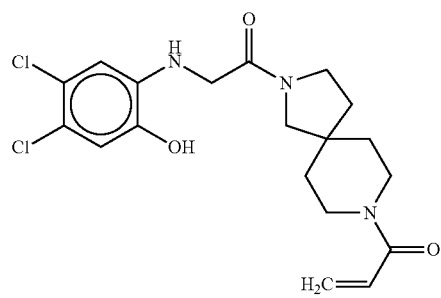 |
| 141 | 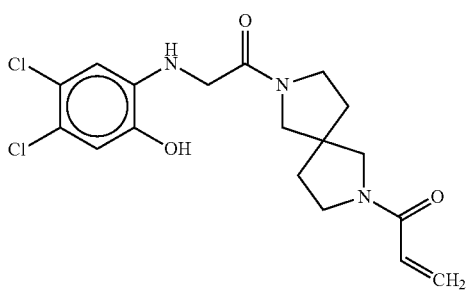 |
| 142 | 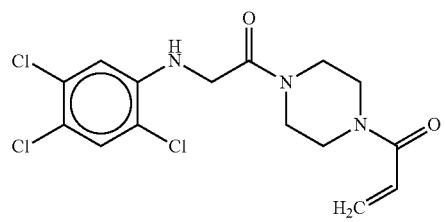 |
| 143 | 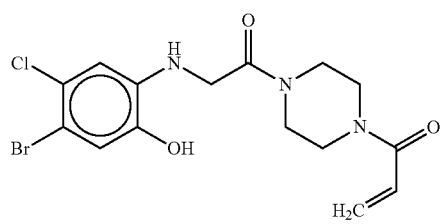 |

TABLE 1-continued

| Compound Number I- | Structure |
|---|---|
| 144 | 5-chloro-4-iodo-2-hydroxyphenyl aminoacetyl piperazine acrylamide |
| 145 | 4,5-dichloro-2-(hydroxymethyl)phenyl aminoacetyl piperazine acrylamide |
| 146 | 5-trifluoromethyl-4-chloro-2-hydroxyphenyl aminoacetyl piperazine acrylamide |
| 147 | 3'-fluoro-4-chloro-6-methoxy-biphenyl aminoacetyl piperazine acrylamide |
| 148 | 4'-fluoro-4-chloro-6-hydroxy-biphenyl aminoacetyl piperazine acrylamide |
| 149 | 4'-cyano-4-chloro-6-hydroxy-biphenyl aminoacetyl piperazine acrylamide |

TABLE 1-continued
| Compound Number I- | Structure |
|---|---|
| 150 | 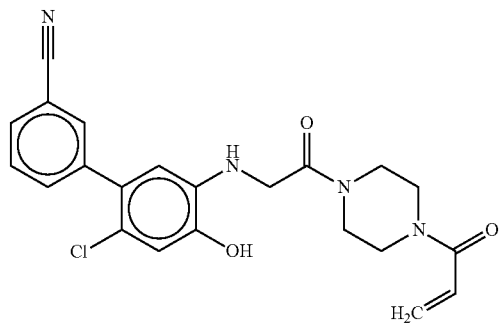 |
| 151 | 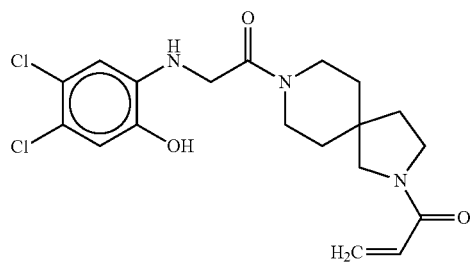 |
| 152 | 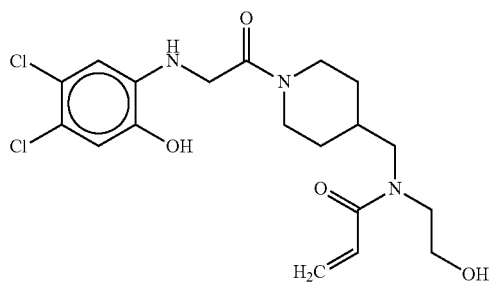 |
| 153 | 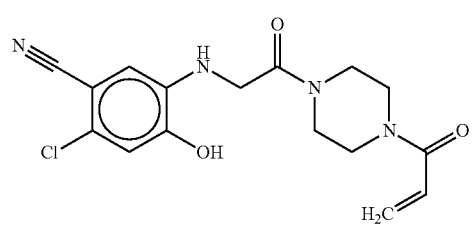 |
| 154 | 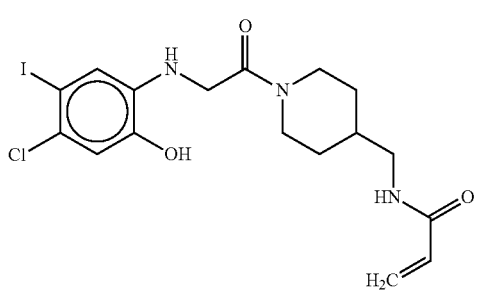 |

TABLE 1-continued

| Compound Number I- | Structure |
|---|---|
| 155 | 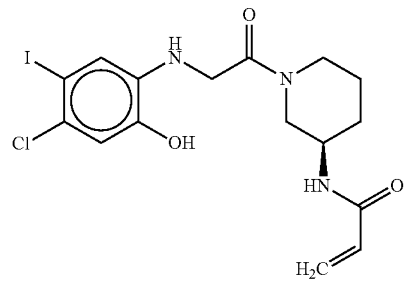 |
| 156 | 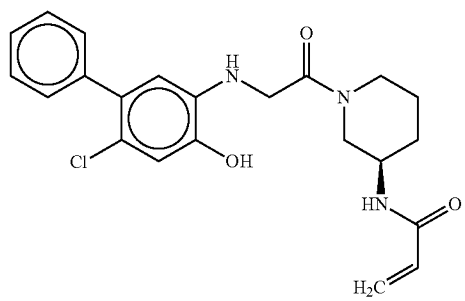 |
| 157 | 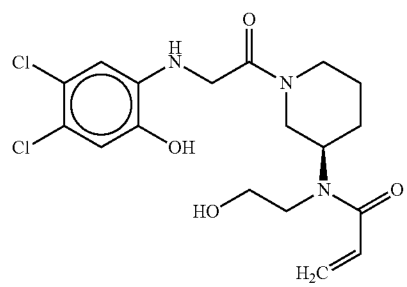 |
| 158 | 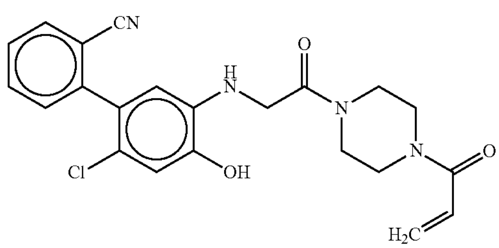 |
| 159 | 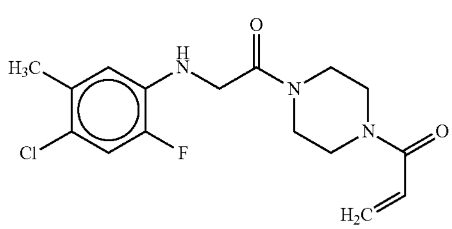 |
| 160 | 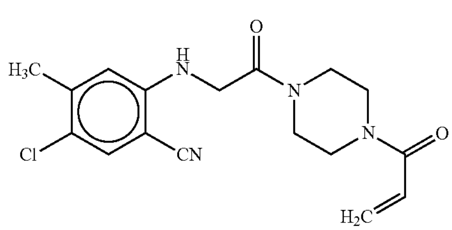 |

TABLE 1-continued

| Compound Number I- | Structure |
|---|---|
| 161 | 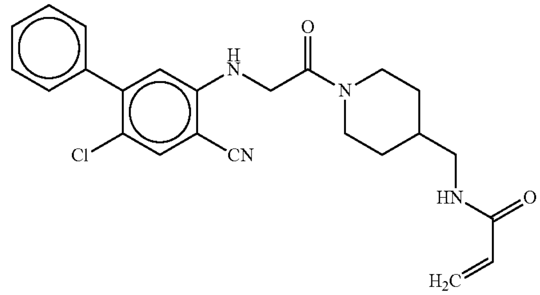 |
| 162 | 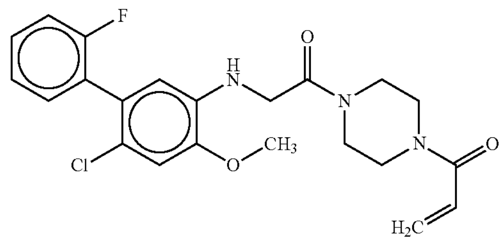 |
| 163 | 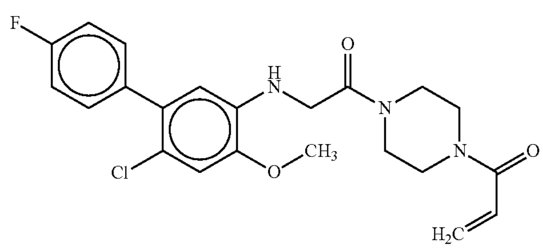 |
| 164 | 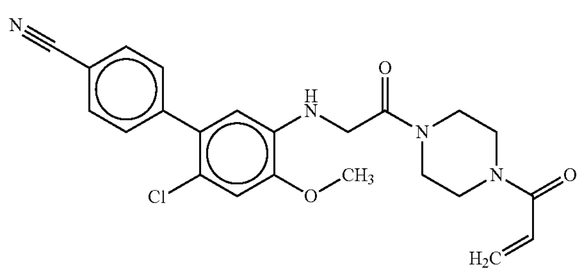 |
| 165 | 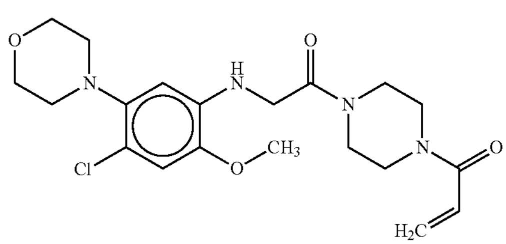 |
| 166 | 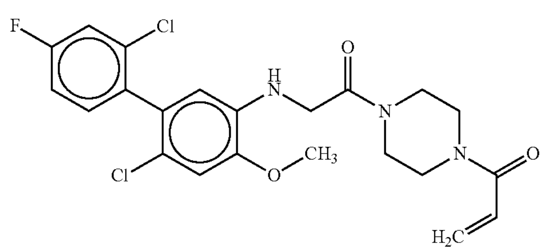 |

TABLE 1-continued
| Compound Number I- | Structure |
|---|---|
| 167 | 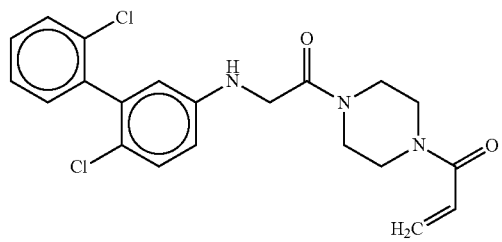 |
| 168 | 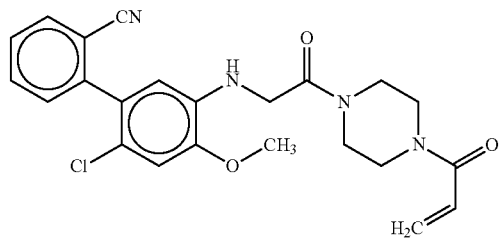 |
| 169 | 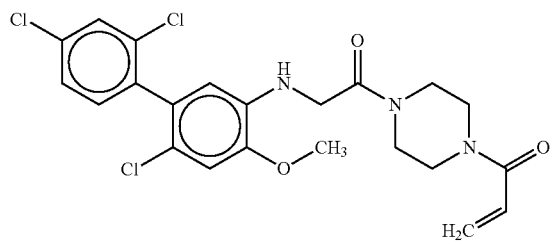 |
| 170 | 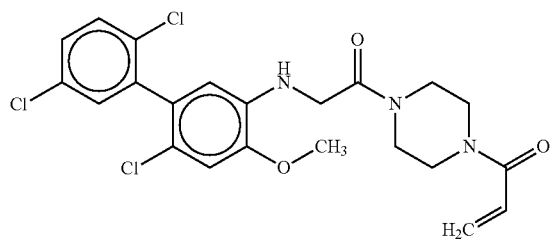 |
| 171 | 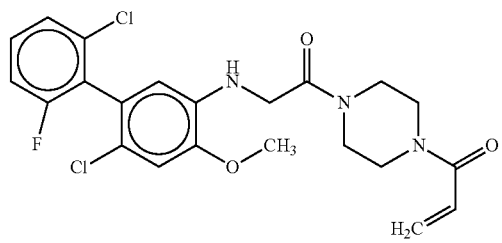 |
| 172 | 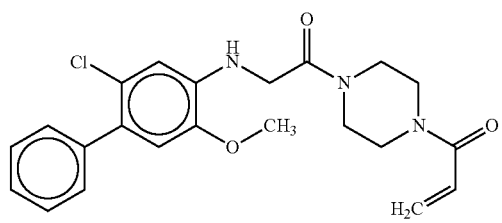 |

TABLE 1-continued
| Compound Number I- | Structure |
|---|---|
| 173 | 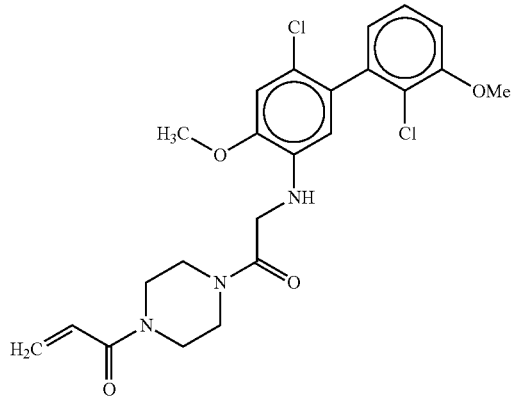 |
| 174 | 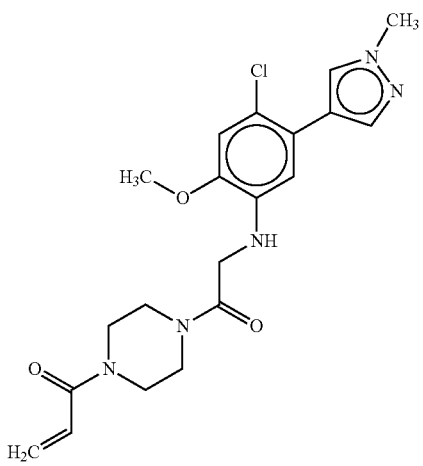 |
| 175 | 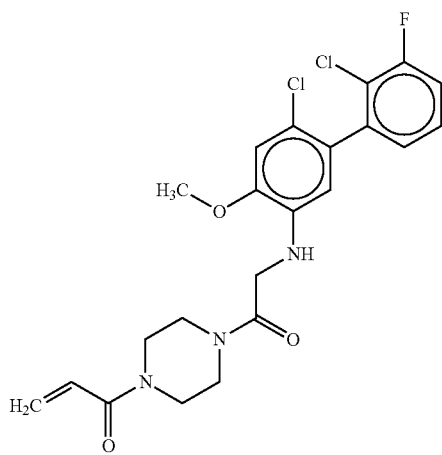 |
| 176 | 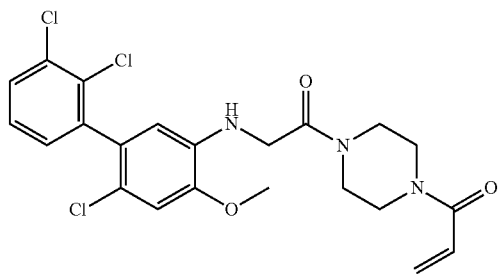 [SMILES: C=CC(=O)N1CCN(C(=O)CNc2cc(-c3cccc(Cl)c3Cl)c(Cl)cc2OC)CC1] |

TABLE 1-continued
| Compound Number I- | Structure |
|---|---|
| 177 | 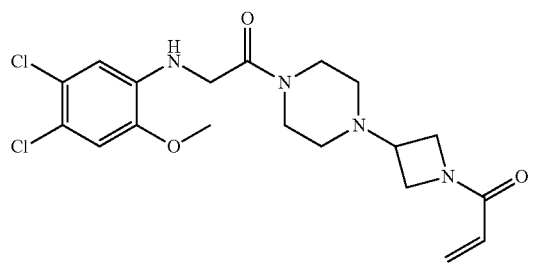 [SMILES: C=CC(=O)N1CC(N2CCN(C(=O)CNc3cc(Cl)c(Cl)cc3OC)CC2)C1] |
| 178 | 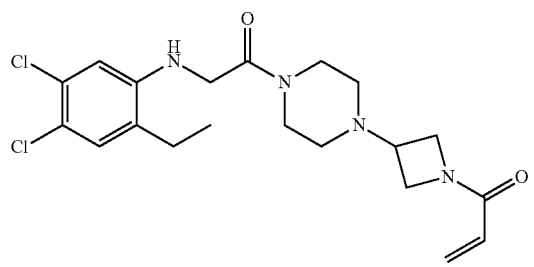 [SMILES: C=CC(=O)N1CC(N2CCN(C(=O)CNc3cc(Cl)c(Cl)cc3CC)CC2)C1] |
| 179 | 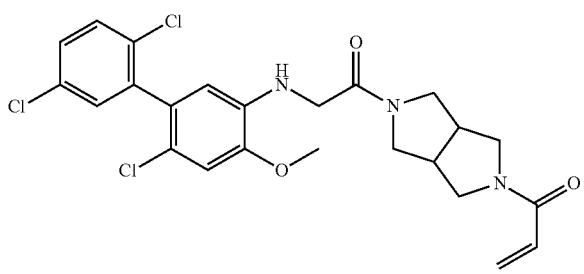 [SMILES: C=CC(=O)N1CC2CN(C(=O)CNc3cc(-c4cc(Cl)ccc4Cl)c(Cl)cc3OC)CC2C1] |
| 180 | 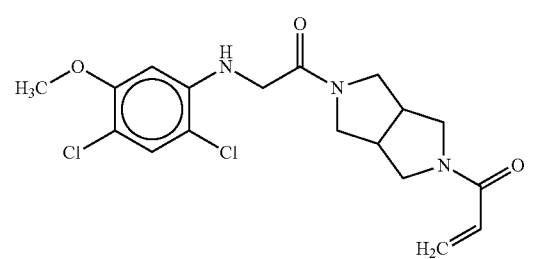 |
| 181 | 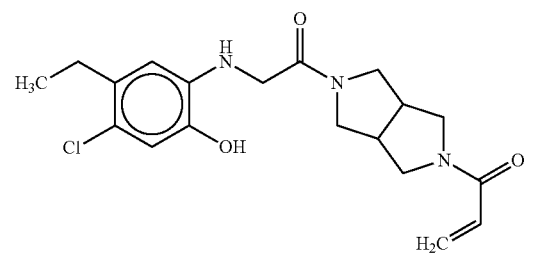 |

TABLE 1-continued
| Compound Number I- | Structure |
|---|---|
| 182 | 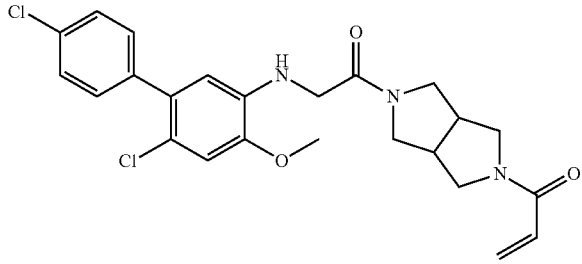 [SMILES: C=CC(=O)N1CC2CN(C(=O)CNc3cc(-c4ccc(Cl)cc4)c(Cl)cc3OC)CC2C1] |
| 183 | 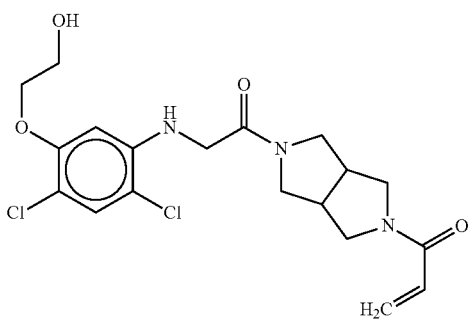 |
| 184 | 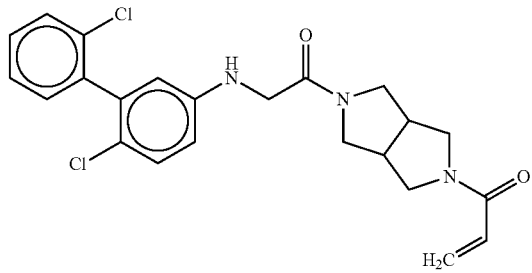 |
| 185 | 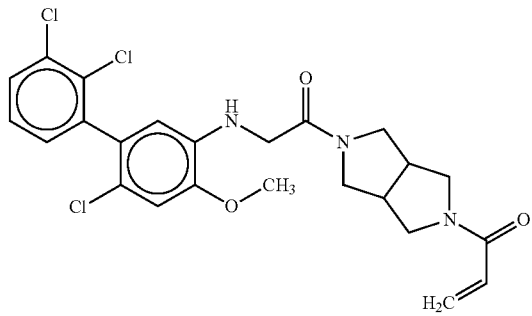 |
| 186 | 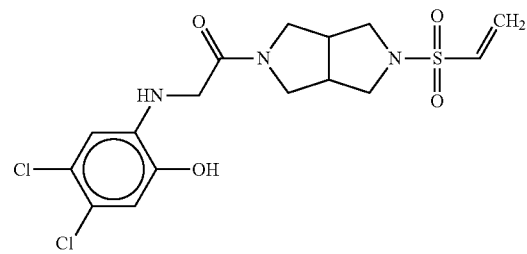 |

TABLE 1-continued
| Compound Number I- | Structure |
|---|---|
| 187 | 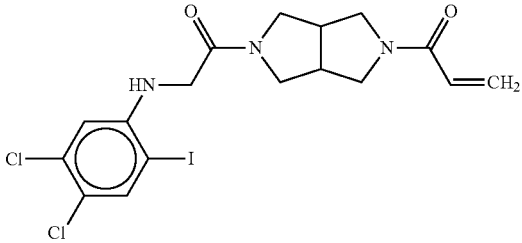 |
| 188 | 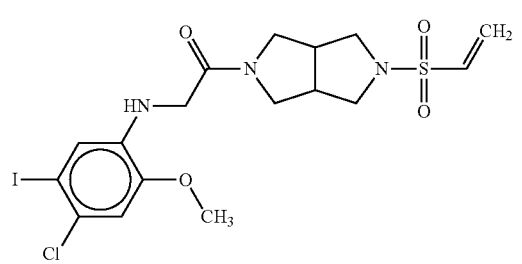 |
| 189 | 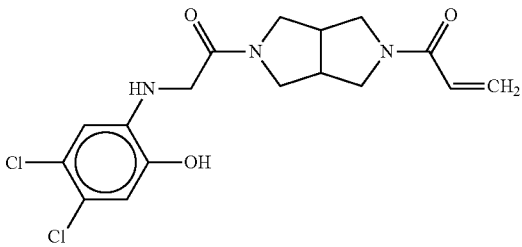 |
| 190 | 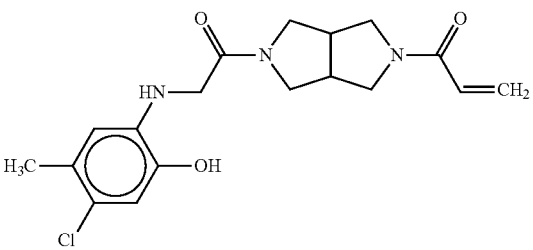 |
| 191 | 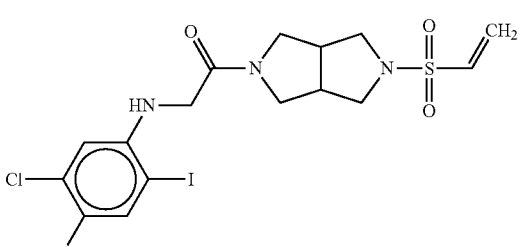 |
| 192 | 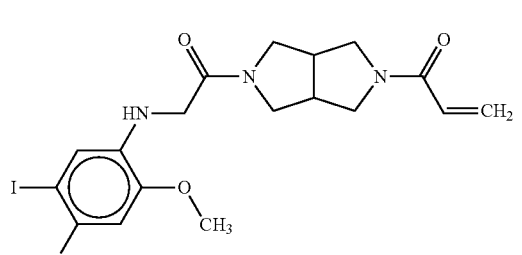 |

TABLE 1-continued
| Compound Number I- | Structure |
|---|---|
| 193 | 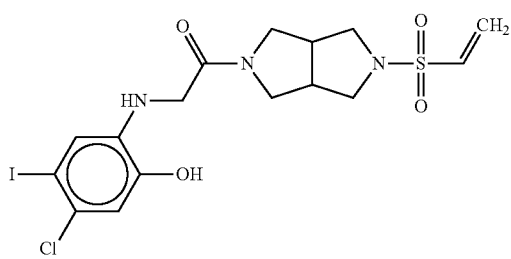 |
| 194 | 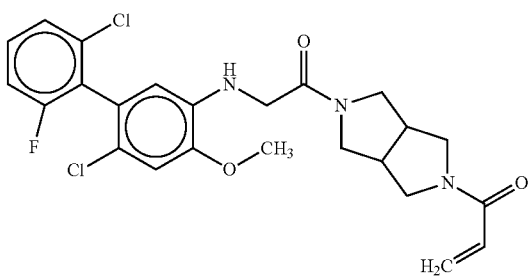 |
| 195 | 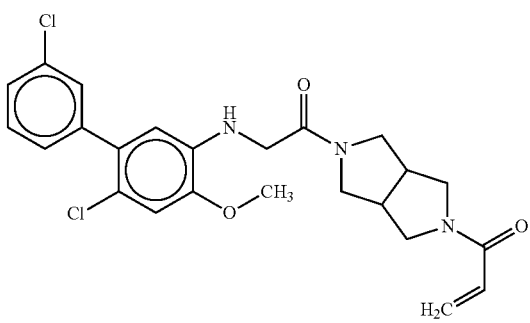 |
| 196 | 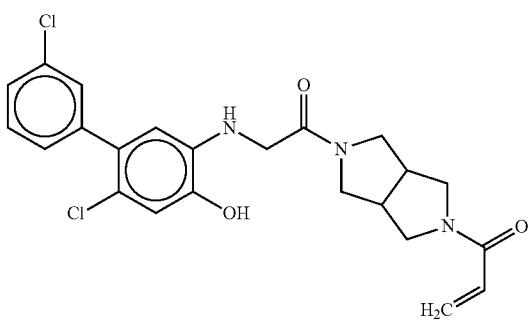 |
| 197 | 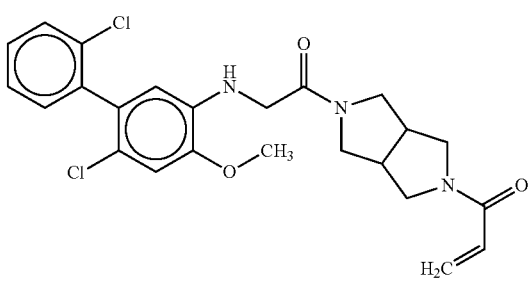 |

TABLE 1-continued
| Compound Number I- | Structure |
|---|---|
| 198 | 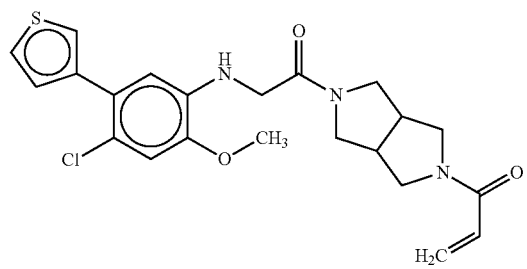 |
| 199 | 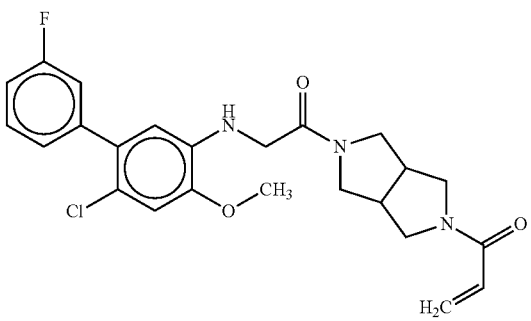 |
| 200 | 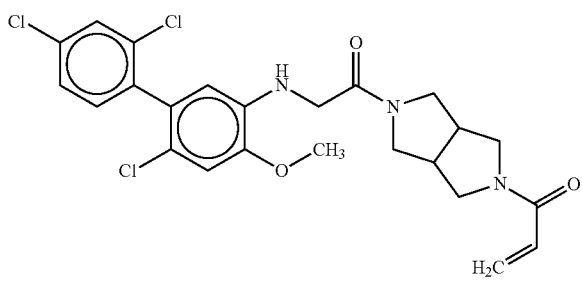 |
| 201 | 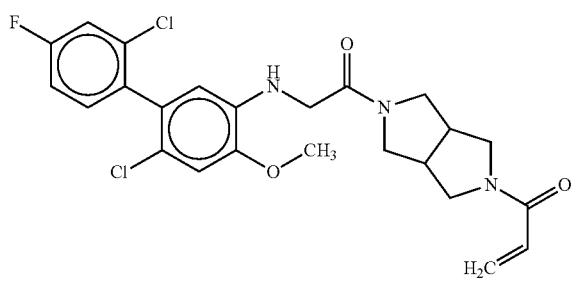 |
| 202 | 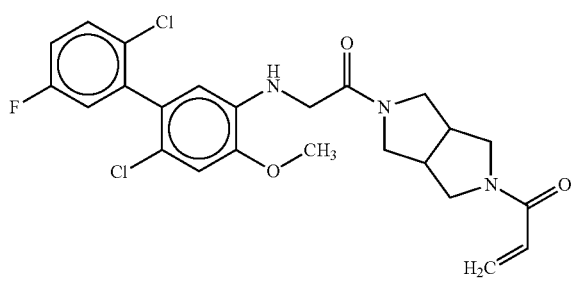 |

TABLE 1-continued
| Compound Number I- | Structure |
|---|---|
| 203 | 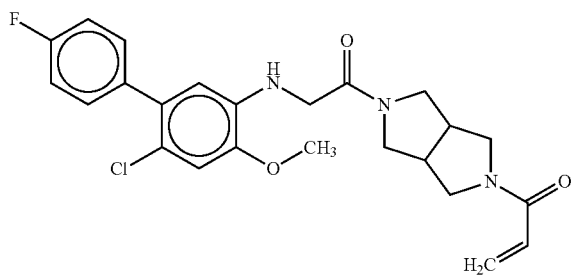 |
| 204 | 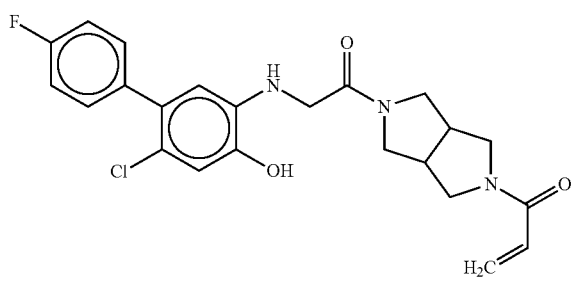 |
| 205 | 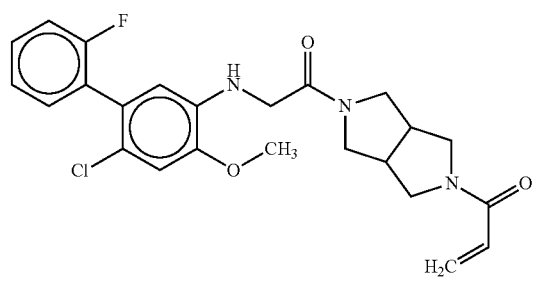 |
| 206 | 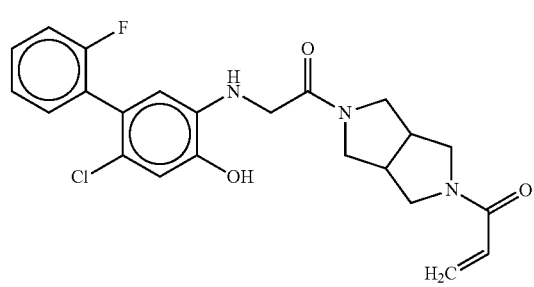 |
| 207 | 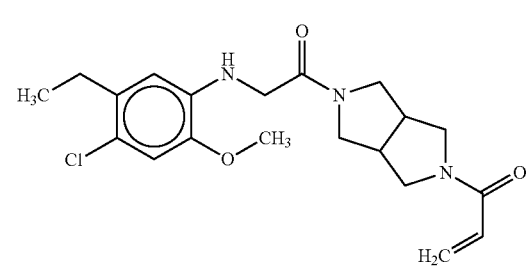 |

TABLE 1-continued
| Compound Number I- | Structure |
|---|---|
| 208 | 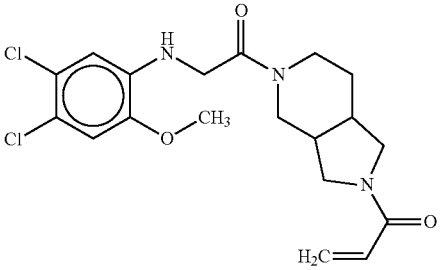 |
| 209 | 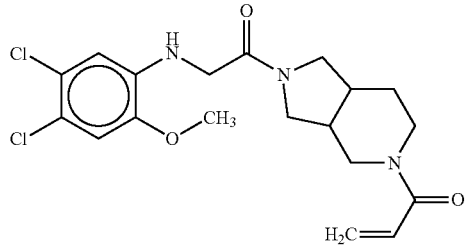 |
| 210 | 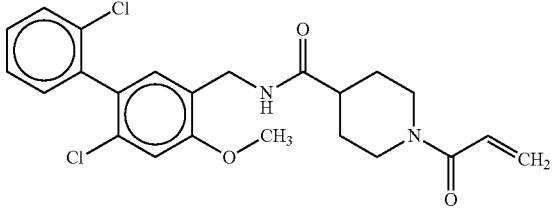 |
| 211 | 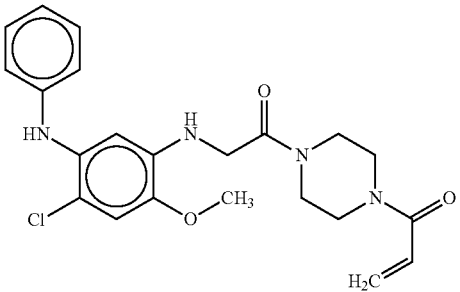 |
| 212 | 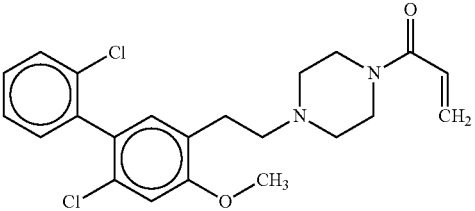 |
| 213 | 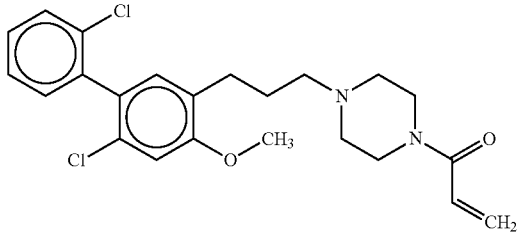 |

TABLE 1-continued
| Compound Number I- | Structure |
|---|---|
| 214 | 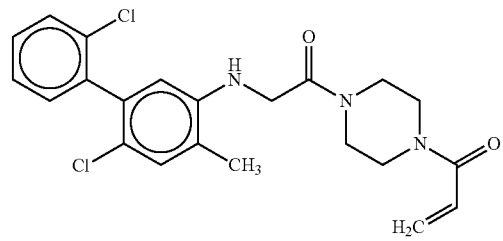 |
| 215 | 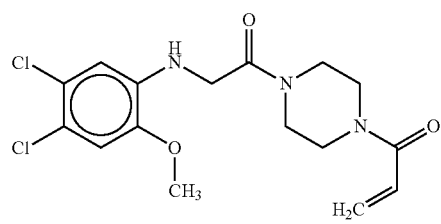 |
| 216 | 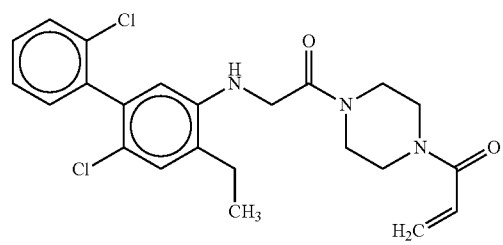 |
| 217 | 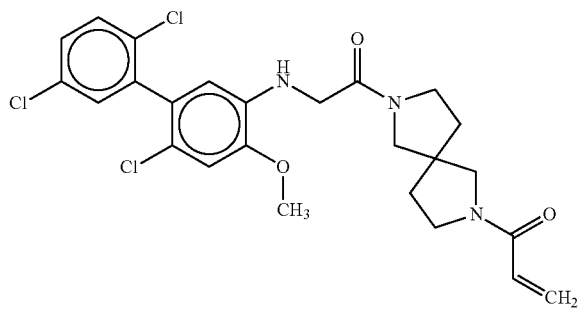 |
| 218 | 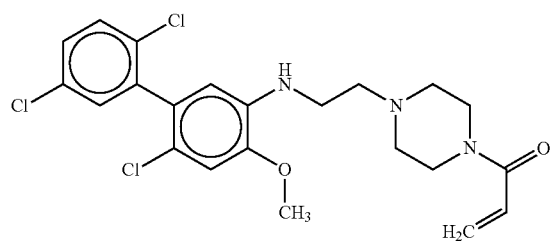 |
| 219 | 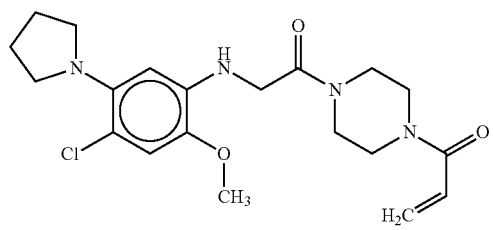 |

TABLE 1-continued
| Compound Number I- | Structure |
|---|---|
| 220 | 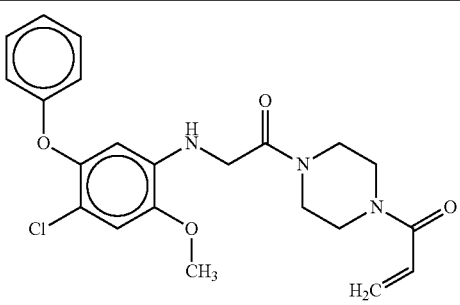 |
| 221 | 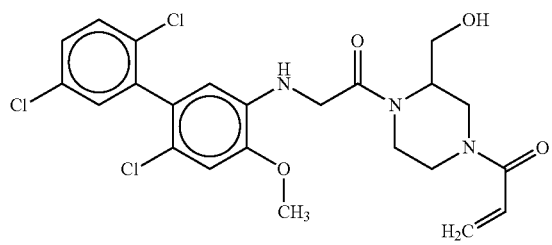 |
| 222 | 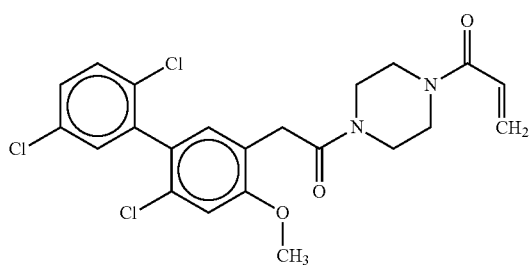 |
| 223 | 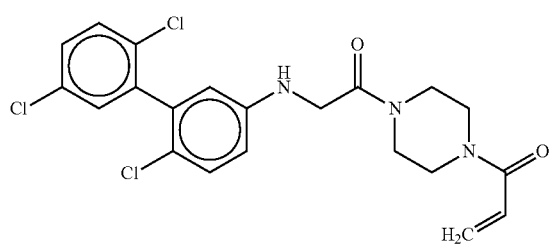 |
| 224 | 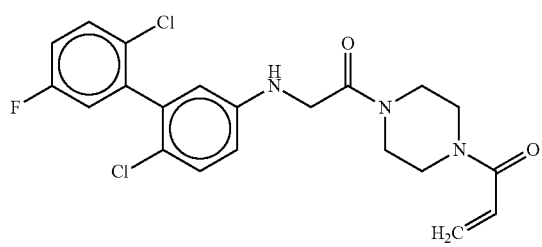 |
| 225 | 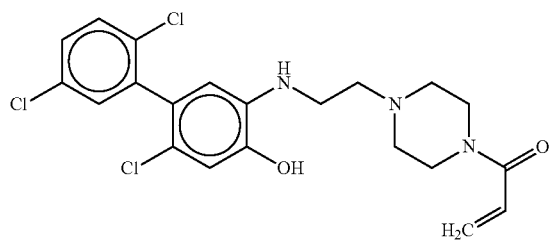 |

TABLE 1-continued
| Compound Number I- | Structure |
|---|---|
| 226 | 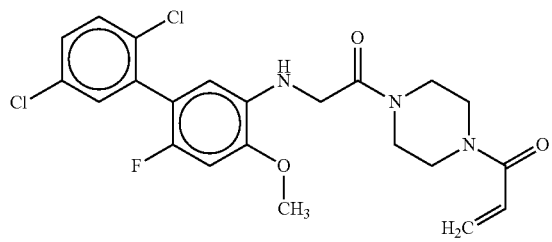 |
| 227 | 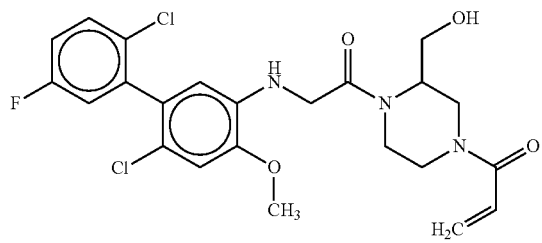 |
| 228 | 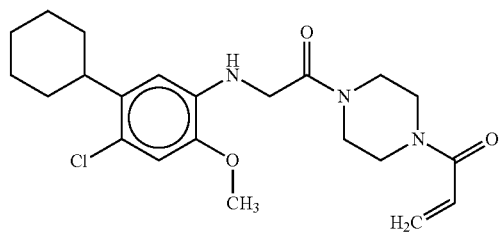 |
| 229 | 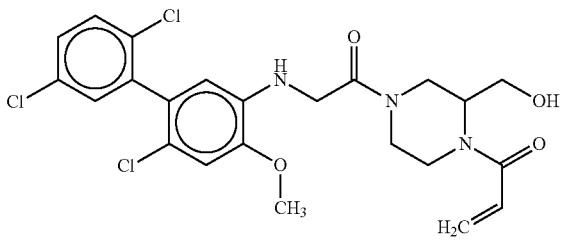 |
| 230 | 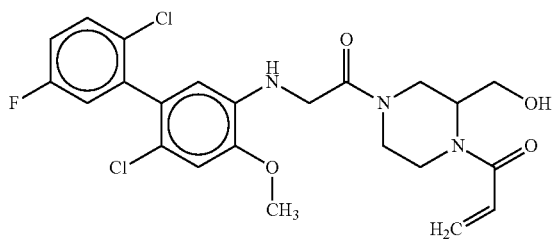 |
| 231 | 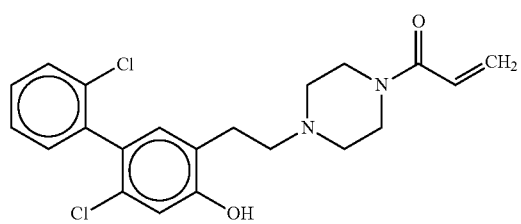 |

TABLE 1-continued
| Compound Number I- | Structure |
|---|---|
| 232 | 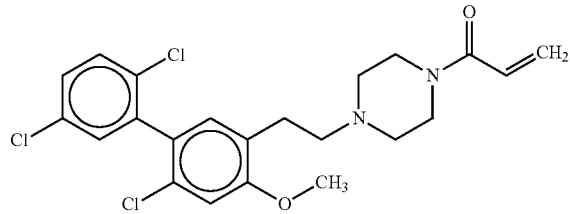 |
| 233 | 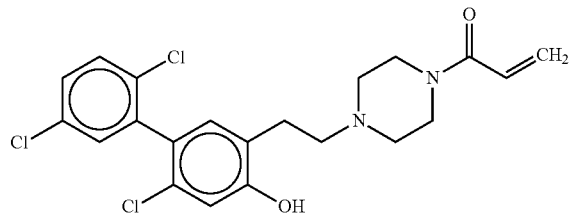 |
| 234 | 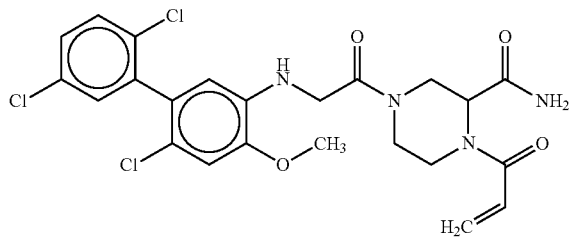 |
| 235 | 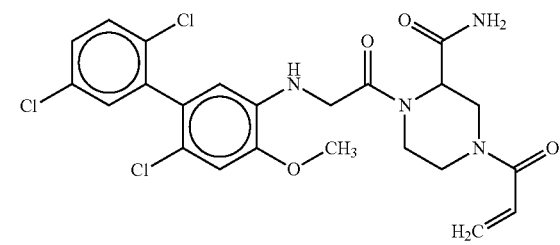 |
| 236 | 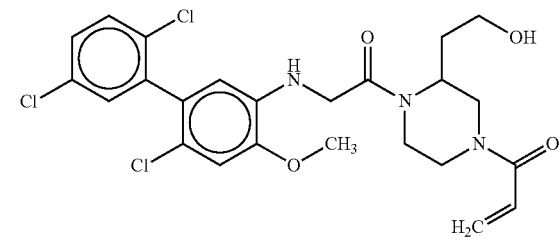 |
| 237 | 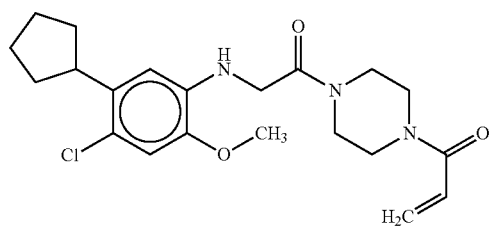 |

TABLE 1-continued
| Compound Number I- | Structure |
|---|---|
| 238 | 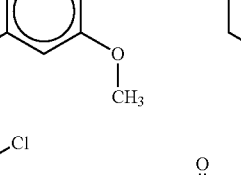 |
| 239 | 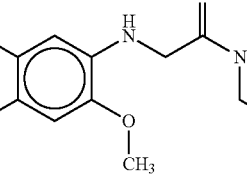 |
| 240 | 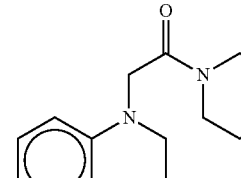 |
| 241 | 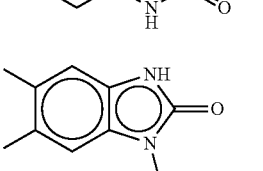 |
| 242 | 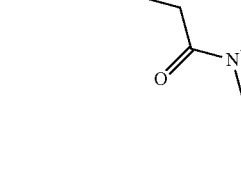 |
| 243 | 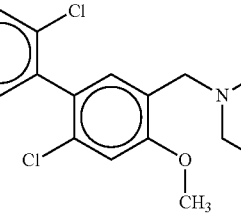 |

TABLE 1-continued
| Compound Number I- | Structure |
|---|---|
| 244 | 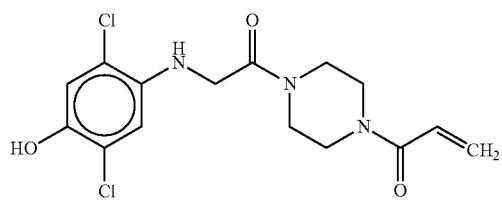 |
| 245 | 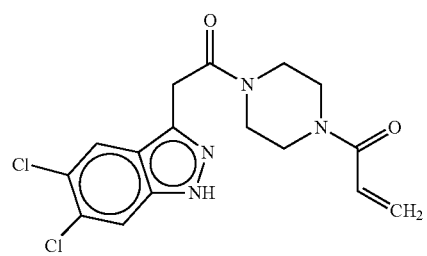 |
| 246 | 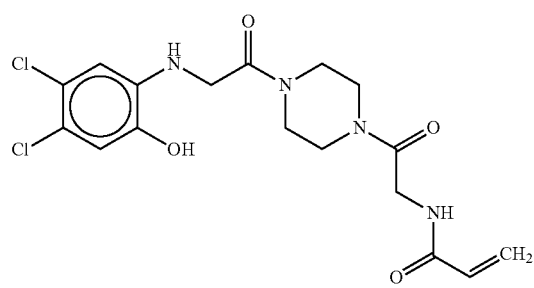 |
| 247 | 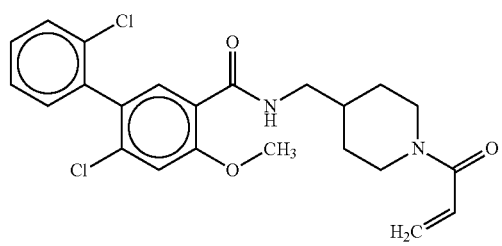 |
| 248 | 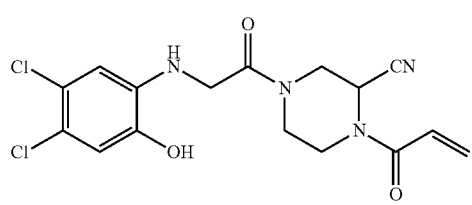 [SMILES: C=CC(=O)N1CCN(C(=O)CNc2cc(Cl)c(Cl)cc2O)CC1C#N] |

TABLE 2
| Compound Number (II-) | Structure |
|---|---|
| 1 | 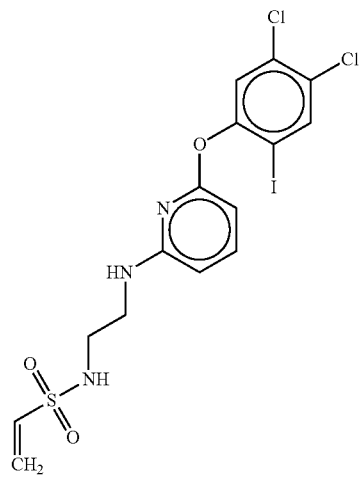 |
| 2 | 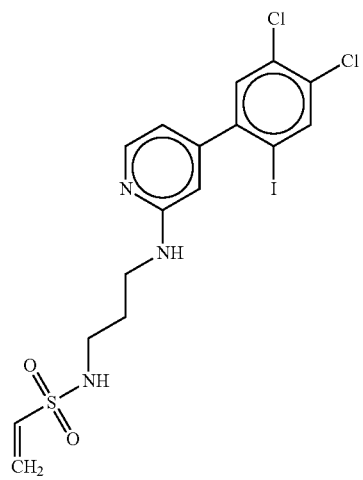 |
| 3 | 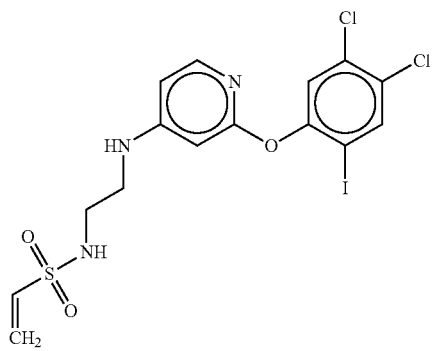 |

TABLE 2-continued

| Compound Number (II-) | Structure |
|---|---|
| 4 | 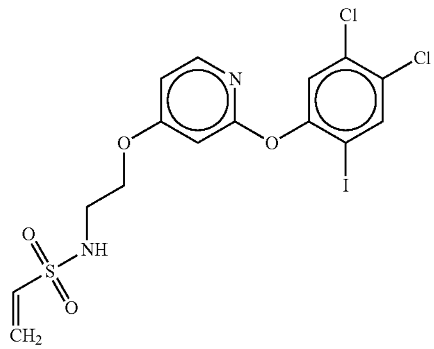 |
| 5 | 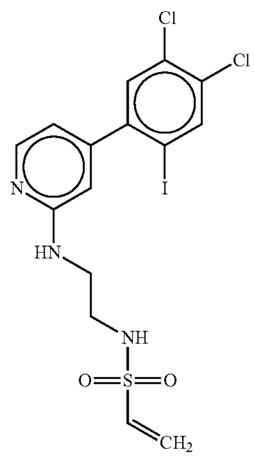 |
| 6 | 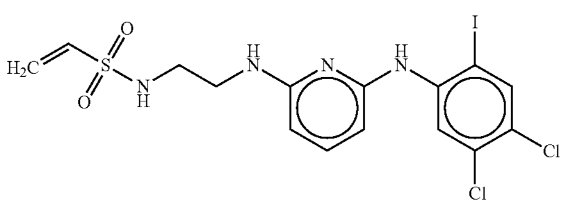 |
| 7 | 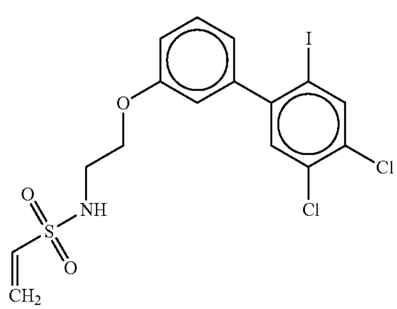 |
| 8 | 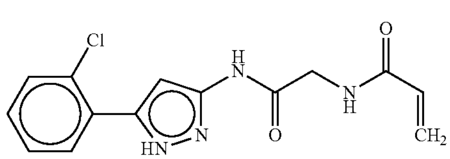 |

TABLE 3

| Compound Number (III-) | Structure |
| --- | --- |
| 1 | 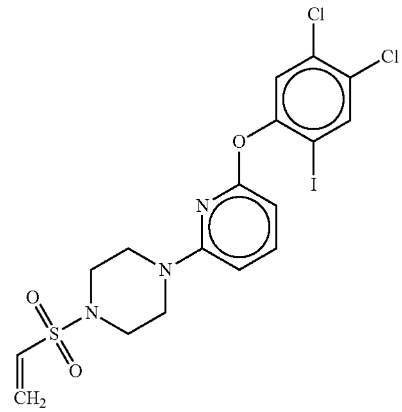 |
| 2 | 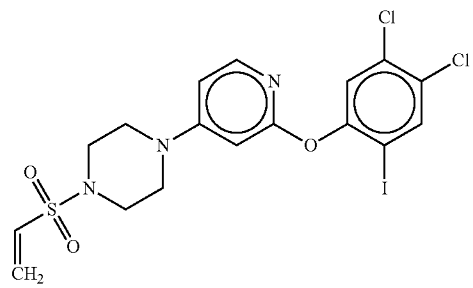 |
| 3 | 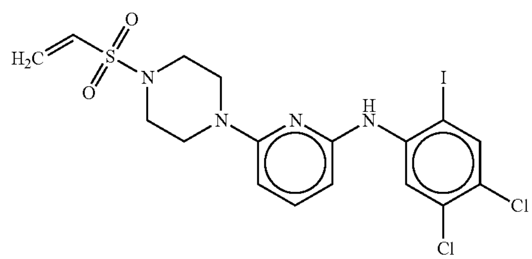 |
| 4 | 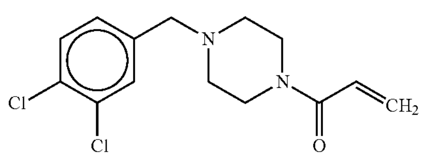 |
| 5 | 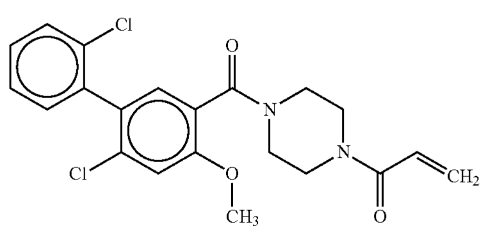 |
| 6 | 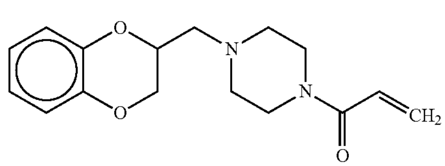 |

TABLE 3-continued
| Compound Number (III-) | Structure |
|---|---|
| 7 | 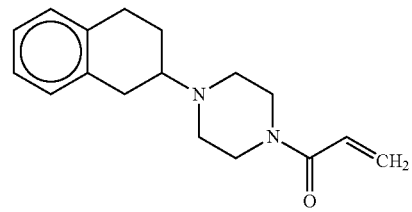 |
| 8 | 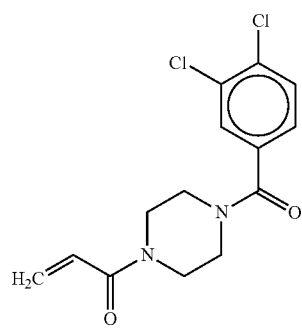 |
| 9 | 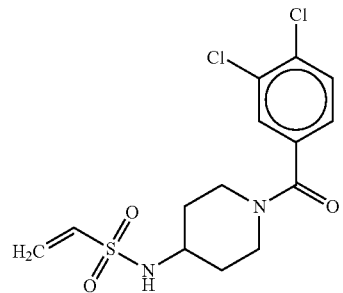 |
| 10 | 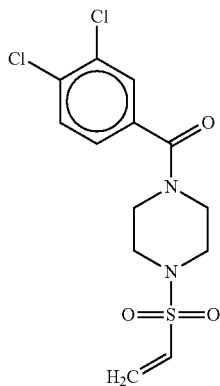 |

TABLE 3-continued

| Compound Number (III-) | Structure |
|---|---|
| 11 | 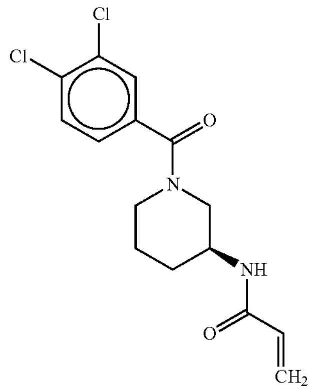 |
| 12 | 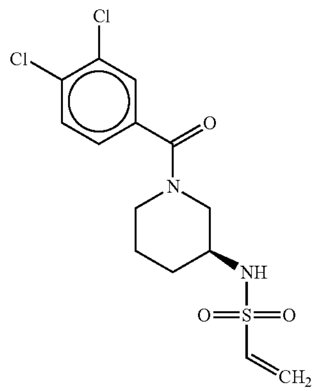 |
| 13 | 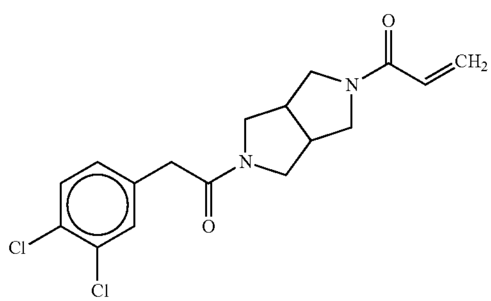 |
| 14 | 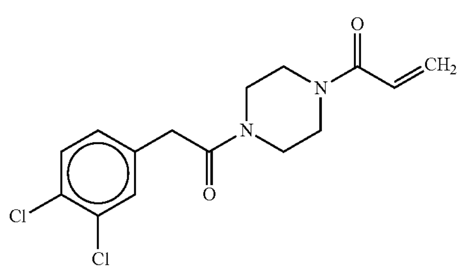 |
| 15 | 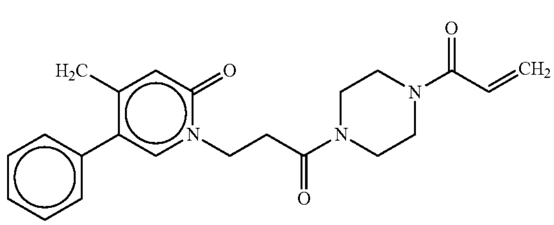 |

TABLE 3-continued

| Compound Number (III-) | Structure |
| --- | --- |
| 16 | 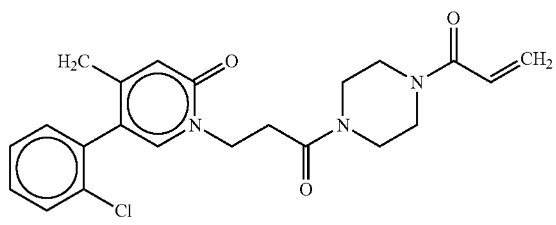 |
| 17 | 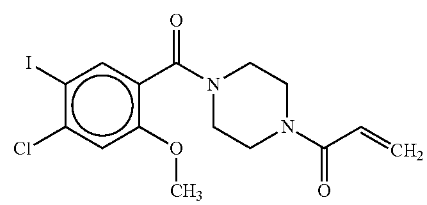 |
| 18 | 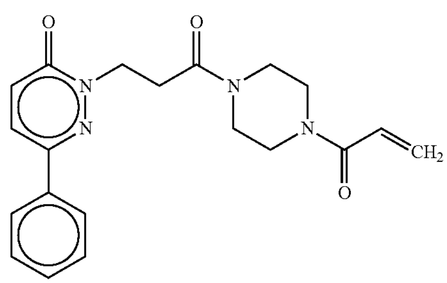 |
| 19 | 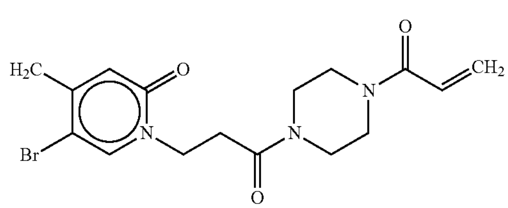 |
| 20 | 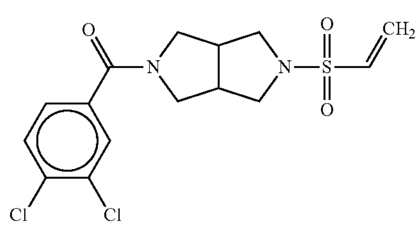 |
| 21 | 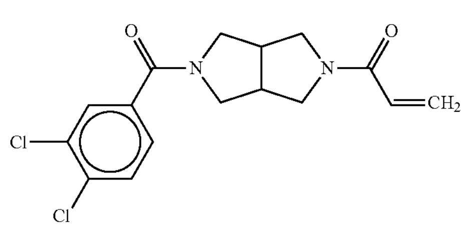 |

TABLE 3-continued

| Compound Number (III-) | Structure |
|---|---|
| 22 | *[Structure: piperazine with acryloyl group connected to pyrimidine bearing NH-C(=O)-(2-chlorophenyl) substituent]* |

TABLE 4

| Compound Number (IV-) | Structure |
|---|---|
| 1 | *[Structure: 1-hydroxy-4-chloronaphthalene-2-carboxamide linked via ethylenediamine to acrylamide]* |
| 2 | *[Structure: quinolin-8-yl amide of 1-acryloylpiperidine-4-carboxylic acid]* |
| 3 | *[Structure: 2-methylpyridin-4-yl amide of 1-acryloylpiperidine-4-carboxylic acid]* |
| 4 | *[Structure: (2-chloro-5-methoxy-4-biphenyl)methylamine coupled to 1-acryloylpiperidine-4-carboxamide]* |
| 5 | *[Structure: N-benzyl 2-(4-acryloylpiperazin-1-yl)acetamide]* |

TABLE 4-continued

| Compound Number (IV-) | Structure |
|---|---|
| 6 | 5-fluoro-4-chloro-2-methoxy-N-(2-(4-acryloylpiperazin-1-yl)ethyl)benzamide |
| 7 | 2'-chloro-4-chloro-4'-methoxy-N-(2-(4-acryloylpiperazin-1-yl)ethyl)-[1,1'-biphenyl]-3-carboxamide |
| 8 | 5-iodo-4-chloro-2-methoxy-N-((1-acryloylpiperidin-4-yl)methyl)benzamide |
| 9 | 2'-chloro-4-chloro-4'-methoxy-N-((1-acryloylpiperidin-4-yl)methyl)-[1,1'-biphenyl]-3-carboxamide |
| 10 | 5-bromo-4-chloro-2-methoxy-benzyl 1-acryloylpiperidine-4-carboxamide |
| 11 | 4,5-dichloro-2-hydroxy-N-(4-acrylamidobenzyl)benzamide |

TABLE 5a

Representative Compounds

| No. | Structure | Name |
|---|---|---|
| V-1 | 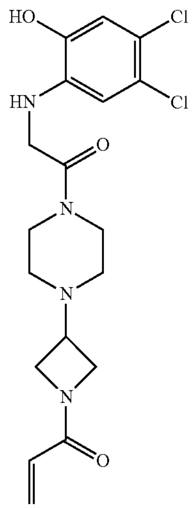 | 1-(3-(4-(2-(4,5-dichloro-2-hydroxyphenylamino)acetyl)piperazin-1-yl)azetidin-1-yl)prop-2-en-1-one |
| V-2 | 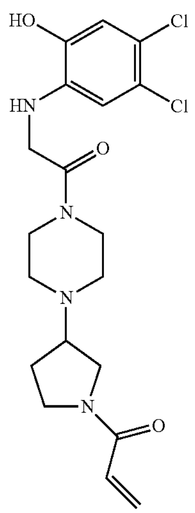 [SMILES: C=CC(=O)N1CCC(N2CCN(C(=O)CNc3cc(Cl)c(Cl)cc3O)CC2)C1] | 1-(3-(4-(2-(4,5-dichloro-2-hydroxyphenylamino)acetyl)piperazin-1-yl)pyrrolidin-1-yl)prop-2-en-1-one |
| V-3 | 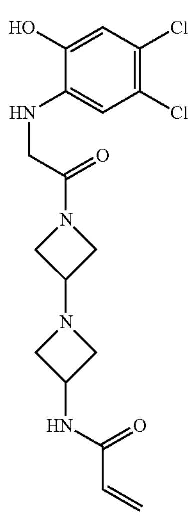 | N-(1'-(2-(4,5-dihcloro-2-hydroxyphenylamino)acetyl)-1,3'-biazetidin-3-yl)acrylamide |
| V-4 | | 1-(4-(1-(2-(4,5-dichloro-2-hydroxyphenylamino)acetyl)pyrrolidin-3-yl)piperazin-1-yl)prop-2-en-1-one |
| V-5 | | 1-(3-(4-(2-(2,4-dichloro-5-methoxyphenylamino)acetyl)piperazin-1-yl)azetidin-1-yl)prop-2-en-1-one |
| V-6 | | 1-(3-(4-(3-(4,5-dichloro-2-hydroxyphenyl)propanoyl)piperazin-1-yl)azetidin-1-yl)prop-2-en-1-one |

TABLE 5a-continued

Representative Compounds

| No. | Structure | Name |
|---|---|---|
| V-7 | 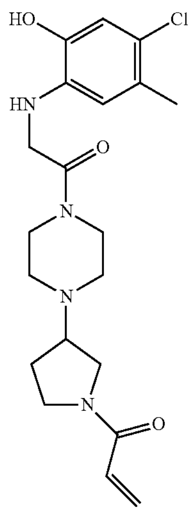 [SMILES: C=CC(=O)N1CCC(N2CCN(C(=O)CNc3cc(C)c(Cl)cc3O)CC2)C1] | 1-(3-(4-(2-(4-chloro-2-hydroxy-5-methylphenylamino)acetyl)piperazin-1-yl)pyrrolidin-1-yl)prop-2-en-1-one |
| V-8 | 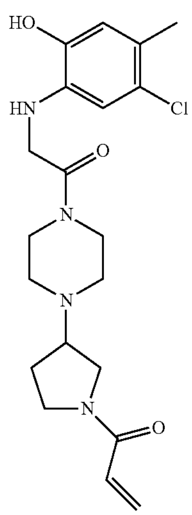 [SMILES: C=CC(=O)N1CCC(N2CCN(C(=O)CNc3cc(Cl)c(C)cc3O)CC2)C1] | 1-(3-(4-(2-(5-chloro-2-hydroxy-4-methylphenylamino)acetyl)piperazin-1-yl)pyrrolidin-1-1-yl)prop-2-en-1-one |
| V-9 | 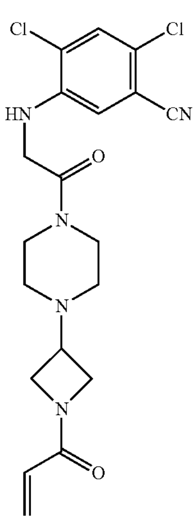 | 5-(2-(4-(1-acryloylazetidin-3-yl)piperazin-1-yl)-2-oxoethylamino)-2,4-dichlorobenzonitrile |
| V-10 | 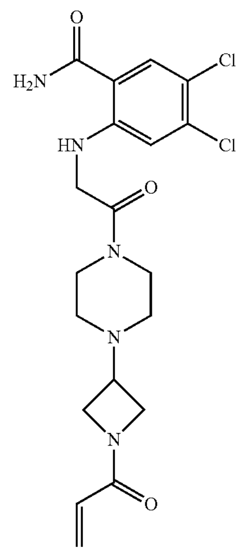 [SMILES: C=CC(=O)N1CC(N2CCN(C(=O)CNc3cc(Cl)c(Cl)cc3C(N)=O)CC2)C1] | 2-(2-(4-(1-acryloylazetidin-3-yl)piperazin-1-yl)-2-oxoethylamino)-4,5-dichlorobenzamide |
| V-11 | 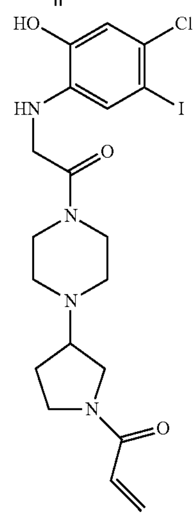 | 1-(3-(4-(2-(4-chloro-2-hydroxy-5-iodophenylamino)acetyl)piperazin-1-yl)pyrrolidin-1-yl)prop-2-en-1-one |
| V-12 | 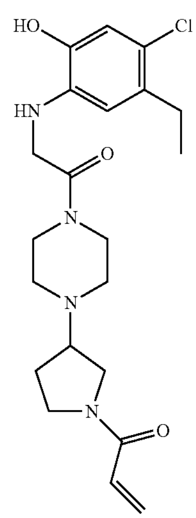 [SMILES: C=CC(=O)N1CCC(N2CCN(C(=O)CNc3cc(CC)c(Cl)cc3O)CC2)C1] | 1-(3-(4-(2-(4-chloro-5-ethyl-2-hydroxyphenylamino)acetyl)piperazin-1-yl)pyrrolidin-1-yl)prop-2-en-1-one |

TABLE 5a-continued

Representative Compounds

| No. | Structure | Name |
|---|---|---|
| V-13 | 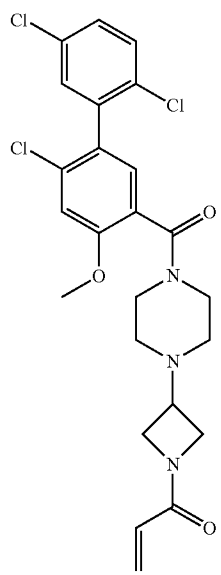 [SMILES: C=CC(=O)N1CC(N2CCN(C(=O)c3cc(-c4cc(Cl)ccc4Cl)c(Cl)cc3OC)CC2)C1] | 1-(3-(4-(2',5',6-trichloro-4-methoxybiphenyl-carbonyl)piperazin-1-yl)azetidin-1-yl)prop-2-en-1-one |
| V-14 | 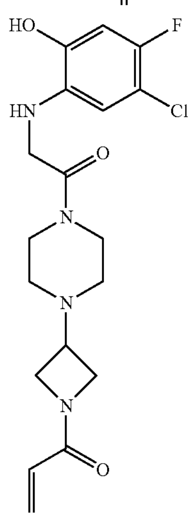 | 1-(3-(4-(2-(5-chloro-4-fluoro-2-hydroxyphenylamino)acetyl)piperazin-1-yl)azetidin-1-yl)prop-2-en-1-one |
| V-15 | 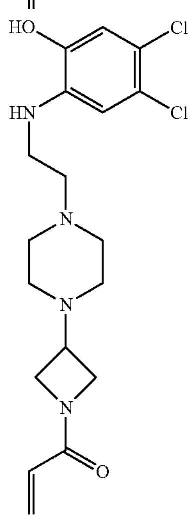 | 1-(3-(4-(2-(4,5-dichloro-2-hydroxyphenylamino)ethyl)piperazin-1-yl)azetidin-1-yl)prop-2-en-1-one |
| V-16 | 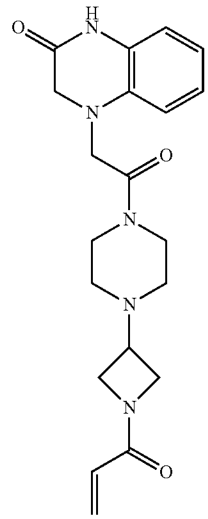 [SMILES: C=CC(=O)N1CC(N2CCN(C(=O)CN3CC(=O)Nc4ccccc43)CC2)C1] | 4-(2-(4-(1-acryloylazetidin-3-yl)piperazin-1-yl)-2-oxoethyl)-3,4-dihydroquinoxalin-2(1H)-one |
| V-17 | 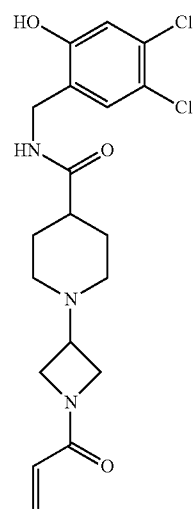 [SMILES: C=CC(=O)N1CC(N2CCC(C(=O)NCc3cc(Cl)c(Cl)cc3O)CC2)C1] | 1-(1-acryloylazetidin-3-yl)-N-(4,5-dichloro-2-hydroxybenzyl)piperidine-4-carboxamide |
| V-18 | 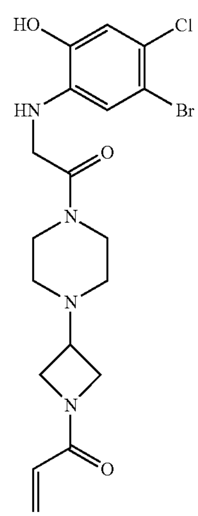 | 1-(3-(4-(2-(5-bromo-4-chloro-2-hydroxyphenylamino)acetyl)piperazin-1-yl)azetidin-1-yl)prop-2-en-1-one |

TABLE 5a-continued

Representative Compounds

| No. | Structure | Name |
|---|---|---|
| V-19 | 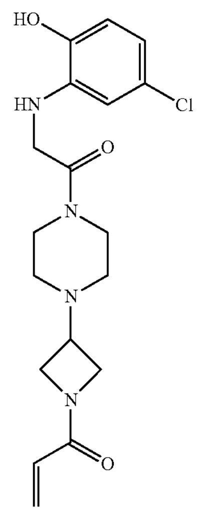 [SMILES: C=CC(=O)N1CC(N2CCN(C(=O)CNc3cc(Cl)ccc3O)CC2)C1] | 1-(3-(4-(2-(5-chloro-2-hydroxyphenylamino)acetyl)piperazin-1-yl)azetidin-1-yl)prop-2-en-1-one |
| V-20 | 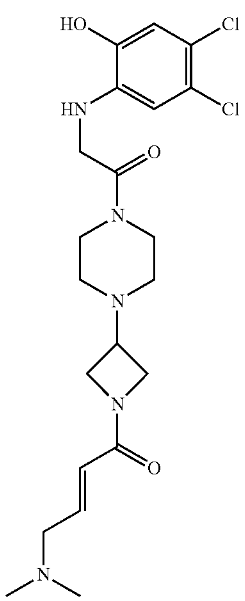 [SMILES: CN(C)C/C=C/C(=O)N1CC(N2CCN(C(=O)CNc3cc(Cl)c(Cl)cc3O)CC2)C1] | (E)-1-(3-(4-((4,5-dichloro-2-hydroxyphenyl)glycyl)piperazin-1-yl)azetidin-1-yl)-4-(dimethylamino)but-2-en-1-one |
| V-21 | 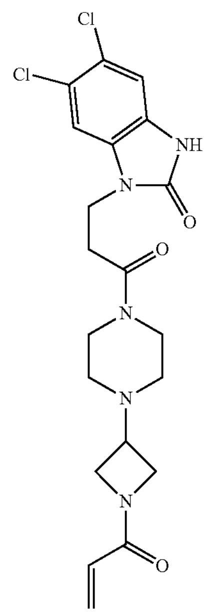 [SMILES: C=CC(=O)N1CC(N2CCN(C(=O)CCn3c(=O)[nH]c4cc(Cl)c(Cl)cc43)CC2)C1] | 1-(3-(4-(1-acryloylazetidin-3-yl)piperazin-1-yl)-3-oxopropyl)-5,6-dichloro-1H-benzo[d]imidazol-2(3H)-one |
| V-22 | 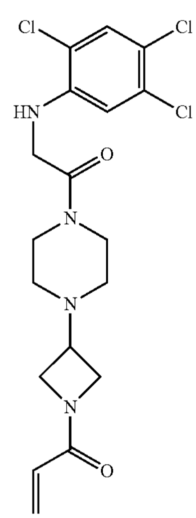 [SMILES: C=CC(=O)N1CC(N2CCN(C(=O)CNc3cc(Cl)c(Cl)cc3Cl)CC2)C1] | 1-(3-(4-(2-(2,4,5-trichlorophenylamino)acetyl)piperazin-1-yl)azetidin-1-yl)prop-2-en-1-one |

TABLE 5a-continued

Representative Compounds

| No. | Structure | Name |
|---|---|---|
| V-23 | 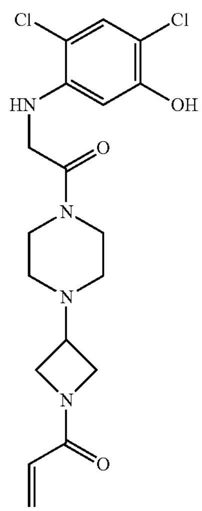 | 1-(3-(4-(2-(2,4-dichloro-5-hydroxyphenylamino)acetyl)piperazin-1-yl)azetidin-1-yl)prop-2-en-1-one |
| V-24 | 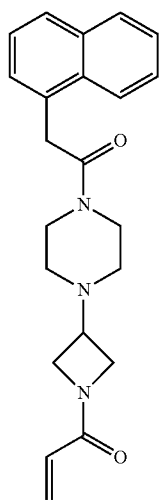 [SMILES: C=CC(=O)N1CC(N2CCN(C(=O)Cc3cccc4ccccc34)CC2)C1] | 1-(3-(4-(2-(naphthalen-1-yl)acetyl)piperazin-1-yl)azetidin-1-yl)prop-2-en-1-one |
| V-25 | 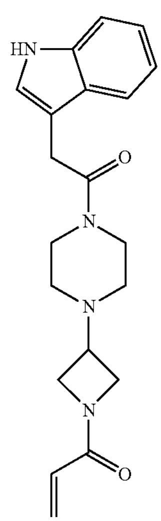 [SMILES: C=CC(=O)N1CC(N2CCN(C(=O)Cc3c[nH]c4ccccc34)CC2)C1] | 1-(3-(4-(2-(1H-indol-3-yl)acetyl)piperazin-1-yl)azetidin-1-yl)prop-2-en-1-one |
| V-26 | 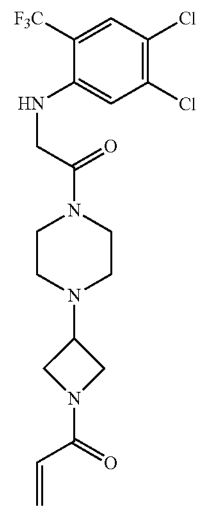 [SMILES: C=CC(=O)N1CC(N2CCN(C(=O)CNc3cc(Cl)c(Cl)cc3C(F)(F)F)CC2)C1] | 1-(3-(4-(2-(4,5-dichloro-2-(trifluoromethyl)phenylamino)acetyl)piperazin-1-yl)azetidin-1-yl)prop-2-en-1-one |
| V-27 | 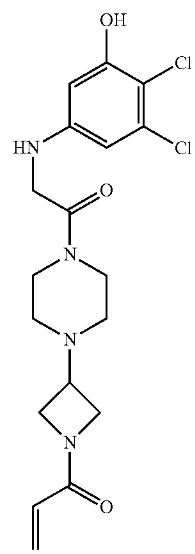 [SMILES: C=CC(=O)N1CC(N2CCN(C(=O)CNc3cc(O)c(Cl)c(Cl)c3)CC2)C1] | 1-(3-(4-(2-(3,4-dichloro-5-hydroxyphenylamino)acetyl)piperazin-1-yl)azetidin-1-yl)prop-2-en-1-one |
| V-28 | 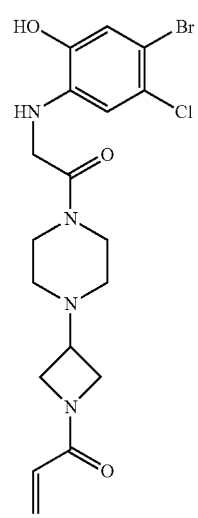 | 1-(3-(4-(2-(4-bromo-5-chloro-2-hydroxyphenylamino)acetyl)piperazin-1-yl)azetidin-1-yl)prop-2-en-1-one |

TABLE 5a-continued

Representative Compounds

| No. | Structure | Name |
|---|---|---|
| V-29 | 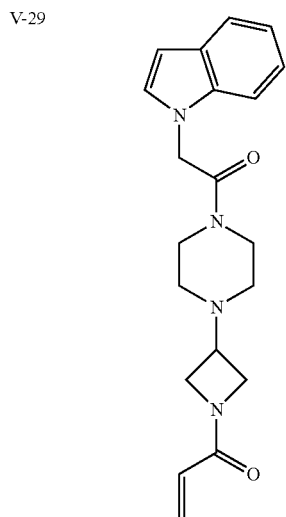 | 1-(3-(4-(2-(1H-indol-1-yl)acetyl)piperazin-1-yl)azetidin-1-yl)prop-2-en-1-one |
| V-30 | 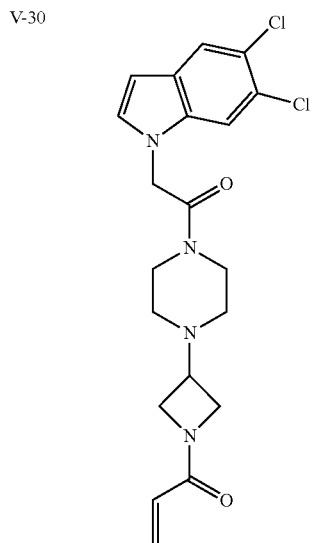 | 1-(3-(4-(2-(5,6-dichloro-1H-indol-1-yl)acetyl)piperazin-1-yl)azetidin-1-yl)prop-2-en-1-one |
| V-31 | 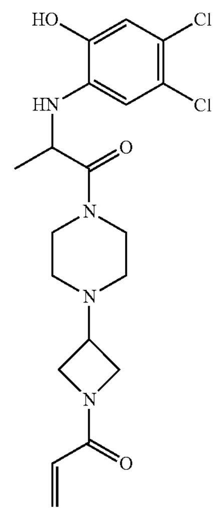 [SMILES: C=CC(=O)N1CC(N2CCN(C(=O)C(C)Nc3cc(Cl)c(Cl)cc3O)CC2)C1] | 1-(3-(4-(2-(4,5-dichloro-2-hydroxyphenylamino)propanoyl)piperazin-1-yl)azetidin-1-yl)prop-2-en-1-one |
| V-32 | 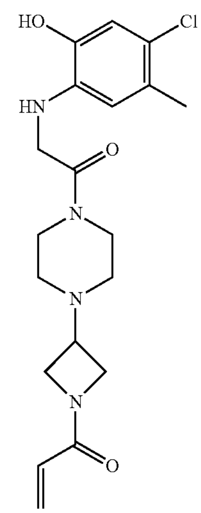 | 1-(3-(4-(2-(4-chloro-2-hydroxy-5-methylphenylamino)acetyl)piperazin-1-yl)azetidin-1-yl)prop-2-en-1-one |
| V-33 | 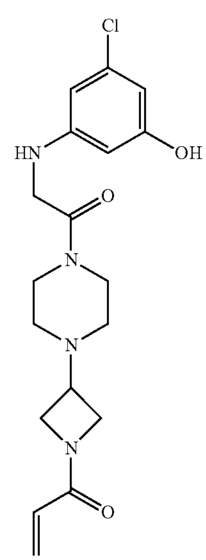 | 1-(3-(4-(2-(3-chloro-5-hydroxyphenylamino)acetyl)piperazin-1-yl)azetidin-1-yl)prop-2-en-1-one |

TABLE 5a-continued

Representative Compounds

| No. | Name |
|---|---|
| V-34 | 1-(3-(4-(2-(2-hydroxy-5-(methylsulfonyl)phenylamino)acetyl)piperazin-1-yl)azetidin-1-yl)prop-2-en-1-one |
| V-35 | 1-(3-(4-(2-(4-chloro-5-cyclopropyl-2-hydroxyphenylamino)acetyl)piperazin-1-yl)azetidin-1-yl)prop-2-en-1-one |
| V-36 | N-(1'-(2-(5-bromo-4-chloro-2-hydroxyphenylamino)acetyl)-1,3'-biazetidin-3-yl)acrylamide |
| V-37 | 1-(3-(4-(2-(4-chloro-2-methoxy-5-(trifluoromethyl)phenylamino)acetyl)piperazin-1-yl)azetidin-1-yl)prop-2-en-1-one |
| V-38 | 1-(3-(4-(2-(5-chlorothiazol-2-ylamino)acetyl)piperazin-1-yl)azetidin-1-yl)prop-2-en-1-one |
| V-39 | 1-(4-(1-(2-(4,5-dichloro-2-hydroxyphenylamino)acetyl)azetidin-3-yl)piperazin-1-yl)prop-2-en-1-one |

TABLE 5a-continued

Representative Compounds

| No. | Structure | Name |
|---|---|---|
| V-40 | 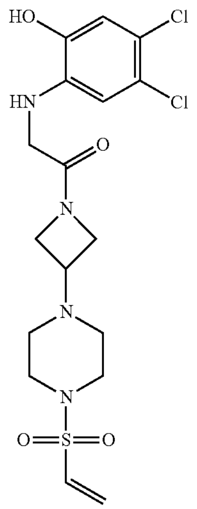 [SMILES: C=CS(=O)(=O)N1CCN(C2CN(C(=O)CNc3cc(Cl)c(Cl)cc3O)C2)CC1] | 2-(4,5-dichloro-2-hydroxyphenylamino)-1-(3-(4-(vinylsulfonyl)piperazin-1-yl)azetidin-1-yl)ethanone |
| V-41 | 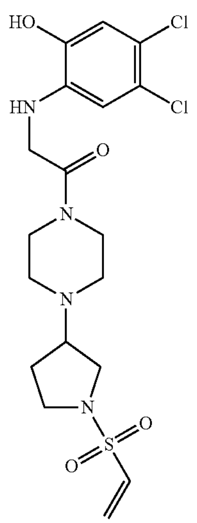 [SMILES: C=CS(=O)(=O)N1CCC(N2CCN(C(=O)CNc3cc(Cl)c(Cl)cc3O)CC2)C1] | 2-(4,5-dichloro-2-hydroxyphenylamino)-1-(4-(1-(vinylsulfonyl)pyrrolidin-3-yl)piperazin-1-yl)ethanone |
| V-42 | 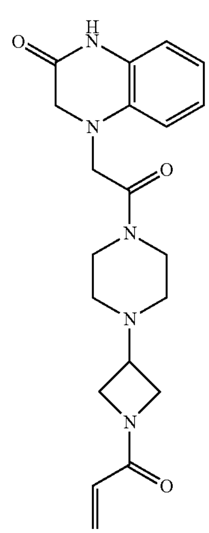 [SMILES: C=CC(=O)N1CC(N2CCN(C(=O)CN3CC(=O)Nc4ccccc43)CC2)C1] | 4-(2-(4-(1-acryloylazetidin-3-yl)piperazin-1-yl)-2-oxoethyl)-3,4-dihydroquinoxalin-2(1H)-one |
| V-43 | 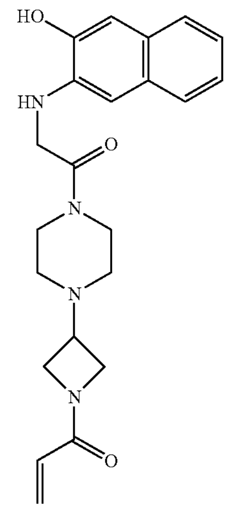 [SMILES: C=CC(=O)N1CC(N2CCN(C(=O)CNc3cc4ccccc4cc3O)CC2)C1] | 1-(3-(4-(2-(3-hydroxynaphthalen-2-ylamino)acetyl)piperazin-1-yl)azetidin-1-yl)prop-2-en-1-one |
| V-44 | 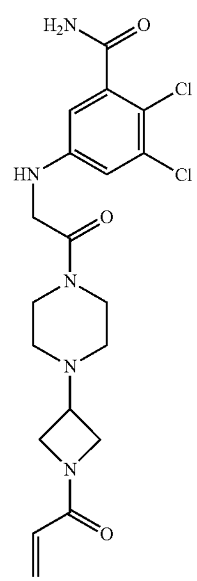 [SMILES: C=CC(=O)N1CC(N2CCN(C(=O)CNc3cc(Cl)c(Cl)c(C(N)=O)c3)CC2)C1] | 5-(2-(4-(1-acryloylazetidin-3-yl)piperazin-1-yl)-2-oxoethylamino)-2,3-dichlorobenzamide |
| V-45 | 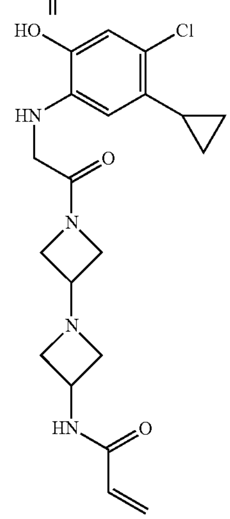 | N-(1'-(2-(4-chloro-5-cyclopropyl-2-hydroxyphenylamino)acetyl)-1,3'-biazetidin-3-yl)acrylamide |

TABLE 5a-continued

Representative Compounds

| No. | Structure | Name |
|---|---|---|
| V-46 | 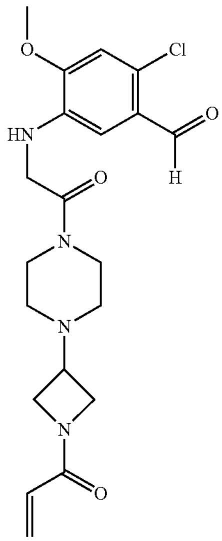 [SMILES: C=CC(=O)N1CC(N2CCN(C(=O)CNc3cc(C=O)c(Cl)cc3OC)CC2)C1] | 5-(2-(4-(1-acryloylazetidin-3-yl)piperazin-1-yl)-2-oxoethylamino)-2-chloro-4-methoxybenzaldehyde |
| V-47 | 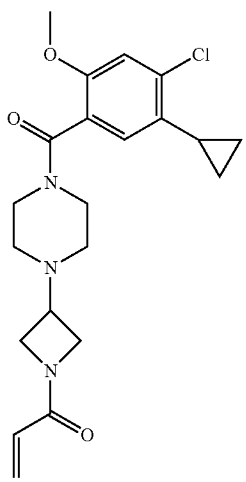 [SMILES: C=CC(=O)N1CC(N2CCN(C(=O)c3cc(C4CC4)c(Cl)cc3OC)CC2)C1] | 1-(3-(4-(4-chloro-5-cyclopropyl-2-methoxybenzoyl)piperazin-1-yl)azetidin-1-yl)prop-2-en-1-one |
| V-48 | 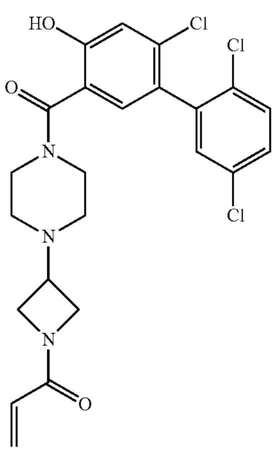 [SMILES: C=CC(=O)N1CC(N2CCN(C(=O)c3cc(-c4cc(Cl)ccc4Cl)c(Cl)cc3O)CC2)C1] | 1-(3-(4-(2',5',6-trichloro-4-hydroxybiphenylcarbonyl)piperazin-1-yl)azetidin-1-yl)prop-2-en-1-one |
| V-49 | | 1-(4-(1-acryloylazetidin-3-yl)piperazin-1-yl)-2-(4,5-dihcloro-2-hydroxyphenylamino)butan-1-one |
| V-50 | | 1-(3-(4-(2-(4-chloro-2-hydroxy-5-isopropylphenylamino)acetyl)piperazin-1-yl)azetidin-1-yl)prop-2-en-1-one |
| V-51 | | 1-(1-acryloylazetidin-3-yl)-4-(2-(4-chloro-5-cyclopropyl-2-hydroxyphenylamino)acetyl)piperazine-2-carboxamide |

TABLE 5a-continued

Representative Compounds

| No. | Structure | Name |
|---|---|---|
| V-52 | 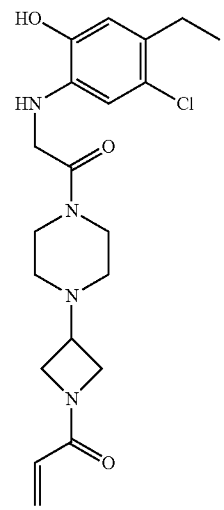 [SMILES: C=CC(=O)N1CC(N2CCN(C(=O)CNc3cc(Cl)c(CC)cc3O)CC2)C1] | 1-(3-(4-(2-(5-chloro-4-ethyl-2-hydroxyphenylamino)acetyl)piperazin-1-yl)azetidin-1-yl)prop-2-en-1-one |
| V-53 | 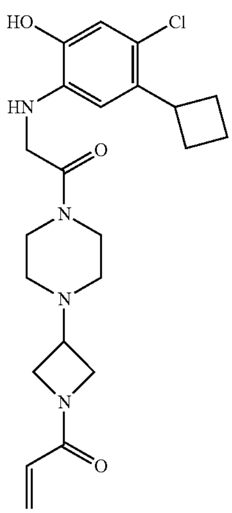 [SMILES: C=CC(=O)N1CC(N2CCN(C(=O)CNc3cc(C4CCC4)c(Cl)cc3O)CC2)C1] | 1-(3-(4-(2-(4-chloro-5-cyclobutyl-2-hydroxyphenylamino)acetyl)piperazin-1-yl)azetidin-1-yl)prop-2-en-1-one |
| V-54 | 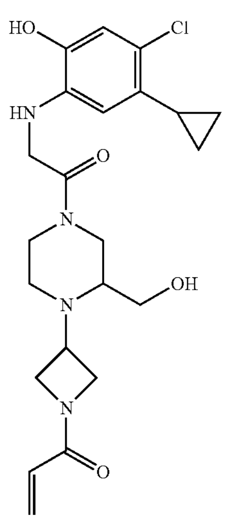 [SMILES: C=CC(=O)N1CC(N2CCN(C(=O)CNc3cc(C4CC4)c(Cl)cc3O)CC2CO)C1] | 1-3-(4-(2-(4-chloro-5-cyclopropyl-2-hydroxyphenylamino)acetyl)-2-(hydroxymethyl)piperazin-1-yl)azetidin-1-yl)prop-2-en-1-one |
| V-55 | | 1-(3-(4-(2-(4-chloro-5-ethyl-2-hydroxyphenylamino)acetyl)piperazin-1-yl)azetidin-1-yl)prop-2-en-1-one |
| V-56 | | 1-(3-(4-(2-(4-chloro-5-(2,2-difluorocyclopropyl)-2-hydroxyphenylamino)acetyl)piperazin-1-yl)azetidin-1-yl)prop-2-en-1-one |
| V-57 | | 1-(3-(4-(2-(4-chloro-2-hydroxy-5-(2,2,2-trifluoroethyl)phenylamino)acetyl)piperazin-1-yl)azetidin-1-yl)prop-2-en-1-one |

TABLE 5a-continued

Representative Compounds

| No. | Structure | Name |
|---|---|---|
| V-58 | 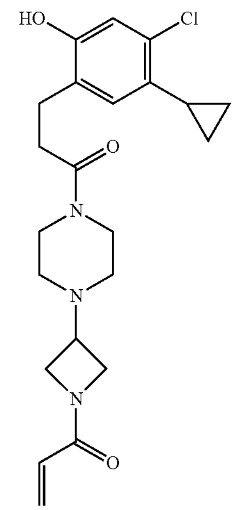 [SMILES: C=CC(=O)N1CC(N2CCN(C(=O)CCc3cc(C4CC4)c(Cl)cc3O)CC2)C1] | 1-(3-(4-(3-(4-chloro-5-cyclopropyl-2-hydroxyphenyl)propanoyl)piperazin-1-yl)azetidin-1-yl)prop-2-en-1-one |
| V-59 | 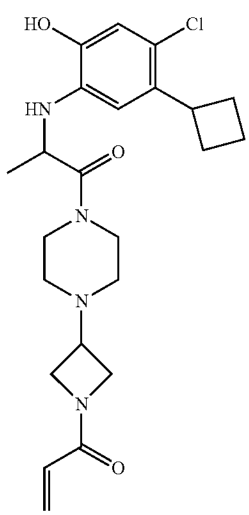 [SMILES: C=CC(=O)N1CC(N2CCN(C(=O)C(C)Nc3cc(C4CCC4)c(Cl)cc3O)CC2)C1] | 1-(3-(4-(2-(4-chloro-5-cyclobutyl-2-hydroxyphenylamino)propanoyl)piperazin-1-yl)azetidin-1-yl)prop-2-en-1-one |
| V-60 | 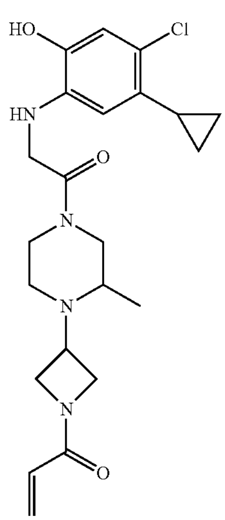 [SMILES: C=CC(=O)N1CC(N2CCN(C(=O)CNc3cc(C4CC4)c(Cl)cc3O)CC2C)C1] | 1-(3-(4-(2-(4-chloro-5-cyclopropyl-2-hydroxyphenylamino)acetyl)-2-methylpiperazin-1-yl)azetidin-1-yl)prop-2-en-1-one |
| V-61 | | 1-(3-(4-(2-(5,6-dichloro-1H-indol-3-yl)acetyl)piperazin-1-yl)azetidin-1-yl)prop-2-en-1-one |
| V-62 | | (E)-1-(4-(1-acryloylazetidin-3-yl)piperazin-1-yl)-3-(4-chloro-5-cyclopropyl-2-hydroxyphenyl)prop-2-en-1-one |
| V-63 | | (S)-1-(3-(4-(2-(4-chloro-5-cyclopropyl-2-hydroxyphenylamino)acetyl)-2-(hydroxymethyl)piperazin-1-yl)azetidin-1-yl)prop-2-en-1-one |

TABLE 5a-continued

Representative Compounds

| No. | Structure | Name |
|---|---|---|
| V-64 | 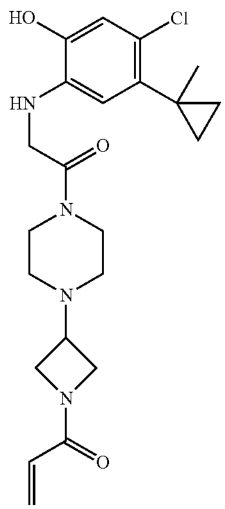 [SMILES: C=CC(=O)N1CC(N2CCN(C(=O)CNc3cc(C4(C)CC4)c(Cl)cc3O)CC2)C1] | 1-(3-(4-(2-(4-chloro-2-hydroxy-5-(1-methylcyclopropyl)phenylamino)acetyl)piperazin-1-yl)azetidin-1-yl)prop-2-en-1-one |
| V-65 | 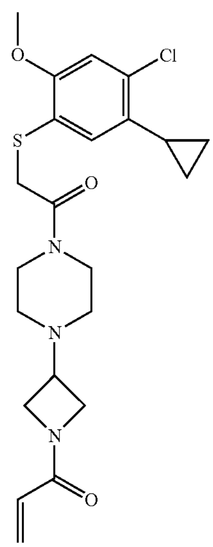 [SMILES: C=CC(=O)N1CC(N2CCN(C(=O)CSc3cc(C4CC4)c(Cl)cc3OC)CC2)C1] | 1-(3-(4-(2-(4-chloro-5-cyclopropyl-2-methoxyphenylthio)acetyl)piperazin-1-yl)azetidin-1-yl)prop-2-en-1-one |
| V-66 | 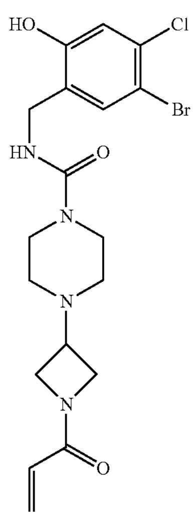 [SMILES: C=CC(=O)N1CC(N2CCN(C(=O)NCc3cc(Br)c(Cl)cc3O)CC2)C1] | 4-(1-acryloylazetidin-3-yl)-N-(5-bromo-4-chloro-2-hydroxybenzyl)piperazine-1-carboxamide |
| V-67 | 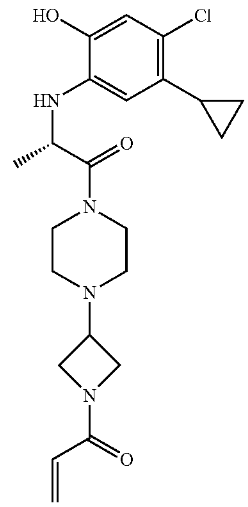 [SMILES: C=CC(=O)N1CC(N2CCN(C(=O)[C@H](C)Nc3cc(C4CC4)c(Cl)cc3O)CC2)C1] | (S)-1-(3-(4-(2-(4-chloro-5-cyclopropyl-2-hydroxyphenylamino)propanoyl)piperazin-1-yl)azetidin-1-yl)prop-2-en-1-one |
| V-68 | 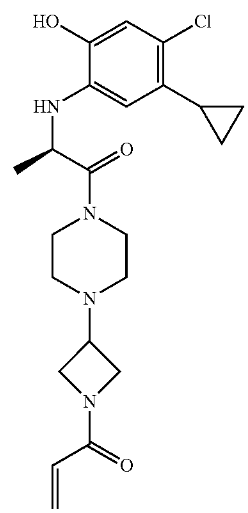 [SMILES: C=CC(=O)N1CC(N2CCN(C(=O)[C@@H](C)Nc3cc(C4CC4)c(Cl)cc3O)CC2)C1] | (R)-1-(3-(4-(2-(4-chloro-5-cyclopropyl-2-hydroxyphenylamino)propanoyl)piperazin-1-yl)azetidin-1-yl)prop-2-en-1-one |
| V-69 | 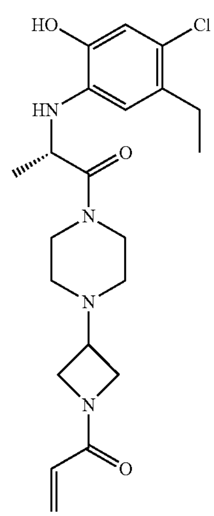 [SMILES: C=CC(=O)N1CC(N2CCN(C(=O)[C@H](C)Nc3cc(CC)c(Cl)cc3O)CC2)C1] | (S)-1-(3-(4-(2-(4-chloro-5-ethyl-2-hydroxyphenylamino)propanoyl)piperazin-1-yl)azetidin-1-yl)prop-2-en-1-one |

TABLE 5a-continued

Representative Compounds

| No. | Structure | Name |
|-----|-----------|------|
| V-70 | 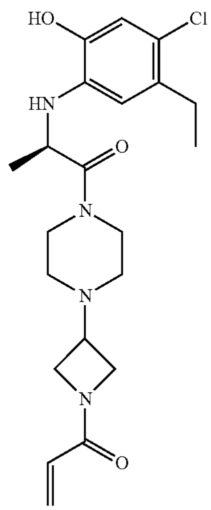 [SMILES: C=CC(=O)N1CC(N2CCN(C(=O)[C@@H](C)Nc3cc(CC)c(Cl)cc3O)CC2)C1] | (R)-1-(3-(4-(2-(4-chloro-5-ethyl-2-hydroxyphenylamino)propanoyl)piperazin-1-yl)azetidin-1-yl)prop-2-en-1-one |
| V-71 | 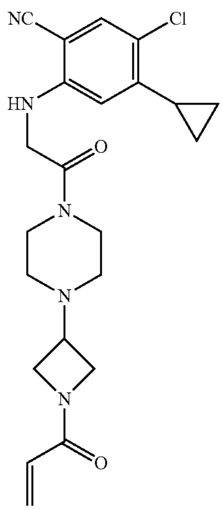 [SMILES: C=CC(=O)N1CC(N2CCN(C(=O)CNc3cc(C4CC4)c(Cl)cc3C#N)CC2)C1] | 2-(2-(4-(1-acryloylazetidin-3-yl)piperazin-1-yl)-2-oxoethylamino)-5-chloro-4-cyclopropylbenzonitrile |
| V-72 | 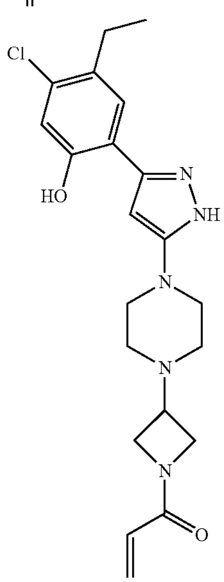 | 1-(3-(4-(3-(4-chloro-5-ethyl-2-hydroxyphenyl)-1H-pyrazol-5-yl)piperazin-1-yl)azetidin-1-yl)prop-2-en-1-one |
| V-73 | | 1-(3-(4-(1-(4-chloro-5-cyclopropyl-2-methoxyphenyl)pyrrolidine-2-carbonyl)piperazin-1-yl)azetidin-1-yl)prop-2-en-1-one |
| V-74 | | 1-(3-(4-(2-(5-chloro-4-ethylpyridin-2-ylamino)acetyl)piperazin-1-yl)azetidin-1-yl)prop-2-en-1-one |
| V-75 | | 1-(3-(4-(2-(4,5-dichloro-7-methoxy-1H-indol-1-yl)acetyl)piperazin-1-yl)azetidin-1-yl)prop-2-en-1-one |

TABLE 5a-continued

Representative Compounds

| No. | Structure | Name |
|---|---|---|
| V-76 | 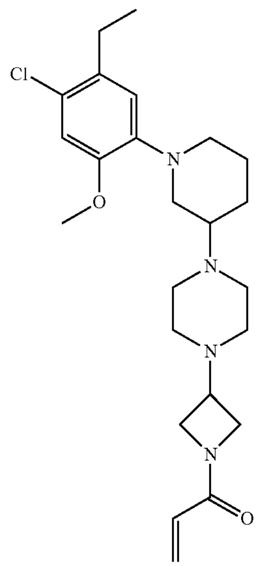 [SMILES: C=CC(=O)N1CC(N2CCN(C3CCCN(c4cc(CC)c(Cl)cc4OC)C3)CC2)C1] | 1-(3-(4-(1-(4-chloro-5-ethyl-2-methoxyphenyl)piperidin-3-yl)piperazin-1-yl)azetidin-1-yl)prop-2-en-1-one |

TABLE 5b

Experimental Mass Spectral Data for Compounds in Table 5

| No. | [M + H⁺] | No. | [M + H⁺] | No. | [M + H⁺] | No. | [M + H⁺] |
|---|---|---|---|---|---|---|---|
| V-1 | 411.30 | V-2 | 425.25 | V-3 | 399.20 | V-4 | 427.30 |
| V-5 | 449.25* | V-6 | 410.25 | V-7 | 429.35* | V-8 | 407.35 |
| V-9 | 422.25 | V-10 | 462.25* | V-11 | 519.25 | V-12 | 443.30* |
| V-13 | 532.25* | V-14 | 395.30 | V-15 | 399.25 | V-16 | 419.25 |
| V-17 | 434.25* | V-18 | 457.35 | V-19 | 379.30 | V-20 | 470.35 |
| V-21 | 450.35 | V-22 | 433.05 | V-23 | 435.25* | V-24 | 386.25* |
| V-25 | 351.35 | V-26 | 487.30* | V-27 | 413.30 | V-28 | 479.20* |
| V-29 | 353.30 | V-30 | 421.30 | V-31 | 449.25* | V-32 | 393.30 |
| V-33 | 377.30⁺ | V-34 | 423.35 | V-35 | 441.30* | V-36 | 445.20 |
| V-37 | 461.30 | V-38 | 368.30⁺ | V-39 | 411.20 | V-40 | 447.25⁺ |
| V-41 | 463.20 | V-42 | 382.40⁺ | V-43 | 417.35* | V-44 | 440.30 |
| V-45 | 405.35 | V-46 | 421.30 | V-47 | 404.35 | V-48 | 494.30 |
| V-49 | 441.30 | V-50 | 421.35 | V-51 | 462.45 | V-52 | 407.40 |
| V-53 | 433.40 | V-54 | 449.35 | V-55 | 407.30 | V-56 | 455.20 |
| V-57 | 461.40 | V-58 | 418.40 | V-59 | 447.40 | V-60 | 433.45 |
| V-61 | 421.25 | V-62 | 416.35 | V-63 | 449.40 | V-64 | 433.35 |
| V-65 | 451.30 | V-66 | 459.25 | V-67 | 433.20 | V-68 | 433.40 |
| V-69 | 421.35 | V-70 | 421.35 | V-71 | 428.35 | V-72 | 416.35 |
| V-73 | 473.90 | V-74 | 392.30 | V-75 | 451.30 | V-76 | 447.85 |

*[M + Na]⁺
⁺[M − H]⁻

TABLE 6

Representative Compounds

| No. | Structure | Name | [M + H]⁺ |
|---|---|---|---|
| VI-1 | 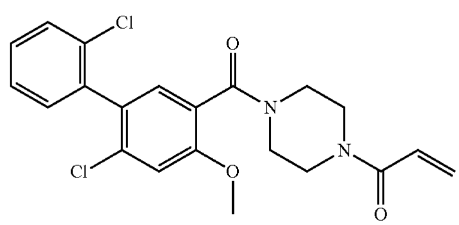 [SMILES: C=CC(=O)N1CCN(C(=O)c2cc(-c3ccccc3Cl)c(Cl)cc2OC)CC1] | 1-(4-(2',6-dichloro-4-methoxybiphenylcarbonyl)piperazin-1-yl)prop-2-en-1-one | 441.20* |
| VI-2 | 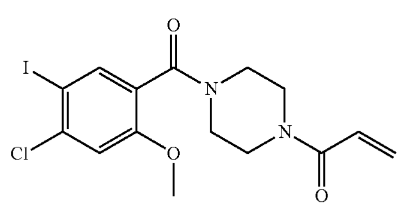 [SMILES: C=CC(=O)N1CCN(C(=O)c2cc(I)c(Cl)cc2OC)CC1] | 1-(4-(4-chloro-5-iodo-2-methoxybenzoyl)piperazin-1-yl)prop-2-en-1-one | 457.05* |
| VI-3 | 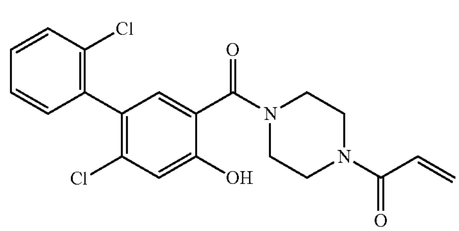 [SMILES: C=CC(=O)N1CCN(C(=O)c2cc(-c3ccccc3Cl)c(Cl)cc2O)CC1] | 1-(4-(2',6-dichloro-4-hydroxybiphenylcarbonyl)piperazin-1-yl)prop-2-en-1-one | 427.15 |

TABLE 6-continued

| No. | Structure | Name | [M + H]⁺ |
|---|---|---|---|
| VI-4 | 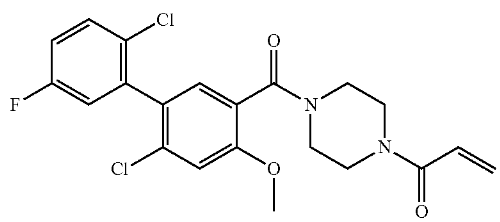 [SMILES: C=CC(=O)N1CCN(C(=O)c2cc(-c3cc(F)ccc3Cl)c(Cl)cc2OC)CC1] | 1-(4-(2',6-dichloro-5'-fluoro-4-methoxybiphenylcarbonyl)piperazin-1-yl)prop-2-en-1-one | 459.15 |
| VI-5 | 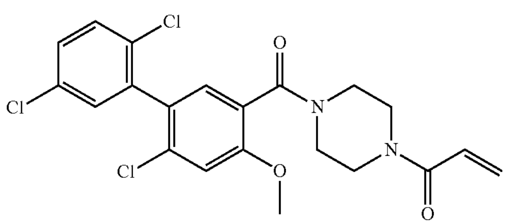 [SMILES: C=CC(=O)N1CCN(C(=O)c2cc(-c3cc(Cl)ccc3Cl)c(Cl)cc2OC)CC1] | 1-(4-(2',5',6-trichloro-4-methoxybiphenylcarbonyl)piperazin-1-yl)prop-2-en-1-one | 453.15 |
| VI-6 | 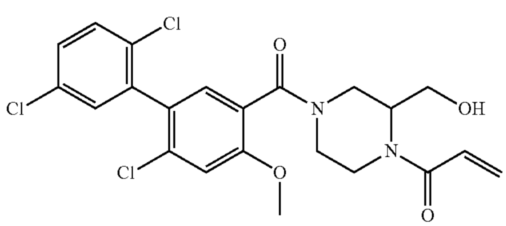 [SMILES: C=CC(=O)N1CCN(C(=O)c2cc(-c3cc(Cl)ccc3Cl)c(Cl)cc2OC)CC1CO] | 1-(2-(hydroxymethyl)-4-(2',5',6-trichloro-4-methoxybiphenylcarbonyl)piperazin-1-yl)prop-2-en-1-one | 483.20# |
| VI-7 | 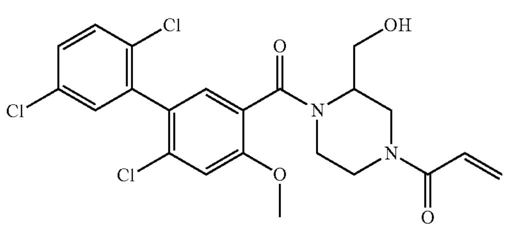 [SMILES: C=CC(=O)N1CCN(C(=O)c2cc(-c3cc(Cl)ccc3Cl)c(Cl)cc2OC)C(CO)C1] | 1-(3-(hydroxymethyl)-4-(2',5',6-trichloro-4-methoxybiphenylcarbonyl)piperazin-1-yl)prop-2-en-1-one | 485.20 |
| VI-8 | 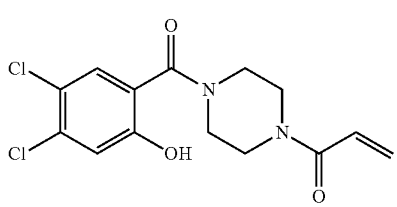 [SMILES: C=CC(=O)N1CCN(C(=O)c2cc(Cl)c(Cl)cc2O)CC1] | 1-(4-(4,5-dichloro-2-hydroxybenzoyl)piperazin-1-yl)prop-2-en-1-one | 327.15 |
| VI-9 | 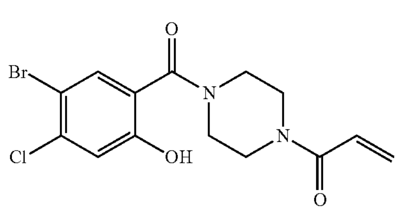 | 1-(4-(5-bromo-4-chloro-2-hydroxybenzoyl)piperazin-1-yl)prop-2-en-1-one | 3.88* |

TABLE 6-continued

Representative Compounds

| No. | Structure | Name | [M + H]+ |
|---|---|---|---|
| VI-10 | 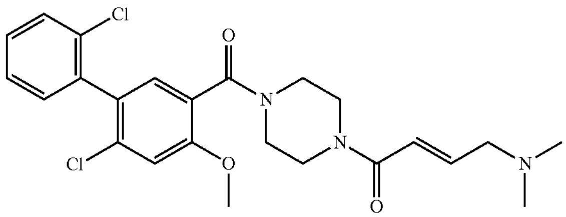 [SMILES: COc1cc(Cl)c(-c2ccccc2Cl)cc1C(=O)N1CCN(C(=O)/C=C/CN(C)C)CC1] | (E)-1-(4-(2',6-dichloro-4-methoxybiphenylcarbonyl)piperazin-1-yl)-4-(dimethylamino)but-2-en-1-one | 476.23 |
| VI-11 | 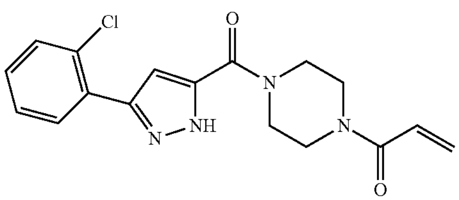 [SMILES: C=CC(=O)N1CCN(C(=O)c2cc(-c3ccccc3Cl)n[nH]2)CC1] | 1-(4-(3-(2-chlorophenyl)-1H-pyrazole-5-carbonyl)piperazin-1-yl)prop-2-en-1-one | 467.20* |
| VI-12 | 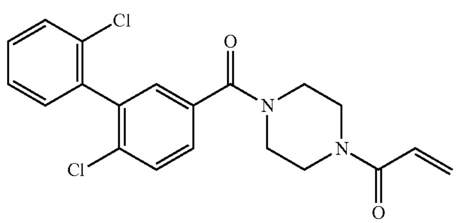 [SMILES: C=CC(=O)N1CCN(C(=O)c2ccc(Cl)c(-c3ccccc3Cl)c2)CC1] | 1-(4-(2',6-dichlorobiphenylcarbonyl)piperazin-1-yl)prop-2-en-1-one | 389.20 |
| VI-13 | 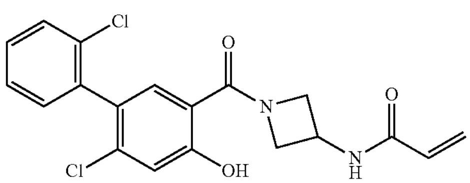 [SMILES: C=CC(=O)NC1CN(C(=O)c2cc(-c3ccccc3Cl)c(Cl)cc2O)C1] | N-(1-(2',6-dichloro-4-hydroxybiphenylcarbonyl)azetidin-3-yl)acrylamide | 389.30 |
| VI-14 | 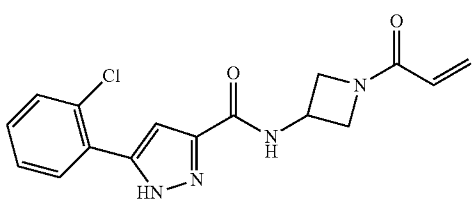 [SMILES: C=CC(=O)N1CC(NC(=O)c2cc(-c3ccccc3Cl)[nH]n2)C1] | N-(1-acryloylazetidin-3-yl)-3-(2-chlorophenyl)-1H-pyrazole-5-carboxamide | 331.15 |
| VI-15 | 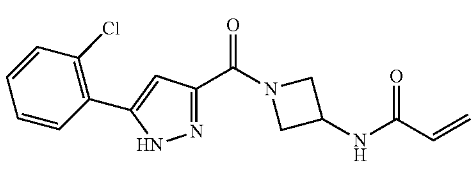 [SMILES: C=CC(=O)NC1CN(C(=O)c2cc(-c3ccccc3Cl)[nH]n2)C1] | N-(1-(3-(2-chlorophenyl)-1H-pyrazole-5-carbonyl)azetidin-3-yl)acrylamide | 331.15 |
| VI-16 | 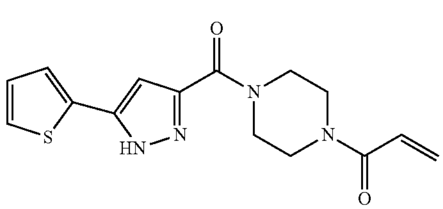 [SMILES: C=CC(=O)N1CCN(C(=O)c2cc(-c3cccs3)[nH]n2)CC1] | 1-(4-(5-(thiophen-2-yl)-1H-pyrazole-3-carbonyl)piperazin-1-yl)prop-2-en-1-one | 339.15 |

TABLE 6-continued

Representative Compounds

| No. | Structure | Name | [M + H]+ |
|---|---|---|---|
| VI-17 | 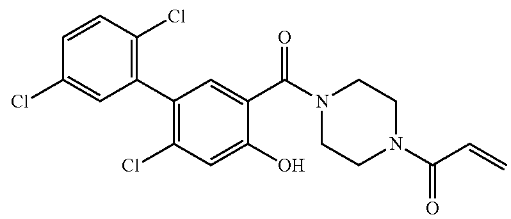 [SMILES: C=CC(=O)N1CCN(C(=O)c2cc(-c3cc(Cl)ccc3Cl)c(Cl)cc2O)CC1] | 1-(4-(2',5',6-trichloro-4-hydroxybiphenylcarbonyl)piperazin-1-yl)prop-2-en-1-one | 438.30+ |
| VI-18 | 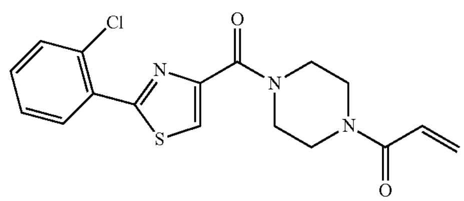 [SMILES: C=CC(=O)N1CCN(C(=O)c2csc(-c3ccccc3Cl)n2)CC1] | 1-(4-(2-(2-chlorophenyl)thiazole-4-carbonyl)piperazin-1-yl)prop-2-en-1-one | 384.15+ |
| VI-19 | 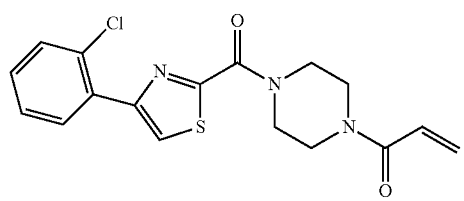 [SMILES: C=CC(=O)N1CCN(C(=O)c2nc(-c3ccccc3Cl)cs2)CC1] | 1-(4-(4-(2-chlorophenyl)thiazole-2-carbonyl)piperazin-1-yl)prop-2-en-1-one | 384.15+ |
| VI-20 | 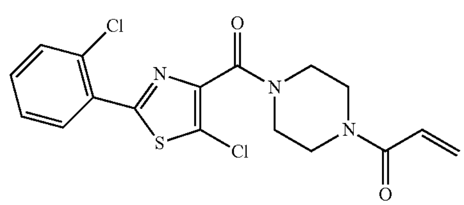 [SMILES: C=CC(=O)N1CCN(C(=O)c2nc(-c3ccccc3Cl)sc2Cl)CC1] | 1-(4-(5-chloro-2-(2-chlorophenyl)thiazole-4-carbonyl)piperazin-1-yl)prop-2-en-1-one | 418.10* |
| VI-21 | 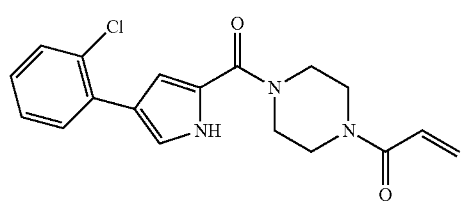 [SMILES: C=CC(=O)N1CCN(C(=O)c2cc(-c3ccccc3Cl)c[nH]2)CC1] | 1-(4-(4-(2-chlorophenyl)-1H-pyrrole-2-carbonyl)piperazin-1-yl)prop-2-en-1-one | 344.20 |
| VI-22 | 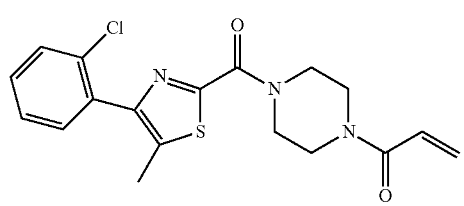 [SMILES: C=CC(=O)N1CCN(C(=O)c2nc(-c3ccccc3Cl)c(C)s2)CC1] | 1-(4-(4-(2-chlorophenyl)-5-methylthiazole-2-carbonyl)piperazin-1-yl)prop-2-en-1-one | 376.25 |
| VI-23 | 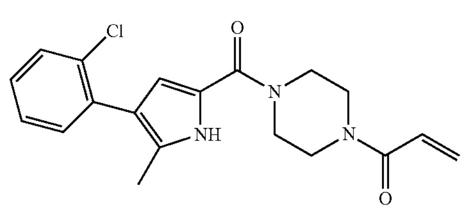 [SMILES: C=CC(=O)N1CCN(C(=O)c2cc(-c3ccccc3Cl)c(C)[nH]2)CC1] | 1-(4-(4-(2-chlorophenyl)-5-methyl-1H-pyrrole-2-carbonyl)piperazin-1-yl)prop-2-en-1-one | 356.35+ |

TABLE 6-continued

Representative Compounds

| No. | Name | [M + H]+ |
|---|---|---|
| VI-24 | (E)-1-(4-(2',6-dichloro-4-hydroxybiphenylcarbonyl)piperazin-1-yl)-4-(dimethylamino)but-2-en-1-one | 462.35 |
| VI-25 | 1-(4-(2'-chloro-5-hydroxybiphenylcarbonyl)piperazin-1-yl)prop-2-en-1-one | 371.25 |
| VI-26 | 1-(4-(2'-chloro-4-hydroxybiphenylcarbonyl)piperazin-1-yl)prop-2-en-1-one | 371.25 |
| VI-27 | 1-(4-(2',6-dichloro-5-hydroxybiphenylcarbonyl)piperazin-1-yl)prop-2-en-1-one | 403.35+ |
| VI-28 | 5-(4-acryloylpiperazine-1-carbonyl)-1-(2,5-dichlorophenyl)-4-hydroxypyridin-2(1H)-one | 422.06 |
| VI-29 | 1-(4-(6-chloro-4-hydroxybiphenylcarbonyl)piperazin-1-yl)prop-2-en-1-one | 371.25 |

TABLE 6-continued

Representative Compounds

| No. | Structure | Name | [M + H]+ |
|---|---|---|---|
| VI-30 | 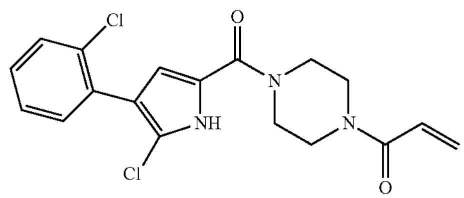 [SMILES: C=CC(=O)N1CCN(C(=O)c2cc(-c3ccccc3Cl)c(Cl)[nH]2)CC1] | 1-(4-(5-chloro-4-(2-chlorophenyl)-1H-pyrrole-2-carbonyl)piperazin-1-yl)prop-2-en-1-one | 378.25+ |
| VI-31 | 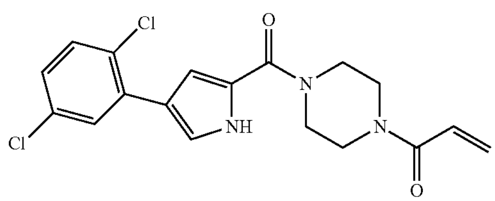 [SMILES: C=CC(=O)N1CCN(C(=O)c2cc(-c3cc(Cl)ccc3Cl)c[nH]2)CC1] | 1-(4-(4-(2,5-dichlorophenyl)-1H-pyrrole-2-carbonyl)piperazin-1-yl)prop-2-en-1-one | 378.20 |
| VI-32 | 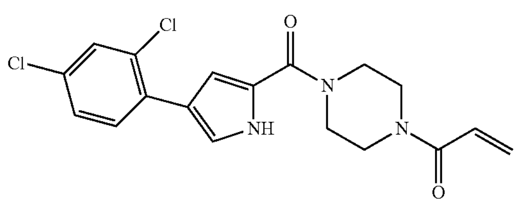 [SMILES: C=CC(=O)N1CCN(C(=O)c2cc(-c3ccc(Cl)cc3Cl)c[nH]2)CC1] | 1-(4-(4-(2,4-dichlorophenyl)-1H-pyrrole-2-carbonyl)piperazin-1-yl)prop-2-en-1-one | 377.90 |
| VI-33 | 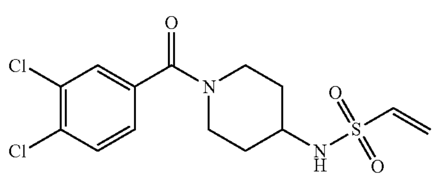 [SMILES: C=CS(=O)(=O)NC1CCN(C(=O)c2ccc(Cl)c(Cl)c2)CC1] | N-(1-(3,4-dichlorobenzoyl)piperidin-4-yl)ethenesulfonamide | 363.02 |
| VI-34 | 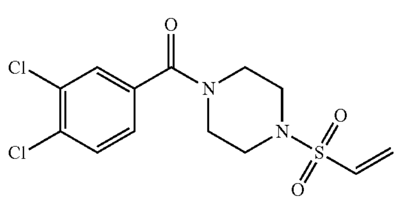 [SMILES: C=CS(=O)(=O)N1CCN(C(=O)c2ccc(Cl)c(Cl)c2)CC1] | (3,4-dichlorophenyl)(4-(vinylsulfonyl)piperazin-1-yl)methanone | 349.04 |
| VI-35 | 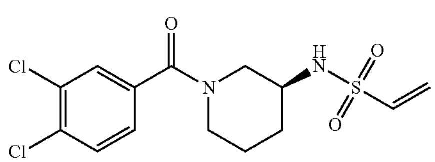 [SMILES: C=CS(=O)(=O)N[C@H]1CCCN(C(=O)c2ccc(Cl)c(Cl)c2)C1] | (S)-N-(1-(3,4-dichlorobenzoyl)piperidin-3-yl)ethenesulfonamide | 363.06 |
| VI-36 | 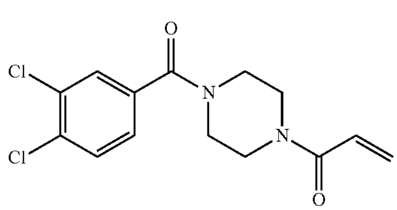 [SMILES: C=CC(=O)N1CCN(C(=O)c2ccc(Cl)c(Cl)c2)CC1] | 1-(4-(3,4-dichlorobenzoyl)piperazin-1-yl)prop-2-en-1-one | 312.99 |

TABLE 6-continued

Representative Compounds

| No. | Structure | Name | [M + H]+ |
|---|---|---|---|
| VI-37 | 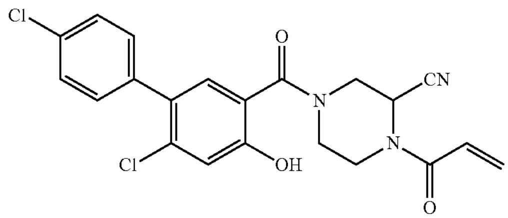 [SMILES: C=CC(=O)N1CCN(C(=O)c2cc(-c3ccc(Cl)cc3)c(Cl)cc2O)CC1C#N] | 1-acryloyl-4-(4',6-dichloro-4-hydroxybiphenylcarbonyl)piperazine-2-carbonitrile | 430.30 |
| VI-38 | 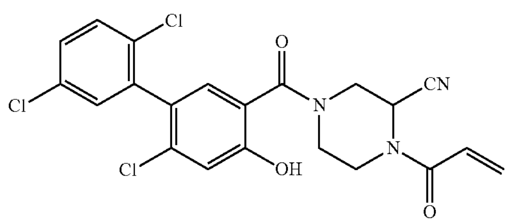 [SMILES: C=CC(=O)N1CCN(C(=O)c2cc(-c3cc(Cl)ccc3Cl)c(Cl)cc2O)CC1C#N] | 1-acryloyl-4-(2',5',6-trichloro-4-hydroxybiphenylcarbonyl)piperazine-2-carbonitrile | 464.30 |
| VI-39 | 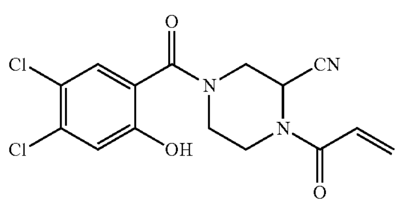 [SMILES: C=CC(=O)N1CCN(C(=O)c2cc(Cl)c(Cl)cc2O)CC1C#N] | 1-acryloyl-4-(4,5-dichloro-2-hydroxybenzoyl)piperazine-2-carbonitrile | 354.15 |
| VI-40 | 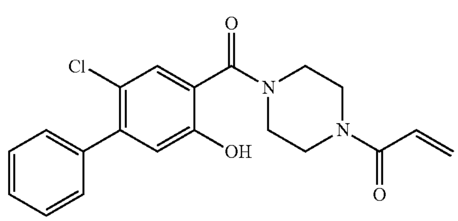 [SMILES: C=CC(=O)N1CCN(C(=O)c2cc(Cl)c(-c3ccccc3)cc2O)CC1] | 1-(4-(2-chloro-5-hydroxybiphenylcarbonyl)piperazin-1-yl)prop-2-en-1-one | 371.25 |
| VI-41 | 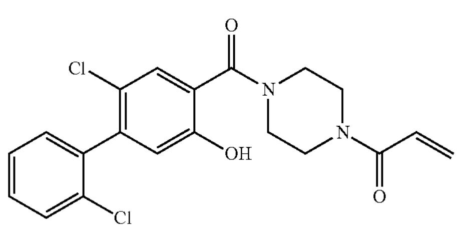 [SMILES: C=CC(=O)N1CCN(C(=O)c2cc(Cl)c(-c3ccccc3Cl)cc2O)CC1] | 1-(4-(2,2'-chloro-5-hydroxybiphenylcarbonyl)piperazin-1-yl)prop-2-en-1-one | 405.25 |
| VI-42 | 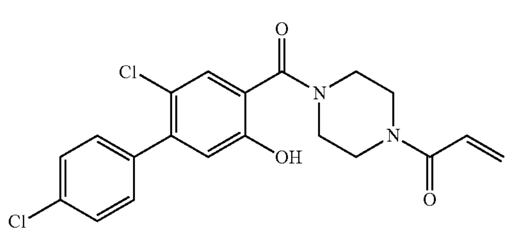 [SMILES: C=CC(=O)N1CCN(C(=O)c2cc(Cl)c(-c3ccc(Cl)cc3)cc2O)CC1] | 1-(4-(2,4'-dichloro-5-hydroxybiphenylcarbonyl)piperazin-1-yl)prop-2-en-1-one | 405.20 |

TABLE 6-continued

Representative Compounds

| No. | Structure | Name | [M + H]+ |
|---|---|---|---|
| VI-43 | 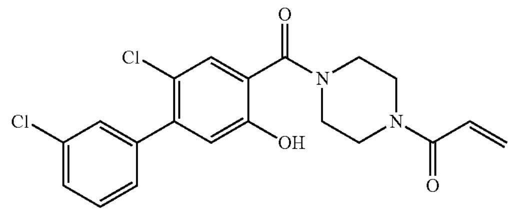 [SMILES: C=CC(=O)N1CCN(C(=O)c2cc(Cl)c(-c3cccc(Cl)c3)cc2O)CC1] | 1-(4-(2,3'-dichloro-5-hydroxybiphenylcarbonyl)piperazin-1-yl)prop-2-en-1-one | 405.25 |

*[M + Na]+
†[M − H]−
[M]

Pharmaceutical Compositions

Other embodiments are directed to pharmaceutical compositions. The pharmaceutical composition comprises any one (or more) of the foregoing compounds and a pharmaceutically acceptable carrier. In some embodiments, the pharmaceutical composition is formulated for oral administration. In other embodiments, the pharmaceutical composition is formulated for injection. In still more embodiments, the pharmaceutical compositions comprise a compound as disclosed herein and an additional therapeutic agent (e.g., anticancer agent). Non-limiting examples of such therapeutic agents are described herein below.

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a compound as described herein is administered in a local rather than systemic manner, for example, via injection of the compound directly into an organ, often in a depot preparation or sustained release formulation. In specific embodiments, long acting formulations are administered by implantation (for example subcutaneously or intramuscularly) or by intramuscular injection. Furthermore, in other embodiments, the drug is delivered in a targeted drug delivery system, for example, in a liposome coated with organ-specific antibody. In such embodiments, the liposomes are targeted to and taken up selectively by the organ. In yet other embodiments, the compound as described herein is provided in the form of a rapid release formulation, in the form of an extended release formulation, or in the form of an intermediate release formulation. In yet other embodiments, the compound described herein is administered topically.

The compounds according to the invention are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that are used in some embodiments. An exemplary dosage is 10 to 30 mg per day. The exact dosage will depend upon the route of administration, the form in which the compound is administered, the subject to be treated, the body weight of the subject to be treated, and the preference and experience of the attending physician.

In some embodiments, a compound of the invention is administered in a single dose. Typically, such administration will be by injection, e.g., intravenous injection, in order to introduce the agent quickly. However, other routes are used as appropriate. In some embodiments, a single dose of a compound of the invention is used for treatment of an acute condition.

In some embodiments, a compound of the invention is administered in multiple doses. In some embodiments, dosing is about once, twice, three times, four times, five times, six times, or more than six times per day. In other embodiments, dosing is about once a month, once every two weeks, once a week, or once every other day. In another embodiment a compound of the invention and another agent are administered together about once per day to about 6 times per day. In another embodiment the administration of a compound of the invention and an agent continues for less than about 7 days. In yet another embodiment the administration continues for more than about 6, 10, 14, 28 days, two months, six months, or one year. In some cases, continuous dosing is achieved and maintained as long as necessary.

Administration of the compounds of the invention may continue as long as necessary. In some embodiments, a compound of the invention is administered for more than 1, 2, 3, 4, 5, 6, 7, 14, or 28 days. In some embodiments, a compound of the invention is administered for less than 28, 14, 7, 6, 5, 4, 3, 2, or 1 day. In some embodiments, a compound of the invention is administered chronically on an ongoing basis, e.g., for the treatment of chronic effects.

In some embodiments, the compounds of the invention are administered in dosages. It is known in the art that due to intersubject variability in compound pharmacokinetics, individualization of dosing regimen is necessary for optimal therapy. Dosing for a compound of the invention may be found by routine experimentation in light of the instant disclosure.

In some embodiments, the compounds described herein are formulated into pharmaceutical compositions. In specific embodiments, pharmaceutical compositions are formulated in a conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients are used as suitable to formulate the pharmaceutical compositions described herein: Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999).

Provided herein are pharmaceutical compositions comprising a compound of structure (I) and a pharmaceutically acceptable diluent(s), excipient(s), or carrier(s). In certain embodiments, the compounds described are administered as pharmaceutical compositions in which compounds of structure (I) are mixed with other active ingredients, as in combination therapy. Encompassed herein are all combinations of actives set forth in the combination therapies section below and throughout this disclosure. In specific embodiments, the pharmaceutical compositions include one or more compounds of structure (I).

A pharmaceutical composition, as used herein, refers to a mixture of a compound of structure (I) with other chemical components, such as carriers, stabilizers, diluents, dispersing agents, suspending agents, thickening agents, and/or excipients. In certain embodiments, the pharmaceutical composition facilitates administration of the compound to an organism. In some embodiments, practicing the methods of treatment or use provided herein, therapeutically effective amounts of compounds of structure (I) provided herein are administered in a pharmaceutical composition to a mammal having a disease, disorder or medical condition to be treated. In specific embodiments, the mammal is a human. In certain embodiments, therapeutically effective amounts vary depending on the severity of the disease, the age and relative health of the subject, the potency of the compound used and other factors. The compounds described herein are used singly or in combination with one or more therapeutic agents as components of mixtures.

In one embodiment, one or more compounds of structure (I) is formulated in an aqueous solutions. In specific embodiments, the aqueous solution is selected from, by way of example only, a physiologically compatible buffer, such as Hank's solution, Ringer's solution, or physiological saline buffer. In other embodiments, one or more compound of structure (I) is/are formulated for transmucosal administration. In specific embodiments, transmucosal formulations include penetrants that are appropriate to the barrier to be permeated. In still other embodiments wherein the compounds described herein are formulated for other parenteral injections, appropriate formulations include aqueous or non-aqueous solutions. In specific embodiments, such solutions include physiologically compatible buffers and/or excipients.

In another embodiment, compounds described herein are formulated for oral administration. Compounds described herein are formulated by combining the active compounds with, e.g., pharmaceutically acceptable carriers or excipients. In various embodiments, the compounds described herein are formulated in oral dosage forms that include, by way of example only, tablets, powders, pills, dragees, capsules, liquids, gels, syrups, elixirs, slurries, suspensions and the like.

In certain embodiments, pharmaceutical preparations for oral use are obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. In specific embodiments, disintegrating agents are optionally added. Disintegrating agents include, by way of example only, cross-linked croscarmellose sodium, polyvinylpyrrolidone, agar, or alginic acid or a salt thereof such as sodium alginate.

In one embodiment, dosage forms, such as dragee cores and tablets, are provided with one or more suitable coating. In specific embodiments, concentrated sugar solutions are used for coating the dosage form. The sugar solutions, optionally contain additional components, such as by way of example only, gum arabic, talc, polyvinylpyrrolidone, carbopol gel, polyethylene glycol, and/or titanium dioxide, lacquer solutions, and suitable organic solvents or solvent mixtures. Dyestuffs and/or pigments are also optionally added to the coatings for identification purposes. Additionally, the dyestuffs and/or pigments are optionally utilized to characterize different combinations of active compound doses.

In certain embodiments, therapeutically effective amounts of at least one of the compounds described herein are formulated into other oral dosage forms. Oral dosage forms include push-fit capsules made of gelatin, as well as soft, sealed capsules made of gelatin and a plasticizer, such as glycerol or sorbitol. In specific embodiments, push-fit capsules contain the active ingredients in admixture with one or more filler. Fillers include, by way of example only, lactose, binders such as starches, and/or lubricants such as talc or magnesium stearate and, optionally, stabilizers. In other embodiments, soft capsules, contain one or more active compound that is dissolved or suspended in a suitable liquid. Suitable liquids include, by way of example only, one or more fatty oil, liquid paraffin, or liquid polyethylene glycol. In addition, stabilizers are optionally added.

In other embodiments, therapeutically effective amounts of at least one of the compounds described herein are formulated for buccal or sublingual administration. Formulations suitable for buccal or sublingual administration include, by way of example only, tablets, lozenges, or gels. In still other embodiments, the compounds described herein are formulated for parental injection, including formulations suitable for bolus injection or continuous infusion. In specific embodiments, formulations for injection are presented in unit dosage form (e.g., in ampoules) or in multi-dose containers. Preservatives are, optionally, added to the injection formulations. In still other embodiments, the pharmaceutical compositions are formulated in a form suitable for parenteral injection as sterile suspensions, solutions or emulsions in oily or aqueous vehicles. Parenteral injection formulations optionally contain formulatory agents such as suspending, stabilizing and/or dispersing agents. In specific embodiments, pharmaceutical formulations for parenteral administration include aqueous solutions of the active compounds in water-soluble form. In additional embodiments, suspensions of the active compounds (e.g., compounds of structure (I)) are prepared as appropriate oily injection suspensions. Suitable lipophilic solvents or vehicles for use in the pharmaceutical compositions described herein include, by way of example only, fatty oils such as sesame oil, or synthetic fatty acid esters, such as ethyl oleate or triglycerides, or liposomes. In certain specific embodiments, aqueous injection suspensions contain substances which increase the viscosity of the suspension, such as sodium carboxymethyl cellulose, sorbitol, or dextran. Optionally, the suspension contains suitable stabilizers or agents which increase the solubility of the compounds to allow for the preparation of highly concentrated solutions. Alternatively, in other embodiments, the active ingredient is in powder form for constitution with a suitable vehicle, e.g., sterile pyrogen-free water, before use.

In still other embodiments, the compounds of structure (I) are administered topically. The compounds described herein are formulated into a variety of topically administrable compositions, such as solutions, suspensions, lotions, gels, pastes, medicated sticks, balms, creams or ointments. Such pharmaceutical compositions optionally contain solubilizers, stabilizers, tonicity enhancing agents, buffers and preservatives.

In yet other embodiments, the compounds of structure (I) are formulated for transdermal administration. In specific embodiments, transdermal formulations employ transdermal delivery devices and transdermal delivery patches and can be lipophilic emulsions or buffered, aqueous solutions, dissolved and/or dispersed in a polymer or an adhesive. In various embodiments, such patches are constructed for continuous, pulsatile, or on demand delivery of pharmaceutical agents. In additional embodiments, the transdermal delivery of the compounds of structure (I) is accomplished by means of iontophoretic patches and the like. In certain embodiments, transdermal patches provide controlled delivery of the compounds of structure (I). In specific embodiments, the rate of absorption is slowed by using rate-controlling membranes or by trapping the compound within a polymer matrix or gel. In alternative embodiments, absorption enhancers are used to increase absorption. Absorption enhancers or carriers include absorbable pharmaceutically acceptable solvents that assist passage through the skin. For example, in one embodiment, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

In other embodiments, the compounds of structure (I) are formulated for administration by inhalation. Various forms suitable for administration by inhalation include, but are not limited to, aerosols, mists or powders. Pharmaceutical compositions of any of compound of structure (I) are conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). In specific embodiments, the dosage unit of a pressurized aerosol is determined by providing a valve to deliver a metered amount. In certain embodiments, capsules and cartridges of, such as, by way of example only, gelatin for use in an inhaler or insufflator are formulated containing a powder mix of the compound and a suitable powder base such as lactose or starch.

In still other embodiments, the compounds of structure (I) are formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

In certain embodiments, pharmaceutical compositions are formulated in any conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients are optionally used as suitable. Pharmaceutical compositions comprising a compound of structure (I) are manufactured in a conventional manner, such as, by way of example only, by means of conventional mixing, dissolving, granulating, dragee-making, levigating, emulsifying, encapsulating, entrapping or compression processes.

Pharmaceutical compositions include at least one pharmaceutically acceptable carrier, diluent or excipient and at least one compound of structure (I), described herein as an active ingredient. The active ingredient is in free-acid or free-base form, or in a pharmaceutically acceptable salt form. In addition, the methods and pharmaceutical compositions described herein include the use of N-oxides, crystalline forms (also known as polymorphs), as well as active metabolites of these compounds having the same type of activity. All tautomers of the compounds described herein are included within the scope of the compounds presented herein. Additionally, the compounds described herein encompass unsolvated as well as solvated forms with pharmaceutically acceptable solvents such as water, ethanol, and the like. The solvated forms of the compounds presented herein are also considered to be disclosed herein. In addition, the pharmaceutical compositions optionally include other medicinal or pharmaceutical agents, carriers, adjuvants, such as preserving, stabilizing, wetting or emulsifying agents, solution promoters, salts for regulating the osmotic pressure, buffers, and/or other therapeutically valuable substances.

Methods for the preparation of compositions comprising the compounds described herein include formulating the compounds with one or more inert, pharmaceutically acceptable excipients or carriers to form a solid, semi-solid or liquid. Solid compositions include, but are not limited to, powders, tablets, dispersible granules, capsules, cachets, and suppositories. Liquid compositions include solutions in which a compound is dissolved, emulsions comprising a compound, or a solution containing liposomes, micelles, or nanoparticles comprising a compound as disclosed herein. Semi-solid compositions include, but are not limited to, gels, suspensions and creams. The form of the pharmaceutical compositions described herein include liquid solutions or suspensions, solid forms suitable for solution or suspension in a liquid prior to use, or as emulsions. These compositions also optionally contain minor amounts of nontoxic, auxiliary substances, such as wetting or emulsifying agents, pH buffering agents, and so forth.

In some embodiments, pharmaceutical composition comprising at least one compound of structure (I) illustratively takes the form of a liquid where the agents are present in solution, in suspension or both. Typically when the composition is administered as a solution or suspension a first portion of the agent is present in solution and a second portion of the agent is present in particulate form, in suspension in a liquid matrix. In some embodiments, a liquid composition includes a gel formulation. In other embodiments, the liquid composition is aqueous.

In certain embodiments, useful aqueous suspensions contain one or more polymers as suspending agents. Useful polymers include water-soluble polymers such as cellulosic polymers, e.g., hydroxypropyl methylcellulose, and water-insoluble polymers such as cross-linked carboxyl-containing polymers. Certain pharmaceutical compositions described herein comprise a mucoadhesive polymer, selected for example from carboxymethylcellulose, carbomer (acrylic acid polymer), poly(methylmethacrylate), polyacrylamide, polycarbophil, acrylic acid/butyl acrylate copolymer, sodium alginate and dextran.

Useful pharmaceutical compositions also, optionally, include solubilizing agents to aid in the solubility of a compound of structure (I). The term "solubilizing agent" generally includes agents that result in formation of a micellar solution or a true solution of the agent. Certain acceptable nonionic surfactants, for example polysorbate 80, are useful as solubilizing agents, as can ophthalmically acceptable glycols, polyglycols, e.g., polyethylene glycol 400, and glycol ethers.

Furthermore, useful pharmaceutical compositions optionally include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Additionally, useful compositions also, optionally, include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Other useful pharmaceutical compositions optionally include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Still other useful compositions include one or more surfactants to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

Still other useful compositions include one or more antioxidants to enhance chemical stability where required. Suitable antioxidants include, by way of example only, ascorbic acid and sodium metabisulfite.

In certain embodiments, aqueous suspension compositions are packaged in single-dose non-reclosable containers. Alternatively, multiple-dose reclosable containers are used, in which case it is typical to include a preservative in the composition.

In alternative embodiments, other delivery systems for hydrophobic pharmaceutical compounds are employed. Liposomes and emulsions are examples of delivery vehicles or carriers useful herein. In certain embodiments, organic solvents such as N-methylpyrrolidone are also employed. In additional embodiments, the compounds described herein are delivered using a sustained-release system, such as semipermeable matrices of solid hydrophobic polymers containing the therapeutic agent. Various sustained-release materials are useful herein. In some embodiments, sustained-release capsules release the compounds for a few weeks up to over 100 days. Depending on the chemical nature and the biological stability of the therapeutic reagent, additional strategies for protein stabilization are employed.

In certain embodiments, the formulations described herein comprise one or more antioxidants, metal chelating agents, thiol containing compounds and/or other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

In some embodiments, the concentration of one or more compounds provided in the pharmaceutical compositions of the present invention is less than 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v or v/v.

In some embodiments, the concentration of one or more compounds of the invention is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v, or v/v.

In some embodiments, the concentration of one or more compounds of the invention is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, approximately 1% to approximately 10% w/w, w/v or v/v.

In some embodiments, the concentration of one or more compounds of the invention is in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, approximately 0.1% to approximately 0.9% w/w, w/v or v/v.

In some embodiments, the amount of one or more compounds of the invention is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of one or more compounds of the invention is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g.

In some embodiments, the amount of one or more compounds of the invention is in the range of 0.0001-10 g, 0.0005-9 g, 0.001-8 g, 0.005-7 g, 0.01-6 g, 0.05-5 g, 0.1-4 g, 0.5-4 g, or 1-3 g.

Kits/Articles of Manufacture

For use in the therapeutic applications described herein, kits and articles of manufacture are also provided. In some embodiments, such kits comprise a carrier, package, or container that is compartmentalized to receive one or more containers such as vials, tubes, and the like, each of the container (s) comprising one of the separate elements to be used in a method described herein. Suitable containers include, for example, bottles, vials, syringes, and test tubes. The containers are formed from a variety of materials such as glass or plastic.

The articles of manufacture provided herein contain packaging materials. Packaging materials for use in packaging pharmaceutical products include those found in, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. For example, the container(s) includes one or more compounds described herein, optionally in a composition or in combination with another agent as disclosed herein. The container(s) optionally have a sterile access port (for example the container is an intravenous solution bag or a vial having a stopper pierceable by a hypodermic injection needle). Such kits optionally comprising a compound with an identifying description or label or instructions relating to its use in the methods described herein.

For example, a kit typically includes one or more additional containers, each with one or more of various materials (such as reagents, optionally in concentrated form, and/or devices) desirable from a commercial and user standpoint for use of a compound described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included. A label is optionally on or associated with the container. For example, a label is on a container when letters, numbers or other characters forming the label are attached, molded or etched into the container itself, a label is associated with a container when it is present within a receptacle or carrier that also holds the container, e.g., as a package insert. In addition, a label is used to indicate that the contents are to be used for a specific therapeutic application. In addition, the label indicates directions for use of the contents, such as in the methods described herein. In certain embodiments, the pharmaceutical compositions is presented in a pack or dispenser device which contains one or more unit dosage forms containing a compound provided herein. The pack for example contains metal or plastic foil, such as a blister pack. Or, the pack or dispenser device is accompanied by instructions for administration. Or, the pack or dispenser is accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In some embodiments, compositions containing a compound provided herein formulated in a compatible pharmaceutical carrier are prepared, placed in an appropriate container, and labeled for treatment of an indicated condition.

Methods

The present invention provides a method of inhibiting Ras-mediated cell signaling comprising contacting a cell with an effective amount of one or more compounds disclosed herein. Inhibition of Ras-mediated signal transduction can be assessed and demonstrated by a wide variety of ways known in the art. Non-limiting examples include a showing of (a) a decrease in GTPase activity of Ras; (b) a decrease in GTP binding affinity or an increase in GDP binding affinity; (c) an increase in K off of GTP or a decrease in K off of GDP; (d) a decrease in the levels of signaling transduction molecules downstream in the Ras pathway, such as a decrease in pMEK level; and/or (e) a decrease in binding of Ras complex to downstream signaling molecules including but not limited to Raf. Kits and commercially available assays can be utilized for determining one or more of the above.

The invention also provides methods of using the compounds or pharmaceutical compositions of the present invention to treat disease conditions, including but not limited to conditions implicated by G12C K-Ras, H-Ras or N-Ras mutation, G12C H-Ras mutation and/or G12C N-Ras mutation (e.g., cancer).

In some embodiments, a method for treatment of cancer is provided, the method comprising administering an effective amount of any of the foregoing pharmaceutical compositions comprising a compound of structure (I) to a subject in need thereof. In some embodiments, the cancer is mediated by a K-Ras, H-Ras or N-Ras G12C mutation. In other embodiments, the cancer is pancreatic cancer, colon cancer, MYH associated polyposis, colorectal cancer or lung cancer.

In some embodiments the invention provides method of treating a disorder in a subject in need thereof, wherein the said method comprises determining if the subject has a K-Ras, H-Ras or N-Ras G12C mutation and if the subject is determined to have the K-Ras, H-Ras or N-Ras G12C mutation, then administering to the subject a therapeutically effective dose of at least one compound of structure (I) or a pharmaceutically acceptable salt, ester, prodrug, tautomer, solvate, hydrate or derivative thereof.

The disclosed compounds strongly inhibit anchorage-independent cell growth and therefore have the potential to inhibit tumor metastasis. Accordingly, in another embodiment the disclosure provides a method for inhibiting tumor metastasis, the method comprising administering an effective amount a pharmaceutical composition of comprising any of the compounds disclosed herein and a pharmaceutically acceptable carrier to a subject in need thereof.

K-Ras, H-Ras or N-Ras G12C mutations have also been identified in hematological malignancies (e.g., cancers that affect blood, bone marrow and/or lymph nodes). Accordingly, certain embodiments are directed to administration of a disclosed compounds (e.g., in the form of a pharmaceutical composition) to a patient in need of treatment of a hematological malignancy. Such malignancies include, but are not limited to leukemias and lymphomas. For example, the presently disclosed compounds can be used for treatment of diseases such as Acute lymphoblastic leukemia (ALL), Acute myelogenous leukemia (AML), Chronic lymphocytic leukemia (CLL), small lymphocytic lymphoma (SLL), Chronic myelogenous leukemia (CML), Acute monocytic leukemia (AMoL) and/or other leukemias. In other embodiments, the compounds are useful for treatment of lymphomas such as all subtypes of Hodgkins lymphoma or non-Hodgkins lymphoma.

Determining whether a tumor or cancer comprises a G12C K-Ras, H-Ras or N-Ras mutation can be undertaken by assessing the nucleotide sequence encoding the K-Ras, H-Ras or N-Ras protein, by assessing the amino acid sequence of the K-Ras, H-Ras or N-Ras protein, or by assessing the characteristics of a putative K-Ras, H-Ras or N-Ras mutant protein. The sequence of wild-type human K-Ras, H-Ras or N-Ras is known in the art, (e.g. Accession No. NP203524).

Methods for detecting a mutation in a K-Ras, H-Ras or N-Ras nucleotide sequence are known by those of skill in the art. These methods include, but are not limited to, polymerase chain reaction-restriction fragment length polymorphism (PCR-RFLP) assays, polymerase chain reaction-single strand conformation polymorphism (PCR-SSCP) assays, real-time PCR assays, PCR sequencing, mutant allele-specific PCR amplification (MASA) assays, direct sequencing, primer extension reactions, electrophoresis, oligonucleotide ligation assays, hybridization assays, TaqMan assays, SNP genotyping assays, high resolution melting assays and microarray analyses. In some embodiments, samples are evaluated for G12C K-Ras, H-Ras or N-Ras mutations by real-time PCR. In real-time PCR, fluorescent probes specific for the K-Ras, H-Ras or N-Ras G12C mutation are used. When a mutation is present, the probe binds and fluorescence is detected. In some embodiments, the K-Ras, H-Ras or N-Ras G12C mutation is identified using a direct sequencing method of specific regions (e.g., exon 2 and/or exon 3) in the K-Ras, H-Ras or N-Ras gene. This technique will identify all possible mutations in the region sequenced.

Methods for detecting a mutation in a K-Ras, H-Ras or N-Ras protein are known by those of skill in the art. These methods include, but are not limited to, detection of a K-Ras, H-Ras or N-Ras mutant using a binding agent (e.g., an antibody) specific for the mutant protein, protein electrophoresis and Western blotting, and direct peptide sequencing.

Methods for determining whether a tumor or cancer comprises a G12C K-Ras, H-Ras or N-Ras mutation can use a variety of samples. In some embodiments, the sample is taken from a subject having a tumor or cancer. In some embodiments, the sample is taken from a subject having a cancer or tumor. In some embodiments, the sample is a fresh tumor/cancer sample. In some embodiments, the sample is a frozen tumor/cancer sample. In some embodiments, the sample is a formalin-fixed paraffin-embedded sample. In some embodiments, the sample is processed to a cell lysate. In some embodiments, the sample is processed to DNA or RNA.

The invention also relates to a method of treating a hyperproliferative disorder in a mammal that comprises administering to said mammal a therapeutically effective amount of a compound of the present invention, or a pharmaceutically acceptable salt, ester, prodrug, solvate, hydrate or derivative thereof. In some embodiments, said method relates to the treatment of cancer such as acute myeloid leukemia, cancer in adolescents, adrenocortical carcinoma childhood, AIDS-related cancers (e.g. Lymphoma and Kaposi's Sarcoma), anal cancer, appendix cancer, astrocytomas, atypical teratoid, basal cell carcinoma, bile duct cancer, bladder cancer, bone cancer, brain stem glioma, brain tumor, breast cancer, bronchial tumors, burkitt lymphoma, carcinoid tumor, atypical teratoid, embryonal tumors, germ cell tumor, primary lymphoma, cervical cancer, childhood cancers, chordoma, cardiac tumors, chronic lymphocytic leukemia (CLL), chronic myelogenous leukemia (CML), chronic myeloproliferative disorders, colon cancer, colorectal cancer, craniopharyngioma, cutaneous T-cell lymphoma, extrahepatic ductal carcinoma in situ (DCIS), embryonal tumors, CNS cancer, endometrial cancer, ependymoma, esophageal cancer, esthesioneuroblastoma, ewing sarcoma, extracranial germ cell tumor, extragonadal germ cell tumor, eye cancer, fibrous histiocytoma of bone, gall bladder cancer, gastric cancer, gastrointestinal carcinoid tumor, gastrointestinal stromal tumors (GIST), germ cell tumor, gestational trophoblastic tumor, hairy cell leukemia, head and neck cancer, heart cancer, liver cancer, hodgkin lymphoma, hypopharyngeal cancer, intraocular melanoma, islet cell tumors, pancreatic neuroendocrine tumors, kidney cancer, laryngeal cancer, lip and oral cavity cancer, liver cancer, lobular carcinoma in situ (LCIS), lung cancer, lymphoma, metastatic squamous neck cancer with occult primary, midline tract carcinoma, mouth cancer multiple endocrine neoplasia syndromes, multiple myeloma/plasma cell neoplasm, mycosis fungoides, myelodysplastic syndromes, myelodysplastic/myeloproliferative neoplasms, multiple myeloma, merkel cell carcinoma, malignant mesothelioma, malignant fibrous histiocytoma of bone and osteosarcoma, nasal cavity and paranasal sinus cancer, nasopharyngeal cancer, neuroblastoma, non-hodgkin lymphoma, non-small cell lung cancer (NSCLC), oral cancer, lip and oral cavity cancer, oropharyngeal cancer, ovarian cancer, pancreatic cancer, papillomatosis, paraganglioma, paranasal sinus and nasal cavity cancer, parathyroid cancer, penile cancer, pharyngeal cancer, pleuropulmonary blastoma, primary central nervous system (CNS) lymphoma, prostate cancer, rectal cancer, transitional cell cancer, retinoblastoma, rhabdomyosarcoma, salivary gland cancer, skin cancer, stomach (gastric) cancer, small cell lung cancer, small intestine cancer, soft tissue sarcoma, T-Cell lymphoma, testicular cancer, throat cancer, thymoma and thymic carcinoma, thyroid cancer, transitional cell cancer of the renal pelvis and ureter, trophoblastic tumor, unusual cancers of childhood, urethral cancer, uterine sarcoma, vaginal cancer, vulvar cancer, or Viral-Induced cancer. In some embodiments, said method relates to the treatment of a non-cancerous hyperproliferative disorder such as benign hyperplasia of the skin (e.g., psoriasis), restenosis, or prostate (e.g., benign prostatic hypertrophy (BPH)).

In certain particular embodiments, the invention relates to methods for treatment of lung cancers, the methods comprise administering an effective amount of any of the above described compound (or a pharmaceutical composition comprising the same) to a subject in need thereof. In certain embodiments the lung cancer is a non-small cell lung carcinoma (NSCLC), for example adenocarcinoma, squamous-cell lung carcinoma or large-cell lung carcinoma. In other embodiments, the lung cancer is a small cell lung carcinoma. Other lung cancers treatable with the disclosed compounds include, but are not limited to, glandular tumors, carcinoid tumors and undifferentiated carcinomas.

Subjects that can be treated with compounds of the invention, or pharmaceutically acceptable salt, ester, prodrug, solvate, tautomer, hydrate or derivative of said compounds, according to the methods of this invention include, for example, subjects that have been diagnosed as having acute myeloid leukemia, acute myeloid leukemia, cancer in adolescents, adrenocortical carcinoma childhood, AIDS-related cancers (e.g. Lymphoma and Kaposi's Sarcoma), anal cancer, appendix cancer, astrocytomas, atypical teratoid, basal cell carcinoma, bile duct cancer, bladder cancer, bone cancer, brain stem glioma, brain tumor, breast cancer, bronchial tumors, burkitt lymphoma, carcinoid tumor, atypical teratoid, embryonal tumors, germ cell tumor, primary lymphoma, cervical cancer, childhood cancers, chordoma, cardiac tumors, chronic lymphocytic leukemia (CLL), chronic myelogenous leukemia (CML), chronic myeloproliferative disorders, colon cancer, colorectal cancer, craniopharyngioma, cutaneous T-cell lymphoma, extrahepatic ductal carcinoma in situ (DCIS), embryonal tumors, CNS cancer, endometrial cancer, ependymoma, esophageal cancer, esthesioneuroblastoma, ewing sarcoma, extracranial germ cell tumor, extragonadal germ cell tumor, eye cancer, fibrous histiocytoma of bone, gall bladder cancer, gastric cancer, gastrointestinal carcinoid tumor, gastrointestinal stromal tumors (GIST), germ cell tumor, gestational trophoblastic tumor, hairy cell leukemia, head and neck cancer, heart cancer, liver cancer, hodgkin lymphoma, hypopharyngeal cancer, intraocular melanoma, islet cell tumors, pancreatic neuroendocrine tumors, kidney cancer, laryngeal cancer, lip and oral cavity cancer, liver cancer, lobular carcinoma in situ (LCIS), lung cancer, lymphoma, metastatic squamous neck cancer with occult primary, midline tract carcinoma, mouth cancer multiple endocrine neoplasia syndromes, multiple myeloma/plasma cell neoplasm, mycosis fungoides, myelodysplastic syndromes, myelodysplastic/myeloproliferative neoplasms, multiple myeloma, merkel cell carcinoma, malignant mesothelioma, malignant fibrous histiocytoma of bone and osteosarcoma, nasal cavity and paranasal sinus cancer, nasopharyngeal cancer, neuroblastoma, non-hodgkin lymphoma, non-small cell lung cancer (NSCLC), oral cancer, lip and oral cavity cancer, oropharyngeal cancer, ovarian cancer, pancreatic cancer, papillomatosis, paraganglioma, paranasal sinus and nasal cavity cancer, parathyroid cancer, penile cancer, pharyngeal cancer, pleuropulmonary blastoma, primary central nervous system (CNS) lymphoma, prostate cancer, rectal cancer, transitional cell cancer, retinoblastoma, rhabdomyosarcoma, salivary gland cancer, skin cancer, stomach (gastric) cancer, small cell lung cancer, small intestine cancer, soft tissue sarcoma, T-Cell lymphoma, testicular cancer, throat cancer, thymoma and thymic carcinoma, thyroid cancer, transitional cell cancer of the renal pelvis and ureter, trophoblastic tumor, unusual cancers of childhood, urethral cancer, uterine sarcoma, vaginal cancer, vulvar cancer, or Viral-Induced cancer. In some embodiments subjects that are treated with the compounds of the invention include subjects that have been diagnosed as having a non-cancerous hyperproliferative disorder such as benign hyperplasia of the skin (e.g., psoriasis), restenosis, or prostate (e.g., benign prostatic hypertrophy (BPH)).

The invention further provides methods of modulating a G12C Mutant K-Ras, H-Ras or N-Ras protein activity by contacting the protein with an effective amount of a compound of the invention. Modulation can be inhibiting or activating protein activity. In some embodiments, the invention provides methods of inhibiting protein activity by contacting the G12C Mutant K-Ras, H-Ras or N-Ras protein with an effective amount of a compound of the invention in solution. In some embodiments, the invention provides methods of inhibiting the G12C Mutant K-Ras, H-Ras or N-Ras protein activity by contacting a cell, tissue, organ that express the protein of interest. In some embodiments, the invention provides methods of inhibiting protein activity in subject including but not limited to rodents and mammal (e.g., human) by administering into the subject an effective amount of a compound of the invention. In some embodiments, the percentage modulation exceeds 25%, 30%, 40%, 50%, 60%, 70%, 80%, or 90%. In some embodiments, the percentage of inhibiting exceeds 25%, 30%, 40%, 50%, 60%, 70%, 80%, or 90%.

In some embodiments, the invention provides methods of inhibiting K-Ras, H-Ras or N-Ras G12C activity in a cell by contacting said cell with an amount of a compound of the invention sufficient to inhibit the activity of K-Ras, H-Ras or N-Ras G12C in said cell. In some embodiments, the invention provides methods of inhibiting K-Ras, H-Ras or N-Ras G12C activity in a tissue by contacting said tissue with an amount of a compound of the invention sufficient to inhibit the activity of K-Ras, H-Ras or N-Ras G12C in said tissue. In some embodiments, the invention provides methods of inhibiting K-Ras, H-Ras or N-Ras G12C activity in an organism by contacting said organism with an amount of a compound of the invention sufficient to inhibit the activity of K-Ras, H-Ras or N-Ras G12C in said organism. In some embodiments, the invention provides methods of inhibiting K-Ras, H-Ras or N-Ras G12C activity in an animal by contacting said animal with an amount of a compound of the invention sufficient to inhibit the activity of K-Ras, H-Ras or N-Ras G12C in said animal. In some embodiments, the invention provides methods of inhibiting K-Ras, H-Ras or N-Ras G12C activity in a mammal by contacting said mammal with an amount of a compound of the invention sufficient to inhibit the activity of K-Ras, H-Ras or N-Ras G12C in said mammal. In some embodiments, the invention provides methods of inhibiting K-Ras, H-Ras or N-Ras G12C activity in a human by contacting said human with an amount of a compound of the invention sufficient to inhibit the activity of K-Ras, H-Ras or N-Ras G12C in said human. The present invention provides methods of treating a disease mediated by K-Ras, H-Ras or N-Ras G12C activity in a subject in need of such treatment.

The present invention also provides methods for combination therapies in which an agent known to modulate other pathways, or other components of the same pathway, or even overlapping sets of target enzymes are used in combination with a compound of the present invention, or a pharmaceutically acceptable salt, ester, prodrug, solvate, tautomer, hydrate or derivative thereof. In one aspect, such therapy includes but is not limited to the combination of one or more compounds of the invention with chemotherapeutic agents, therapeutic antibodies, and radiation treatment, to provide a synergistic or additive therapeutic effect.

Many chemotherapeutics are presently known in the art and can be used in combination with the compounds of the invention. In some embodiments, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens.

Non-limiting examples are chemotherapeutic agents, cytotoxic agents, and non-peptide small molecules such as Gleevec® (Imatinib Mesylate), Velcade® (bortezomib), Casodex (bicalutamide), Iressa® (gefitinib), and Adriamycin as well as a host of chemotherapeutic agents. Non-limiting examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, Casodex™, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofuran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (TAXOL™, Bristol-Myers Squibb Oncology, Princeton, N.J.) and docetaxel (TAXOTERE™, Rhone-Poulenc Rorer, Antony, France); retinoic acid; esperamicins; capecitabine; and pharmaceutically acceptable salts, acids or derivatives of any of the above. Also included as suitable chemotherapeutic cell conditioners are anti-hormonal agents that act to regulate or inhibit hormone action on tumors such as anti-estrogens including for example tamoxifen, (Nolvadex™), raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; camptothecin-11 (CPT-11); topoisomerase inhibitor RFS 2000; difluoromethylomithine (DMFO). Where desired, the compounds or pharmaceutical composition of the present invention can be used in combination with commonly prescribed anti-cancer drugs such as Herceptin®, Avastin®, Erbitux®, Rituxan®, Taxol®, Arimidex®, Taxotere®, ABVD, AVICINE, Abagovomab, Acridine carboxamide, Adecatumumab, 17-N-Allylamino-17-demethoxygeldanamycin, Alpharadin, Alvocidib, 3-Aminopyridine-2-carboxaldehyde thiosemicarbazone, Amonafide, Anthracenedione, Anti-CD22 immunotoxins, Antineoplastic, Antitumorigenic herbs, Apaziquone, Atiprimod, Azathioprine, Belotecan, Bendamustine, BIBW 2992, Biricodar, Brostallicin, Bryostatin, Buthionine sulfoximine, CBV (chemotherapy), Calyculin, cell-cycle nonspecific antineoplastic agents, Dichloroacetic acid, Discodermolide, Elsamitrucin, Enocitabine, Epothilone, Eribulin, Everolimus, Exatecan, Exisulind, Ferruginol, Forodesine, Fosfestrol, ICE chemotherapy regimen, IT-101, Imexon, Imiquimod, Indolocarbazole, Irofulven, Laniquidar, Larotaxel, Lenalidomide, Lucanthone, Lurtotecan, Mafosfamide, Mitozolomide, Nafoxidine, Nedaplatin, Olaparib, Ortataxel, PAC-1, Pawpaw, Pixantrone, Proteasome inhibitor, Rebeccamycin, Resiquimod, Rubitecan, SN-38, Salinosporamide A, Sapacitabine, Stanford V, Swainsonine, Talaporfin, Tariquidar, Tegafur-uracil, Temodar, Tesetaxel, Triplatin tetranitrate, Tris(2-chloroethyl)amine, Troxacitabine, Uramustine, Vadimezan, Vinflunine, ZD6126 or Zosuquidar.

This invention further relates to a method for using the compounds or pharmaceutical compositions provided herein, in combination with radiation therapy for inhibiting abnormal cell growth or treating the hyperproliferative disorder in the mammal. Techniques for administering radiation therapy are known in the art, and these techniques can be used in the combination therapy described herein. The administration of the compound of the invention in this combination therapy can be determined as described herein.

Radiation therapy can be administered through one of several methods, or a combination of methods, including without limitation external-beam therapy, internal radiation therapy, implant radiation, stereotactic radiosurgery, systemic radiation therapy, radiotherapy and permanent or temporary interstitial brachytherapy. The term "brachytherapy," as used herein, refers to radiation therapy delivered by a spatially confined radioactive material inserted into the body at or near a tumor or other proliferative tissue disease site. The term is intended without limitation to include exposure to radioactive isotopes (e.g. At-211, I-131, I-125, Y-90, Re-186, Re-188, Sm-153, Bi-212, P-32, and radioactive isotopes of Lu). Suitable radiation sources for use as a cell conditioner of the present invention include both solids and liquids. By way of non-limiting example, the radiation source can be a radionuclide, such as I-125, I-131, Yb-169, Ir-192 as a solid source, I-125 as a solid source, or other radionuclides that emit photons, beta particles, gamma radiation, or other therapeutic rays. The radioactive material can also be a fluid made from any solution of radionuclide(s), e.g., a solution of I-125 or I-131, or a radioactive fluid can be produced using a slurry of a suitable fluid containing small particles of solid radionuclides, such as Au-198, Y-90. Moreover, the radionuclide(s) can be embodied in a gel or radioactive micro spheres.

Without being limited by any theory, the compounds of the present invention can render abnormal cells more sensitive to treatment with radiation for purposes of killing and/or inhibiting the growth of such cells. Accordingly, this invention further relates to a method for sensitizing abnormal cells in a mammal to treatment with radiation which comprises administering to the mammal an amount of a compound of the present invention or pharmaceutically acceptable salt, ester, prodrug, solvate, hydrate or derivative thereof, which amount is effective is sensitizing abnormal cells to treatment with radiation. The amount of the compound, salt, or solvate in this method can be determined according to the means for ascertaining effective amounts of such compounds described herein.

The compounds or pharmaceutical compositions of the invention can be used in combination with an amount of one or more substances selected from anti-angiogenesis agents, signal transduction inhibitors, antiproliferative agents, glycolysis inhibitors, or autophagy inhibitors.

Anti-angiogenesis agents, such as MMP-2 (matrix-metalloproteinase 2) inhibitors, MMP-9 (matrix-metalloprotienase 9) inhibitors, and COX-11 (cyclooxygenase 11) inhibitors, can be used in conjunction with a compound of the invention and pharmaceutical compositions described herein. Anti-angiogenesis agents include, for example, rapamycin, temsirolimus (CCI-779), everolimus (RAD001), sorafenib, sunitinib, and bevacizumab. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931,788 (published Jul. 28, 1999), WO 90/05719 (published May 31, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain Patent Application No. 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are incorporated herein in their entireties by reference. Preferred MMP-2 and MMP-9 inhibitors are those that have little or no activity inhibiting MMP-1. More preferred, are those that selectively inhibit MMP-2 and/or AMP-9 relative to the other matrix-metalloproteinases (i.e., MAP-1, MMP-3, MMP-4, MMP-5, MMP-6, MMP-7, MMP-8, MMP-10, MMP-11, MMP-12, and MMP-13). Some specific examples of MMP inhibitors useful in the invention are AG-3340, RO 32-3555, and RS 13-0830.

Autophagy inhibitors include, but are not limited to chloroquine, 3-methyladenine, hydroxychloroquine (Plaquenil™), bafilomycin A1, 5-amino-4-imidazole carboxamide riboside (AICAR), okadaic acid, autophagy-suppressive algal toxins which inhibit protein phosphatases of type 2A or type 1, analogues of cAMP, and drugs which elevate cAMP levels such as adenosine, LY204002, N6-mercaptopurine riboside, and vinblastine. In addition, antisense or siRNA that inhibits expression of proteins including but not limited to ATG5 (which are implicated in autophagy), may also be used.

The invention also relates to a method of and to a pharmaceutical composition for treating a cardiovascular disease in a mammal which comprises an amount of a compound of the invention, or a pharmaceutically acceptable salt, ester, prodrug, solvate, tautomer, hydrate or derivative thereof, or an isotopically-labeled derivative thereof, and an amount of one or more therapeutic agents use for the treatment of cardiovascular diseases.

Exemplary agents for use in cardiovascular disease applications are anti-thrombotic agents, e.g., prostacyclin and salicylates, thrombolytic agents, e.g., streptokinase, urokinase, tissue plasminogen activator (TPA) and anisoylated plasminogen-streptokinase activator complex (APSAC), anti-platelets agents, e.g., acetyl-salicylic acid (ASA) and clopidrogel, vasodilating agents, e.g., nitrates, calcium channel blocking drugs, anti-proliferative agents, e.g., colchicine and alkylating agents, intercalating agents, growth modulating factors such as interleukins, transformation growth factor-beta and congeners of platelet derived growth factor, monoclonal antibodies directed against growth factors, anti-inflammatory agents, both steroidal and non-steroidal, and other agents that can modulate vessel tone, function, arteriosclerosis, and the healing response to vessel or organ injury post intervention. Antibiotics can also be included in combinations or coatings comprised by the invention. Moreover, a coating can be used to effect therapeutic delivery focally within the vessel wall. By incorporation of the active agent in a swellable polymer, the active agent will be released upon swelling of the polymer.

In some embodiments, the compounds described herein are formulated or administered in conjunction with liquid or solid tissue barriers also known as lubricants. Examples of tissue barriers include, but are not limited to, polysaccharides, polyglycans, seprafilm, interceed and hyaluronic acid.

In some embodiments, medicaments which are administered in conjunction with the compounds described herein include any suitable drugs usefully delivered by inhalation for example, analgesics, e.g. codeine, dihydromorphine, ergotamine, fentanyl or morphine; anginal preparations, e.g. diltiazem; antiallergics, e.g. cromoglycate, ketotifen or nedocromil; anti-infectives, e.g. cephalosporins, penicillins, streptomycin, sulphonamides, tetracyclines or pentamidine; antihistamines, e.g. methapyrilene; anti-inflammatories, e.g. beclomethasone, flunisolide, budesonide, tipredane, triamcinolone acetonide or fluticasone; antitussives, e.g. noscapine; bronchodilators, e.g. ephedrine, adrenaline, fenoterol, formoterol, isoprenaline, metaproterenol, phenylephrine, phenylpropanolamine, pirbuterol, reproterol, rimiterol, salbutamol, salmeterol, terbutalin, isoetharine, tulobuterol, orciprenaline or (−)-4-amino-3,5-dichloro-α-[[[6-[2-(2-pyridinyl)ethoxy]hexyl]-amino]methyl]benzenemethanol; diuretics, e.g. amiloride; anticholinergics e.g. ipratropium, atropine or oxitropium; hormones, e.g. cortisone, hydrocortisone or prednisolone; xanthines e.g. aminophylline, choline theophyllinate, lysine theophyllinate or theophylline; and therapeutic proteins and peptides, e.g. insulin or glucagon. It will be clear to a person skilled in the art that, where appropriate, the medicaments are used in the form of salts (e.g. as alkali metal or amine salts or as acid addition salts) or as esters (e.g. lower alkyl esters) or as solvates (e.g. hydrates) to optimize the activity and/or stability of the medicament.

Other exemplary therapeutic agents useful for a combination therapy include but are not limited to agents as described above, radiation therapy, hormone antagonists, hormones and their releasing factors, thyroid and antithyroid drugs, estrogens and progestins, androgens, adrenocorticotropic hormone; adrenocortical steroids and their synthetic analogs; inhibitors of the synthesis and actions of adrenocortical hormones, insulin, oral hypoglycemic agents, and the pharmacology of the endocrine pancreas, agents affecting calcification and bone turnover: calcium, phosphate, parathyroid hormone, vitamin D, calcitonin, vitamins such as water-soluble vitamins, vitamin B complex, ascorbic acid, fatsoluble vitamins, vitamins A, K, and E, growth factors, cytokines, chemokines, muscarinic receptor agonists and antagonists; anticholinesterase agents; agents acting at the neuromuscular junction and/or autonomic ganglia; catecholamines, sympathomimetic drugs, and adrenergic receptor agonists or antagonists; and 5-hydroxytryptamine (5-HT, serotonin) receptor agonists and antagonists.

Therapeutic agents can also include agents for pain and inflammation such as histamine and histamine antagonists, bradykinin and bradykinin antagonists, 5-hydroxytryptamine (serotonin), lipid substances that are generated by biotransformation of the products of the selective hydrolysis of membrane phospholipids, eicosanoids, prostaglandins, thromboxanes, leukotrienes, aspirin, nonsteroidal anti-inflammatory agents, analgesic-antipyretic agents, agents that inhibit the synthesis of prostaglandins and thromboxanes, selective inhibitors of the inducible cyclooxygenase, selective inhibitors of the inducible cyclooxygenase-2, autacoids, paracrine hormones, somatostatin, gastrin, cytokines that mediate interactions involved in humoral and cellular immune responses, lipid-derived autacoids, eicosanoids, β-adrenergic agonists, ipratropium, glucocorticoids, methylxanthines, sodium channel blockers, opioid receptor agonists, calcium channel blockers, membrane stabilizers and leukotriene inhibitors.

Additional therapeutic agents contemplated herein include diuretics, vasopressin, agents affecting the renal conservation of water, rennin, angiotensin, agents useful in the treatment of myocardial ischemia, anti-hypertensive agents, angiotensin converting enzyme inhibitors, β-adrenergic receptor antagonists, agents for the treatment of hypercholesterolemia, and agents for the treatment of dyslipidemia.

Other therapeutic agents contemplated include drugs used for control of gastric acidity, agents for the treatment of peptic ulcers, agents for the treatment of gastroesophageal reflux disease, prokinetic agents, antiemetics, agents used in irritable bowel syndrome, agents used for diarrhea, agents used for constipation, agents used for inflammatory bowel disease, agents used for biliary disease, agents used for pancreatic disease. Therapeutic agents used to treat protozoan infections, drugs used to treat Malaria, Amebiasis, Giardiasis, Trichomoniasis, Trypanosomiasis, and/or Leishmaniasis, and/or drugs used in the chemotherapy of helminthiasis. Other therapeutic agents include antimicrobial agents, sulfonamides, trimethoprim-sulfamethoxazole quinolones, and agents for urinary tract infections, penicillins, cephalosporins, and other, β-lactam antibiotics, an agent comprising an aminoglycoside, protein synthesis inhibitors, drugs used in the chemotherapy of tuberculosis, *mycobacterium avium* complex disease, and leprosy, antifungal agents, antiviral agents including nonretroviral agents and antiretroviral agents.

Examples of therapeutic antibodies that can be combined with a compound of the invention include but are not limited to anti-receptor tyrosine kinase antibodies (cetuximab, panitumumab, trastuzumab), anti CD20 antibodies (rituximab, tositumomab), and other antibodies such as alemtuzumab, bevacizumab, and gemtuzumab.

Moreover, therapeutic agents used for immunomodulation, such as immunomodulators, immunosuppressive agents, tolerogens, and immunostimulants are contemplated by the methods herein. In addition, therapeutic agents acting on the blood and the blood-forming organs, hematopoietic agents, growth factors, minerals, and vitamins, anticoagulant, thrombolytic, and antiplatelet drugs.

For treating renal carcinoma, one may combine a compound of the present invention with sorafenib and/or avastin. For treating an endometrial disorder, one may combine a compound of the present invention with doxorubincin, taxotere (taxol), and/or cisplatin (carboplatin). For treating ovarian cancer, one may combine a compound of the present invention with cisplatin (carboplatin), taxotere, doxorubincin, topotecan, and/or tamoxifen. For treating breast cancer, one may combine a compound of the present invention with taxotere (taxol), gemcitabine (capecitabine), tamoxifen, letrozole, tarceva, lapatinib, PD0325901, avastin, herceptin, OSI-906, and/or OSI-930. For treating lung cancer, one may combine a compound of the present invention with taxotere (taxol), gemcitabine, cisplatin, pemetrexed, Tarceva, PD0325901, and/or avastin.

Further therapeutic agents that can be combined with a compound of the invention are found in Goodman and Gilman's "The Pharmacological Basis of Therapeutics" Tenth Edition edited by Hardman, Limbird and Gilman or the Physician's Desk Reference, both of which are incorporated herein by reference in their entirety.

The compounds described herein can be used in combination with the agents disclosed herein or other suitable agents, depending on the condition being treated. Hence, in some embodiments the one or more compounds of the invention will be co-administered with other agents as described above. When used in combination therapy, the compounds described herein are administered with the second agent simultaneously or separately. This administration in combination can include simultaneous administration of the two agents in the same dosage form, simultaneous administration in separate dosage forms, and separate administration. That is, a compound described herein and any of the agents described above can be formulated together in the same dosage form and administered simultaneously. Alternatively, a compound of the invention and any of the agents described above can be simultaneously administered, wherein both the agents are present in separate formulations. In another alternative, a compound of the present invention can be administered just followed by and any of the agents described above, or vice versa. In some embodiments of the separate administration protocol, a compound of the invention and any of the agents described above are administered a few minutes apart, or a few hours apart, or a few days apart.

The examples and preparations provided below further illustrate and exemplify the compounds of the present invention and methods of preparing such compounds. It is to be understood that the scope of the present invention is not limited in any way by the scope of the following examples and preparations. In the following examples, and throughout the specification and claims, molecules with a single chiral center, unless otherwise noted, exist as a racemic mixture. Those molecules with two or more chiral centers, unless otherwise noted, exist as a racemic mixture of diastereomers. Single enantiomers/diastereomers may be obtained by methods known to those skilled in the art.

EXAMPLES

Example 1

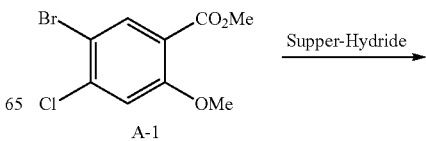

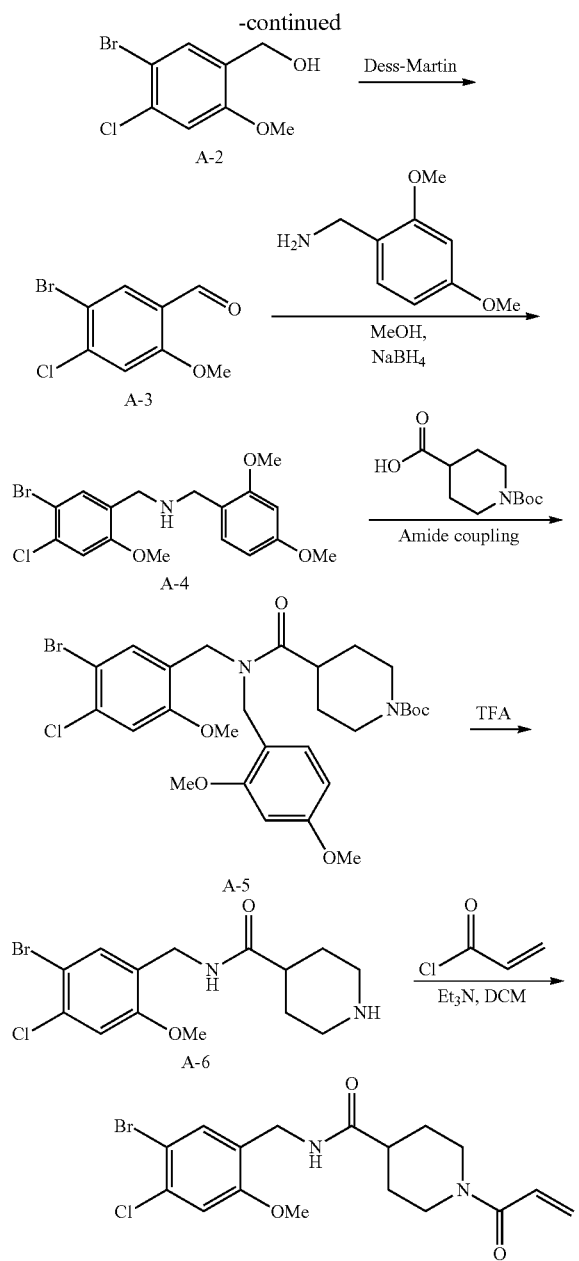

5-Bromo-4-chloro-2-methoxyphenyl)methanol

To a solution of methyl 5-bromo-4-chloro-2-methoxybenzoate (1.0 g, 3.6 mmol) in dry THF (10 mL) at 0° C., supper-Hydride (1.0 M, 10 mL) was added and the resulting mixture was stirred at room temperature overnight. The mixture was partitioned between ethyl acetate and water. The organic layer was dried over Na$_2$SO$_4$, filtered and concentrated in vacuo to afford the desired product. The crude product was used directly in the next step without further purification.

5-Bromo-4-chloro-2-methoxybenzaldehyde

To the solution of 5-bromo-4-chloro-2-methoxyphenyl) methanol in dry DCM (5 mL), Dess-Martin reagent (607 mg) was added and the resulting mixture was stirred at room temperature overnight. The mixture was partitioned between DCM and water. The organic layer was dried over Na$_2$SO$_4$, filtered and concentrated in vacuo. The residue was purified via Isolera One (silica cartridge, 0-60% ethyl acetate/hexanes) to afford the desired product (200 mg, 56% yield). $^1$H NMR (300 MHz, CDCl$_3$) δ: 10.33 (s, 1H), 8.04 (s, 1H), 7.12 (s, 1H), 3.39 (s, 3H).

N-(5-bromo-4-chloro-2-methoxybenzyl)-1-(2,4-dimethoxyphenyl)methanamine

The solution of 5-bromo-4-chloro-2-methoxybenzaldehyde (300 mg, 1.2 mmol) and 2,4-dimethoxybenzyl amine (167 mg, 1.2 mmol) in MeOH/DCM (4:1, 10 mL) was stirred at room temperature for 5 h. To this mixture, NaBH$_4$ (100 mg, 13 mmol) was added in two portions. The mixture stirred for 1 h and then partitioned between DCM and water. The organic layer was washed with brine, dried over Na$_2$SO$_4$, filtered and concentrated in vacuo to afford the desired product. The crude product was used directly in the next step without further purification.

tert-Butyl 4-((5-bromo-4-chloro-2-methoxybenzyl) (2,4-dimethoxybenzyl)carbamoyl)piperidine-1-carboxylate The mixture of N-(5-bromo-4-chloro-2-methoxybenzyl)-1-(2,4-dimethoxyphenyl)methanamine (190 mg, 0.47 mmol), 1-(tert-butoxycarbonyl)piperidine-4-carboxylic acid (109 mg, 0.47 mmol), HATU (180 mg, 0.47 mmol) and Et$_3$N (101 mg, 1 mmol) in DMF (5 mL) was stirred at room temperature for 4 h. The mixture was partitioned between ethyl acetate and water. The organic layer was washed with brine, dried over Na$_2$SO$_4$, filtered and concentrated in vacuo to afford the desired product. The crude product was used directly in the next step without further purification.

N-(5-Bromo-4-chloro-2-methoxybenzyl)piperidine-4-carboxamide

The crude tert-Butyl 4-((5-bromo-4-chloro-2-methoxybenzyl)(2,4-dimethoxybenzyl)carbamoyl)piperidine-1-carboxylate was dissolved in 50% TFA in DCM (10 mL) and the resulting mixture was stirred at room temperature for 2 h. The mixture was concentrated in vacuo and the residue was partitioned between DCM and saturate NaHCO$_3$ aqueous solution. The organic layer was washed with brine, dried over Na$_2$SO$_4$, filtered and concentrated in vacuo to afford the desired product.

1-Acryloyl-N-(5-bromo-4-chloro-2-methoxybenzyl) piperidine-4-carboxamide

To a solution of N-(5-Bromo-4-chloro-2-methoxybenzyl) piperidine-4-carboxamide obtained from above step in DCM (10 mL) at 0° C., Et$_3$N (0.2 mL, 1.43 mmol) and acryloyl chloride (36.2 mg, 0.4 mmol) were added sequentially and the mixture was stirred at room temperature for 1 h. The mixture was partitioned between DCM and water. The organic layer was washed with brine, dried over Na$_2$SO$_4$, filtered and concentrated in vacuo. The residue was purified via Isolera One (silica cartridge, 0-3% MeOH/DCM) to afford the desired product (13 mg). $^1$H NMR (300 MHz, DMSO-d6) δ: 8.27 (t, J=5.6 Hz, 1H), 7.37 (s, 1H), 7.26 (s, 1H), 6.81 (dd, J=10.4, 18.8 Hz, 1H), 6.08 (dd, J=2.4, 16.7 Hz, 1H), 5.66 (dd, J=2.4, 10.4 Hz, 1H), 4.40 (d, J=12.8 Hz, 1H), 4.17 (d, J=5.8 Hz, 2H), 4.07 (d, J=13.1 Hz, 1H), 3.83 (s, 3H), 3.07 (t, J=12.0 Hz, 1 H), 2.68 (t, J=12.7 Hz, 1 H), 2.48-2.50 (m, 1H), 1.75 (d, J=10.8 Hz, 2 H), 1.47-1.51 (m, 2H). ESI-MS m/z: 417.05 [M+H]⁺.

Example 2

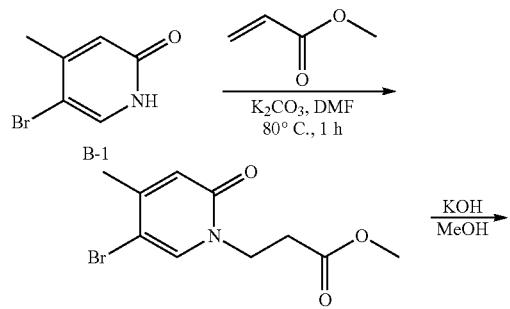

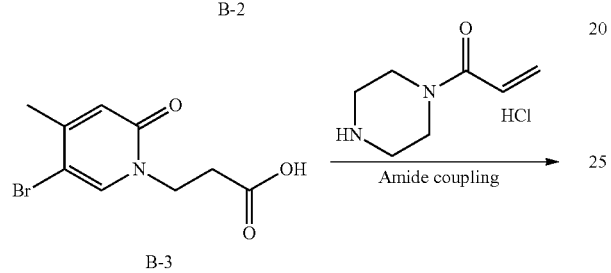

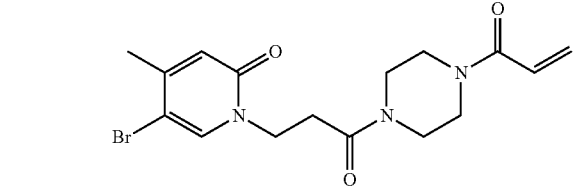

Methyl 3-(5-bromo-4-methyl-2-oxopyridin-1(2H)-yl)propanoate

To a solution of 5-bromo-4-methylpyridin-2(1H)-one (1.0 g, 5.3 mmol) in DMF (10 mL), $K_2CO_3$ (1.5 g, 10.6 mmol) was added, followed by addition of methyl acrylate (0.91 g, 10.6 mmol) at 80° C. The mixture was stirred at 80° C. for 1 h. The mixture was allowed to cool to room temperature and then partitioned between ethyl acetate and water. The organic layer was washed with brine, dried over $Na_2SO_4$, filtered and concentrated in vacuo. The residue was used directly in the next step without further purification.

3-(5-Bromo-4-methyl-2-oxopyridin-1(2H)-yl)propanoic acid

To a solution of the crude product from above step in MeOH (20 mL), aqueous KOH (2M, 5 mL) was added and the resulting mixture was stirred at room temperature overnight. The mixture was acidified with con. HCl and then extracted with ethyl acetate. The organic layer was washed with brine, dried over $Na_2SO_4$, filtered and concentrated in vacuo. The crude product was used directly in the next step without further purification.

1-(3-(4-Acryloylpiperazin-1-yl)-3-oxopropyl)-5-bromo-4-methylpyridin-2(1H)-one

A mixture of 3-(5-Bromo-4-methyl-2-oxopyridin-1(2H)-yl)propanoic acid (112 mg, 0.43 mmol), 1-(piperazin-1-yl) prop-2-en-1-one (80 mg, 0.43 mmol), HATU (163 mg, 0.43 mmol) and $Et_3N$ (0.2 mL, 1.43 mmol) in DMF (5 mL) was stirred at room temperature for 2 h. The mixture was partitioned between ethyl acetate and water. The organic layer was washed with brine, dried over $Na_2SO_4$, filtered and concentrated in vacuo. The residue was purified via Isolera One (silica cartridge, 0-6% MeOH/DCM) to afford the desired product (22.8 mg, 14 yield). ¹H NMR (300 MHz, CDCl₃) δ: 7.73 (s, 1H), 6.55 (dd, J=10.5, 16.7 Hz, 1H), 6.46 (s, 1H), 6.32 (dd, J=1.8, 16.8 Hz, 1H), 5.75 (dd, J=1.8, 10.5 Hz, 1H), 4.20 (t, J=6.0 Hz, 2H), 3.4-3.6 (m, 8H), 2.86 (t, J=6.0 Hz, 2H), 2.22 (s, 3H). ESI-MS m/z: 382.05 [M+H]⁺.

Example 3

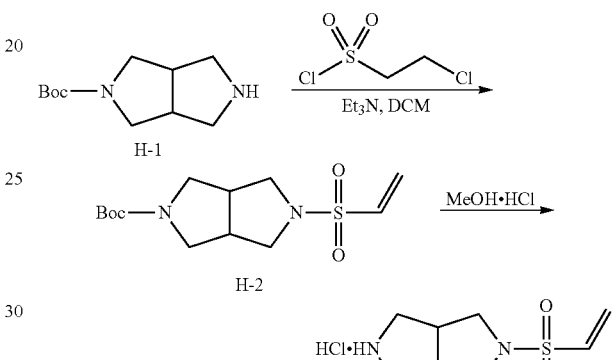

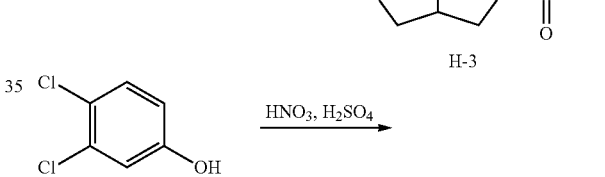

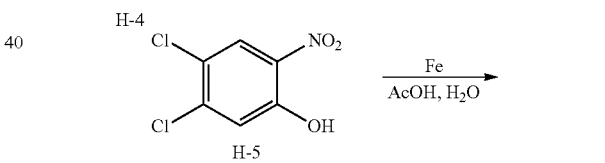

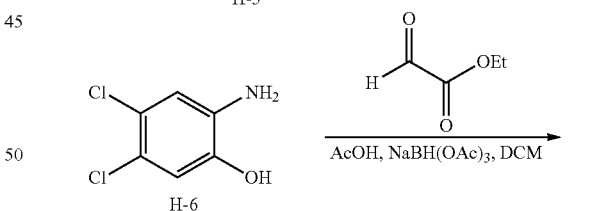

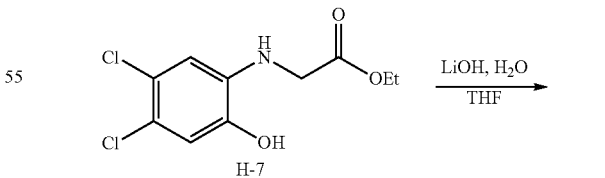

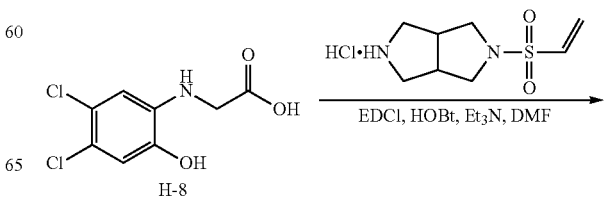

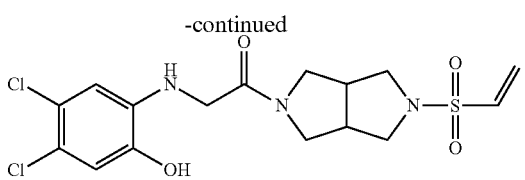

tert-Butyl 5-(vinylsulfonyl)hexahydropyrrolo[3,4-c]pyrrole-2(1H)-carboxylate To a stirred mixture of tert-butyl hexahydropyrrolo[3,4-c]pyrrole-2(1H)-carboxylate (1.0 g, 4.71 mmol) in DCM (20 mL) at 0° C., Et₃N (1.43 g, 14.1 mmol) was added. The mixture was stirred at 0° C. for 5 min, and then a solution of 2-chloroethanesulfonyl chloride (0.77 g, 4.71 mmol) in DCM (5 mL) was added dropwise. The resulting mixture was stirred at room temperature for 0.5 h. The reaction mixture was poured into water (20 mL) and extracted with DCM (30 mL×3). The combined organic layer was washed with brine (15 mL×3), dried over anhydrous Na₂SO₄, filtered and concentrated in vacuo. The residue was purified by flash column chromatography on silica gel (10-50% ethyl acetate/petroleum ether) to afford the desired product (0.5 g, 35% yield) as a solid.

2-(Vinylsulfonyl)octahydropyrrolo[3,4-c]pyrrole

A mixture of tert-butyl 5-(vinylsulfonyl)hexahydropyrrolo[3,4-c]pyrrole-2(1H)-carboxylate (150 mg, 0.50 mmol) in HCl/MeOH (20 mL, 2.86 M) was stirred at room temperature for 1 h. The mixture was concentrated in vacuo to afford the crude product (110 mg) as a solid which was used directly in next step without further purification.

4,5-Dichloro-2-nitrophenol

To a solution of 3,4-dichlorophenol (30 g, 185 mmol) in DCM (300 mL) at −15° C., sulfuric acid (24 g, 278 mmol) was added. To this mixture, nitric acid (19 g, 194 mmol) was added dropwise (over 20 min) and the temperature was controlled between −15° C. to −5° C. The resulting mixture was stirred at 0° C. for 1 h. The mixture was poured into ice and extracted with ethyl acetate. The combined organic layer was washed with water, saturate NaHCO₃ aqueous solution and brine, dried over Na₂SO₄ and then concentrated in vacuo. The residue was purified by flash column chromatography on silica gel (petroleum ether/ethyl acetate=100:1) to afford the desired product (16 g, 42% yield) as a solid.

2-Amino-4,5-dichlorophenol

To a stirred solution of 4,5-dichloro-2-nitrophenol (15 g, 72 mmol) in acetic acid (150 mL) and water (450 mL), iron powder (16 g, 285 mmol) was added in portions. The resulting mixture was stirred at 50° C. for 2 h. The mixture was allowed to cool to room temperature, filtered, and the cake was rinsed with ethyl acetate. The filtrate was extracted with ethyl acetate. The organic layer was washed with water, NaHCO₃ (aq.) and brine, dried over Na₂SO₄ and concentrated in vacuo to afford the desired product (10 g, 78%).

Ethyl 2-((4,5-dichloro-2-hydroxyphenyl)amino)acetate

To a solution of 2-amino-4,5-dichlorophenol (2.0 g, 11.3 mmol) and ethyl-2-oxoacetate (2.26 g, 12.42 mmol) in DCM (50 mL) at room temperature, AcOH (1 mL) was added and the resulting mixture was stirred for 1 h. To this mixture, NaBH(OAc)₃ (7.2 g, 33.9 mmol) was added and then stirred for 16 h. The mixture was concentrated in vacuo and the residue was suspended in DCM. The mixture was filtered through a pad of Celite and the filtrate was washed with brine. The organic layer was dried over anhydrous Na₂SO₄, filtered and concentrated in vacuo. The residue was purified by flash column chromatography on silica gel (petroleum ether/ethyl acetate=10:1) to afford the desired product (2.4 g, 81% yield) as a solid.

2-((4,5-Dichloro-2-hydroxyphenyl)amino)acetic acid

To a solution of ethyl 2-((4,5-dichloro-2-hydroxyphenyl)amino)acetate (2 g, 7.6 mmol) in of 4:1 mixture of tetrahydrofuran and water (30 mL) at room temperature, LiOH.H₂O (3.2 g, 76 mmol) were added and the resulting mixture was stirred for 30 min and then acidified with aqueous HCl (1N) to adjust the pH to 3-5. The mixture was extracted with ethyl acetate (40 mL×3). The combined organic layer was washed with brine (40 mL×3), dried over anhydrous Na₂SO₄, filtered and concentrated in vacuo to afford the crude product (2 g) which was used directly in the next step without further purification.

2-((4,5-dichloro-2-hydroxyphenyl)amino)-1-(5-(vinylsulfonyl)hexahydropyrrolo[3,4-c]pyrrol-2(1H)-yl)ethanone To a stirred solution of 2-((4,5-dichloro-2-hydroxyphenyl)amino)acetic acid (90 mg, 0.385 mmol) in DMF (15 mL) at room temperature, 2-(vinylsulfonyl)octahydropyrrolo[3,4-c]pyrrole (110 mg, 0.46 mmol) was added followed by HOBt (78.05 mg, 0.58 mmol), EDCI.HCl (110.7 mg, 0.46 mmol) and Et₃N (116.7 mg, 1.2 mmol). The reaction mixture was stirred at room temperature for 1 h. The reaction mixture was partitioned between ethyl acetate and brine. The organic layer was dried over anhydrous Na₂SO₄, filtered and concentrated in vacuo. The residue was purified by flash column chromatography on silica gel (10-50% ethyl acetate/dichloroethane) to afford the desired product (20 mg, 10% yield) as a solid. ¹H NMR (400 MHz, DMSO-d6)δ: 10.17 (s, 1H), 6.91 (dd, J=10.0, 16.4 Hz, 1H), 6.79 (s, 1H), 6.62 (s, 1H), 6.17-6.10 (m, 2H), 5.25 (t, J=4.0 Hz, 1H), 3.85-3.82 (m, 2H), 3.71-3.66 (m, 1H), 3.61-3.56 (m, 1H), 3.45-3.39 (m, 3H), 3.29-3.25 (m, 1H), 3.09-3.00 (m, 3H), 2.92-2.89 (m, 1H). ESI-MS m/z: 420.1 [M+H]⁺.

Example 4

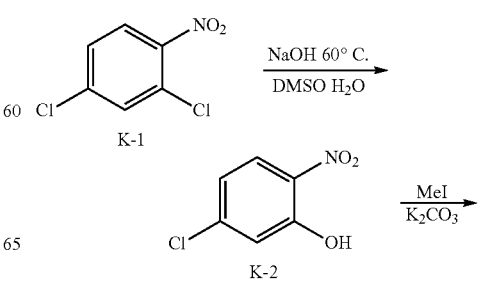

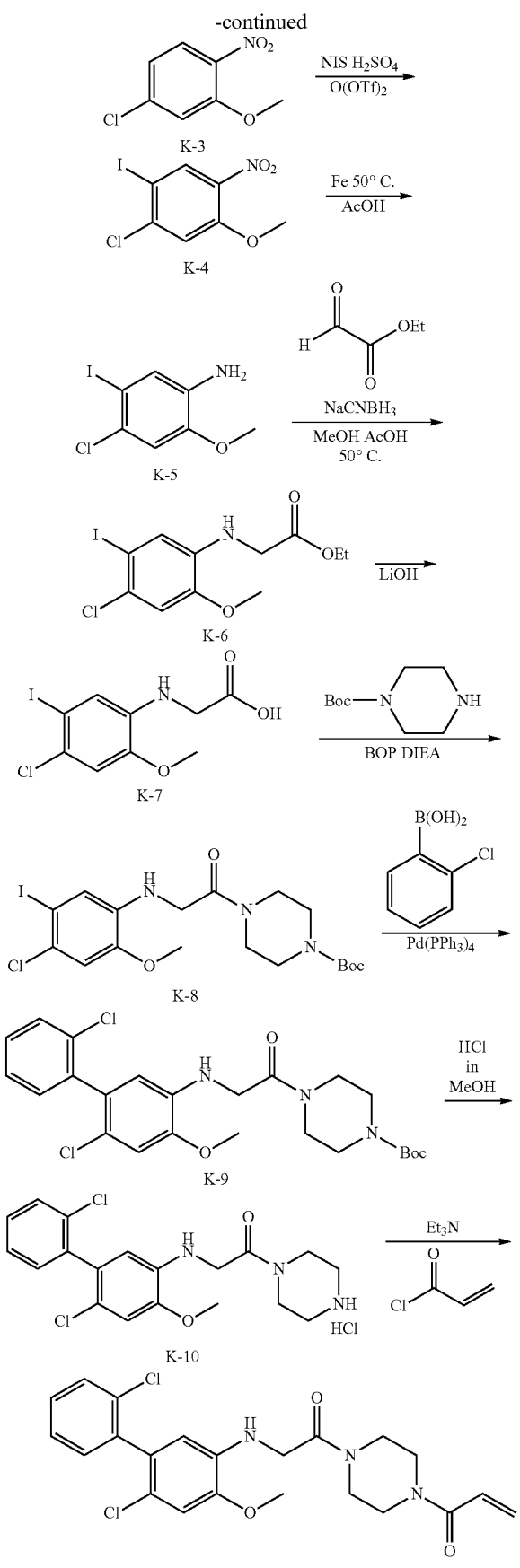

5-Chloro-2-nitrophenol

To a solution of 2,4-dichloro-1-nitrobenzene (100 g, 0.52 mol) in DMSO (200 mL), aqueous solution of NaOH (41.6 g, 1.04 mol) in water (42 mL) was added and the resulting mixture was stirred 60° C. for 16 h. The mixture was allowed to cool to room temperature, poured to ice water, and then acidified with aqueous HCl (1M) to adjusted the pH to 3-4. The mixture was extracted with ethyl acetate. The combined organic layer was washed with brine, dried over $Na_2SO_4$, filtered and concentrated in vacuo. The residue was used directly in the next step (80 g, 88% yield).

4-Chloro-2-methoxy-1-nitrobenzene

To a solution of 5-chloro-2-nitrophenol (40 g, 0.23 mol) in DMF (200 mL), $K_2CO_3$ (47.6 g, 0.345 mol) and iodomethane (49 g, 0.345 mol) were added and the resulting mixture was stirred at room temperature for 16 h. The mixture was partitioned between ethyl acetate and water. The organic layer was washed with brine, dried over $MgSO_4$, filtered and concentrated in vacuo. The residue was purified by flash column chromatography on silica gel (petroleum ether) to afford the desired product (30 g, 70% yield).

1-Chloro-2-iodo-5-methoxy-4-nitrobenzene

To a solution of $H_2SO_4$ (600 mL, 90%), trifluoromethanesulfonic anhydride (11.3 g, 0.04 mol) and NIS (49.68 g, 0.22 mol) were added and resulting mixture was stirred at room temperature for 1 h. To this mixture, 4-chloro-2-methoxy-1-nitrobenzene (69 g, 0.368 mol) was added quickly. The mixture was stirred for 1 h, and then NIS (33.12 g, 0.148 mol) was slowly added to the mixture. The mixture was stirred at room temperature for 1 h and then was poured into ice-water. The precipitate collected by filtration, rinsed with water, aqueous $NaSO_3$ and $NaHCO_3$ solutions, and then dried in vacuo to afford the desired product (113 g, 98% yield).

4-Chloro-5-iodo-2-methoxybenzenamine

To a solution of 1-chloro-2-iodo-5-methoxy-4-nitrobenzene (113 g, 0.361 mol) in acetic acid (1 L) and water (50 mL) at 50° C., Fe (50.5 g, 0.903 mol) was added and the resulting mixture was stirred at 50° C. for 2 h. The mixture was allowed to cool to room temperature and then poured into ice-water. The precipitate was collected by filtration and rinsed with water. This crude product was dissolved with ethyl acetate (1 L) and filtered. The filtrate was washed with saturated $NaHCO_3$ solution and brine. The organic layer was dried over $MgSO_4$, filtered, and concentrated in vacuo to afford the desired product (87 g, 85% yield).

Ethyl 2-(4-chloro-5-iodo-2-methoxyphenylamino)acetate

To a solution of 4-chloro-5-iodo-2-methoxybenzenamine (6 g, 21.2 mmol) in MeOH (50 mL) at room temperature, AcOH (3 drops) and ethyl glyoxalate (5.6 g, 27.5 mmol, 50% in toluene) were added. The mixture was stirred at room temperature for 2 h and then sodium cyanoborohydride (5.32 g, 84.8 mmol) was added to the mixture. The resulting mixture was stirred at 50° C. for 16 h. The mixture was allowed to cool to room temperature, and partitioned between ethyl acetate and water. The organic layer was dried over $MgSO_4$, filtered, and concentrated in vacuo to afford the crude product (8.6 g).

2-(4-Chloro-5-iodo-2-methoxyphenylamino)acetic acid

To a solution of ethyl 2-(4-chloro-5-iodo-2-methoxyphenylamino)acetate (8.6 g, 22.9 mmol) in THF (50 mL) and water (50 mL), LiOH.H₂O (1.96 g, 45.9 mmol) was added and the resulting mixture was stirred at room temperature for 2 h. The mixture was washed with 20% ethyl acetate/petroleum ether. The aqueous layer was acidified with aqueous HCl (1 M) to adjust PH to 3-4 and extracted with ethyl acetate. The organic layer was dried over MgSO₄, filtered, and concentrated in vacuo to afford the desired product (5 g, 64% yield).

tert-Butyl 4-(2-(4-chloro-5-iodo-2-methoxyphenylamino)acetyl)piperazine-1-carboxylate To a solution of 2-(4-chloro-5-iodo-2-methoxyphenylamino)acetic acid (280 mg, 0.83 mmol) and tert-butyl piperazine-1-carboxylate (185 mg, 0.99 mmol) in DMF (10 mL) at room temperature, BOP (550 mg, 1.25 mmol) and DIEA (321 mg, 2.4 9 mmol) were added and the resulting mixture was stirred at room temperature for 1 h. The mixture was partitioned between ethyl acetate and water. The organic layer was washed brine, dried over MgSO₄, filtered and concentrated in vacuo. The residue was purified by flash column chromatography on silica gel (petroleum ether/ethyl acetate=3:1) to afford the desired product (350 mg, 68.7% yield). ESI-MS m/z: 510.3[M+1]⁺.

tert-Butyl-4-(2-(5-(2-Chlorophenyl)-4-chloro-2-methoxyphenylamino)acetyl)piperazine-1-carboxylate To a solution of tert-butyl 4-(2-(4-chloro-5-iodo-2-methoxyphenylamino)acetyl)piperazine-1-carboxylate (200 mg, 0.4 mmol) and 2-chlorophenylboronic acid (69 mg, 0.44 mmol) in 1,4-dioxane (10 mL) and water (2 mL), Pd(PPh₃)₄ (40 mg, 0.035 mmol) and Na₂CO₃ (212 mg, 2 mmol) were added. The mixture was stirred at 80° C. for 16 h. The mixture was allowed to cool to room temperature and concentrated in vacuo. The residue was purified by flash column chromatography on silica gel (petroleum ether/ethyl acetate=4:1) to afford the desire product (150 mg, 76% yield).

2-(5-(2-Chlorophenyl)-4-chloro-2-methoxyphenylamino)-1-(piperazin-1-yl)ethanone To a solution of tert-butyl-4-(2-(5-(2-chlorophenyl)-4-chloro-2-methoxyphenylamino)acetyl)piperazine-1-carboxylate (150 mg, 0.304 mmol) in DCM (2 mL), a solution of HCl in MeOH (10 mL, 29 mmol) was added. The mixture was stirred at room temperature for 1 h and then concentrated in vacuo to afford the crude product which was used in the next step without further purification.

1-(4-(2-(4-chloro-5-(2-Chlorophenyl)-2-methoxyphenylamino)acetyl)piperazin-1-yl)prop-2-en-1-one To a solution of the crude 2-(5-(2-Chlorophenyl)-4-chloro-2-methoxyphenylamino)-1-(piperazin-1-yl)ethanone (0.304 mmol) and Et₃N in DCM (5 mL) at 0° C., acryloyl chloride (27.5 mg, 0.304 mmol) was slowly added and the resulting mixture was stirred at room temperature for 1 h. The mixture was quenched with saturated NaHCO₃ solution and extracted with DCM. The organic layer was washed with brine, dried over MgSO₄, filtered and concentrated in vacuo. The residue was purified by flash column chromatography on silica gel to afford the desired product (80 mg, 58.7% yield, 2 steps). ¹H NMR (400 MHz, DMSO-d6) δ: 7.55-7.52 (m, 1H), 7.45-7.39 (m, 2H), 7.32-7.29 (m, 1H), 6.97 (s, 1H), 6.80 (dd, J=10.4, 16.4 Hz, 1H), 6.54 (s, 1H), 6.12 (dd, J=2.0, 16.8 Hz, 1H), 5.70 (dd, J=2.0, 10.4 Hz, 1H), 5.35 (bs., 1H), 3.93 (d, J=4.0 Hz, 2H), 3.89 (s, 1H), 3.55-3.49 (m, 8H). ESI-MS m/z: 448.2[M+H]⁺.

Example 5

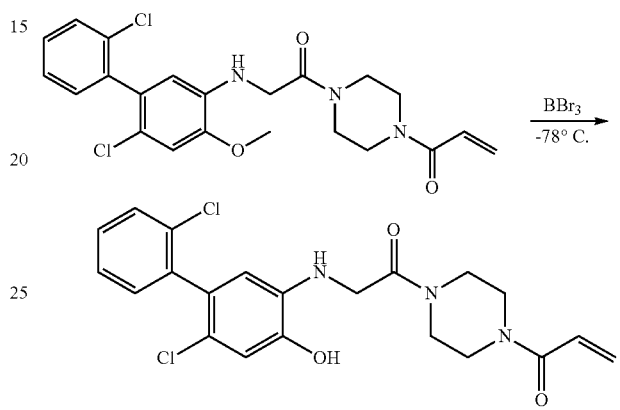

1-(4-(2-(4-chloro-2-hydroxy-5-(2-Chlorophenyl)phenylamino)acetyl)piperazin-1-yl)prop-2-en-1-one To a solution of 1-(4-(2-(4-chloro-5-(2-Chlorophenyl)-2-methoxyphenylamino)acetyl)piperazin-1-yl)prop-2-en-1-one (70 mg, 0.147 mmol) in DCM (15 mL)-78° C. under argon, BBr₃ (187 mg, 0.754 mmol) was added. The mixture was stirred at room temperature for 1 h. The mixture was poured into ice water and extracted ethyl acetate. The organic layer was dried over MgSO₄, filtered and concentrated in vacuo. The residue was purified by flash column chromatography on silica gel (dichloromethane/methanol=40:1) to afford the desired product (15 mg, 24% yield). ¹H NMR (400 MHz, DMSO-d6) δ: 10.08 (s, 1H), 7.53-7.51 (m, 1H), 7.41-7.37 (m, 2H), 7.30-7.28 (m, 1H), 6.84-6.77 (m, 2H), 6.48 (s, 1H), 6.12 (dd, J=2.4, 16.4 Hz, 1H), 5.70 (dd, J=2.0, 10.4 Hz, 1H), 5.24 (t, J=4.0 Hz, 1H), 3.90 (d, J=4.4 Hz, 2H), 3.56-3.49 (m, 8H). ESI-MS m/z: 434.2[M+H]⁺.

Example 6

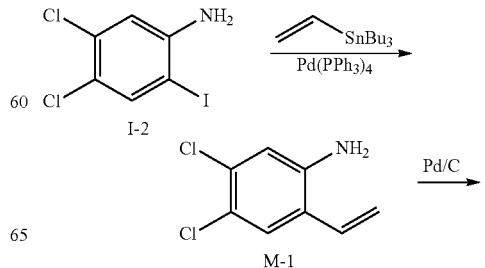

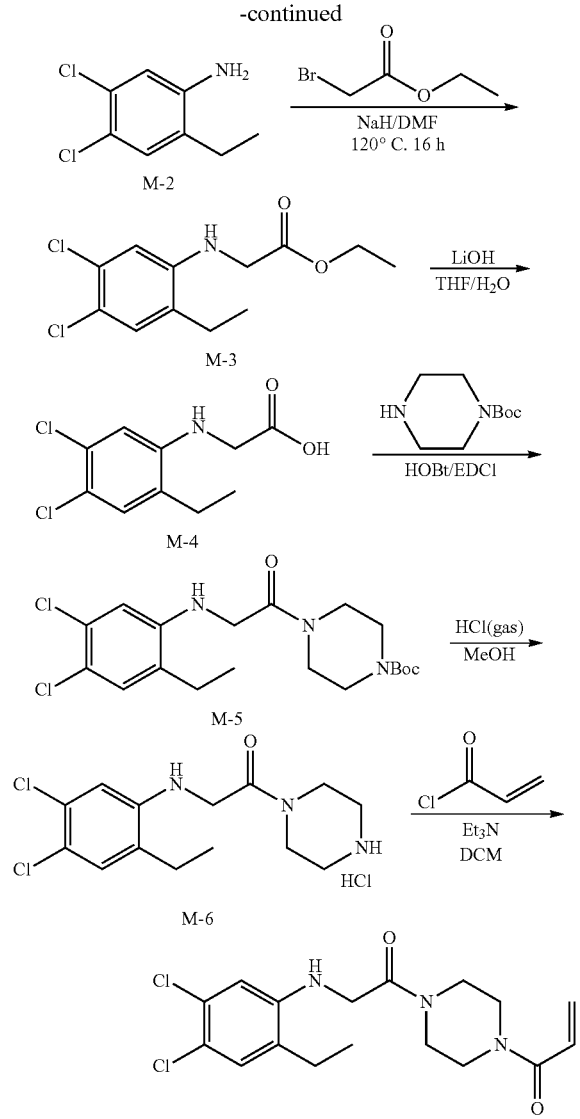

4,5-Dichloro-2-vinylbenzenamine

A mixture of 4,5-dichloro-2-iodobenzenamine (6 g, 20.8 mmol), tributyl(vinyl)stannane (6.6 g, 20.8 mmol), Pd(PPh$_3$)$_4$ (2.4 g, 2.1 mmol) in toluene (60 mL) was stirred at reflux under argon for 6 h. The mixture was allowed to cool to room temperature, quenched with aqueous KF solution and then extracted with ethyl acetate. The organic layer was washed with brine, dried over Na$_2$SO$_4$, filtered and concentrated in vacuo. The residue was purified by flash column chromatography on silica gel (petroleum ether/ethyl acetate=4:1) to afford the desired product (3.0 g, 76.7% yield) as a colorless oil.

4,5-Dichloro-2-ethylbenzenamine

A mixture of 4,5-dichloro-2-vinylbenzenamine (3.0 g, 15.95 mmol), Pd/C (3.3 g, 10%) in MeOH (20 mL) was stirred at room temperature under H$_2$ (1 atm) atmosphere for 4 h. The mixture was filtered and the filtrate was concentrated in vacuo to afford the desired product (2.4 g, 80% yield).

Ethyl 2-(4,5-dichloro-2-ethylphenylamino)acetate

To a stirring solution of 4,5-dichloro-2-ethylbenzenamine (600 mg, 3.15 mmol) in DMF at 0° C., NaH (150 mg, 3.78 mmol) was added in portions. After stirring for 30 min, ethyl 2-bromoacetate (789 mg, 4.74 mmol) was added to the mixture. The resulting mixture was stirred at 120° C. for 16 h. The mixture was allowed to cool to room temperature, poured into ice-water and extracted with ethyl acetate. The organic layer was washed with brine, dried over Na$_2$SO$_4$ and concentrated. The residue was purified by flash column chromatography on silica gel (petroleum ether/ethyl acetate=5:1) to afford the desired product (380 mg, 44.7% yield) as a yellow solid.

2-(4,5-Dichloro-2-ethylphenylamino)acetic acid

A mixture of ethyl 2-(4,5-dichloro-2-ethylphenylamino)acetate (390 mg, 1.41 mmol) and LiOH.H$_2$O (592 mg, 14.1 mmol) in THF (8 mL) and water (2 mL) was stirred at room temperature for 2 h. The mixture was concentrated in vacuo and the residue was dissolved in H$_2$O and diluted with ethyl acetate. The mixture was acidified with aqueous HCl (10%) to adjust the pH to 3-4 and then extracted with ethyl acetate. The organic layer was dried over Na$_2$SO$_4$, filtered and concentrated in vacuo to afford the desired product (300 mg, 85.75% yield) as a yellow solid. ESI-MS m/z: 246.2 [M–H]$^-$.

tert-Butyl 4-(2-(4,5-dichloro-2-ethylphenylamino)acetyl)piperazine-1-carboxylate To a stirred mixture of 2-(4,5-dichloro-2-ethylphenylamino)acetic acid (100 mg, 0.403 mmol), Et$_3$N (122 mg, 1.21 mmol) in DCM (3 mL) at 0° C., EDCI.HCl (123 mg, 0.604 mmol) and HOBt (8 2 mg, 0.604 mmol) were added. The resulting mixture was stirred at 0° C. for 30 min, and then tert-butyl piperazine-1-carboxylate (90 mg, 0.483 mmol) was added. The mixture was stirred at room temperature for 16 h and partitioned between ethyl acetate and water. The organic layer was washed with brine, dried over Na$_2$SO$_4$, filtered and concentrated in vacuo. The residue was purified by flash column chromatography on silica gel (petroleum ether/ethyl acetate=5:1) to afford the desired product (120 mg, 71.5% yield) as an off-white solid. ESI-MS m/z: 414.3 [M–H]$^-$.

2-(4,5-Dichloro-2-ethylphenylamino)-1-(piperazin-1-yl)ethanone hydrochloride A mixture of tert-butyl 4-(2-(4,5-dichloro-2-ethylphenylamino)acetyl)piperazine-1-carboxylate (120 mg, 0.288 mmol) in HCl/MeOH (2.86 M, 10 mL) was stirred at room temperature for 1 h. The mixture was concentrated in vacuo to afford the crude product (82 mg) as a yellow solid which was used directly in the next step without further purification.

1-(4-(2-(4,5-Dichloro-2-ethylphenylamino)acetyl)piperazin-1-yl)prop-2-en-1-one To a mixture of above crude 2-(4,5-dichloro-2-ethylphenylamino)-1-(piperazin-1-yl)ethanone hydrochloride (82 mg) and Et$_3$N (69 mg, 0.686 mmol) in DCM (3 mL) 0° C., a solution of acryloyl chloride (23 mg, 0.251 mmol) in DCM (1 mL) was added. The resulting mixture was stirred at room temperature for 1 h and then was quenched withed saturated NaHCO$_3$ solution. The mixture was diluted with ethyl acetate, washed with saturated NaHCO$_3$ solution and brine, dried over Na$_2$SO$_4$ and concentrated in vacuo. The residue was purified by flash column chromatography on silica gel (DCM/MeOH=30:1) to afford the desired product (20 mg, 18.76% yield, 2 steps) as an off-white solid. $^1$H NMR (400 MHz, CDCl$_3$) δ: 7.11 (s, 1H), 6.58 (dd, J=10.4, 16.4 Hz, 1H), 6.54 (s, 1H), 6.36 (dd, J=1.6, 16.4 Hz, 1H), 5.79 (dd, J=1.6, 10.4 Hz, 1H), 5.08 (bs., 1H), 3.89-3.52 (m, 10H), 2.52 (q, J=7.2 Hz, 2H), 1.29-1.26 (t, J=7.6 Hz, 3H). ESI-MS m/z: 370.2[M+H]$^+$.

Example 7

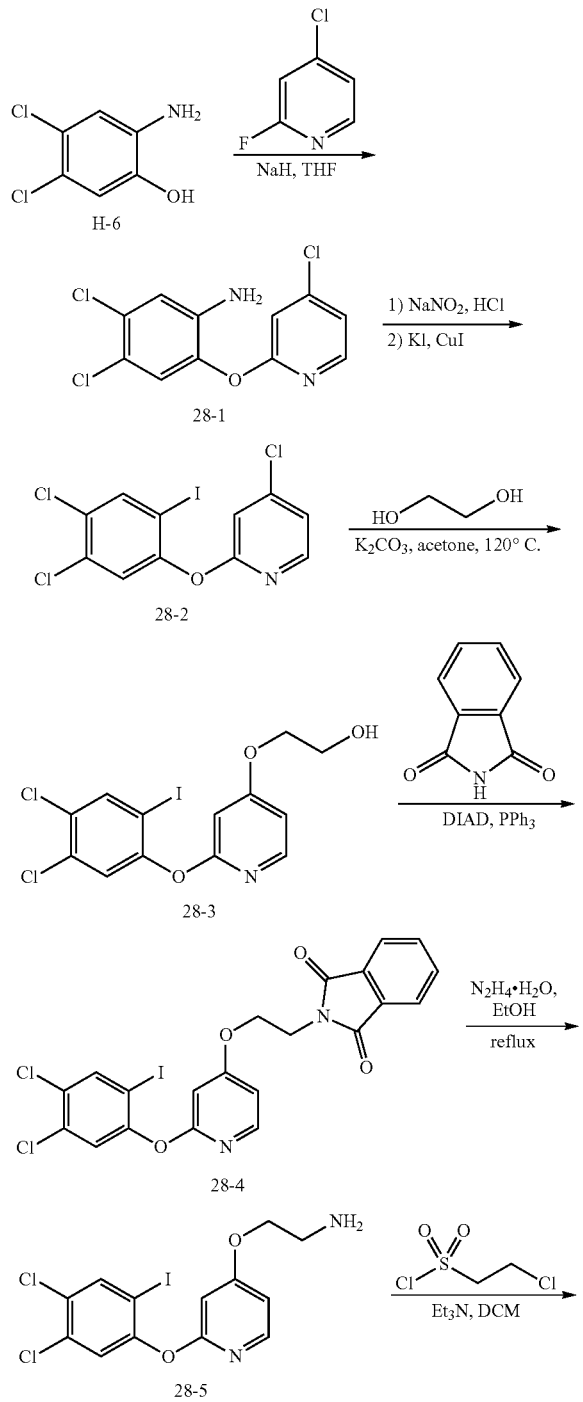

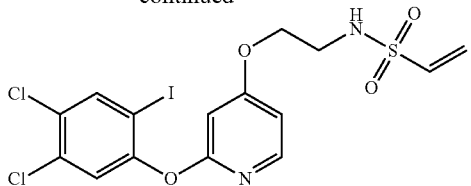

2-(4-chloropyridin-2-yloxy)-4,5-dichlorobenzenamine

To a solution of 2-amino-4,5-dichlorophenol (1.5 g, 8.47 mmol) in THF (20 mL) at 0° C., NaH (60% dispersed in oil, 373 mg, 9.33 mmol) was added and the resulting mixture was stirred for 20 min. To this mixture, 4-chloro-2-fluoropyridine (1.67 g, 12.7 mmol) was added and the resulting mixture was stirred at reflux under argon for 15 h. The mixture was allowed to cool to room temperature and concentrated in vacuo. The residue was purified by flash column chromatography on silica gel (petroleum ether/ethyl acetate=20:1 to 10:1) to afford the desired product (1.1 g, 45% yield). ESI-MS m/z: 287.0 [M−H]$^-$.

2-(4,5-Dichloro-2-iodophenoxy)-4-chloropyridine

The mixture of 2-(4-chloropyridin-2-yloxy)-4,5-dichlorobenzenamine (1.0 g, 3.47 mmol) in concentrated HCl (5 mL) and H$_2$O (15 mL) was cooled to −10° C.-0° C., NaNO$_2$ (0.359 g, 5.21 mmol) was added and the resulting mixture was stirred at this temperature for 50 min. This mixture was added dropwise to the mixture of KI (10 g, 60.2 mmol), CuI (330 mg, 1.73 mmol) in H$_2$O (40 mL) and then stirred at room temperature for 15 h. The mixture was partitioned between ethyl acetate and water. The organic layer was washed withed brine, dried over Na$_2$SO$_4$ and concentrated. The residue was purified by flash column chromatography on silica gel (petroleum ether/ethyl acetate=30:1) to afford the desired product (900 mg, 65% yield). ESI-MS m/z: 399.9[M+H]$^+$.

2-(2-(4,5-Dichloro-2-iodophenoxy)pyridin-4-yloxy) ethanol

A mixture of 2-(4,5-dichloro-2-iodophenoxy)-4-chloropyridine (0.45 g, 1.128 mmol), ethane-1,2-diol (4 mL, 71.89 mmol), K$_2$CO$_3$ (0.45 mg, 3.26 mmol) in acetone (6 mL) was stirred at 120° C. for 5 h. The mixture was poured into water and extracted with ethyl acetate. The organic layer was washed withed brine, dried over Na$_2$SO$_4$ and concentrated. The residue was purified by flash column chromatography on silica gel (petroleum ether/ethyl acetate=20:1 to 4:1) to afford the desired product (160 mg, 33% yield). ESI-MS m/z: 426.0 [M+H]$^+$.

2-(2-(2-(4,5-Dichloro-2-iodophenoxy)pyridin-4-yloxy)ethyl)isoindoline-1,3-dione

A mixture of 2-(2-(4,5-dichloro-2-iodophenoxy)pyridin-4-yloxy)ethanol (130 mg, 0.31 mmol), isoindoline-1,3-dione (54 mg, 0.37 mmol), PPh$_3$ (160 mg, 0.61 mmol) in THF (5 mL) at 0° C., DIAD (123 mg, 0.61 mmol) was added. The resulting mixture was allowed to warm to room temperature and stirred for 15 h. The mixture was concentrated in vacuo and the residue was purified by flash column chromatography on silica gel (petroleum ether/ethyl acetate=20:1 to 5:1) to afford the desired product (120 mg, 71% yield). ESI-MS m/z: 555.0[M+H]⁺.

2-(2-(4,5-Dichloro-2-iodophenoxy)pyridin-4-yloxy)ethanamine

The mixture of 2-(2-(2-(4,5-dichloro-2-iodophenoxy)pyridin-4-yloxy)ethyl)isoindoline-1,3-dione (120 mg, 0.22 mmol), $N_2H_4 \cdot H_2O$ (106 mg, 1.80 mmol) and EtOH (5 mL) was stirred at reflux for 1 h. The mixture was allowed to cool to room temperature and then concentrated in vacuo. The residue was slurried in DCM (5 mL) and MeOH (1 mL). The precipitate was removed by filtration, and the filtrate was concentrated in vacuo. The residue was purified by flash column chromatography on silica gel (DCM/MeOH=10:1) to afford the desired product (35 mg, 38% yield).

N-(2-(2-(4,5-Dichloro-2-iodophenoxy)pyridin-4-yloxy)ethyl)ethenesulfonamide

To a mixture of 2-(2-(4,5-dichloro-2-iodophenoxy)pyridin-4-yloxy)ethanamine (30 mg, 0.07 mmol), $Et_3N$ (35.7 mg, 0.35 mmol) in DCM (5 mL), 2-chloroethanesulfonyl chloride (11.5 mg, 0.07 mmol) was added and the resulting mixture was stirred at room temperature for 1 h. Then solvent was removed under reduced pressure. The residue was taken in THF (2 mL) and $H_2O$ (2 mL), then $K_2CO_3$ (100 mg) was added and the resulting mixture was stirred at room temperature for 1 h. The mixture was partitioned between DCM and water. The organic layer was washed with brine, dried over $Na_2SO_4$ and concentrated. The residue was purified by flash column chromatography on silica gel (DCM/ethyl acetate=5:1) to afford the desired product (56 mg, 56% yield). ¹H NMR (400 MHz, $CDCl_3$) δ: 7.98 (d, J=5.6 Hz, 1H), 7.92 (s, 1H), 7.25 (s, 1H), 6.61-6.57 (m, 2H), 6.47 (d, J=2.0 Hz, 1H), 6.32 (d, J=16.4 Hz, 1H), 6.00 (d, J=10.0 Hz, 1H), 4.77 (t, J=5.2 Hz, 1H), 4.18 (t, J=5.2 Hz, 2H), 3.51-3.47 (m, 2H). ESI-MS m/z: 515.0[M+H]⁺.

Example 8

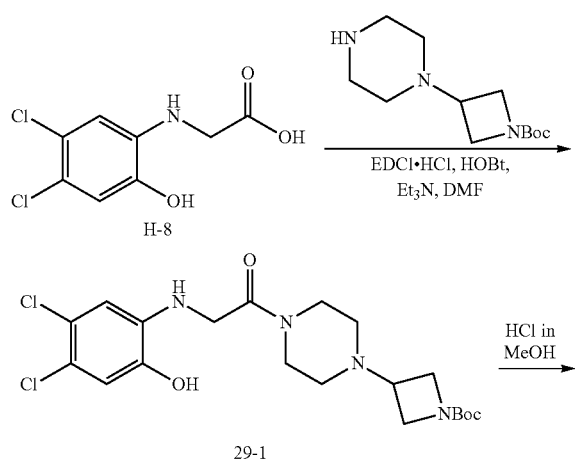

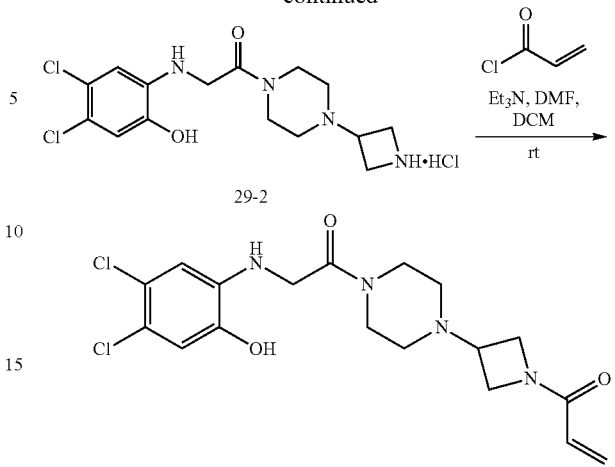

tert-Butyl 3-(4-(2-(4,5-dichloro-2-hydroxyphenylamino)acetyl)piperazin-1-yl)azetidine-1-carboxylate A mixture of 2-(4,5-dichloro-2-hydroxyphenylamino)acetic acid (500 mg, 2.12 mmol), tert-butyl 3-(piperazin-1-yl)azetidine-1-carboxylate (565 mg, 2.34 mmol), EDCI.HCl (488 mg, 2.54 mmol), HOBt (343 mg, 2.54 mmol), $Et_3N$ (428 mg, 4.24 mmol) in DMF (20 mL) was stirred at room temperature for 15 h. The mixture was poured into water and extracted with ethyl acetate. The organic layer was washed withed saturated aqueous $NaHCO_3$ solution and brine, dried over $Na_2SO_4$ and concentrated in vacuo. The residue was purified by flash column chromatography on silica gel (DCM/MeOH=30:1) to afford the desired product (300 mg, 31% yield). ESI-MS m/z: 457.4 [M–H]⁻.

2-(4,5-Dichloro-2-hydroxyphenylamino)-1-(4-(azetidin-3-yl)piperazin-1-yl)ethanone hydrochloride A mixture of tert-butyl 3-(4-(2-(4,5-dichloro-2-hydroxyphenylamino)acetyl)piperazin-1-yl)azetidine-1-carboxylate (150 mg, 0.33 mmol) in HCl-MeOH (20 mL, 57 mmol) was stirred at room temperature for 1 h. The mixture was concentrated in vacuo to afford the crude product (130 mg) which was used directly in the next step without further purification.

1-(3-(4-(2-(4,5-Dichloro-2-hydroxyphenylamino)acetyl)piperazin-1-yl)azetidin-1-yl)prop-2-en-1-one 2-(4,5-dichloro-2-hydroxyphenylamino)-1-(4-(azetidin-3-yl)piperazin-1-yl)ethanone hydrochloride (120 mg, 0.30 mmol) was added to the mixture of $Et_3N$ (0.2 mL, 1.44 mmol) in DCM (10 mL) followed by addition of DMF (1 drop). The mixture was stirred for 5 min and then acryloyl chloride (27 mg, 0.30 mmol) was added. The resulting mixture was stirred at room temperature for 1 h, poured into water and then extracted with MeOH/DCM. The organic layer was washed with brine, dried over $Na_2SO_4$ and concentrated. The residue was purified by flash column chromatography on silica gel (DCM/MeOH/$NH_3 \cdot H_2O$=50:1:0.1 to 20:1:0.2) to afford the desired product (30 mg, 24% yield). ¹H NMR (400 MHz, DMSO-d6) δ: 10.17 (s, 1H), 6.78 (s, 1H), 6.71 (s, 1H), 6.30 (dd, J=10.4, 17.2 Hz, 1H), 6.09 (dd, J=2.0, 17.2 Hz, 1H), 5.67 (dd, J=2.4, 10.4 Hz, 1H), 5.32 (t, J=4.4 Hz, 1H), 4.26-4.22 (m, 1H), 4.11-4.04 (m, 1H), 3.93-3.91 (m, 3H), 3.79-3.75 (m, 3H), 3.52-3.51 (m, 4H), 3.19-3.16 (m, 1H), 2.36-2.30 (m, 4H). ESI-MS m/z: 411.2 [M−H]⁻.

Example 9

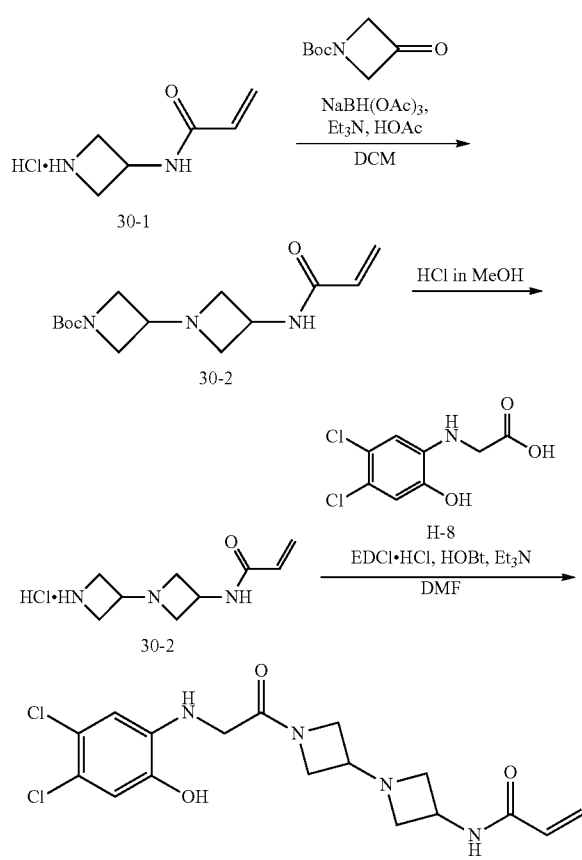

tert-Butyl 3-(3-(acrylamido)azetidin-1-yl)azetidine-1-carboxylate

To a mixture of N-(azetidin-3-yl)acrylamide hydrochloride (500 mg, 3.40 mmol), tert-butyl 3-oxoazetidine-1-carboxylate (684 mg, 4.0 mmol), Et₃N (343 mg, 3.40 mmol) and AcOH (100 mg, 0.167 mmol) in DCM (20 mL), NaBH(OAc)₃ (2.16 g, 10.2 mmol) was added, and the resulting mixture was stirred at room temperature for 16 h. The mixture was poured into water and extracted with ethyl acetate. The organic layer was washed with saturated NaHCO₃ solution and brine, dried over Na₂SO₄ and concentrated in vacuo. The residue was purified by flash column chromatography on silica gel (DCM/MeOH=100:1 to 20:1) to afford the desired product (300 mg, 31% yield).

N-(1-(Azetidin-3-yl)azetidin-3-yl)acrylamide hydrochloride

A mixture of tert-butyl 3-(3-(acrylamido)azetidin-1-yl)azetidine-1-carboxylate (300 mg, 1.07 mmol) in HCl-MeOH (30 mL, 86 mmol) was stirred at room temperature for 1 h. The mixture was concentrated in vacuo to afford the crude product (250 mg) which was used directly in the next step without further purification.

N-(1-(1-(2-(4,5-Dichloro-2-hydroxyphenylamino) acetyl)azetidin-3-yl)azetidin-3-yl)acrylamide A mixture of 2-(4,5-dichloro-2-hydroxyphenylamino)acetic acid (120 mg, 0.51 mmol), EDCI.HCl (147 mg, 0.77 mmol), HOBt (83 mg, 0.61 mmol), Et₃N (154 mg, 1.53 mmol) in DMF (20 mL) was stirred at room temperature for 5 min and then N-(1-(azetidin-3-yl)azetidin-3-yl)acrylamide hydrochloride (150 mg, 0.69 mmol) was added. The resulting mixture was stirred at room temperature for 15 h. The mixture was poured into water and extracted with ethyl acetate. The organic layer was washed with saturated NaHCO₃ solution and brine, dried over Na₂SO₄ and concentrated in vacuo. The residue was purified by flash column chromatography on silica gel (DCM/MeOH/NH₃.H₂O=100:10:1.5) to afford the desired product (6 mg, 3% yield). ¹H NMR (400 MHz, DMSO-d6) δ: 10.19 (s, 1H), 8.59 (d, J=8.0 Hz, 1H), 6.79 (s, 1H), 6.55 (s, 1H), 6.20 (dd, J=10.0, 16.8 Hz, 1H), 6.09 (dd, J=2.0, 16.8 Hz, 1H), 5.62 (dd, J=2.0, 9.6 Hz, 1H), 5.20 (t, J=4.0 Hz, 1H), 4.40-4.35 (m, 1H), 4.19-4.15 (m, 1H), 3.96-3.88 (m, 2H), 3.73-3.69 (m, 3H), 3.53-3.45 (m, 3H), 3.00-2.96 (m, 2H). ESI-MS m/z: 399.2[M+H]⁺.

Example 10

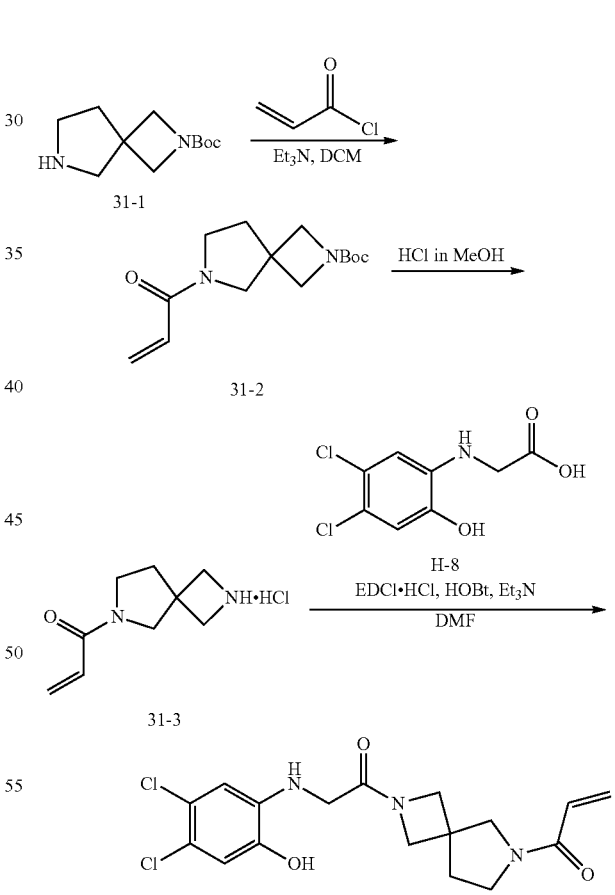

2,6-Diaza-spiro[3.4]octane-6-acryloyl-2-carboxylic acid tert-butyl ester

To a mixture of 2,6-diaza-spiro[3.4]octane-2-carboxylic acid tert-butyl ester (80 mg, 0.38 mmol), Et₃N (0.2 mL, 1.44 mmol) in DCM (20 mL), acryloyl chloride (34 mg, 0.38 mmol) was added and the resulting mixture was stirred at room temperature for 1 h. The mixture was poured into water and extracted with ethyl acetate. The organic layer was washed with saturated NaHCO₃ solution and brine, dried over Na₂SO₄ and concentrated in vacuo. The residue was purified by flash column chromatography on silica gel (DCM/MeOH=40:1) to afford the desired product (50 mg, 50% yield). ESI-MS m/z: 289.2[M+Na]⁺.

1-(2,6-Diazaspiro[3.4]octan-6-yl)prop-2-en-1-one

A mixture of 2,6-diaza-spiro[3.4]octane-6-acryloyl-2-carboxylic acid tert-butyl ester (50 mg, 0.19 mmol) in HCl/MeOH (10 mL, 29 mmol) was stirred at room temperature for 1 h. The mixture was concentrated in vacuo to afford the crude product (40 mg) which was used directly in the next step without further purification.

1-(2-((4,5-Dichloro-2-hydroxyphenyl)glycyl)-2,6-diazaspiro[3.4]octan-6-yl)prop-2-en-1-one The mixture of 2-(4,5-dichloro-2-hydroxyphenylamino) acetic acid (47 mg, 0.2 mmol), 1-(2,6-diazaspiro[3.4]octan-6-yl)prop-2-en-1-one (40 mg, 0.2 mmol), EDCI.HCl (46 mg, 0.24 mmol), HOBt (32 mg, 0.24 mmol) and Et₃N (0.61 mg, 0.6 mmol) in DMF (10 mL) was stirred at room temperature for 2 h. The mixture was poured into water and extracted with ethyl acetate. The organic layer was washed withed saturated NaHCO₃ solution and brine, dried over Na₂SO₄ and concentrated in vacuo. The residue was purified by flash column chromatography on silica gel (DCM/MeOH=30:1) to afford the desired product (13 mg, 17% yield). ¹H NMR (400 MHz, DMSO-d6) δ: 10.17 (s, 1H), 6.78 (s, 1H), 6.60-6.50 (m, 2H), 6.13 (dt, J=2.4, 16.4 Hz, 1H), 5.67 (dd, J=2.4, 10.4 Hz, 1H), 5.19 (dd, J=5.2, 10.0 Hz, 1H), 4.16-4.07 (m, 2H), 3.90-3.83 (m, 2H), 3.75-3.72 (m, 3H), 3.61-3.52 (m, 2H), 3.42-3.39 (m, 1H), 2.16-2.13 (m, 1H), 2.06-2.03 (m, 1H). ESI-MS m/z: 382.3 [M−H]⁻.

Example 11

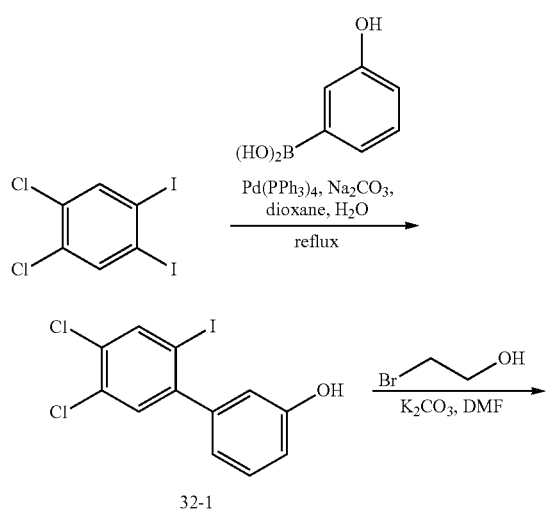

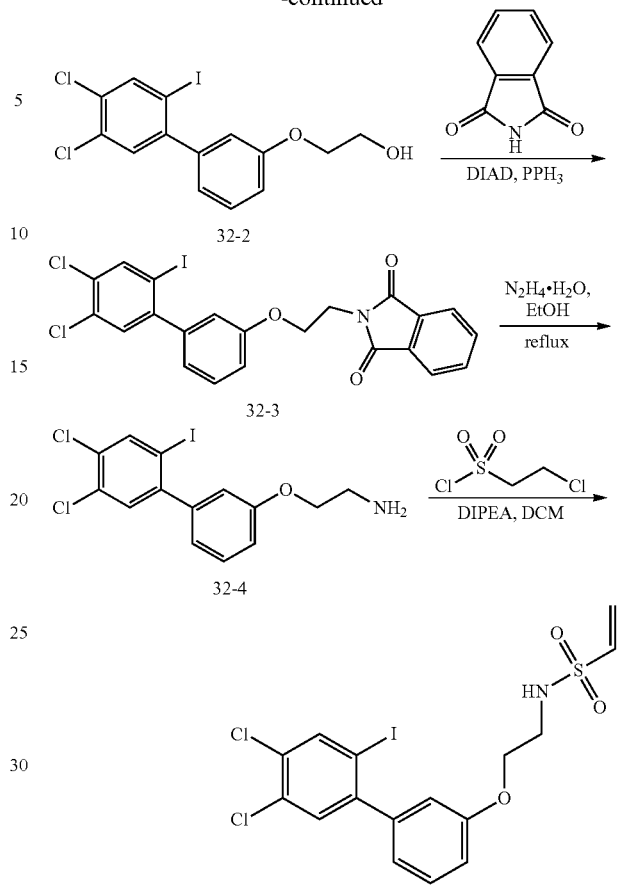

3-(4,5-Dichloro-2-iodophenyl)phenol

A mixture of 1,2-dichloro-4,5-diiodobenzene (1.5 g, 3.76 mmol), 3-hydroxyphenylboronic acid (0.52 g, 3.76 mmol), Na₂CO₃ (1.99 g, 18.8 mmol) and Pd(PPh₃)₄ (0.35 g, 0.30 mmol), in 1,4-dioxane (10 mL) and water (2 mL) was stirred at reflux under argon for 16 h. The mixture was allowed to cool to room temperature and then concentrated in vacuo. The residue was purified by flash column chromatography on silica gel (petroleum ether/ethyl acetate=20:1) to afford the desired product (300 mg, 22% yield). ESI-MS m/z: 362.9 [M−H]⁻.

2-[3-(4,5-Dichloro-2-iodo)phenoxy]ethanol

A mixture of 3-(4,5-dichloro-2-iodophenyl)phenol (0.3 g, 0.82 mmol), 2-bromoethanol (0.20 g, 1.65 mmol), K₂CO₃ (0.57 g, 4.12 mmol) in DMF (5 mL) was stirred at 100° C. under nitrogen for 16 h. The mixture was allowed to cool to room temperature and partitioned between ethyl acetate and brine. The organic layer was dried over Na2SO4, filtered and concentrated in vacuo. The residue was purified by flash column chromatography on silica gel (petroleum ether/ethyl acetate=4:1) to afford the desired product (150 mg, 45% yield).

N-(2-((4',5'-Dichloro-2'-iodo-[1,1'-biphenyl]-3-yl) oxy)ethyl)ethenesulfonamide

The title compound was prepared from 2-[3-(4,5-dichloro-2-iodo)phenoxy]ethanol in three steps followed the procedure described in Example 28. $^1$H NMR (400 MHz, CDCl$_3$) δ: 8.01 (s, 1H), 7.37-7.33 (m, 2H), 6.94-6.91 (m, 2H), 6.81-6.80 (m, 1H), 6.57 (dd, J=10.0, 16.8 Hz, 1H), 6.30 (d, J=16.4 Hz, 1H), 5.97 (d, J=10.0 Hz, 1H), 4.77 (t, J=6.0 Hz, 1H), 4.14 (t, J=5.2 Hz, 2H), 3.49-3.45 (m, 2H). ESI-MS m/z: 496.0 [M−H]$^-$.

Example 12

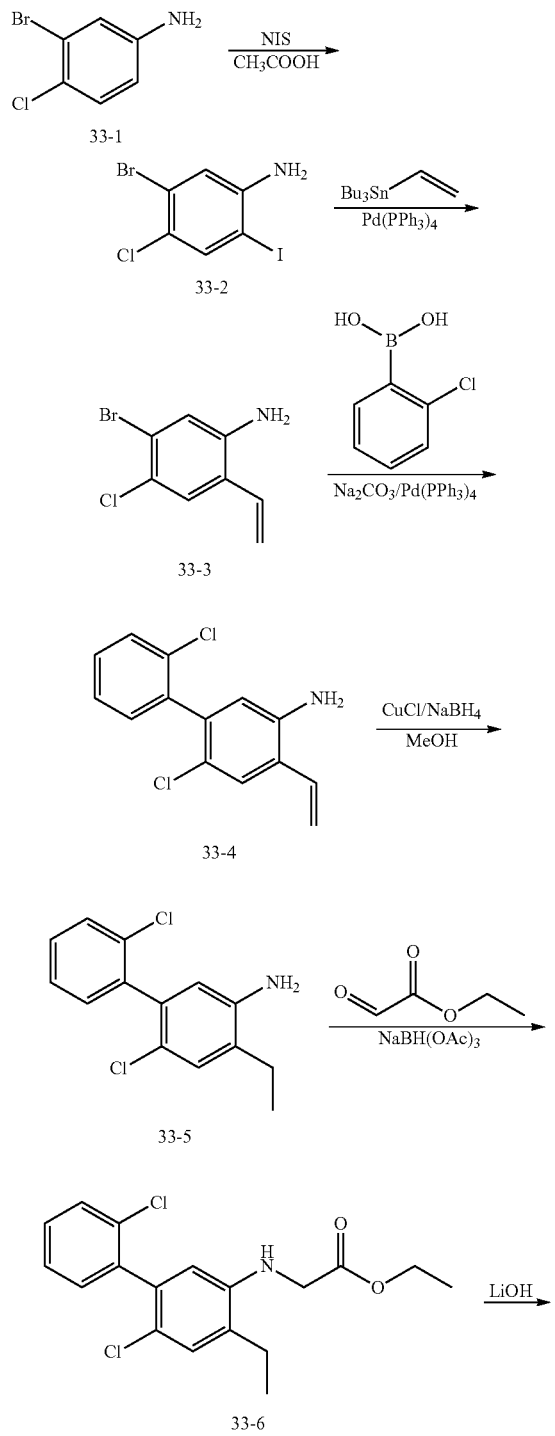

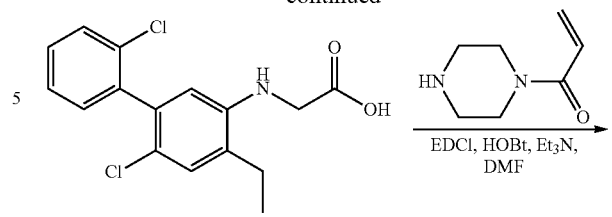

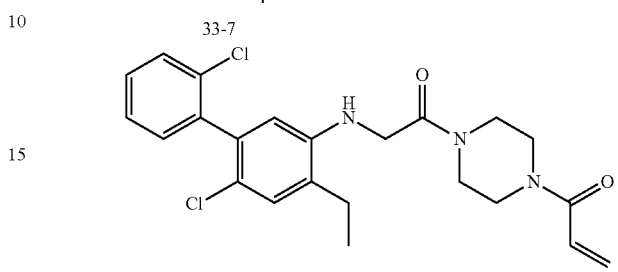

5-Bromo-4-chloro-2-iodobenzenamine

To a solution of 3-bromo-4-chlorobenzenamine (10.0 g, 48.5 mmol) in CH3COOH (50 mL), NIS (10.9 g, 48.5 mmol) was added in portions and the resulting mixture was stirred at room temperature for 16 h. The mixture was concentrated in vacuo. The residue was dissolved in ethyl acetate, washed with saturated NaHCO$_3$ solution and brine, dried over Na$_2$SO$_4$ and concentrated in vacuo. The residue was purified by flash column chromatography on silica gel (petroleum ether/ethyl acetate=50:1) to afford the desired product (2.5 g, 15.5% yield). ESI-MS m/z: 329.9 [M−H]$^-$.

5-Bromo-4-chloro-2-vinylbenzenamine

A mixture of 5-bromo-4-chloro-2-iodobenzenamine (2.5 g, 7.51 mmol), tributyl(vinyl)stannane (2.4 g, 7.51 mmol), Pd(PPh$_3$)$_4$ (867 mg, 0.75 mmol) in toluene (25 mL) was stirred at reflux under argon for 16 h. The reaction mixture was allowed to cool to room temperature and quenched with aqueous KF solution. The mixture was partitioned between ethyl acetate and water. The organic layer was washed with brine, dried over Na$_2$SO$_4$ and concentrated. The residue was purified by flash column chromatography on silica gel (petroleum ether/ethyl acetate=20:1) to afford the desired product (1.0 g, 57.4% yield). ESI-MS m/z: 232.2[M+H]$^+$.

2',6-Dichloro-4-vinyl-[1,1'-biphenyl]-3-amine

A mixture of 5-bromo-4-chloro-2-vinylbenzenamine (600 mg, 2.6 mmol), 2-chlorophenylboronic acid (1.25 g, 12.9 mmol), Pd(PPh$_3$)$_4$ (300 mg, 0.26 mmol), Na$_2$CO$_3$ (1.4 g, 13.0 mmol) in 1,4-dioxane (20 mL) and water (5 mL) was stirred at reflux under argon for 16 h. The mixture was allowed to cool to room temperature and then concentrated in vacuo. The residue was purified by flash column chromatography on silica gel (petroleum ether/ethyl acetate=30:1) to afford the desired product (500 mg, 73.1% yield). ESI-MS m/z: 263.1 [M+H]$^+$.

2',6-Dichloro-4-ethyl-[1,1'-biphenyl]-3-amine

A mixture of 2',6-dichloro-4-vinyl-[1,1'-biphenyl]-3-amine (500 mg, 1.9 mmol), CuCl (225 mg, 2.28 mmol) in MeOH (10 mL) at 0° C., NaBH$_4$ (722 mg, 19 mmol) was added in portions and the resulting mixture was stirred at room temperature for 20 min. The reaction was quenched with water and extracted with ethyl acetate. The organic layer was washed with brine, dried over Na$_2$SO$_4$ and concentrated in vacuo. The residue was purified by flash column chromatography on silica gel (petroleum ether/ethyl acetate=30:1) to afford the desired product (300 mg, 59.4% yield). ESI-MS m/z: 266.0[M+H]$^+$.

1-(4-(2-((2',6-Dichloro-4-ethyl-[1,1'-biphenyl]-3-yl)amino)acetyl)piperazin-1-yl)prop-2-en-1-one The title compound was prepared from 2',6-dichloro-4-ethyl-[1,1'-biphenyl]-3-amine in three steps followed the procedure described in Example 20 and the following procedure for the amide formation.

2-((2',6-dichloro-4-ethyl-[1,1'-biphenyl]-3-yl)amino)acetic acid (150 mg, 0.466 mmol) and Et$_3$N (235 mg, 2.33 mmol) in DMF (5 mL) at 0° C., EDCI.HCl (178 mg, 0.932 mmol) and HOBt (126 mg, 0.932 mmol) were added and the resulting mixture was stirred at 0° C. for 30 min. To this mixture, tert-butyl piperazine-1-carboxylate (123 mg, 0.698 mmol) was added and then stirred at room temperature for 16 h. The reaction mixture was partitioned between ethyl acetate and water. The organic layer was washed with brine, dried over Na$_2$SO$_4$ and concentrated in vacuo. The residue was purified by flash column chromatography on silica gel (DCM/MeOH=50:1) to afford the desired product (45 mg, 21.7% yield). $^1$H NMR (400 MHz, DMSO-d6) δ: 7.56-7.54 (m, 1H), 7.43-7.41 (m, 2H), 7.32-7.30 (m, 1H), 7.14 (s, 1H), 6.81 (dd, J=10.4, 16.4 Hz, 1H), 6.54 (s, 1H), 6.13 (dd, J=2.4, 16.8 Hz, 1H), 5.71 (dd, J=2.0, 10.4 Hz, 1H), 5.25 (bs., 1H), 3.96 (d, J=4.4 Hz, 2H), 3.56-3.52 (m, 8H), 2.54 (q, J=7.2 Hz, 2H), 1.23 (t, J=7.2 Hz, $^3$H). ESI-MS m/z: 444.3 [M−H]$^−$.

Example 13

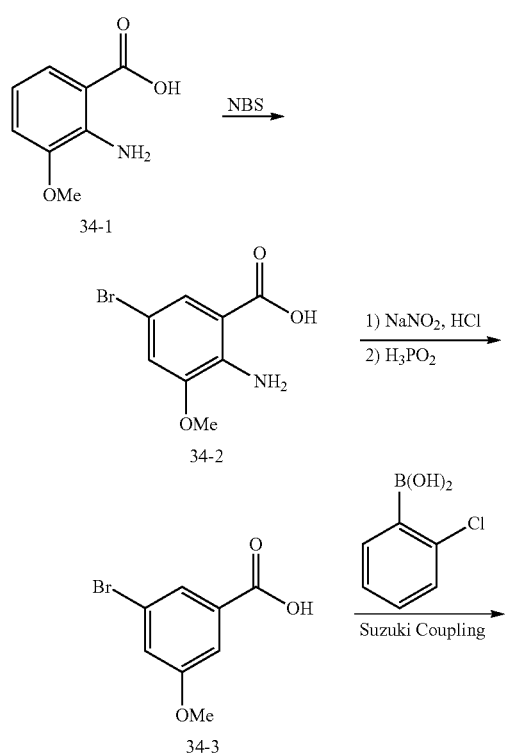

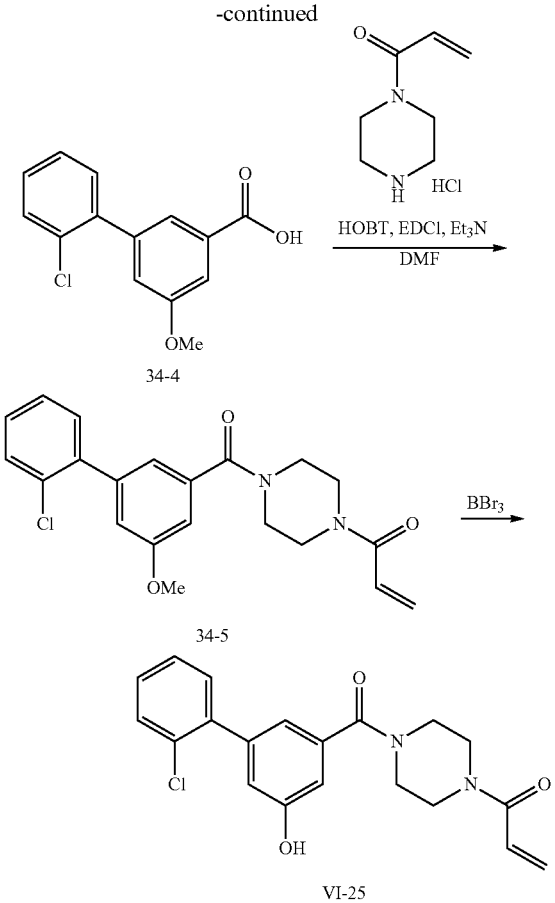

2-Amino-5-bromo-3-methoxybenzoic acid

To a solution of 2-amino-3-methoxybenzoic acid (5 g, 29.9 mmol) in MeOH (35 mL) at −5° C., NBS (5.59 g, 31.4 mmol) was added and the resulting mixture was stirred at 0° C. for 16 h. The mixture was partitioned between ethyl acetate and water. The organic layer was washed with brine, dried over MgSO$_4$, filtered and concentrated in vacuo to afford the crude product (4 g, 54% yield). ESI-MS m/z: 244.2 [M−H]$^−$.

3-Bromo-5-methoxybenzoic acid

To a solution of 2-amino-5-bromo-3-methoxybenzoic acid (4 g, 16.3 mmol) in water (20 mL) at 0° C., conc. HCl (7.5 mL, 90 mmol) and THF (20 mL) were added. The mixture was stirred for 30 min, and then NaNO$_2$ (3.16 g, 45.8 mmol) was added. The resulting mixture was stirred for 2 h and then hypophosphorous acid (5.1 g, 76 mmol, 50% in H$_2$O) was added to the reaction. The mixture was stirred at room temperature for 16 h. The precipitate was collected by filtration, washed with water and dried in vacuo to afford the desired product (3.2 g, 85% yield). ESI-MS m/z: 229.2 [M−H]$^−$.

3-(2-Chlorophenyl)-5-methoxybenzoic acid

To a solution of 3-bromo-5-methoxybenzoic acid (1 g, 4.06 mmol) and 2-chlorophenylboronic acid (1.27 g, 8.13 mmol) in 1,4-dioxane (10 mL) and water (2 mL), Pd(PPh$_3$)$_4$ (468 mg, 0.40 mmol) and Na$_2$CO$_3$ (2.15 g, 20.3 mmol) were added and the resulting mixture was stirred at 80° C. for 16 h. The mixture was allowed to cool to room temperature and acidified with aqueous HCl (1.0 M) to adjust the pH to 3-4. The mixture was extracted with ethyl acetate. The organic layer was dried over MgSO₄, filtered and concentrated in vacuo to afford the desired product (800 mg, 75% yield) without further purification. ESI-MS m/z: 361.2 [M–H]⁻.

1-(4-(2'-Chloro-5-methoxy-[1,1'-biphenyl]-3-carbonyl)piperazin-1-yl)prop-2-en-1-one To a solution of tert-butyl 4-acryloylpiperazine-1-carboxylate (260 mg, 1.07 mmol) in DCM (2 mL), a solution of HCl in MeOH (10 mL, 28.6 mmol) was added and the resulting mixture was stirred at room temperature for 1 h. The mixture was concentrated in vacuo. The residue was added to the solution of 3-(2-chlorophenyl)-5-methoxybenzoic acid (280 mg, 1.07 mmol), HOBt (290 mg, 2.17 mmol), EDCI.HCl (410 mg, 2.17 mmol) and Et₃N (324 mg, 3.21 mmol) in DMF (10 mL). The resulting mixture was stirred at room temperature for 16 h and partitioned between DCM and saturated NaHCO₃ solution. The organic layer was dried over MgSO₄, filtered and concentrated in vacuo. The residue was purified by flash column chromatography on silica gel (dichloromethane/methanol=50:1) to afford the desired product (200 mg, 52% yield). ESI-MS m/z: 385.2[M+H]⁺.

1-(4-(2'-Chloro-5-hydroxy-[1,1'-biphenyl]-3-carbonyl)piperazin-1-yl)prop-2-en-1-one (VI-25)

To a solution of 1-(4-(2'-chloro-5-methoxy-[1,1'-biphenyl]-3-carbonyl)piperazin-1-yl)prop-2-en-1-one (100 mg, 0.26 mmol) in DCM (15 mL) at −78° C., BBr₃ (650 mg, 2.6 mmol) was added and the resulting mixture was stirred at room temperature for 1 h. The mixture was poured into ice-water, basified with sat NaHCO₃ aqueous solution to adjust the pH to 7-8 and extracted with ethyl acetate. The organic layer was dried over MgSO₄, filtered and concentrated in vacuo. The residue was purified by flash column chromatography on silica gel (dichloromethane/methanol=50:1) to afford the desired product (25 mg, 26% yield). ¹H NMR (400 MHz, DMSO-d6) δ: 9.96 (s, 1H), 7.58-7.56 (m, 1H), 7.42-7.40 (m, 3H), 6.89-6.75 (m, 4H), 6.14 (dd, J=2.0, 16.8 Hz, 1H), 5.71 (dd, J=2.0, 10.0 Hz, 1H), 3.68-3.44 (m, 8H). ESI-MS m/z: 371.2[M+H]⁺.

Example 14

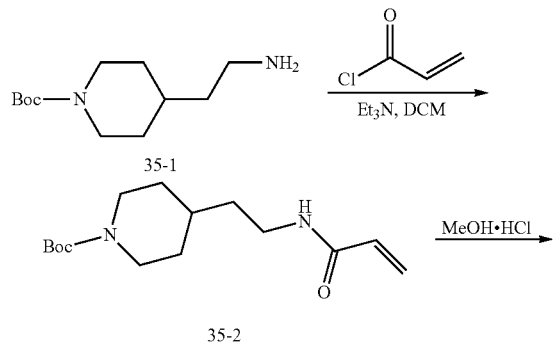

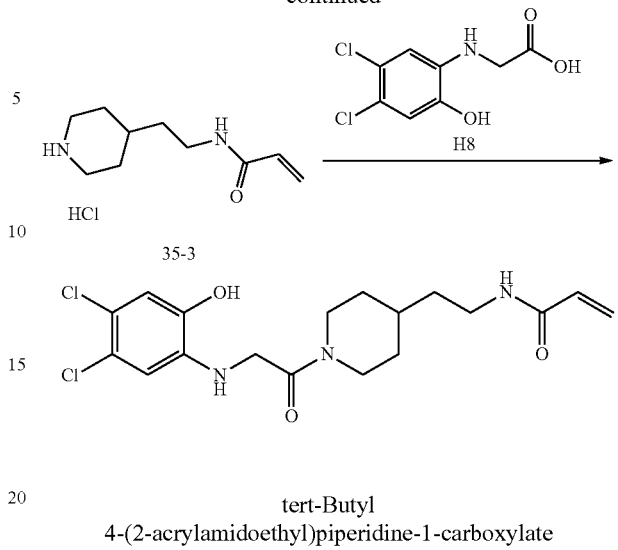

tert-Butyl 4-(2-acrylamidoethyl)piperidine-1-carboxylate

To a stirred mixture of tert-butyl 4-(2-aminoethyl)piperidine-1-carboxylate (1.0 g, 4.38 mmol) in DCM (20 mL) at 0° C., Et₃N (1.33 g, 13.14 mmol) was added and the resulting mixture was stirred at 0° C. for 5 min. To this mixture, a solution of acryloyl chloride (0.39 g, 4.38 mmol) in DCM (5 mL) was added dropwise. The resulting mixture was stirred at room temperature for 30 min. The reaction mixture was poured into water (20 mL) and extracted with DCM (30 mL×3). The combined organic layer was washed with brine (15 mL×3), dried over anhydrous Na₂SO₄, filtered and concentrated in vacuo. The residue was purified by flash column chromatography on silica gel (10-50% ethyl acetate/dichloroethane) to afford the desired product (0.6 g, 50% yield) as a solid.

N-(2-(Piperidin-4-yl)ethyl)acrylamide

A mixture of tert-butyl 4-(2-acrylamidoethyl)piperidine-1-carboxylate (600 mg, 2.13 mmol) in HCl/MeOH (60 mL, 2.86 M) was stirred at room temperature for 1 h. The mixture was concentrated in vacuo to yield the crude product (550 mg) as a solid which was used directly in the next step without further purification.

N-(2-(1-(2-((4,5-Dichloro-2-hydroxyphenyl)amino) acetyl)piperidin-4-yl)ethyl)acrylamide To a stirred solution of 2-((4,5-dichloro-2-hydroxyphenyl) amino)acetic acid (200 mg, 0.85 mmol) in DMF (30 mL) at room temperature, N-(2-(piperidin-4-yl)ethyl)acrylamide (222.8 mg, 1.02 mmol) was added followed by HOBt (172.9 mg, 1.28 mmol), EDCI.HCl (244.7 mg, 1.28 mmol) and Et₃N (257.9 mg, 2.55 mmol). The reaction mixture was stirred at room temperature for 1 h and then partitioned between ethyl acetate and brine. The organic layer was dried over anhydrous Na₂SO₄, filtered and concentrated in vacuo. The residue was purified by flash column chromatography on silica gel (1-3% methanol/dichloroethane) to afford the desired product (120 mg, 29% yield) as a solid. ¹H NMR (400 MHz, DMSO-d6) δ: 10.15 (s, 1H), 8.07 (t, J=5.2 Hz, 1H), 6.78 (s, 1H), 6.72 (s, 1H), 6.18 (dd, J=10.0, 17.2 Hz, 1H), 6.06 (dd, J=2.4, 17.2 Hz, 1H), 5.56 (dd, J=2.4, 10.4 Hz, 1H), 5.34 (t, J=4.0 Hz, 1H), 4.36 (d, J=12.8 Hz, 1H), 3.94-3.87 (m, 3H), 3.20-3.15 (m, 2H), 2.98-2.92 (m, 1H), 2.63-2.57 (m, 1H), 1.74-1.69 (m, 2H), 1.57-1.52 (m, 1H), 1.41-1.35 (m, 2H), 1.12-0.95 (m, 2H). ESI-MS m/z: 400.4[M+H]⁺.

Example 15

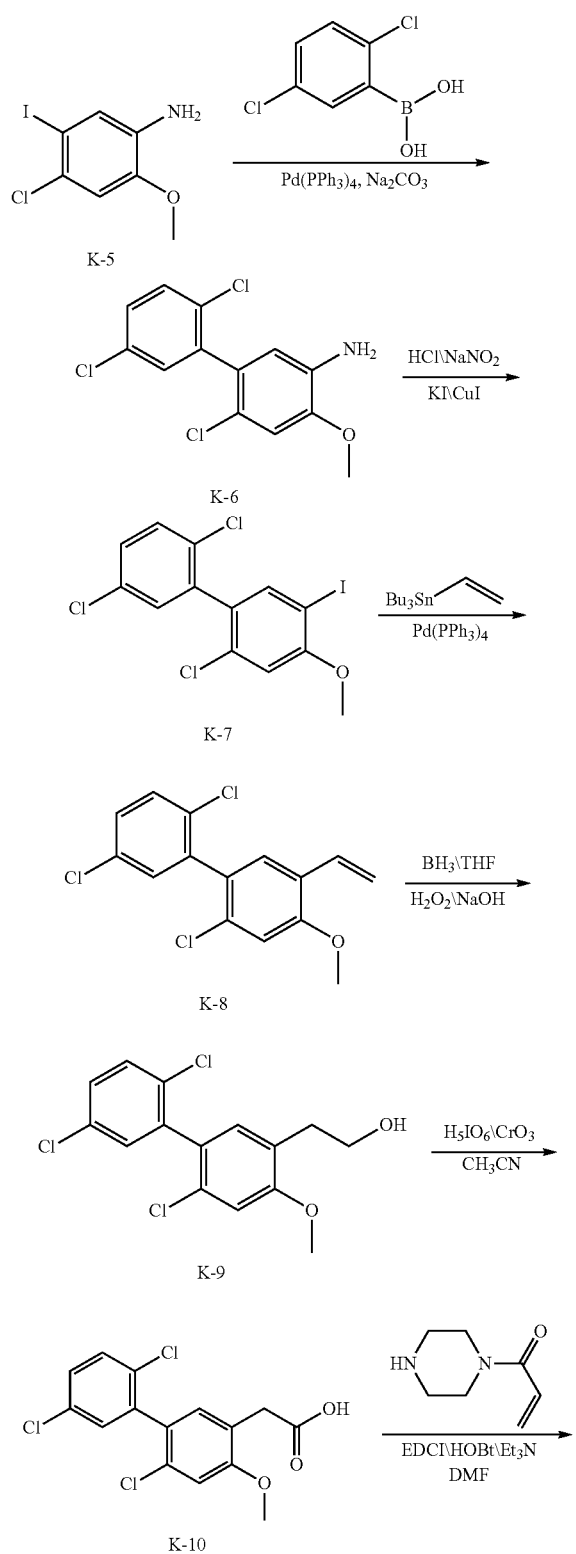

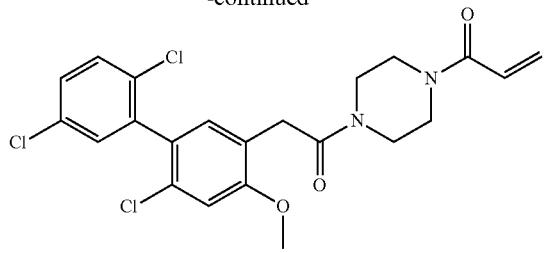

2',5',6-Trichloro-4-methoxy-[1,1'-biphenyl]-3-amine

A mixture of 4-chloro-5-iodo-2-methoxybenzenamine (4.1 g, 14.5 mmol), 2,5-dichlorophenylboronic acid (3.3 g, 17.4 mmol), Pd(PPh$_3$)$_4$ (500 mg, 1.45 mmol) and Na$_2$CO$_3$ (4.7 g, 43.5 mmol) in 1,4-dioxane (150 mL) and water (15 mL) was stirred at 80° C. under argon for 16 h. The mixture was allowed to cool to room temperature, and then partitioned between ethyl acetate and water. The organic layer was washed with brine, dried over Na$_2$SO$_4$ and concentrated in vacuo. The residue was purified by flash column chromatography on silica gel (petroleum ether/ethyl acetate=20:1) to afford the desired product (3.3 g, 75.8% yield) as an off-white solid.

2,2',5'-Trichloro-5-iodo-4-methoxy-1,1'-biphenyl

A mixture of 2',5',6-trichloro-4-methoxy-[1,1'-biphenyl]-3-amine (1.0 g, 3.3 mmol) in conc. HCl (10 mL) and water (10 mL) at 0° C., NaNO$_2$ (350 mg, 5 mmol) was added in portions and the resulting solution was stirred at −5-0° C. for 30 min. To this mixture, a solution of KI (2.2 g, 13.2 mmol) in H$_2$O (10 mL) and CuI (630 mg, 3.3 mmol) was added slowly. The resulting solution was stirred at room temperature for 45 min and then extracted with ethyl acetate. The organic layer was washed with saturated NaHCO$_3$ aqueous solution and brine, dried over Na$_2$SO$_4$ and concentrated in vacuo. The residue was purified by flash column chromatography on silica gel (petroleum ether/ethyl acetate=20:1) to afford the desired product (1.17 g, 87% yield) as a dark oil.

2,2',5'-Trichloro-4-methoxy-5-vinyl-1,1'-biphenyl

A mixture of 2,2',5'-trichloro-5-iodo-4-methoxy-1,1'-biphenyl (1.17 g, 2.9 mmol), tributyl(vinyl)stannane (1.1 g, 3.5 mmol), Pd(PPh$_3$)$_4$ (670 mg, 0.6 mmol) in toluene (30 mL) was stirred at reflux under argon for 6 h. The reaction mixture was quenched with KF aqueous solution and then extracted with ethyl acetate. The organic layer was washed with brine, dried over Na$_2$SO$_4$ and concentrated in vacuo. The residue was purified by flash column chromatography on silica gel (petroleum ether/DCM=100:1) to afford the desired product (310 mg, 35% yield) as a white solid.

2-(2',5',6-Trichloro-4-methoxy-[1,1'-biphenyl]-3-yl) ethanol

To a stirring solution of 2,2',5'-trichloro-4-methoxy-5-vinyl-1,1'-biphenyl (310 mg, 1 mmol) in THF (15 mL) under nitrogen at room temperature, BH$_3$ (2 mL, 1N) was added. After stirring for 8 h, a mixture of NaOH (160 mg, 4 mmol) in water (3 mL) and H$_2$O$_2$ (30% in H$_2$O, 0.3 g, 4 mmol) was added and the resulting mixture was stirred for 6 h. The reaction was quenched with NaHCO$_3$ aqueous solution and extracted with ethyl acetate. The organic layer was washed with brine, dried over $Na_2SO_4$ and concentrated in vacuo. The residue was purified by flash column chromatography on silica gel (petroleum ether/ethyl acetate=4:1) to afford the desired product (180 mg, 54% yield) as a colorless oil.

2-(2',5',6-Trichloro-4-methoxy-[1,1'-biphenyl]-3-yl)acetic acid

To a solution of 2-(2',5',6-Trichloro-4-methoxy-[1,1'-biphenyl]-3-yl)ethanol (180 mg, 0.54 mmol) in CH3CN (20 mL) at 0° C., $H_5IO_5$\$CrO_3$ (3.7 mL, 1.63 mmol, 0.44 M in water) was added and the resulting mixture was stirred at 0° C. for 1 h. The reaction was quenched with $Na_2HPO_4$ and diluted with ethyl acetate. The organic layer was washed with brine, dried over $Na_2SO_4$ and concentrated in vacuo to afford the product (110 mg, 59% yield) as a colorless oil. ESI-MS m/z: 343.1 [M–H]⁻.

1-(4-(2-(2',5',6-Trichloro-4-methoxy-[1,1'-biphenyl]-3-yl)acetyl)piperazin-1-yl)prop-2-en-1-one To a solution of 2-(2',5',6Ttrichloro-4-methoxy-[1,1'-biphenyl]-3-yl)acetic acid (110 mg, 0.318 mmol) $Et_3N$ (96 mg, 0.954 mmol) in DMF (3 mL) at 0° C., EDCI.HCl (92 mg, 0.477 mmol) and HOBt (65 mg, 0.477 mmol) were added and the resulting mixture was stirred at 0° C. for 30 min. To this mixture, 1-(piperazin-1-yl)prop-2-en-1-one (67 mg, 0.382 mmol) was added. The resulting mixture was stirred at room temperature for 16 h and then partitioned between ethyl acetate and water. The organic layer was washed with brine, dried over $Na_2SO_4$ and concentrated in vacuo. The residue was purified by flash column chromatography on silica gel (DCM/MeOH=30:1) to afford the desired product (37 mg, 24.97% yield) as an off-white solid. ¹H NMR (400 MHz, DMSO-d6) δ: 7.61 (d, J=8.4 Hz, 1H), 7.52 (dd, J=2.4, 8.8 Hz, 1H), 7.40 (d, J=2.4 Hz, 1H), 7.20 (s, 1H), 7.10 (s, 1H), 6.81 (dd, J=10.8, 15.2 Hz, 1H), 6.13 (dd, J=2.4, 16.8 Hz, 1H), 5.71 (dd, J=2.0, 10.4 Hz, 1H), 3.84 (s, 3H), 3.67 (s, 2H), 3.54-3.41 (m, 8H). ESI-MS m/z: 467.1[M+H]⁺.

Example 16

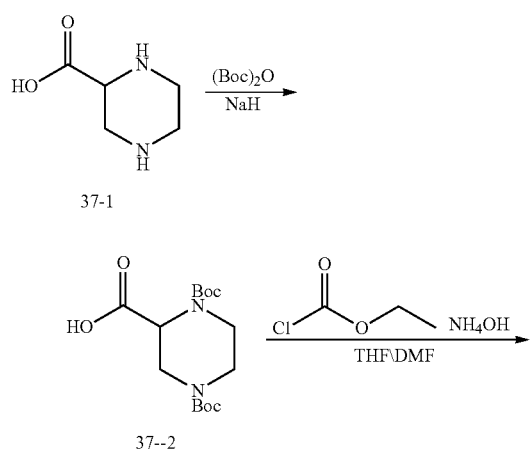

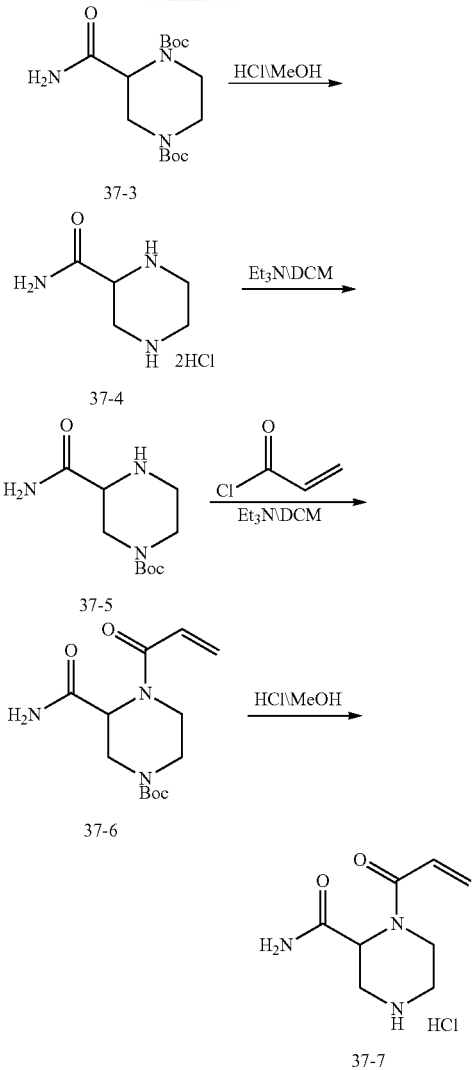

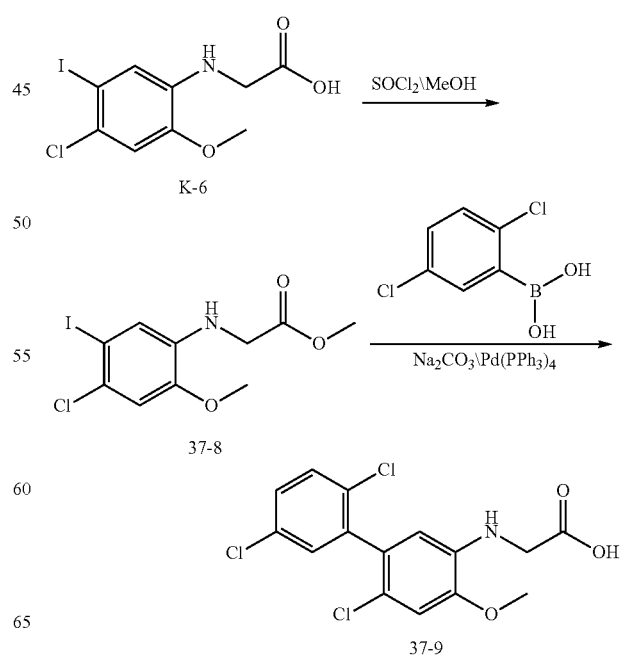

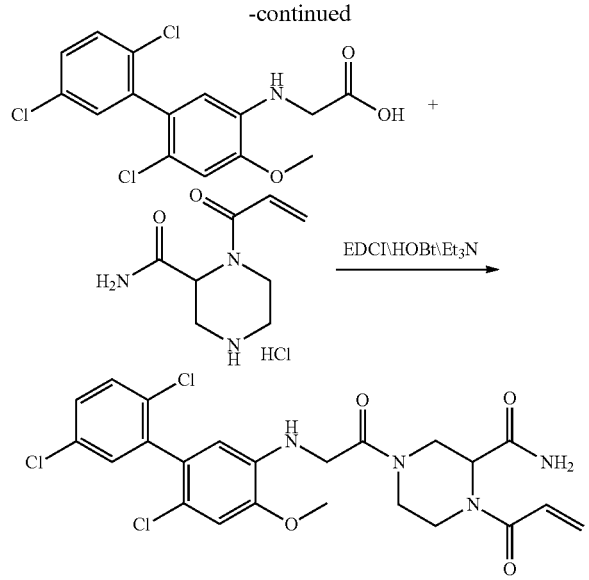

Methyl 2-(4-chloro-5-iodo-2-methoxyphenylamino)acetate

A mixture of tert-butyl 2-(4-chloro-5-iodo-2-methoxyphenylamino)acetic acid (3.0 g, 8.7 mmol), SOCl$_2$ (3 mL) in MeOH (20 mL) was stirred at reflux for 2 h. The mixture was concentrated in vacuo to yield the crude product (3.1 g) as a yellow solid.

2-((2',5',6-Trichloro-4-methoxy-[1,1'-biphenyl]-3-yl)amino)acetic acid

A mixture of methyl 2-(4-chloro-5-iodo-2-methoxyphenylamino)acetate (5.0 g, 14.08 mmol), 2,5-dichlorophenylboronic acid (4.03 g, 21.12 mmol), Pd(PPh$_3$)$_4$ (1.626 g, 1.04 mmol), Na$_2$CO$_3$ (4.477 g, 42.24 mmol) in 1,4-dioxane (100 mL) and water (20 mL) was stirred at reflux under argon for 6 h. Then reaction mixture was allowed to cool to room temperature, quenched with water and acidified with HCl (10% in water) to adjust the pH to 3-4. The mixture was extracted with ethyl acetate, washed with brine, dried over Na$_2$SO$_4$ and concentrated in vacuo. The residue was purified by flash column chromatography on silica gel (50% petroleum ether/ethyl acetate) to afford the desired product (3 g, 59% yield) as an off-white solid. ESI-MS m/z: 360.2 [M–H]$^-$.

1,4-di(tert-Butoxycarbonyl)piperazine-2-carboxylic acid

To a solution of piperazine-2-carboxylic acid (21.2 g, 0.16 mol) in 1,4-dioxane at 0° C., NaOH (80 mL, 400 mmol) was added slowly (over 15 min) followed by (Boc)$_2$O (71 g, 33 mol) and the resulting mixture was stirred at room temperature for 16 h. The mixture was concentrated in vacuo. The residue was dissolved in water (100 mL), acidified with conc. HCl at 0° C. to adjust the pH to 2-3 and then extracted with ethyl acetate. The organic layer was washed with brine, dried over Na$_2$SO$_4$ and concentrated in vacuo to afford the product (44.2 g, 83.7% yield) as an off-white solid.

di-tert-Butyl 2-carbamoylpiperazine-1,4-dicarboxylate

To a solution of 1,4-di(tert-butoxycarbonyl)piperazine-2-carboxylic acid (8.21 g, 24.85 mmol) was dissolved in THF (50 mL) and Et$_3$N (20 mL) at 0° C., ethyl chloroformate (2.8 g, 26.1 mmol) was added dropwise. After stirring at –5-0° C. for 1 h, NH$_4$OH (20 mL) was added and the resulting solution was stirred at room temperature for 1 h. The mixture was poured into water and extracted with ethyl acetate. The organic layer was washed with 1N NaOH and brine, dried over Na$_2$SO$_4$ and concentrated in vacuo to give the product (7.5 g, 91.7% yield) as an off-white solid.

Piperazine-2-carboxamide dihydrochloride

A mixture of di-tert-butyl 2-carbamoylpiperazine-1,4-dicarboxylate (7.5 g, 22.79 mmol), in HCl/MeOH (75 mL, 2.86; N) was stirred at room temperature for 16 h. The mixture was concentrated in vacuo to yield the product (4.58 g, 100% yield) as a yellow solid.

tert-Butyl 3-carbamoylpiperazine-1-carboxylate

To a solution of piperazine-2-carboxamide dihydrochloride (2.02 g, 10 mmol) and Et$_3$N (3.03 g, 30 mmol) in DCM (40 mL) at 0° C., (Boc)$_2$O (2.18 g, 10 mmol) was added dropwise (over 1 h). The resulting solution was stirred at room temperature for 16 h and then partitioned between ethyl acetate and water. The organic layer was washed with brine, dried over Na$_2$SO$_4$ and concentrated in vacuo. The residue was purified by flash column chromatography on silica gel (DCM/MeOH=30:1) to afford the desired product (1.1 g, 48.0% yield).

tert-Butyl 4-acryloyl-3-carbamoylpiperazine-1-carboxylate

To a solution of tert-butyl 3-carbamoylpiperazine-1-carboxylate (300 mg, 1.31 mmol) and Et$_3$N (396 mg, 3.93 mmol) in DCM (5 mL) at 0° C., acryloyl chloride (130 mg, 1.44 mmol) in DCM (1 mL) was added and the resulting mixture was stirred at room temperature for 1.5 h. The mixture was partitioned between DCM and saturated NaHCO$_3$ aqueous solution. The organic layer was washed with saturated NaHCO$_3$ and brine, dried over Na$_2$SO$_4$ and concentrated in vacuo. The residue was purified by flash column chromatography on silica gel (DCM/MeOH=30:1) to afford the desired product (200 mg, 53.9% yield) as an off-white solid.

1-Acryloylpiperazine-2-carboxamide hydrochloride

A mixture of tert-butyl 4-acryloyl-3-carbamoylpiperazine-1-carboxylate (200 mg, 0.706 mmol) in HCl/MeOH (20 mL, 2.86; N) was stirred at room temperature for 1 h. The mixture was concentrated in vacuo to yield the crude product (160 mg) as a yellow solid which was used directly in next step without further purification.

1-Acryloyl-4-(2-((2',5',6-trichloro-4-methoxy-[1,1'-biphenyl]-3-yl)amino)acetyl)piperazine-2-carboxamide 2-((2',5',6-Trichloro-4-methoxy-[1,1'-biphenyl]-3-yl)amino)acetic acid (231 mg, 0.641 mmol) and Et$_3$N (592 mg, 2.564 mmol) in DMF (3 mL) at 0° C., EDCI.HCl (184 mg, 0.961 mmol) and HOBt (134 mg, 0.961 mmol) were added and the resulting mixture was stirred at 0° C. for 30 min. To this mixture, the above 1-acryloylpiperazine-2-carboxamide hydrochloride (160 mg) was added and stirred at room temperature for 16 h. The mixture was partitioned between ethyl acetate and water. The organic layer was washed with brine, dried over Na₂SO₄ and concentrated in vacuo. The residue was purified by flash column chromatography on silica gel (DCM/MeOH=30:1) to afford the desired product (10 mg, 2.97% yield) as an off-white solid. ¹H NMR (400 MHz, DMSO-d6) δ: 7.60-7.38 (m, 3H), 6.70-6.99 (m, 1H), 6.86-6.78 (m, 1H), 6.54-6.49 (m, 1H), 6.16-6.10 (m, 1H), 5.76-5.69 (m, 1H), 5.32-5.31 (m, 1H), 4.93-4.84 (m, 1H), 4.93-4.84 (m, 1H), 4.70-4.62 (m, 1H), 4.35-4.32 (m, 1H), 4.04-3.96 (m, 2H), 3.89-3.63 (m, 1H), 2.90-2.86 (m, 1H). ESI-MS m/z: 525.2[M+H]⁺.

into ice-water, basified with saturated NaHCO₃ solution to adjust the pH to 8-9, and extracted with DCM. The organic layer was dried over anhydrous sodium sulfate, filtered and concentrated in vacuo. The residue was purified by flash column chromatography on silica gel (dichloromethane/methanol=20:1) to afford the desired product (10 mg, 5% yield). ¹H NMR (400 MHz, DMSO-d6) δ: 10.6 (s, 1H), 7.57-7.33 (m, 5H), 7.12 (s, 1H), 7.05 (s, 1H), 6.80 (m, 1H), 6.15-6.11 (dd, J=2, 16.8 Hz, 1H), 5.72-5.70 (m, 1H), 3.6 (m, 8H). ESI-MS m/z: 405.3[M+H]⁺.

Example 17

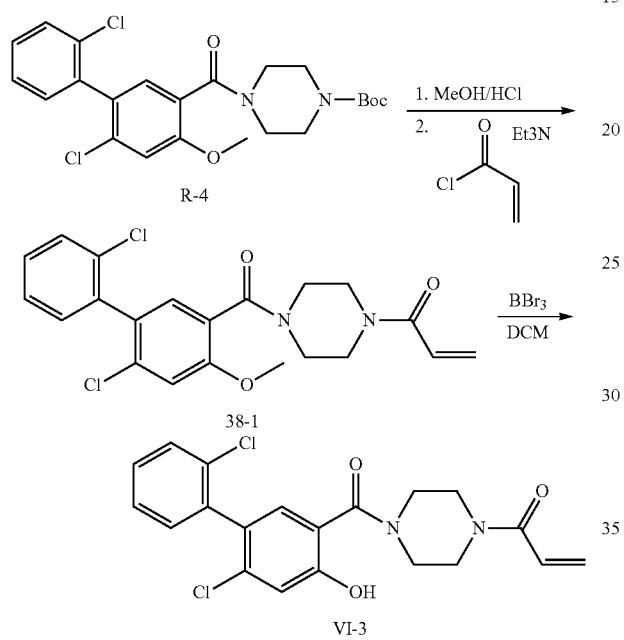

Example 18

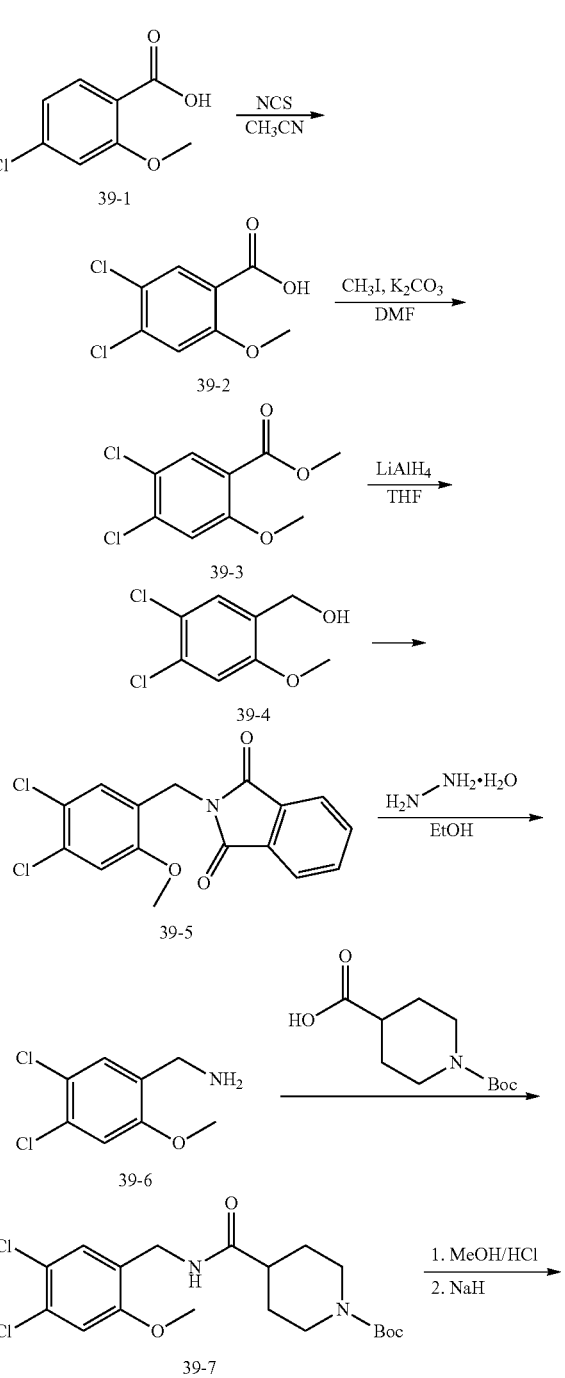

1-(4-(2',6-dichloro-4-methoxy-[1,1'-biphenyl]-3-carbonyl)piperazin-1-yl)prop-2-en-1-one tert-Butyl 4-(2',6-dichloro-4-methoxy-[1,1'-biphenyl]-3-carbonyl)piperazine-1-carboxylate (200 mg, 0.43 mmol) was stirred in HCl in MeOH (2.86 M, 10 mL) for 1 h. The mixture was concentrated in vacuo to yield the crude product. The residue was dissolved in DCM (15 mL), triethylamine (0.5 mL), acryloyl chloride (40 mg, 0.43 mmol) was added to the mixture. The reaction mixture was stirred at room temperature for 30 min, poured into water, and extracted with DCM. The organic layer was washed with water and brine, dried over Na₂SO₄ and concentrated in vacuo. The residue was purified by flash column chromatography on silica gel (dichloromethane/methanol=50:1) to afford the desired product (16 mg, 10% yield) as white solid. ESI-MS m/z: 419.2 [M+H]⁺.

1-(4-(2',6-Dichloro-4-hydroxy-[1,1'-biphenyl]-3-carbonyl)piperazin-1-yl)prop-2-en-1-one (VI-3)

To a solution of 1-(4-(2',6-Dichloro-4-methoxy-[1,1'-biphenyl]-3-carbonyl)piperazin-1-yl)prop-2-en-1-one (200 mg, 0.48 mmol) in DCM (15 mL) at −60° C., BBr₃ (0.6 g, 2.4 mmol) was added dropwise and the resulting mixture was stirred at room temperature for 1 h. The mixture was poured

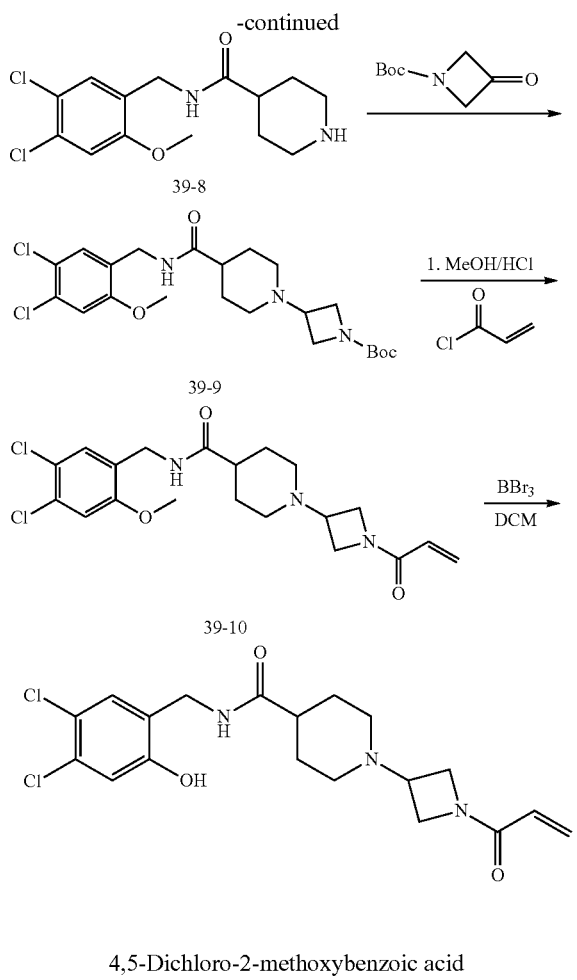

4,5-Dichloro-2-methoxybenzoic acid

A mixture of 4-chloro-2-methoxybenzoic acid (10 g, 53.6 mmol) and NCS (35 g, 19.2 mmol) in acetonitrile (200 mL) was stirred at room temperature for 48 h. The mixture was poured into water and extracted with ethyl acetate. The organic layer was washed with water and brine, dried over $Na_2SO_4$ and concentrated in vacuo to get the crude product (23.3 g).

Methyl 4,5-dichloro-2-methoxybenzoate

A mixture of 4,5-dichloro-2-methoxybenzoic acid (8.2 g, 37 mmol) and $K_2CO_3$ (11.8 g, 111 mmol) in DMF (100 mL), CH3I (6.3 g, 44 mmol) was added dropwise and the resulting mixture was stirred at room temperature for 16 h. The mixture was partitioned between ethyl acetate and water. The organic layer was washed with water and brine, dried over $Na_2SO_4$, and concentrated in vacuo. The residue was purified by flash column chromatography on silica gel (petroleum ether/ethyl acetate=10:1) to afford the desired product.

(4,5-Dichloro-2-methoxyphenyl)methanol

To a mixture of $LiAlH_4$ (2.42 g, 64 mmol) in THF (40 mL) at −40° C. under argon, a solution of methyl 4,5-dichloro-2-methoxybenzoate (6 g, 26 mmol) in THF (50 mL) was added dropwise. The reaction mixture was stirred at −5° C. to 5° C. for 1 h. The mixture was cooled to −20° C. and then water (2 mL) and NaOH (15%) aqueous were added. The resulting mixture was stirred for 15 min. The solid was filtered, and the cake rinsed with ethyl acetate. The combined filtrate was dried over $Na_2SO_4$ and concentrated in vacuo to afford the crude product (4.6 g).

2-(4,5-Dichloro-2-methoxybenzyl)isoindoline-1,3-dione

To a mixture of 4,5-dichloro-2-methoxyphenyl)methanol (4.5 g, 22 mmol), isoindoline-1,3-dione (9.6 g, 65 mmol) and $PPh_3$ (17 g, 65 mmol) in THF (100 mL) at room temperature, DIAD (13 g, 65 mmol) was added and the resulting mixture was stirred at room temperature for 16 h. The mixture was partitioned between ethyl acetate and water. The organic layer was washed brine, dried over $Na_2SO_4$, concentrated in vacuo. The residue was purified by flash column chromatography on silica gel (petroleum ether/ethyl acetate=10:1) to afford the desired product.

(4,5-Dichloro-2-methoxyphenyl)methanamine

To a solution of 2-(4,5-dichloro-2-methoxybenzyl)isoindoline-1,3-dione (1.8 g, 5 mmol) in EtOH (5 mL), hydrazine hydrate (1.34 g, 27 mmol) was added and the resulting mixture was stirred at reflux for 1 h. The mixture was concentrated in vacuo and the residue was purified by flash column chromatography on silica gel (dichloromethane/methanol=20:1) to afford the desired product (0.8 g, 78% yield).

tert-Butyl 4-((4,5-dichloro-2-methoxybenzyl)carbamoyl)piperidine-1-carboxylate The mixture of (4,5-dichloro-2-methoxyphenyl)methanamine (0.8 g, 3.90 mmol), 1-(tert-butoxycarbonyl)piperidine-4-carboxylic acid (0.88 g, 3.84 mmol), BOP (2 g, 1.16 mmol) and DIEA (1.6 g, 2.91 mmol) in DMF (20 mL) was stirred at room temperature for 1 h. The mixture was poured into water and extracted with ethyl acetate. The organic layer was washed with water and brine, dried over $Na_2SO_4$ and concentrated in vacuo. The residue was purified by flash column chromatography on silica gel (dichloromethane/methanol=100:1) to afford the desired product (0.987 g, 62% yield). ESI-MS m/z: 415.4 $[M-H]^-$.

N-(4,5-Dichloro-2-methoxybenzyl)piperidine-4-carboxamide

The mixture of 4-((4,5-dichloro-2-methoxybenzyl)carbamoyl)piperidine-1-carboxylate (987 mg, 2.37 mmol) in HCl/MeOH (20 mL, 57.2 mmol) was stirred at room temperature for 1 h. Then the solvent was evaporated in vacuo and the residue was dissolved with dichloromethane (5 mL). To this mixture, NaH (85 mg, 3.55 mmol) was added. Then the resulting mixture was stirred at room temperature for 30 min. The solvent was removed under reduced pressure to yield the crude product (800 mg).

tert-butyl 3-(4-(4,5-Dichloro-2-methoxybenzylcarbamoyl)piperidin-1-yl)azetidine-1-carboxylate A mixture of N-(4,5-dichloro-2-methoxybenzyl)piperidine-4-carboxamide (750 mg, 2.37 mmol), tert-butyl 3-oxoazetidine-1-carboxylate (607 mg, 3.55 mmol), AcOH (1 mL) and MeOH (5 mL) was stirred at reflux for 2 h. To this mixture, $NaBH_3(CN)$ (0.74 g, 11.85 mmol) was added and the resulting mixture was stirred at 60° C. for 16 h. The mixture was allowed to cool to room temperature and partitioned between $NH_4Cl$ aqueous solution and ethyl acetate.

The organic layer was washed with water and brine, dried over Na$_2$SO$_4$ and concentrated in vacuo. The residue was purified by flash column chromatography on silica gel (dichloromethane/methanol=50:1) to afford the desired product (220 mg, 18% yield). ESI-MS m/z: 472.3[M+H]$^+$.

1-(1-Acryloylazetidin-3-yl)-N-(4,5-dichloro-2-methoxybenzyl)piperidine-4-carboxamide A mixture of tert-butyl 3-(4-(4,5-dichloro-2-methoxybenzylcarbamoyl)piperidin-1-yl)azetidine-1-carboxylate (210 mg, 0.44 mmol) in HCl/MeOH (10 mL, 2.86 M) was stirred at room temperature for 1 h. The mixture was concentrated in vacuo to yield the crude residue. The residue was dissolved in DCM (5 mL), triethylamine (0.5 mL) and acryloyl chloride (40 mg, 0.43 mmol) were added. The reaction mixture was stirred at room temperature for 30 min and then partitioned between DCM and water. The organic layer was washed with water and brine, dried over Na$_2$SO$_4$ and concentrated in vacuo. The residue was purified by flash column chromatography on silica gel (dichloromethane/methanol=50:1) to afford the desired product (150 mg, 82% yield).

N-(4,5-Dichloro-2-hydroxybenzyl)-1-(1-acryloylazetidin-3-yl)piperidine-4-carboxamide To a solution of 1-(1-acryloylazetidin-3-yl)-N-(4,5-dichloro-2-methoxybenzyl)piperidine-4-carboxamide (150 mg, 0.35 mmol) in DCM (15 mL) at −60° C., BBr$_3$ (0.6 g, 2.4 mmol) was added dropwise. The resulting mixture was allowed to warm to room temperature and stirred for 1 h. The mixture was poured into ice-water, basified with saturated NaHCO$_3$ solution to adjust the pH to 8-9, and then extracted with DCM. The organic layer was dried over anhydrous sodium sulfate and concentrated in vacuo. The residue was purified by flash column chromatography on silica gel (dichloromethane/methanol=20:1) to afford the desired product (34 mg, 24% yield). $^1$H NMR (400 MHz, DMSO-d6) δ: 10.34 (s, 1H), 8.2-8.25 (m, 1H), 7.2 (s, 1H), 7.0 (s, 1H), 6.91 (s, 1H), 6.33-6.27 (m, 1H), 6.12-6.07 (dd, J=2.4, 12.4 Hz, 1H), 5.68-5.65 (dd, J=2.4, 10.4 Hz, 1H), 4.24-4.20 (m, 1H), 4.17-4.14 (m, 2H), 4.14-3.99 (m, 1H), 3.94-3.90 (m, 1H), 3.73-3.70 (m, 1H), 3.10 (s, 1H), 2.84-2.80 (m, 2H), 2.22 (m, 1H), 1.80 (s, 2H), 1.73-1.71 (m, 2H), 1.63-1.57 (m, 2H). ESI-MS m/z: 412.2[M+H]$^+$.

Example 19

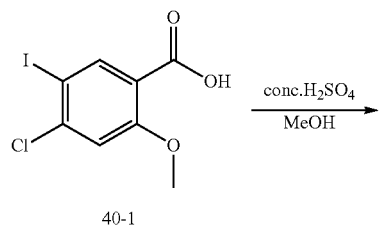

40-1

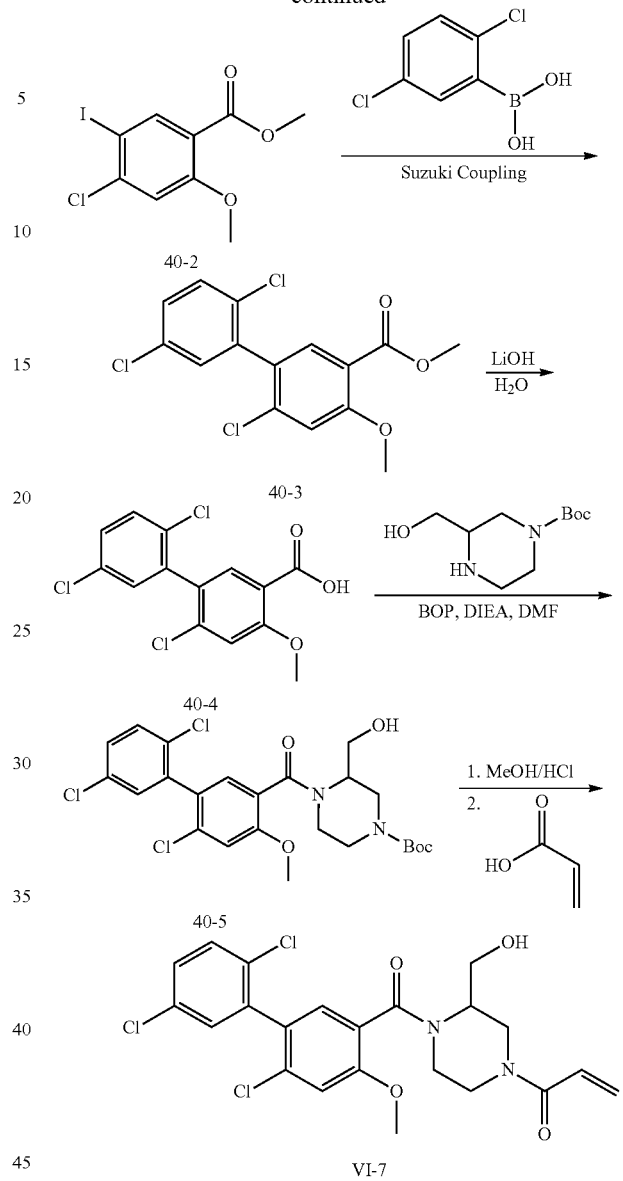

Methyl 4-chloro-5-iodo-2-methoxybenzoate

A mixture of 4-chloro-5-iodo-2-methoxybenzoic acid (2 g, 6.41 mmol) concentrated sulfuric acid (1.5 mL) in MeOH (50 mL) was stirred at reflux for 16 h. The mixture was allowed to cool to room temperature and partitioned between water and ethyl acetate. The organic layer was washed with water and brine, dried over Na$_2$SO$_4$ and concentrated in vacuo to afford the desired product (1.85 g, 85% yield) as a yellow oil.

Methyl 2',5',6-trichloro-4-methoxy-[1,1'-biphenyl]-3-carboxylate

A mixture of Methyl 4-chloro-5-iodo-2-methoxybenzoate (1.8 g, 5.51 mmol), (2,5-dichlorophenyl)boronic acid (2.1 g, 11.03 mmol), Pd(PPh$_3$)$_4$ (403 mg, 0.55 mmol), Na$_2$CO$_3$ (1.75 g, 16.54 mmol) in 1,4-dioxane (50 mL) and water (5 mL) was stirred at reflux under argon for 16 h. The mixture was filtered and filtrate was concentrated in vacuo. The residue was purified by flash column chromatography on silica gel (petroleum ether/ethyl acetate=20:1) to afford the desired product (1.6 g, 85% yield).

1-(3-(Hydroxymethyl)-4-(2',5',6-trichloro-4-methoxy-[1,1'-biphenyl]-3-carbonyl)piperazin-1-yl)prop-2-en-1-one (VI-7)

The title compound was prepared from methyl 2',5',6-trichloro-4-methoxy-[1,1'-biphenyl]-3-carboxylate in three steps followed the procedure described in Example 20.

tert-butyl3-(hydroxymethyl)-4-(2',5',6-trichloro-4-methoxy-[1,1'-biphenyl]-3-carbonyl)piperazine-1-carboxylate (420 mg, 0.79 mmol) was stirred in HCl in MeOH (2.85N). The solvent was removed under reduced pressure to yield the crude reside which was dissolved in DMF (20 mL), acrylic acid (57 mg, 0.79 mmol), BOP (421 mg, 0.95 mmol) and DIEA (409 mg, 3.17 mmol) were added. The reaction was stirred at room temperature for 1 h. The resulting mixture was poured into water, extracted with ethyl acetate and washed with water and brine. The combined organic layer was dried over $Na_2SO_4$, filtered and concentrated. The residue was purified by column chromatography on silica gel (dichloromethane/methanol=60:1) to afford the desired product (92 mg, 24% yield). $^1$H NMR (400 MHz, DMSO-d6) δ: 7.64-7.20 (m, 5H), 6.83-6.70 (m, 1H), 6.16-6.11 (d, 1H), 5.74-5.71 (d, 1H), 6.91 (s, 1H), 5.08-4.01 (m, 3H), 3.90-3.86 (d, 3H), 3.49-3.22 (m, 2H), 2.93-2.74 (m, 2H), 2.89-2.67 (m, 2H). ESI-MS m/z: 451.2 [M−H]$^−$.

Example 20 tert-Butyl 4-(4-bromo-1H-pyrrole-2-carbonyl)piperazine-1-carboxylate

To a mixture of 4-bromo-1H-pyrrole-2-carboxylic acid (800 mg, 4.21 mmol), tert-butylpiperazine-1-carboxylate (822 mg, 4.42 mmol), BOP (2.2 g, 5.05 mmol) in DMF (5 mL), DIEA (1.63 g, 12.63 mmol) was added and the resulting mixture was stirred at room temperature for 1 h. The mixture was poured into water and extracted with ethyl acetate. The organic layer was washed with water and brine, dried over $Na_2SO_4$ and concentrated in vacuo to afford the crude product (920 mg, 61% yield) which was used directly in the next step without purification.

tert-Butyl 4-(4-(2,4-dichlorophenyl)-1H-pyrrole-2-carbonyl)piperazine-1-carboxylate A mixture of tert-butyl 4-(4-bromo-1H-pyrrole-2-carbonyl)piperazine-1-carboxylate (350 mg, 0.98 mmol), (2,4-dichlorophenyl) boronic acid (280 mg, 1.47 mmol), Pd(PPh$_3$)$_4$ (116 mg, 0.1 mmol), Na$_2$CO$_3$ (312 mg, 2.94 mmol) in 1,4-dioxane (10 mL) and water (2 mL) was stirred at reflux under argon for 16 h. The mixture was allowed to cool to room temperature and concentrated in vacuo. The residue was purified by flash column chromatography on silica gel (petroleum ether/ethyl acetate=30:1) to afford the desired product (273 mg, 59% yield).

1-(4-(4-(2,4-Dichlorophenyl)-1H-pyrrole-2-carbonyl)piperazin-1-yl)prop-2-en-1-one (VI-32)

The mixture of tert-butyl 4-(4-(2,4-dichlorophenyl)-1H-pyrrole-2-carbonyl)piperazine-1-carboxylate (270 mg, 0.64 mmol) in HCl/MeOH (20 mL, 57.2 mmol) was stirred for 1 h. The mixture was concentrated in vacuo and the residue was dissolved in DMF (5 mL). To this mixture, acrylic acid (50 mg, 0.7 mmol), BOP (437 mg, 0.72 mmol) and DIEA (248 mg, 1.92 mmol) were added. The reaction mixture was stirred at room temperature for 1 h. The mixture was partitioned between ethyl acetate and water. The organic layer was washed with brine, dried over $Na_2SO_4$ and concentrated in vacuo. The residue was purified by flash column chromatography on silica gel (dichloromethane/methanol=60:1) to afford the desired product (40 mg, 27% yield) as a white solid. $^1$H NMR (400 MHz, DMSO-d6) δ: 11.88 (s, 1H), 7.66-7.63 (m, 2H), 7.43 (m, 1H), 7.38 (s, 1H), 6.91 (s, 1H), 6.85-6.78 (m, 1H), 6.18-6.13 (dd, J=2.4, 12.4 Hz, 1H), 5.74-5.71 (dd, J=2.4, 10.4 Hz, 1H), 3.76 (s, 4H), 3.68-3.63 (m, 4H). ESI-MS m/z: 377.3 [M−H]$^−$.

Example 21

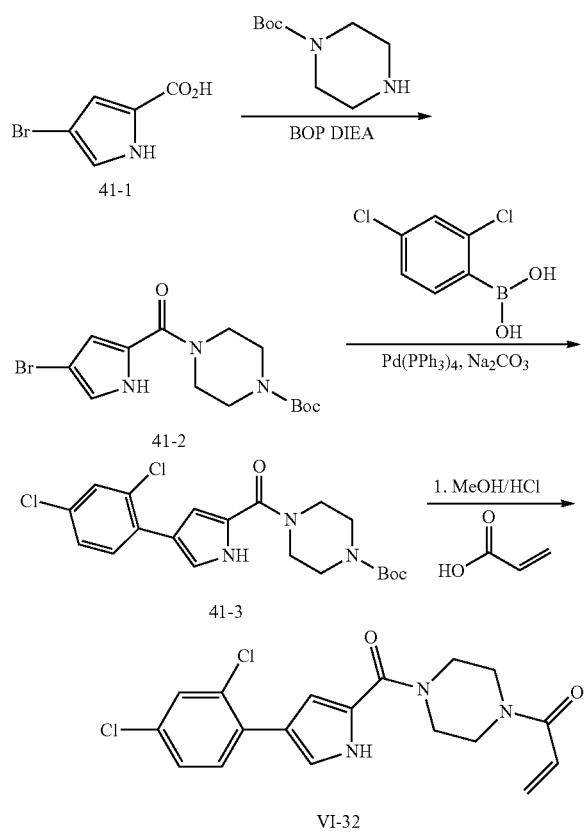

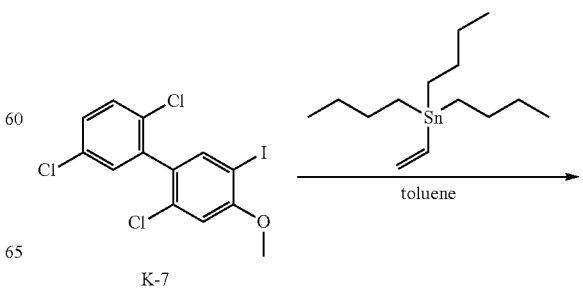

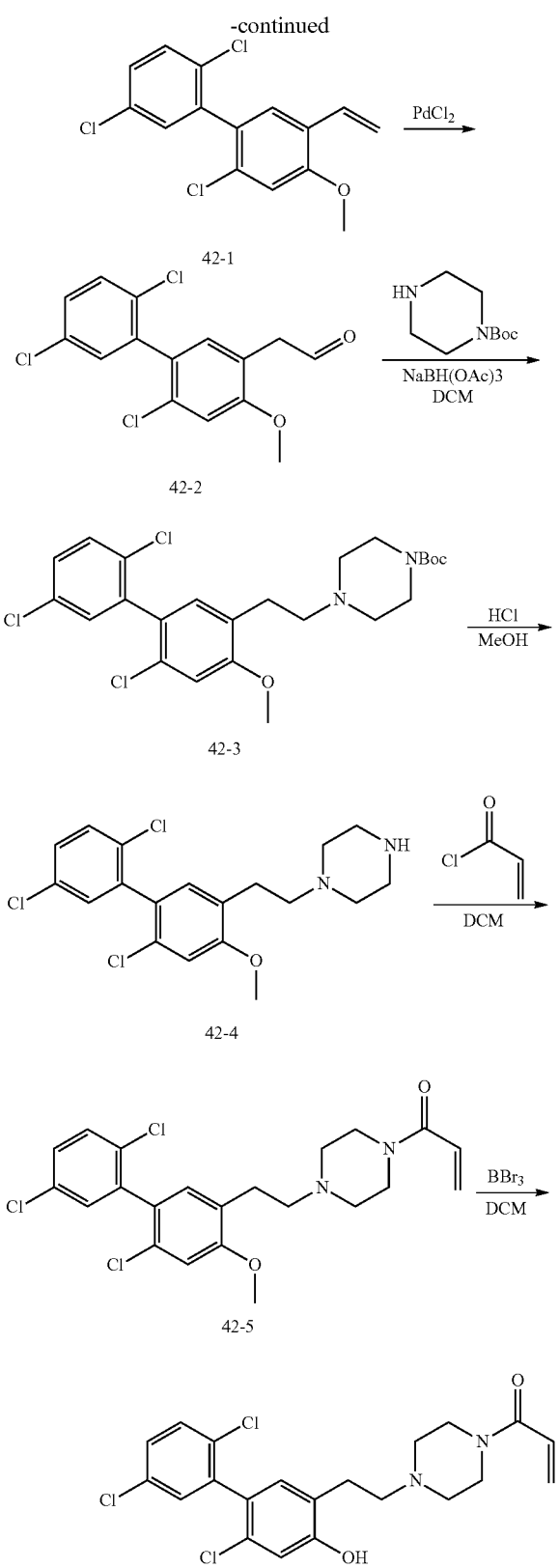

2,2',5'-Trichloro-4-methoxy-5-vinylbiphenyl

To a stirred solution of 2,2',5'-trichloro-5-iodo-4-methoxybiphenyl (3.4 g, 8.3 mmol) in toluene (100 mL) at room temperature, tributyl(vinyl)stannane (3.1 g, 9.9 mmol) was added followed by Pd(PPh$_3$)$_4$ (2 g, 1.7 mmol). The reaction mixture was degassed and back-filled with nitrogen (several cycles) and then stirred at reflux for 16 h. The mixture was allowed to cool to room temperature, a solution of KF (1.72 g, 29.7 mmol) in H$_2$O (10 mL) was added and then stirred for 1 h. The mixture was partitioned between ethyl acetate and water. The organic layer was dried over anhydrous Na$_2$SO$_4$, filtered and concentrated in vacuo. The residue was purified by flash column chromatography on silica gel (1-2% ethyl acetate/petroleum ether) to afford the desired product (2.4 g, 92% yield) as a white solid 2-(2',5',6-Trichloro-4-methoxybiphenyl-3-yl)acetaldehyde To a mixture of 2,2',5'-trichloro-4-methoxy-5-vinylbiphenyl (1.0 g, 3.2 mmol) in anhydrous DMF (10 mL), PdCl$_2$ (1.14 g, 6.4 mmol) was added and the resulting mixture was stirred at room temperature under nitrogen for 16 h. To this mixture, water (0.5 mL) was added and the resulting mixture was stirred at room temperature for another 6 h. The mixture was partitioned between ethyl acetate and water. The organic layer was washed with water, dried over anhydrous Na$_2$SO$_4$, filtered and concentrated in vacuo. The residue was purified by flash column chromatography on silica gel (1-3% ethyl acetate/petroleum ether) to afford the desired product (300 mg, 29% yield) as a white solid.

tert-Butyl 4-(2-(2',5',6-trichloro-4-methoxybiphenyl-3-yl)ethyl)piperazine-1-carboxylate To a stirred solution of 2-(2',5',6-trichloro-4-methoxybiphenyl-3-yl)acetaldehyde (300 mg, 0.92 mmol) in DCM (20 mL) at room temperature, tert-butyl piperazine-1-carboxylate (205 mg, 1.1 mmol) was added followed by drops of AcOH. The reaction mixture was stirred at room temperature for 1 h, and then NaBH(OAc)$_3$ (1.95 g, 9.2 mmol) was added. The resulting mixture was stirred at reflux for 16 h. The mixture was allowed to cool to room temperature, diluted with water and extracted with DCM. The organic layer was dried over anhydrous Na$_2$SO$_4$, filtered and concentrated in vacuo. The residue was purified by flash column chromatography on silica gel (1-33% ethyl acetate/petroleum ether) to afford the desired product (350 mg, 77% yield) as a white solid.

1-(4-(2-(2',5',6-Trichloro-4-hydroxybiphenyl-3-yl)ethyl)piperazin-1-yl)prop-2-en-1-one The title compound was prepared from tert-butyl 4-(2-(2',5',6-trichloro-4-methoxybiphenyl-3-yl)ethyl)piperazine-1-carboxylate in three steps following the procedure described in Example 18. $^1$H NMR (400 MHz, DMSO-d6) δ: 10.96 (bs., 1H), 7.54-7.59 (d, J=8.6 Hz, 1H), 7.47-7.50 (m, 1H), 7.39-7.40 (d, J=2.6 Hz, 1H), 7.08 (s, 1H), 6.94 (s, 1H), 6.77-6.84 (m, 1H), 6.09 (dd, J=2.1, 17.0 Hz, 1H), 5.65 (dd, J=2.6, 10.7

Hz, 1H), 3.50 (m, 4H), 2.72-2.76 (m, 2H), 2.54-2.57 (m, 2H), 2.47-2.50 (m, 4H). ESI-MS m/z: 439.1[M+H]⁺.

Example 22

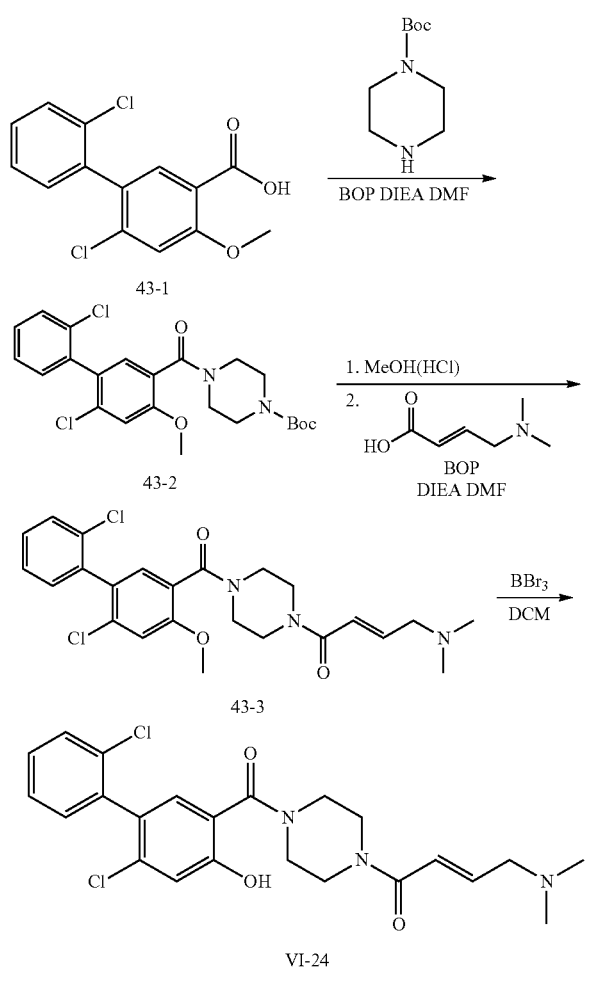

tert-Butyl 4-(2',6-dichloro-4-methoxy-[1,1'-biphenyl]-3-carbonyl)piperazine-1-carboxylate To a stirred solution of 2',6-dichloro-4-methoxy-[1,1'-biphenyl]-3-carboxylic acid (500 mg, 1.68 mmol) in DMF (10 mL) at room temperature, tert-butyl piperazine-1-carboxylate (345 mg, 1.85 mmol), BOP (892 mg, 2.02 mmol) and DIEA (542 mg, 4.2 mmol) were added and the resulting mixture was stirred at room temperature for 2 h. The reaction mixture was diluted with ethyl acetate and washed with brine. The organic layer was dried over anhydrous Na₂SO₄, filtered and concentrated in vacuo. The residue was purified by flash column chromatography on silica gel (dichloromethane/methanol=50:1) to afford the desired product (550 mg, 70% yield). ESI-MS m/z: 465.4[M+H]⁺.

(E)-1-(4-(2',6-dichloro-4-methoxy-[1,1'-biphenyl]-3-carbonyl)piperazin-1-yl)-4-(dimethylamino)but-2-en-1-one A mixture of tert-Butyl 4-(2',6-dichloro-4-methoxy-[1,1'-biphenyl]-3-carbonyl)piperazine-1-carboxylate (550 mg, 1.18 mmol) in HCl/MeOH (20 mL, 57.2 mmol) was stirred at room temperature for 1 h. The solvent was removed under reduced pressure to yield the crude product. The crude residue was dissolved with DMF (10 mL), 4-(dimethylamino)but-2-enoic acid (215 mg, 0.47 mmol), BOP (627 mg, 1.42 mmol) and DIEA (610 mg, 4.73 mmol) was added. The resulting mixture was stirred at room temperature for 2 h. The reaction mixture was diluted with ethyl acetate and washed with brine. The organic layer was dried over anhydrous Na₂SO₄, filtered and concentrated in vacuo. The residue was purified by flash column chromatography on silica gel (dichloromethane/methanol=50:1) to afford the desired product (450 mg, 80% yield, 2 steps). ESI-MS m/z: 476.4[M+H]⁺.

(E)-1-(4-(2',6-dichloro-4-hydroxy-[1,1'-biphenyl]-3-carbonyl)piperazin-1-yl)-4-(dimethylamino)but-2-en-1-one (VI-24)

A solution of (E)-1-(4-(2',6-dichloro-4-methoxy-[1,1'-biphenyl]-3-carbonyl)piperazin-1-yl)-4-(dimethylamino)but-2-en-1-one (270 mg, 0.57 mmol) in DCM (5 mL) at −78° C., BBr₃ (1.43 g, 5.7 mmol) was added dropwise. The resulting mixture was stirred at room temperature for 2 h. The mixture was poured into ice-water, basified with the aqueous NaHCO₃ to adjust the pH to 7 and then extracted with DCM (3×20 mL). The organic layer was dried over Na₂SO₄ and concentrated in vacuo. The residue was purified by column chromatography on silica gel (dichloromethane/methanol=50:1) to afford the desired product (150 mg, 57% yield). ¹HNMR (400 MHz, DMSO-d6) δ: 13.12 (s, 1H), 8.02 (s, 1H), 7.81 (s, 1H), 6.81 (m, 1H), 6.13 (dd, J=2.8, 16.8 Hz, 1H), 5.71 (dd, J=2.0, 10.4 Hz, 1H), 4.10 (s, 2H), 3.50-3.60 (m, 8H). ESI-MS m/z: 462.4[M+H]⁺.

Example 23

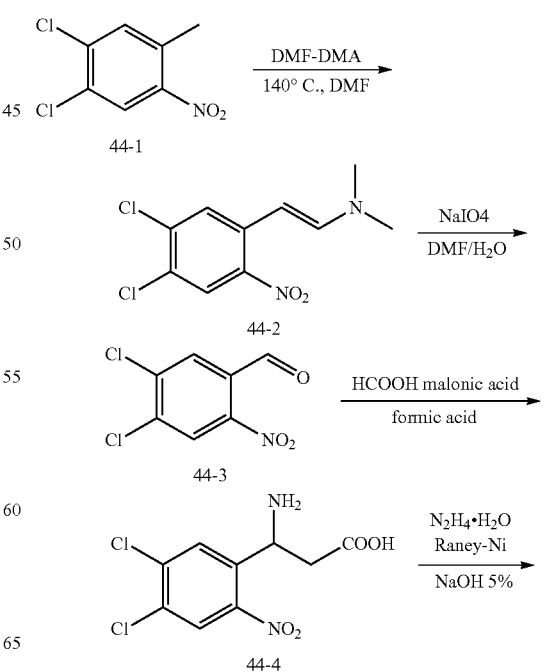

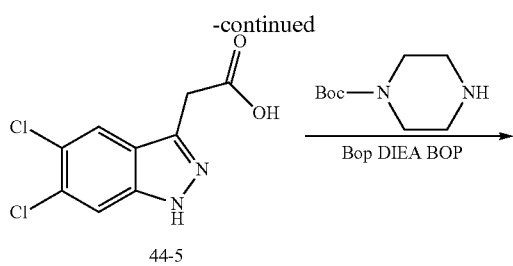
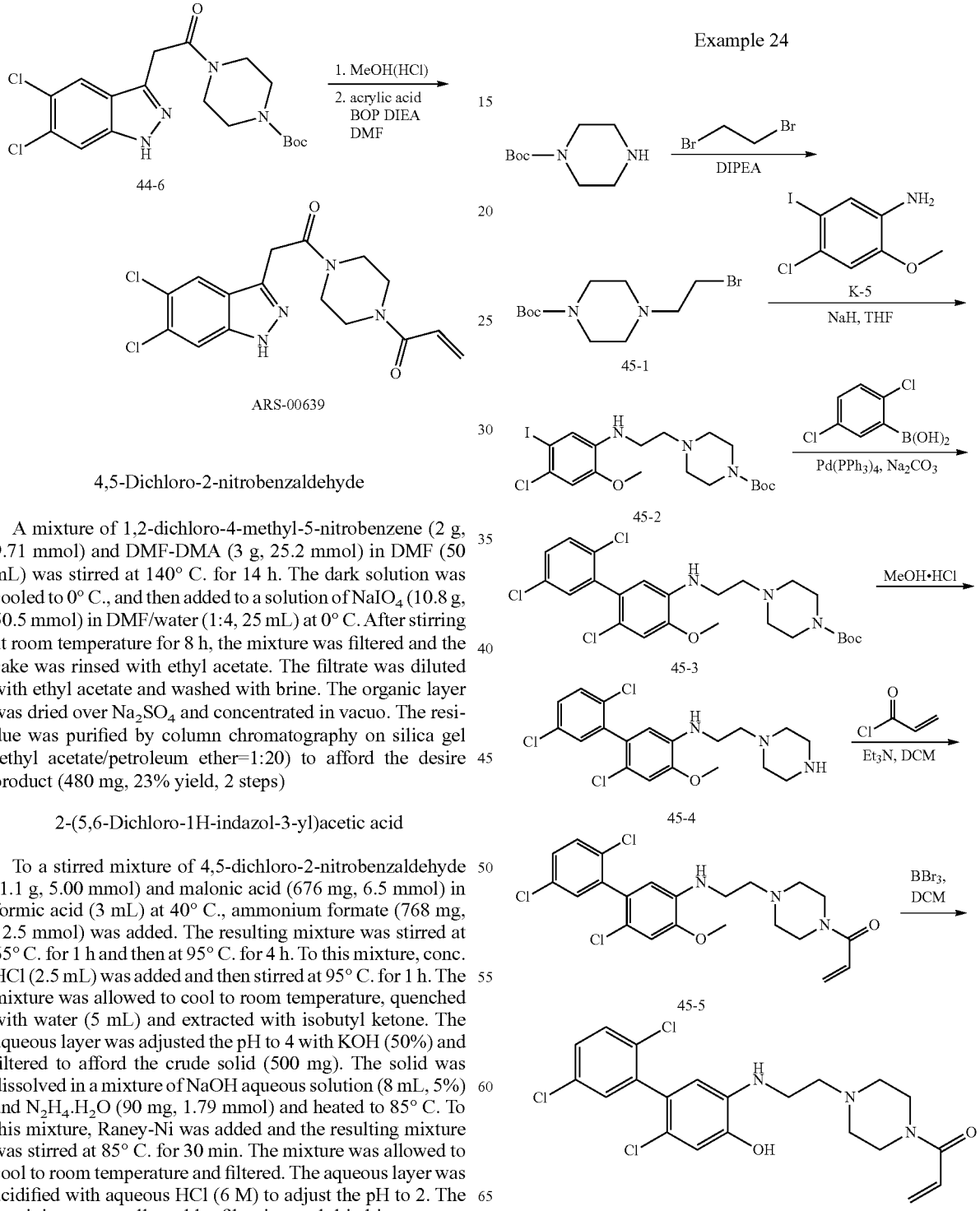

4,5-Dichloro-2-nitrobenzaldehyde

A mixture of 1,2-dichloro-4-methyl-5-nitrobenzene (2 g, 9.71 mmol) and DMF-DMA (3 g, 25.2 mmol) in DMF (50 mL) was stirred at 140° C. for 14 h. The dark solution was cooled to 0° C., and then added to a solution of NaIO$_4$ (10.8 g, 50.5 mmol) in DMF/water (1:4, 25 mL) at 0° C. After stirring at room temperature for 8 h, the mixture was filtered and the cake was rinsed with ethyl acetate. The filtrate was diluted with ethyl acetate and washed with brine. The organic layer was dried over Na$_2$SO$_4$ and concentrated in vacuo. The residue was purified by column chromatography on silica gel (ethyl acetate/petroleum ether=1:20) to afford the desire product (480 mg, 23% yield, 2 steps)

2-(5,6-Dichloro-1H-indazol-3-yl)acetic acid

To a stirred mixture of 4,5-dichloro-2-nitrobenzaldehyde (1.1 g, 5.00 mmol) and malonic acid (676 mg, 6.5 mmol) in formic acid (3 mL) at 40° C., ammonium formate (768 mg, 12.5 mmol) was added. The resulting mixture was stirred at 65° C. for 1 h and then at 95° C. for 4 h. To this mixture, conc. HCl (2.5 mL) was added and then stirred at 95° C. for 1 h. The mixture was allowed to cool to room temperature, quenched with water (5 mL) and extracted with isobutyl ketone. The aqueous layer was adjusted the pH to 4 with KOH (50%) and filtered to afford the crude solid (500 mg). The solid was dissolved in a mixture of NaOH aqueous solution (8 mL, 5%) and N$_2$H$_4$.H$_2$O (90 mg, 1.79 mmol) and heated to 85° C. To this mixture, Raney-Ni was added and the resulting mixture was stirred at 85° C. for 30 min. The mixture was allowed to cool to room temperature and filtered. The aqueous layer was acidified with aqueous HCl (6 M) to adjust the pH to 2. The precipitate was collected by filtration and dried in vacuo to afford the desired product (250 mg, yield 22%, 2 steps).

1-(4-(2-(5,6-Dichloro-1H-indazol-3-yl)acetyl)piperazin-1-yl)prop-2-en-1-one

The title compound was prepared from 2-(5,6-dichloro-1H-indazol-3-yl)acetic acid in three steps followed the procedure described in Example 40. $^1$H NMR (400 MHz, DMSO-d6) δ: 7.56 (m, 1H), 7.33-7.45 (m, 3H), 7.12 (s, 1H), 7.07 (s, 1H), 6.62 (s, 2H), 3.60 (m, 8H), 3.10 (s, 2H), 2.20 (s, 6H). ESI-MS m/z: 367.2[M+H]$^+$.

Example 24 tert-Butyl 4-(2-bromoethyl)piperazine-1-carboxylate

A mixture of tert-butyl piperazine-1-carboxylate (5.0 g, 26.9 mmol), 1,2-dibromoethane (25 mL), DIPEA (3.5 g, 26.9 mmol) was stirred at 30° C. under argon for 72 h. The solvent was removed under reduced pressure and the residue was purified by column chromatography on silica gel (1-2% methanol/dichloroethane) to afford the desired product (2.8 g, 36% yield) as a solid. ESI-MS m/z: 293.1[M+1]$^+$.

tert-Butyl 4-(2-((4-chloro-5-iodo-2-methoxyphenyl)amino)ethyl)piperazine-1-carboxylate To a stirred solution of 4-chloro-5-iodo-2-methoxyaniline (968 mg, 3.42 mmol) in anhydrous THF (20 mL) at 0° C., NaH (60% in mineral oil, 205.2 mg, 5.13 mmol) was added and the resulting mixture was stirred at reflux under nitrogen for 1 h. To this mixture, tert-butyl-4-(2-bromoethyl)piperazine-1-carboxylate (500 mg, 1.71 mmol) was added and the resulting mixture was stirred at room temperature for 15 h. The mixture was concentrated in vacuo and the residue was partitioned between ethyl acetate and brine. The organic layer was dried over anhydrous Na$_2$SO$_4$, filtered and concentrated in vacuo. The residue was purified by flash column chromatography on silica gel (10-30% ethyl acetate/petroleum ether) to afford the desired product (180 mg, 21% yield) as a solid.

tert-Butyl-4-(2-((2',5',6-trichloro-4-methoxy-[1,1'-biphenyl]-3-yl)amino)ethyl)piperazine-1-carboxylate A mixture of tert-butyl 4-(2-((4-chloro-5-iodo-2-methoxyphenyl)amino)ethyl)piperazine-1-carboxylate (180 mg, 0.36 mmol), (2,5-dichlorophenyl)boronic acid (138.9 mg, 0.72 mmol), Na$_2$CO$_3$ (114.5 mg, 1.08 mmol), Pd(PPh$_3$)$_4$ (42 mg, 0.036 mmol) in 1,4-dioxane (20 mL) and water (5 mL) was stirred at 90° C. under argon for 16 h. The mixture was allowed to cool to room temperature and then concentrated in vacuo. The residue was purified by column chromatography on silica gel (petroleum ether/ethyl acetate=5:1) to afford the desired product (135 mg, 73% yield) as a solid. ESI-MS m/z: 514.3[M+H]$^+$.

1-(4-(2-((2',5',6-Trichloro-4-hydroxy-[1,1'-biphenyl]-3-yl)amino)ethyl)piperazin-1-yl)prop-2-en-1-one The title compound was prepared from tert-butyl-4-(2-((2',5',6-trichloro-4-methoxy-[1,1'-biphenyl]-3-yl)amino)ethyl)piperazine-1-carboxylate in three steps followed the procedure described in Example 18. $^1$H NMR (400 MHz, DMSO-d6) δ: 10.04 (s, 1H), 7.56 (d, J=8.4 Hz, 1H), 7.48-7.45 (m, 1H), 7.37 (d, J=2.8 Hz, 1H), 6.79 (dd, J=10.4, 16.8 Hz, 1H), 6.77 (s, 1H), 6.40 (s, 1H), 6.09 (dd, J=2.4, 16.4 Hz, 1H), 5.67 (dd, J=2.4, 10.4 Hz, 1H), 4.88 (bs., 1H), 3.54-3.51 (m, 4H), 3.11 (d, J=4.8 Hz, 2H), 2.55 (t, J=6.0 Hz, 2H), 2.39-2.38 (m, 4H). ESI-MS m/z: 454.1[M+H]$^+$.

Example 25

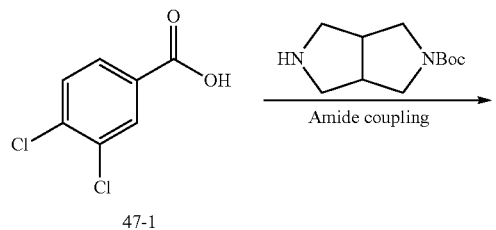

47-1

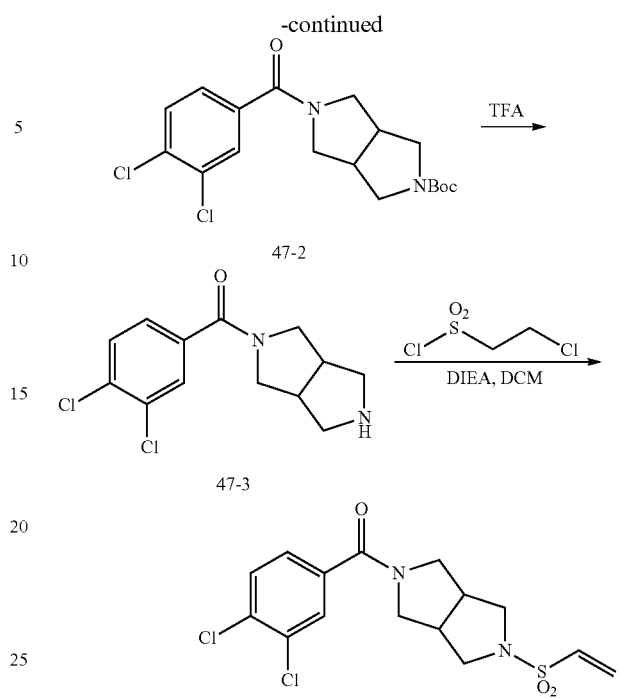

tert-butyl 5-(3,4-dichlorobenzoyl)hexahydropyrrolo[3,4-c]pyrrole-2(1H)-carboxylate To a solution of acid 3,4-dichlorobenzoic acid (0.45 g, 2.36 mmol), tert-butyl hexahydropyrrolo[3,4-c]pyrrole-2(1H)-carboxylate (0.5 g, 2.36 mmol) and HOBt (0.4 g, 2.83 mmol) in DMF (15 mL), EDCI.HCl (0.54 g, 2.83 mmol) and DIEA (1.5 g, 11.5 mmol) were added. The mixture was stirred at room temperature overnight and then partitioned between ethyl acetate and water. The organic layer was washed with brine, dried over Na$_2$SO$_4$, filtered and concentrated in vacuo to afford the crude product which was used directly in the next step.

(3,4-dichlorophenyl)(hexahydropyrrolo[3,4-c]pyrrol-2(1H)-yl)methanone tert-Butyl 5-(3,4-dichlorobenzoyl)hexahydropyrrolo[3,4-c]pyrrole-2(1H)-carboxylate (crude product from above step) was dissolved in 50% TFA in DCM (10 mL) and the resulting mixture was stirred at room temperature for 3 h. The mixture was concentrated in vacuo. The residue was dissolved in ethyl acetate and washed with saturated NaHCO$_3$ aqueous solution. The organic layer was dried over Na$_2$SO$_4$, filtered and concentrated in vacuo to afford the crude product. The crude product was used directly in the next step without further purification.

(3,4-Dichlorophenyl)(5-(vinylsulfonyl)hexahydropyrrolo[3,4-c]pyrrol-2(1H)-yl)methanone To a solution of (3,4-dichlorophenyl)(hexahydropyrrolo[3,4-c]pyrrol-2(1H)-yl)methanone (100 mg, 0.35 mmol) in DCM (10 mL) at 0° C., Et$_3$N (106 mg, 1 mmol) was added followed by sulfonyl chloride (60 mg, 0.37 mmol). The resulting mixture was stirred at room temperature overnight. The mixture was partitioned between DCM and water. The organic layer was dried over Na$_2$SO$_4$, filtered and concentrated in vacuo. The residue was purified by Isolera One (silica gel cartridge, 10-100% ethyl acetate/hexanes) to afford the desired product (14 mg, 11%). ¹H NMR (300 MHz, CDCl₃) δ: 7.60 (d, J=2.0 Hz, 1H), 7.51 (d, J=8.2 Hz, 1H), 7.35 (dd, J=2.0, 8.2 Hz, 1H), 6.50 (dd, J=9.9, 16.5 Hz, 1H), 6.30 (d, J=16.6 Hz, 1H), 6.09 (d, J=9.9 Hz, 1H), 2.90-4.10 (m, 10H). ESI-MS m/z: 375.0[M+H]⁺.
Example 26
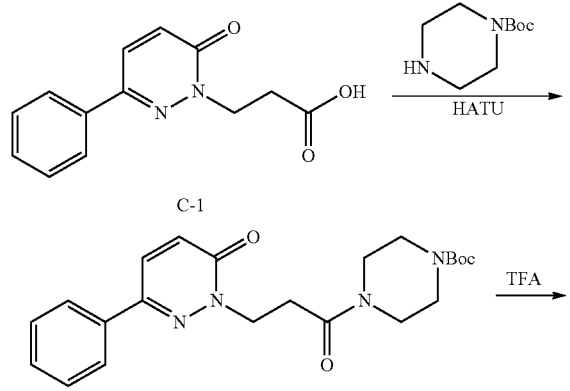
Example 27
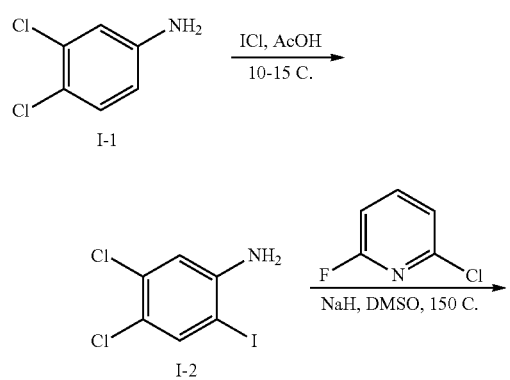
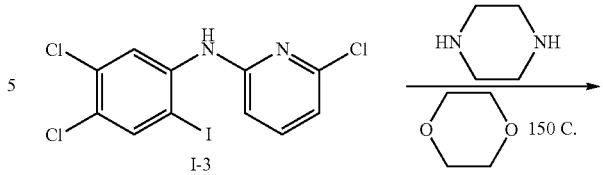
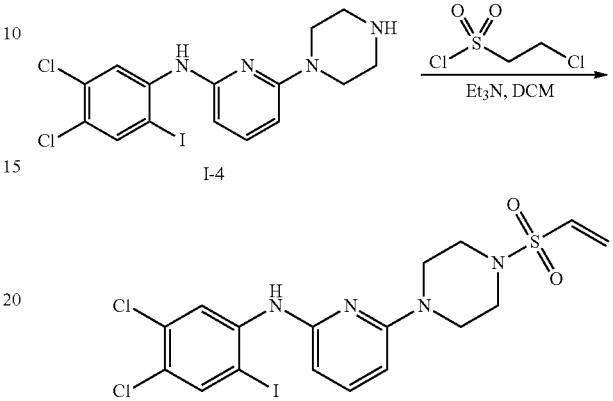
Example 28
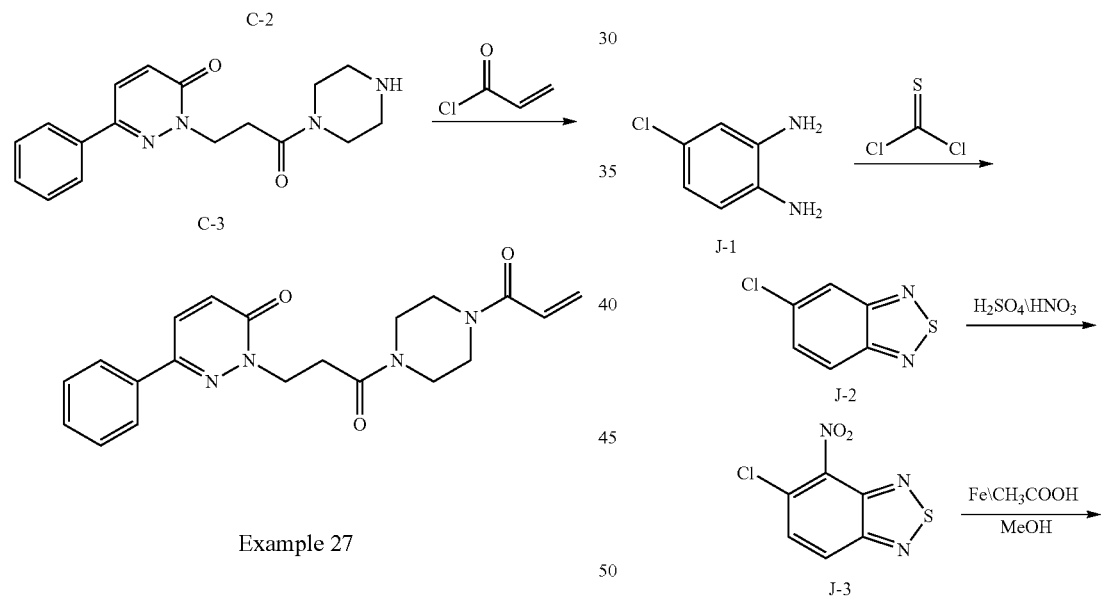
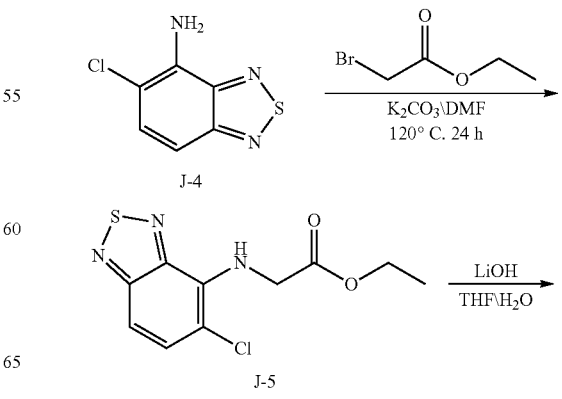

299
-continued
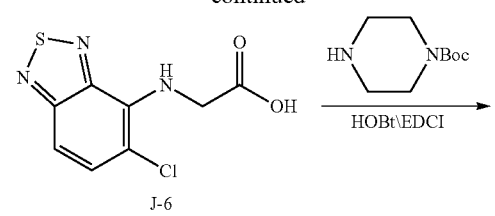
J-6
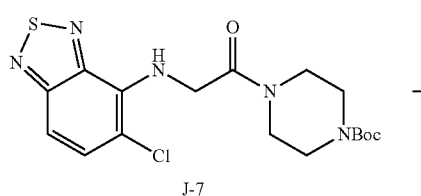
J-7
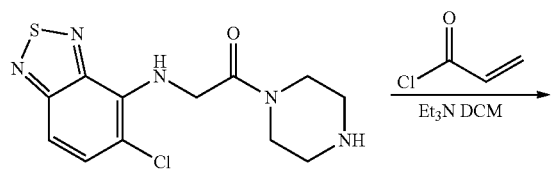
J-8
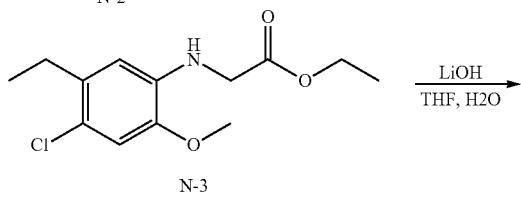
Example 29
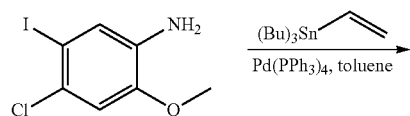
K-5
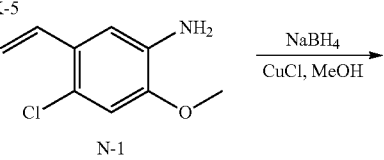
N-1
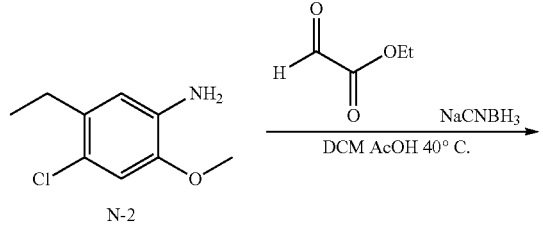
N-2
N-3
300
-continued
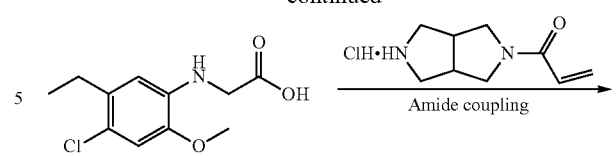
N-4
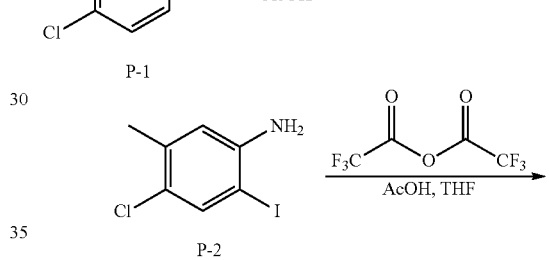
Example 30
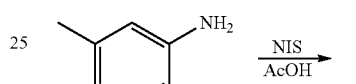
P-1
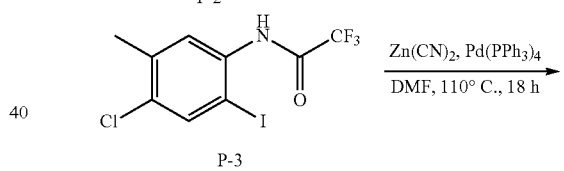
P-2
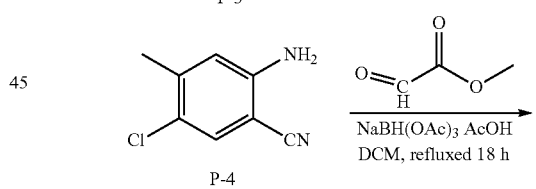
P-3
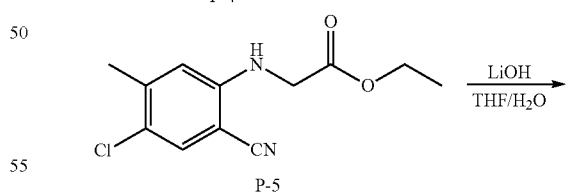
P-4
P-5
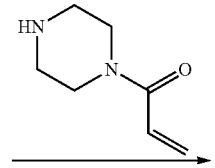
P-6

301
-continued
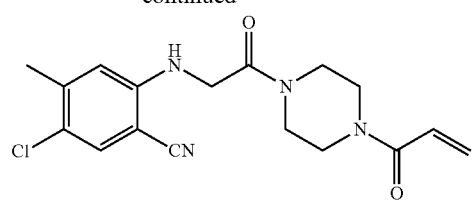
Example 31
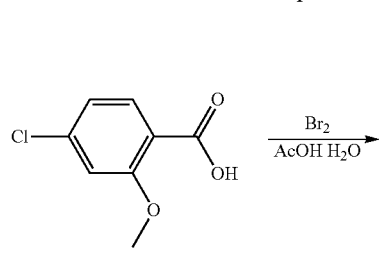
R-1
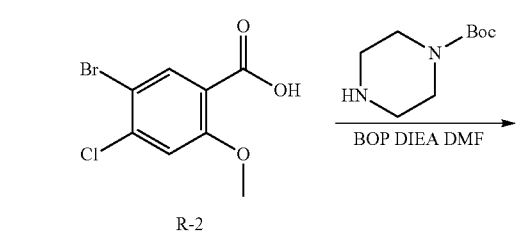
R-2
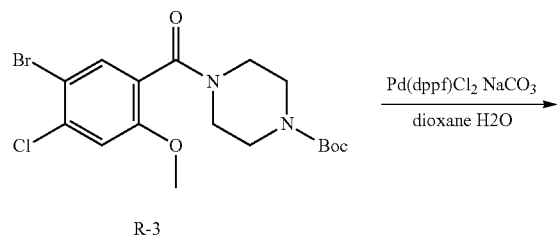
R-3
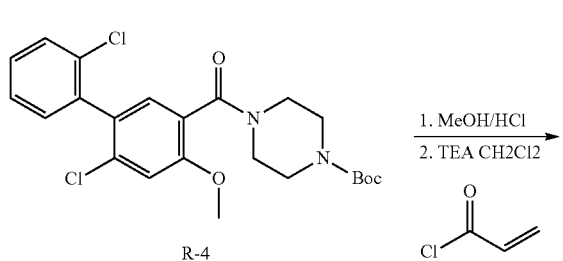
R-4
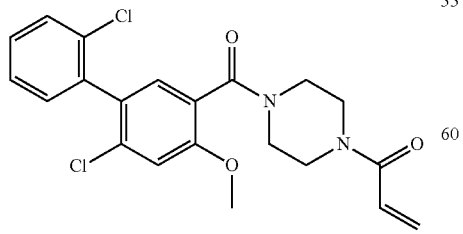
VI-1
302
Example 32
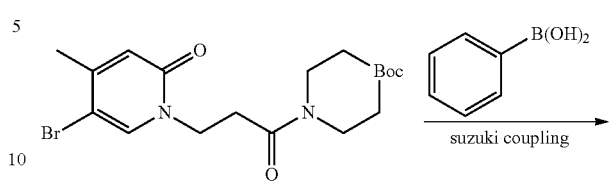
B-4
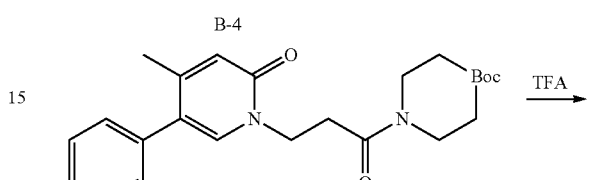
U-1
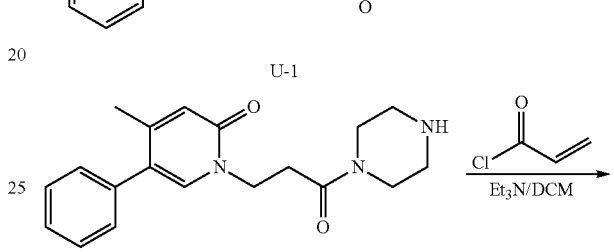
U-2
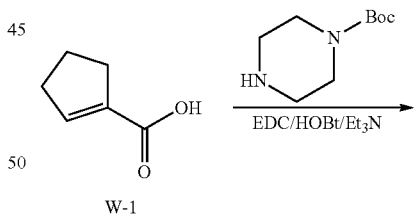
Example 33
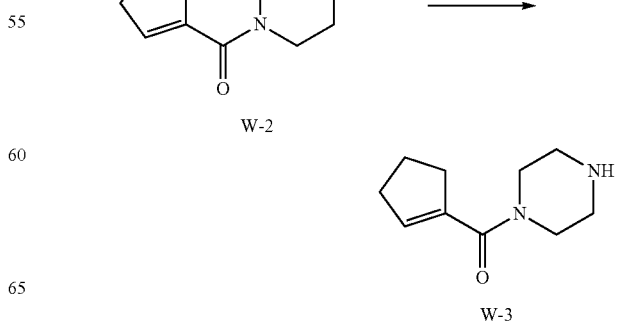
W-1, W-2, W-3

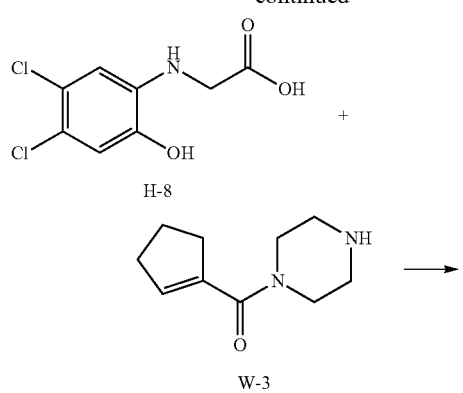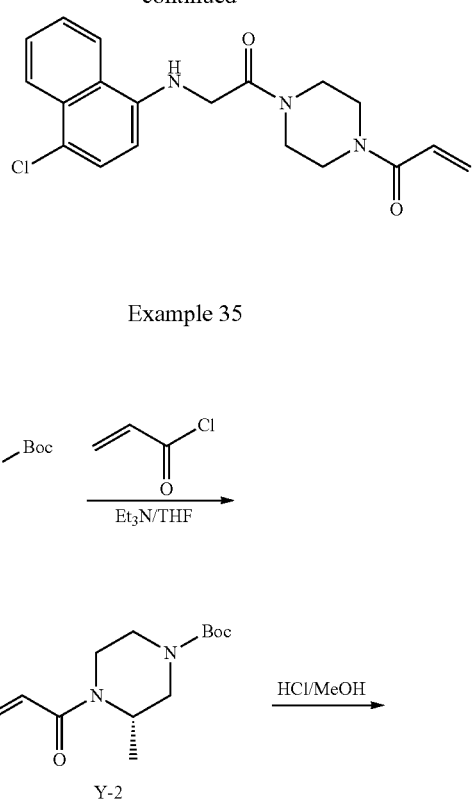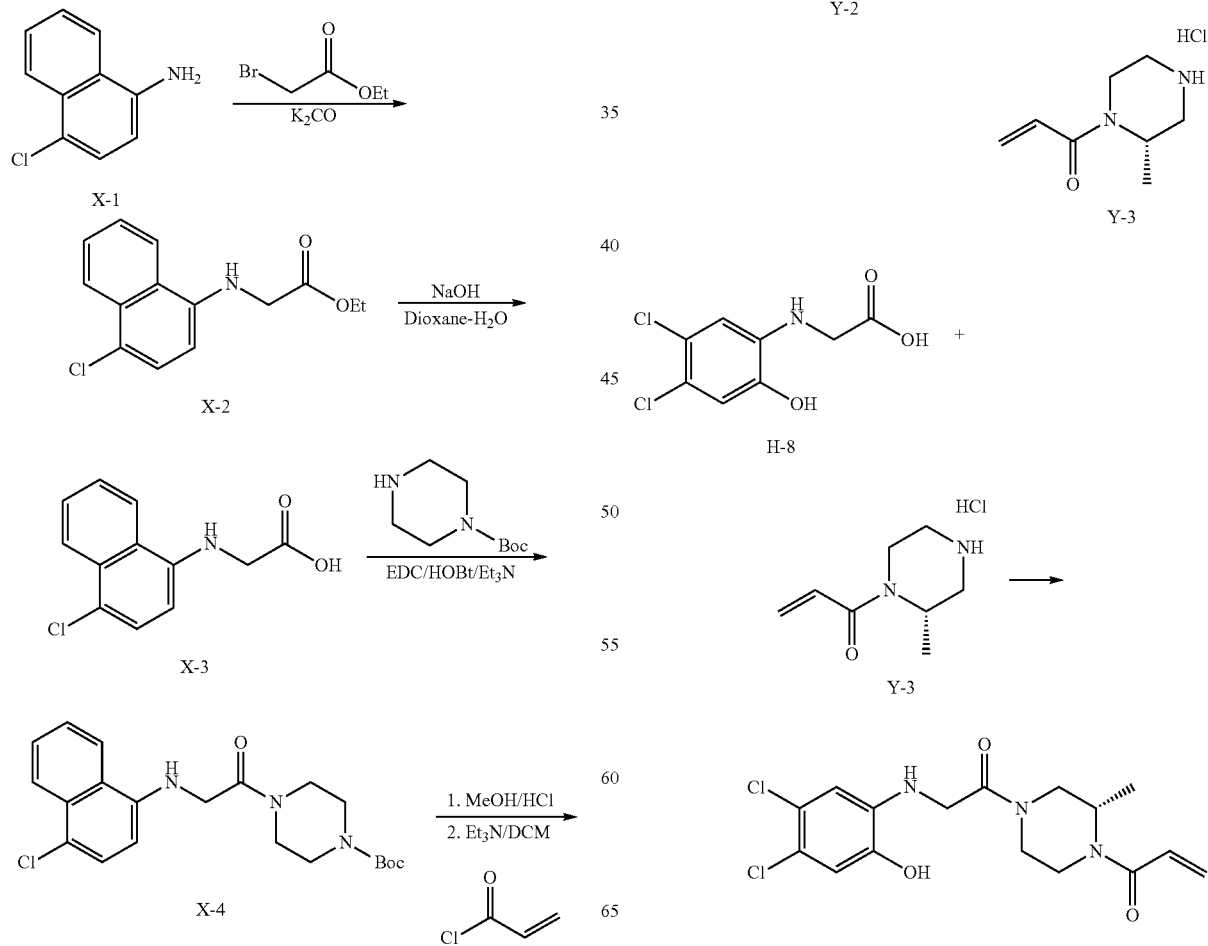
Example 34
Example 35

Example 36

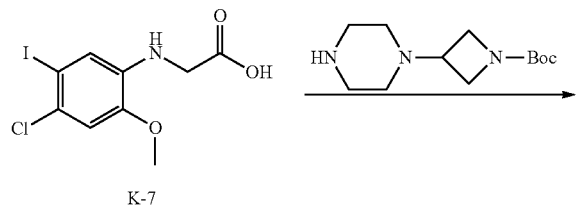

K-7

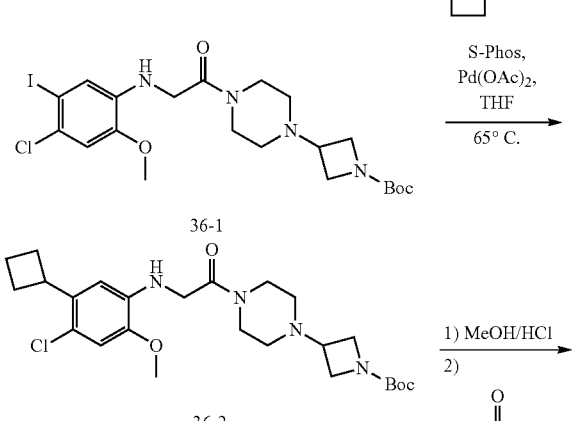

36-1

36-2

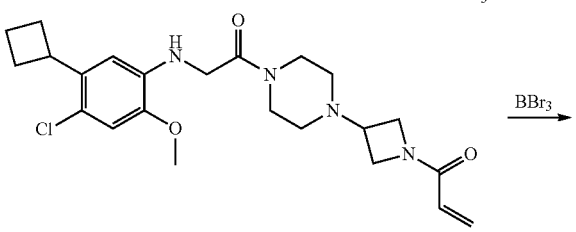

36-3

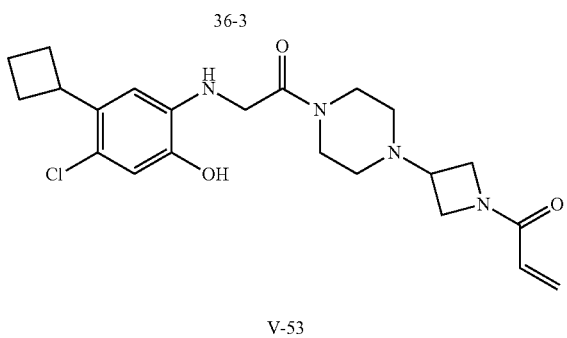

V-53 tert-Butyl 3-(4-(2-(4-Chloro-5-iodo-2-methoxyphenylamino)acetyl)piperazin-1-yl)azetidine-1-carboxylate To a solution of 2-(4-chloro-5-iodo-2-methoxyphenylamino)acetic acid (2.0 g, 5.88 mmol), tert-butyl 3-(piperazin-1-yl)azetidine-1-carboxylate (1.84 g, 7.64 mmol), EDCI·HCl (2.26 g, 11.76 mmol), and HOBt (1.59 g, 11.76 mmol) in DMF (3 mL) at 0° C., Et₃N (3.28 mL, 23.52 mmol) was added. The resulting mixture was stirred at RT for 16 h and then partitioned between ethyl acetate and water. The organic layer was washed with brine, dried over Na₂SO₄ and concentrated in vacuo. The residue was washed by a mixture of ethyl acetate/petroleum ether=1:5 to afford the desired product (2.24 g, 67% yield) as a white solid. ESI-MS m/z: 565.4[M+H]⁺.

tert-Butyl 3-(4-(2-(4-chloro-5-cyclobutyl-2-methoxyphenylamino)acetyl)piperazin-1-yl)azetidine-1-carboxylate A mixture of tert-butyl 3-(4-(2-(4-chloro-5-iodo-2-methoxyphenylamino)acetyl)piperazin-1-yl)azetidine-1-carboxylate (697 mg, 1.24 mmol), cyclobutylzinc bromide (4.46 mL, 2.23 mmol, 0.5 M in THF), Pd(OAc)₂ (56 mg, 0.248 mmol), and S-Phos (102 mg, 0.248 mmol) in THF (15 mL) was stirred at 65° C. under argon for 16 h. The mixture was allowed to cool to RT, quenched with aqueous NH₄Cl solution and then extracted with ethyl acetate. The organic layer was washed with brine, dried over Na₂SO₄, filtered and concentrated in vacuo. The residue was purified by flash column chromatography on silica gel (methanol/dichloromethane=1:30) to afford the desired product (596 mg, 98% yield) as a brown oil. ESI-MS m/z: 493.5[M+H]⁺.

1-(3-(4-(2-(4-Chloro-5-cyclobutyl-2-hydroxyphenylamino)acetyl)piperazin-1-yl)azetidin-1-yl)prop-2-en-1-one (V-53)

The title compound was prepared from tert-butyl 3-(4-(2-(4-chloro-5-cyclobutyl-2-methoxyphenylamino)acetyl)piperazin-1-yl)azetidine-1-carboxylate in three steps according to the procedure described in Example 17. ¹H NMR (400 MHz, DMSO-d6) δ: 9.66 (s, 1H), 6.63 (s, 1H), 6.52 (s, 1H), 6.31 (dd, J=10.2, 16.9 Hz, 1H), 6.10 (dd, J=2.1, 16.8 Hz, 1H), 5.68 (dd, J=2.1, 10.2 Hz, 1H), 5.16 (t, J=4.4 Hz, 1H), 4.27-4.23 (m, 1H), 4.08-4.04 (m, 1H), 3.97-3.93 (m, 3H), 3.80-3.76 (m, 1H), 3.65-3.59 (m, 1H), 3.56-3.54 (m, 4H), 3.20-3.14 (m, 1H), 2.40-2.25 (m, 4H), 2.20-2.15 (m, 2H), 2.09-2.05 (m, 2H), 1.97-1.90 (m, 1H), 1.80-1.74 (m, 1H). ESI-MS m/z: 433.4[M+H]⁺.

Example 37

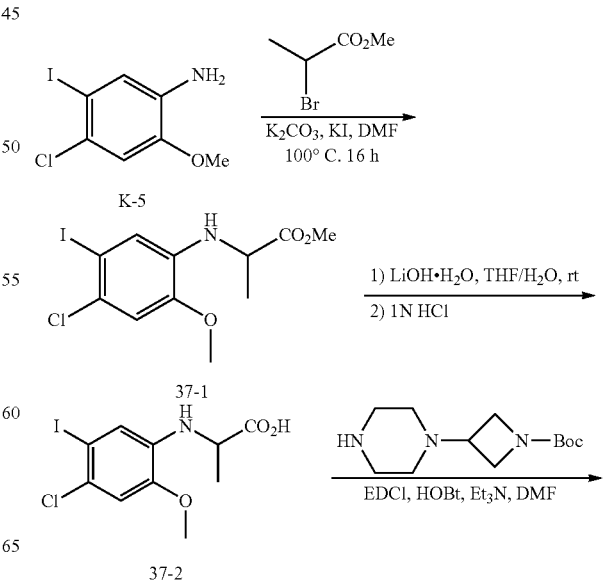

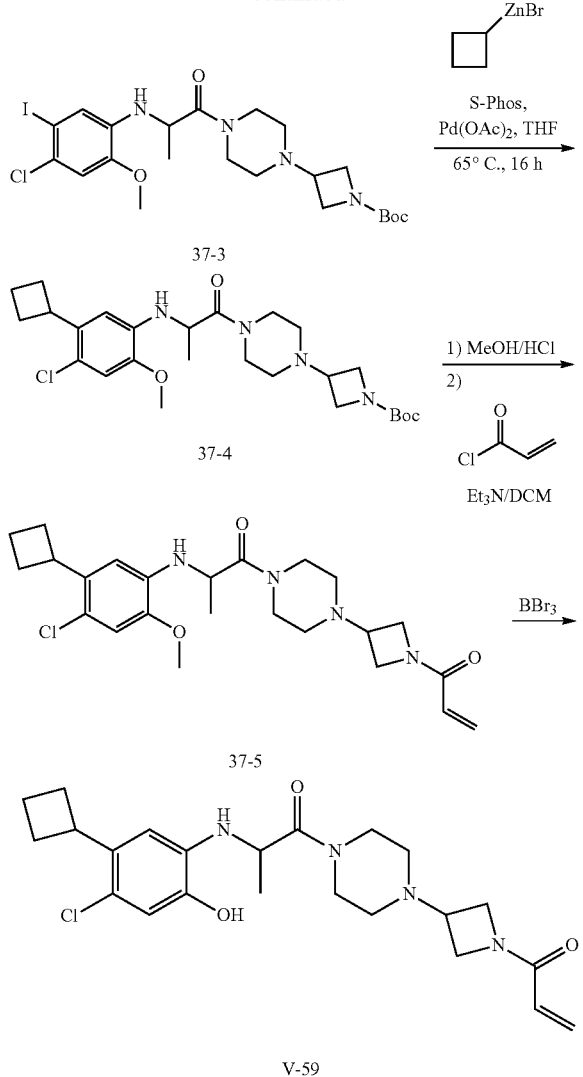

Methyl 2-(4-chloro-5-iodo-2-methoxyphenylamino)propanoate

A mixture of tert-butyl 4-chloro-5-iodo-2-methoxybenzenamine (2 g, 7.07 mmol), methyl 2-bromopropanoate (1.17 g, 7.07 mmol), $K_2CO_3$ (1.94 g, 14.14 mmol) and KI (0.235 g, 1.414 mmol) in DMF (25 mL) was stirred at 100° C. for 16 h. The mixture was allowed to cool to RT, quenched with aqueous $NaHCO_3$ solution and then extracted with ethyl acetate. The organic layer was washed with brine, dried over $Na_2SO_4$, filtered and concentrated in vacuo. The residue was purified by flash column chromatography on silica gel (ethyl acetate/petroleum ether=1:20) to afford the desired product (1.12 g, 43% yield) as a yellow solid. ESI-MS m/z: 370.1[M+H]$^+$.

2-(4-Chloro-5-iodo-2-methoxyphenylamino)propanoic acid

To a solution of methyl 2-(4-chloro-5-iodo-2-methoxyphenylamino)propanoate (1.12 g, 3.04 mmol) in mixture of tetrahydrofuran (20 mL) and water (10 mL) at RT, $LiOH.H_2O$ (0.51 g, 12.16 mmol) was added and the resulting mixture was stirred for 1 h. The aqueous phase was washed with TBME and then acidified with aqueous HCl (1N) to adjust the pH to 5. The mixture was extracted with ethyl acetate. The organic layer was washed with brine, dried over anhydrous $Na_2SO_4$, filtered and concentrated in vacuo to afford the crude product (760 mg) which was used directly in the next step without further purification. ESI-MS m/z: 356.1[M+H]$^+$.

Tert-Butyl 3-(4-(2-((4-Chloro-5-iodo-2-methoxyphenyl)amino)propanoyl)piperazin-1-yl)azetidine-1-carboxylate To a solution of 2-(4-chloro-5-iodo-2-methoxyphenylamino)propanoic acid (760 mg, 2.13 mmol), tert-butyl 3-(piperazin-1-yl)azetidine-1-carboxylate (669 mg, 2.78 mmol), EDCI.HCl (818 mg, 4.26 mmol), HOBt (575 mg, 4.26 mmol) in DMF (8 mL) at 0° C., $Et_3N$ (861 mg, 8.52 mmol) was added. The resulting mixture was stirred at RT for 16 h and then partitioned between ethyl acetate and water. The organic layer was washed with saturated $NaHCO_3$ solution and brine, dried over $Na_2SO_4$ and concentrated in vacuo. The residue was purified by flash column chromatography on silica gel (ethyl acetate/petroleum ether=1:1) to afford the desired product (673 mg, 55% yield) as a white solid. ESI-MS m/z: 579.4 [M+H]$^+$.

Tert-Butyl 3-(4-(2-((4-Chloro-5-cyclobutyl-2-methoxyphenyl)amino)propanoyl)piperazin-1-yl)azetidine-1-carboxylate A mixture of tert-butyl 3-(4-(2-((4-chloro-5-iodo-2-methoxyphenyl)amino)propanoyl)piperazin-1-yl)azetidine-1-carboxylate (673 mg, 1.162 mmol), cyclobutylzinc bromide (5.11 mL, 2.556 mmol, 0.5 M in THF), $Pd(Oac)_2$ (52 mg, 0.23 mmol), S-Phos (95 mg, 0.23 mmol) in THF (10 mL) was stirred at 65° C. under argon for 16 h. The mixture was allowed to cool to RT, quenched with aqueous $NH_4Cl$ solution and then extracted with ethyl acetate. The organic layer was washed with brine, dried over $Na_2SO_4$, filtered and concentrated in vacuo. The residue was purified by flash column chromatography on silica gel (ethyl acetate/petroleum ether=1:1) to afford the desired product (565 mg, 96% yield) as a light yellow solid. ESI-MS m/z: 507.6[M+H]$^+$.

1-(3-(4-(2-((4-Chloro-5-cyclobutyl-2-hydroxyphenyl)amino)propanoyl)piperazin-1-yl)azetidin-1-yl)prop-2-en-1-one (V-59)

The title compound was prepared from tert-butyl 3-(4-(2-((4-chloro-5-cyclobutyl-2-methoxyphenyl)amino)propanoyl)piperazin-1-yl)azetidine-1-carboxylate in three steps according to the procedure described in Example 17. $^1$H NMR (400 MHz, DMSO-d6) δ: 9.63 (s, 1H), 6.62 (s, 1H), 6.49 (s, 1H), 6.30 (dd, J=10.1, 16.8 Hz, 1H), 6.10 (d, J=18.7 Hz, 1H), 5.68 (d, J=10.4 Hz, 1H), 4.86 (d, J=9.2 Hz, 1H), 4.69-4.63 (m, 1H), 4.27-4.23 (m, 1H), 4.07-4.03 (m, 1H), 3.97-3.62 (m, 1H), 3.82-3.76 (m, 2H), 3.64-3.55 (m, 3H), 3.77-3.11 (m, 1H), 2.44-2.15 (m, 6H), 2.08-1.90 (m, 4H), 1.80-1.72 (m, 2H), 1.97-1.90 (m, 1H), 1.24 (d, J=6.4 Hz, 3H). ESI-MS m/z: 447.4[M+H]$^+$.

Example 38

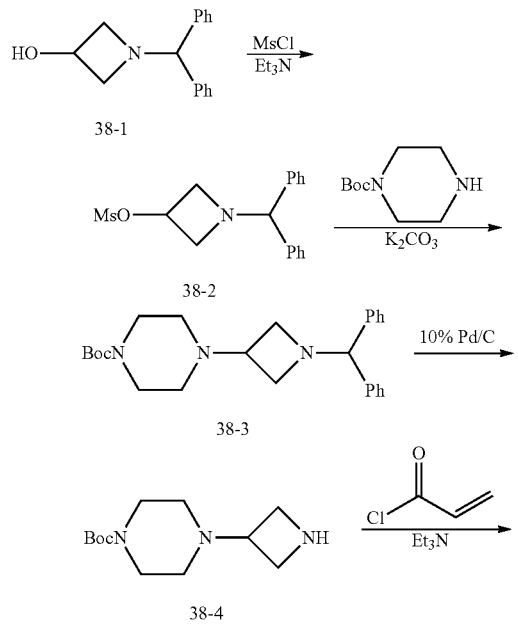

1-Benzhydrylazetidin-3-yl methanesulfonate

A mixture of 1-benzhydrylazetidin-3-ol (20.0 g, 83.68 mmol) and Et$_3$N (12.68 g, 125.52 mmol) in DCM (200 mL) at 0° C., MsCl (11.447 mg, 100.41 mmol) was added in portions and the resulting solution was stirred at RT for 1 h. The reaction mixture was diluted with ethyl acetate and washed with brine. The organic layer was dried over anhydrous Na$_2$SO$_4$, filtered and concentrated in vacuo to afford the desired product (26.526 g, 100% yield).

tert-Butyl 4-(1-benzhydrylazetidin-3-yl)piperazine-1-carboxylate

A mixture of 1-benzhydrylazetidin-3-yl methanesulfonate (26.53 g, 83.68 mmol), tert-butyl piperazine-1-carboxylate (18.68 g, 100.41 mmol) and K$_2$CO$_3$ (23.09 g, 163.36 mmol) in CH3CN (200 mL) was stirred at 80° C. for 16 h. The reaction mixture was cooled to RT and diluted with ethyl acetate and washed with brine. The organic layer was dried over anhydrous Na$_2$SO$_4$, filtered and concentrated in vacuo. The residue was purified by flash column chromatography on silica gel (dichloromethane/methanol=50:1) to afford the desired product (25.5 g, 80% yield).

tert-Butyl 4-(azetidi-3-yl)piperazine-1-carboxylate

A mixture of tert-butyl 4-(1-benzhydrylazetidin-3-yl)piperazine-1-carboxylate (10.0 g, 24.57 mmol) and 10% Pd\C (2.5 g) in MeOH (100 mL) was stirred under H$_2$ atmosphere at 50° C. for 48 h. The reaction mixture was cooled to RT and filtered. The filtrate was diluted concentrated in vacuo to afford a crude desire product (6.7 g) as a colorless oil.

tert-Butyl 4-(1-acryloylazetidin-3-yl)piperazine-1-carboxylate

A mixture of tert-butyl 4-(azetidi-3-yl)piperazine-1-carboxylate (6.7 g, 27.80 mmol) and Et$_3$N (8.43 g, 83.40 mmol) in DCM (100 mL) at 0° C., acryloyl chloride (3.77 g, 41.7 mmol) was added in portions and the resulting solution was stirred at RT for 1 h. The reaction mixture was diluted with DCM and washed with brine. The organic layer was dried over anhydrous Na$_2$SO$_4$, filtered and concentrated in vacuo. The residue was purified by column chromatography on silica gel (dichloromethane/methanol=50:1) to afford the desired product (3.6 g, 49.66% yield, 2 steps). $^1$H NMR (400 MHz, DMSO-d6) δ: 6.30 (dd, J=10.4, 16.8 Hz, 1H), 6.09 (dd, J=2.4, 17.2 Hz, 1H), 5.67 (dd, J=2.4, 10.4 Hz, 1H), 4.22 (t, J=8, 1H), 4.03-4.00 (m, 1H), 3.94-3.90 (m, 1H), 3.75-3.70 (m, 1H), 3.32 (t, J=8.8 Hz, 4H), 3.10-3.18 (m, 1H), 2.22-2.30 (m, 1H), 1.40 (s, 9H).

Example 39

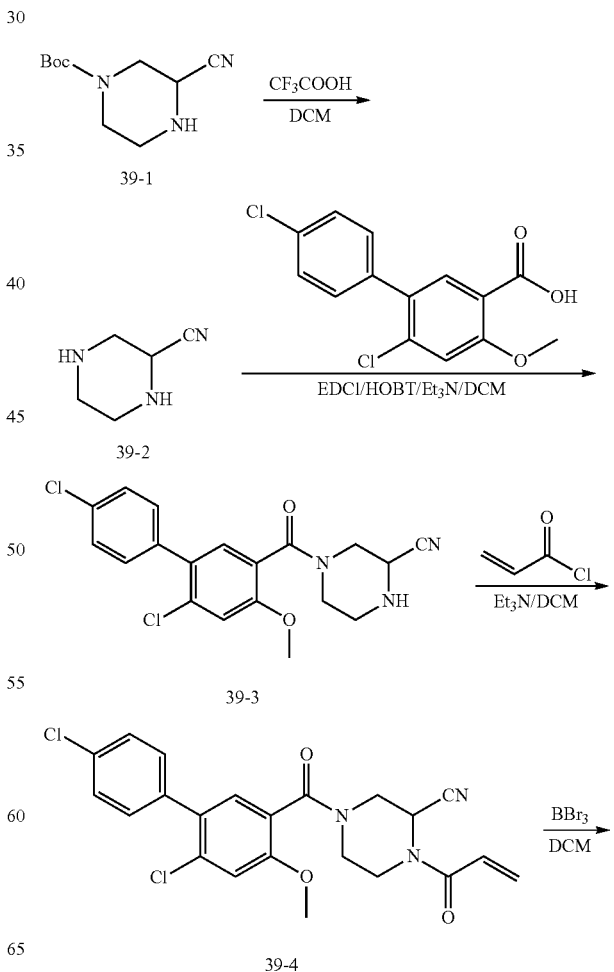

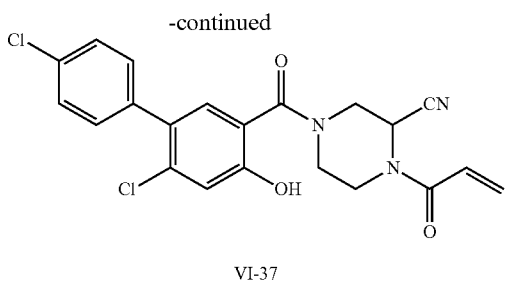

VI-37

Piperazine-2-carbonitrile

To a mixture of tert-butyl 3-cyanopiperazine-1-carboxylate (200 mg, 0.95 mmol) in dichloromethane (10 mL), $CF_3COOH$ (2 mL) was added and the resulting was stirred at RT for 1 h. The mixture was concentrated in vacuo to afford the crude product.

4-(4',6-Dichloro-4-methoxy-[1,1'-biphenyl]-3-carbonyl)piperazine-2-carbonitrile

To a mixture of 4',6-dichloro-4-methoxy-[1,1'-biphenyl]-3-carboxylic acid (309 mg, 1.04 mmol), EDCI (272 mg, 1.43 mmol), HOBt (195 mg, 1.43 mmol), $Et_3N$ (288 mg, 2.85 mmol) in dichloromethane (10 mL) at 0° C., piperazine-2-carbonitrile was added at 0° C. and the resulting mixture was stirred at RT for 8 h. The mixture was partitioned between dichloromethane and water. The organic layer was washed brine, dried over $MgSO_4$, filtered and concentrated in vacuo. The residue was purified by flash column chromatography on silica gel (dichloromethane/methanol=50:1) to afford the desired product (225 mg, 61% yield). ESI-MS m/z: 444.3[M+H]$^+$.

1-Acryloyl-4-(4',6-dichloro-4-hydroxy-[1,1'-biphenyl]-3-carbonyl)piperazine-2-carbonitrile (VI-37)

The title compound was prepared from 4-(4',6-dichloro-4-methoxy-[1,1'-biphenyl]-3-carbonyl)piperazine-2-carbonitrile in two steps according to the procedure described in Example 17. $^1H$ NMR (400 MHz, $CDCl_3$) δ: 9.24 (s, 1H), 7.44-7.33 (m, 5H), 7.20 (s, 1H), 6.57-6.45 (m, 2H), 6.79 (s, 1H), 5.94-5.91 (m, 1H), 5.75 (s, 1H), 4.62-4.61 (m, 1H), 4.50-4.46 (m, 1H), 4.06 (s, 1H), 3.61 (s, 1H), 3.36-3.33 (m, 1H), 3.16-3.10 (m, 1H). ESI-MS m/z: 428.4[M+H]$^+$.

Example 40

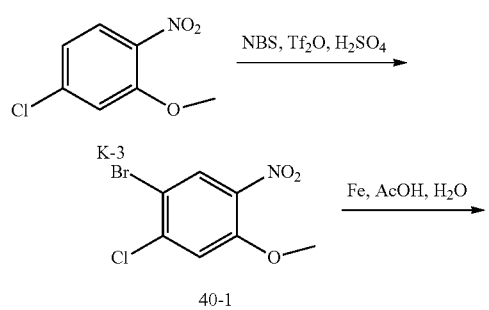

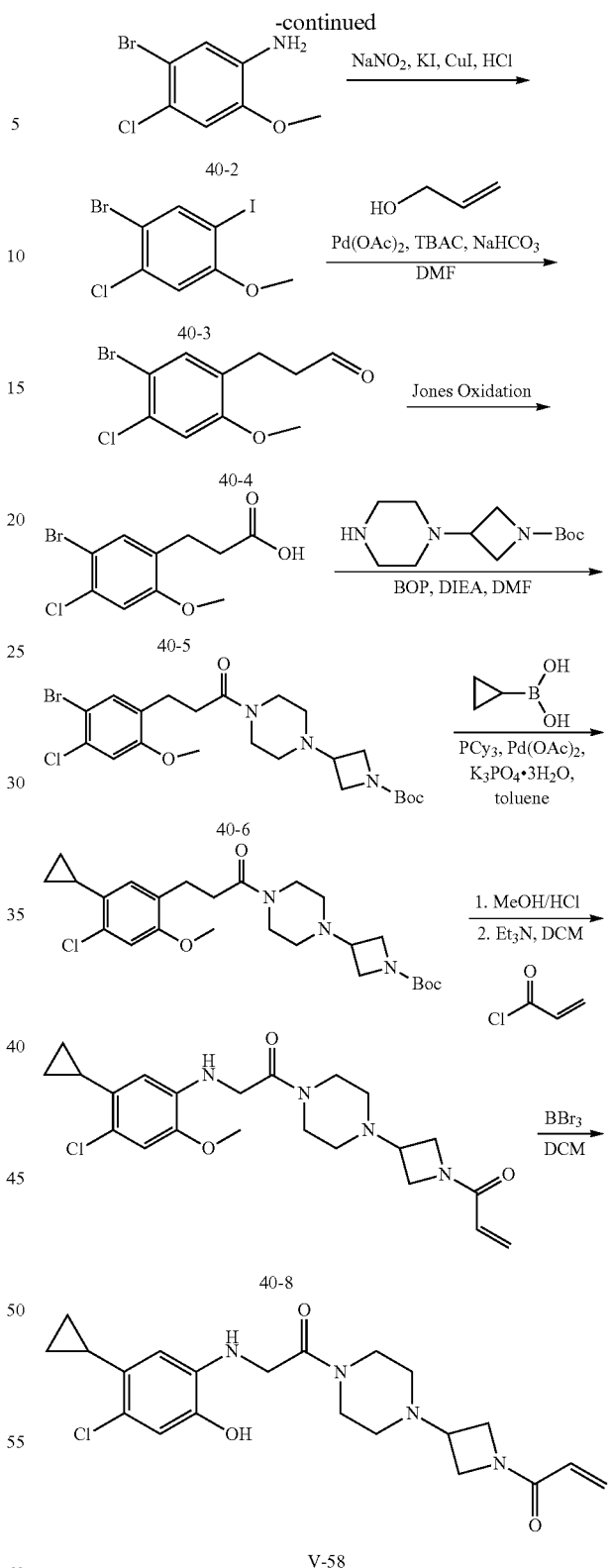

5-Bromo-4-chloro-2-methoxybenzenamine

The title compound was prepared from 4-chloro-2-methoxy-1-nitrobenzene in two steps according to the procedure described in Example 4.

1-Bromo-2-chloro-5-iodo-4-methoxybenzene

To a mixture of 5-bromo-4-chloro-2-methoxyaniline (3 g, 12.7 mmol) in 6N HCl (60 mL, 360 mmol) at 0° C., a solution of NaNO$_2$ (963 mg, 13.9 mmol) in water (20 mL) was added dropwise while keeping the internal temperature around 0° C. KI (10.5 g, 63.4 mmol) and CuI (4.8 g, 25.4 mmol) were dissolved in water (20 mL) and added to the stirred reaction mixture. The reaction was kept at 5° C. for 2 h. The reaction mixture was extracted with ethyl acetate. The combined organic layer was washed with water, Na$_2$SO$_3$ (aq, 10%) and brine, dried over anhydrous Na$_2$SO$_4$, an concentrated. The residue was purified by flash column chromatography on silica gel (ethyl acetate/petroleum ether=1:100) to afford the desired product (3.2 g, 73% yield).

3-(5-Bromo-4-chloro-2-methoxyphenyl)propanal

A mixture of 1-bromo-2-chloro-5-iodo-4-methoxybenzene (3.2 g, 9.2 mmol), prop-2-en-1-ol (1.3 g, 23.0 mmol), Pd(OAc)$_2$ (206 mg, 0.9 mmol), TBAC (2.56 g, 9.2 mmol), NaHCO$_3$ (2.3 g, 27.6 mmol) in DMF (50 mL) was stirred under Argon at 60° C. for 16 h. The mixture was allowed to cool to RT, and then partitioned between ethyl acetate and water. The combined organic layer was washed with brine, dried over anhydrous Na$_2$SO$_4$ and concentrated. The residue was purified by flash column chromatography on silica gel (ethyl acetate/petroleum ether=1:20) to afford the desired product (860 mg, 34% yield).

3-(5-Bromo-4-chloro-2-methoxyphenyl)propanoic acid

To a stirred solution of Jones reagent (3 mL, 5.4 mmol, 2.8 M) in acetone (20 mL), 3-(5-bromo-4-chloro-2-methoxyphenyl)propanal (860 mg, 3.1 mmol) was added. The reaction was stirred at RT for 12 h, quenched with iso-propylalcohol and then stirred for 10 min. The resulting mixture was diluted with water, extracted with ethyl acetate. The combined organic layer was washed with water and brine, dried over Na$_2$SO$_4$ and concentrated. The residue was purified by flash column chromatography on silica gel (ethyl acetate/petroleum ether=1:1) to afford the desired product (358 mg, 38% yield). ESI-MS m/z: 291.1[M+H]$^-$.

tert-Butyl-3-(4-(3-(5-bromo-4-chloro-2-methoxyphenyl)propanoyl)piperazin-1-yl)azetidine-1-carboxylate To a stirred solution of 3-(5-bromo-4-chloro-2-methoxyphenyl)propanoic acid (350 mg, 1.2 mmol) in DMF (30 mL) at RT, tert-butyl 3-(piperazin-1-yl)azetidine-1-carboxylate (317 mg, 1.3 mmol), BOP (731 mg, 1.4 mmol) and DIEA (461 mg, 3.6 mmol) were added and the mixture was stirred at RT for 1 h. The reaction mixture was partitioned between ethyl acetate and water. The organic layer was washed with brine and dried over anhydrous Na$_2$SO$_4$, filtered and concentrated in vacuo. The residue was purified by flash column chromatography on silica gel (dichloromethane/methanol=50:1) to afford the desired product (285 mg, 46% yield).

tert-Butyl 3-(4-(3-(4-chloro-5-cyclopropyl-2-hydroxyphenyl)propanoyl)piperazin-1-yl)azetidine-1-carboxylate A mixture of tert-butyl 3-(4-(3-(5-bromo-4-chloro-2-methoxyphenyl)propanoyl)piperazin-1-yl)azetidine-1-car-
boxylate (280 mg, 0.54 mmol), cyclopropylboronic acid (185 mg, 2.2 mmol), K$_3$PO$_4$.3H$_2$O (444 mg, 1.9 mmol), tricyclohexylphosphine (30 mg, 0.1 mmol), Pd(OAc)$_2$ (24 mg, 0.11 mmol) in toluene (10 mL) and water (1 mL) was stirred at reflux under argon for 16 h. The mixture was allowed to cool to RT and concentrated in vacuo. The residue was purified by flash column chromatography on silica gel (dichloromethane/methanol=60:1) to afford the desired product (194 mg, 75% yield). ESI-MS m/z: 477.3[M+H]$^+$.

1-(3-(4-(3-(4-Chloro-5-cyclopropyl-2-hydroxyphenyl)propanoyl)piperazin-1-yl)azetidin-1-yl)prop-2-en-1-one (V-58)

The title compound was prepared from tert-butyl 3-(4-(3-(4-chloro-5-cyclopropyl-2-hydroxyphenyl)propanoyl)piperazin-1-yl)azetidine-1-carboxylate in three steps according to the procedure described in Example 17. $^1$H NMR (400 MHz, DMSO-d6) δ: 9.68 (s, 1H), 6.79 (s, 1H), 6.74 (s, 1H), 6.33-6.26 (m, 1H), 6.12-6.07 (dd, J=1.9, 17.2 Hz, 1H), 5.68-5.65 (dd, J=2.0, 10.2 Hz, 1H), 4.24-4.20 (m, 1H), 4.05-4.01 (m, 1H), 3.94-3.90 (m, 1H), 3.76-3.72 (m, 1H), 3.45-3.42 (m, 4H), 3.13-3.11 (m, 1H), 2.69-2.65 (m, 2H), 2.53-2.51 (m, 2H), 2.25-2.23 (bs, 4H), 1.97-1.93 (m, 1H), 0.90-0.86 (m, 1H), 0.60-0.55 (m, 1H). ESI-MS m/z: 418.4[M+H]$^+$.

Example 41

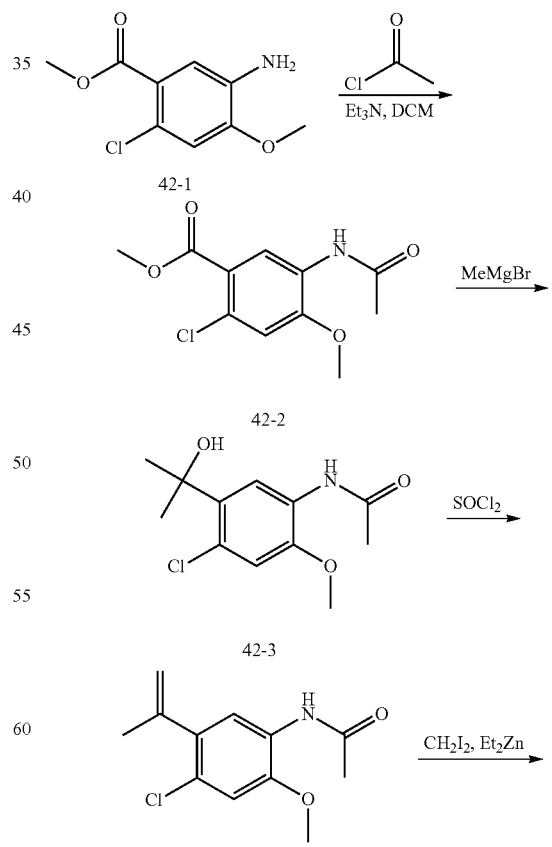

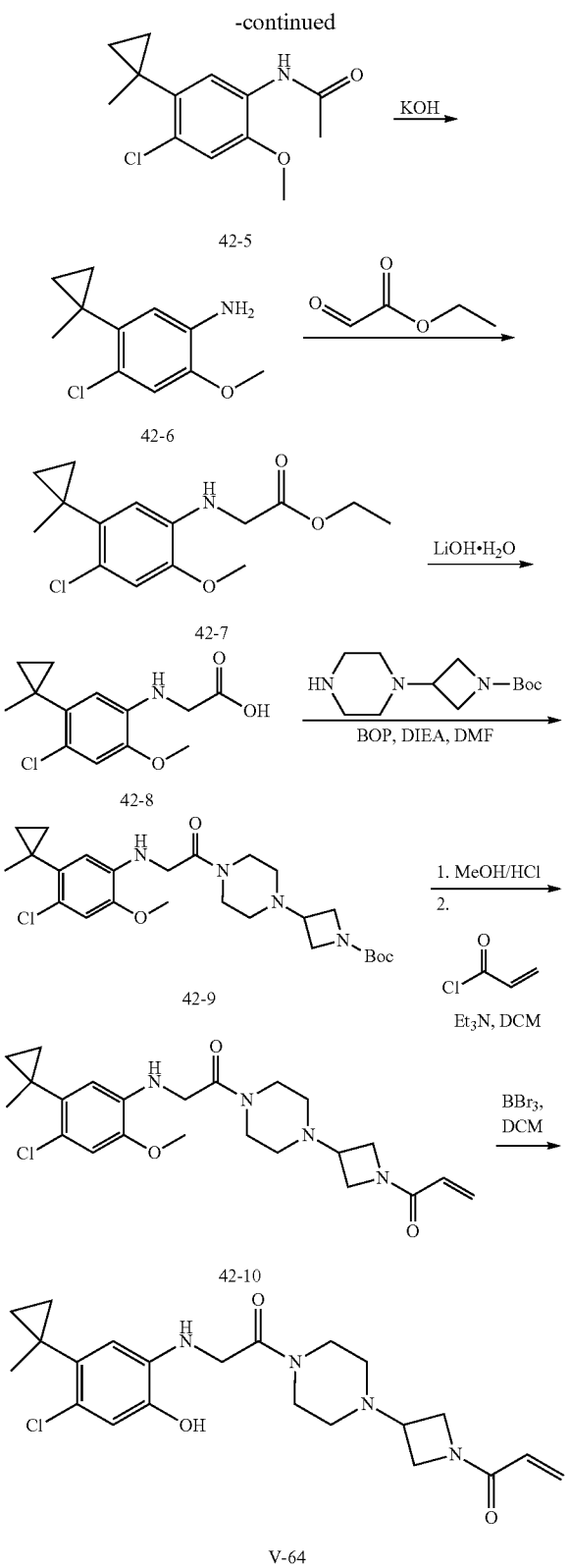

added dropwise and the resulting mixture was stirred for 12 h. The reaction mixture was partitioned between dichloromethane and water. The organic layer was washed with saturated NaHCO₃ solution and brine, dried over anhydrous $Na_2SO_4$ and concentrated in vacuo. The residue was purified by flash column chromatography on silica gel (ethyl acetate/petroleum ether=1:1) to afford the desired product (2.7 g, 63% yield).

N-(4-Chloro-5-(2-hydroxypropan-2-yl)-2-methoxyphenyl)acetamide

To a solution of methyl 5-acetamido-2-chloro-4-methoxybenzoate (2.7 g, 11.1 mmol), in THF (40 mL) at −40° C. under Argon, methylmagnesium bromide (21 mL, 21 mmol, 1M in ether) was added dropwise while keeping the internal temperature at −40° C. Then the mixture was allowed to warm to RT, and stirred for 2 h. The reaction mixture was poured into ice-cooled $NH_4Cl$ (10%) solution, and extracted with ethyl acetate. The combined organic layer was washed with water and brine, dried over anhydrous $Na_2SO_4$ and concentrated in vacuo to afford the desire product (2.3 g, 80% yield).

N-(4-Chloro-2-methoxy-5-(prop-1-en-2-yl)phenyl)acetamide

To a solution of N-(4-chloro-5-(2-hydroxypropan-2-yl)-2-methoxyphenyl)acetamide (3.2 g, 12.4 mmol) in DCM (20 mL) at −5° C., $SOCl_2$ (3.7 g, 37.25 mmol) was added dropwise. The mixture was warmed to RT, and then stirred at reflux for 2 h. The reaction mixture was concentrated and the residue was purified by flash column chromatography on silica gel (ethyl acetate/petroleum ether=3:1) to afford the desired product (1.9 g, 64% yield).

N-(4-Chloro-2-methoxy-5-(1-methylcyclopropyl)phenyl)acetamide

To a solution of N-(4-chloro-2-methoxy-5-(prop-1-en-2-yl)phenyl)acetamide (1.0 g, 4.17 mmol) in toluene (20 mL) at 0° C., $CH_2I_2$ (5.6 g, 20.86 mmol) and $Et_2Zn$ (41.7 mL, 41.7 mmol, 1.0 M in hexane) was added. The mixture was kept at 0° C. for 30 min, and then stirred at RT for 16 h. The reaction mixture was quenched with saturated $NH_4Cl$ solution and stirred for 15 min. The mixture was concentrated in vacuo to remove toluene and the resulting mixture was extracted with dichloromethane. The combined organic layer was washed with water and brine, dried over anhydrous $Na_2SO_4$, concentrated to afford the desired product (820 mg, 77% yield).

4-Chloro-2-methoxy-5-(1-methylcyclopropyl)aniline

A mixture of N-(4-chloro-2-methoxy-5-(1-methylcyclopropyl)phenyl)acetamide (820 mg, 3.23 mmol), KOH (1.8 g, 32.3 mmol), ethanol (40 mL) and water (20 mL) was stirred at reflux for 12 h. The reaction mixture was extracted with ethyl acetate. The combined organic layer was washed with water and brine, dried over anhydrous $Na_2SO_4$ and filtered. The filtrate was concentrated in vacuo and the residue was purified by flash column chromatography on silica gel (ethyl acetate/petroleum ether=20:1) to afford the desired product (460 mg, 67% yield). ESI-MS m/z: 212.4[M+H]⁺.

Ethyl 2-((4-chloro-2-methoxy-5-(1-methylcyclopropyl)phenyl)amino)acetate

To a solution of 4-chloro-2-methoxy-5-(1-methylcyclopropyl)aniline (450 mg, 2.13 mmol) in MeOH (20 mL) at RT, AcOH (3 drops) and ethyl glyoxalate (326 mg, 3.19 mmol, 50% in toluene) were added. The mixture was stirred at RT for 2 h and then sodium cyanoborohydride (403 mg, 6.39 mmol) was added to the mixture. The resulting mixture was stirred at 50° C. for 16 h. The mixture was allowed to cool to RT, and partitioned between ethyl acetate and water. The organic layer was dried over MgSO$_4$, filtered, and concentrated in vacuo to afford the crude product (636 mg). ESI-MS m/z: 298.2[M+H]$^+$.

2-((4-Chloro-2-methoxy-5-(1-methylcyclopropyl) phenyl)amino)acetic acid

To a solution of ethyl 2-((4-chloro-2-methoxy-5-(1-methylcyclopropyl)phenyl)amino)acetate (630 mg, 2.12 mmol) in THF (15 mL) and water (5 mL), LiOH.H$_2$O (889 mg, 21.2 mmol) was added and the resulting mixture was stirred at RT for 2 h. The mixture was washed with 20% ethyl acetate/petroleum ether. The aqueous layer was acidified with aqueous HCl (1N) to adjust pH to 3-4 and extracted with ethyl acetate. The organic layer was dried over MgSO$_4$, filtered and concentrated in vacuo to afford the desired product (200 mg, 33% yield).

tert-Butyl 3-(4-(2-((4-chloro-2-methoxy-5-(1-methylcyclopropyl)phenyl)amino)acetyl)piperazin-1-yl) azetidine-1-carboxylate To a solution of 2-((4-chloro-2-methoxy-5-(1-methylcyclopropyl)phenyl)amino)acetic acid (110 mg, 0.41 mmol) and tert-butyl 3-(piperazin-1-yl)azetidine-1-carboxylate (118 mg, 0.49 mmol) in DMF (15 mL) at RT, BOP (217 mg, 0.49 mmol) and DIEA (159 mg, 1.23 mmol) were added and the resulting mixture was stirred at RT for 1 h. The mixture was partitioned between ethyl acetate and water. The organic layer was washed with brine, dried over MgSO$_4$, filtered and concentrated in vacuo to afford the desired product (192 mg, 95% yield).

1-(3-(4-(2-((4-Chloro-2-hydroxy-5-(1-methylcyclopropyl)phenyl)amino)acetyl)piperazin-1-yl)azetidin-1-yl)prop-2-en-1-one (V-64)

The title compound was prepared from tert-butyl 3-(4-(2-((4-chloro-2-methoxy-5-(1-methylcyclopropyl)phenyl) amino)acetyl)piperazin-1-yl)azetidine-1-carboxylate in three steps according to the procedure described in Example 17. $^1$H NMR (400 MHz, DMSO-d6) δ: 9.70 (s, 1H), 6.64 (s, 1H), 6.51 (s, 1H), 6.35-6.28 (m, 1H), 6.13-6.08 (dd, J=1.9, 17.9 Hz, 1H), 5.69-5.66 (dd, J=2.1, 10.1 Hz, 1H), 5.13-5.11 (m, 1H), 4.25-4.23 (m, 1H), 4.08-4.05 (m, 1H), 3.95-3.91 (m, 3H), 3.80-3.76 (m, 1H), 3.53 (bs, 4H), 3.18-3.16 (m, 1H), 2.38-2.31 (m, 4H), 1.26 (s, 3H), 0.72-0.64 (m, 4H). ESI-MS m/z: 434.4[M+H]$^+$.

Example 42

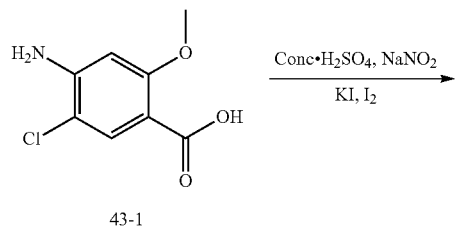

43-1

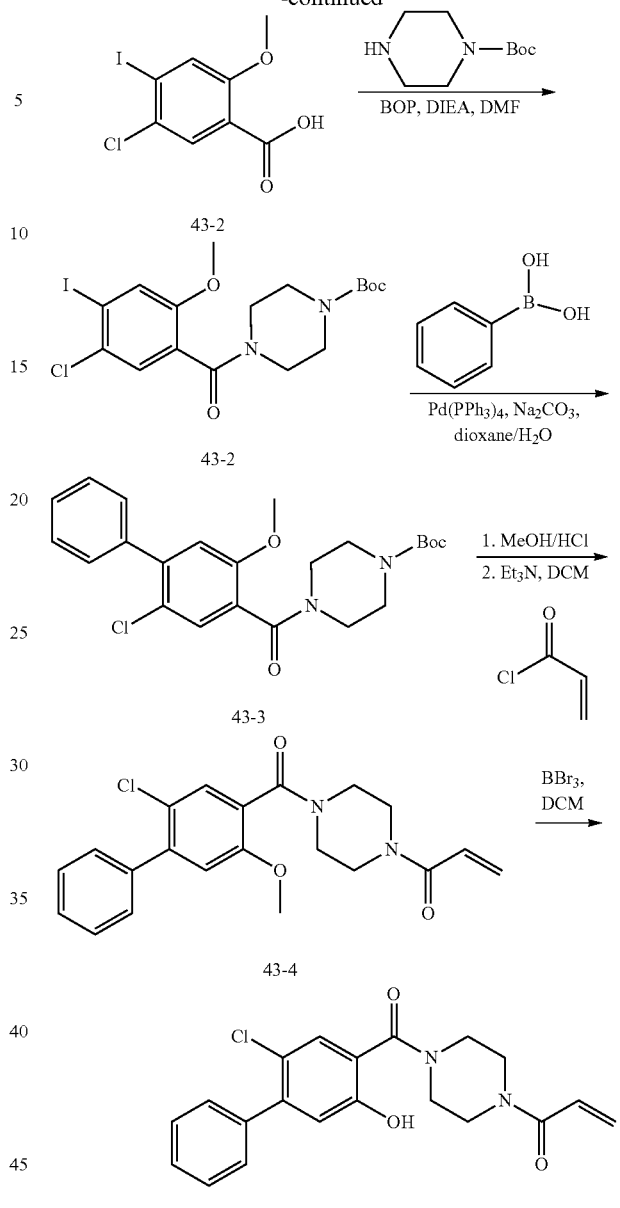

5-Chloro-4-iodo-2-methoxybenzoic acid

To a stirred solution of 4-amino-5-chloro-2-methoxybenzoic acid (5 g, 24.8 mmol) in water (10 mL) at 0° C., concentrated sulfuric acid (50 mL) was added. Then a solution of NaNO$_2$ (1.9 g, 27.3 mmol) in water (10 mL) was added dropwise while keeping the internal temperature around 0° C. KI (4.5 g, 27.3 mmol) and I$_2$ (3.5 g, 13.64 mmol) were dissolved in water and added dropwise to the stirred reaction mixture. The reaction was stirred at 5° C. for 2 h and then extracted with ethyl acetate. The organic layer was washed with water, Na$_2$SO$_3$ (aq, 10%) and brine, dried over anhydrous Na$_2$SO$_4$ and concentrated in vacuo to afford desired product (1.55 g, 19% yield). ESI-MS m/z: 311.1[M+H]$^+$.

tert-Butyl 4-(5-chloro-4-iodo-2-methoxybenzoyl) piperazine-1-carboxylate

To a stirred solution of 5-chloro-4-iodo-2-methoxybenzoic acid (1.55 g, 4.9 mmol) in DMF (30 mL) at RT, tert-butyl piperazine-1-carboxylate (1.02 g, 5.5 mmol), BOP (2.63 g, 25.9 mmol) and DIEA (1.92 g, 14.9 mmol) were added and the resulting mixture was stirred at RT for 1 h. The reaction mixture was extracted with ethyl acetate and washed with brine. The organic layer was dried over anhydrous $Na_2SO_4$, filtered and concentrated in vacuo. The residue was purified by flash column chromatography on silica gel (dichloromethane/methanol=50:1) to afford the desired product (1.96 g, 76% yield).

tert-Butyl-4-(2-chloro-5-methoxy-[1,1'-biphenyl]-4-carbonyl)piperazine-1-carboxylate A mixture of tert-butyl 4-(5-chloro-4-iodo-2-methoxybenzoyl)piperazine-1-carboxylate (300 mg, 0.56 mmol), phenylboronic acid (82 mg, 0.67 mmol), $Pd(PPh_3)_4$ (129 mg, 0.1 mmol), $Na_2CO_3$ (180 mg, 1.68 mmol) in 1,4-dioxane (10 mL) and water (2 mL) was stirred at reflux under argon for 16 h. The mixture was allowed to cool to room temperature and concentrated in vacuo. The residue was purified by flash column chromatography on silica gel (petroleum ether/ethyl acetate=30:1) to afford the desired product (219 mg, 80% yield).

1-(4-(2-Chloro-5-hydroxy-[1,1'-biphenyl]-4-carbonyl)piperazin-4-carbonyl)piperazin-1-yl)prop-2-en-1-one (VI-42)

The title compound was prepared from tert-butyl-4-(2-chloro-5-methoxy-[1,1'-biphenyl]-4-carbonyl)piperazine-1-carboxylatein three steps according to the procedure described in Example 17. $^1$H NMR (400 MHz, DMSO-d6) δ: 10.40 (s, 1H), 7.50-7.41 (m, 5H), 7.35 (s, 1H), 6.89 (s, 1H), 6.84 (m, 1H), 6.17-6.13 (d, 1H), 5.73-5.71 (m, 1H), 3.63 (s, 6H), 3.30 (s, 2H). ESI-MS m/z: 371.2[M+H]$^+$.

Example 43

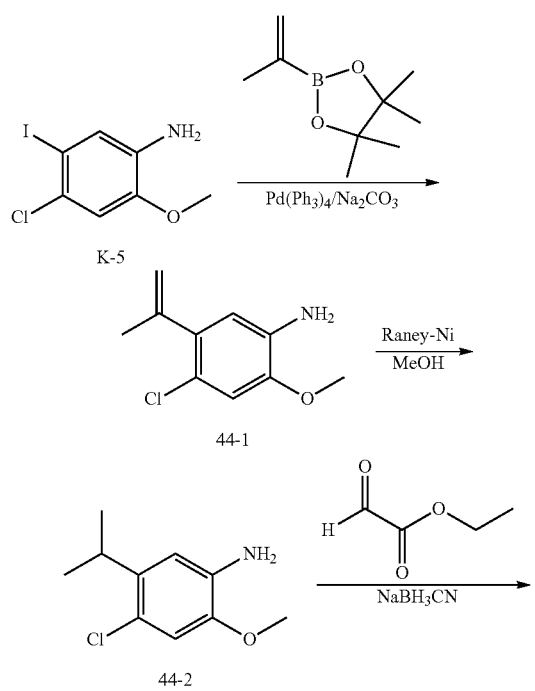

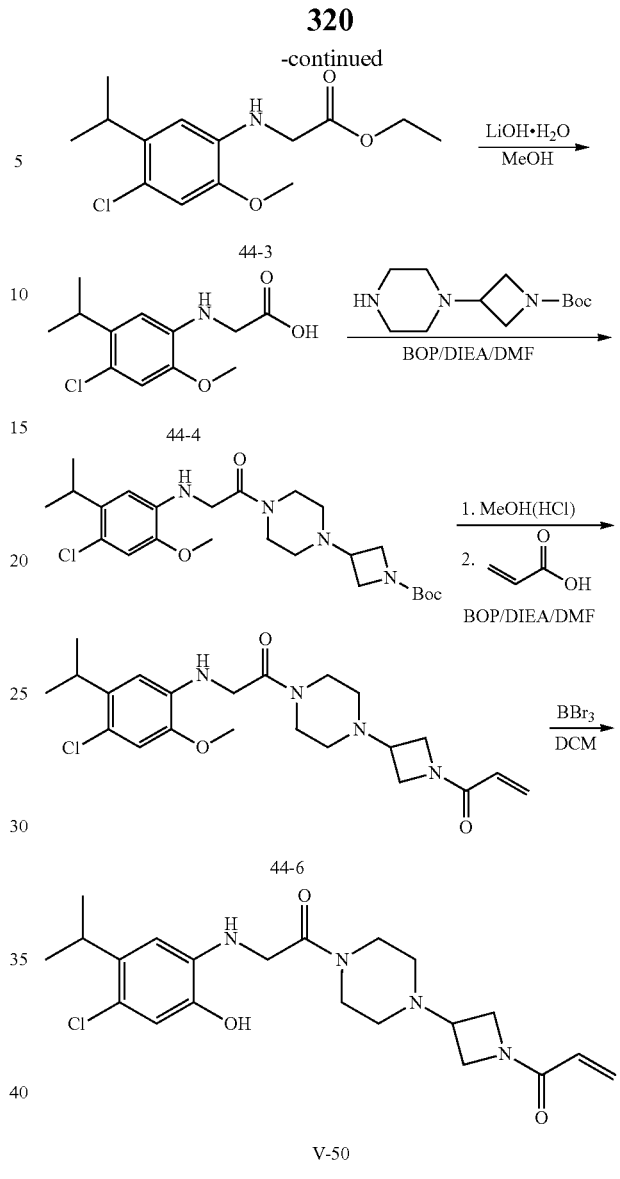

4-Chloro-2-methoxy-5-(prop-1-en-2-yl)benzenamine

A mixture of 4-chloro-5-iodo-2-methoxybenzenamine (1.0 g, 3.53 mmol), 4,4,5,5-tetramethyl-2-(prop-1-en-2-yl)-1,3,2-dioxaborolane (889 mg, 5.29 mmol), $Pd(PPh_3)_4$ (363 mg, 0.353 mmol), $Na_2CO_3$ (1.12 g, 10.6 mmol) in DME (10 mL) and water (3 mL) was stirred at reflux under argon for 6 h. The reaction mixture was allowed to cool to RT and extracted with ethyl acetate. The organic layer was washed with brine, dried over $Na_2SO_4$ and concentrated in vacuo. The residue was purified by flash column chromatography on silica gel (5% petroleum ether/ethyl acetate) to afford the desired product (173 mg, 25% yield) as an off-white solid. ESI-MS m/z: 198.5[M+H]$^+$.

4-Chloro-5-isopropyl-2-methoxybenzenamine

A mixture of 4-chloro-2-methoxy-5-(prop-1-en-2-yl)benzenamine (160 mg, 0.81 mmol), Raney-Ni (20 mg) in MeOH (5 mL) was stirred at RT under $H_2$ (1 atm) atmosphere for 8 h. The mixture was filtered and the filtrate was concentrated in vacuo to afford the desired product (150 mg, 93% yield).

321 tert-Butyl 3-(4-(2-(4-chloro-5-isopropyl-2-methoxyphenylamino)acetyl)piperazin-1-yl)azetidine-1-carboxylate The title compound was prepared from 4-chloro-5-isopropyl-2-methoxybenzenamine in three steps according to the procedure described in Example 42.

1-(3-(4-(2-(4-Chloro-5-isopropyl-2-methoxyphenylamino)acetyl)piperazin-1-yl)azetidin-1-yl)prop-2-en-1-one A mixture of tert-butyl 3-(4-(2-(4-chloro-5-isopropyl-2-methoxyphenylamino)acetyl)piperazin-1-yl)azetidine-1-carboxylate (102 mg, 0.212 mmol) in HCl/MeOH (2.86 M, 5 mL) was stirred at RT for 1 h. The mixture was concentrated in vacuo to afford the crude product, the crude was dissolved in DMF (5 mL) at RT, acrylic acid (17 mg, 0.233 mmol), BOP (113 mg, 0.254 mmol) and DIEA (82 mg, 0.636 mmol) were added and the resulting mixture was stirred at RT for 1 h. The mixture was partitioned between ethyl acetate and water. The organic layer was washed brine, dried over MgSO$_4$, filtered and concentrated in vacuo. The residue was purified by flash column chromatography on silica gel (dichloromethane/methanol=50:1) to afford the desired product (77 mg, 85% yield, 2 steps). ESI-MS m/z: 435.4[M+H]$^+$.

322

1-(3-(4-(2-(4-Chloro-2-hydroxy-5-isopropylphenylamino)acetyl)piperazin-1-yl)azetidin-1-yl)prop-2-en-1-one (V-50)

To a solution of 1-(3-(4-(2-(4-chloro-5-isopropyl-2-methoxyphenylamino)acetyl)piperazin-1-yl)azetidin-1-yl)prop-2-en-1-one (77 mg, 0.18 mmol) in DCM (15 mL) at −60° C., BBr$_3$ (443 mg, 1.8 mmol) was added dropwise and the resulting mixture was stirred at RT for 1 h. The mixture was cooled to −60° C., MeOH was added dropwise and then basified with Et$_3$N to adjust the pH to 8-9. The mixture was poured into water and extracted with dichloromethane. The organic layer was dried over anhydrous Na$_2$SO$_4$, filtered and concentrated in vacuo. The residue was purified by flash column chromatography on silica gel (dichloromethane/methanol=50:1) to afford the desired product (25 mg, 33% yield). $^1$H NMR (400 MHz, DMSO-d6) δ: 9.50 (bs, 1H), 6.62 (s, 1H), 6.470 (s, 1H), 6.30 (m, 1H), 6.10 (dd, J=2.4, 17.2 Hz, 1H), 5.68 (dd, J=2.0, 10.4 Hz, 1H), 5.14 (m, 1H), 4.25 (m, 1H), 4.06 (m, 1H), 3.96 (m, 1H), 3.91 (m, 2H), 3.78 (m, 1H), 3.54 (m, 4H), 3.17 (m, 2H), 2.35 (m, 4H), 1.21 (m, 6H). ESI-MS m/z: 421.4[M+H]$^+$.

Example 44

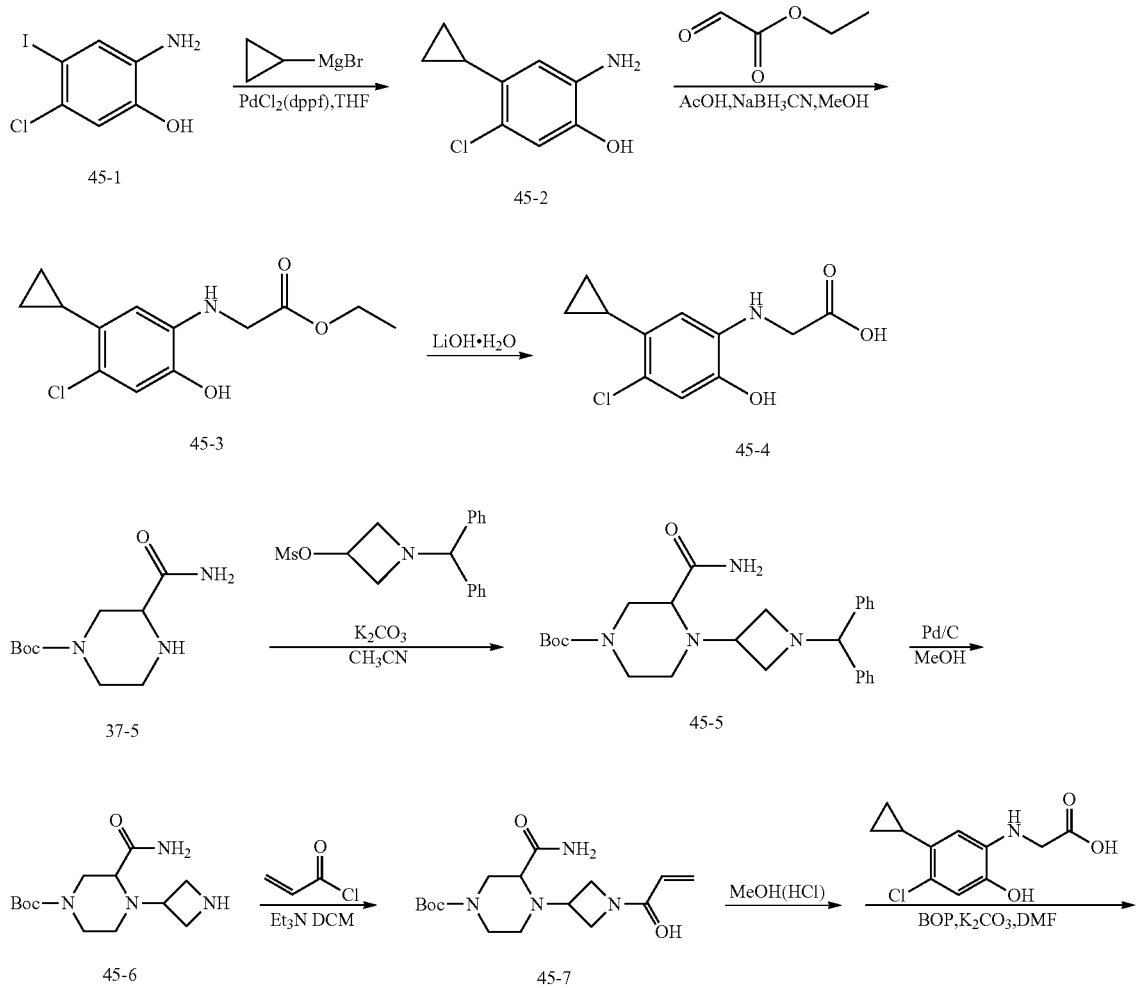

-continued

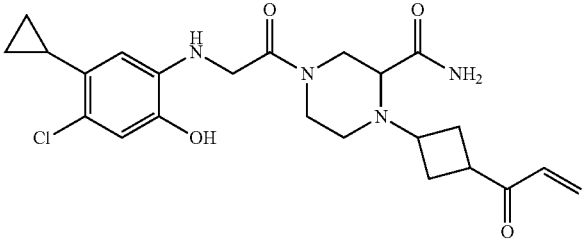

V-51

2-Amino-5-chloro-4-cyclopropylphenol

To a mixture of 2-amino-5-chloro-4-iodophenol (500 mg, 1.9 mmol), PdCl$_2$(dppf) (136 mg, 0.19 mmol) in THF (10 mL) under argon at RT, cyclopropylmagnesium bromide (16 mL, 11.4 mmol, 0.7 M in THF) was added and the mixture was stirred at reflux for 15 h. The mixture was allowed to cool to RT, and partitioned between ethyl acetate and water. The organic layer was washed with brine, dried over Na$_2$SO$_4$ and concentrated. The residue was purified by flash column chromatography on silica gel (10-20% ethyl acetate/hexanes) to afford the desired product (220 mg, 63% yield) as a brown solid. $^1$H NMR (400 MHz, DMSO-d6) δ: 9.27 (s, 1H), 6.62 (s, 1H), 6.22 (s, 1H), 4.53 (s, 2H), 1.89-1.93 (m, 1H), 0.83-0.87 (m, 2H), 0.46-0.49 (m, 2H).

Ethyl 2-(4-chloro-5-cyclopropyl-2-hydroxyphenylamino)acetate

To a solution of 2-amino-5-chloro-4-cyclopropylphenol (200 mg, 1.01 mmol) in MeOH (20 mL) at RT, AcOH (3 drops) and ethyl glyoxalate (416 mg, 2.02 mmol, 50% in toluene) were added. The mixture was stirred at RT for 2 h and then sodium cyanoborohydride (190 mg, 3.03 mmol) was added to the mixture. The resulting mixture was stirred at 40° C. for 15 h. The mixture was allowed to cool to RT and partitioned between ethyl acetate and water. The organic layer was washed with brine, dried over Na$_2$SO$_4$ and concentrated. The residue was purified by flash column chromatography on silica gel (10-20% methanol/dichloromethane) to afford the desired product (290 mg, 100% yield) as a solid. $^1$H NMR (400 MHz, DMSO-d6) δ: 9.63 (s, 1H), 6.66 (s, 1H), 5.93 (s, 1H), 5.07 (t, J=6.4 Hz, 1H), 4.12 (q, J=7.2 Hz, 2H), 3.91 (d, J=6.4 Hz, 2H), 1.92-1.97 (m, 1H), 1.20 (t, J=6.8 Hz, 2H), 0.84-0.87 (m, 2H), 0.51-0.55 (m, 2H).

2-(4-Chloro-5-cyclopropyl-2-hydroxyphenylamino)acetic acid

To a solution of ethyl 2-(4-chloro-5-cyclopropyl-2-hydroxyphenylamino)acetate (290 mg, 0.89 mmol) in of 4:1 mixture of tetrahydrofuran and water (30 mL) at RT, LiOH.H$_2$O (226 mg, 5.34 mmol) was added and the resulting mixture was stirred for 2 h at 60° C. The mixture was acidified with aqueous HCl (1N) to adjust the pH to 3-5 and then extracted with ethyl acetate. The organic layer was washed with brine, dried over anhydrous Na$_2$SO$_4$, filtered and concentrated in vacuo to afford the product (100 mg, 47% yield). $^1$H NMR (400 MHz, DMSO-d6) δ: 9.64 (s, 1H), 6.66 (s, 1H), 5.96 (s, 1H), 3.81 (s, 2H), 1.89-1.96 (m, 1H), 0.84-0.87 (m, 2H), 0.54-0.56 (m, 2H).

tert-Butyl 4-(1-benzhydrylazetidin-3-yl)-3-carbamoylpiperazine-1-carboxylate A mixture of 1-benzhydrylazetidin-3-yl methanesulfonate (2.69 g, 8.5 mmol), K$_2$CO$_3$ (1.76 g, 12.8 mmol), tert-butyl 3-carbamoylpiperazine-1-carboxylate (1.95 g, 8.5 mmol) in CH3CN (40 mL) was stirred at reflux for 16 h. The mixture was partitioned between ethyl acetate and water. The organic layer was washed with water and brine, dried over Na$_2$SO$_4$, and concentrated in vacuo. The residue was purified by flash column chromatography on silica gel (dichloromethane/methanol=50:1) to afford the desired product. (2.08 g, 54% yield).

tert-Butyl 4-(azetidin-3-yl)-3-carbamoylpiperazine-1-carboxylate

A mixture of 4-chloro-2-methoxy-5-(prop-1-en-2-yl)benzenamine (1 g, 2.22 mmol), Pd/C (300 mg) in MeOH (25 mL) was stirred at 50° C. under H$_2$ (1 atm) atmosphere for 12 h. The mixture was cooled and filtered. The filtrate was concentrated in vacuo to afford the desired product (640 mg, 100% yield).

tert-Butyl 4-(1-acryloylazetidin-3-yl)-3-carbamoylpiperazine-1-carboxylate

To a solution of tert-butyl 4-(azetidin-3-yl)-3-carbamoylpiperazine-1-carboxylate (640 mg, 2.22 mmol) and Et$_3$N (463 mg, 4.58 mmol) in DCM (10 mL) at 0° C., acryloyl chloride (248 mg, 2.74 mmol) was added dropwise and the resulting mixture was stirred at RT for 1.5 h. The mixture was partitioned between dichloromethane and saturated NaHCO$_3$ solution. The organic layer was washed with saturated brine, dried over Na$_2$SO$_4$ and concentrated in vacuo. The residue was purified by flash column chromatography on silica gel (dichloromethane/methanol=50:1) to afford the desired product (350 mg, 47% yield).

1-(1-acryloylazetidin-3-yl)-4-(2-(4-chloro-5-cyclopropyl-2-hydroxyphenylamino)acetyl)piperazine-2-carboxamide (V-51)

A mixture of tert-butyl 4-(1-acryloylazetidin-3-yl)-3-carbamoylpiperazine-1-carboxylate (120 mg, 0.35 mmol) in HCl/MeOH (2.86 M, 10 mL) was stirred at RT for 1 h. The mixture was concentrated in vacuo to afford the crude residue. It was dissolved in DMF (5 mL) at 0° C., 2-(4-chloro-5-cyclopropyl-2-hydroxyphenylamino)acetic acid (31 mg, 0.427 mmol), BOP (206 mg, 0.466 mmol) and K$_2$CO$_3$ (150 mg, 1.164 mmol) were added and the resulting mixture was stirred at RT for 1 h. The mixture was partitioned between ethyl acetate and water. The organic layer was washed brine, dried over MgSO$_4$, filtered and concentrated in vacuo. The residue was purified by flash column chromatography on silica gel (dichloromethane/methanol=20:1) to afford the desired product (126 mg, 75% yield, 2 steps). $^1$H NMR (400 MHz, DMSO-d6) δ: 9.63 (bs, 1H), 7.53 (d, 1H), 7.26-6.94 (m, 2H), 6.67 (s, 1H), 6.34-6.27 (m, 1H), 6.10 (m, 2H), 5.68 (d, J=10.4, 1H), 5.08 (m, 1H), 4.30 (m, 2H), 3.93 (m, 6H), 3.52 (m, 2H), 3.29 (m, 1H), 3.15 (m, 1H), 3.06 (m, 1H), 2.47 (m, 1H), 1.98 (m, 1H), 0.87 (m, 2H), 0.64 (m, 2H). ESI-MS m/z: 462.5[M+H]$^+$.

Example 45

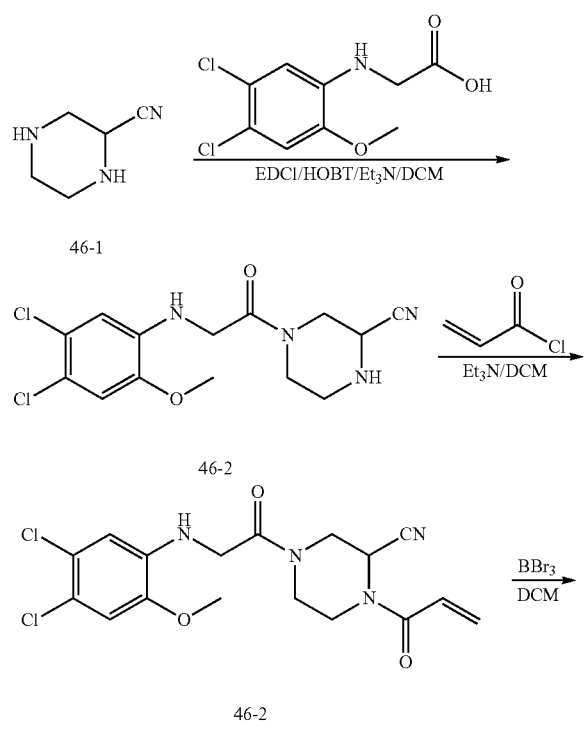

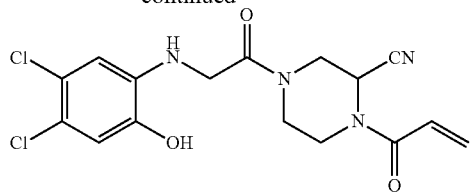

VI-39

4-(2-(4,5-Dichloro-2-methoxyphenylamino)acetyl) piperazine-2-carbonitrile

To a mixture of 2-(4,5-dichloro-2-methoxyphenylamino) acetic acid (260 mg, 1.04 mmol), EDCI (273 mg, 1.43 mmol), HOBt (194 mg, 1.43 mmol) and Et$_3$N (288 mg 2.85 mmol) in DCM (10 mL) at 0° C., piperazine-2-carbonitrile was added. The resulting mixture was stirred at RT for 8 h. The mixture was partitioned between dichloromethane and water. The organic layer was washed with brine, dried over MgSO$_4$, filtered and concentrated in vacuo. The residue was purified by flash column chromatography on silica gel (dichloromethane/methanol=50:1) to afford the desired product (108 mg, 30% yield).

1-acryloyl-4-(2-(4,5-dichloro-2-hydroxyphenylamino)acetyl)piperazine-2-carbonitrile (VI-39)

The title compound was prepared from 4-(2-(4,5-dichloro-2-methoxyphenylamino)acetyl)piperazine-2-carbonitrile in two steps according to the procedure described in Example 17. $^1$H NMR (400 MHz, DMSO-d6) δ: 10.3 (s, 1H), 6.90 (m, 1H), 6.87 (s, 1H), 6.73 (s, 1H), 6.28 (d, J=16.4 Hz, 1H), 5.88 (d, J=10.4 Hz, 1H), 5.68 (m, 1H), 5.33 (m, 1H), 4.66 (m, 1H), 4.40 (m, 1H), 4.02 (m, 2H), 3.22 (m, 1H), 3.04 (m, 1H), 2.91 (m, 1H). ESI-MS m/z: 383.2[M+H]$^+$.

Example 46

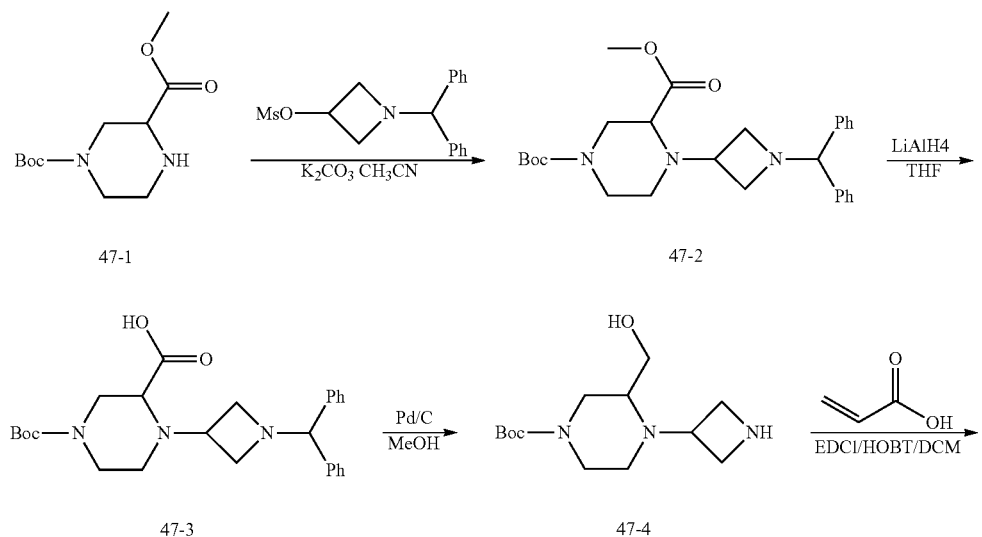

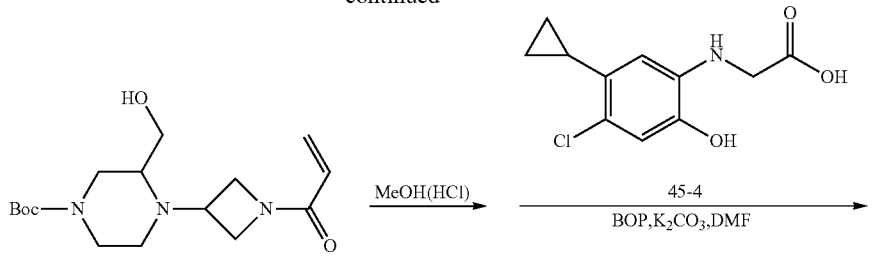

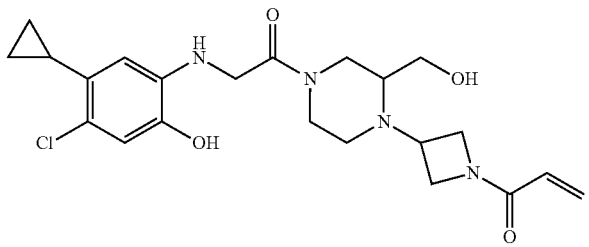

1-tert-Butyl 3-methyl 4-(1-benzhydrylazetidin-3-yl) piperazine-1,3-dicarboxylate A mixture of 1-benzhydrylazetidin-3-yl methanesulfonate (2.4 g, 7.56 mmol), tert-butyl methyl piperazine-1,3-dicarboxylate (1.85 g, 7.56 mmol), $K_2CO_3$ (1.6 g, 11.34 mmol) in CH3CN (40 mL) was stirred at reflux for 16 h. The mixture was partitioned between ethyl acetate and water. The organic layer was washed with water and brine, dried over $Na_2SO_4$, and concentrated in vacuo. The residue was purified by flash column chromatography on silica gel (10% petroleum ether/ethyl acetate) to afford the desired product (1.85 g, 51% yield).

tert-Butyl 4-(1-benzhydrylazetidin-3-yl)-3-(hydroxymethyl)piperazine-1-carboxylate To a mixture of $LiAlH_4$ (500 mg, 13.5 mmol) in THF (40 mL) at −40° C. under argon, a solution of 1-tert-butyl 3-methyl 4-(1-benzhydrylazetidin-3-yl)piperazine-1,3-dicarboxylate (1.8 g, 3.87 mmol) in THF (10 mL) was added dropwise. The reaction mixture was stirred at −5° C. to 5° C. for 1 h and cooled to −20° C. Then water (2 mL) and NaOH (15%) aqueous were added. The resulting mixture was stirred for 15 min. The solid was filtered, and the cake rinsed with ethyl acetate. The combined filtrate was dried over $Na_2SO_4$ and concentrated in vacuo to afford the product (1.6 g, 94% yield).

1-(3-(4-(2-(4-Chloro-5-cyclopropyl-2-hydroxyphenylamino)acetyl)-2-(hydroxymethyl)piperazin-1-yl)azetidin-1-yl)prop-2-en-1-one (V-54)

The title compound was prepared from 4-(2-(4,5-dichloro-2-methoxyphenylamino)acetyl)piperazine-2-carbonitrile in four steps according to the procedure described in Example 44. $^1$H NMR (400 MHz, DMSO-d6) δ: 9.68 (bs, 1H), 6.67 (s, 1H), 6.35-6.27 (m, 1H), 6.12-6.05 (m, 2H), 5.67 (dd, J=1.6, 10.4 Hz, 1H), 5.11 (m, 1H), 4.82-4.63 (m, 1H), 4.24 (m, 1H), 4.13 (m, 1H), 3.95 (m, 1H), 3.88 (m, 2H), 3.85 (m, 1H), 3.77-3.67 (m, 2H), 3.20 (m, 1H), 3.15 (m, 1H), 2.76-2.60 (m, 2H), 2.40 (m, 1H), 1.95 (m, 1H), 0.87 (m, 2H), 0.62 (m, 2H). ESI-MS m/z: 449.4[M+H]$^+$.

Example 47

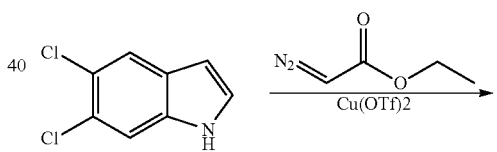

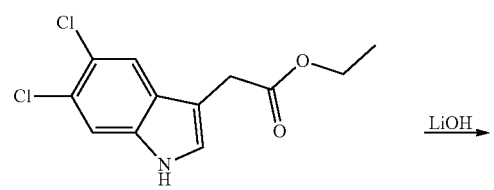

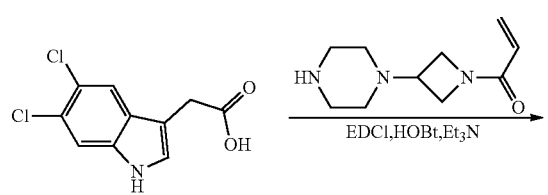

Example 48

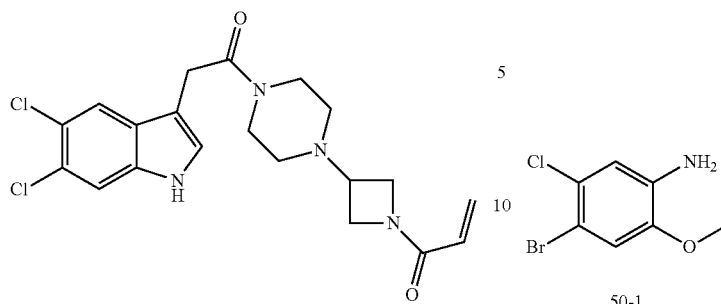

V-61

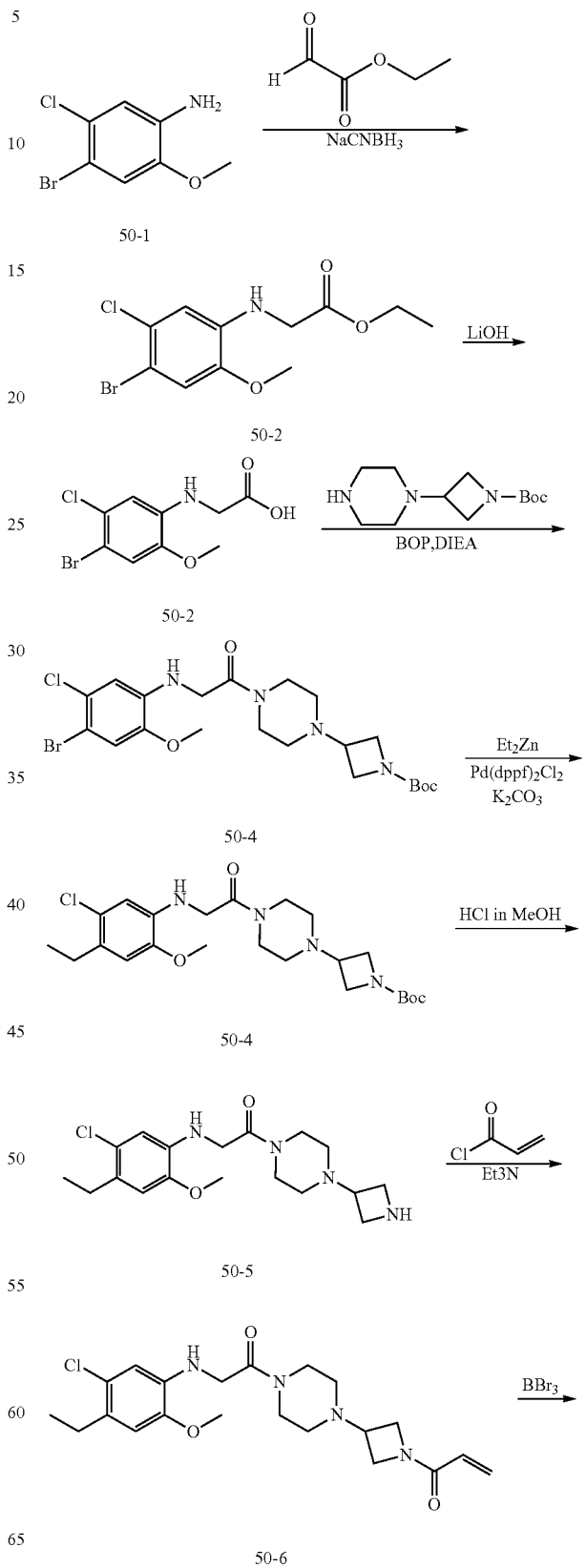

Ethyl 2-(5,6-dichloro-1H-indol-3-yl)acetate

To a mixture of 5,6-dichloro-1H-indole (1.0 g, 5.37 mmol), Cu(OTf)$_2$ (194 mg, 0.537 mmol) in DCM (15 mL) at RT, ethyl 2-diazoacetate (918 mg, 8.05 mmol) was added dropwise. The resulting mixture was stirred at RT for 16 h, quenched with water, and then extracted dichloromethane. The organic layer was dried over Na$_2$SO$_4$, filtered and concentrated in vacuo. The residue was purified by Prep-HPLC to afford the desired product (120 mg, 8.2% yield) as light yellow solid. ESI-MS m/z: 272.1[M+H]$^+$.

2-(5,6-Dichloro-1H-indol-3-yl)acetic acid

A mixture of ethyl 2-(5,6-dichloro-1H-indol-3-yl)acetate (120 mg, 0.44 mmol), LiOH (90 mg, 2.20 mmol) in THF (3 mL) and H$_2$O (1 mL) was stirred at RT for 16 h. The solution was poured into water, adjusted pH to 3-4 with 1N HCl and extracted with ethyl acetate. The organic layer was dried over Na$_2$SO$_4$ and concentrated in vacuo to afford the desired product (90 mg, 84.5% yield) as a yellow solid.

1-(3-(4-(2-(5,6-Dichloro-1H-indol-3-yl)acetyl)piperazin-1-yl)azetidin-1-yl)prop-2-en-1-one (V-61)

A mixture of 2-(5,6-dichloro-1H-indol-3-yl)acetic acid (90 mg, 0.372 mmol), 1-(3-(piperazin-1-yl)azetidin-1-yl)prop-2-en-1-one (87 mg, 0.446 mmol), EDCI.HCl (107 mg, 0.558 mmol), HOBt (75 mg, 0.558 mmol) in DMF (3 mL) at 0° C., Et$_3$N (112 mg, 1.11 mmol) was added. The resulting mixture was stirred at RT for 16 h. The mixture was partitioned between ethyl acetate and water. The organic layer was washed with brine, dried over Na$_2$SO$_4$ and concentrated in vacuo. The residue was purified by flash column chromatography on silica gel (dichloromethane/methanol=30:1) to afford the desired product (12 mg, 7.66% yield) as an off-white solid. $^1$H NMR (400 MHz, DMSO-d6) δ:11.19 (bs, 1H), 7.79 (s, 1H), 7.59 (s, 1H), 7.35 (d, 1H), 6.28 (dd, J=9.6, 16.8 Hz, 1H), 6.09 (dd, J=2.4, 17.2 Hz, 1H), 5.66 (dd, J=2.4, 10.4 Hz, 1H), 4.21-4.18 (m, 1H), 4.02-3.98 (m, 1H), 3.93-3.88 (m, 1H), 3.78 (s, 2H), 3.74-3.70 (m, 1H), 3.53-3.47 (m, 4H), 3.10-3.07 (m, 1H), 2.25-2.19 (m, 4H). ESI-MS m/z: 423.3[M+1].

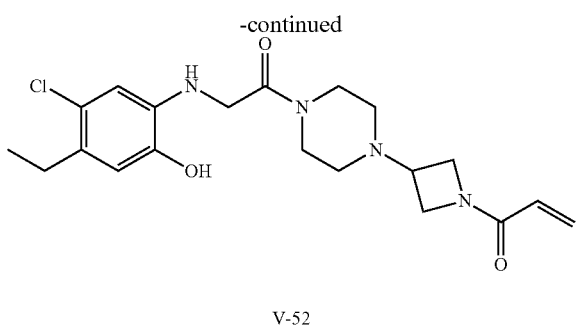

V-52 tert-Butyl 3-(4-(2-(4-bromo-5-chloro-2-methoxyphenylamino)acetyl)piperazin-1-yl)azetidine-1-carboxylate The title compound was prepared from 4-bromo-5-chloro-2-methoxybenzenamine in three steps according to the procedure described in Example 4.

tert-Butyl 3-(4-(2-(5-chloro-4-ethyl-2-methoxyphenylamino)acetyl)piperazin-1-yl)azetidine-1-carboxylate To a mixture of tert-butyl 3-(4-(2-(4-bromo-5-chloro-2-methoxyphenylamino)acetyl)piperazin-1-yl)azetidine-1-carboxylate (100 mg, 0.193 mmol), Pd(dppf)$_2$Cl$_2$ (29 mg, 0.04 mmol) and K$_2$CO$_3$ (55 mg, 0.386 mmol) in DMF (10 mL) at RT, Et$_2$Zn (0.8 mL, 0.8 mmol, 1.0 M in hexane) was added. The resulting mixture was stirred at 80° C. for 16 h. The mixture was partitioned between ethyl acetate and water. The organic layer was washed with brine, dried over Na$_2$SO$_4$ and concentrated in vacuo. The residue was purified by flash column chromatography on silica gel (dichloromethane/methanol=50:1) to afford the crude product (100 mg). ESI-MS m/z: 467.5[M+1]$^+$.

1-(3-(4-(2-(5-Chloro-4-ethyl-2-hydroxyphenylamino)acetyl)piperazin-1-yl)azetidin-1-yl)prop-2-en-1-one (V-52)

The title compound was prepared from tert-butyl 3-(4-(2-(5-chloro-4-ethyl-2-methoxyphenylamino)acetyl)piperazin-1-yl)azetidine-1-carboxylate in 3 steps according to the procedure described in Example 17. $^1$H NMR (400 MHz, DMSO-d6) δ: 9.6 (s, 1H), 6.6 (s, 1H), 6.5 (s, 1H), 6.3 (dd, J=10.4, 17.2 Hz, 1H), 6.1 (dd, J=2.4, 17.2 Hz, 1H), 5.7 (dd, J=2.4, 10.4 Hz, 1H), 5.1 (t, J=4.4 Hz, 1H), 4.2 (t, J=8 Hz, 1H), 4.1 (dd, J=4.8, 8.8 Hz, 1H), 3.95 (dd, J=7.2, 10.0 Hz, 1H), 3.9 (d, J=4.4 Hz, 2H), 3.8 (dd, J=4.8, 10.4 Hz, 1H), 3.6-3.5 (m, 4H), 3.2-3.1 (m, 1H), 3.1-3.0 (m, 1H), 2.5-2.3 (m, 4H), 1.1 (t, J=7.2 Hz, 3H); ESI-MS m/z: 407.4[M+H]$^+$.

Example 49

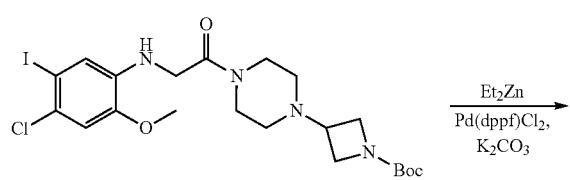

36-1

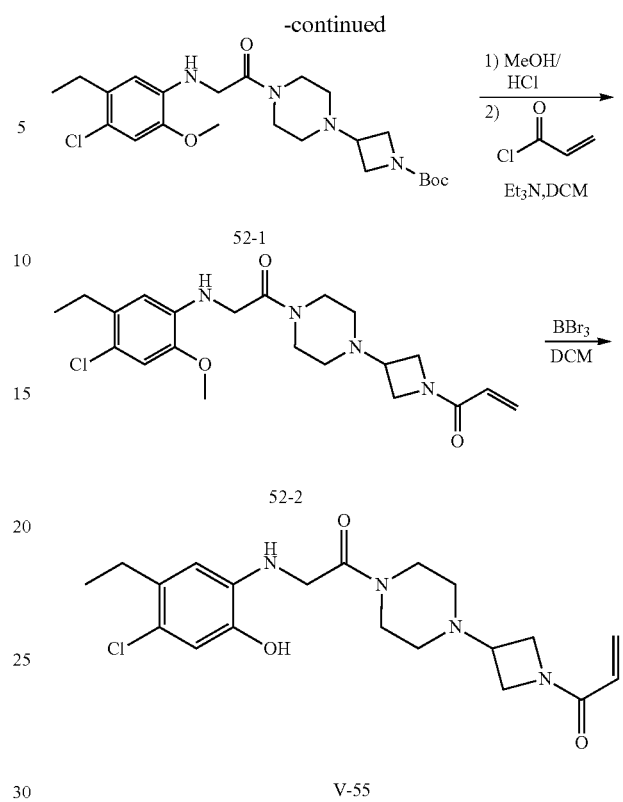

V-55 tert-Butyl 3-(4-(2-((4-chloro-5-ethyl-2-methoxyphenyl)amino)acetyl)piperazin-1-yl) azetidine-1-carboxylate The title compound was prepared from tert-butyl 3-(4-(2-(4-chloro-5-iodo-2-methoxyphenylamino)acetyl)piperazin-1-yl)azetidine-1-carboxylate in one step according to the procedure described in Example 50.

1-(3-(4-(2-(4-chloro-5-ethyl-2-hydroxyphenylamino)acetyl)piperazin-1-yl)azetidin-1-yl)prop-2-en-1-one (V-55)

The title compound was prepared from tert-butyl3-(4-(2-((4-chloro-5-ethyl-2-methoxyphenyl)amino)acetyl)piperazin-1-yl) azetidine-1-carboxylate in three steps according to the procedure described in Example 17. $^1$H NMR (400 MHz, DMSO-d6) δ:9.67 (s, 1H), 6.66 (s, 1H), 6.47 (s, 1H), 6.30 (dd, J=10.5, 16.9 Hz, 1H), 6.12 (dd, J=1.7, 16.7 Hz, 1H), 5.69 (dd, J=1.7, 16.7 Hz, 1H), 5.1 (m, 1H), 4.26 (m, 1H), 4.07 (m, 1H), 3.96 (m, 1H), 3.88 (d, J=4.4, 2H), 3.78 (m, 1H), 3.53 (m, 4H), 3.17 (m, 1H), 2.54 (m, 2H), 2.37 (m, 4H), 1.14 (m, 3H). ESI-MS m/z: 407.3[M+H]$^+$.

Example 50

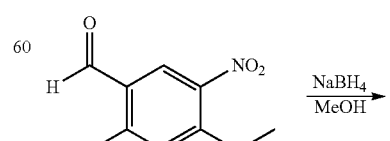

53-1

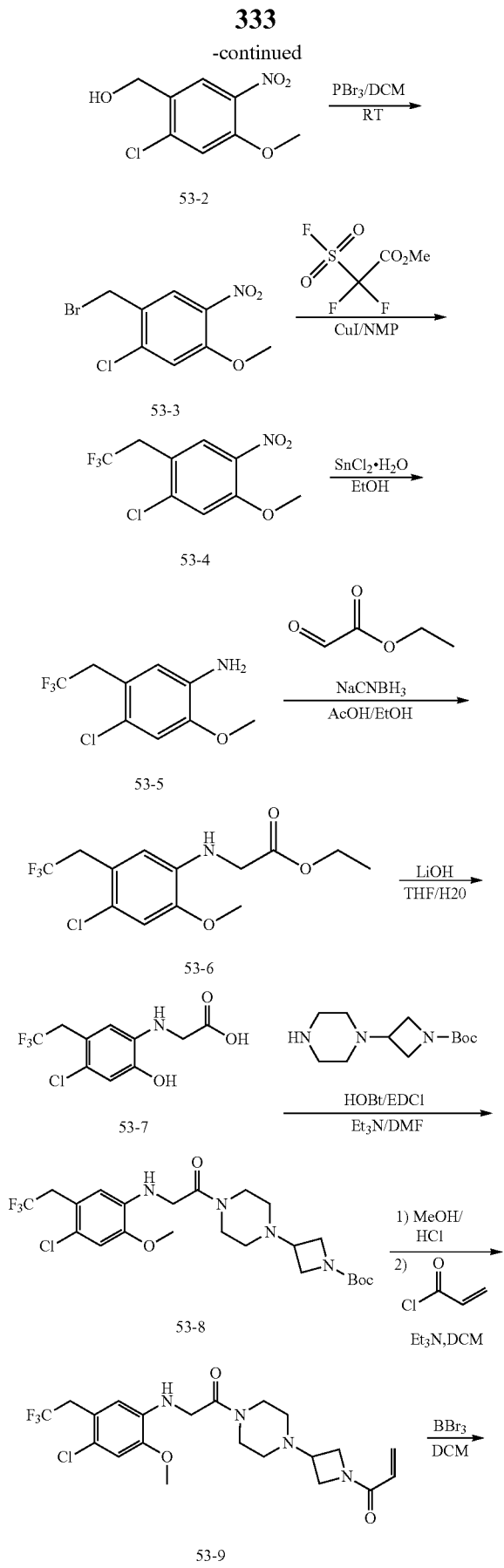

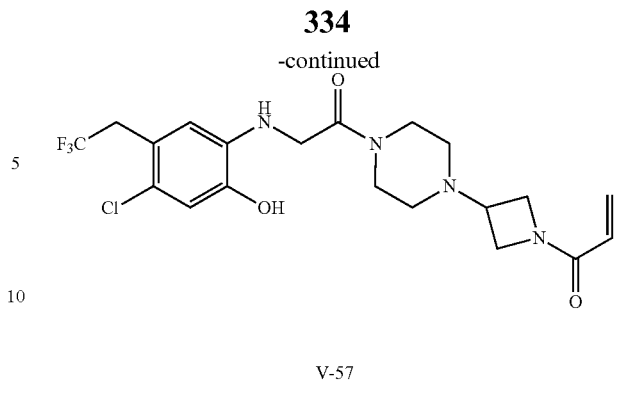

V-57

(2-Chloro-4-methoxy-5-nitrophenyl)methanol

To a solution of 2-chloro-4-methoxy-5-nitrobenzaldehyde (6.0 g, 29 mmol) in MeOH at 0° C. (50 mL), sodium borohydride (4.45 g, 117 mmol) was added in portions and the resulting mixture was stirred at RT for 30 min. The mixture was concentrated in vacuo. The residue was dissolved in ethyl acetate, washed with brine, dried over $Na_2SO_4$ and concentrated in vacuo. The residue was purified by flash column chromatography on silica gel (petroleum ether/ethyl acetate=10:1) to afford the desired product (5.0 g, 78.4% yield).

1-(Bromomethyl)-2-chloro-4-methoxy-5-nitrobenzene

To a solution of (2-chloro-4-methoxy-5-nitrophenyl)methanol (5.0 g, 23 mmol) in dichloromethane (50 mL) at 0° C., tribromophosphine (3.08 g, 11.5 mmol) was added in portions and the resulting mixture was stirred at RT for 2 h. The mixture was poured into ice-water and extracted with dichloromethane. The organic layer was washed with brine, dried over $Na_2SO_4$ and concentrated in vacuo. The residue was purified by flash column chromatography on silica gel (petroleum ether/ethyl acetate=10:1) to afford the desired product (3.5 g, 54.2% yield).

1-Chloro-5-methoxy-4-nitro-2-(2,2,2-trifluoroethyl)benzene

A mixture of (2-chloro-4-methoxy-5-nitrophenyl)methanol (3.5 g, 12.5 mmol), methyl 2,2-difluoro-2-(fluorosulfonyl)acetate (4.8 g, 25 mmol), copper iodide (617 mg, 3.25 mmol) in NMP (20 mL) was stirred at 80° C. for 24 h under Argon. After cooled to RT, the reaction mixture was dissolved in ethyl acetate, washed with brine, dried over $Na_2SO_4$ and concentrated in vacuo. The residue was purified by flash column chromatography on silica gel (petroleum ether/ethyl acetate=100:1) to afford the desired product (1.2 g, 36.4% yield). $^1$H NMR (400 MHz, DMSO-d6) δ: 8.15 (s, 1H), 7.60 (s, 1H), 3.98 (s, 3H), 3.89 (dd, J=1.7, 11.2 Hz, 2H).

4-Chloro-2-methoxy-5-(2,2,2-trifluoroethyl)aniline

A mixture of 1-chloro-5-methoxy-4-nitro-2-(2,2,2-trifluoroethyl)benzene (1.2 g, 4.51 mmol), tin(II) chloride dehydrate (5.0 g, 22.5 mmol) in EtOH (20 mL) was stirred at reflux for 2 h. After cooled to RT, the reaction mixture was added saturated $NaHCO_3$ solution to adjusted pH to 7-8 and then extracted with ethyl acetate. The organic layer washed with brine, dried over $Na_2SO_4$ and concentrated in vacuo to afford the desired product (900 mg, 85% yield). $^1$H NMR (400 MHz, DMSO-d6) δ: 7.29 (s, 1H), 7.11 (s, 1H), 5.41 (s, 2H), 4.21 (s, 3H), 3.99 (dd, J=1.7, 11.2 Hz, 2H).

1-(3-(4-(2-((4-Chloro-2-hydroxy-5-(2,2,2-trifluoroethyl)phenyl)amino)acetyl)piperazin-1-yl)azetidin-1-yl)prop-2-en-1-one (V-57)

The title compound was prepared from 4-chloro-2-methoxy-5-(2,2,2-trifluoroethyl)aniline in six steps according to the procedure described in Example 41. $^1$H NMR (400 MHz, DMSO-d6) δ: 10.08 (s, 1H), 6.74 (s, 1H), 6.59 (s, 1H), 6.34 (dd, J=10.5, 16.9 Hz, 1H), 6.12 (dd, J=1.7, 16.7 Hz, 1H), 5.69 (dd, J=1.7, 16.7 Hz, 1H), 5.22 (m, 1H), 4.24 (m, 1H), 4.04 (m, 1H), 3.94 (m, 1H), 3.88 (d, J=4.4 Hz, 2H), 3.78 (m, 1H), 3.57 (m, 2H), 3.54 (m, 4H), 3.18 (m, 1H), 2.37 (m, 4H). ESI-MS m/z: 461.2[M+H]$^+$.

Example 51

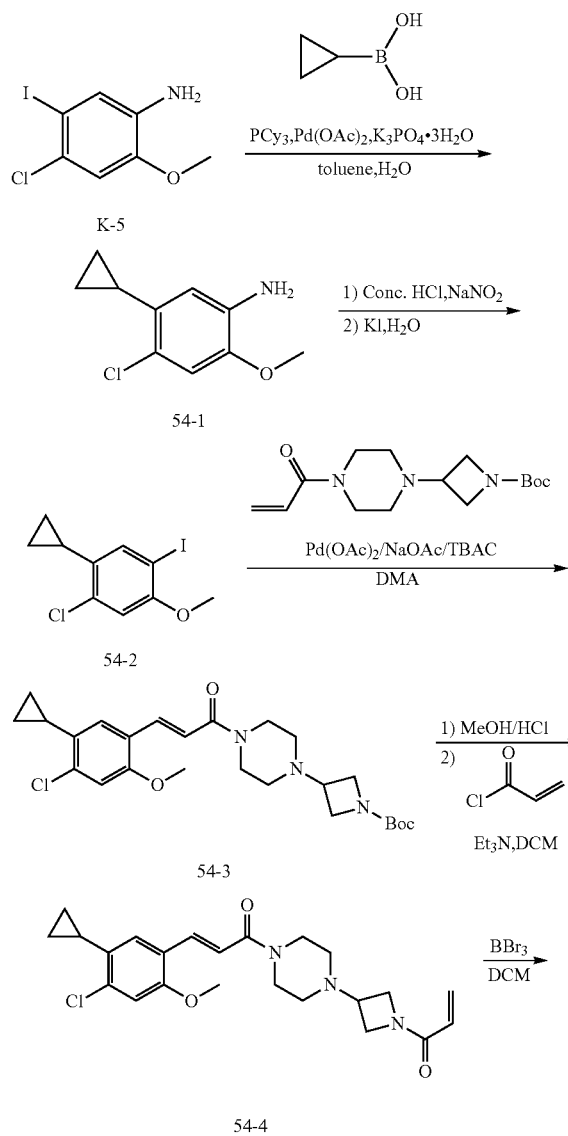

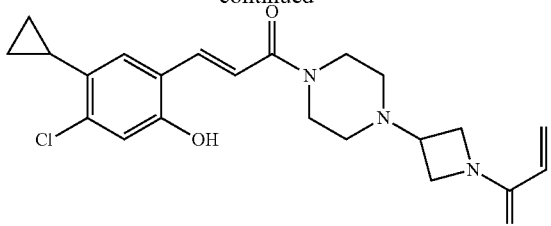

V-62

4-Chloro-5-cyclopropyl-2-methoxybenzenamine

A mixture of 4-chloro-5-iodo-2-methoxyaniline (5.0 g, 17.6 mmol), cyclopropylboronic acid (1.8 g, 21.1 mmol), Pd(OAc)$_2$ (314 mg, 1.4 mmol), tricyclohexylphosphine (500 mg, 17.6 mmol), K$_3$PO$_4$·3H$_2$O (16.4 g, 61.6 mmol) in toluene (62.5 mL) and H$_2$O (3 mL) was stirred at 80° C. under argon for 16 h. The mixture was allowed to cool to RT, and then partitioned between ethyl acetate and water. The organic layer was washed with brine, dried over Na$_2$SO$_4$ and concentrated in vacuo. The residue was purified by flash column chromatography on silica gel (petroleum ether/ethyl acetate=10:1) to afford the desired product (3.1 g, 88.5% yield). ESI-MS m/z: 198.2[M+H]$^+$.

1-Chloro-2-cyclopropyl-4-iodo-5-methoxybenzene

To a mixture of 4-chloro-5-cyclopropyl-2-methoxyaniline (2.2 g, 11.05 mmol), conc. HCl (12 mL) and water (12 mL) at 0° C., the solution of sodium nitrate (762.8 mg, 11.05 mmol) in water (2.5 mL) was added dropwise. After stirring at 0° C. for 15 min, a solution of KI (1.83 g, 11.05 mmol) in water (5 mL) was added dropwise. The resulting mixture was stirred at RT for 4 h, poured into water (20 mL) and then extracted with dichloromethane. The organic layer was washed with brine, dried over anhydrous Na$_2$SO$_4$, filtered and concentrated in vacuo. The residue was purified by flash column chromatography on silica gel (0-10% ethyl acetate/petroleum ether) to afford the desired product (680 mg, 20% yield) as a solid. $^1$H NMR (400 MHz, DMSO-d6) δ: 7.37 (s, 1H), 7.08 (s, 1H), 3.84 (s, 3H), 2.00 (m, 1H), 0.89 (m, 2H), 0.65 (m, 1H).

(E)-1-(4-(1-Acryloylazetidin-3-yl)piperazin-1-yl)-3-(4-chloro-5-cyclopropyl-2-methoxyphenyl)prop-2-en-1-one A mixture of 1-chloro-2-cyclopropyl-4-iodo-5-methoxybenzene (300 mg, 0.974 mmol), tert-butyl 3-(4-acryloylpiperazin-1-yl)azetidine-1-carboxylate (431 mg, 1.46 mmol), Pd(OAc)$_2$ (54.6 mg, 0.243 mmol), sodium acetate (239 mg, 2.92 mmol), tetrabutylammonium chloride (539 mg, 1.95 mmol) in DMF (7 mL) was stirred at 100° C. for 24 h. The mixture was partitioned between ethyl acetate and water. The organic layer was washed with brine, dried over Na$_2$SO$_4$, filtered and concentrated in vacuo to purified by silica gel (dichloromethane/methanol=40:1) to afford the desired product (350 mg, 84% yield). ESI-MS m/z: 476.2[M+H]$^+$.

(E)-1-(4-(1-Acryloylazetidin-3-yl)piperazin-1-yl)-3-(4-chloro-5-cyclopropyl-2-hydroxyphenyl)prop-2-en-1-one (V-62)

The title compound was prepared from (E)-1-(4-(1-acryloylazetidin-3-yl)piperazin-1-yl)-3-(4-chloro-5-cyclopropyl-2-methoxyphenyl)prop-2-en-1-one in three steps according to the procedure described in Example 17. ¹H NMR (400 MHz, DMSO-d6) δ: 10.3 (s, 1H), 7.71 (m, 1H), 7.30 (s, 1H), 7.22 (m, 1H), 6.93 (s, 1H), 6.34 (dd, J=10.5, 16.9 Hz, 1H), 6.12 (dd, J=1.7, 16.7 Hz, 1H), 5.66 (dd, J=1.7, 16.7 Hz, 1H), 4.26 (m, 1H), 4.08 (m, 1H), 3.94 (m, 1H), 3.79 (m, 1H), 3.69 (m, 2H), 3.58 (m, 2H), 3.18 (m, 1H), 2.33 (m, 4H), 1.99 (m, 1H), 0.92 (m, 2H), 0.73 (m, 2H). ESI-MS m/z: 416[M+H]⁺.

Example 52

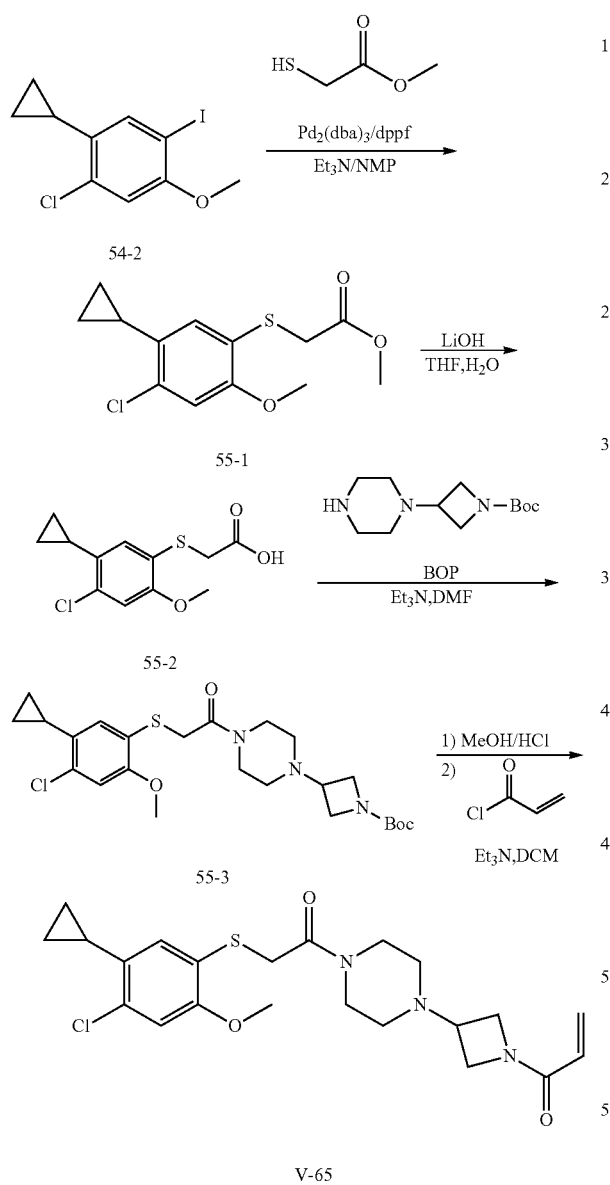

V-65

Methyl 2-((4-chloro-5-cyclopropyl-2-methoxyphenyl)thio)acetate

A mixture of 1-chloro-2-cyclopropyl-4-iodo-5-methoxybenzene (380 mg, 1.23 mmol), Pd₂(dba)₃ (56 mg, 0.061 mmol), methyl 2-mercaptoacetate (196 mg, 1.85 mmol), 1,1'-Bis(diphenylphosphino)ferrocene (136 mg, 0.246 mmol), Et₃N (372 mg, 3.69 mmol) in NMP (8 mL) was stirred under argon at 80° C. for 24 h. After cooled to RT, the reaction mixture was extracted with ethyl acetate. The organic layer was washed with brine, dried over Na₂SO₄ and concentrated in vacuo. The residue was purified by flash column chromatography on silica gel (petroleum ether/ethyl acetate=20:1) to afford the desired product (340 mg, 92% yield). ¹H NMR (400 MHz, DMSO-d6) δ: 7.05 (s, 1H), 6.81 (s, 1H), 3.84 (s, 2H), 3.82 (s, 3H), 3.62 (s, 3H), 2.00 (m, 1H), 0.94 (m, 2H), 0.64 (m, 2H).

1-(3-(4-(2-(4-Chloro-5-cyclopropyl-2-methoxyphenylthio)acetyl)piperazin-1-yl)azetidin-1-yl)prop-2-en-1-one (V-65)

The title compound was prepared from methyl 2-((4-chloro-5-cyclopropyl-2-methoxyphenyl)thio)acetate in four steps according to the procedure described in Example 40. ¹H NMR (400 MHz, DMSO-d6) δ: 7.03 (s, 1H), 6.93 (s, 1H), 6.31 (dd, J=10.5, 16.9 Hz, 1H), 6.11 (dd, J=1.7, 16.7 Hz, 1H), 5.68 (dd, J=1.7, 16.7 Hz, 1H), 4.25 (m, 1H), 4.04 (m, 1H), 3.88 (s, 2H) 3.81 (s, 3H), 3.75 (m, 1H), 3.52 (m, 4H), 3.16 (m, 1H), 2.36-2.25 (m, 4H), 2.02 (m, 1H), 0.93 (m, 2H), 0.66 (m, 2H). ESI-MS m/z: 450[M+H]⁺.

Example 53

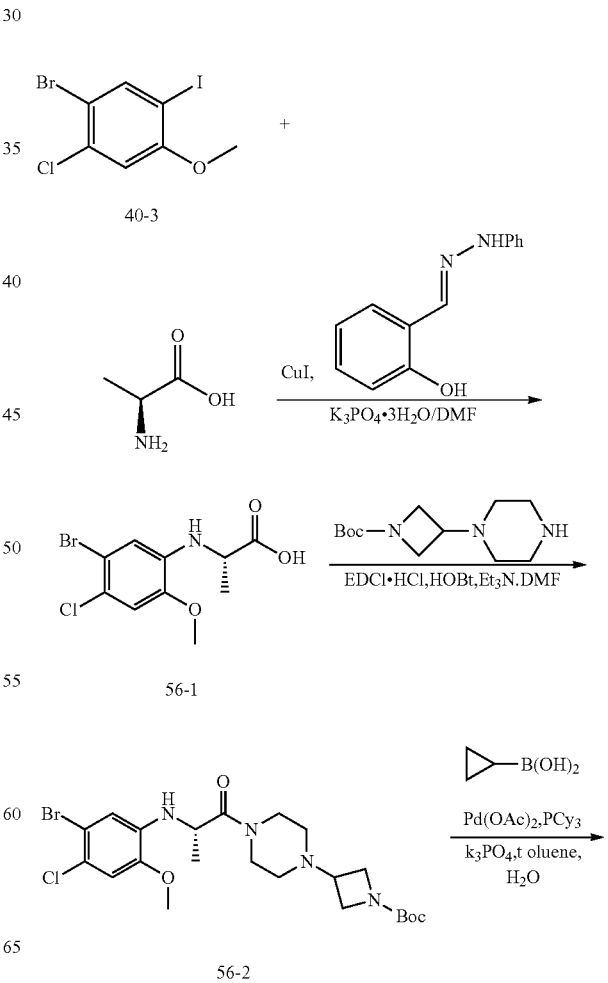

339

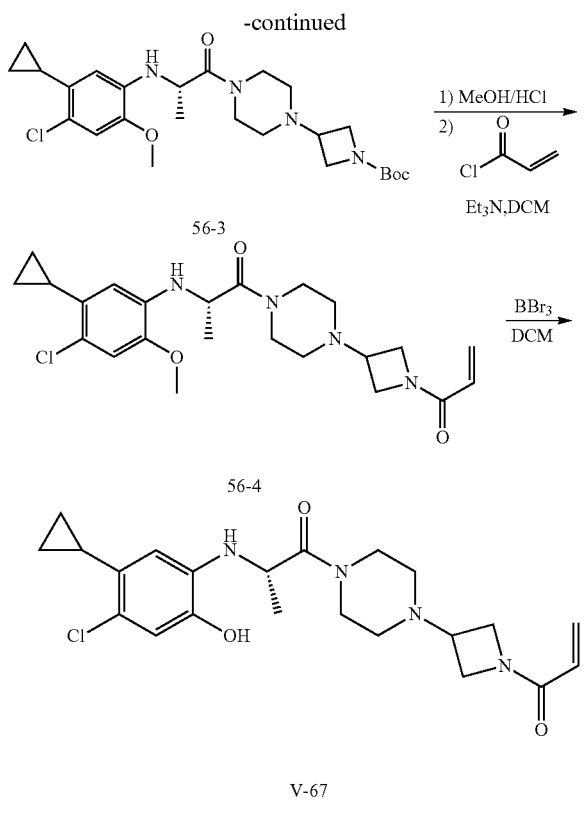

(S)-2-(5-Bromo-4-chloro-2-methoxyphenylamino)propanoic acid

A mixture of 1-bromo-2-chloro-5-iodo-4-methoxybenzene (3 g, 8.64 mmol), (S)-2-aminopropanoic acid (769 mg, 8.64 mmol), CuI (164 mg, 0.864 mmol), 2-hydroxybenzaldehyde phenylhydrazone (366 mg, 1.73 mmol), $K_3PO_4 \cdot 3H_2O$ (4.6 g, 17.28 mmol) in DMF (10 mL) was stirred under argon at 80° C. for 16 h. The mixture was allowed to cool to RT, $H_2O$ and $Et_2O$ were added to the solution. The resulting solution was partitioned into two phases, the aqueous phase was separated, and the organic layer was extracted with 5% NaOH. The combined aqueous phase was acidified to pH 4 with 20% HCl, and then extracted with $Et_2O$. The resulting organic layer was dried over $MgSO_4$ and concentrated in vacuo to afford the desired product (1.7 g, 64% yield). ESI-MS m/z: 306.1[M+H]$^-$ (S)-tert-Butyl 3-(4-(2-((5-bromo-4-chloro-2-methoxyphenyl)amino)propanoyl)piperazin-1-yl)azetidine-1-carboxylate To a solution of (S)-2-(5-bromo-4-chloro-2-methoxyphenylamino)propanoic acid (1.6 g, 5.21 mmol), tert-butyl 3-(piperazin-1-yl)azetidine-1-carboxylate (1.88 g, 7.82 mmol), EDCI.HCl (2.0 g, 10.42 mmol), HOBt (1.41 g, 10.42 mmol) in DMF (20 mL) at 0° C., $Et_3N$ (1.58 g, 15.63 mmol) was added. The resulting mixture was stirred at RT for 16 h and then partitioned between ethyl acetate and water. The organic layer was washed with brine, dried over $Na_2SO_4$ and concentrated in vacuo. The residue was purified by flash column chromatography on silica gel (methanol/dichloroethane=1:50) to afford the desired product (2.1 g, 76% yield). ESI-MS m/z: 531.3[M+H]$^+$.

340

((S)-tert-Butyl 3-(4-(2-((4-chloro-5-cyclopropyl-2-methoxyphenyl)amino)propanoyl)piperazin-1-yl)azetidine-1-carboxylate A mixture of (S)-tert-butyl 3-(4-(2-((5-bromo-4-chloro-2-methoxyphenyl)amino)propanoyl)piperazin-1-yl)azetidine-1-carboxylate (700 mg, 1.32 mmol), cyclopropylboronic acid (114 mg, 1.32 mmol), Pd(OAc)$_2$ (15 mg, 0.066 mmol), tricyclohexylphosphine (37 mg, 0.132 mmol), $K_3PO_4 \cdot 3H_2O$ (974 mg, 4.62 mmol) in DMF (10 mL) and $H_2O$ (0.5 mL) was stirred under argon at 80° C. for 16 h. The mixture was allowed to cool to RT, and then partitioned between ethyl acetate and water. The organic layer was washed with brine, dried over $Na_2SO_4$ and concentrated in vacuo. The residue was purified by flash column chromatography on silica gel (methanol/dichloroethane=1:100) to afford the desired product (400 mg, 62%). ESI-MS m/z: 493.2[M+H]$^+$.

(S)-1-(3-(4-(2-((4-Chloro-5-cyclopropyl-2-hydroxyphenyl)amino)propanoyl)piperazin-1-yl)azetidin-1-yl)prop-2-en-1-one (V-67)

The title compound was prepared from (S)-tert-butyl 3-(4-(2-((4-chloro-5-cyclopropyl-2-methoxyphenyl)amino)propanoyl)piperazin-1-yl)azetidine-1-carboxylate in three steps according to the procedure described in Example 17. $^1$H NMR (400 MHz, DMSO-d6) δ: 9.69 (s, 1H), 6.66 (s, 1H), 6.29 (dd, J=10.5, 16.9 Hz, 1H), 6.12 (dd, J=1.7, 16.7 Hz, 1H), 6.05 (s, 1H), 5.68 (dd, J=1.7, 16.7 Hz, 1H), 4.84 (m, 1H), 4.61 (m, 1H), 4.24 (m, 1H), 4.06 (m, 1H), 3.94 (m, 1H), 3.78 (m, 4H), 3.55 (m, 1H), 2.43-2.17 (m, 4H), 1.97 (m, 1H), 0.88 (m, 2H), 0.63 (m, 2H). ESI-MS m/z: 433.3[M+H]$^+$.

Example 54

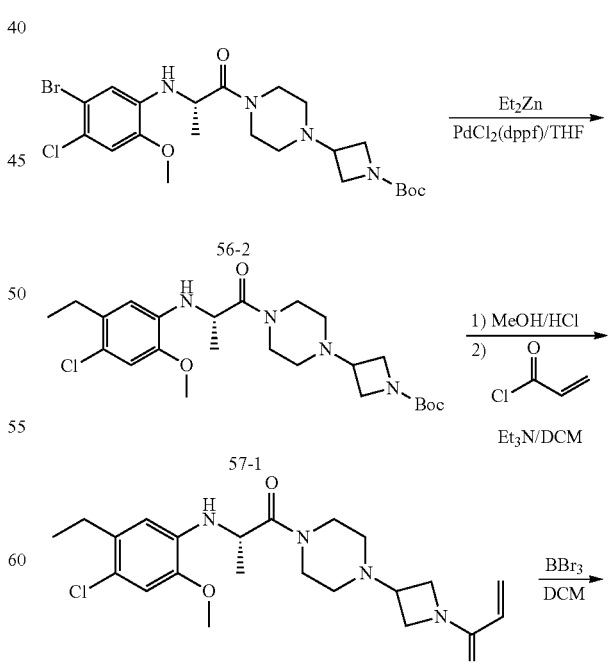

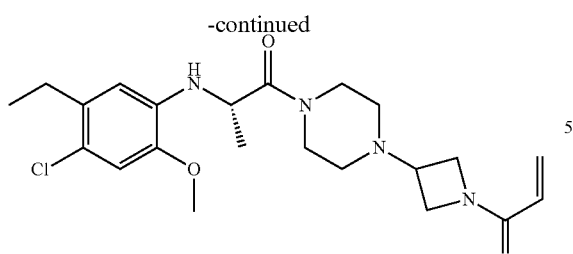

V-69

(S)-tert-Butyl 3-(4-(2-((4-chloro-5-ethyl-2-methoxyphenyl)amino)propanoyl)piperazin-1-yl)azetidine-1-carboxylate To a solution of (S)-tert-butyl 3-(4-(2-((5-bromo-4-chloro-2-methoxyphenyl)amino)propanoyl)piperazin-1-yl)azetidine-1-carboxylate (400 mg, 0.75 mmol), PdCl$_2$(dppf) (95 mg, 0.13 mmol) in THF (20 mL) at RT, Et$_2$Zn (2.86 mL, 2.86 mmol, 1.0 M in hexane) was added. The resulting mixture was stirred under argon at 80° C. for 4 h and then partitioned between ethyl acetate and water. The organic layer was washed with brine, dried over Na$_2$SO$_4$ and concentrated in vacuo. The residue was purified by flash column chromatography on silica gel (methanol/dichloroethane=1:80) to afford the desired product (250 mg, 69% yield). ESI-MS m/z: 481.2 [M+H]$^+$.

(S)-1-(3-(4-(2-((4-Chloro-5-ethyl-2-hydroxyphenyl)amino)propanoyl)piperazin-1-yl)azetidin-1-yl)prop-2-en-1-one (V-69)

The title compound was prepared from (S)-tert-butyl 3-(4-(2-((4-chloro-5-ethyl-2-methoxyphenyl)amino)propanoyl)piperazin-1-yl)azetidine-1-carboxylate in three steps according to the procedure described in Example 17. $^1$H NMR (400 MHz, DMSO-d6) δ: 9.61 (s, 1H), 6.64 (s, 1H), 6.48 (s, 1H), 6.29 (dd, J=10.5, 16.9 Hz, 1H), 6.12 (dd, J=1.7, 16.7 Hz, 1H), 5.68 (dd, J=1.7, 16.7 Hz, 1H), 4.89 (m, 1H), 4.61 (m, 1H), 4.25 (m, 1H), 4.06 (m, 1H), 3.94 (m, 1H), 3.72-3.53 (m, 4H), 3.16 (m, 1H), 2.5 (m, 2H), 2.43-2.17 (m, 4H), 1.21 (dd, 3H), 1.15 (m, 3H). ESI-MS m/z: 406.2[M+H]$^+$.

Example 55

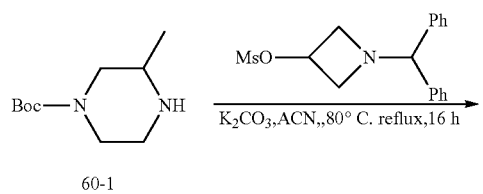

60-1

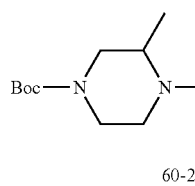

60-2

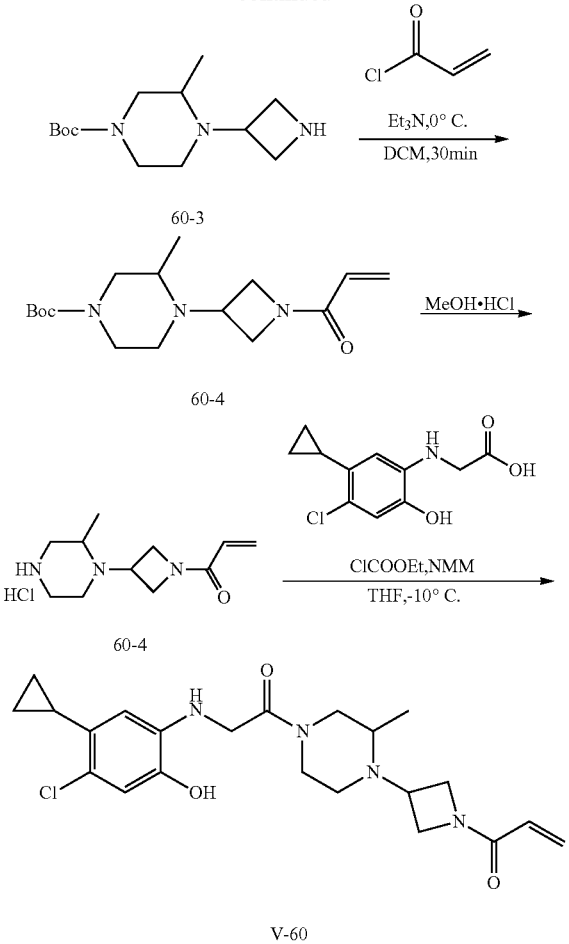

V-60 tert-Butyl 4-(1-acryloylazetidin-3-yl)-3-methylpiperazine-1-carboxylate

The title compound was prepared from tert-butyl 3-methylpiperazine-1-carboxylate in three steps according to the procedure described in Example 38.

1-(3-(2-Methylpiperazin-1-yl)azetidin-1-yl)prop-2-en-1-one hydrochloride

The mixture of tert-butyl 4-(1-acryloylazetidin-3-yl)-3-methylpiperazine-1-carboxylate (62 mg, 0.199 mmol) in MeOH/HCl (20 mL, 2.9 M) was stirred at RT for 1 h. The mixture was concentrated in vacuo to afford the crude product (59 mg). The crude product was used directly in the next step without further purification.

1-(3-(4-(2-((4-Chloro-5-cyclopropyl-2-hydroxyphenyl)amino)acetyl)$_2$=methylpiperazin-1-yl)azetidin-1-yl)prop-2-en-1-one (V-60)

To the mixture of 2-((4-chloro-5-cyclopropyl-2-hydroxyphenyl)amino)acetic acid (30 mg, 0.124 mmol) and NMM (50 mg, 0.496 mmol) in dry THF (30 mL) at −10° C., ethyl chloroformate (15 mg, 0.136 mmol) was added and the resulting mixture was stirred at −10° C. for 45 min. Then it was added a mixture of 1-(3-(2-methylpiperazin-1-yl)azetidin-1-yl)prop-2-en-1-one hydrochloride (37 mg, 0.149 mmol), Et₃N (50 mg, 0.496 mmol) and dichloromethane (3 mL). The resulting mixture was stirred at RT for 30 min. The mixture was partitioned between ethyl acetate and water. The organic layer was washed with saturated NaHCO₃ solution and brine, dried over Na₂SO₄, filtered and concentrated in vacuo. The residue was purified with column chromatography on silica gel (dichloromethane/methanol=40:1) to afford the desired product (10 mg, 18.6% yield) as a white solid. ¹H NMR (400 MHz, DMSO-d6) δ: 9.65 (s, 1H), 6.66 (s, 1H), 6.34-6.27 (m, 1H), 6.10-6.07 (m, 2H), 5.68-5.65 (d, J=10.4 Hz, 1H), 5.12 (m, 1H), 4.29-4.19 (m, 1H), 4.12-4.10 (m, 1H), 4.08-3.81 (m, 4H), 3.78 (s, 4H), 2.63 (m, 2H), 2.25 (m, 1H), 1.96 (m, 1H), 1.24 (s, 1H), 0.96-0.87 (m, 5H), 0.63 (m, 2H). ESI-MS m/z: 433.5[M+H]⁺.

Example 56

4-Bromo-5-chloro-2-nitrobenzamide

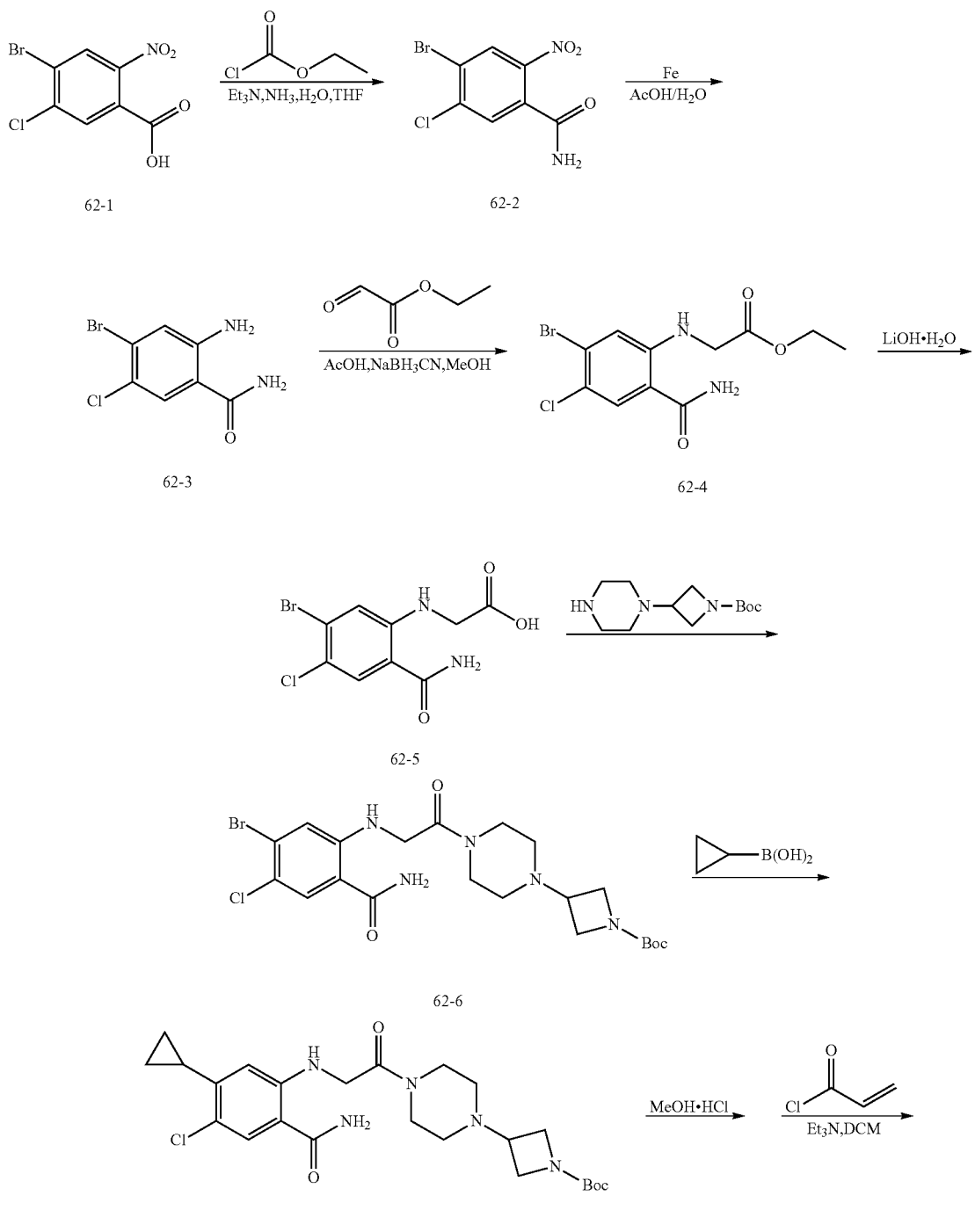

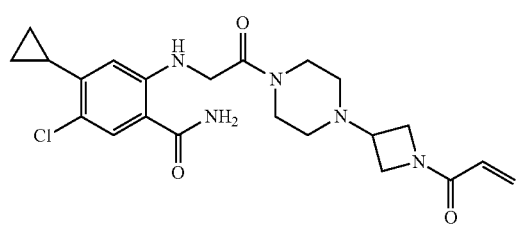

62-8

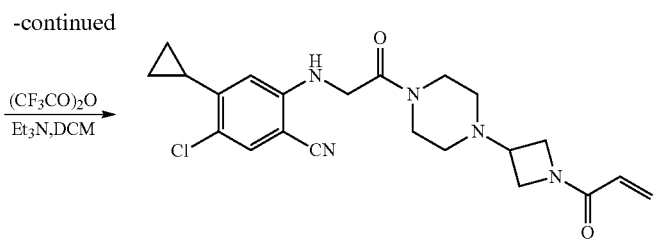

62-8

A mixture of 4-bromo-5-chloro-2-nitrobenzoic acid (1.3 g, 4.63 mmol), Et$_3$N (1.4 g, 13.9 mmol) in THF (20 mL) at 0° C., ethyl chloroformate (1.5 g, 13.9 mmol) was added. The resulting mixture was stirred at 0° C. for 1 h. Then NH$_3$.H$_2$O (4 mL) was added and stirred for 0.5 h. The mixture was extracted with ethyl acetate. The organic layer was washed with brine, dried over anhydrous Na$_2$SO$_4$, filtered and concentrated in vacuo to afford the crude product (900 mg).

2-Amino-4-bromo-5-chlorobenzamide

To a solution of 4-bromo-5-chloro-2-nitrobenzamide (900 mg, 3.2 mmol) in AcOH (20 mL) and water (5 mL) at 70° C., Fe powder (900 mg, 16.1 mmol) was added and the resulting mixture was stirred at 70° C. for 1 h. The mixture was allowed to cool to RT and poured into ice-water. The precipitate was collected by filtration and rinsed with water. This crude product was dissolved with ethyl acetate and filtered. The filtrate was washed with saturated NaHCO$_3$ solution and brine. The organic layer was dried over MgSO$_4$, filtered, and concentrated in vacuo to afford the desired product (770 mg, 97% yield). ESI-MS m/z: 250.1[M+H]$^+$.

tert-Butyl 3-(4-(2-((5-bromo-2-carbamoyl-4-chlorophenyl)amino)acetyl)piperazin-1-yl)azetidine-1-carboxylate The title compound was prepared from 2-amino-4-bromo-5-chlorobenzamide in three steps according to the procedure described in Example 41. ESI-MS m/z: 532.5[M+H]$^+$.

tert-Butyl 3-(4-(2-((2-carbamoyl-4-chloro-5-cyclopropylphenyl)amino)acetyl)piperazin-1-yl)azetidine-1-carboxylate To a solution of tert-butyl 3-(4-(2-((5-bromo-2-carbamoyl-4-chlorophenyl)amino)acetyl)piperazin-1-yl)azetidine-1-carboxylate (350 mg, 0.66 mmol) and cyclopropylboronic acid (226 mg, 2.64 mmol) in toluene (10 mL) and water (2 mL), Pd(OAc)$_2$ (15 mg, 0.07 mmol), PCy$_3$ (37 mg, 0.132 mmol) and K$_3$PO$_4$ (487 mg, 2.31 mmol) were added. The mixture was stirred at 80° C. for 16 h. The mixture was allowed to cool to RT and concentrated in vacuo. The residue was purified by flash column chromatography on silica gel (1-5% methanol/dichloroethane) to afford the desired product (150 mg, 46% yield) as a solid.

2-((2-(4-(1-Acryloylazetidin-3-yl)piperazin-1-yl)-2-oxoethyl)amino)-5-chloro-4-cyclopropylbenzamide The title compound was prepared from tert-butyl 3-(4-(2-((2-carbamoyl-4-chloro-5-cyclopropylphenyl)amino)acetyl)piperazin-1-yl)azetidine-1-carboxylate in two steps according to the procedure described in Example 17. ESI-MS m/z: 446.4[M+H]$^+$.

2-((2-(4-(1-Acryloylazetidin-3-yl)piperazin-1-yl)-2-oxoethyl)amino)-5-chloro-4-cyclopropylbenzonitrile (V-71)

A mixture of 2-((2-(4-(1-acryloylazetidin-3-yl)piperazin-1-yl)-2-oxoethyl)amino)-5-chloro-4-cyclopropylbenzamide (3 0 mg, 0.067 mmol) and Et$_3$N (41 mg, 0.404 mmol) in DCM (10 mL) at RT, trifluoroacetic anhydride (56 mg, 0.268 mmol) was added. The resulting mixture was stirred at RT for 0.5 h, poured into water and then extracted with dichloromethane. The organic layer was washed with brine, dried over Na$_2$SO$_4$ and concentrated. The residue was purified by flash column chromatography on silica gel (1-4% methanol/dichloroethane) to afford the desired product (20 mg, 72% yield). $^1$H NMR (400 MHz, DMSO-d6) δ: 7.60 (s, 1H), 6.34-6.30 (m, 1H), 6.27 (s, 1H), 6.12-6.07 (m, 1H), 6.01-5.99 (t, J=4 Hz, 1H), 5.69-5.65 (m, 1H), 4.26-4.22 (m, 1H), 4.07-4.04 (m, 3H), 3.96-3.92 (m, 1H), 3.80-3.76 (m, 1H), 3.53-3.51 (m, 4H), 3.19-3.13 (m, 1H), 2.45-2.30 (m, 4H), 2.16-2.09 (m, 1H), 1.08-1.03 (m, 2H), 0.87-0.80 (m, 2H). ESI-MS m/z: 428.4[M+H]$^+$.

Example 57

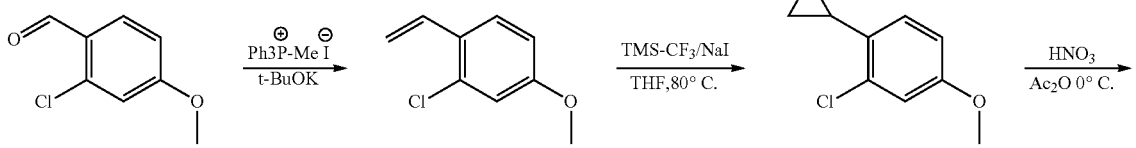

63-1     63-2     63-3

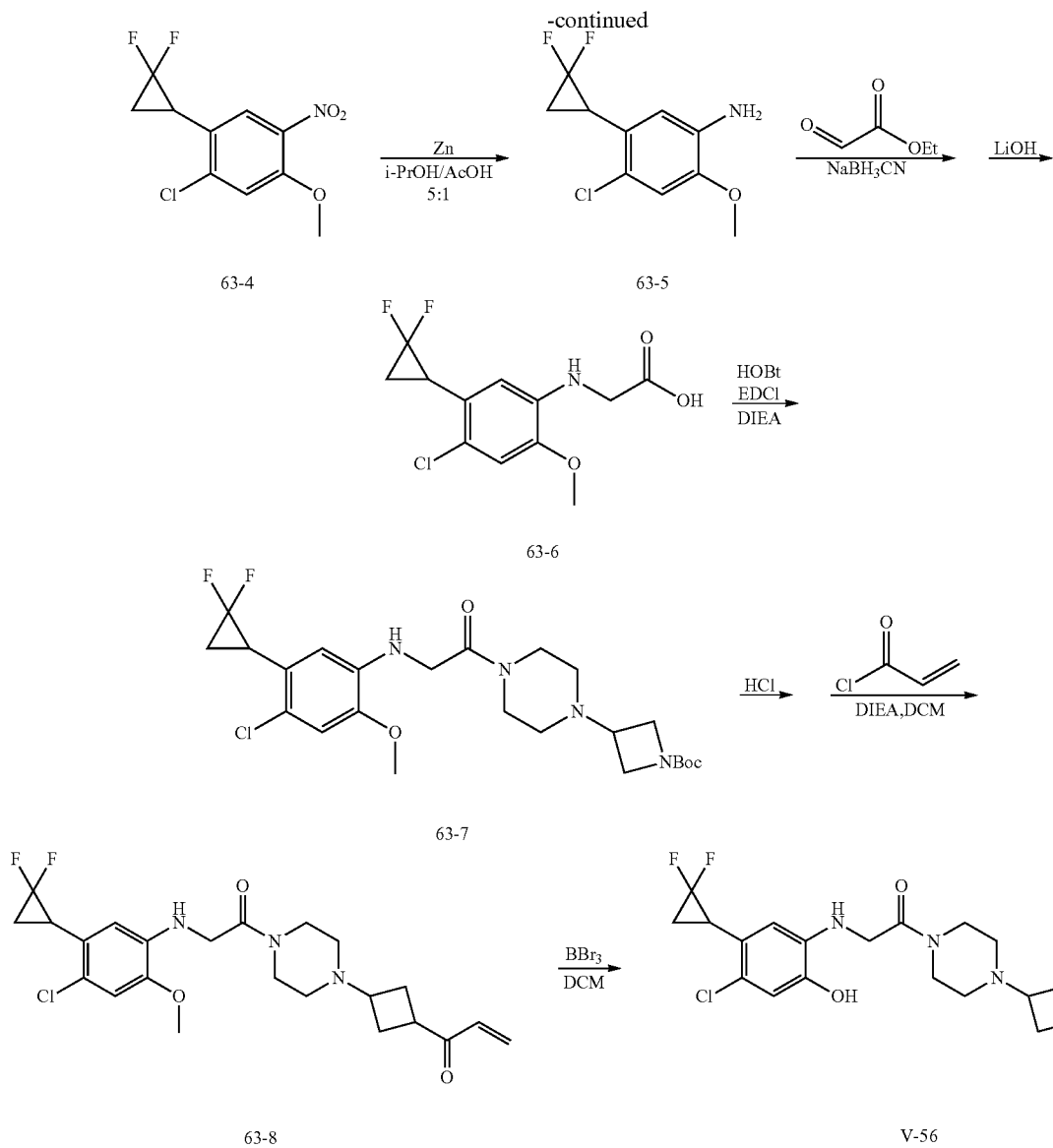

2-Chloro-4-methoxy-1-vinylbenzene

To a suspension of phosphonium salt (2.05 g, 5 mmol) in THF (50 mL), was added t-BuOK (0.84 g, 7.5 mmol). The mixture turned to yellow and was kept stirring at RT for 1 h. 2-Chloro-4-methoxybenzaldehyde (0.85 g, 5 mmol) was added to the mixture. The mixture was stirred for 24 h, diluted with sat. NaHCO3 and then extracted with hexane. Organic layer was dried over $Na_2SO_4$, filtered and concentrated in vacuo. The residue was purified by Isolera One (100% hexanes to afford the desired product (0.45 g, 53% yield). $^1$H NMR (CDCl$_3$, δ): 7.49 (d, J=6.8 Hz, 1H), 7.03 (dd, J=8.8, 14.0 Hz, 1H), 6.90 (d, J=2.0, 1H), 6.79 (dd, J=2.0, 6.8 Hz, 1H), 5.62 (d, J=14.0 Hz, 1H), 5.26 (d, J=8.8 Hz, 1H), 3.80 (s, 3H).

2-Chloro-1-(2,2-difluorocyclopropyl)-4-methoxybenzene

The solution of 2-chloro-4-methoxy-1-vinylbenzene (290 mg, 1.72 mmol) in dry THF (4 mL) was degassed, and then TMS-CF$_3$ and NaI were added. The mixture was stirred at 80° C. overnight. TLC (100% Hexane) showed the reaction as complete. The mixture was diluted with hexane (20 mL). The inorganic salt was removed by filtration. The filtrate was concentrate in vacuo. The residue was purified via Isolera One (Hexane=100%).

1-Chloro-2-(2,2-difluorocyclopropyl)-5-methoxy-4-nitrobenzene

To a solution of 2-chloro-1-(2,2-difluorocyclopropyl)-4-methoxybenzene (328 mg, 1.5 mmol) in Ac$_2$O (2 mL), was added HNO$_3$ (10 drops) at 0° C. The mixture was stirred from 0° C. to rt. Ac$_2$O was removed in vacuo. The residue was diluted with DCM and washed with water. The organic layer was dried over $Na_2SO_4$. The solvent was removed in vacuo. The residue was purified via Isolera One (EtOAc/Hexane=0-15%) to afford the desired product. $^1$H NMR (CDCl$_3$, δ): 7.77 (s, 1H), 7.16 (s, 1H), 3.98 (s, 3H), 2.78-2.90 (m, 1H), 1.90-1.98 (m, 1H), 1.60-1.68 (m, 1H). ESI-MS m/z: 264.1[M+H]$^+$.

4-Chloro-5-(2,2-difluorocyclopropyl)-2-methoxyaniline

The above obtained 1-chloro-2-(2,2-difluorocyclopropyl)-5-methoxy-4-nitrobenzene was dissolved in 10 mL of co-solvent of AcOH/1-PrOH (1:5). Zn dust was added to the mixture. The mixture was stirred at 60° C. for 30 min. The solvent was removed in vacuo. The residue was diluted was DCM and the inorganic salt was removed by filtration. The filtrate was concentrated to give crude product which was used in next step without further purification.

1-(3-(4-((4-chloro-5-(2,2-difluorocyclopropyl)-2-hydroxyphenyl)glycyl)piperazin-1-yl)azetidin-1-yl)prop-2-en-1-one (V-56)

The title compound was prepared from 4-chloro-5-(2,2-difluorocyclopropyl)-2-methoxyaniline in 6 steps according to the procedure described in Example 41.

$^1$H NMR (CDCl$_3$, δ): 9.90 (s, 1H), 6.73 (s, 1H), 6.40 (s, 1H), 6.30 (dd, J=8.4, 13.6 Hz, 1H), 6.10 (dd, J=1.6, 12.0 Hz, 1H), 5.66 (dd, J=1.6, 8.4 Hz, 1H), 5.18 (t, J=3.2, 3.6 Hz, 1H), 4.24 (t, J=6.0, 6.8 Hz, 1H), 4.03-4.08 (m, 1H), 3.86-3.97 (m, 3H), 3.74-3.80 (m, 1H), 3.52 (br. s, 4H), 3.13-3.20 (m, 1H), 2.77-2.87 (m, 1H), 2.25-2.43 (m, 4H), 1.87-1.97 (m, 2H). ESI-MS m/z: 455.2[M+H]$^+$.

Example 58

Biochemical Assay of the Compounds

Test compounds were prepared as 10 mM stock solutions in DMSO (Fisher cat#BP-231-100). KRAS G12CI-169, his-tagged protein, GDP-loaded was diluted to 2 μm in buffer (20 mM Hepes, 150 mM NaCl, 1 mM MgCl$_2$). Compounds were tested for activity as follows:

Compounds were diluted to 50× final test concentration in DMSO in 96-well storage plates. Compound stock solutions were vortexed before use and observed carefully for any sign of precipitation. Dilutions were as follow:

For 100 μM final compound concentration, compounds were diluted to 5000 μM (5 μl 10 mM compound stock+5 μl DMSO and mixed well by pipetting.

For 30 μM final compound concentration, compounds were diluted to 1500 μM (3 μl 10 mM compound stock+17 μl DMSO) and mixed well by pipetting.

For 10 μM final compound concentration, compounds were diluted to 500 μM (2 μl 10 mM compound stock+38 μl DMSO) and mixed well by pipetting.

49 μl of the stock protein solution was added to each well of a 96-well PCR plate (Fisher cat#1423027). 1 μl of the diluted 50× compounds were added to appropriate wells in the PCR plate using 12-channel pipettor. Reactions were mixed carefully and thoroughly by pipetting up/down with a 200 μl multi-channel pipettor. The plate was sealed well with aluminum plate seal, and stored in a drawer at room temperature for 2 hrs or 24 hrs. 5 μl of 2% formic acid (Fisher cat#A117) in DI H$_2$O was then added to each well followed by mixing with a pipette. The plate was then resealed with aluminum seal and stored on dry ice until analyzed as described below.

The above described assays were analyzed by mass spectrometry according to the following procedure:

The MS instrument is set to positive polarity, 2 GHz resolution, and low mass (1700) mode and allowed to equilibrate for 30 minutes. The instrument is then calibrated, switched to acquisition mode and the appropriate method loaded.

After another 30 minute equilibration time, a blank batch (i.e., buffer) is run to ensure equipment is operating properly. The samples are thawed at 37° C. for 10 minutes, briefly centrifuged, and transfer to the bench top. Wells A1 and H12 are spiked with 1 uL 500 uM internal standard peptide, and the plates centrifuged at 2000×g for 5 minutes. The method is then run and masses of each individual well recorded.

The masses (for which integration data is desired) for each well are pasted into the platemap and exported from the analysis. Masses for the internal standards are exported as well. The data at 50 ppm is extracted for the +19 charge state, and identity of well A1 is assigned using the internal standard spike and integrated. Peak data is exported as a TOF list and the above steps are repeated individually, for the +20, 21, 22, 23, 24, and 25 charge states.

Other in vitro analyses are as follows:

Inhibition of Cell Growth:

The ability of the subject compounds to inhibit Ras-mediated cell growth is assessed and demonstrated as follows. Cells expressing a wildtype or a mutant Ras are plated in white, clear bottom 96 well plates at a density of 5,000 cells per well. Cells are allowed to attach for about 2 hours after plating before a compound disclosed herein is added. After certain hours (e.g., 24 hours, 48 hours, or 72 hours of cell growth), cell proliferation is determined by measuring total ATP content using the Cell Titer Glo reagent (Promega) according to manufacturer's instructions. Proliferation EC50s is determined by analyzing 8 point compound dose responses at half-log intervals decreasing from 100 μM.

Inhibition of Ras-Mediated Signaling Transduction:

The ability of the compounds disclosed herein in inhibiting Ras-mediated signaling is assessed and demonstrated as follows. Cells expressing wild type or a mutant Ras (such as G12C, G12V, or G12A) are treated with or without (control cells) a subject compound. Inhibition of Ras signaling by one or more subject compounds is demonstrated by a decrease in the steady-state level of phosphorylated MEK, and/or Raf binding in cells treated with the one or more of the subject compounds as compared to the control cells.

Inhibition of Ras-Mediated Signaling Transduction:

The ability of the compounds disclosed herein in inhibiting Ras-mediated signaling is assessed and demonstrated as follows. Cells expressing wild type or a mutant Ras (such as G12C, G12V, or G12A) are treated with or without (control cells) a subject compound. Inhibition of Ras signaling by one or more subject compounds is demonstrated by percentage binding of compound to the G12C mutated Ras protein in cells treated with the one or more of the subject compounds as compared to the control cells.

Inhibition of Ras-Mediated Signaling Transduction:

The ability of the compounds disclosed herein in inhibiting Ras-mediated signaling is assessed and demonstrated as follows. Cells expressing wild type or a mutant Ras (such as G12C, G12V, or G12A) are treated with or without (control cells) a subject compound. Inhibition of Ras signaling by one or more subject compounds is demonstrated by a decrease in binding of Ras complex to downstream signaling molecules (for example Raf) in cells treated with the one or more of the subject compounds as compared to the control cells.

The compounds in Tables 1-6 were tested according to the above procedures. Results for the compounds of Tables 5 and 6 are presented below. Each of the compounds in Tables 5 and 6 were found to covalently bind to KRAS G12C to the extent of at least about 5% (i.e., at least about 5% of the protein present in the well was found to be covalently bound to test compound).

TABLE 7a

Activity of Representative Compounds*

| No. | Binding % | No. | Binding % | No. | Binding % | No. | Binding % |
|---|---|---|---|---|---|---|---|
| V-1 | ++++ | V-2 | +++ | V-3 | ++++ | V-4 | +++ |
| V-5 | + | V-6 | + | V-7 | ++ | V-8 | ++ |
| V-9 | + | V-10 | + | V-11 | ++++ | V-12 | +++ |
| V-13 | ++ | V-14 | +++ | V-15 | + | V-16 | + |
| V-17 | ++ | V-18 | ++++ | V-19 | +++ | V-20 | ++ |
| V-21 | + | V-22 | + | V-23 | + | V-24 | + |
| V-25 | + | V-26 | + | V-27 | ++ | V-28 | +++ |
| V-29 | + | V-30 | + | V-31 | ++++ | V-32 | ++++ |
| V-33 | + | V-34 | + | V-35 | ++++ | V-36 | ++++ |
| V-37 | ++ | V-38 | + | V-39 | +++ | V-40 | ++++ |
| V-41 | ++++ | V-42 | + | V-43 | ++++ | V-44 | + |
| V-45 | ++++ | V-46 | + | V-47 | + | V-48 | ++ |
| V-49 | ++++ | N/A | N/A | N/A | N/A | N/A | N/A |

*Binding activity determined at 24 hrs.
+ indicates binding activity from 5% to 15%
++ indicates binding activity greater than 15% and up to 25%
+++ indicates binding activity greater than 25% and up to 50%
++++ indicates binding activity greater than 50%

TABLE 7b

Activity of Representative Compounds*

| No. | Binding % | No. | Binding % | No. | Binding % | No. | Binding % |
|---|---|---|---|---|---|---|---|
| V-50 | ++ | V-51 | ++ | V-52 | + | V-53 | ++ |
| V-54 | ++ | V-55 | ++ | V-56 | ++ | V-57 | ++ |
| V-58 | + | V-59 | ++ | V-60 | ++ | V-61 | + |
| V-62 | + | V-63 | ++ | V-64 | ++ | V-65 | + |
| V-66 | + | V-67 | ++ | V-68 | ++ | V-69 | ++ |
| V-70 | ++ | V-71 | + | V-72 | + | V-73 | + |
| V-74 | + | V-75 | + | V-76 | N/A | N/A | N/A |

*Binding activity determined at 2 hrs.
+ indicates binding activity from 5% to 20%
++ indicates binding activity greater than 20%

TABLE 8a

Activity of Representative Compounds*

| No. | Binding % | No. | Binding % | No. | Binding % | No. | Binding % |
|---|---|---|---|---|---|---|---|
| VI-1 | + | VI-2 | ++ | VI-3 | ++++ | VI-4 | ++ |
| VI-5 | ++++ | VI-6 | ++ | VI-7 | +++ | VI-8 | + |
| VI-9 | + | VI-10 | + | VI-11 | + | VI-12 | +++ |
| VI-13 | + | VI-14 | + | VI-15 | + | VI-16 | + |
| VI-17 | ++++ | VI-18 | + | VI-19 | + | VI-20 | + |
| VI-21 | ++ | VI-22 | + | VI-23 | +++ | VI-24 | ++++ |
| VI-25 | +++ | VI-26 | ++ | VI-27 | +++ | VI-28 | ++ |
| VI-29 | +++ | VI-30 | ++ | VI-31 | + | VI-32 | ++++ |
| VI-33 | + | VI-34 | +++ | VI-35 | ++ | VI-36 | + |

*Binding activity determined at 24 hrs.
+ indicates binding activity from 5% to 10%
++ indicates binding activity greater than 10% and up to 20%
+++ indicates binding activity greater than 20% and up to 30%
++++ indicates binding activity greater than 30%

TABLE 8b

Activity of Representative Compounds*

| No. | Binding % | No. | Binding % | No. | Binding % | No. | Binding % |
|---|---|---|---|---|---|---|---|
| VI-37 | ++ | VI-38 | ++ | VI-39 | ++ | VI-40 | + |
| VI-41 | + | VI-42 | + | VI-43 | + | N/A | N/A |

*Binding activity determined at 2 hrs.
+ indicates binding activity from 5% to 20%
++ indicates binding activity greater than 20%

Example 59

Assessing Inhibition of Cell Proliferation by Compound I-189

Figure 4:
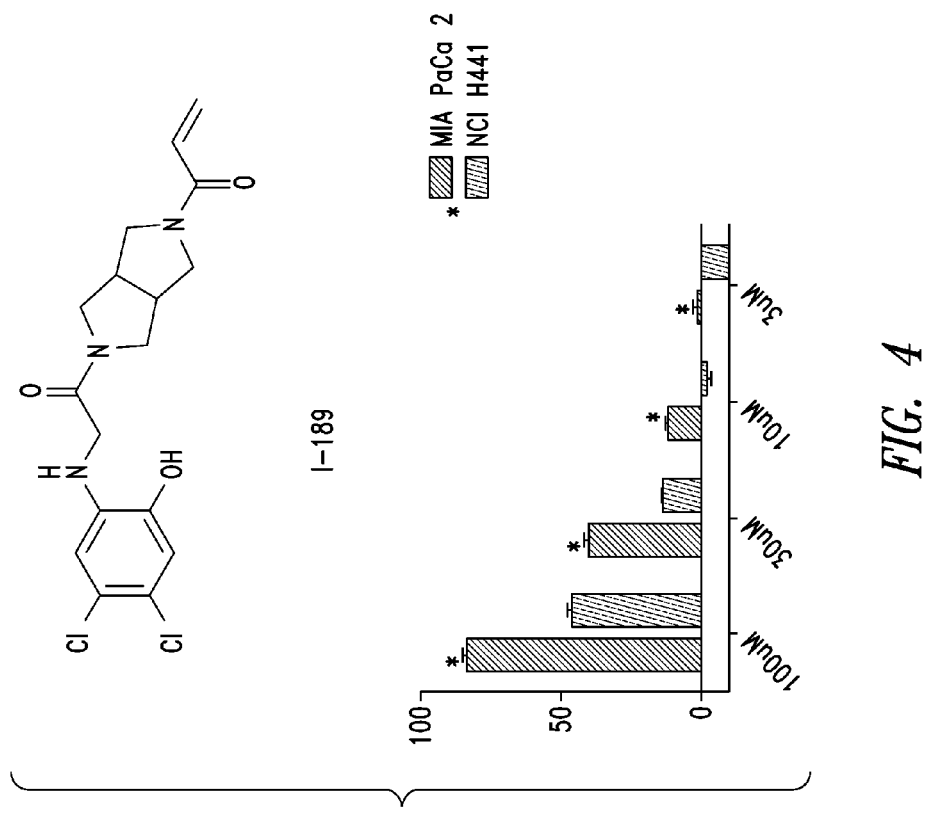
FIG. 4 shows the results of cell potency assay for the compound I-189.

Two cancer cell lines, NCI H441 (human lung adenenocarcinoma cells comprising a G12V mutation) and MIA paca-2 (human pancreatic carcinoma comprising a G12C mutation) were used in this experiment. Both the cell lines were treated with compound I-189 at a concentration of 100 μM, 30 μM, 10 μM and 3 μM and cell potency was measured as described in Example 1. The results of this experiment are shown in FIG. 4.

Example 60

Comparison of Cell Proliferation Inhibition by Compound I-189, I-92 and I-94

Figure 5:
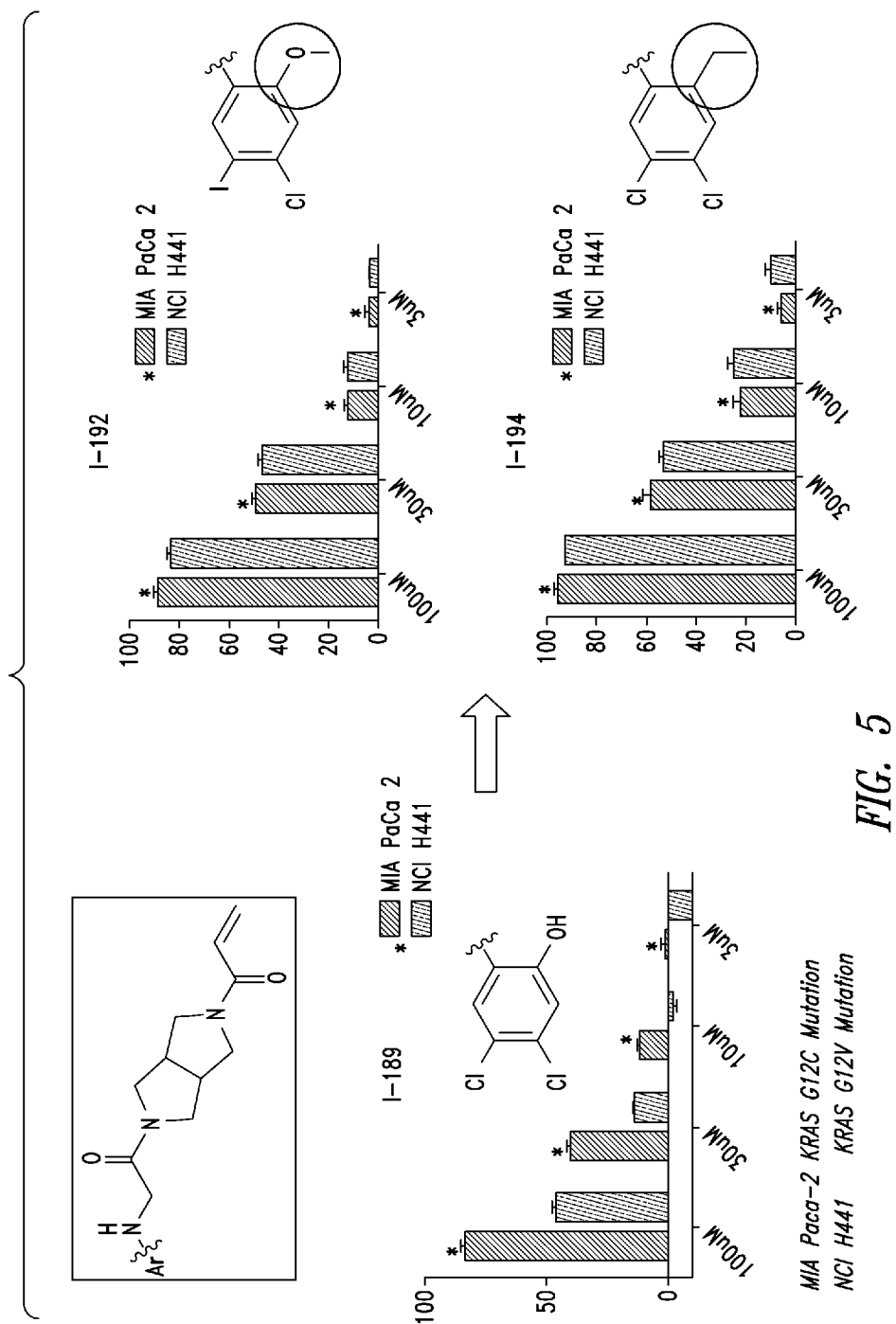
FIG. 5 shows the results of comparison of cell potency assay for the compound I-189, I-92 and I-94.

The results of these SAR studies are shown in FIG. 5. Two cancer cell lines, NCI H441 (human lung adenenocarcinoma cells comprising a G12V mutation) and MIA paca-2 (human pancreatic carcinoma comprising a G12C mutation) were used in this experiment. Both the cell lines were treated with compound I-189 at a concentration of 100 μM, 30 μM, 10 μM and 3 μM and cell potency was measured. Similar experiments were performed with compounds I-192 and I-94.

Example 61

Comparison of Cell Proliferation Inhibition by Compound I-92 and I-95

Figure 6:
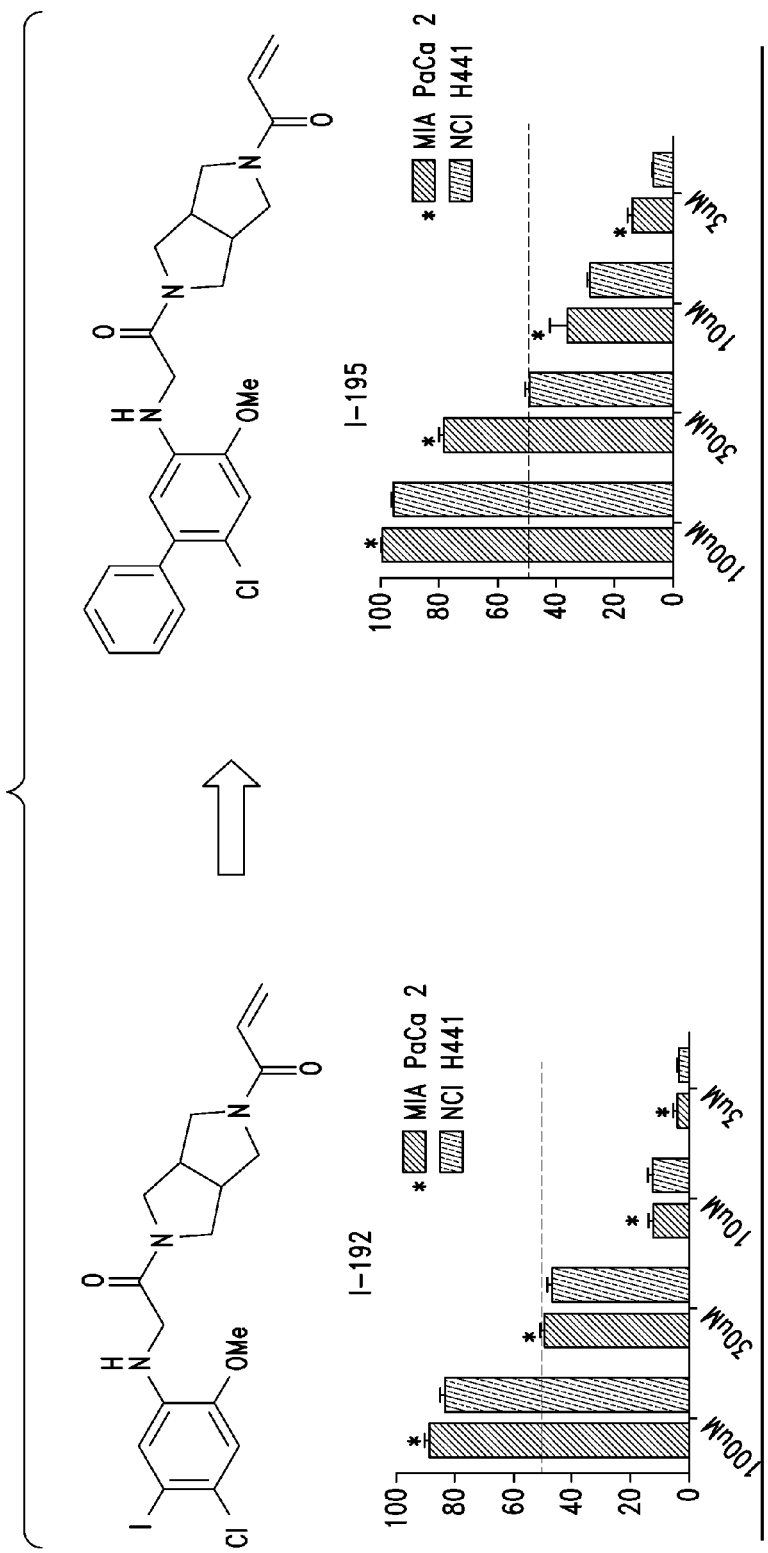
FIG. 6 shows the results of comparison of cell potency assay for the compound I-92 and I-95.

The results of these studies are shown in FIG. 6. Two cancer cell lines, NCI H441 (human lung adenenocarcinoma cells comprising a G12V mutation) and MIA paca-2 (human pancreatic carcinoma comprising a G12C mutation) were used in this experiment. Both the cell lines were treated with compound I-192 at a concentration of 100 μM, 30 μM, 10 μM and 3 μM and cell potency was measured. Similar experiments were performed with compound I-95.

Example 62

Comparison of Cell Proliferation Inhibition by Compound I-66, I-45 and I-91

Figure 7:
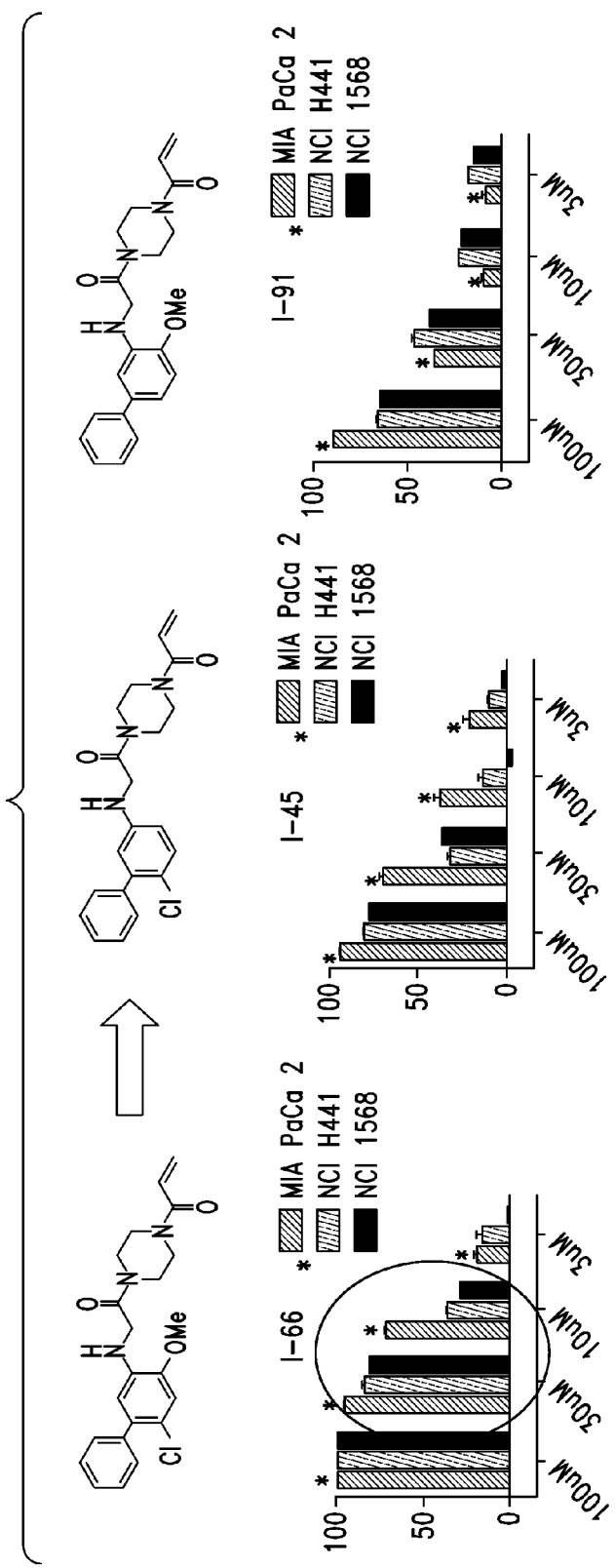
FIG. 7 shows the results of comparison of cell potency assay for the compound I-66, I-45 and I-91.

The results of these studies are shown in FIG. 7. Two cancer cell lines, NCI H441 (human lung adenenocarcinoma cells comprising a G12V mutation) and MIA pancreatic carcinoma comprising a G12C mutation) were used in this experiment. Both the cell lines were treated with compound I-66 at a concentration of 100 μM, 30 μM, 10 μM and 3 µM and cell potency was measured. Similar experiments were performed with compounds I-45 and I-91.

Example 63

Comparison of Cell Proliferation Inhibition by Compound I-47, I-42 and I-60

Figure 8:
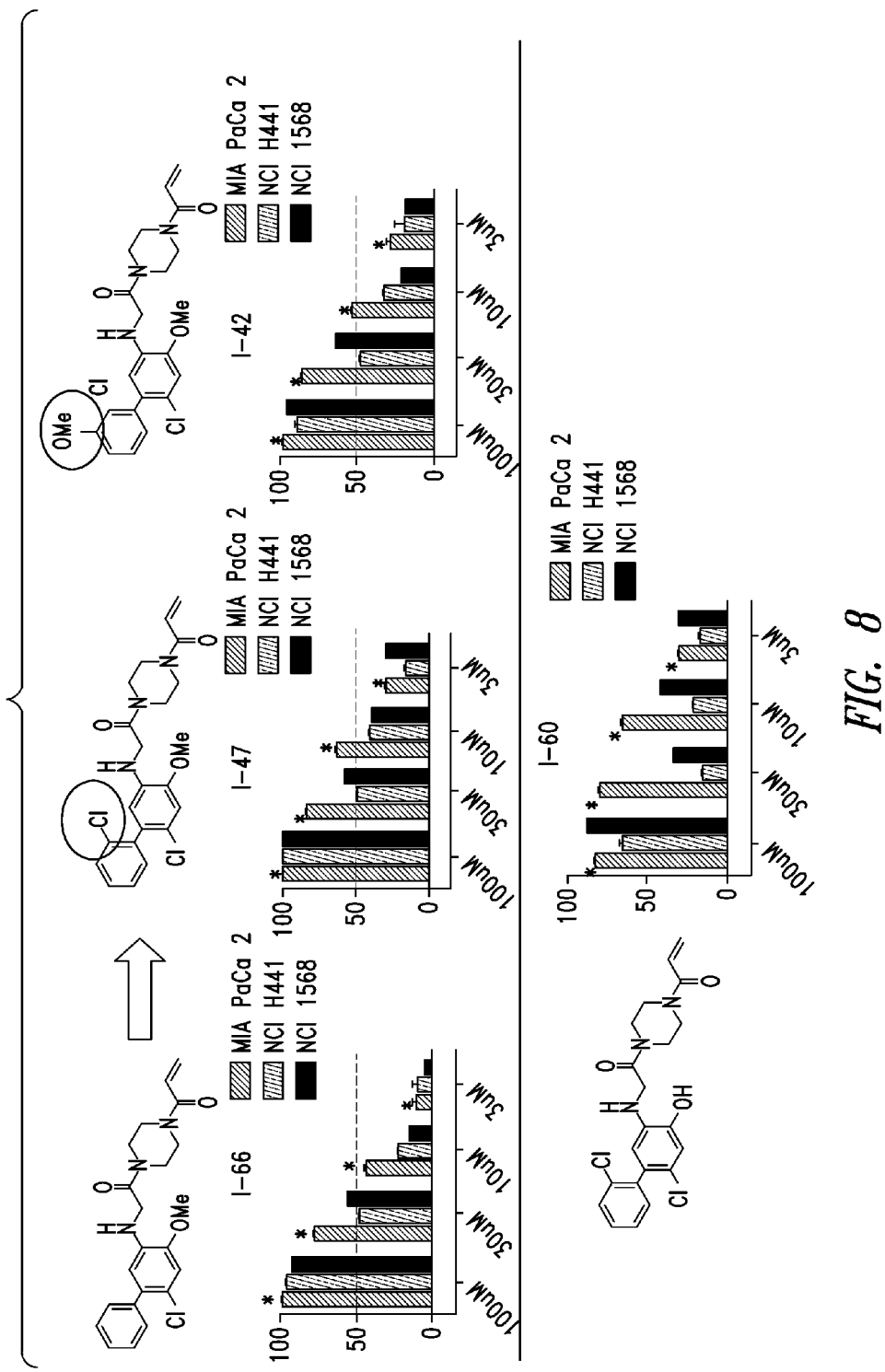
FIG. 8 shows the results of comparison of cell potency assay for the compound I-47, I-42 and I-60.

The results of these studies are shown in FIG. 8. Three cell lines, NCI H441 (human lung adenenocarcinoma cells), NCI 1568 (lung adenenocarcinoma cells) and MIA paca-2 (human pancreatic carcinoma) were used in this experiment. Both the cell lines were treated with compound I-66 at a concentration of 100 µM, 30 µM, 10 µM and 3 µM and cell potency was measured. Similar experiments were performed with compounds I-47, I-42 and I-60.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, including but not limited to U.S. patent application No. 61/852,123, filed Mar. 15, 2013 and U.S. patent application No. 61/889,480, filed Oct. 10, 2013, are incorporated herein by reference, in their entirety. Aspects of the embodiments can be modified, if necessary to employ concepts of the various patents, applications and publications to provide yet further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

From the foregoing it will be appreciated that, although specific embodiments of the invention have been described herein for purposes of illustration, various modifications may be made without deviating from the spirit and scope of the invention. Accordingly, the invention is not limited except as by the appended claims.

The invention claimed is:

1. A compound having the following structure (V):

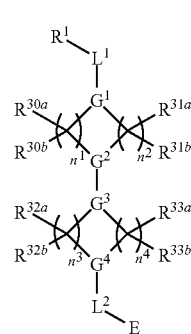

(V)

or a pharmaceutically acceptable salt, tautomer, or stereoisomer thereof, wherein:
$R^1$ is aryl;
$R^{30a}$ and $R^{30b}$ are, at each occurrence, independently H, —OH, —NH$_2$, —CO$_2$H, cyano, cyanoalkyl, $C_1$-$C_6$alkyl, $C_3$-$C_8$cycloalkyl, hydroxylalkyl, aminoalkyl, carboxylalkyl or aminocarbonyl; or $R^{30a}$ and $R^{30b}$ join to form a carbocyclic or heterocyclic ring; or $R^{30a}$ is H, —OH, —NH$_2$, —CO$_2$H, cyano, $C_1$-$C_6$alkyl, $C_3$-$C_8$cycloalkyl, hydroxylalkyl, aminoalkyl, carboxylalkyl or aminocarbonyl and $R^{30b}$ joins with $R^{31b}$ to form a carbocyclic or heterocyclic ring;
$R^{31a}$ and $R^{31b}$ are, at each occurrence, independently H, —OH, —NH$_2$, —CO$_2$H, cyano, cyanoalkyl, $C_1$-$C_6$alkyl, $C_3$-$C_8$cycloalkyl, hydroxylalkyl, aminoalkyl, carboxylalkyl or aminocarbonyl; or $R^{31a}$ and $R^{31b}$ join to form a carbocyclic or heterocyclic ring; or $R^{31a}$ is H, —OH, —NH$_2$, —CO$_2$H, cyano, $C_1$-$C_6$alkyl, $C_3$-$C_8$cycloalkyl, hydroxylalkyl, aminoalkyl, carboxylalkyl or aminocarbonyl and $R^{31b}$ joins with $R^{30}$ b to form a carbocyclic or heterocyclic ring;
$R^{32a}$ and $R^{32b}$ are, at each occurrence, independently H, —OH, —NH$_2$, —CO$_2$H, cyano, cyanoalkyl, $C_1$-$C_6$alkyl, $C_3$-$C_8$cycloalkyl, hydroxylalkyl, aminoalkyl, carboxylalkyl or aminocarbonyl; or $R^{32a}$ and $R^{32b}$ join to form a carbocyclic or heterocyclic ring; or $R^{32a}$ is H, —OH, —NH$_2$, —CO$_2$H, cyano, $C_1$-$C_6$alkyl, $C_3$-$C_8$cycloalkyl, hydroxylalkyl, aminoalkyl, carboxylalkyl or aminocarbonyl and $R^{32b}$ joins with $R^{33b}$ to form a carbocyclic or heterocyclic ring;
$R^{33a}$ and $R^{33b}$ are, at each occurrence, independently H, —OH, —NH$_2$, —CO$_2$H, cyano, cyanoalkyl, $C_1$-$C_6$alkyl, $C_3$-$C_8$cycloalkyl, hydroxylalkyl, aminoalkyl, carboxylalkyl or aminocarbonyl; or $R^{33a}$ and $R^{33b}$ join to form a carbocyclic or heterocyclic ring; or $R^{33a}$ is H, —OH, —NH$_2$, —CO$_2$H, cyano, $C_1$-$C_6$alkyl, $C_3$-$C_8$cycloalkyl, hydroxylalkyl, aminoalkyl, carboxylalkyl or aminocarbonyl and $R^{33b}$ joins with $R^{32b}$ to form a carbocyclic or heterocyclic ring;
$L^1$ heteroalkylene, heterocycloalkylene, heteroarylene, heteroalkylenecarbonyl, heterocycloalkylenecarbonyl or heteroarylenecarbonyl;
$L^2$ is a bond or alkylene;
$G^1$, $G^2$, $G^3$ and $G^4$ are each independently N or CR, where R is H, cyano, halo or $C_1$-$C_6$alkyl;
$n^1$, $n^2$, $n^3$ and $n^4$ are each independently 1, 2 or 3; and
E is an electrophilic moiety capable of forming a covalent bond with the cysteine residue at position 12 of a K-Ras, H-Ras or N-Ras G12C mutant protein.

2. The compound of claim 1, wherein the compound has the following structure (Vb):

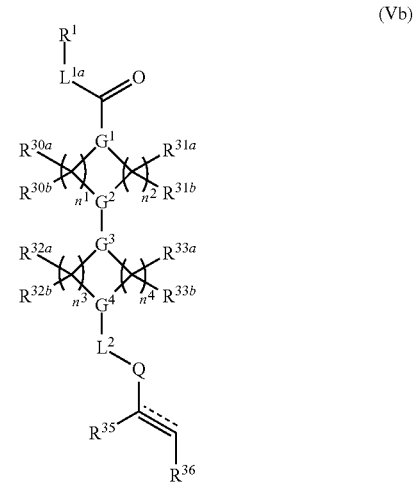

(Vb)

wherein:

L$^{1a}$ is heteroalkylene, heterocycloalkylene or heteroarylene;

Q is —C(=O)—, —NR$^{34}$C(=O)—, —S(=O)$_2$— or —NR$^{34}$S(=O)$_2$—;

R$^{34}$ is H, C$_1$-C$_6$alkyl or hydroxylalkyl;

≡ is a carbon-carbon double bond or a carbon-carbon triple bond; and

R$^{35}$ and R$^{36}$ are each independently H, cyano, C$_1$-C$_6$alkyl, aminoalkyl, alkylaminoalkyl, or hydroxylalkyl or R$^{35}$ and R$^{36}$ join to form a carbocyclic or heterocyclic ring when ≡ is a double bond; or R$^{35}$ is absent and R$^{36}$ is H, C$_1$-C$_6$alkyl, aminoalkyl, alkylaminoalkyl or hydroxylalkyl when ≡ is a triple bond.

3. The compound of claim 2, wherein the compound is selected from the group consisting of (Vc), (Vd), (Ve) and (Vf):

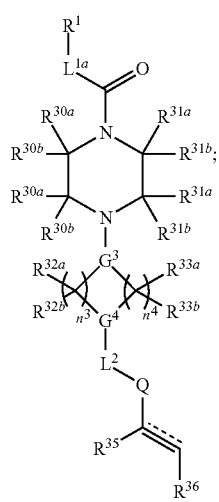

(Vc)

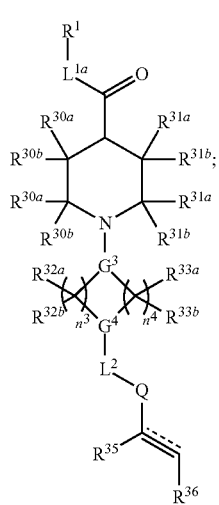

(Vd)

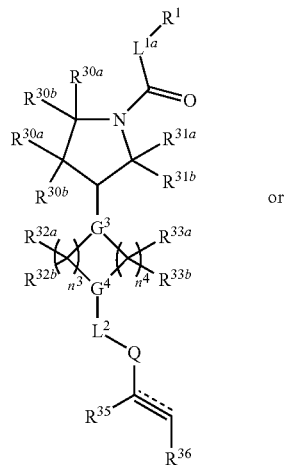

(Ve)

or

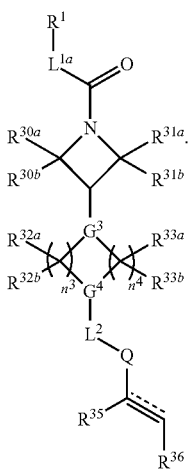

(Vf)

4. The compound of claim 2, wherein the compound is selected from the group consisting of (Vg), (Vh), (Vi) and (Vj):

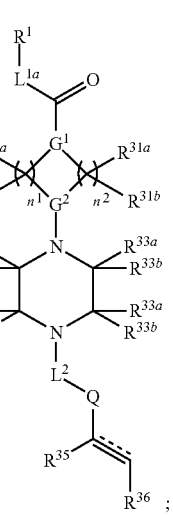

(Vg)

(Vh)
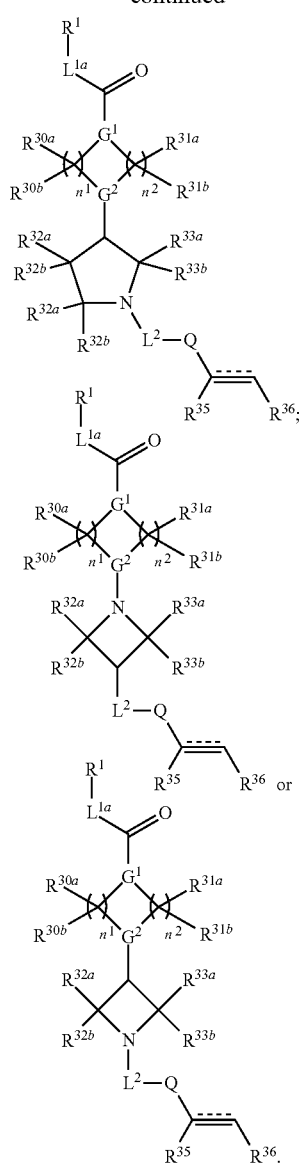
(Vi)
(Vj)
5. The compound of claim 2, wherein the compound is selected from the group consisting of (Vk), (Vl), (Vm), (Vn); (Vo) and (Vp):
(Vk)
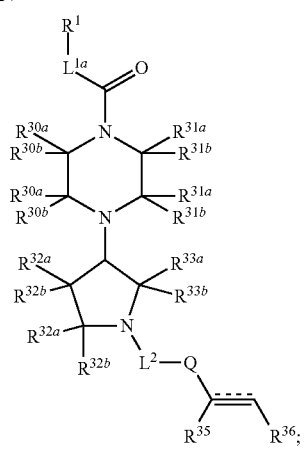
(Vl)
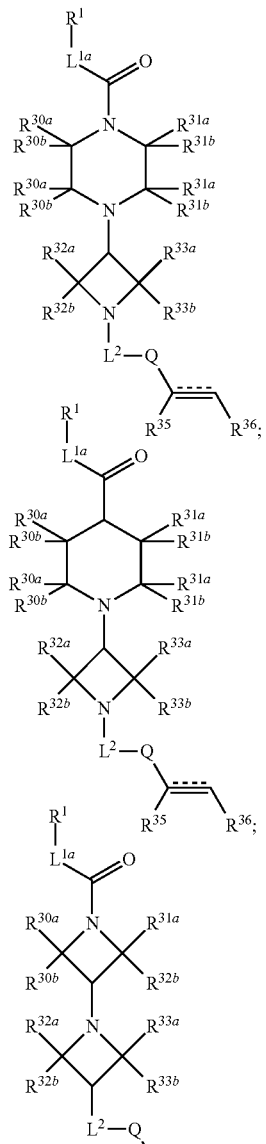
(Vm)
(Vn)
(Vo)
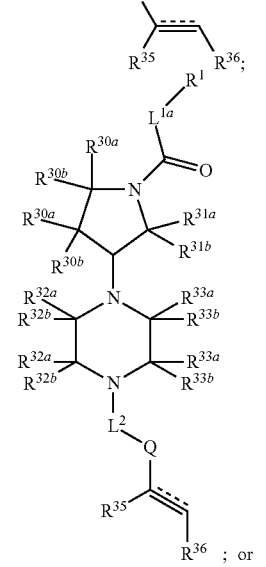
; or

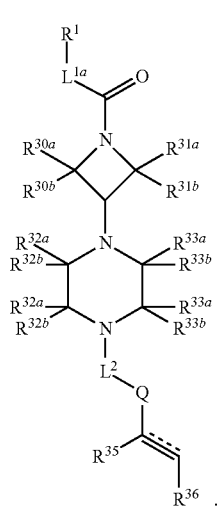

(Vp)

6. The compound of claim 1, wherein the aryl is naphthyl.

7. The compound of claim 1, wherein the aryl is phenyl.

8. The compound of claim 1, wherein the wherein the aryl is substituted with one or more substituents selected from the group consisting of halo, hydroxyl, cyano, aminocarbonyl, formyl, $C_1$-$C_6$alkyl, $C_1$-$C_6$alkylsulfonyl, $C_1$-$C_6$haloalkyl, $C_3$-$C_8$cycloalkyl, $C_1$-$C_6$alkoxy, $C_1$-$C_6$hydroxylalkyl, $C_1$-$C_6$alkoxyalkyl, $C_1$-$C_6$-aminoalkyl, aliphatic heterocyclyl, heteroaryl and aryl.

9. The compound of claim 8, wherein the substituents are selected from the group consisting of fluoro, chloro, bromo, iodo, hydroxyl, cyano, methyl, ethyl, isopropyl, methylsulfonyl, methoxy, aminocarbonyl, trifluoromethyl, 2,2,2-trifluorethyl, cyclobutyl, cyclopropyl and phenyl, wherein the cyclopropyl, cyclibutyl and phenyl are optionally substituted with one or more substituents selected from $C_1$-$C_6$alkyl, halo, hydroxyl and cyano.

10. The compound of claim 9, wherein the substituents are selected from the group consisting of fluoro, chloro, bromo, iodo, hydroxyl, methyl, ethyl, cyclobutyl and cyclopropyl, wherein the cyclopropyl and cyclobutyl are optionally substituted with one or more substituents selected from $C_1$-$C_6$alkyl, halo, hydroxyl and cyano.

11. The compound of claim 10, wherein the substituents are selected from the group consisting of fluoro, chloro, bromo, hydroxyl and cyclopropyl, wherein the cyclopropyl is optionally substituted with one or more substituents selected from $C_1$-$C_6$alkyl, halo, hydroxyl and cyano.

12. The compound of claim 1, wherein $R^1$ is selected from the group consisting of:

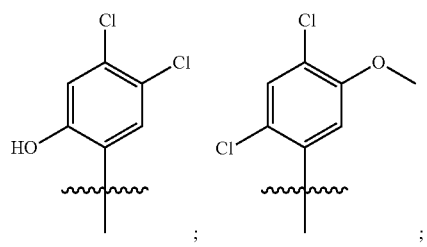

;

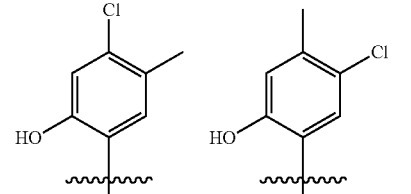

;

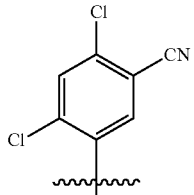

;

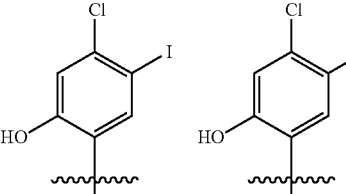

;

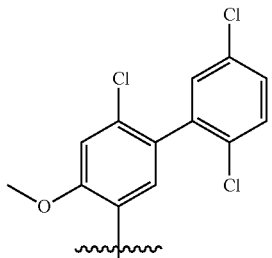

;

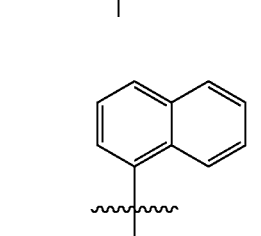

;

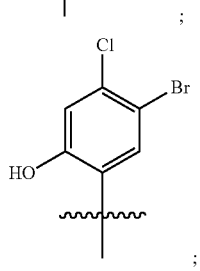

;

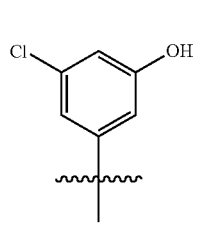

;

361
-continued
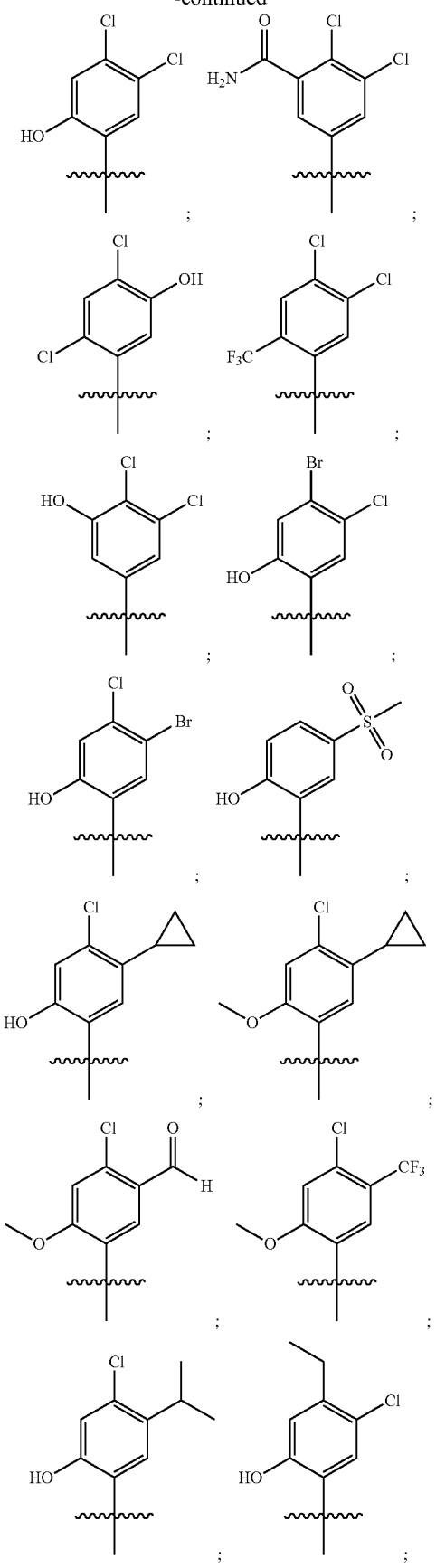
362
-continued
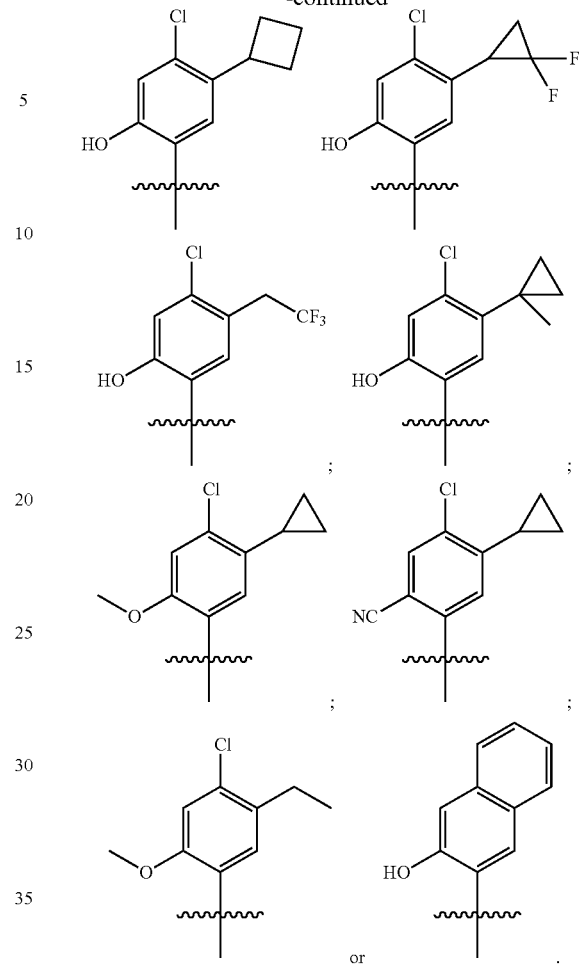
or
13. The compound of claim 2, wherein Q is —C(=O)—.
14. The compound of claim 2, wherein each of $R^{35}$ and $R^{36}$ are H.
15. The compound of claim 1, wherein E is selected from the group consisting of:
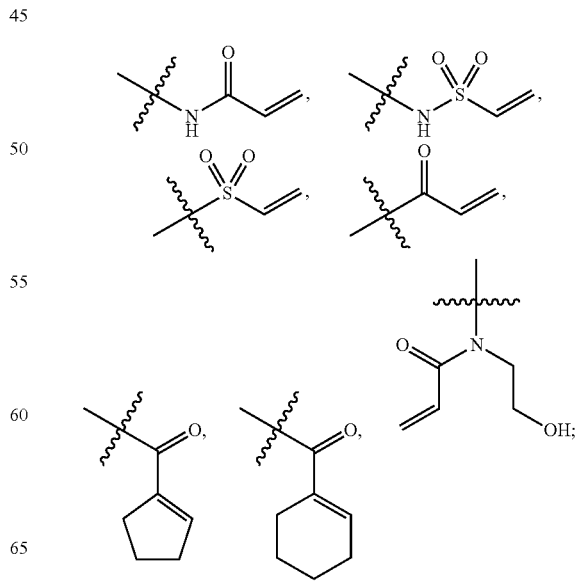

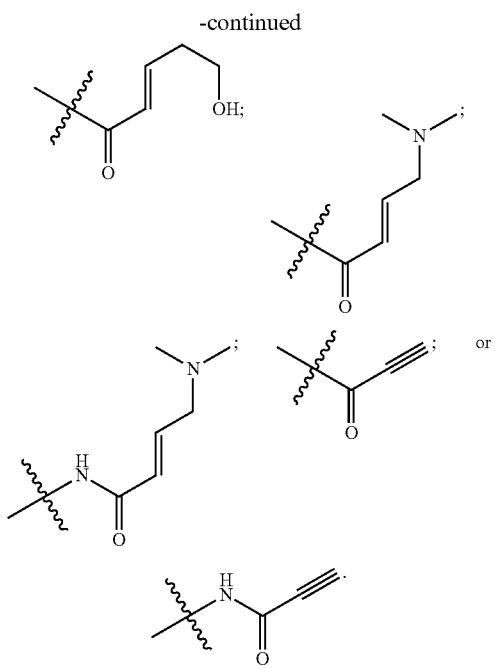

16. The compound of claim 2, wherein $L^{1a}$ is heteroalkylene or heterocycloalkylene.

17. The compound of claim 16, wherein $L^{1a}$ is aminoalkylene or thioalkylene.

18. The compound of claim 17, wherein $L^{1a}$ is selected from the group consisting of:

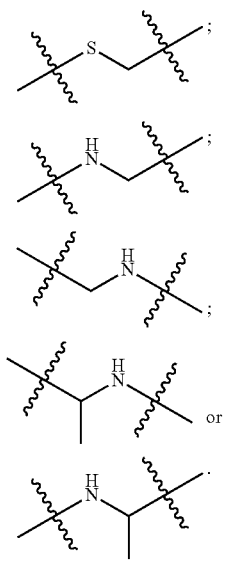

19. The compound of claim 1, wherein $L^2$ is a bond.

20. The compound of claim 1, wherein each of $R^{30a}$, $R^{30b}$, $R^{31a}$, $R^{31b}$, $R^{32a}$, $R^{32b}$, $R^{33a}$ and $R^{33b}$ is H.

21. The compound of claim 1, wherein at least one of $R^{30a}$, $R^{30b}$, $R^{31a}$, $R^{31b}$, $R^{32a}$, $R^{32b}$, $R^{33a}$ and $R^{33b}$ is hydroxylalkyl.

22. The compound of claim 1, wherein at least one of $R^{30a}$, $R^{30b}$, $R^{31a}$, $R^{31b}$, $R^{32a}$, $R^{32b}$, $R^{33a}$ and $R^{33b}$ is $C_1$-$C_6$alkyl.

23. The compound of claim 1, wherein the compound is selected from the group consisting of:

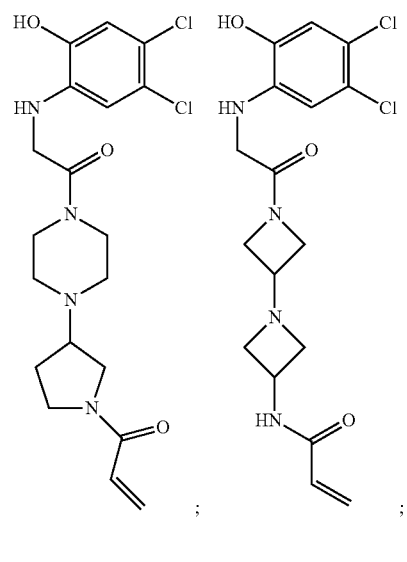

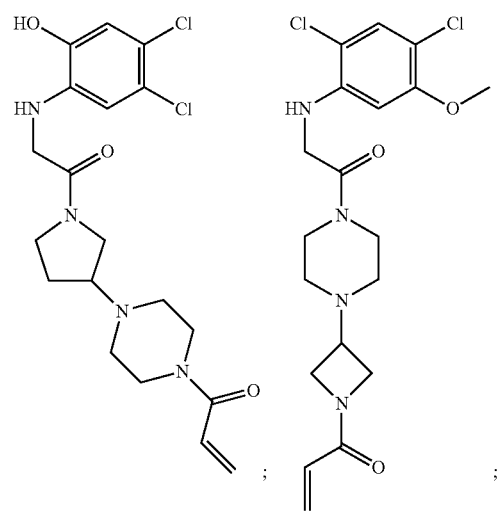

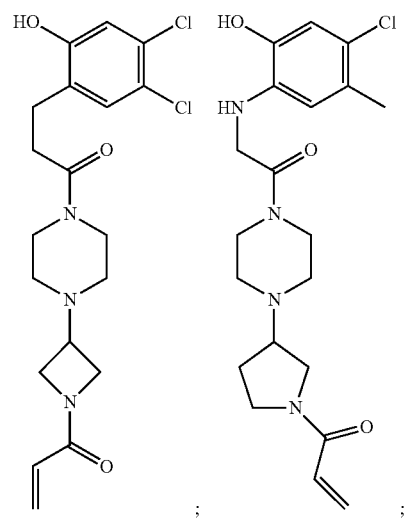

365
-continued
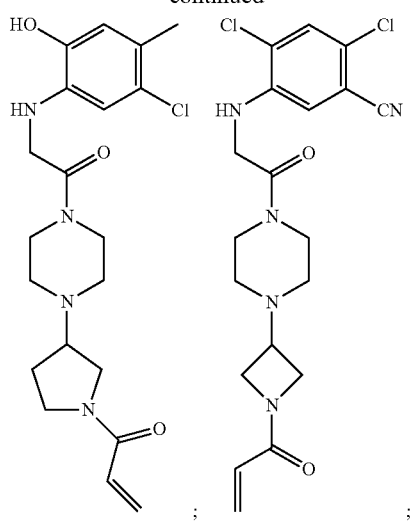
;
366
-continued
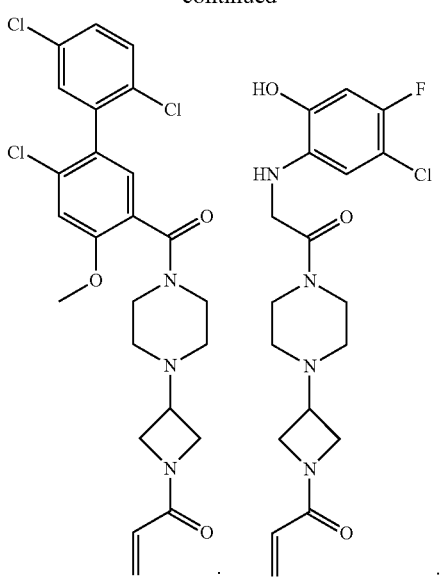
;
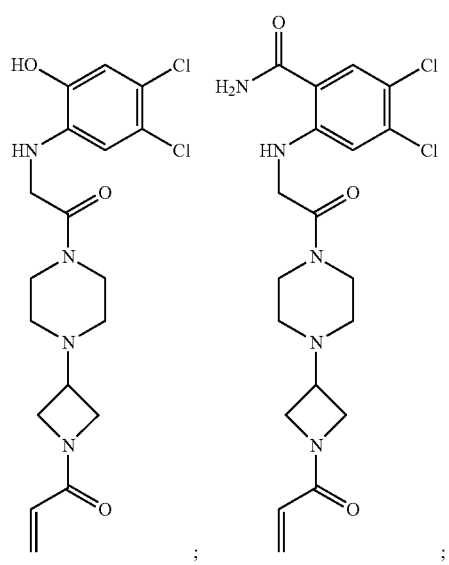
;
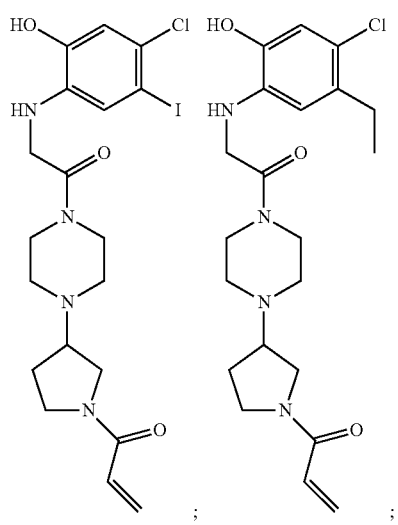
;

367
-continued
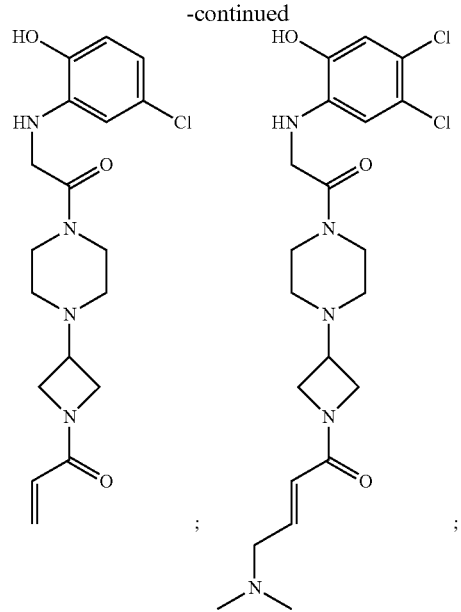
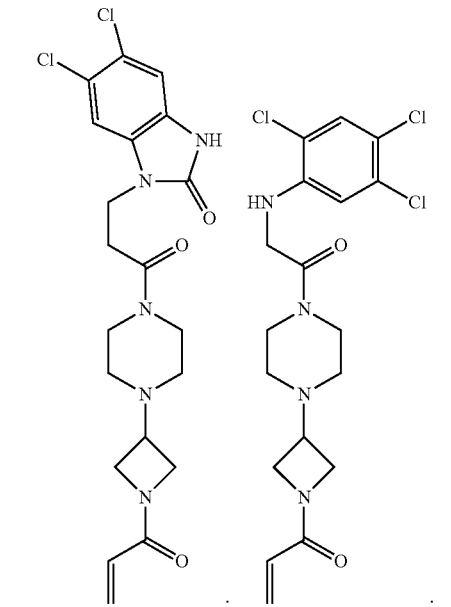
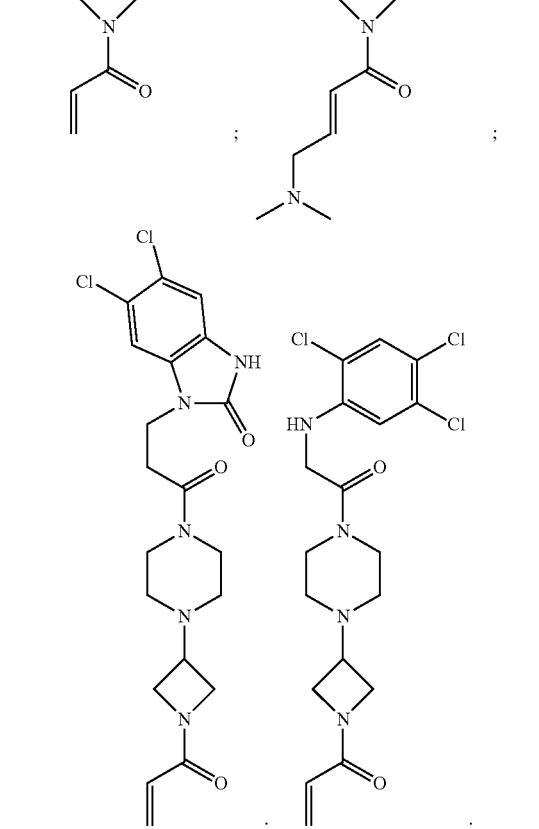
368
-continued
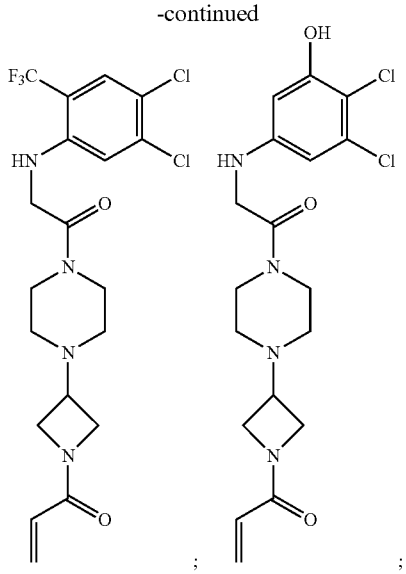
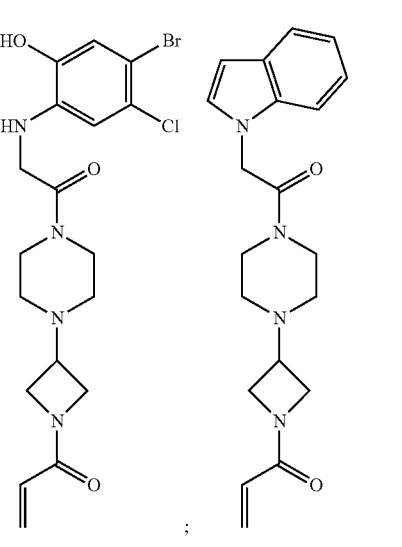
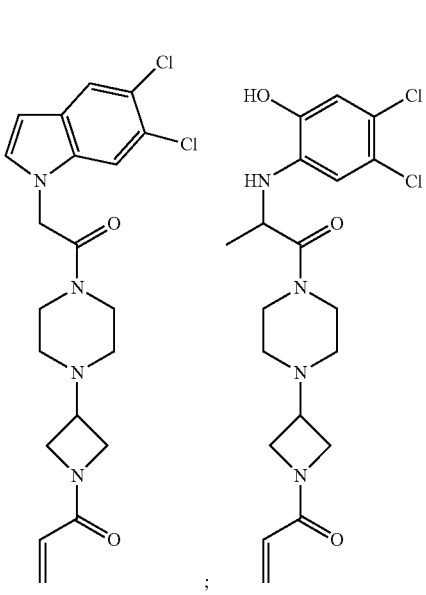

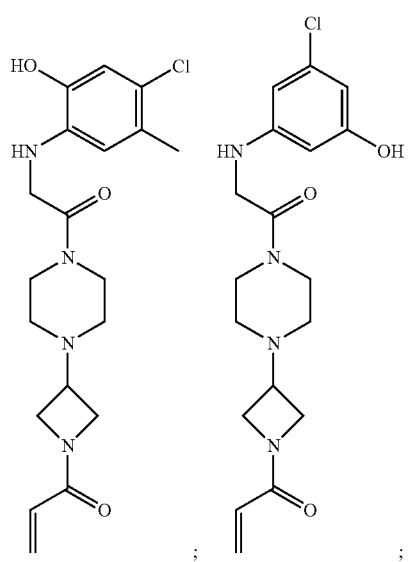
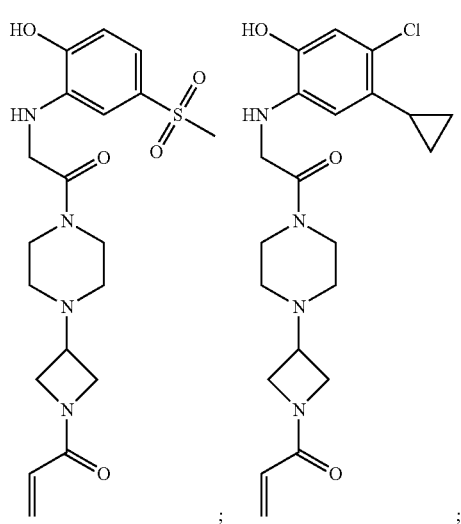
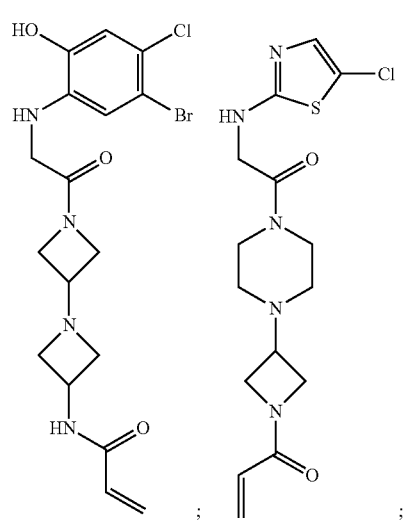
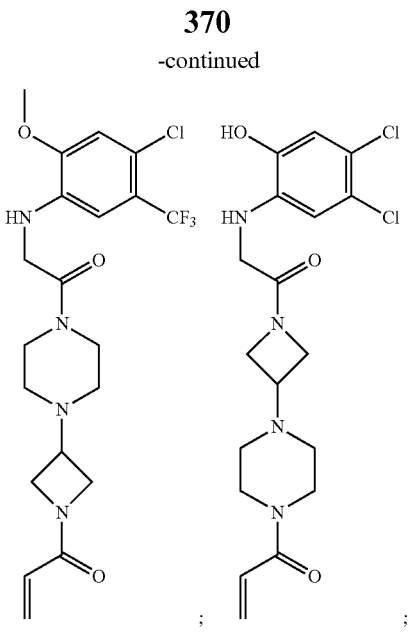
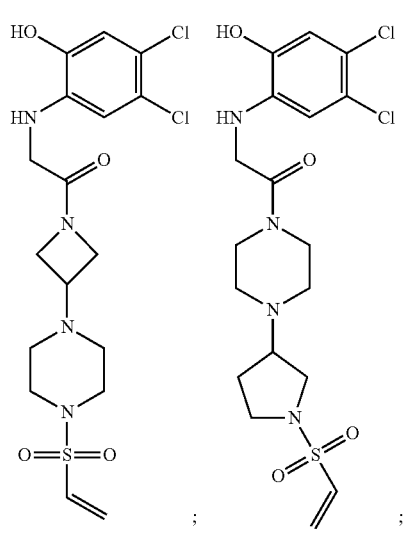
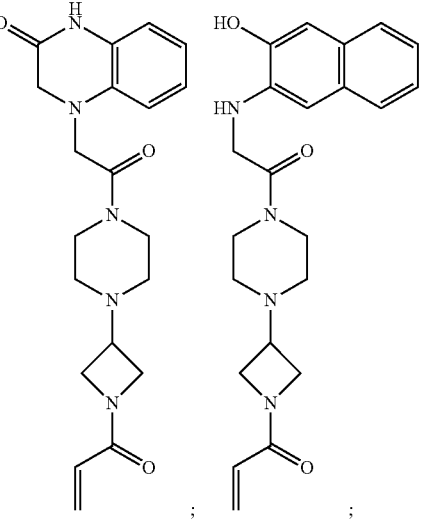

371
-continued
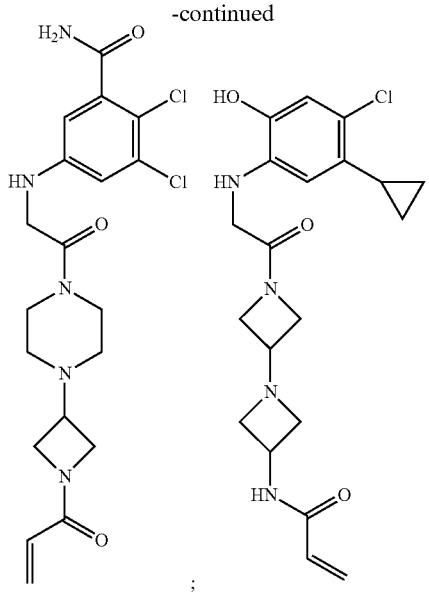
372
-continued
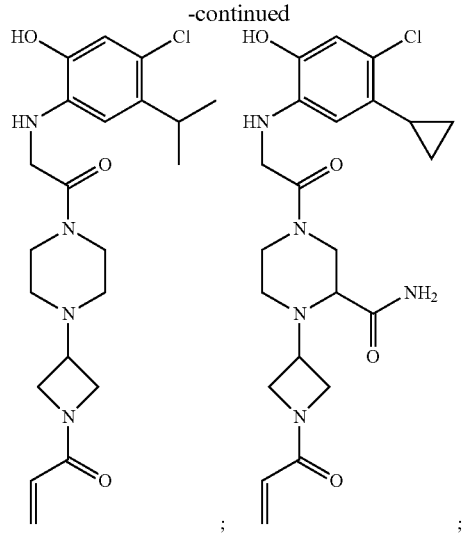
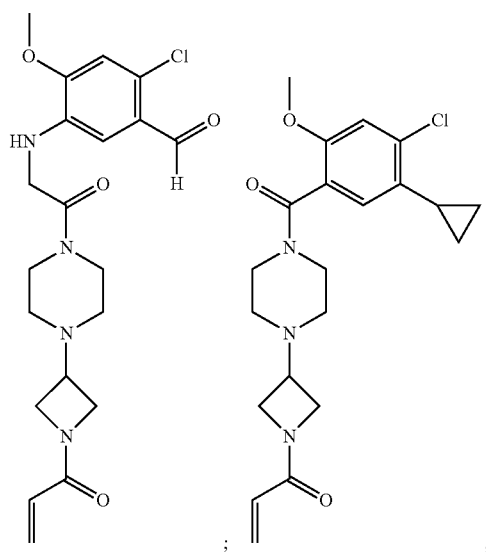
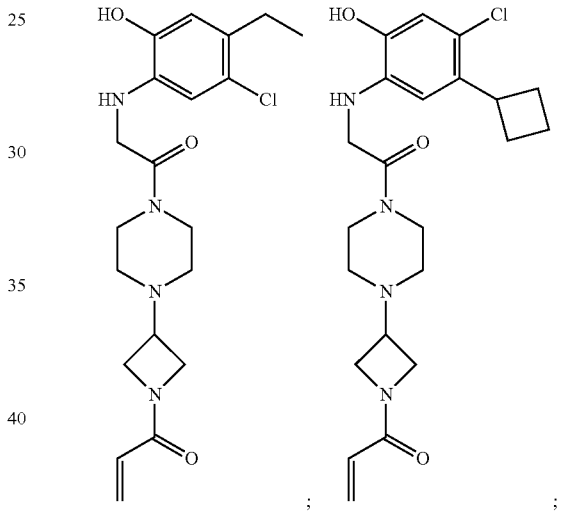
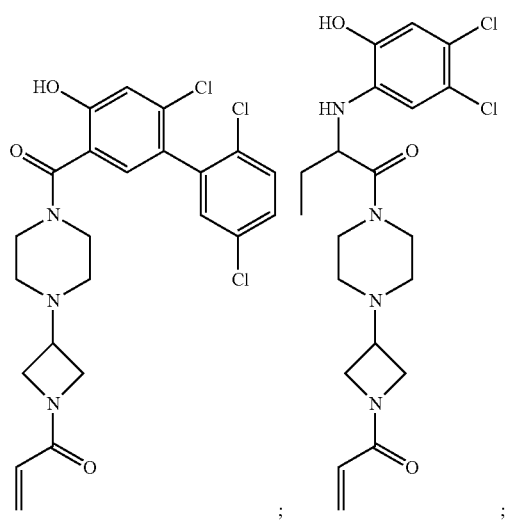
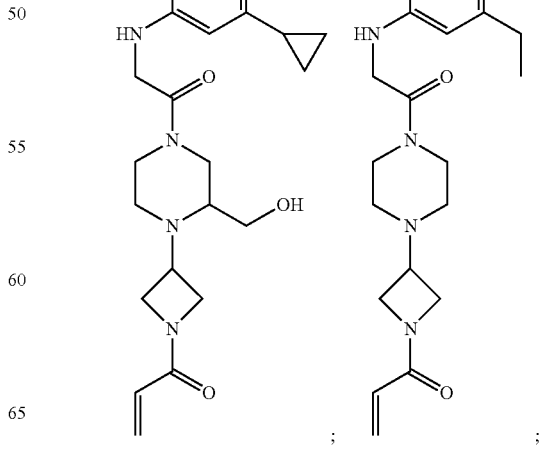

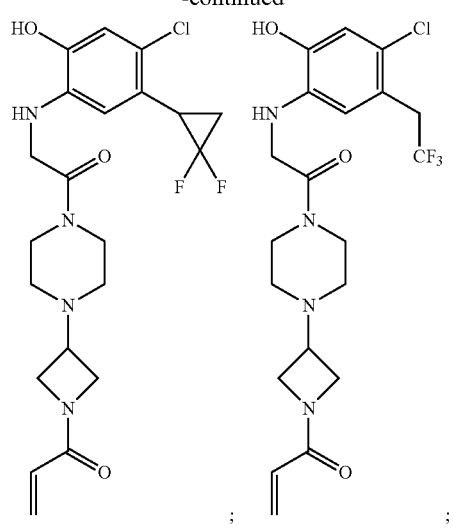
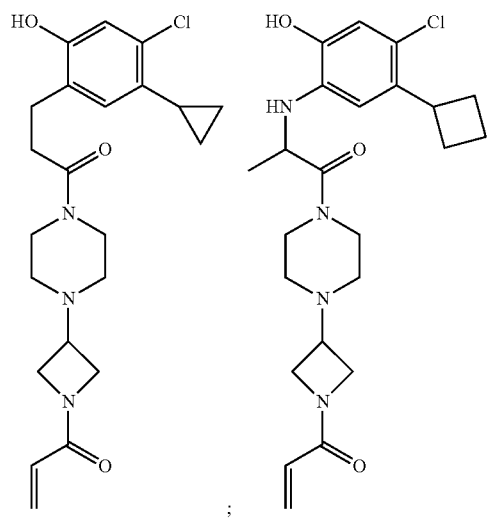
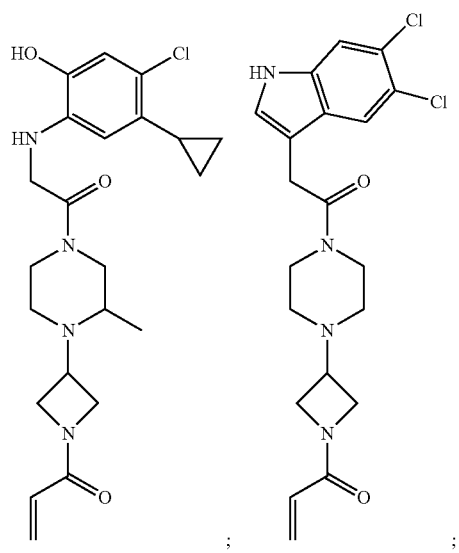
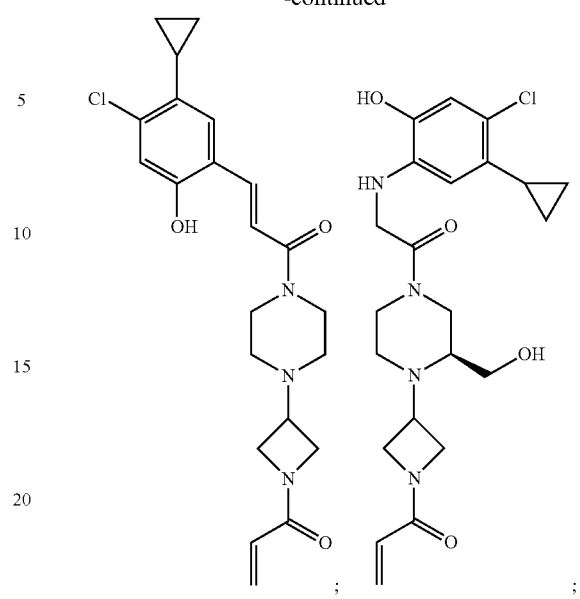
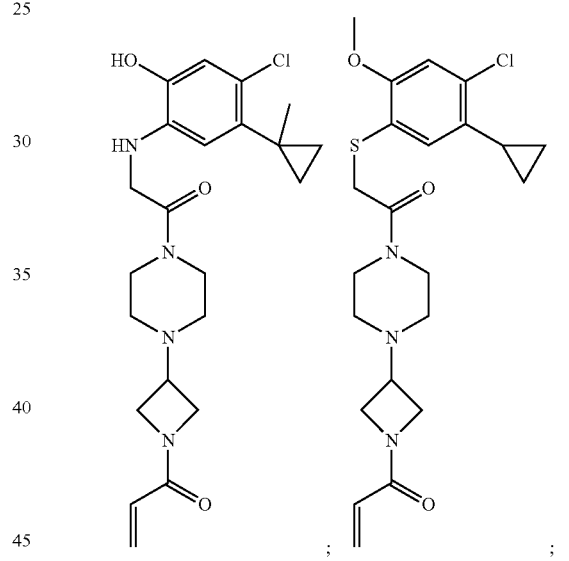
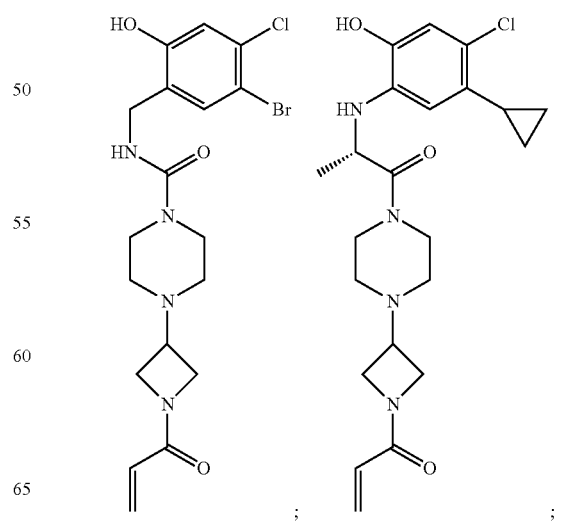

-continued
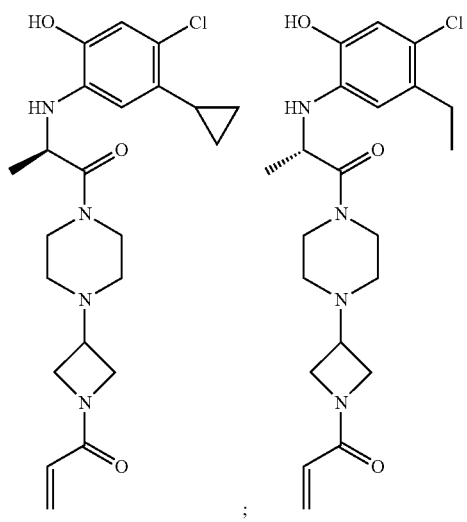
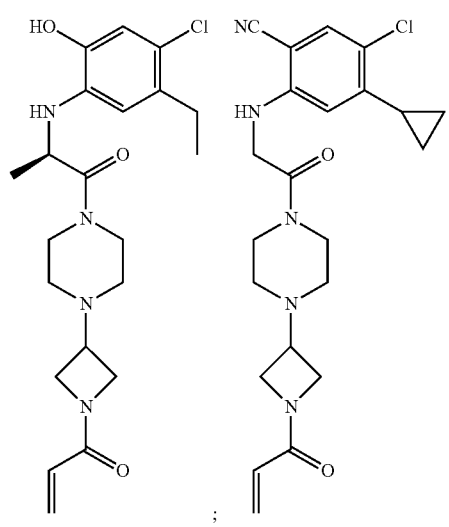
-continued
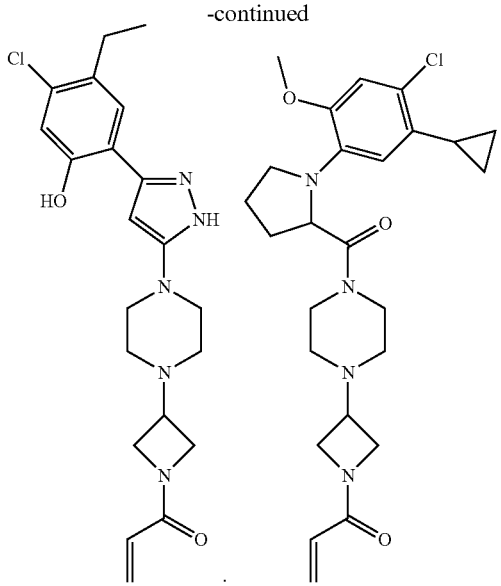
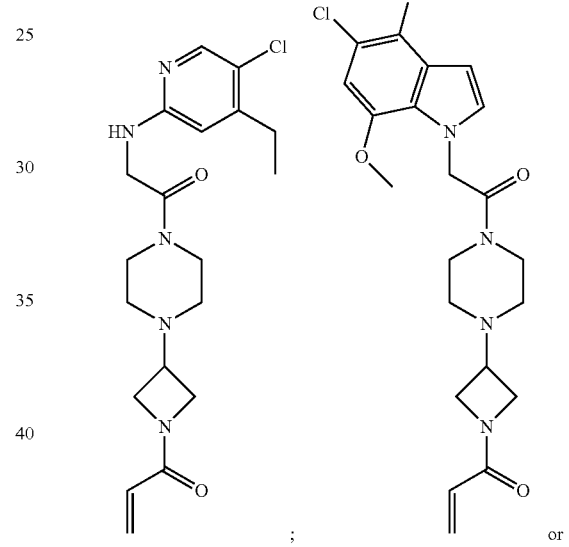
24. A pharmaceutical composition comprising a compound of claim 1 and a pharmaceutically acceptable carrier.
* * * * *